US010889811B2

(12) United States Patent
Vasquez et al.

(10) Patent No.: US 10,889,811 B2
(45) Date of Patent: Jan. 12, 2021

(54) ANTIBODY LIBRARIES

(71) Applicant: Adimab, LLC, Lebanon, NH (US)

(72) Inventors: Maximiliano Vasquez, Palo Alto, CA (US); Arvind Sivasubramanian, Santa Clara, CA (US); Michael Feldhaus, Grantham, NH (US)

(73) Assignee: Adimab, LLC, Lebanon, NH (US)

( * ) Notice: Subject to any disclaimer, the term of this patent is extended or adjusted under 35 U.S.C. 154(b) by 107 days.

(21) Appl. No.: 16/126,987

(22) Filed: Sep. 10, 2018

(65) Prior Publication Data

US 2018/0371454 A1 Dec. 27, 2018

Related U.S. Application Data

(62) Division of application No. 15/151,626, filed on May 11, 2016, now Pat. No. 10,138,478, which is a division of application No. 13/810,570, filed as application No. PCT/US2011/044063 on Jul. 14, 2011, now Pat. No. 9,354,228.

(60) Provisional application No. 61/365,194, filed on Jul. 16, 2010.

(51) Int. Cl.

| | |
|---|---|
| ***C40B 50/06*** | (2006.01) |
| ***C12N 15/10*** | (2006.01) |
| ***C07K 16/00*** | (2006.01) |
| ***G01N 33/543*** | (2006.01) |
| *C40B 40/08* | (2006.01) |
| *G16B 35/00* | (2019.01) |
| *G16C 20/60* | (2019.01) |

(52) U.S. Cl.

CPC .......... *C12N 15/1089* (2013.01); *C07K 16/00* (2013.01); *G01N 33/543* (2013.01); *C07K 2317/21* (2013.01); *C07K 2317/565* (2013.01); *C07K 2317/567* (2013.01); *C40B 40/08* (2013.01); *C40B 50/06* (2013.01); *G16B 35/00* (2019.02); *G16C 20/60* (2019.02)

(58) Field of Classification Search

None

See application file for complete search history.

(56) References Cited

U.S. PATENT DOCUMENTS

| | | | |
|---|---|---|---|
| 4,946,778 | A | 8/1990 | Ladner et al. |
| 5,118,605 | A | 6/1992 | Urdea |
| 5,223,409 | A | 6/1993 | Ladner et al. |
| 5,283,173 | A | 2/1994 | Fields et al. |
| 5,380,833 | A | 1/1995 | Urdea |
| 5,525,490 | A | 6/1996 | Erickson et al. |

(Continued)

FOREIGN PATENT DOCUMENTS

| | | | |
|---|---|---|---|
| DE | 19624562 | A1 | 1/1998 |
| EP | 0469897 | A2 | 2/1992 |

(Continued)

OTHER PUBLICATIONS

Abbas et al., "Cellular and Molecular Immunology", 4th ed., p. 43, Figure 3-1,. W.B. Saunders Co. (2000).

(Continued)

*Primary Examiner* — Christian C Boesen

(74) *Attorney, Agent, or Firm* — Choate, Hall & Stewart LLP; Brenda Herschbach Jarrell; Meaghan E. Bychowski

(57) ABSTRACT

The present invention overcomes the inadequacies inherent in the known methods for generating libraries of antibody-encoding polynucleotides by specifically designing the libraries with directed sequence and length diversity.

18 Claims, 15 Drawing Sheets

Specification includes a Sequence Listing.

(56) References Cited

U.S. PATENT DOCUMENTS

| | | | |
|---|---|---|---|
| 5,530,101 | A | 6/1996 | Queen et al. |
| 5,565,332 | A | 10/1996 | Hoogenboom et al. |
| 5,571,698 | A | 11/1996 | Ladner et al. |
| 5,618,920 | A | 4/1997 | Robinson et al. |
| 5,658,727 | A | 8/1997 | Barbas et al. |
| 5,688,666 | A | 11/1997 | Bass et al. |
| 5,695,941 | A | 12/1997 | Brent et al. |
| 5,723,323 | A | 3/1998 | Kauffman et al. |
| 5,733,743 | A | 3/1998 | Johnson et al. |
| 5,739,281 | A | 4/1998 | Thogersen et al. |
| 5,750,373 | A | 5/1998 | Garrard et al. |
| 5,767,260 | A | 6/1998 | Whitlow et al. |
| 5,780,279 | A | 7/1998 | Matthews et al. |
| 5,798,208 | A | 8/1998 | Crea |
| 5,811,238 | A | 9/1998 | Stemmer et al. |
| 5,814,476 | A | 9/1998 | Kauffman et al. |
| 5,817,483 | A | 10/1998 | Kauffman et al. |
| 5,821,047 | A | 10/1998 | Garrard et al. |
| 5,824,514 | A | 10/1998 | Kauffman et al. |
| 5,830,663 | A | 11/1998 | Embleton et al. |
| 5,837,242 | A | 11/1998 | Holliger et al. |
| 5,837,500 | A | 11/1998 | Ladner et al. |
| 5,840,479 | A | 11/1998 | Little et al. |
| 5,846,765 | A | 12/1998 | Matthews et al. |
| 5,858,657 | A | 1/1999 | Winter et al. |
| 5,858,671 | A | 1/1999 | Jones |
| 5,863,765 | A | 1/1999 | Berry et al. |
| 5,866,344 | A | 2/1999 | Georgiou |
| 5,869,250 | A | 2/1999 | Cheng et al. |
| 5,871,907 | A | 2/1999 | Winter et al. |
| 5,872,215 | A | 2/1999 | Osbourne et al. |
| 5,885,793 | A | 3/1999 | Griffiths et al. |
| 5,888,773 | A | 3/1999 | Jost et al. |
| 5,917,018 | A | 6/1999 | Thogersen et al. |
| 5,922,545 | A | 7/1999 | Mattheakis et al. |
| 5,928,868 | A | 7/1999 | Liu et al. |
| 5,935,831 | A | 8/1999 | Quax et al. |
| 5,948,620 | A | 9/1999 | Hurd et al. |
| 5,955,275 | A | 9/1999 | Kamb |
| 5,962,255 | A | 10/1999 | Griffiths et al. |
| 5,965,368 | A | 10/1999 | Vidal et al. |
| 5,969,108 | A | 10/1999 | McCafferty et al. |
| 5,976,862 | A | 11/1999 | Kauffman et al. |
| 5,994,515 | A | 11/1999 | Hoxie |
| 5,994,519 | A | 11/1999 | Osbourn et al. |
| 6,010,884 | A | 1/2000 | Griffiths et al. |
| 6,017,732 | A | 1/2000 | Jespers et al. |
| 6,027,910 | A | 2/2000 | Klis et al. |
| 6,040,136 | A | 3/2000 | Garrard et al. |
| 6,057,098 | A | 5/2000 | Buechler et al. |
| 6,057,101 | A | 5/2000 | Nandabalan et al. |
| 6,072,036 | A | 6/2000 | Marasco et al. |
| 6,083,693 | A | 7/2000 | Nandabalan et al. |
| 6,114,147 | A | 9/2000 | Frenken et al. |
| 6,132,963 | A | 10/2000 | Brent et al. |
| 6,140,471 | A | 10/2000 | Johnson et al. |
| 6,159,705 | A | 12/2000 | Trueheart et al. |
| 6,171,795 | B1 | 1/2001 | Korman et al. |
| 6,172,197 | B1 | 1/2001 | McCafferty et al. |
| 6,180,336 | B1 | 1/2001 | Osbourn et al. |
| 6,187,535 | B1 | 2/2001 | LeGrain et al. |
| 6,200,759 | B1 | 3/2001 | Dove et al. |
| 6,225,447 | B1 | 5/2001 | Winter et al. |
| 6,248,516 | B1 | 6/2001 | Winter et al. |
| 6,291,158 | B1 | 9/2001 | Winter et al. |
| 6,291,159 | B1 | 9/2001 | Winter et al. |
| 6,291,160 | B1 | 9/2001 | Lerner et al. |
| 6,291,161 | B1 | 9/2001 | Lerner et al. |
| 6,291,650 | B1 | 9/2001 | Winter et al. |
| 6,300,064 | B1 | 10/2001 | Knappik et al. |
| 6,300,065 | B1 | 10/2001 | Kieke et al. |
| 6,319,690 | B1 | 11/2001 | Little et al. |
| 6,342,588 | B1 | 1/2002 | Osbourn et al. |
| 6,358,733 | B1 | 3/2002 | Motwani et al. |
| 6,406,863 | B1 | 6/2002 | Zhu et al. |
| 6,410,246 | B1 | 6/2002 | Zhu et al. |
| 6,410,271 | B1 | 6/2002 | Zhu et al. |
| 6,420,113 | B1 | 7/2002 | Buechler et al. |
| 6,423,538 | B1 | 7/2002 | Wittrup et al. |
| 6,489,123 | B2 | 12/2002 | Osbourn et al. |
| 6,492,107 | B1 | 12/2002 | Kauffman et al. |
| 6,492,123 | B1 | 12/2002 | Holliger et al. |
| 6,492,160 | B1 | 12/2002 | Griffiths et al. |
| 6,521,404 | B1 | 2/2003 | Griffiths et al. |
| 6,531,580 | B1 | 3/2003 | Huse et al. |
| 6,544,731 | B1 | 4/2003 | Griffiths et al. |
| 6,545,142 | B1 | 4/2003 | Winter et al. |
| 6,555,313 | B1 | 4/2003 | Griffiths et al. |
| 6,569,641 | B1 | 5/2003 | Kauffman et al. |
| 6,582,915 | B1 | 6/2003 | Griffiths et al. |
| 6,589,527 | B1 | 7/2003 | Winter et al. |
| 6,589,741 | B2 | 7/2003 | Pluckthun et al. |
| 6,593,081 | B1 | 7/2003 | Griffiths et al. |
| 6,610,472 | B1 | 8/2003 | Zhu et al. |
| 6,653,443 | B2 | 11/2003 | Zhang et al. |
| 6,664,048 | B1 | 12/2003 | Wanker et al. |
| 6,680,192 | B1 | 1/2004 | Lerner et al. |
| 6,696,245 | B2 | 2/2004 | Winter et al. |
| 6,696,248 | B1 | 2/2004 | Knappik et al. |
| 6,696,251 | B1 | 2/2004 | Wittrup et al. |
| 6,699,658 | B1 | 3/2004 | Wittrup et al. |
| 6,706,484 | B1 | 3/2004 | Knappik et al. |
| 6,753,136 | B2 | 6/2004 | Lohning |
| 6,806,079 | B1 | 10/2004 | McCafferty et al. |
| 6,828,422 | B1 | 12/2004 | Achim et al. |
| 6,833,441 | B2 | 12/2004 | Wang et al. |
| 6,846,634 | B1 | 1/2005 | Tomlinson et al. |
| 6,916,605 | B1 | 7/2005 | McCafferty et al. |
| 6,919,183 | B2 | 7/2005 | Fandl et al. |
| 6,969,586 | B1 | 11/2005 | Lerner et al. |
| 7,005,503 | B2 | 2/2006 | Hua et al. |
| 7,063,943 | B1 | 6/2006 | McCafferty et al. |
| 7,083,945 | B1 | 8/2006 | Chen et al. |
| 7,094,571 | B2 | 8/2006 | Harvey et al. |
| 7,138,496 | B2 | 11/2006 | Hua et al. |
| 7,166,423 | B1 | 1/2007 | Miltenyi et al. |
| 7,189,841 | B2 | 3/2007 | Lerner et al. |
| 7,208,293 | B2 | 4/2007 | Ladner et al. |
| 7,435,553 | B2 | 10/2008 | Fandl et al. |
| 7,465,787 | B2 | 12/2008 | Wittrup et al. |
| 7,569,357 | B2 | 8/2009 | Kranz et al. |
| 10,138,478 | B2 | 11/2018 | Vasquez et al. |
| 2001/0037016 | A1 | 11/2001 | Ning et al. |
| 2001/0041333 | A1 | 11/2001 | Short et al. |
| 2002/0004215 | A1 | 1/2002 | Osbourn et al. |
| 2002/0026653 | A1 | 2/2002 | Allen et al. |
| 2002/0037280 | A1 | 3/2002 | Lieber et al. |
| 2002/0169284 | A1 | 11/2002 | Ashkenazi et al. |
| 2002/0177170 | A1 | 11/2002 | Luo et al. |
| 2002/0197691 | A1 | 12/2002 | Sugiyama |
| 2003/0022240 | A1 | 1/2003 | Luo et al. |
| 2003/0091995 | A1 | 5/2003 | Buechler et al. |
| 2003/0114659 | A1 | 6/2003 | Winter et al. |
| 2003/0130496 | A1 | 7/2003 | Winter et al. |
| 2003/0148372 | A1 | 8/2003 | Tomlinson et al. |
| 2003/0165988 | A1 | 9/2003 | Hua et al. |
| 2003/0190674 | A1 | 10/2003 | Griffiths et al. |
| 2003/0228302 | A1 | 12/2003 | Crea |
| 2003/0232333 | A1 | 12/2003 | Ladner et al. |
| 2003/0232395 | A1 | 12/2003 | Hufton |
| 2004/0038921 | A1 | 2/2004 | Kreutzer et al. |
| 2004/0110941 | A2 | 6/2004 | Winter et al. |
| 2004/0146976 | A1 | 7/2004 | Wittrup et al. |
| 2004/0157214 | A1 | 8/2004 | McCafferty et al. |
| 2004/0157215 | A1 | 8/2004 | McCafferty et al. |
| 2004/0219611 | A1 | 11/2004 | Racher |
| 2005/0202512 | A1 | 9/2005 | Tomlinson et al. |
| 2006/0003334 | A1 | 1/2006 | Achim et al. |
| 2006/0019260 | A1 | 1/2006 | Lerner et al. |
| 2006/0159673 | A1 | 7/2006 | Kojima |
| 2006/0166252 | A1 | 7/2006 | Ladner et al. |
| 2006/0234302 | A1 | 10/2006 | Hoet et al. |
| 2006/0257937 | A1 | 11/2006 | Ladner |
| 2007/0031879 | A1 | 2/2007 | Ley et al. |

(56) References Cited

U.S. PATENT DOCUMENTS

| | | | |
|---|---|---|---|
| 2007/0099267 A1 | 5/2007 | Harvey et al. | |
| 2007/0258954 A1 | 11/2007 | Iverson et al. | |
| 2008/0108514 A1 | 5/2008 | Mattheus Hoogenboom | |
| 2008/0153712 A1 | 6/2008 | Crea | |
| 2008/0171059 A1 | 7/2008 | Howland et al. | |
| 2009/0082213 A1 | 3/2009 | Horowitz et al. | |
| 2009/0181855 A1 | 7/2009 | Vasquez et al. | |
| 2010/0009866 A1 | 1/2010 | Prinz et al. | |
| 2010/0056386 A1 | 3/2010 | Vasquez et al. | |
| 2010/0292103 A1 | 11/2010 | Ladner | |
| 2011/0009280 A1 | 1/2011 | Hufton et al. | |
| 2011/0082054 A1 | 4/2011 | Ladner | |
| 2011/0118147 A1 | 5/2011 | Ladner | |
| 2011/0136695 A1 | 6/2011 | Crea | |
| 2011/0172125 A1 | 7/2011 | Ladner | |
| 2016/0244750 A1 | 8/2016 | Vasquez et al. | |

FOREIGN PATENT DOCUMENTS

| | | |
|---|---|---|
| EP | 1438400 A1 | 7/2004 |
| JP | H05-68599 A | 3/1993 |
| WO | WO-88/01649 A1 | 3/1988 |
| WO | WO-88/06630 A1 | 9/1988 |
| WO | WO-94/01567 A1 | 1/1994 |
| WO | WO-94/07922 A1 | 4/1994 |
| WO | WO-94/18330 A1 | 8/1994 |
| WO | WO-95/26400 A1 | 10/1995 |
| WO | WO-97/08320 A1 | 3/1997 |
| WO | WO-97/20923 A1 | 6/1997 |
| WO | WO-97/49809 A1 | 12/1997 |
| WO | WO-98/49198 A1 | 11/1998 |
| WO | WO-99/06834 A2 | 2/1999 |
| WO | WO-99/28502 A1 | 6/1999 |
| WO | WO-99/36569 A1 | 7/1999 |
| WO | WO-99/50461 A1 | 10/1999 |
| WO | WO-99/53049 A1 | 10/1999 |
| WO | WO-99/55367 A1 | 11/1999 |
| WO | WO-00/18905 A1 | 4/2000 |
| WO | WO-00/54057 A1 | 9/2000 |
| WO | WO-01/79229 A2 | 10/2001 |
| WO | WO-01/79481 A2 | 10/2001 |
| WO | WO-02/055718 A2 | 7/2002 |
| WO | WO-03/029456 A1 | 4/2003 |
| WO | WO-2004/065611 A1 | 8/2004 |
| WO | WO-2005/007121 A2 | 1/2005 |
| WO | WO-2005023993 A2 | 3/2005 |
| WO | WO-2005/054273 A2 | 6/2005 |
| WO | WO-2006/138700 A2 | 12/2006 |
| WO | WO-2007/054816 A2 | 5/2007 |
| WO | WO-2007/056441 A2 | 5/2007 |
| WO | WO-2008/019366 A2 | 2/2008 |
| WO | WO-2008/042754 A2 | 4/2008 |
| WO | WO-2008/053275 A2 | 5/2008 |
| WO | WO-2008067547 A2 | 6/2008 |
| WO | WO-2009/036379 A2 | 3/2009 |
| WO | WO-2009/132287 A2 | 10/2009 |
| WO | WO-2010/005863 A1 | 1/2010 |
| WO | WO-2010/054007 A1 | 5/2010 |
| WO | WO-2010/105256 A1 | 9/2010 |
| WO | WO-2012/009568 A2 | 1/2012 |

OTHER PUBLICATIONS

Abbas et al., Cellular and Molecular Immunology, Fourth Edition—Section III Maturation, Activation, and Regulation of Lymphocytes, 125-133 (2000).

Adams, G.P. and Schier, R., "Generating Improved Single-Chain Fv Molecules for Tumor Targeting" Journal of Immunological Methods, 231:249-260 (1999).

Adams, G.P. and Weiner, L. M., "Monoclonal antibody therapy of cancer" Nature Biotechnology, 23(9) 1147-1157 (2005).

Akamatsu, Y. et al., "Construction of a human Ig combinatorial library from genomic V segments and synthetic CDR3 fragments" J. Immunol., 51(9):4651-4659 (1993).

Allen, J.B. et al., "Finding prospective partners in the library: the two-hybrid system and phage display find a match" TIBS, 20:(12):511-516 (1995).

Alt, F.W. and Baltimore, D., "Joining of Immunoglobulin Heavy Chain Gene Segments: Implications from a Chromosome with Evidence of Three D-JH Fusions" PNAS, 79:4118-4122 (1982).

Arden, B., "Conserved motifs in T-cell receptor CDR1 and CDR2: implications for ligand and CDS co-receptor binding" Current Opinion In Immunology, Current Biology LTD., 10(1):74-81 (1998).

Aronheim, Ami et al., "Isolation of an AP-1 Repressor by a Novel Method for Detecting Protein-Protein Interactions" Molecular and Cellular Biology, 17(6):3094-3102 (1997).

Aujame, L. et al., "High affinity human antibodies by phage display" Human Antibodies, 8(4):155-168 (1997).

Ayala, M. et al., "Variable region sequence modulates periplasmic export of a single-chain Fv antibody fragment in *Escherichia coli*" BioTechniques, 18(5):832-838, 840-2 (1995).

Bahler et al., "Clonal Salivary Gland Infiltrates Associated with Myoepithelial Sialadenitis (Sjogren's Syndrome) Begin as Nonmalignant Antigen-Selected Expansions", Blood, 91(6):1864-1872 (1998).

Bakkus et al., "Evidence that Multiple Myeloma Ig Heavy Chain VDJ Genes Contain Somatic Mutations but Show no Intraclonal Variation", Blood, 80(9):2326-2335 (1992).

Balint, R.F. and Larrick, J.W., "Antibody engineering by parsimonious mutagenesis" Gene, 137:109-118 (1993).

Barbas et al., "Molecular Profile of an Antibody Response to HIV-1 as Probed by Combinatorial Libraries", J. Mol. Bioi., 230:812-823 (1993).

Barbas, C.F. 3rd et al., "Human autoantibody recognition of DNA" Proc. Natl. Acad. Sci., 92:2529-2533 (1995).

Barbas, C.F. 3rd et al., "Semisynthetic combinatorial antibody libraries: a chemical solution to the diversity problem" Proceedings of the National Academy of Sciences of USA, 89:4457-4461 (1992).

Barbas, C.F. 3rd, et al., "Assembly of combinatorial antibody libraries on phage surfaces: The gene III site" Proc. Natl. Acad. Sci., 88:7978-7982 (1991).

Basu, M. et al., "Synthesis of compositionally unique DNA by terminal deoxynucleotidyl transferase" Biochem. Biophys. Res. Comm., 111(3):1105-1112 (1983).

Bhatia, S.K. et al., "Rolling adhesion kinematics of yeast engineered to express selectins" Biotech. Prog., 19:1033-1037 (2003).

Binz, H.K. et al., "Engineering novel binding proteins from nonimmunoglobulin domains" Nat. Biotechnol., 23(10):1257-1268 (2005).

Bird, R.E. et al., "Single-chain antigen-binding proteins" Science, 242(4877):423-426 (1988).

Boder and Wittrup, "Yeast Surface Display for Directed Evolution of Protein Expression, Affinity, and Stability" Methods in Enzymology 328:430-444 (2000).

Boder and Wittrup, "Yeast surface display system for antibody engineering" pp. 283 (1996).

Boder et al., "Yeast Surface Display of a Noncovalent MHC Class II Heterodimer Complexed With Antigenic Peptide" Biotechnology and Bioengineering 92(4):485-491 (2005).

Boder, E.T. and Jiang, W., "Engineering Antibodies for Cancer Therapy" Annu. Rev. Chem. Biomol. Eng. 2:53-75 (2011).

Boder, E.T. and Wittrup, K.D., "Optimal screening of surface-displayed polypeptide libraries" Biotechnol Prog.,14(1):55-62 (1998).

Boder, E.T. and Wittrup, K.D., "Yeast surface display for screening combinatorial polypeptide libraries" Nat Biotechnol.,15(6):553-7 (1997).

Boder, E.T. et al., "Directed evolution of antibody fragments with monovalent femtomolar antigen-binding affinity" Proc Natl Acad Sci USA, 97(20):10701-5 (2000).

Borth, N. et al., "Efficient selection of high-producing subclones during gene amplification of recombinant Chinese hamster ovary cells by flow cytometry and cell sorting" Biotechnol. and Bioengin., 71(4):266-273 (2000-2001).

Bradbury, A., "Display Technologies Expand Their Horizons" TIBTECH 17:137-138 (1999).

Bradbury, A., "Molecular Library Technologies at the Millennium", TIBTECH 18:132-133 (2000).

(56) References Cited

OTHER PUBLICATIONS

Bradbury, A., "Recent advances in phage display: the report of the Phage Club first meeting" Immunotechnology, 3(3):227-231 (1997).
Breitling, F. et al., "A surface expression vector for antibody screening" Gene, 104(2):147-153 (1991).
Brezinschek, H.P. et al., "Analysis of the human VH gene repertoire. Differential effects of selection and somatic hypermutation on human peripheral CD5(+)/IgM+ and CD5(−)/IgM+ B cells" The American Society for Clinical Investigation, Inc., 99(10):2488-2501 (1997).
Broder, Y.C. et al., "The ras recruitment system, a novel approach to the study of protein-protein interactions" Current Biology 8(20):1121-1124 (1998).
Brophy et al., "A yeast display system for engineering functional peptide-MHC complexes" Journal of Immunological Methods 272:235-246 (2003).
Burke et al., "Methods in Yeast Genetics", pp. 40-41 (2000).
Burton, D.R. et al., "A large array of human monoclonal antibodies to type 1 human immunodeficiency virus from combinatorial libraries of asymptomatic seropostive individuals" Proc. Natl. Acad. Sci., 88(22):10134-10137 (1991).
Canaán-Haden, L., "Purification and application of a single-chain Fv antibody fragment specific to hepatitis B virus surface antigen" BioTechniques, 19(4) 606-608, 610, 612 passim(1995).
Cappellaro et al., "Mating type-specific cell—cell recognition of *Saccharomyces cerevisiae*: cell wall attachment and active sites of a- and alpha-agglutinin1" The EMBO Journal 13(20)4737-4744 (1994).
Carroll et al., "Absence of Ig V Region Gene Somatic Hypermutation in Advanced Burkitt's Lymphoma", J. Immunol.,143(2):692-698 (1989).
Casset, F.et al., "A peptide mimetic of an anti-CD4 monoclonal antibody by rational design" Biochemical and Biophysical Research Communications, 307(1):198-205, (2003).
Castelli, L.A. et al., "High-level secretion of correctily processed beta-lactamase from *Saccharomyces ceravisiae* using a high-copy-number secretion vector" Biomolecular Research Institute, 142(1):113-117 (1994).
Caton, A.J. and Koprowski, H., "Influenza virus hemagglutinin-specific antibodies isolated from a combinatorial expression library are closely related to the immune response of the donor" Proc. Natl. Acad. Science, USA, 87(16):6450-6454 (1990).
Cattaneo, A. and Biocca, S., "The selection of intracellular antibodies" TIBTECH, 17:115-120 (1999).
Chang, C.N. et al., "Expression of antibody Fab domains on bacteriophage surfaces. Potential use for antibody selection" J. Immunol, 147(10):3610-3614. (1991).
Chang, H.C. et al., "A general method for facilitating heterodimeric pairing between two proteins: Application to expression of alpha and beta T-cell receptor extracellular segments" Proc Natl. Acad. Sci., USA, 91:11408-11412 (1994).
Chaudhary, V.K. et al., "A rapid method of cloning functional variable-region antibody genes in *Escherichia coli* as single-chain immunotoxins" Proc. Natl. Acad. Sci., 87(3):1066-1070 (1990).
Chen, W. et al., "Characterization of germline antibody libraries from human umbilical cord blood and selection of monoclonal antibodies to viral envelope glycoproteins: Implications for mechanisms of immune evasion and design of vaccine immunogens" Biochem. Biophys. Res. Commun. 1-6 (2012).
Chiswell, David and McCaffery, John, "Phage antibodies: will new 'coliclonal' antibodies replace monoclonal antibodies?" TIBTECH, 10(3):80-84 (1992).
Cho et al., "A yeast surface display system for the discovery of ligands that trigger cell activation" journal of Immunological Methods 220:179-188 (1998).
Chothia, C. and Lesk, A.M., "Canonical structures for the hypervariable regions of immunoglobulins" J. Mol. Biol., 196(4):901-917 (1987).
Chothia, C. et al., "Conformations of immunoglobulin hypervariable regions" Nature, 342(6252):877-883 (1989).
Chothia, C. et al., "Structural repertoire of the human VH segments" J. Mol. Biol., 227(3):799-817 (1992).
Cioe, L., Cloning and Nucleotide Sequence of a Mouse Erythrocyte beta-Spectrin cDNA, Blood, 70:915-920 (1987).
Clackson, T. and Wells, J.A., "In vitro selection from protein and peptide libraries" Trends Biotechnol., 12(5):173-184 (1994).
Clackson, T. et al., "Making antibody fragments using phage display libraries" Nature, 352(6336):624-628 (1991).
Co, M.S. and Queen, C., "Humanized antibodies for therapy" Nature, 351(6326):501-502 (1991).
Colby et al., "Development of a Human Light Chain Variable Domain (VL) Intracellular Antibody Specific for the Amino Terminus of Huntingtin via Yeast Surface Display" J. Mol. Biol. 901-912 (2004).
Collins, A.M. et al., "Partitioning of rearranged Ig genes by mutation analysis demonstrates D-D fusion and V gene replacement in the expressed human repertoire" J. Immunol., 172(1):340-348 (2004).
Collins, A.M. et al., "The reported germline repertoire of human immunoglobulin kappa chain genes is relatively complete and accurate" Immunogenetics, 60(11):669-676 (2008).
Corbett, S.J. et al., "Sequence of the human immunoglobulin diversity (D) segment locus: a systematic analysis provides no evidence for the use of DIR segments, nverted D egments, "minor" D segments or D-D recombination" J. Mol. Bioi., 270:587-597 (1997).
Courtney, B.C. et al., "A phage display vector with improved stability, applicability and ease of manipulation", Gene, 165(1):139-140 (1995).
Couto, J.R. et al., "Designing human consensus antibodies with minimal positional templates", Cancer Res., (23 Suppl):5973s-5977s (1995).
Crameri, R. and Suter, M., "Display of biologically active proteins on the surface of filamentous phages: a cDNA cloning system for selection of functional gene products linked to the genetic information responsible for their production" Gene, 137(1):69-75 (1993).
Cwirla, S.E., et al., "Peptides on phage: a vast library of peptides for identifying ligands" Proc. Natl. Acad. Sci. USA, 87(16):6378-6382 (1990).
Davi et al., "High Frequency of Somatic Mutations in the VH Genes Expressed in Prolymphocytic Leukemia", Blood, 88 (10):3953-3961 (1996).
Davies, J. and Riechmann, L., "Affinity improvement of single antibody VH domains: residues in all three hypervariable regions affect antigen binding" Immunotechnology 2(3):169-179 (1996).
de Haard et al., "A Large Non-immunized Human Fab Fragment Phage Library That Permits Rapid Isolation and Kinetic Analysis of High Affinity Antibodies" Journal of Biological Chemistry, 274(26):18218-18230 (1999).
De Jaeger, G. et al., "Analysis of the interaction between single-chain variable fragments and their antigen in a reducing intracellular environment using the two-hybrid system" FEBS Lett., 467(2-3):316-320 (2000).
de Kruif, J. et al., "Selection and application of human single chain Fv antibody fragments from a semi-synthetic phage antibody display library with designed CDR3 regions" J. Mol. Biol. 248(1):97-105 (1995).
Delves, P.J. "Antibody production: essential techniques" John Wiley & Sons, New York, pp. 90-113 (1997).
DiPietro et al., "Limited number of immunoglobulin VH regions expressed in the mutant rabbit 'Alicia'", Eur. J. Immunol., 20:1401-1404 (1990).
Dranginis et al., "A Biochemical Guide to Yeast Adhesins: Glycoproteins for Social and Antisocial Occasions" Microbiology and Molecular Biology Reviews 71(2)282-294 (2007).
Esposito et al., "Phage display of a human antibody against Clostridium tetani toxin", Gene, 148:167-168 (1994).
Fan, Z. et al., "Three-dimensional structure of an Fv from a human IgM immunoglobulin" J. Mol. Biol., 228(1):188-207 (1992).
Fellouse, F.A. et al., "High-throughput Generation of Synthetic Antibodies from Highly Functional Minimalist Phage-displayed Libraries" J. Mol. Biol. 373(4):924-940 (2007).
Fellouse, F.A. et al., "Molecular Recognition by a Binary Code" J. Mol, Biol. 348(5):1153-1162 (2005).

(56) References Cited

OTHER PUBLICATIONS

Fellouse, F.A. et al., "Synthetic antibodies from a four-amino-acid code: a dominant role for tyrosine in antigen recognition" PNAS, 101(34):12467-12472 (2004).
Fields, S. and Sternglanz, R., "The two-hybrid system: an assay for protein-protein interactions" Trends Genet.,10(8):286-292 (1994).
Fields. S. and Song, O., "A novel genetic system to detect protein-protein interactions" Nature, 340(6230):245-246 (1989).
Firth, A.E. and Patrick, W.M., "Glue-It and Pedel-AA: new programmes for analyzing protein diversity in randomized libraries" Nucleic Acids Res., 36:W281-W285 (2008).
Flyak, A. et al., In silico analysis of the structure of variable domains of mouse single-chain antibodies specific to the human recombinant interferon beta1b, Cytol Genet, 43(1):54-60 (2009).
Foote, J. and Winter, G., Antibody Framework Residues Affecting the Conformation of the Hypervariable Loops, J. Mol. Biol., 224:487-499 (1992).
Frazer, J. K., and J. D. Capra, "Immunoglobulins: Structure and Function", in Fundamental Immunology, Fourth Edition, William E. Paul, ed., Lippincot-Raven Publishers, Philadelphia, pp. 41-43 and 51-52 (1999).
Frykman, S. and Srienc, F., "Quantitating secretion rates of individual cells: design of secretion assays" Biotechnol. & Bioeng., 59(2):214-226 (1998).
Fuh, G., "Synthetic antibodies as therapeutics" Expert Opin. Biol. Ther., 7(1):73-87 (2007).
Fusco, et al., In vivo construction of cDNA libraries for use in the yeast two-hybrid system. Yeast, 15(8):715-720 (1999).
Gietz et al., "Improved method for high efficiency transformation of intact yeast cells" Nucleic Acids Res., 20(6):1425 (1992).
Gietz, R.D. and R.H. Schiestl, "Transforming Yeast with DNA" Methods in Molecular and Cellular Biology (Invited Chapter), 5:255-269 (1995).
Gilfillan, S. et al., "Efficient immune responses in mice lacking N-region diversity" Eur. J. Immunol., 25(11):3115-3122 (1995).
Griffin et al., "Blockade of T Cell Activation Using a Surface-Linked Single-Chain Antibody to CTLA-4 (CD152)" J Immunol. 64(9):4433-4442 (2000).
Griffiths, A.D. et al., "Isolation of high affinity human antibodies directly from large synthetic repertoires," EMBO J., 13(14):3245-3260 (1994).
Griffiths, A.D. et al., Human anti-self antibodies with high specificity from phage display libraries, EMBO J., 12(2):725-734 (1993).
Hamilton and Gerngross, "Glycosylation engineering in yeast: the advent of fully humanized yeast" Current Opinion in Biotechnology 18:387-392 (2007).
Hanes, J. et al., "Picomolar affinity antibodies from a fully synthetic naive library selected and evolved by ribosome display" Nat Biotechnol. 18:(12):1287-1292 (2000).
Hasan, N. and Szybalski, W., "Control of cloned gene expression by promoter inversion in vivo: construction of improved vectors with a multiple cloning site and the Ptac promoter" Gene, 56(1):145-151 (1987).
Hawkins, R.E. and Winter, G., "Cell selection strategies for making antibodies from variable gene libraries: trapping the memory pool" Eur. J. Immunol., 22(3):867-870 (1992).
He, M. and Taussig, M.J., "Antibody-ribosome-mRNA (ARM) complexes as efficient selection particles for in vitro display and evolution of antibody combining sites" Nucleic Acids Res., 25(24):5132-5134 (1997).
Hoet, R.M. et al., "Generation of high-affinity human antibodies by combining donor-derived and synthetic complementarity-determining-region diversity" Nat. Biotechnol., 23(3):344-348 (2005).
Hoet, R.M. et al., "The importance of the light chain for the epitope specificity of human anti-U1 small nuclear RNA autoantibodies present in systemic lupus erythematosus patients" Journal of Immunology,163(6):3304-3312 (1999).
Holler et al., "In vitro evolution of a T cell recepto with high affinity for peptide / MHC" Proc. Natl. Acad. Sci. 97(10):5387-5392 (2000).
Holmes, P. and Al-Rubeai, M., "Improved cell line development by a high throughput affinity capture surface display technique to select for high secretors" J. Immunol. Methods, 230(1-2):141-147 (1999).
Hoogenboom and Chames, "Natural and designer binding sites made by phage display technology" Immunology Today 21(8):371-378 (2000).
Hoogenboom, H.R. and Winter, G., "By-passing immunisation. Human antibodies from synthetic repertoires of germline VH gene segments rearranged in vitro" J. Mol. Biol., 227(2):381-388 (1992).
Hoogenboom, H.R. et al., "Antibody phage display technology and its applications" Immunotechnology, 4(1):1-20 (1998).
Hoogenboom, H.R. et al., "Multi-subunit proteins on the surface of filamentous phage: methodologies for displaying antibody (Fab) heavy and light chains" Nucleic Acids Research, 19(15):4133-4137 (1991).
Hoogenboom, H.R., "Designing and optimizing library selection strategies for generating high-affinity antibodies" Trends Biotechnol. 15(2):62-70 (1997).
Horwitz A.H. et al., "Secretion of functional antibody and Fab fragments from yeast cells" Proc. Natl. Acad. Sci. USA, 85(22):8678-8682 (1988).
Hoshino, Y. et al., "The rational design of a synthetic polymer nanoparticle that neutralizes a toxic peptide in vivo" PNAS 109(1):33-38 (2012).
Hua, S.B. et al., "Construction of a modular yeast two-hybrid cDNA library from human EST clones for the human genome protein linkage map" Gene, 215(1):143-152 (1998).
Hua, S.B. et al., "Minimum length sequence homology required for in vivo cloning by homologous recombination in yeast" Plasmid, 38(2):91-96 (1997).
Huang et al., "A Majority of Ig H Chain eDNA of Normal Human Adult Blood Lymphocytes Resembles eDNA for Fetal Ig and Natural Autoantibodies", J. Immunol., 151:5290-5300 (1993).
Huang, D. and Shusta, E.V. et al., "Secretion and surface display of green fluorescent protein using the yeast *Saccharomyces cerevisiae*" Biotechnol. Prog., 21(2):349-357 (2005).
Hubberstey and Wildeman, "Use of interplasmid recombination to generate stable selectable markers for yeast transformation: application to studies of actin gene control" Genome 33(5):696-706 (1990).
Huse, W.D. et al., "Generation of a large combinatorial library of the immunoglobin repertoire in phage lambda" Science 246(4935):1275-1281 (1989).
Huston, J.S. et al., "Protein engineering of antibody binding sites: recovery of specific activity in an anti-digoxin single-chain Fv analogue produced in *Escherichia coli*" Proc. Natl. Acad. Sci. USA 85(16):5879-5883 (1988).
Imai and Yamamoto, "The fission yeast mating pheromone P-factor: its molecular structure, gene structure, and ability to induce gene expression and G1 arrest in the mating partner" Genes & Development 8:328-338 (1993).
International Preliminary Report of Patentability for PCT/US2011/044063, dated Jan. 31, 2013.
International Search Report and the Written Opinion of the International Searching Authority for PCT/US2011/044063, dated Feb. 14, 2012.
Ivanov, I.I. et al., "Development of the expressed Ig CDR-H3 repertoire is marked by focusing of constraints in length, amino acid use, and charge that are first established in early B cell progenitors," J. Immunol., 174(12):7773-7780 (2005).
Ivanovski et al., "Somatic Hypermutation, Clonal Diversity, and Preferential Expression of the VH 51p1/VL kv325 Immunoglobin Gene Combination in Hepatitis C Virus-Associated Immunocytomas", Blood, 91(7):2433-2442 (1998).
Jackson, K.J., et al., "Identifying highly mutated IGHD genes in the junctions of rearranged human immunoglobulin heavy chain genes," J. Immunol. Methods, 324(1-2):26-37 (2007).
Jirholt, P. et al., "Exploiting sequence space: shuffling in vivo formed complementarity determining regions into a master framework", Gene, 215(2):471-476 (1998).
Johns M. et al., "In vivo selection of sFv from phage display libraries" J. Immunol. Methods, 239(1-2):137-151 (2000).

(56) References Cited

OTHER PUBLICATIONS

Juul, L. et al., "The normally expressed kappa immunoglobulin light chain gene repertoire and somatic mutations studied by single-sided specific polymerase chain reaction (PCR); frequent occurrence of features often assigned to autoimmunity" Clin. Exp. Immunol., 109(1):194-203 (1997).
Kang, A.S. et al., "Linkage of recognition and replication functions by assembling combinatorial antibody Fab libraries along phage surfaces" Proc. Natl. Acad. Sci., 88(10):4363-4666 (1991).
Karu et al., "Recombinant Antibody Technology" ILAR Journal 37(3) pp. 1-9 (1995).
Kieke et al., "High Affinity T Cell Receptors from Yeast Display Libraries Block T Cell Activation by Superantigens" J. Mol. Biol. 307:1305-1315 (2001).
Kieke, M.C. et al., "Isolation of anti-T cell receptor scFv mutants by yeast surface display". Protein Eng. 10(11):1303-1310 (1997).
Kieke, M.C. et al., "Selection of functional T cell receptor mutants from a yeast surface-display library" Proc. Natl. Acad. Sci. USA, 96(10):5651-5656 (1999).
Klein, R. et al., "Expressed human immunoglobulin kappa genes and their hypermutation" Eur. J. Immunol., 23(12):3248-3262 (1993).
Knappik, A. et al., "Fully synthetic human combinatorial antibody libraries (HuCAL) based on modular consensus frameworks and CDRs randomized with trinucleotides" J. Mol. Biol., 296(1):57-86 (2000).
Koiwai, O. et al., "Isolation and characterization of bovine and mouse terminal deoxynucleotidyltransferase cDNAs expressible in mammalian cells" Nucleic Acids Res., 14(14):5777-5792 (1986).
Kokubu F. et al., Complete structure and organization of immunoglobulin heavy chain constant region genes in a phylogenetically primitive vertebrate, The EMBO Journal, 7(7):1979-1988 (1988).
Kontermann, R.E. and Müller, R., "Intracellular and cell surface displayed single-chain diabodies", J. Immunol. Methods, 226(1-2):179-188 (1999).
Kostrub, C.F. et al., "Use of gap repair in fission yeast to obtain novel alleles of specific genes" Nucleic Acids Research, 26(20):4783-4784 (1998).
Kranz and Voss, "Restricted reassociation of heavy and light chains from hapten-specific monoclonal antibodies" Proc. Natl. Acad. Sci. 78(9):5807-5811 (1981).
Kretzschmar, T. and von Rüden, T., "Antibody discovery: phage display" Curr. Opin. Biotechnol., 13(6):598-602 (2002).
Lake, D.F. et al., "Generation of diverse single-chain proteins using a universal (Gly4-Ser)3 encoding oligonucleotide" BioTechniques, 19(5):700-702 (1995).
Lee, C.E., et al., "Reconsidering the human immunoglobulin heavy-chain locus: 1. An evaluation of the expressed human IGHD gene repertoire" Immunogenetics, 57(12):917-925 (2006).
Lee, C.V. et al., "High-affinity human antibodies from phage-displayed synthetic Fab libraries with a single framework scaffold" J. Mol. Biol. 340(5):1073-1093 (2004).
Lee, S.Y. et al., "Microbial cell-surface display" Trends Biotechnol., 21(1):45-52 (2003).
Leonard, B. et al., "Co-expression of antibody fab heavy and light chain genes from separate evolved compatible replicons in *E. coli*" J. Immunol. Methods, 317(1-2):56-63 (2006).
Lerner, R.A. et al.,"Antibodies without immunization" Science,258(5086):1313-314 (1992).
Lewin, B., "Genes V", p. 99, Oxford University Press (1994).
Lieber et al., "Lymphoid V(D)J recombination: Nucleotide insertion at signal joints as well as coding joints", Proc. Natl. Acad. Sci. USA, 85:8588-8592 (1988).
Lieber, M.R., "Site-specific recombination in the immune system", FASEB J., 5:2934-2944 (1991).
Lin et al., "Display of a functional hetero-oligomeric catalytic antibody on the yeast cell surface" Appl. Microbiol. Biotechnol. 62:226-232 (2003).
Little, M. et al., "Generation of a large complex antibody library from multiple donors" J. Immunol Methods, 231(1-2):3-9 (1999).
Liu et al., "Normal Human IgD+IgM- Germinal Center B Cells can Express up to 80 Mutations in the Variable Region of their IgD Transcripts", Immunity, 4:603-613 (1996).
Liu, Q. et al., "Rapid construction of recombinant DNA by the univector plasmid-fusion system" Methods Enzymol. 328:530-49 (2000).
Love J.C. et al., "A microengraving method for rapid selection of single cells producing antigen-specific antibodies" Nature Biotechnol. 24(6):703-707 (2006).
Lowman, H.B. et al., "Selecting high-affinity binding proteins by monovalent phage display" Biochemistry, 30(45):10832-10838 (1991).
Ma et al., "Association of Transport-Defective Light Chains with Immunoglobulin Heavy Chain Binding Protein" Molecular Immunology 27(7):623-630 (1990).
Ma, H. et al., "Plasmid construction by homologous recombination in yeast" Gene, 58(2-3):201-216 (1987).
MacCallum, R.M. et al., "Antibody-antigen interactions: contact analysis and binding site topography" J. Mol. Biol., 262(5):732-745 (1996).
Manivasakam and Schiestl, High efficiency transformation of *Saccharomyces cerevisiae* by electroporation Nucleic Acids Research 21(18)4414-4415 (1993).
Manz, R. et al., "Analysis and sorting of live cells according to secreted molecules, relocated to a cell-surface affinity matrix" Proc. Natl. Acad. Sci. USA, 92(6):1921-1925 (1995).
Marks, J.D. et al., "By-passing Immunization. Human Antibodies from V-gene Libraries Displayed on Phage" J. Mol. Biol., 222(3):581-597 (1991).
Marks, J.D. et al., "By-passing Immunization: building high affinity human antibodies by chain shuffling" Biotechnology (NY), 10(7):779-783 (1992).
Martin, A.C., "Accessing the Kabat antibody sequence database by computer" Proteins, 25(1):130-133 (1996).
Martin, A.C.and Thornton, J.M., "Structural families in loops of homologous proteins: automatic classification, modelling and application to antibodies" J. Mol. Biol., 263(5):800-815 (1996).
Matolcsy et al., "Molecular Characterization of IgA- and/or IgG-Switched Chronic Lymphocytic Leukemia B Cells", Blood, 89(5):1732-1739 (1997).
Matsuda, F. et al., "The complete nucleotide sequence of the human immunoglobulin heavy chain variable region locus" J. Exp. Med., 188(11):2151-2162 (1998).
Mattila, P.S. et al., "Extensive allelic sequence variation in the J region of the human immunoglobulin heavy chain gene locus" Eur. J. Immunol., 9(:)2578-2582 (1995).
Mazor Y. et al., "Isolation of engineered, full-length antibodies from libraries expressed in *Escherichia coli*" Nature Biotecnol., 25(5):563-565 (2007).
McCafferty, J. et al., "Phage antibodies: filamentous phage displaying antibody variable domains" Nature, 348(6301):552-554 (1990).
McCormack, W.T., Comparison of latent and nominal rabbit Ig VHa1 allotype cDNA sequences. J. Immunol., 141(6):2063-2071 (1988).
Mcintosh et al., "Analysis of Immunoglobulin Gk Antithyroid Peroxidase Antibodies from Different Tissues in Hashimoto's Thyroiditis", J. Clin. Endocrinol. Metab., 82(11):3818-3825 (1997).
Mimran, A. et al., "GCN4-Based Expression System (pGES): Translationally Regulated Yeast Expression Vectors" BioTechniques, 28(3):552-554, 556, 558-560 (2000).
Mollova, S. et al., "Visualising the immune repertoire" BMC Systems Biology, 1(S1):P30 (2007).
Mouquet et al., "Enhanced HIV-1 neutralization by antibody heteroligation", PNAS, published on line before printing, Jan. 4, 2012, doi:10.1073/pnas.1120059109.
Mullinax, R.L. et al., "Identification of human antibody fragment clones specific for tetanus toxoid in a bacteriophage lambda immunoexpression library" Proc. Natl. Acad. Sci., 87(20):8095-8099 (1990).
Mézard, C. et al., "Recombination between similar but not identical DNA sequences during yeast transformation occurs within short stretches of identity" Cell, 70(4):659-670 (1992).

(56) References Cited

OTHER PUBLICATIONS

Nakamura, Y. et al., "Development of novel whole-cell immunoadsorbents by yeast surface display of the IgG-binding domain" Appl. Microbiol. Biotechnol., 57(4):500-505 (2001).
Nissim et al., "Antibody fragments from a 'single pot' phage display library as immunochemical reagents", The EMBO Journal, 13(3):692-698 (1994).
Oldenburg, K.R et al., "Recombination-mediated PCR-directed plasmid construction in vivo in yeast" Nucleic Acids Res, 25(2):451-452 (1997).
Onda, T. et al., "A phage display system for detection of T cell receptor-antigen interactions" Mol Immunol., 32(17-18):1387-1397 (1995).
Orr et al., "Rapid Method for Measuring ScFv Thermal Stability by Yeast Surface Display" Biotechnol. Prog. 19:631-638 (2003).
Panka, D.J. et al., "Variable region framework differences result in decreased or increased affinity of variant anti-digoxin antibodies" Proc. Natl. Acad. Sci. USA, 85(9):3080-3084 (1988).
Parthasarathy, R. et al., "An immobilized biotin ligase: surface display of *Escherichia coli* BirA on *Saccharomyces cerevisiae*" Biotechnol. Prog., 21(6):1627-1631 (2005).
Pasqualini, R. and Ruoslahti, E., "Organ targeting in vivo using phage display peptide libraries" Nature, 380(6572):364-366 (1996).
Patel et al., "Parallel selection of antibody libraries on phage and yeast surfaces via a cross-species display" Protein Engineering, Design & Selection, pp. 1-9 (2011).
Patrick, W.M. et al., "User-friendly algorithms for estimating completeness and diversity in randomized protein-encoding libraries" Protein Engineering, 16(6):451-457 (2003).
Pearson, B.M. et al., "Construction of PCR-ligated long flanking homology cassettes for use in the functional analysis of six unknown open reading frames from the left and right arms of *Saccharomyces cerevisiae* chromosome XV" Yeast, 14(4):391-399 (1998).
Pepper et al., "A Decade of Yeast Surface Display Technology: Where Are We Now?" Combinatorial Chemistry & High Throughput Screening 11:127-134 (2008).
Persson, M.A. et al., "Generation of diverse high-affinity human monoclonal antibodies by repertoire cloning" Proc. Natl. Acad. Sci. USA, 88(6):2432-2436 (1991).
Philibert, P. et al., "A focused antibody library for selected scFvs expressed at high levels in the cytoplasm" BMC Biotechnol., 7:81 (2007).
Pini, A. et al., "Design and use of a phage display library. Human antibodies with subnanomolar affinity against a marker of angiogenesis eluted from a two-dimensional gel" Journal of Biological Chemistry, 273(34):21769-21776 (1998).
Pluckthun, A., "Antibody engineering: Advances from the use of *Escherichia coli* expression systems" Biotechnology (NY) 9(6):545-551 (1991).
Pogue and Goodnow, "Gene Dose-dependent Maturation and Receptor Editing of B Cells Expressing Immumoglobulin (Ig)G1 or IgM/IgG1 Tail Antigen Receptors" J. Exp. Med 191(6) 1031-1043 (2000).
Powell, Richard and McLane, Kathryn Evans, "Construction, assembly and selection of combinatorial antibody libraries." Genetic Engineering with PCR (Horton and Tait, Eds. 1998), vol. 5 of The Current Innovations in Molecular Biol series, Horizon Scientific Press, pp. 155-172.
Prabakaran, P. et al., "Expressed antibody repertoires in human cord blood cells: 454 sequencing and IMGT/High V-QUEST analysis of germline gene usage, junctional diversity, and somatic mutations" Immunogenetics (2011), pp. 1-14.
Prabakaran, P. et al., Supplemental "Expressed antibody repertoires in human cord blood cells: 454 sequencing and IMGT/High V-QUEST analysis of germline gene usage, junctional diversity, and somatic mutations" Immunogenetics (2011), pp. 1-6.
Proba, K. et al., "Antibody scFv fragments without disulfide bonds made by molecular evolution". J Mol Biol. 275(2):245-253 (1998).
Pörtner-Taliana, A. et al., "In vivo selection of single-chain antibodies using a yeast two-hybrid system", J. Immunol. Methods, 238(1-2):161-172 (2000).
Rader, C and Barbas, C.F. 3rd, "Phage display of combinatorial antibody libraries" Curr. Opin. Biotechnol., 8(4):503-508 (1997).
Rader, C. et al., "A phage display approach for rapid antibody humanization: designed combinatorial V gene libraries" Proc. Natl. Acad. Sci. USA, 95(15):8910-8915 (1998).
Rajan, S. and Sidhu, S., "Simplified Synthetic Antibody Libraries" Methods in Enzymology 202 3-23 (2012).
Rakestraw, J.A. and Wittrup, K.D., "Dissertation Abstracts International", 68(1B):43, abstract only (2006).
Rakestraw, J.A. et al., "A Flow Cytometric Assay for Screening Improved Heterologous Protein Secretion in Yeast." Biotechnol. Prog., 22(4):1200-1208 (2006).
Rauchenberger, R. et al., "Human combinatorial Fab library yielding specific and functional antibodies against the human fibroblast growth factor receptor 3" J. Biol. Chem., 278(40):38194-38205 (2003).
Raymond, C.K. et al., "General method for plasmid construction using homologous recombination" BioTechniques, 26(1):134-138, 140-141 (1999).
Retter, I. et al., "VBASE2, an integrative V gene database" Nucleic Acids Res., 33:D671-D674 (2005).
Rhoden, J.J. and Wittrup, K.D., "Dose Dependence of Intratumoral Perivascular Distribution of Monoclonal Antibodies" Journal of Pharmaceutical Sciences 101(2): 860-867 (2012).
Roitt, I. et al., "Immunoglobulins: A Family of Proteins", in Immunology, Sixth Edition, Mosby, Harcourt Publishers Limited, London, pp. 67-70 and 80 (2001).
Roman, T. et al., Evolution of specific antigen recognition: size reduction and restricted length distribution of the CDRH3 regions in the rainbow trout, Eur J Immunol, 25(1):269-73 (1995).
Rothe, C. et al., The Human Combinatorial Antibody Library HuCAL GOLD Combines Diversification of All Six CDRs According to the Natural Immune System with a Novel Display Method for Efficient Selection of High-Affinity Antibodies, J. Mol. Biol., 376:1182-1200 (2008).
Rudikoff, S. et al., "Single amino acid substitution altering antigen-binding specificity" Proc. Natl. Acad. Sci. USA, 79(6):1979-1983 (1982).
Ruiz, M. et al., "The human immunoglobulin heavy diversity (IGHD) and joining (IGHJ) segments." Exp. Clin. Irnrnunogenet, 16(3):173-184 (1999).
Ryu, D.D. and Nam, D.H., "Recent progress in biomolecular engineering" Biotechnol Prog, 16(1):2-16 (2000).
Saada, R. et al., "Models for antigen receptor gene rearrangement: CDR3 length" Immunol. Cell Biol., 85(4):323-332 (2007).
Sahota et al., "Ig VH Gene Mutational Patterns Indicate Different Tumor Cell Status in Human Myeloma and Monoclonal Gammopathy of Undetermined Significance", Blood, 87(2):746-755 (1996).
Sblattero, D. and Bradbury, A., "A definitive set of oligonucleotide primers for amplifying human V regions" Immunotechnology, 3(4):271-278 (1998).
Sblattero, D. and Bradbury, A., "Exploiting recombination in single bacteria to make large phage antibody libraries" Nat. Biotechnol., 18(1):75-80 (2000).
Scaviner, D. et al., "Protein displays of the human immunoglobulin heavy, kappa and lambda variable and joining regions." Exp. Clin. Immunogenet., 16(4):234-240 (1999).
Schable, K.F. and Zachau, H.G., "The variable genes of the human immunoglobulin kappa locus" Biol. Chem. Hoppe Seyler, 374(11):1001-1022 (1993).
Schoonbroodt, S. et al., "Oligonucleotide-assisted cleavage and ligation: a novel directional DNA cloning technology to capture cDNAs. Application in the construction of a human immune antibody phage-display library" Nucleic Acids Research, 33(9):e81:2-14 (2005).
Schreuder et al., "Immobilizing proteins on the surface of yeast cells" Trends Biotechnol. 14(4)115-120 (1996).
Schreuder et al., "Targeting of a Heterologous Protein to the Cell Wall of *Saccharamyces cerevisiae*" Yeast 9:399-409 (1993).

(56) References Cited

OTHER PUBLICATIONS

Schwager, J. et al., Amino acid sequence of heavy chain from Xenopus levis IgM deduced from cDNA sequence: Implications for evolution of immunoglobulin domains, Proc. Natl. Acad. Sci. USA, 85:2245-2249 (1988).
Seed, B., "Developments in expression cloning." Current Opinion in Biotechnology, 6(5):567-573 (1995).
Sharifmoghadam, et al., "The fission yeast Map4 protein is a novel adhesin required for mating" FEBS Letters 580:4457-4462 (2006).
Sheets, M.D. et al., "Efficient construction of a large nonimmune phage antibody library: The production of high-affinity human single-chain antibodies to protein antigens." Proc. Natl. Acad. Sci. USA, 95(11):6157-6162 (1998).
Shen et al., "Delineation of Functional Regions within the Subunits of the *Saccharomyces cerevisiae* Cell Adhesion Molecule a-Agglutinin" The Journal of Biological Chemistry 276(19):15768-15775 (2001).
Shimoda et al., "Natural polyreactive immunoglobulin A antibodies produced in mouse Peyer's patches", Immunology, 97:9-17 (1999).
Short, M.K. et al., "Contribution of antibody heavy chain CDR1 to digoxin binding analyzed by random mutagenesis of phage-displayed Fab 26-10" J. Biol. Chem., 270(48):28541-28550 (1995).
Shusta, E.V. et al., "Directed evolution of a stable scaffold forT-cell receptor engineering" Nat. Biotechnol.,18(7):754-759 (2000).
Shusta, E.V. et al., "Yeast Polypeptide Fusion Surface Display Levels Predict Thermal Stability and Soluble Secretion Efficiency" J. Mol. Biol. 292 949-956 (1999).
Sidhu, S.S, et al., "Phage-displayed antibody libraries of synthetic heavy chain complementarity determining regions" J. Mol. Biol. 338(2):229-310 (2004).
Skerra, A., "Alternative non-antibody scaffolds for molecular recognition" Current Opin. Biotechnol. 18(4):295-304 (2007).
Smith, G., "Homologous Recombination Near and Far from DNA Breaks: Alternative Roles and Contrasting Views" Annu Rev Genet 35:243-274 (2001).
Smith, G.P. and Petrenko, V.A., "Phage Display" Chern. Rev., 97(2):391-410 (1997).
Soderlind, E. et al., "Domain libraries: synthetic diversity for de novo design of antibody V-regions" Gene, 160(2): 269-272 (1995).
Soderlind, E. et al., "The immune diversity in a test tube—non-immunised antibody libraries and functional variability in defined protein scaffolds" Combinatorial Chemistry & High Throughput Screening, 4(5):409-416 (2001).
Souriau and Hudson, "Recombinant antibodies for cancer diagnosis and therapy" Expert Opin. Biol. Ther. 1(5):845-855 (2001).
Souto-Carneiro, M.M. et al., "Characterization of the Hurnan Ig Heavy Chain Antigen Binding Complementarity Determining Region 3 Using a Newly Developed Software Algorithm, JOINSOLVER," J. Immunol., 172(11):6790-6802 (2004).
Starwalt et al., "Directed evolution of a single-chain class II MHC product by yeast display" Protein Engineering 16(2):147-156 (2003).
Stewart, A.K. et al., "High-frequency representation of a single VH gene in the expressed human B cell repertoire" J. Exp. Med., 177(2):409-418 (1993).
Stohl, W. and Hilbert, D.M., "The discovery and development of belimumab: the anti-BLyS-lupus connection" Nature Biology 30(1):69-77 (2012).
Struhl et al., "High-frequency transformation of yeast: Autonomous replication of hybrid DNA molecules" Proc. Natl. Acad. Sci. 76(3):1035-1039 (1979).
Suzuki, M. et al., "Light chain determines the binding property of human anti-dsDNA IgG autoantibodies" Biochem. Biophys. Res. Commun., 271(1):240-243 (2000).
Swers et al., "Integrated Mimicry of B Cell Antibody Mutagenesis Using Yeast Homologous Recombination" Mol. Biotechnol. 46:57-69 (2011).
Swers, J.S. et al., "Shuffled antibody libraries created by in vivo homologous recombination and yeast surface display" Nuc. Acids. Res. 32(3), e36, 1-8 (2004).
Tavladoraki, P. et al., "Transgenic plants expressing a functional single-chain Fv antibody are specifically protected from virus attack" Nature, 366(6454):469-472 (1993).
Terskikh, A.V. et al., "Peptabody": A new type of high avidity binding protein Proc. Natl. Acad., 94(5):1663-1668 (1997).
Tomlinson, I.M. et al., "The repertoire of human germline VH sequences reveals about fifty groups of VH segments with different hypervariable loops" Journal of Molecular Biology, 227(3):776-798 (1992).
Tomlinson, I.M. et al., "The structural repertoire of the human V kappa domain" EMBO J., 14(18):4628-4638 (1995).
Tsurushita, N. et al., "Phage display vectors for in vivo recombination of immunoglobulin heavy and light chain genes to make large combinatorial libraries" Gene, 172(1):59-63 (1996).
Ueda and Tanaka, "Cell Surface Engineering of Yeast: Construction of Arming Yeast with Biocatalyst" Journal of Bioscience and Bioengineering 90(2):125:136 (2000).
Ueda, M. and Tanaka, A., "Genetic immobilization of proteins on the yeast cell surface" Biotechnology Advances, 18(2):121-140 (2000).
van den Beucken et al., "Affinity maturation of Fab antibody fragments by fluorescent-activated cell sorting of yeast-displayed libraries" FEBS Letters 546:288-294 (2003).
VanAntwerp and Wittrup, "Fine Affinity Discrimination by Yeast Surface Display and Flow Cytometry" Biotechnol. Prog. 16:31-37 (2000).
Vander Vaart, J.M. et al., "Comparison of cell wall proteins of *Saccharomyces cerevisiae* as anchors for cell surface expression of heterologous proteins" Appl. Environ. Microbiol., 63(2):615-620 (1997).
Vaswani, S.K. and Hamilton, R.G., "Humanized antibodies as potential therapeutic drugs" Ann. Allergy Athma Immunol., 81(2):105-115 (1998).
Vendel, M.C. et al., "Secretion from bacterial versus mammalian cells yields a recombinant scFv with variable folding properties" Arch. Biochem. Biophys. 1-6 (2012).
Visintin. M. et al., "Selection of antibodies for intracellular function using a two-hybrid in vivo system.", Proc. Natl. Acad. Sci. USA 96(21):11723-11728 (1999).
Volpe, J.M. and Kepler, T.B., "Genetic correlates of autoreactivity and autoreactive potential in human Ig heavy chains" Immunome Res., 5:1 (2009).
Volpe, J.M. et al., "SoDA: Implementation of a 3D Alignment Algorithm for Inference of Antigen Receptor Recombinations," Bioinforrnatics, 22(4):438-444 (2006).
Vugmeyster, Y. et al., "Complex Pharmacokinetics of a Humanized Antibody Against Human Amyloid Beta Peptide, Anti-Abeta Ab2, in Nonclinical Species" Pharm Res, 28:1696-1706 (2011).
Walhout, A.J. et al., "GATEWAY recombinational cloning: application to the cloning of large numbers of open reading frames or ORFeomes" Methods in Enzymology, 328:575-92 (2000).
Wang, Y. et al., "Many human immunoglobulin heavy-chain IGHV gene polymorphisms have been reported in error" Immunol. Cell. Biol., 86(2):111-115 (epub 2007-2008).
Weaver-Feldhaus, J.M. et al., "Yeast mating for combinatorial Fab library generation and surface display" FEBS Lett., 564(1-2):24-34 (2004).
Welschof et al., "Amino acid sequence based PCR primers for amplification of rearranged human heavy and light chain immunoglobulin variable region genes", J. Immunol. Meth., 179:203-214 (1995).
Wen et al., "T cells recognize the VH complementarity-determining region 3 of the idiotypic protein of B cell non-Hodgkin's lymphoma", Eur. J. Immunol., 27:1043-1047 (1997).
Wentz, A.E. and Shusta, E.V., "A novel high-throughput screen reveals yeast genes that increase secretion of heterologous proteins" Appl. Environ. Microbiol., 73(4):1189-1198 (2007).
Winkler et al., "Analysis of immunoglobulin variable region genes from human IgG anti-DNA hybridomas", Eur. J. Immunol., 22:1719-1728 (1992).
Winter G. and Milstein C., "Man-made antibodies" Nature, 349(6307):293-299 (1991).

(56) References Cited

OTHER PUBLICATIONS

Winter, Greg, "Synthetic human antibodies and a strategy for protein engineering", FEBS Letters, 430:92-94 (1998).
Wood et al., "The synthesis and in vivo assembly of functional antibodies in yeast" Nature 314:(6010)446-449 (1985).
Woods and Gietz, "High-Efficiency Transformation of Plasmid DNA into Yeast", Methods in Molecular Biology, 177:85-97 (2001).
Wu, H. et al., "Humanization of a murine monoclonal antibody by simultaneous optimization of framework and CDR residues" J. Mol. Biol., 294(1):151-162 (1999).
Wörn, A. and Plückthun, A., "An intrinsically stable antibody scFv fragment can tolerate the loss of both disulfide bonds and fold correctly." FEBS Lett., 427(3):357-361 (1998).
Xu, J.L. and Davis, M.M., "Diversity in the CDR3 region of V(H) is sufficient for most antibody specificities" Immunity, 13(1):37-45 (2000).
Yang, W.P. et al., "CDR walking mutagenesis for the affinity maturation of a potent human anti-HIV-1 antibody into the picomolar range" J. Molecular Biology, 254(3):392-403 (1995).
Yeung and Wittrup, "Quantitative Screening of Yeast Surface-Displayed Polypeptide Libraries by Magnetic Bead Capture" Biotechnol. Prog. 18(2):212-220 (2002).
Zemlin, M. et al., "Expressed murine and human CDR-H3 intervals of equal length exhibit distinct repertoires that differ in their amino acid composition and predicted range of structures" J. Mol. Biol. 334(4):733-749 (2003).
Zeng et al., "CD146, an epithelial-mesenchymal transition inducer, is associated with triple-negative breast cancer", published on line before print Dec. 30, 2011, doi:1010.1073/pnas.1111053108.
Zucconi, A. et al., "Domain repertoires as a tool to derive protein recognition rules" FEBS Letters, 480(1):49-54 (2000).

FIGURE 4

| | | |
|---|---|---|
| IGHJ3-02 | - | **AT**GCTTTTGATATCT...TCTTCAG |
| IGHJ3-02-1 | Mutate 5' doublet | **NN**TGCTTTTGATATCT...TCTTCAG |
| IGHJ3-02-2 | Delete 5' codon | GCTTTTGATATCT...TCTTCAG |
| IGHJ3-02-3 | Mutate 5' doublet | **NN**TTTTGATATCT...TCTTCAG |
| IGHJ3-02-4 | Delete 5' codon | TTTGATATCT...TCTTCAG |
| IGHJ3-02-5 | Mutate 5' doublet | **NN**TGATATCT...TCTTCAG |

| | | |
|---|---|---|
| IGHJ1-01 | - | GCTGAATACTTCCAG...TCCTCAG |
| IGHJ1-01-1 | Mutate 5' doublet | **NN**TGAATACTTCCAG...TCCTCAG |
| IGHJ1-01-2 | Delete 5' codon | GAATACTTCCAG...TCCTCAG |
| IGHJ1-01-3 | Mutate 5' doublet | **NN**ATACTTCCAG...TCCTCAG |
| IGHJ1-01-4 | Delete 5' codon | TACTTCCAG...TCCTCAG |
| IGHJ1-01-5 | Mutate 5' doublet | **NN**CTTCCAG...TCCTCAG |

| | | |
|---|---|---|
| IGHJ2-01 | - | **C**TACTGGTACTTCGA...TCCTCAG |
| IGHJ2-01-1 | Mutate 5' doublet | **NN**ACTGGTACTTCGA...TCCTCAG |
| IGHJ2-01-2 | Delete 5' codon | CTGGTACTTCGA...TCCTCAG |
| IGHJ2-01-3 | Mutate 5' doublet | **NN**GGTACTTCGA...TCCTCAG |
| IGHJ2-01-4 | Delete 5' codon | GTACTTCGA...TCCTCAG |
| IGHJ2-01-5 | Mutate 5' doublet | **NN**ACTTCGA...TCCTCAG |

FIGURE 8

Based on a set of CDRH3 sequences derived from 55 clinically relevant human mAbs

| Amino acid mismatches in Kabat-H3 region | LUA-141 | Exemplary Library Design 3 (EDLD-3) | Extended Diversity Library Design (EDLD) |
|---|---|---|---|
| 0 | 4 | 7 | 25 |
| 1 | 16 | 27 | 15 |
| 2 | 19 | 5 | 9 |
| 3-or-more | 16 | 16 | 6 |
| Total | 55 | 55 | 55 |

| Library | LUA-141 | Exemplary Library Design 3 | Human H3 |
|---|---|---|---|
| Average | 14.37 | 13.94 | 13.99 |
| Stdev | 2.82 | 3.35 | 3.55 |
| Shortest | 5 | 2 | 2 |
| Longest | 26 | 28 | 35 |

| Set: | Boyd | ELD-3 | Extended Diversity |
| --- | --- | --- | --- |
| r2-to-Boyd | 1.00 | 0.986 | 0.990 |
| Mean | 14.27 | 13.99 | 14.47 |
| Standard Deviation | 4.02 | 3.35 | 3.47 |
| Shortest | 1 | 2 | 2 |
| Longest | 39 | 28 | 30 |

ANTIBODY LIBRARIES

CROSS REFERENCE TO RELATED APPLICATIONS

This application is a divisional of U.S. application Ser. No. 15/151,626, filed on May 11, 2016, which is a divisional of U.S. application Ser. No. 13/810,570, filed on Apr. 1, 2013, which is a national phase entry under 35 U.S.C. § 371 of International Application No. PCT/US2011/044063, filed on Jul. 14, 2011, which claims priority to U.S. Provisional Application No. 61/365,194, filed on Jul. 16, 2010. The disclosure of each of U.S. application Ser. No. 15/151,626; U.S. application Ser. No. 13/810,570 and U.S. Provisional Application No. 61/365,194 are hereby incorporated herein by reference in their entirety.

SEQUENCE LISTING

In accordance with 37 CFR 1.52(e)(5), a Sequence Listing in the form of a text file (entitled "2009186_0225_Sequence_Listing.txt" created on Sep. 7, 2018 May 10, 2016 and 2,508,889 bytes in size) is incorporated by reference in its entirety.

BACKGROUND

Antibodies have profound relevance as research tools and in diagnostic and therapeutic applications. However, the identification of useful antibodies is difficult and once identified, antibodies often require considerable redesign or "humanization" before they are suitable for therapeutic applications in humans.

Many methods for identifying antibodies involve display of libraries of antibodies derived by amplification of nucleic acids from B cells or tissues. Some of these methods have utilized synthetic libraries. However, many of these approaches have limitations. For example, most human antibody libraries known in the art contain only the antibody sequence diversity that can be experimentally captured or cloned from a biological source (e.g., B cells). Accordingly, such libraries may over-represent some sequences, while completely lacking or under-representing other sequences, particularly those binding human antigens. Most synthetic libraries known in the art have other limitations, such as the occurrence of unnatural (i.e., non-human) amino acid sequence motifs that have the potential to be immunogenic.

Accordingly, a need exists for diverse antibody libraries that contain candidate antibodies that are non-immunogenic (i.e., are human) and have desired properties (e.g., the ability to recognize a broad variety of antigens). However, obtaining such libraries requires balancing the competing objectives of generating diverse libraries while still maintaining the human character of the sequences within the library. The current invention provides antibody libraries that have these and other desirable features, and methods of making and using such libraries.

SUMMARY

The invention provides, among other things, improvements in the design and production of synthetic libraries that mimic the diversity of the natural human repertoire of CDRH3, CDRL3, heavy chain, light chain, and/or full-length (intact) antibody sequences. In some embodiments the invention defines and provides methods of generating theoretical segment pools of TN1, DH, N2, and H3-JH segments to consider for inclusion in a physical manifestation of a library (e.g., polynucleotide or polypeptide) comprising or encoding CDRH3 sequences (e.g., an antibody library). In certain embodiments the invention defines and provides methods of matching the individual members of these theoretical segment pools to a reference set of CDRH3 sequences, to determine the frequency of occurrence (or segment usage weight) of each of the segments in the theoretical segment pool in the reference set. While any set of CDRH3 sequences may be used as a reference set, the invention also defines and provides methods of generating particular reference sets or subsets of interest. For example, among other things, the present invention provides methods for filtering an original reference set to obtain a provided reference set with a preimmune character. Also provided are methods to define and/or identify segments that occur within the CDRH3 sequences in the reference set but not in the theoretical segment pool. Such segments can be added to a theoretical segment pool, for example in order to be considered for inclusion in a physical library. Although the frequency of occurrence of a particular segment in a reference set is useful to select segments for inclusion in a physical library, the invention also provides a number of physicochemical and biological properties that can be used (alone or together with any other criterion or criteria) to select segments for inclusion in a physical library.

In some embodiments the invention provides libraries that differ from certain other libraries known in the art in that they are not sitewise-stochastic in composition or sequence, and are therefore intrinsically less random than these certain other libraries of the art (see e.g., Example 14 of US Pub. No. 2009/0181855, incorporated by reference in its entirety, for a discussion of information content and randomness). In some embodiments, degenerate oligonucleotides may be used to further increase the diversity of the members of a library while further improving matching with a reference set of sequences (e.g., CDRH3, CDRL3, heavy chain, light chain, and/or full-length (intact) antibody sequences).

The invention also provides libraries whose members have sequences that are related to one another in that they would be selected for inclusion in a physical library by performing the analyses described herein, for example by generating a CDRH3 reference set as in Example 3; generating theoretical segment pools as in Examples 5-7; matching the members of a theoretical segment pool to the reference set as in Examples 4 and 8; and selecting members of the theoretical segment pool for inclusion in a physical library as in Examples 8-9. Also provided are methods of further increasing diversity in certain sequences by utilizing degenerate oligonucleotides as in Examples 12-16.

In some embodiments, the present invention provides polynucleotide and polypeptide libraries comprising CDRH3, CDRL3, heavy chain, light chain, and/or full-length (intact) antibody sequences, and methods of making and using such libraries.

In some embodiments, the invention provides libraries comprising, consisting essentially of, or consisting of any of the libraries or theoretical segment pools described herein.

In some embodiments, the present invention recognizes that by mimicking the in vivo activity of the enzyme TdT computationally, theoretical segment pools can be generated and subsequently matched to large reference datasets of CDR sequences to choose, for inclusion in a library, those theoretical segments that best recapitulate the CDR sequences in the reference data sets.

In certain embodiments, the invention provides libraries of polynucleotides comprising at least about $10^4$ polynucleotides encoding CDRH3 polypeptides with the structure: [TN1]-[DH]-[N2]-[H3-JH], wherein: TN1 is a polypeptide corresponding to any of the TN1 polypeptides of Tables 9-10 and 18-26, or a polypeptide produced by translation of any of the TN1 polynucleotides of Tables 25-26; DH is a polypeptide corresponding to any of the DH polypeptides of Tables 9, 11, 17-25 and 28, or a polypeptide produced by translation of any of the DH-encoding polynucleotides of Tables 16, 25 and 27; N2 is a polypeptide corresponding to any of the N2 polypeptides of Tables 9, 12, 18-25 and 30, or a polypeptide produced by translation of any of the N2-encoding polynucleotides of Tables 25 and 29; and H3-JH is a polypeptide corresponding to any of the H3-JH polypeptides of Tables 9, 13, 15, 18-25 and 32, or a polypeptide produced by translation of any of the H3-JH-encoding polynucleotides of Tables 14, 25 and 31.

In some embodiments, the invention provides libraries wherein at least about 1%, 5%, or 10% of the sequences in the library have the structure provided above, or that of any of the libraries provided herein.

In certain embodiments, the invention provides libraries comprising polynucleotides encoding CDRH3 polypeptides produced by the sets of TN1, DH, N2, and H3-JH polypeptides provided in any one of Tables 23-25.

In some embodiments, the invention provides libraries comprising polynucleotides encoding CDRH3 polypeptides produced by the set of TN1 polypeptides provided in Table 26, the set of DH polypeptides provided in Table 28, the set of N2 polypeptides provided in Table 30 and the set of H3-JH polypeptides provided in Table 32.

In certain embodiments, the invention provides libraries whose members show (or encode polypeptides that show) at least a certain percent identity with the polypeptides described above, for example, a library comprising at least about $10^4$ polynucleotides encoding CDRH3 polypeptides with the structure: [TN1]-[DH]-[N2]-[H3-JH], wherein: TN1 is a polypeptide at least about 80%, 90%, or 95% identical to any of the TN1 polypeptides of Tables 9-10 and 18-26, or a polypeptide at least about 80%, 90%, or 95% identical to a polypeptide produced by translation of any of the TN1 polynucleotides of Tables 25-26; DH is a polypeptide at least about 80%, 90%, or 95% identical to any of the DH polypeptides of Tables 9, 11, 17-25 and 28, or a polypeptide at least about 80%, 90%, or 95% identical to a polypeptide produced by translation of any of the DH-encoding polynucleotides of Tables 16, 25 and 27; N2 is a polypeptide at least about 80%, 90%, or 95% identical to any of the N2 polypeptides of Tables 9, 12, 18-25 and 30, or a polypeptide at least about 80%, 90%, or 95% identical to a polypeptide produced by translation of any of the N2-encoding polynucleotides of Tables 25 and 29; and H3-JH is a polypeptide at least about 80%, 90%, or 95% identical to any of the H3-JH polypeptides of Tables 9, 13, 15, 18-25 and 32, or a polypeptide at least about 80%, 90%, or 95% identical to a polypeptide produced by translation of any of the H3-JH-encoding polynucleotides of Tables 14, 25 and 31.

In some embodiments, the invention provides libraries comprising polynucleotides encoding light chain variable regions, wherein the light chain variable regions are selected from the group consisting of: (a) a VK1-05 sequence varied at one or more of positions 4, 49, and 46; (b) a VK1-12 sequence varied at one or more of positions 4, 49, 46, and 66; (c) a VK1-33 sequence varied at one or more of positions 4, 49, and 66; (d) a VK1-39 sequence varied at one or more of positions 4, 49, and 46; (e) a VK2-28 sequence varied at one or more of positions 2, 4, 46, and 49; (f) a VK3-11 sequence varied at one or more of positions 2, 4, 36, and 49; (g) a VK3-15 sequence varied at one or more of positions 2, 4, 48, and 49; (h) a VK3-20 sequence varied at one or more of positions 2, 4, 48, and 49; and/or (i) a VK4-1 sequence varied at one or more of positions 4, 46, 49, and 66.

In certain embodiments, the invention provides libraries comprising polynucleotides encoding light chain variable regions that comprise polypeptide sequences at least about 80%, 90%, or 95% identical to two or more of the light chain polypeptide sequences provided in Table 3.

In some embodiments, the invention provides libraries wherein the light chain variable regions comprise the polypeptide sequences provided in Table 3.

In certain embodiments, the invention provides libraries comprising polynucleotides encoding light chain variable regions, wherein the L3-VL polypeptide sequences of the light chain variable regions are varied at two or three residues between positions 89 to 94, inclusive, in comparison to an L3-VL germline sequence. In some embodiments, libraries containing a single light chain germline sequence and its variants are provided. In certain embodiments, variants produced from different light chain germline sequences can be combined to produce libraries encoding multiple light chain germline sequences and their variants. Any of the light chain L3-VL germline sequences provided herein may be varied at two or three residues between positions 89 to 94, inclusive, and one of ordinary skill in the art will recognize that any other L3-VL sequence can also be varied according to the principles described herein to produce libraries provided by the invention. In some embodiments, the present invention comprises libraries containing polynucleotides that encode antibody light chain variable regions, wherein the antibody light chain variable regions comprise one or more of the following L3-VL sequences: (i) an amino acid sequence that is identical to an L3-VL germline sequence (e.g., see Table 1); (ii) an amino acid sequence that contains two substitutions between residues 89-94, inclusive, in comparison to an L3-VL germline sequence; and (iii) an amino acid sequence that contains three substitutions between residues 89-94, inclusive, in comparison to an L3-VL germline sequence. In some embodiments, each antibody light chain variable region on a library includes one or more of the above L3-VL sequences. In some embodiments, such a library is combined with one or more sets of other nucleic acids that may or may not encode antibody light chain variable regions, and may or may not contain such L3-VL sequences. In some embodiments, the present invention comprises libraries containing polynucleotides that encode an antibody light chain variable region having an amino acid sequence as set forth in Table 4, or a polynucleotide sequence as set forth in one or more of Tables 5-7, wherein two or three residues at positions 89-94, inclusive, are varied.

In some embodiments, the present invention comprises libraries containing polynucleotides that encode an antibody light chain variable region, wherein, across the library, all encoded antibody light chain variable regions are identical to one another except for substitutions of residues at positions between residue 89 and residue 94, inclusive and further wherein, across the library, sequences of any two encoded antibody light chain variable regions differ from one another at not more than 3 positions.

In some embodiments, the invention provides libraries comprising polynucleotides encoding light chain variable regions comprising polypeptide sequences at least about 80%, 90%, or 95% identical to polypeptides produced by translation of two or more of the polynucleotide sequences provided in Tables 5-7. In certain embodiments all members of the library are at least about 80%, 90%, or 95% identical to polypeptides produced by translation of two or more of the polynucleotide sequences provided in Tables 5-7.

In certain embodiments, the invention provides a library comprising light chain variable regions that comprise the polypeptides produced by translation of the polynucleotide sequences provided in Tables 5-7. In certain embodiments, all members of the library comprise the polypeptides produced by translation of the polynucleotide sequences provided in Tables 5-7.

In some embodiments, any of the libraries described herein as containing or encoding CDRL3 and/or light chain variable regions, contains or encodes such CDRL3 and/or light chain variable regions in the context of complete light chains. Furthermore, in some embodiments, such libraries (and/or complete light chain libraries) further contain or encode one or more heavy chain CDRH3, variable domains, or intact heavy chains. In some embodiments, provided libraries include or encode intact antibodies such as, for example, intact intact IgGs.

In some embodiments, provided libraries include or encode human antibodies or antibody fragments; in some such embodiments, provided libraries include or encode intact human antibodies.

In certain embodiments, the invention provides libraries that comprise nucleic acid vectors containing library nucleic acids described herein. In many embodiments, each such library member comprises the same vector.

In some embodiments, the invention provides host cells containing one or more provided libraries, for example including a vector. In some embodiments the host cell is a yeast, and in certain embodiments the yeast is *Saccharomyces cerevisiae.*

In some embodiments, the invention provides antibodies isolated from the libraries described herein.

In certain embodiments, the invention provides kits containing any of the libraries described herein.

In some embodiments, the invention provides representations of libraries and/or theoretical segment pools in a computer readable format, for example, the TN1 polypeptides of Tables 10, 23-25 and 26; the DH polypeptides of Tables 11, 23-25 and 28; the N2 polypeptides of Tables 12, 23-25 and 30; the H3-JH polypeptides of Tables 13, 15, 17, 23-25 and 32; the TN1 polynucleotides of Tables 25-26; the DH polynucleotides of Tables 25 and 27; the N2 polynucleotides of Tables 25 and 29; and/or the H3-JH polynucleotides of Tables 25 and 31.

In certain embodiments, the invention provides a representation of the polynucleotide sequences of the Human Preimmune Set (Appendix A), or the polypeptide expression products thereof, in a computer readable format.

In some embodiments, the invention provides a method of making synthetic polynucleotides encoding a CDRH3 library, comprising: (a) providing a theoretical segment pool containing TN1, DH, N2, and H3JH segments; (b) providing a reference set of CDRH3 sequences; (c) utilizing the theoretical segment pool of (a) to identify the closest match (es) to each CDRH3 sequence in the reference set of (b); (d) selecting segments from the theoretical segment pool for inclusion in a synthetic library; and (e) synthesizing the synthetic CDRH3 library. In certain embodiments, the invention provides libraries made by this method. In some embodiments, the segments selected for inclusion in the synthetic library are selected according to their segment usage weight in the reference set of CDRH3 sequences.

In certain embodiments, the invention provides a method of making synthetic polynucleotides encoding a CDRL3 library, comprising: (i) obtaining a reference set of light chain sequences, wherein the reference set contains light chain sequences with VL segments originating from the same IGVL germline gene and/or its allelic variants; (ii) determining which amino acids occur at each of the CDRL3 positions in the reference set that are encoded by the IGVL gene; (iii) synthesizing light chain variable domain encoding sequences wherein two positions between positions 89 and 94, inclusive, contain degenerate codons encoding two or more of the five most frequently occurring amino acid residues at the corresponding positions in the reference set; and (iv) synthesizing the polynucleotides encoding the CDRL3 library. In certain embodiments, the invention provides libraries made by this method.

In some embodiments, the invention provides a method of using any of the libraries of the invention to isolate an antibody binding an antigen, comprising contacting the polypeptide expression products of said libraries with an antigen and isolating polypeptide expression products that bind to the antigen.

In certain embodiments, the number of N-linked glycosylation sites, deamidation motifs, and/or Cys residues in the libraries of the invention are reduced or eliminated in comparison to libraries produced by amplification of a repertoire from a biological source.

The invention provides a number of polynucleotide and polypeptide sequences and segments that can be used to build larger polynucleotide and polypeptide sequences (e.g., TN1, DH, N2, and H3-JH segments that can be used to build CDRH3). One of ordinary skill in the art will readily recognize that in some instances these sequences can be more succinctly represented by providing consensus sequences after alignment of the sequences provided by the invention, and that these consensus sequences fall within the scope of the invention and may be used to more succinctly represent any of the sequences provided herein.

BRIEF DESCRIPTION OF THE DRAWING

FIG. 4 shows the application of a provided method used to generate nucleotide sequences (SEQ ID NOS 8748-8759, respectively, in order of appearance) encoding the parent H3-JH segments.

that match CDRH3 sequences from Lee-666 and Boyd-3000 with zero, one, two, three, or more than three amino acid mismatches.

FIG. 8 shows that Exemplary Library Design 3 (ELD-3) and the Extended Diversity Library Design both return better matches to clinically relevant CDRH3 sequences than the LUA-141 library.

Figure 9:
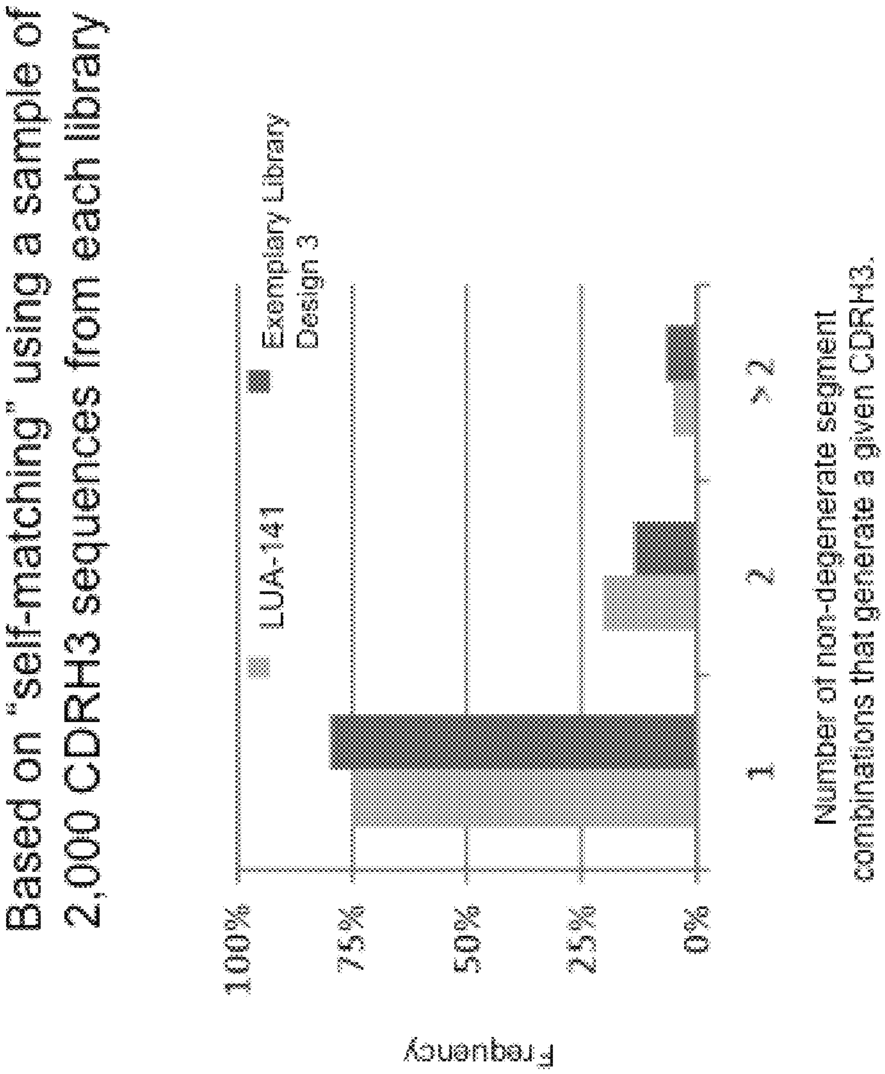

FIG. 9 shows that the combinatorial efficiency of Exemplary Library Design 3 (ELD-3) is greater than that of the LUA-141 library. Specifically, the ELD-3 segments are more likely to yield a unique CDRH3 than the LUA-141 library segments.

Figure 10:
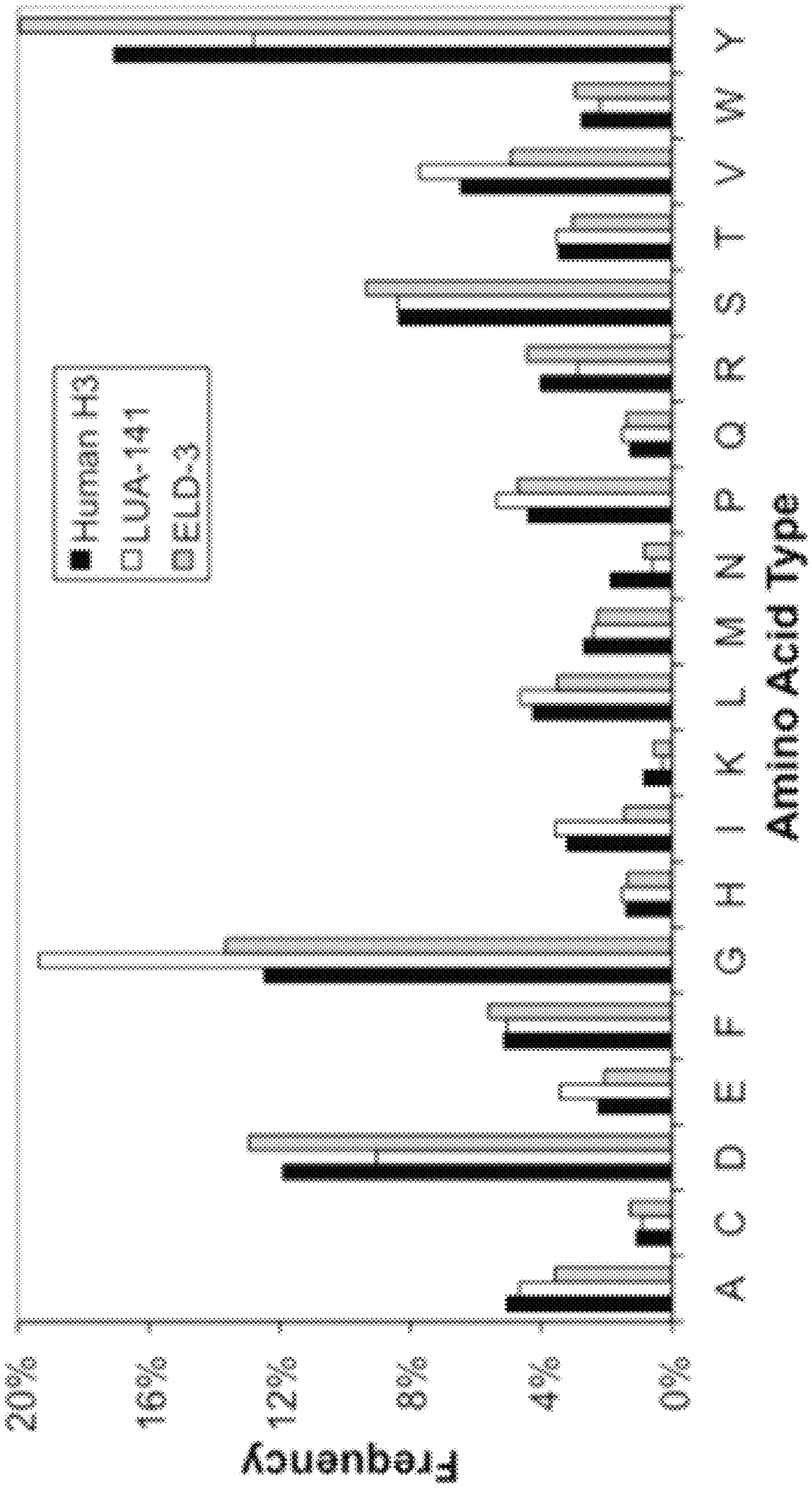

FIG. 10 shows the amino acid compositions of the Kabat-CDRH3s of LUA-141, Exemplary Library Design 3 (ELD-3), and Human CDRH3 sequences from the HPS (Human H3).

Figure 11:
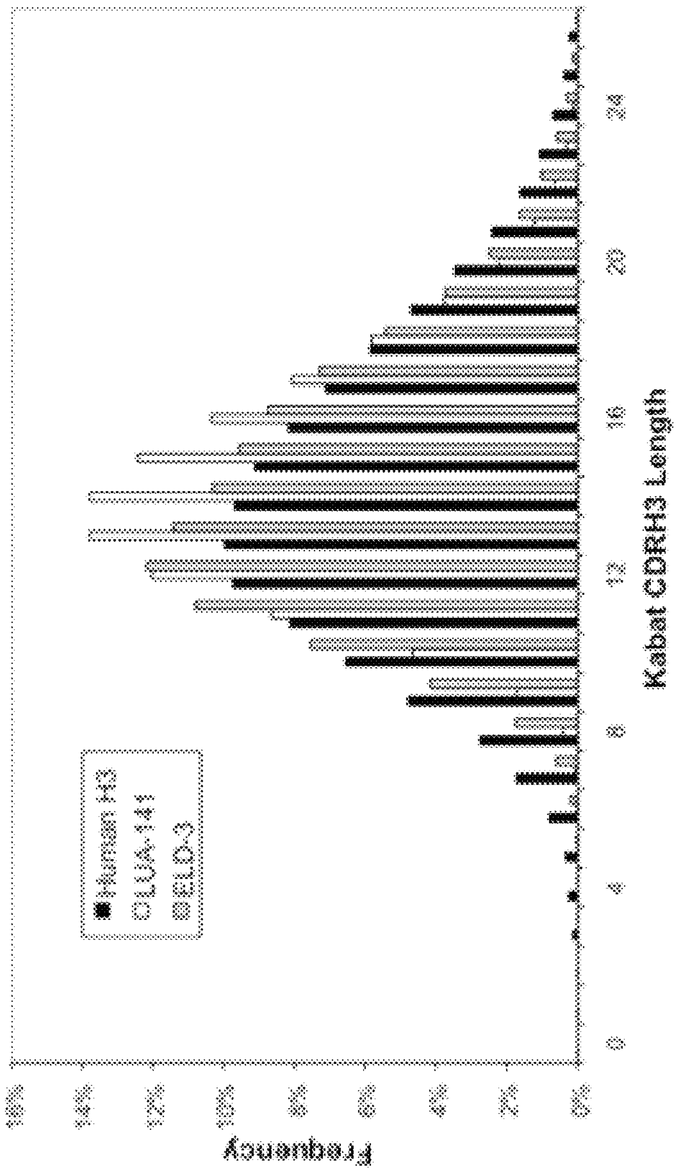

FIG. 11 shows the Kabat-CDRH3 length distribution of LUA-141, Exemplary Library Design 3 (ELD-3), and Human CDRH3 sequences from the HPS (Human H3).

Figure 12:
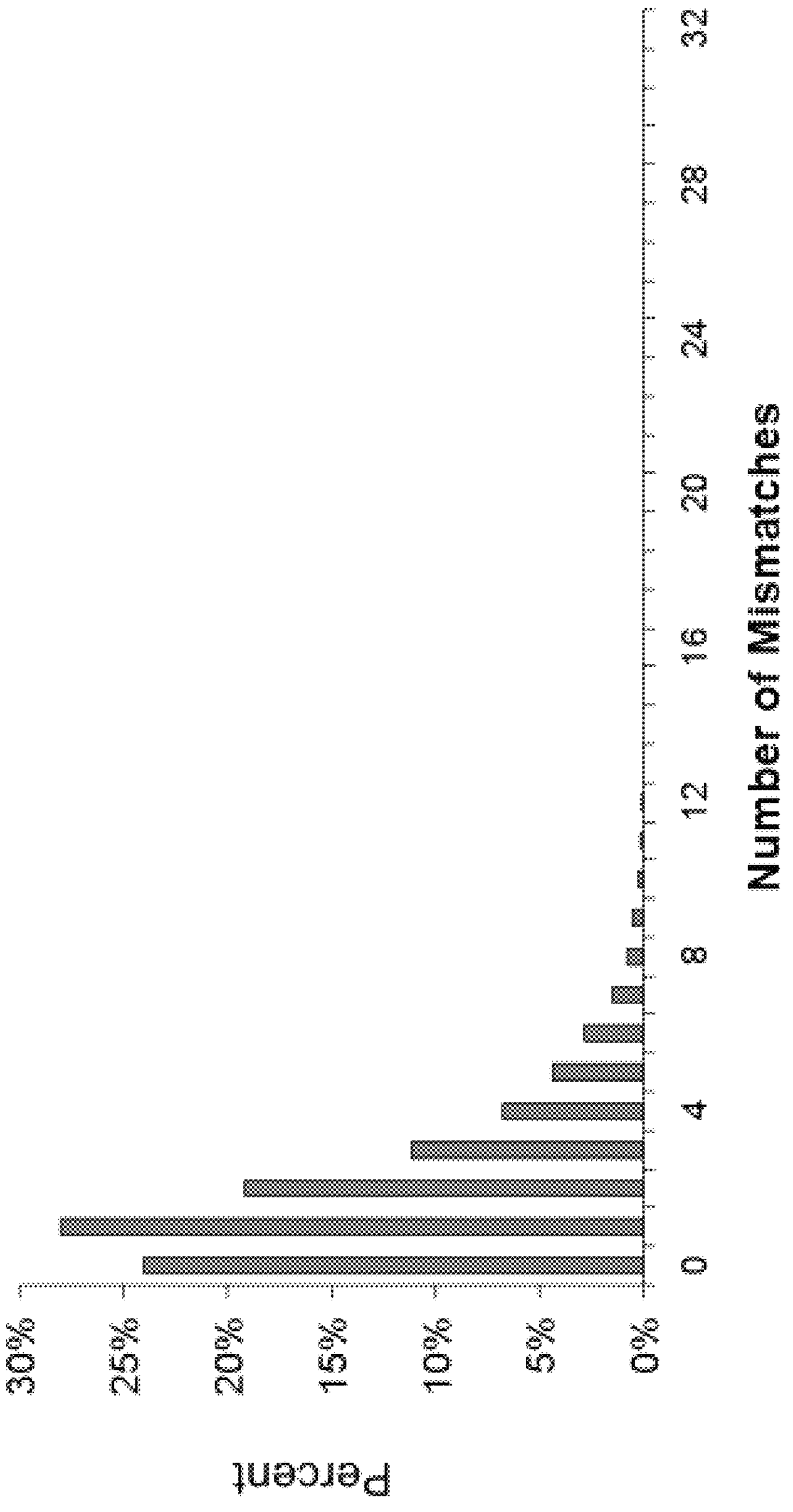
Figure 13:
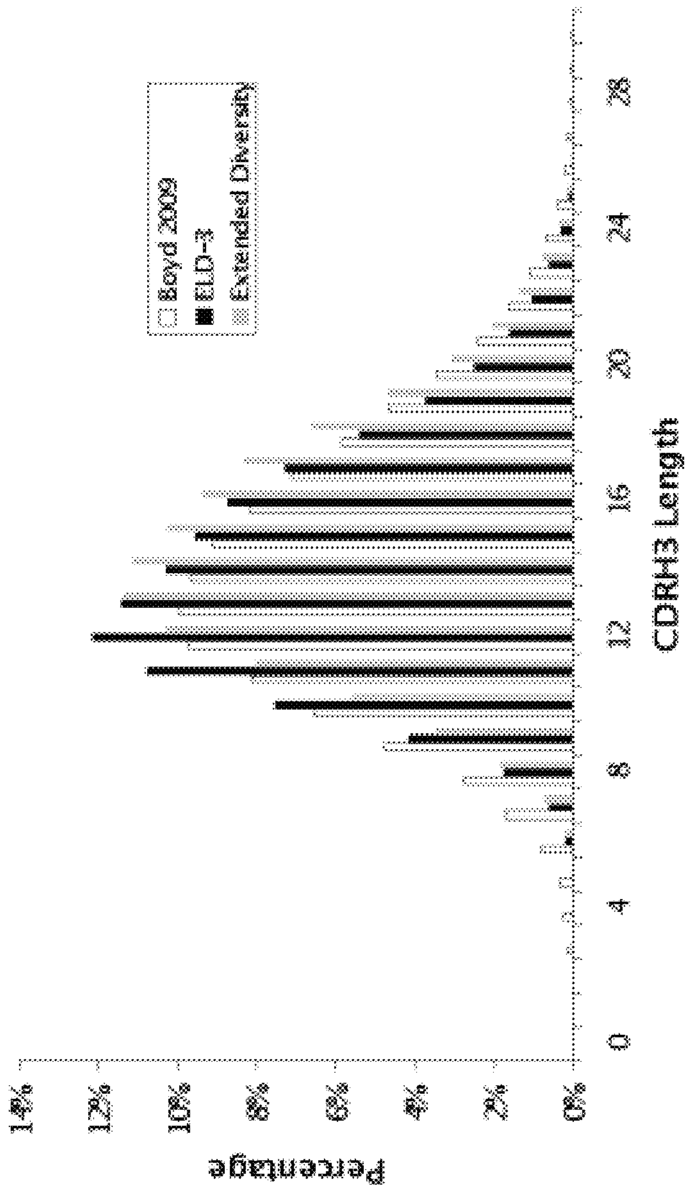

FIG. 12 shows the percentage of CDRH3 sequences in the Extended Diversity library that match CDRH3 sequences from Boyd et al. with zero to thirty-two amino acid mismatches FIG. 13 shows the Kabat-CDRH3 length distribution of Exemplary Library Design 3 ("ELD-3"), the Extended Diversity Library Design ("Extended Diversity") and human CDRH3 sequences from the Boyd et al. data set ("Boyd 2009").

Figure 14:
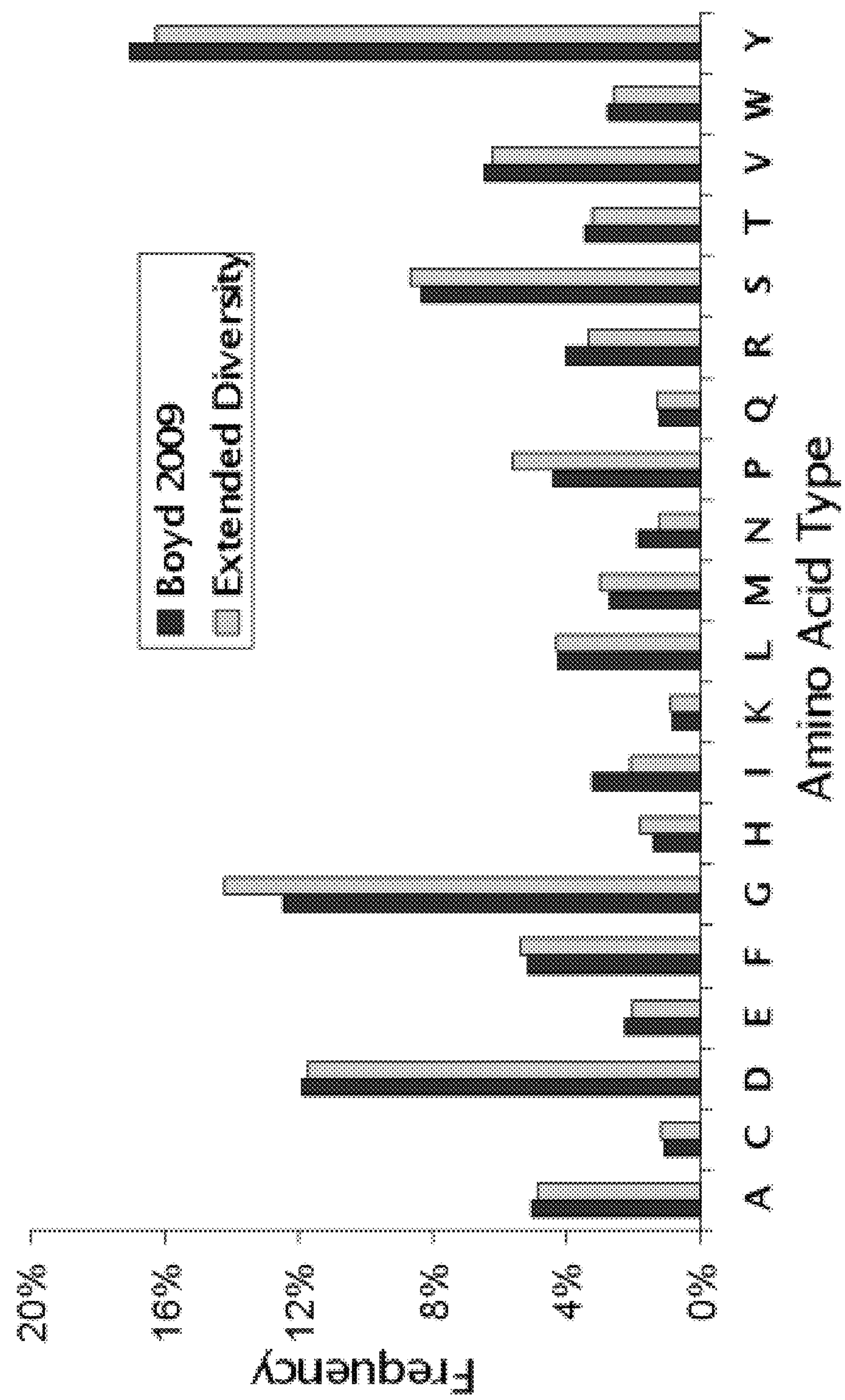

FIG. 14 shows the amino acid compositions of the Kabat-CDRH3s of the Extended Diversity Library Design ("Extended Diversity") and human CDRH3 sequences from the Boyd et al. dataset ("Boyd 2009").

Figure 15:
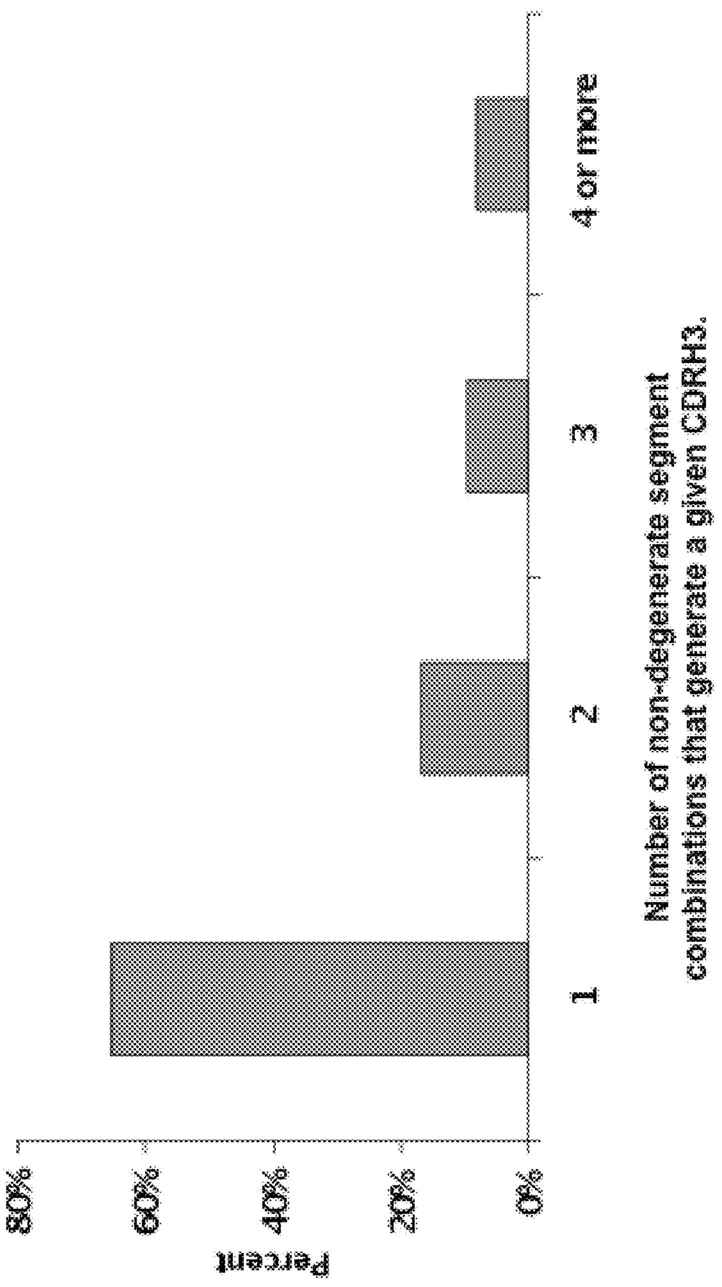

FIG. 15 shows the combinatorial efficiency of the Extended Diversity Library Design by matching 20,000 randomly selected sequences from the (same) design. About 65% of the sequences appear only once in the design and about 17% appear twice.

DETAILED DESCRIPTION OF CERTAIN EMBODIMENTS OF THE INVENTION

The present invention provides, among other things, polynucleotide and polypeptide libraries, methods of producing and using the libraries, kits containing the libraries, and computer readable forms of representations of libraries and/or theoretical segment pools disclosed herein. Libraries taught in this application can be described, at least in part, in terms of components (e.g., polynucleotide or polypeptide "segments") from which they are assembled. Among other things, the present invention specifically provides and contemplates these polynucleotide or polypeptide segments, methods of producing and using such segments, and kits and computer readable forms of representations that include such library segments.

In certain embodiments, the invention provides antibody libraries specifically designed based on sequences and CDR length distribution in a naturally occurring human antibody repertoire. It is estimated that, even in the absence of antigenic stimulation, an individual human makes at least about $10^7$ different antibody molecules (Boyd et al., Science Translational Medicine, 2009, 1: 1). The antigen-binding sites of many antibodies can cross-react with a variety of related but different epitopes. In addition, the human antibody repertoire is large enough to ensure that there is an antigen-binding site to fit almost any potential epitope, albeit potentially with low affinity.

The mammalian immune system has evolved unique genetic mechanisms that enable it to generate an almost unlimited number of different light and heavy chains in a remarkably economical way, by combinatorially joining chromosomally separated gene segments prior to transcription. Each type of immunoglobulin (Ig) chain (i.e., kappa light, lambda light, and heavy) is synthesized by combinatorial assembly of DNA sequences, selected from two or more families of gene segments, to produce a single polypeptide chain. Specifically, the heavy chains and light chains each consist of a variable region and a constant (C) region. The variable regions of the heavy chains are encoded by DNA sequences assembled from three families of gene sequences: variable (IGHV), diversity (IGHD), and joining (IGHJ). The variable regions of light chains are encoded by DNA sequences assembled from two families of gene sequences for each of the kappa and lambda light chains: variable (IGLV) and joining (IGLJ). Each variable region (heavy and light) is also recombined with a constant region, to produce a full-length immunoglobulin chain.

While combinatorial assembly of the V, D and J gene segments make a substantial contribution to antibody variable region diversity, further diversity is introduced in vivo, at the pre-B cell stage, via imprecise joining of these gene segments and the introduction of non-templated nucleotides at the junctions between the gene segments (see e.g., U.S. Pub. No. 2009/0181855, which is incorporated by reference in its entirety, for more information).

After a B cell recognizes an antigen, it is induced to proliferate. During proliferation, the B cell receptor locus undergoes an extremely high rate of somatic mutation that is far greater than the normal rate of genomic mutation. The mutations that occur are primarily localized to the Ig variable regions and comprise substitutions, insertions and deletions. This somatic hypermutation enables the production of B cells that express antibodies possessing enhanced affinity toward an antigen. Such antigen-driven somatic hypermutation fine-tunes antibody responses to a given antigen.

Synthetic antibody libraries of the instant invention have the potential to recognize any antigen, including antigens of human origin. The ability to recognize antigens of human origin may not be present in other antibody libraries, such as antibody libraries prepared from human biological sources (e.g., from human cDNA), because self-reactive antibodies are removed by the donor's immune system via negative selection.

Still further, the present invention provides strategies that streamline and/or simplify certain aspects of library development and/or screening. For example, in some embodiments, the present invention permits use of cell sorting technologies (e.g., fluorescence activated cell sorting, FACS) to identify positive clones, and therefore bypasses or obviates the need for the standard and tedious methodology of generating a hybridoma library and supernatant screening.

Yet further, in some embodiments, the present invention provides libraries and/or sublibraries that accommodate multiple screening passes. For example, in some embodiments, provided libraries and/or sublibraries can be screened multiple times. In some such embodiments, individual provided libraries and/or sublibraries can be used to discover additional antibodies against many targets.

Before further description of the invention, certain terms are defined.

DEFINITIONS

Unless defined otherwise, all technical and scientific terms used herein have the meaning commonly understood by one of ordinary skill in the art relevant to the invention. Unless otherwise specified, the Kabat numbering system is used throughout the application. The definitions below supplement those in the art and are directed to the embodiments described in the current application.

The term “amino acid” or “amino acid residue,” as would be understood by one of ordinary skill in the art, typically refers to an amino acid having its art recognized definition such as an amino acid selected from the group consisting of: alanine (Ala or A); arginine (Arg or R); asparagine (Asn or N); aspartic acid (Asp or D); cysteine (Cys or C); glutamine (Gln or Q); glutamic acid (Glu or E); glycine (Gly or G); histidine (His or H); isoleucine (Ile or I): leucine (Leu or L); lysine (Lys or K); methionine (Met or M); phenylalanine (Phe or F); proline (Pro or P); serine (Ser or S); threonine (Thr or T); tryptophan (Trp or W); tyrosine (Tyr or Y); and valine (Val or V), although modified, synthetic, or rare amino acids may be used as desired. Generally, amino acids can be grouped as having a non-polar side chain (e.g., Ala, Cys, Ile, Leu, Met, Phe, Pro, Val); a negatively charged side chain (e.g., Asp, Glu); a positively charged side chain (e.g., Arg, His, Lys); or an uncharged polar side chain (e.g., Asn, Cys, Gln, Gly, His, Met, Phe, Ser, Thr, Trp, and Tyr).

As would be understood by those of ordinary skill in the art, the term “antibody” is used herein in the broadest sense and specifically encompasses at least monoclonal antibodies, polyclonal antibodies, multi-specific antibodies (e.g., bispecific antibodies), chimeric antibodies, humanized antibodies, human antibodies, and antibody fragments. An antibody is a protein comprising one or more polypeptides substantially or partially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes.

The term “antibody binding region” refers to one or more portions of an immunoglobulin or antibody variable region capable of binding an antigen(s). Typically, the antibody binding region is, for example, an antibody light chain (or variable region or one or more CDRs thereof), an antibody heavy chain (or variable region or one or more CDRs thereof), a heavy chain Fd region, a combined antibody light and heavy chain (or variable regions thereof) such as a Fab, $F(ab)_2$, single domain, or single chain antibodies (scFv), or any region of a full length antibody that recognizes an antigen, for example, an IgG (e.g., an IgG1, IgG2, IgG3, or IgG4 subtype), IgA1, IgA2, IgD, IgE, or IgM antibody.

“Antibody fragments” comprise a portion of an intact antibody, for example, one or more portions of the antigen-binding region thereof. Examples of antibody fragments include Fab, Fab', $F(ab')_2$, and Fv fragments, diabodies, linear antibodies, single-chain antibodies, and multi-specific antibodies formed from intact antibodies and antibody fragments.

The term “antibody of interest” refers to an antibody that has a property of interest that is identified and/or isolated from a library of the invention. Exemplary properties of interest include, for example, but are not limited to, binding to a particular antigen or epitope, binding with a certain affinity, cross-reactivity, blocking a binding interaction between two molecules, and/or eliciting a certain biological effect.

The term “canonical structure,” as understood by those of ordinary skill in the art, refers to the main chain conformation that is adopted by the antigen binding (CDR) loops. From comparative structural studies, it has been found that five of the six antigen binding loops have only a limited repertoire of available conformations. Each canonical structure can be characterized by the torsion angles of the polypeptide backbone. Correspondent loops between antibodies may, therefore, have very similar three dimensional structures, despite high amino acid sequence variability in most parts of the loops (Chothia and Lesk, J. Mol. Biol., 1987, 196: 901; Chothia et al., Nature, 1989, 342: 877; Martin and Thornton, J. Mol. Biol., 1996, 263: 800, each of which is incorporated by reference in its entirety). Furthermore, there is a relationship between the adopted loop structure and the amino acid sequences surrounding it. As is known in the art, the conformation of a particular canonical class is determined by the length of the loop and the amino acid residues residing at key positions within the loop, as well as within the conserved framework (i.e., outside of the loop). Assignment to a particular canonical class can therefore be made based on the presence of these key amino acid residues. The term “canonical structure” may also include considerations as to the linear sequence of the antibody, for example, as catalogued by Kabat (Kabat et al., in “Sequences of Proteins of Immunological Interest,” $5^{th}$ Edition, U.S. Department of Heath and Human Services, 1992). The Kabat numbering scheme is a widely adopted standard for numbering the amino acid residues of an antibody variable domain in a consistent manner, and is used herein unless indicated otherwise. Additional structural considerations can also be used to determine the canonical structure of an antibody. For example, those differences not fully reflected by Kabat numbering can be described by the numbering system of Chothia et al. and/or revealed by other techniques, for example, crystallography and two or three-dimensional computational modeling. Accordingly, a given antibody sequence may be placed into a canonical class which allows for, among other things, identifying appropriate chassis sequences (e.g., based on a desire to include a variety of canonical structures in a library). Kabat numbering of antibody amino acid sequences and structural considerations as described by Chothia et al., and their implications for construing canonical aspects of antibody structure, are described in the literature.

The terms “CDR”, and its plural “CDRs”, refer to a complementarity determining region (CDR) of which three make up the binding character of a light chain variable region (CDRL1, CDRL2 and CDRL3) and three make up the binding character of a heavy chain variable region (CDRH1, CDRH2 and CDRH3). CDRs contribute to the functional activity of an antibody molecule and are separated by amino acid sequences that comprise framework regions. The exact definitional CDR boundaries and lengths are subject to different classification and numbering systems. CDRs may therefore be referred to by Kabat, Chothia, contact or other boundary definitions, including for example the CDRH3 numbering system described below. Despite differing boundaries, each of these systems has some degree of overlap in what constitutes the so called “hypervariable regions” within the variable region. CDR definitions according to these systems may therefore differ in length and boundary areas with respect to the adjacent framework region. See, for example Kabat et al., in “Sequences of Proteins of Immunological Interest,” $5^{th}$ Edition, U.S. Department of Health and Human Services, 1992; Chothia et al., J. Mol. Biol., 1987, 196: 901; and MacCallum et al., J. Mol. Biol., 1996, 262: 732, each of which is incorporated by reference in its entirety.

The “CDRH3 numbering system” used herein defines the first amino acid of CDRH3 as being at position 95 and the last amino acid of CDRH3 as position 102. Note that this is a custom numbering system that is not according to Kabat. The amino acid segment, beginning at position 95 is called "TN1" and, when present, is assigned numbers 95, 96, 96A, 96B, etc. Note that the nomenclature used in the current application is slightly different from that used in U.S. Publication Nos. 2009/0181855 and 2010/0056386, and WO/2009/036379. In those applications, position 95 was designated a "Tail" residue, while here, the Tail (T) has been combined with the N1 segment, to produce one segment, designated "TN1." The TN1 segment is followed by the "DH" segment, which is assigned numbers 97, 97A, 97B, 97C, etc. The DH segment is followed by the "N2" segment, which, when present, is numbered 98, 98A, 98B, etc. Finally, the most C-terminal amino acid residue of the "H3-JH" segment is designated as number 102. The residue directly before (N-terminal) it, when present, is 101, and the one before (if present) is 100. The rest of the H3-JH amino acids are numbered in reverse order, beginning with 99 for the amino acid just N-terminal to 100, 99A for the residue N-terminal to 99, and so forth for 99B, 99C, etc. Examples of CDRH3 sequence residue numbers may therefore include the following:

```
13 Amino Acid CDR-H3 with TN1 and N2
(95) (96) (96A) (97) (97A) (97B) (97C) (97D)  (98)  (99) (100) (101) (102)
|----------------|----------------------------------|----|------------------------|
 TN1                    DH                      N2          H3-JH

10 Amino Acid CDR-H3 without TN1 and N2
(97) (97A) (97B) (97C) (97D) (97E) (97F) (97G) (101) (102)
|----------------------------------------------------------|-------------|
                         DH                            H3-JH
```

"Chassis" of the invention are portions of the antibody heavy chain variable (IGHV) or light chain variable (IGLV) domains that are not part of CDRH3 or CDRL3, respectively. A chassis of the invention is defined as the portion of the variable region of an antibody beginning with the first amino acid of FRM1 and ending with the last amino acid of FRM3. In the case of the heavy chain, the chassis includes the amino acids including from position 1 to position 94. In the case of the light chains (kappa and lambda), the chassis are defined as including from position 1 to position 88. The chassis of the invention may contain certain modifications relative to the corresponding germline variable domain sequences. These modifications may be engineered (e.g., to remove N-linked glycosylation sites) or naturally occurring (e.g., to account for naturally occurring allelic variation). For example, it is known in the art that the immunoglobulin gene repertoire is polymorphic (Wang et al., Immunol. Cell. Biol., 2008, 86: 111; Collins et al., Immunogenetics, 2008, 60: 669, each incorporated by reference in its entirety); chassis, CDRs and constant regions representative of these allelic variants are also encompassed by the invention. In some embodiments, the allelic variant(s) used in a particular embodiment of the invention may be selected based on the allelic variation present in different patient populations, for example, to identify antibodies that are non-immunogenic in these patient populations. In certain embodiments, the immunogenicity of an antibody of the invention may depend on allelic variation in the major histocompatibility complex (MHC) genes of a patient population. Such allelic variation may also be considered in the design of libraries of the invention. In certain embodiments of the invention, the chassis and constant regions are contained in a vector, and a CDR3 region is introduced between them via homologous recombination.

As used herein, a sequence designed with "directed diversity" has been specifically designed to contain both sequence diversity and length diversity. Directed diversity is not stochastic.

As used herein, the term "diversity" refers to a variety or a noticeable heterogeneity. The term "sequence diversity" refers to a variety of sequences which are collectively representative of several possibilities of sequences, for example, those found in natural human antibodies. For example, CDRH3 sequence diversity may refer to a variety of possibilities of combining the known human TN1, DH, N2, and H3-JH segments to form CDRH3 sequences. The CDRL3 sequence diversity (kappa or lambda) may refer to a variety of possibilities of combining the naturally occurring light chain variable region contributing to CDRL3 (i.e., "L3-VL") and joining (i.e., "L3-JL") segments, to form CDRL3 sequences. As used herein, "H3-JH" refers to the portion of the IGHJ gene contributing to CDRH3. As used herein, "L3-VL" and "L3-JL" refer to the portions of the IGLV and IGLJ genes (kappa or lambda) contributing to CDRL3, respectively.

As used herein, the term "expression" refers to steps involved in the production of a polypeptide including, but not limited to, transcription, post-transcriptional modification, translation, post-translational modification, and secretion.

The term "framework region" refers to the art-recognized portions of an antibody variable region that exist between the more divergent (i.e., hypervariable) CDRs. Such framework regions are typically referred to as frameworks 1 through 4 (FRM1, FRM2, FRM3, and FRM4) and provide a scaffold for the presentation of the six CDRs (three from the heavy chain and three from the light chain) in three dimensional space, to form an antigen-binding surface.

The term "full-length heavy chain" refers to an immunoglobulin heavy chain that contains each of the canonical structural domains of an immunoglobulin heavy chain, including the four framework regions, the three CDRs, and the constant region.

The term "full-length light chain" refers to an immunoglobulin light chain that contains each of the canonical structural domains of an immunoglobulin light chain, including the four framework regions, the three CDRs, and the constant region.

The term "germline-like," when used with respect to the CDRL3 sequences of the light chains of the invention, means those sequences consisting of combinations of: (i) the first six wild-type residues contributed to CDRL3 by the IGVL germline gene (i.e., positions 89 to 94 in the Kabat numbering system; "L" is kappa or lambda); and (ii) one of several amino acid sequences, two one to four amino acids in length, largely, but not exclusively, derived from the JL segment ("L," again is kappa or lambda). For kappa CDRL3 sequences of the most common lengths (i.e., 8, 9, and 10 residues), the sequences of (ii) number twenty and are: FT, LT, IT, RT, WT, YT, [X]T, [X]PT, [X]FT, [X]LT, [X]IT, [X]RT, [X]WT, [X]YT, [X]PFT, [X]PLT, [X]PIT, [X]PRT, [X]PWT and [X]PYT, where [X] corresponds to the amino acid residue found at position 95 (Kabat) in the respective VK germline sequence. X is most commonly P, but may also be S or any other amino acid residue found at position 95 of a VK germline sequence. For eight exemplified VK chassis exemplified herein, the corresponding 160 germline-like sequences, (i.e., 20 sequences of two to four amino acids in length combined with positions 89 to 94 of each of eight VK germline sequences) are provided in Table 1. A similar approach is applied to define germline-like CDRL3 sequences for lambda light chains. As for the kappa sequences described above, the intact, un-mutated portions of CDRL3 encoded by the IGVL genes (in this case, IGVλ) would be combined with the sequences largely, but not exclusively, derived from the Jλ segment. Here, the latter sequences (corresponding to (ii), above), number five and are: YV, VV, WV, AV or V. In addition, and as described in Example 7 of US 2009/0818155, one could further allow for variation at the last position of the Vλ-gene-encoded portion of CDRL3 by considering partial codons, while still considering the resulting sequences "germline-like." More specifically, the entire "minimalist library" of Example 7 in US 2009/0818155 would be defined as "germline-like." One of ordinary skill in the art will readily recognize that these methods can be extended to other VK and Vλ sequences.

The term "genotype-phenotype linkage," as understood by those of ordinary skill in the art, refers to the fact that the nucleic acid (genotype) encoding a protein with a particular phenotype (e.g., binding an antigen) can be isolated from a library. For the purposes of illustration, an antibody fragment expressed on the surface of a phage can be isolated based on its binding to an antigen (e.g., U.S. Pat. No. 5,837,500). The binding of the antibody to the antigen simultaneously enables the isolation of the phage containing the nucleic acid encoding the antibody fragment. Thus, the phenotype (antigen-binding characteristics of the antibody fragment) has been "linked" to the genotype (nucleic acid encoding the antibody fragment). Other methods of maintaining a genotype-phenotype linkage include those of Wittrup et al. (U.S. Pat. Nos. 6,300,065, 6,331,391, 6,423, 538, 6,696,251, 6,699,658, and U.S. Pub. No. 20040146976, each of which is incorporated by reference in its entirety), Miltenyi (U.S. Pat. No. 7,166,423, incorporated by reference in its entirety), Fandl (U.S. Pat. No. 6,919,183, US Pub No. 20060234311, each incorporated by reference in its entirety), Clausell-Tormos et al. (Chem. Biol., 2008, 15: 427, incorporated by reference in its entirety), Love et al. (Nat. Biotechnol., 2006, 24: 703, incorporated by reference in its entirety), and Kelly et al. (Chem. Commun., 2007, 14: 1773, incorporated by reference in its entirety). The term can be used to refer to any method which localizes an antibody protein together with the gene encoding the antibody protein, in a way in which they can both be recovered while the linkage between them is maintained.

The term "heterologous moiety" is used herein to indicate the addition of a moiety to an antibody wherein the moiety is not part of a naturally-occurring antibody. Exemplary heterologous moieties include drugs, toxins, imaging agents, and any other compositions which might provide an activity that is not inherent in the antibody itself.

As used herein, the term "host cell" is intended to refer to a cell comprising a polynucleotide of the invention. It should be understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

As used herein, the term "human antibody CDR library" includes at least a polynucleotide or polypeptide library which has been designed to represent the sequence diversity and length diversity of naturally occurring CDRs in human antibodies (e.g., the term "CDR" in "human antibody CDR library" may be substituted with "CDRL1," "CDRL2," "CDRL3," "CDRH1," "CDRH2," and/or "CDRH3"). Known human CDR sequences are represented in various data sets, including Jackson et al., J. Immunol Methods, 2007, 324: 26; Martin, Proteins, 1996, 25: 130; Lee et al., Immunogenetics, 2006, 57: 917, Boyd et al., Science Translational Medicine, 2009, 1: 1, and WO/2009/036379, each of which is incorporated by reference in its entirety, and the HPS, which is provided in Appendix A.

The term "Human Preimmune Set," or "HPS," refers to a reference set of 3,571 curated human preimmune heavy chain sequences corresponding to the GI Nos. provided in Appendix A.

An "intact antibody" is one comprising full-length heavy- and light-chains (i.e., four frameworks, three CDRs, and a constant region for each of the heavy and light chains). An intact antibody is also referred to as a "full-length" antibody.

The term "length diversity" refers to a variety in the length of a family of nucleotide or amino acid sequence. For example, in naturally occurring human antibodies, the heavy chain CDR3 sequence varies in length, for example, from about 2 amino acids to over about 35 amino acids, and the light chain CDR3 sequence varies in length, for example, from about 5 to about 16 amino acids.

The term "library" refers to a set of entities comprising two or more entities having diversity as described herein, and/or designed according to the methods of the invention. For example, a "library of polynucleotides" refers to a set of polynucleotides comprising two or more polynucleotides having diversity as described herein, and/or designed according to the methods of the invention. A "library of polypeptides" refers to a set of polypeptides comprising two or more polypeptides having diversity as described herein, and/or designed according to the methods of the invention. A "library of synthetic polynucleotides" refers to a set of polynucleotides comprising two or more synthetic polynucleotides having diversity as described herein, and/or designed according to the methods of the invention. Libraries where all members are synthetic are also encompassed by the invention. A "human antibody library" refers to a set of polypeptides comprising two or more polypeptides having diversity as described herein, and/or designed according to the methods of the invention, for example a library designed to represent the sequence diversity and length diversity of naturally occurring human antibodies. In some embodiments, the term "library" may refer to a set of entities sharing similar structural or sequence characteristics, for example, a "heavy chain library," "light chain library," "antibody library," and/or "CDRH3 library."

The term "physical realization" refers to a portion of a theoretical (e.g., computer-based) or synthetic (e.g., oligonucleotide-based) diversity that can actually be physically sampled, for example, by any display methodology. Exemplary display methodology include: phage display, ribosomal display, and yeast display. For synthetic sequences, the size of the physical realization of a library depends on (1) the fraction of the theoretical diversity that can actually be synthesized, and (2) the limitations of the particular screening method. Exemplary limitations of screening methods include the number of variants that can be screened in a particular assay (e.g., ribosome display, phage display, yeast display) and the transformation efficiency of the host cells (e.g., yeast, mammalian cells, bacteria) which are used in a screening assay. For the purposes of illustration, given a library with a theoretical diversity of $10^{12}$ members, an exemplary physical realization of the library (e.g., in yeast, bacterial cells, or ribosome display) that can maximally include $10^{11}$ members will, therefore, sample about 10% of the theoretical diversity of the library. However, if fewer than $10^{11}$ members of the library with a theoretical diversity of $10^{12}$ are synthesized, and the physical realization of the library can maximally include $10^{11}$ members, less than 10% of the theoretical diversity of the library is sampled in the physical realization of the library. Similarly, a physical realization of the library that can maximally include more than $10^{12}$ members would "oversample" the theoretical diversity, meaning that each member may be present more than once (assuming that the entire $10^{12}$ theoretical diversity is synthesized).

The term "polynucleotide(s)" refers to nucleic acids such as DNA molecules and RNA molecules and analogs thereof (e.g., DNA or RNA generated using nucleotide analogs or using nucleic acid chemistry). As desired, the polynucleotides may be made synthetically, e.g., using art-recognized nucleic acid chemistry or enzymatically using, e.g., a polymerase, and, if desired, be modified. Typical modifications include methylation, biotinylation, and other art-known modifications. In addition, the nucleic acid molecule can be single-stranded or double-stranded and, where desired, linked to a detectable moiety. The representation of nucleotide bases herein follows International Union of Pure and Applied Chemistry (IUPAC) nomenclature (see U.S. Pub. No. 2009/0181855, incorporated by reference in its entirety).

"Preimmune" antibody libraries have sequence diversities and length diversities similar to naturally occurring human antibody sequences before these sequences have undergone negative selection and/or somatic hypermutation. For example, the set of sequences described in Lee et al. (Immunogenetics, 2006, 57: 917, incorporated by reference in its entirety) and the Human Preimmune Set (HPS) described herein (see Appendix A) are believed to represent sequences from the preimmune repertoire. In certain embodiments of the invention, the sequences of the invention will be similar to these sequences (e.g., in terms of composition and length).

As used herein, the term "sitewise stochastic" describes a process of generating a sequence of amino acids, where only the amino acid occurrences at the individual positions are considered, and higher order motifs (e.g., pair-wise correlations) are not accounted for (e.g., see Knappik, et al., J Mol Biol, 2000, 296: 57, and analysis provided in U.S. Publication No. 2009/0181855, each incorporated by reference in its entirety).

The term "split-pool synthesis" refers to a procedure in which the products of a plurality of individual first reactions are combined (pooled) and then separated (split) before participating in a plurality of second reactions. For example, U.S. Publication No. 2009/0181855 (incorporated by reference in its entirety) describes the synthesis of 278 DH segments (products), each in a separate reaction. After synthesis, these 278 segments are combined (pooled) and then distributed (split) amongst 141 columns for the synthesis of the N2 segments. This enables the pairing of each of the 278 DH segments with each of 141 N2 segments.

As used herein, "stochastic" describes a process of generating a random sequence of nucleotides or amino acids, which is considered as a sample of one element from a probability distribution (e.g., see U.S. Pat. No. 5,723,323).

As used herein, the term "synthetic polynucleotide" refers to a molecule formed through a chemical process, as opposed to molecules of natural origin, or molecules derived via template-based amplification of molecules of natural origin (e.g., immunoglobulin chains cloned from populations of B cells via PCR amplification are not "synthetic" as used herein). In some instances, for example, when referring to libraries of the invention that comprise multiple segments (e.g., TN1, DH, N2, and/or H3-JH), the invention encompasses libraries in which at least one, two, three, or four of the aforementioned components is synthetic. By way of illustration, a library in which certain components are synthetic, while other components are of natural origin or derived via template-based amplification of molecules of natural origin, would be encompassed by the invention. Libraries that are fully synthetic would, of course, also be encompassed by the invention.

The term "theoretical diversity" refers to the maximum number of variants in a library design. For example, given an amino acid sequence of three residues, where residues one and three may each be any one of five amino acid types and residue two may be any one of 20 amino acid types, the theoretical diversity is $5\times20\times5=500$ possible sequences. Similarly if sequence X is constructed by combination of 4 amino acid segments, where segment 1 has 100 possible sequences, segment 2 has 75 possible sequences, segment 3 has 250 possible sequences, and segment 4 has 30 possible sequences, the theoretical diversity of fragment X would be $100\times75\times200\times30$, or $5.6\times10^5$ possible sequences.

The term "theoretical segment pool" refers to a set of polynucleotide or polypeptide segments that can be used as building blocks to assemble a larger polynucleotide or polypeptide. For example, a theoretical segment pool containing TN1, DH, N2, and H3-JH segments can be used to assemble a library of CDRH3 sequences by concatenating them combinatorially to form a sequence represented by [TN1]-[DH]-[N2]-[H3-JH], and synthesizing the corresponding oligonucleotide(s). The term "theoretical segment pool" can apply to any set of polynucleotide or polypeptide segments. Thus, while a set of TN1, DH, N2, and H3-JH segments are collectively considered a theoretical segment pool, each of the individual sets of segments also comprise a theoretical segment pool, specifically a TN1 theoretical segment pool, a DH theoretical segment pool, an N2 theoretical segment pool, and an H3-JH theoretical segment pool. Any subsets of these theoretical segment pools containing two or more sequences can also be considered theoretical segment pools.

The term "unique," as used herein, refers to a sequence that is different (e.g., has a different chemical structure) from every other sequence within the designed set (e.g., the theoretical diversity). It should be understood that there are likely to be more than one copy of many unique sequences from the theoretical diversity in a particular physical realization. For example, a library comprising three unique sequences at the theoretical level may comprise nine total members if each sequence occurs three times in the physical realization of the library. However, in certain embodiments, each unique sequence may occur only once, less than once, or more than once.

The term "variable" refers to the portions of the immunoglobulin domains that exhibit variability in their sequence and that are involved in determining the specificity and binding affinity of a particular antibody (i.e., the "variable domain(s)"). Variability is not evenly distributed throughout the variable domains of antibodies; it is concentrated in sub-domains of each of the heavy and light chain variable regions. These sub-domains are called "hypervariable" regions or "complementarity determining regions" (CDRs). The more conserved (i.e., non-hypervariable) portions of the variable domains are called the "framework" regions (FRM). The variable domains of naturally occurring heavy and light chains each comprise four FRM regions, largely adopting a β-sheet configuration, connected by three hypervariable regions, which form loops connecting, and in some cases forming part of, the β-sheet structure. The hypervariable regions in each chain are held together in close proximity by the FRM and, with the hypervariable regions from the other chain, contribute to the formation of the antigen-binding site (see Kabat et al. Sequences of Proteins of Immunological Interest, 5th Ed. Public Health Service, National Institutes of Health, Bethesda, Md., 1991, incorporated by reference in its entirety). The constant domains are not directly involved in antigen binding, but exhibit various effector functions, such as, for example, antibody-dependent, cell-mediated cytotoxicity and complement activation.

Libraries of the invention containing "VKCDR3" sequences and "VλCDR3" sequences refer to the kappa and lambda sub-sets of the light chain CDR3 (CDRL3) sequences, respectively. Such libraries may be designed with directed diversity, to collectively represent the length and sequence diversity of the human antibody CDRL3 repertoire. "Preimmune" versions of these libraries have similar sequence diversities and length diversities as naturally occurring human antibody CDRL3 sequences before these sequences undergo negative selection and/or somatic hypermutation. Known human CDRL3 sequences are represented in various data sets, including the NCBI database, WO/2009/036379, and Martin, Proteins, 1996, 25: 130 each incorporated by reference in its entirety.

General Design of Libraries

Antibody libraries provided by the present invention may be designed to reflect certain aspects of the preimmune repertoire as created by the human immune system. Certain libraries of the invention are based on rational design informed by collections of human V, D, and J genes, and large databases of human heavy and light chain sequences (e.g., publicly known germline sequences and sequences from Jackson et al., J. Immunol Methods, 2007, 324: 26; Lee et al., Immunogenetics, 2006, 57: 917; Boyd et al., Science Translational Medicine, 2009, 1: 1-8, each incorporated by reference in its entirety; and sequences compiled from rearranged VK and Vλ sequences (see WO/2009/036379, also incorporated by reference in its entirety). Additional information may be found, for example, in Scaviner et al., Exp. Clin. Immunogenet., 1999, 16: 234; Tomlinson et al., J. Mol. Biol., 1992, 227: 799; and Matsuda et al., J. Exp. Med., 1998, 188: 2151, each incorporated by reference in its entirety.

In certain embodiments of the invention, segments representing the possible V, D, and J diversity found in the human repertoire, as well as junctional diversity (i.e., TN1 and N2), are synthesized de novo as single or double-stranded DNA oligonucleotides. In certain embodiments of the invention, oligonucleotides encoding CDR sequences are introduced into yeast along with one or more acceptor vectors containing heavy or light chain chassis sequences and constant domains. No primer-based PCR amplification or template-directed cloning steps from mammalian cDNA or mRNA are employed. Through standard homologous recombination, the recipient yeast recombines the CDR segments with the acceptor vectors containing the chassis sequences and constant regions, to create a properly ordered synthetic, full-length human heavy chain and/or light chain immunoglobulin library that can be genetically propagated, expressed, presented, and screened. One of ordinary skill in the art will readily recognize that the acceptor vector can be designed so as to produce constructs other than full-length human heavy chains and/or light chains. For example, in certain embodiments of the invention, the chassis may be designed to encode portions of a polypeptide encoding an antibody fragment or subunit of an antibody fragment, so that a sequence encoding an antibody fragment, or subunit thereof, is produced when the oligonucleotide cassette containing the CDR is recombined with the acceptor vector.

Thus, in certain embodiments, the invention provides a synthetic, preimmune human antibody repertoire the repertoire comprising:

(a) one or more selected human antibody heavy chain chassis (i.e., amino acids 1 to 94 of the heavy chain variable region, using Kabat's definition);

(b) a CDRH3 repertoire (described more fully below), designed based on the human IGHD and IGHJ germline sequences, and the extraction of TN1 and N2 sequences from reference sets of human CDRH3 sequences, the CDRH3 repertoire comprising (i) a TN1 segment; (ii) a DH segment; (iii) an N2 segment; (iv) an H3-JH segment.

(c) one or more selected human antibody kappa and/or lambda light chain chassis; and (d) a CDRL3 repertoire designed based on the human IGLV and IGLJ germline sequences, wherein "L" may be a kappa or lambda light chain.

The instant invention also provides methods for producing and using such libraries, as well as libraries comprising one or more immunoglobulin domains or antibody fragments. Design and synthesis of each component of the antibody libraries of the invention is provided in more detail below.

Design of Antibody Library Chassis Sequences

In certain embodiments, provided libraries are constructed from selected chassis sequences that are based on naturally occurring variable domain sequences (e.g., IGHV and IGLV genes). The selection of such chassis sequences can be done arbitrarily, or through the definition of certain pre-determined criteria. For example, the Kabat database, an electronic database containing non-redundant rearranged antibody sequences, can be queried for those heavy and light chain germline sequences that are most frequently represented. An algorithm such as BLAST, or a more specialized tool such as SoDA (Volpe et al., Bioinformatics, 2006, 22: 438-44, incorporated by reference in its entirety), can be used to compare rearranged antibody sequences with germline sequences (e.g., using the V BASE2 database; see, for example, Retter et al., Nucleic Acids Res., 2005, 33: D671-D674, incorporated by reference in its entirety), or similar collections of human V, D, and J genes, to identify germline families that are most frequently used to generate functional antibodies.

Several criteria can be utilized for the selection of chassis for inclusion in the libraries of the invention. For example, sequences that are known (or have been determined) to express poorly in yeast, or other organisms used in the invention (e.g., bacteria, mammalian cells, fungi, or plants) can be excluded from the libraries. Chassis may also be chosen based on the representation of their corresponding germline genes in the peripheral blood of humans. In certain embodiments of the invention, it may be desirable to select chassis that correspond to germline sequences that are highly represented in the peripheral blood of humans. In some embodiments, it may be desirable to select chassis that correspond to germline sequences that are less frequently represented, for example, to increase the canonical diversity of the library. Therefore, chassis may be selected to produce libraries that represent the largest and most structurally diverse group of functional human antibodies.

In certain embodiments of the invention, less diverse chassis may be utilized, for example, if it is desirable to produce a smaller, more focused library with less chassis variability and greater CDR variability. In some embodiments of the invention, chassis may be selected based on both their expression in a cell of the invention (e.g., a yeast cell) and the diversity of canonical structures represented by the selected sequences. One may therefore produce a library with a diversity of canonical structures that express well in a cell of the invention.

Design of Heavy Chain Chassis Sequences

The design and selection of heavy chain chassis sequences that can be used in the current invention is described in detail in U.S. Publication Nos. 2009/0181855 and 2010/0056386, and WO/2009/036379, each of which is incorporated by reference in its entirety, and is therefore described only briefly here.

In general, VH domains of the library comprise three components: (1) a VH "chassis," which includes amino acids 1 to 94 (using Kabat numbering), (2) the CDRH3, which is defined herein to include the Kabat CDRH3 proper (positions 95-102), and (3) the FRM4 region, including amino acids 103 to 113 (Kabat numbering). The overall VH domain structure may therefore be depicted schematically (not to scale) as:

```
(1) . . . (94)                         (95) . . . (102)  (103) . . . (113)
|---------------------------------------|-----------------|-----------------|
VH Chassis                              CDRH3             FRM4
```

In certain embodiments of the invention, the VH chassis of the libraries may comprise from about Kabat residue 1 to about Kabat residue 94 of one or more of the following IGHV germline sequences: IGHV1-2, IGHV1-3, IGHV1-8, IGHV1-18, IGHV1-24, IGHV1-45, IGHV1-46, IGHV1-58, IGHV1-69, IGH8, IGH56, IGH100, IGHV3-7, IGHV3-9, IGHV3-11, IGHV3-13, IGHV3-15, IGHV3-20, IGHV3-21, IGHV3-23, IGHV3-30, IGHV3-33, IGHV3-43, IGHV3-48, IGHV3-49, IGHV3-53, IGHV3-64, IGHV3-66, IGHV3-72, IGHV3-73, IGHV3-74, IGHV4-4, IGHV4-28, IGHV4-31, IGHV4-34, IGHV4-39, IGHV4-59, IGHV4-61, IGHV4-B, IGHV5-51, IGHV6-1, and/or IGHV7-4-1. In some embodiments of the invention, a library may contain one or more of these sequences, one or more allelic variants of these sequences, or encode an amino acid sequence at least about 99.9%, 99.5%, 99%, 98.5%, 98%, 97.5%, 97%, 96.5%, 96%, 95.5%, 95%, 94.5%, 94%, 93.5%, 93%, 92.5%, 92%, 91.5%, 91%, 90.5%, 90%, 89%, 88%, 87%, 86%, 85%, 84%, 83%, 82%, 81%, 80%, 77.5%, 75%, 73.5%, 70%, 65%, 60%, 55%, or 50% identical to one or more of these sequences. One of ordinary skill in the art will recognize that given the chassis definition provided above, any IGHV-encoding sequence can be adapted for use as a chassis of the invention. As exemplified in U.S. Publication Nos. 2009/0181855 and 2010/0056386, and WO/2009/036379 (each incorporated by reference in its entirety), these chassis can also be varied, particularly by altering the amino acid residues in the CDRH1 and CDRH2 regions, further increasing the diversity of the library.

Design of Light Chain Chassis Sequences

The design and selection of light chain chassis sequences that can be used in the current invention is described in detail in U.S. Publication Nos. 2009/0181855 and 2010/0056386, and WO/2009/036379, each of which is incorporated by reference in its entirety, and is therefore described only briefly here. The light chain chassis of the invention may be based on kappa and/or lambda light chain sequences.

The VL domains of the library comprise three primary components: (1) a VL "chassis", which includes amino acids 1 to 88 (using Kabat numbering), (2) the CDRL3, which is defined herein to include the Kabat CDRL3 proper (positions 89-97), and (3) the FRM4 region, including amino acids 98 to 107 (Kabat numbering). The overall VL domain structure may therefore be depicted schematically (not to scale) as:

```
(1) . . . (88)                         (89) . . . (97)  (98) . . . (107)
|---------------------------------------|-----------------|-----------------|
VL Chassis                              CDRL3             FRM4
```

In certain embodiments of the invention, the VL chassis of the libraries include one or more chassis based on IGKV germline sequences. In certain embodiments of the invention, the VL chassis of the libraries may comprise from about Kabat residue 1 to about Kabat residue 88 of one or more of the following IGKV germline sequences: IGKV1-05, IGKV1-06, IGKV1-08, IGKV1-09, IGKV1-12, IGKV1-13, IGKV1-16, IGKV1-17, IGKV1-27, IGKV1-33, IGKV1-37, IGKV1-39, IGKV1D-16, IGKV1D-17, IGKV1D-43, IGKV1D-8, IGK54, IGK58, IGK59, IGK60, IGK70, IGKV2D-26, IGKV2D-29, IGKV2D-30, IGKV3-11, IGKV3-15, IGKV3-20, IGKV3D-07, IGKV3D-11, IGKV3D-20, IGKV4-1, IGKV5-2, IGKV6-21, and/or IGKV6D-41. In some embodiments of the invention, a library may contain one or more of these sequences, one or more allelic variants of these sequences, or encode an amino acid sequence at least about 99.9%, 99.5%, 99%, 98.5%, 98%, 97.5%, 97%, 96.5%, 96%, 95.5%, 95%, 94.5%, 94%, 93.5%, 93%, 92.5%, 92%, 91.5%, 91%, 90.5%, 90%, 89%, 88%, 87%, 86%, 85%, 84%, 83%, 82%, 81%, 80%, 77.5%, 75%, 73.5%, 70%, 65%, 60%, 55%, or 50% identical to one or more of these sequences.

In certain embodiments of the invention, the VL chassis of the libraries include one or more chassis based on IGλV germline sequences. In certain embodiments of the invention, the VL chassis of the libraries may comprise from about Kabat residue 1 to about Kabat residue 88 of one or more of the following IGλV germline sequences: IGλV3-1, IGλV3-21, IGλ44, IGλV1-40, IGλV3-19, IGλV1-51, IGλV1-44, IGλV6-57, IGλ11, IGλV3-25, IGλ53, IGλV3-10, IGλV4-69, IGλV1-47, IGλ41, IGλV7-43, IGλV7-46, IGλV5-45, IGλV4-60, IGλV10-54, IGλV8-61, IGλV3-9, IGλV1-36, IGλ48, IGλV3-16, IGλV3-27, IGλV4-3, IGλV5-39, IGλV9-49, and/or IGλV3-12. In some embodiments of the invention, a library may contain one or more of these sequences, one or more allelic variants of these sequences, or encode an amino acid sequence at least about 99.9%, 99.5%, 99%, 98%, 97%, 96%, 95%, 94%, 93%, 92%, 91%, 90%, 85%, 80%, 75%, 70%, 65%, 60%, 55%, or 50% identical to one or more of these sequences.

One of ordinary skill in the art will recognize that given the chassis definition provided above, any IGKV- or IGλV-encoding sequence can be adapted for use as a chassis of the invention.

Design and Selection of TN1, DH, N2, and H3-JH Segments

The human germline repertoire contains at least six IGHJ genes (IGHJ1, IGHJ2, IGHJ3, IGHJ4, IGHJ5, and IGHJ6; included in Table 14, where the primary allele is designated "01," and selected allelic variants are designated "02" or "03"), and at least 27 IGHD genes (Table 16, including allelic variants). In some embodiments, the invention comprises a library of CDRH3 polypeptide sequences, or polynucleotide sequences encoding CDRH3 sequences, the library comprising members of any of the theoretical segment pools disclosed herein.

A person of ordinary skill in the art will recognize that not every segment in a theoretical segment pool provided herein is necessary to produce a functional CDRH3 library of the invention. Therefore, in certain embodiments, a CDRH3 library of the invention will contain a subset of the segments of any of the theoretical segment pools described herein. For example, in certain embodiments of the invention, at least about 15, 30, 45, 60, 75, 90, 100, 105, 120, 135, 150, 165, 180, 195, 200, 210, 225, 240, 255, 270, 285, 300, 320, 340, 360, 380, 400, 420, 440, 460, 480, 500, 520, 540, 560, 580, 600, 620, 640, or 643 of the H3-JH segments of any of the theoretical segment pools provided herein, or generated by the methods described herein, are included in a library. In some embodiments of the invention, at least about 15, 30, 45, 60, 75, 90, 100, 105, 120, 135, 150, 165, 180, 195, 200, 250, 300, 350, 400, 450, 500, 550, 600, 650, 700, 750, 800, 850, 900, 950, 1000, 1050, 1100, 1111, 2000, 3000, 4000, 5000, 6000, 7000, 14000, 21000, 28000, 35000, 42000, 49000, 56000, 63000, or 68374 of the DH segments of any of the theoretical segment pools provided herein, or generated by the methods described herein, are included in a library. In some embodiments of the invention, at least about 10, 20, 30, 40, 50, 60, 70, 80, 90, 100, 110, 120, 130, 140, 141, 150, 160, 170, 180, 190, or 200, 220, 240, 260, 280, 300, 320, 340, 360, 380, 400, 420, 424, 440, 460, 480, 500, 550, 600, 650, 700, 727, 750, 800, 850, 900, 950, or 1000 of the TN1 and/or N2 segments of any of the theoretical segment pools provided herein, or generated by the methods described herein, are included in a library. In certain embodiments, a library of the invention may contain less than a particular number of polynucleotide or polypeptide segments, where the number of segments is defined using any one of the integers provided above for the respective segment. In some embodiments of the invention, a particular numerical range is defined, using any two of the integers provided above as lower and upper boundaries of the range, inclusive or exclusive. All combinations of the integers provided, which define an upper and lower boundary, are contemplated.

In certain embodiments, the invention provides CDRH3 libraries comprising at least about 1%, 2.5%, 5%, 10%, 15%, 20%, 25%, 30%, 40%, 45%, 50%, 55%, 60%, 65%, 70%, 75%, 80%, 85%, 90%, 95%, or 99% of the segments from any of the theoretical segment pools provided herein. For example, the invention provides libraries comprising at least about 1%, 2.5%, 5%, 10%, 15%, 20%, 25%, 30%, 40%, 45%, 50%, 55%, 60%, 65%, 70%, 75%, 80%, 85%, 90%, 95%, or 99% of the TN1, DH, N2, and/or H3-JH segments from any of the theoretical segment pools provided herein. In some embodiments of the invention, a particular percentage range is defined, using any two of the percentages provided above as lower and upper boundaries of the range, inclusive or exclusive. All combinations of the percentages provided, which define an upper and lower boundary, are contemplated.

In some embodiments of the invention, at least about 1%, 2.5%, 5%, 10%, 15%, 20%, 25%, 30%, 40%, 45%, 50%, 55%, 60%, 65%, 70%, 75%, 80%, 85%, 90%, 95%, or 99% of the H3-JH, DH, TN1, and/or N2 segments in a CDRH3 library are H3-JH, DH, TN1, and/or N2 segments of any of the theoretical segment pools provided herein, or generated by the methods described herein. In some embodiments of the invention, at least about 1%, 2.5%, 5%, 10%, 15%, 20%, 25%, 30%, 40%, 45%, 50%, 55%, 60%, 65%, 70%, 75%, 80%, 85%, 90%, 95%, or 99% of the H3-JH, DH, TN1, and/or N2 segments of antibodies isolated from a CDRH3 library (e.g., by binding to a particular antigen and/or generic ligand through one or more rounds of selection) are H3-JH, DH, TN1, and/or N2 segments of any of the theoretical segment pools provided herein, or generated by methods described herein. In certain embodiments, a CDRH3 library of the invention may contain less than a particular percentage of H3-JH, DH, TN1, and/or N2 segments of any of the theoretical segment pools provided herein, or generated by the methods described herein, where the number of segments is defined using any one of the percentages provided above for the respective segment. In some embodiments of the invention, a particular percentage range is defined, using any two of the percentages provided above as lower and upper boundaries of the range, inclusive or exclusive. All combinations of the percentages provided, which define an upper and lower boundary, are contemplated.

One of ordinary skill in the art will appreciate, upon reading the disclosure herein. that given the TN1, DH, N2, and/or H3-JH segments of any of the theoretical segment pools provided herein, or generated by the methods described herein, similar TN1, DH, N2, and/or H3-JH segments, and corresponding CDRH3 libraries, could be produced which, while not 100% identical to those provided in terms of their sequences, may be functionally very similar. Such theoretical segment pools and CDRH3 libraries also fall within the scope of the invention. A variety of techniques well-known in the art could be used to obtain these additional sequences, including the mutagenesis techniques provided herein. Therefore, each of the explicitly enumerated embodiments of the invention can also be practiced using segments that share a particular percent identity to any of the segments of any of the theoretical segment pools provided herein, or generated by the methods described herein. For example, each of the previously described embodiments of the invention can be practiced using TN1, DH, N2, and/or H3-JH segments that are at least about 50%, 55%, 60%, 65%, 70%, 75%, 80%, 85%, 90%, 91%, 92%, 93%, 94%, 95%, 96%, 97%, 98%, 99%, 99.5%, or 99.9% identical to the TN1, DH, N2, and/or H3-JH segments of any of the theoretical segment pools provided herein, or generated by the methods described herein.

In some embodiments, the invention provides libraries produced from one or more VH chassis sequences combined with one or more TN1 segments, one or more DH segments, one or more N2 segments, and one or more H3-JH segments. In certain embodiments at least 1, 2, 5, 10, 20, 50, 75, or 100, of each chassis, TN1, DH, N2, or H3-JH segments are included in a library of the invention.

In some embodiments, the invention provides a method of selecting TN1, DH, N2, and H3-JH segments from a theoretical segment pool for inclusion in a synthetic CDRH3 library, comprising:

(i) providing a theoretical segment pool containing one or more of TN1, DH, N2, and H3-JH segments;
(ii) providing a reference set of CDRH3 sequences;
(iii) utilizing the theoretical segment pool of (i) to identify the closest match(es) to each CDRH3 sequence in the reference set of (ii); and
(iv) selecting segments from the theoretical segment pool for inclusion in a synthetic library.

In some embodiments, the selection process of (iv) can optionally involve any number of additional criteria, including the frequency of occurrence of the segments of (i) in the reference set of (ii); the corresponding segmental usage weights; and any physicochemical properties (see all numerical indices on the world wide web at genome.jp/aaindex/) of the segments (e.g., hydrophobicity, alpha-helical propensity, and/or isoelectric point). Optionally, TN1 and/or N2 segments that do not occur in the theoretical segment pool of (i) but that are found in the reference set of (ii) may be identified and added to prospective theoretical segment pools to produce theoretical segment pools with increased TN1 and/or N2 diversity in the prospective theoretical segment pools and/or synthetic libraries of the invention.

Any characteristic or set of characteristics of the segments can be used to choose them for inclusion in the library, including for example one or more biological properties (e.g., immunogenicity, stability, half-life) and/or one or more physicochemical properties such as the numerical indices provided above. In some embodiments, at least 1, 2, 3, 4, 5, 6, 7, 8, 9, 10, 11, 12, 13, 14, 15 or more such properties is used to select segments for inclusion in a library of the invention. Physiochemical properties included in the index provided above can include, for example, ANDN920101 alpha-CH chemical shifts (Andersen et al., 1992); ARGP820101 Hydrophobicity index (Argos et al., 1982); ARGP820102 Signal sequence helical potential (Argos et al., 1982); ARGP820103 Membrane-buried preference parameters (Argos et al., 1982); BEGF750101 Conformational parameter of inner helix (Beghin-Dirkx, 1975); BEGF750102 Conformational parameter of beta-structure (Beghin-Dirkx, 1975); BEGF750103 Conformational parameter of beta-turn (Beghin-Dirkx, 1975); BHAR880101 Average flexibility indices (Bhaskaran-Ponnuswamy, 1988); BIGC670101 Residue volume (Bigelow, 1967); BIOV880101 Information value for accessibility; average fraction 35% (Biou et al., 1988); BIOV880102 Information value for accessibility; average fraction 23% (Biou et al., 1988); BROC820101 Retention coefficient in TFA (Browne et al., 1982); BROC820102 Retention coefficient in HFBA (Browne et al., 1982); BULH740101 Transfer free energy to surface (Bull-Breese, 1974); BULH740102 Apparent partial specific volume (Bull-Breese, 1974); BUNA790101 alpha-NH chemical shifts (Bundi-Wuthrich, 1979); BUNA790102 alpha-CH chemical shifts (Bundi-Wuthrich, 1979); BUNA790103 Spin-spin coupling constants 3JHalpha-NH (Bundi-Wuthrich, 1979); BURA740101 Normalized frequency of alpha-helix (Burgess et al., 1974); BURA740102 Normalized frequency of extended structure (Burgess et al., 1974); CHAM810101 Steric parameter (Charton, 1981); CHAM820101 Polarizability parameter (Charton-Charton, 1982); CHAM820102 Free energy of solution in water, kcal/mole (Charton-Charton, 1982); CHAM830101 The Chou-Fasman parameter of the coil conformation (Charton-Charton, 1983); CHAM830102 A parameter defined from the residuals obtained from the best correlation of the Chou-Fasman parameter of beta-sheet (Charton-Charton, 1983); CHAM830103 The number of atoms in the side chain labelled 1+1 (Charton-Charton, 1983); CHAM830104 The number of atoms in the side chain labelled 2+1 (Charton-Charton, 1983); CHAM830105 The number of atoms in the side chain labelled 3+1 (Charton-Charton, 1983); CHAM830106 The number of bonds in the longest chain (Charton-Charton, 1983); CHAM830107 A parameter of charge transfer capability (Charton-Charton, 1983); CHAM830108 A parameter of charge transfer donor capability (Charton-Charton, 1983); CHOC750101 Average volume of buried residue (Chothia, 1975); CHOC760101 Residue accessible surface area in tripeptide (Chothia, 1976); CHOC760102 Residue accessible surface area in folded protein (Chothia, 1976); CHOC760103 Proportion of residues 95% buried (Chothia, 1976); CHOC760104 Proportion of residues 100% buried (Chothia, 1976); CHOP780101 Normalized frequency of beta-turn (Chou-Fasman, 1978a); CHOP780201 Normalized frequency of alpha-helix (Chou-Fasman, 1978b); CHOP780202 Normalized frequency of beta-sheet (Chou-Fasman, 1978b); CHOP780203 Normalized frequency of beta-turn (Chou-Fasman, 1978b); CHOP780204 Normalized frequency of N-terminal helix (Chou-Fasman, 1978b); CHOP780205 Normalized frequency of C-terminal helix (Chou-Fasman, 1978b); CHOP780206 Normalized frequency of N-terminal non helical region (Chou-Fasman, 1978b); CHOP780207 Normalized frequency of C-terminal non helical region (Chou-Fasman, 1978b); CHOP780208 Normalized frequency of N-terminal beta-sheet (Chou-Fasman, 1978b); CHOP780209 Normalized frequency of C-terminal beta-sheet (Chou-Fasman, 1978b); CHOP780210 Normalized frequency of N-terminal non beta region (Chou-Fasman, 1978b); CHOP780211 Normalized frequency of C-terminal non beta region (Chou-Fasman, 1978b); CHOP780212 Frequency of the 1st residue in turn (Chou-Fasman, 1978b); CHOP780213 Frequency of the 2nd residue in turn (Chou-Fasman, 1978b); CHOP780214 Frequency of the 3rd residue in turn (Chou-Fasman, 1978b); CHOP780215 Frequency of the 4th residue in turn (Chou-Fasman, 1978b); CHOP780216 Normalized frequency of the 2nd and 3rd residues in turn (Chou-Fasman, 1978b); CIDH920101 Normalized hydrophobicity scales for alpha-proteins (Cid et al., 1992); CIDH920102 Normalized hydrophobicity scales for beta-proteins (Cid et al., 1992); CIDH920103 Normalized hydrophobicity scales for alpha+beta-proteins (Cid et al., 1992); CIDH920104 Normalized hydrophobicity scales for alpha/beta-proteins (Cid et al., 1992); CIDH920105 Normalized average hydrophobicity scales (Cid et al., 1992); COHE430101 Partial specific volume (Cohn-Edsall, 1943); CRAJ730101 Normalized frequency of middle helix (Crawford et al., 1973); CRAJ730102 Normalized frequency of beta-sheet (Crawford et al., 1973); CRAJ730103 Normalized frequency of turn (Crawford et al., 1973); DAWD720101 Size (Dawson, 1972); DAYM780101 Amino acid composition (Dayhoff et al., 1978a); DAYM780201 Relative mutability (Dayhoff et al., 1978b); DESM900101 Membrane preference for cytochrome b: MPH89 (Degli Esposti et al., 1990); DESM900102 Average membrane preference: AMP07 (Degli Esposti et al., 1990); EISD840101 Consensus normalized hydrophobicity scale (Eisenberg, 1984); EISD860101 Solvation free energy (Eisenberg-McLachlan, 1986); EISD860102 Atom-based hydrophobic moment (Eisenberg-McLachlan, 1986); EISD860103 Direction of hydrophobic moment (Eisenberg-McLachlan, 1986); FASG760101 Molecular weight (Fasman, 1976); FASG760102 Melting point (Fasman, 1976); FASG760103 Optical rotation (Fasman, 1976); FASG760104 pK-N (Fasman, 1976); FASG760105 pK-C (Fasman, 1976); FAUJ830101 Hydrophobic parameter pi (Fauchere-Pliska, 1983); FAUJ880101 Graph shape index (Fauchere et al., 1988); FAUJ880102 Smoothed upsilon steric parameter (Fauchere et al., 1988); FAUJ880103 Normalized van der Waals volume (Fauchere et al., 1988); FAUJ880104 STERIMOL length of the side chain (Fauchere et al., 1988); FAUJ880105 STERIMOL minimum width of the side chain (Fauchere et al., 1988); FAUJ880106 STERIMOL maximum width of the side chain (Fauchere et al., 1988); FAUJ880107 N.m.r. chemical shift of alpha-carbon (Fauchere et al., 1988); FAUJ880108 Localized electrical effect (Fauchere et al., 1988); FAUJ880109 Number of hydrogen bond donors (Fauchere et al., 1988); FAUJ880110 Number of full nonbonding orbitals (Fauchere et al., 1988); FAUJ880111 Positive charge (Fauchere et al., 1988); FAUJ880112 Negative charge (Fauchere et al., 1988); FAUJ880113 pK-a (RCOOH) (Fauchere et al., 1988); FINA770101 Helix-coil equilibrium constant (Finkelstein-Ptitsyn, 1977); FINA910101 Helix initiation parameter at posision i−1 (Finkelstein et al., 1991); FINA910102 Helix initiation parameter at posision i, i+1, i+2 (Finkelstein et al., 1991); FINA910103 Helix termination parameter at posision j−2,j−1,j (Finkelstein et al., 1991); FINA910104 Helix termination parameter at posision j+1 (Finkelstein et al., 1991); GARJ730101 Partition coefficient (Garel et al., 1973); GEIM800101 Alpha-helix indices (Geisow-Roberts, 1980); GEIM800102 Alpha-helix indices for alpha-proteins (Geisow-Roberts, 1980); GEIM800103 Alpha-helix indices for beta-proteins (Geisow-Roberts, 1980); GEIM800104 Alpha-helix indices for alpha/beta-proteins (Geisow-Roberts, 1980); GEIM800105 Beta-strand indices (Geisow-Roberts, 1980); GEIM800106 Beta-strand indices for beta-proteins (Geisow-Roberts, 1980); GEIM800107 Beta-strand indices for alpha/beta-proteins (Geisow-Roberts, 1980)

GEIM800108 Aperiodic indices (Geisow-Roberts, 1980); GEI M800109 Aperiodic indices for alpha-proteins (Geisow-Roberts, 1980); GEIM800110 Aperiodic indices for beta-proteins (Geisow-Roberts, 1980); GEIM800111 Aperiodic indices for alpha/beta-proteins (Geisow-Roberts, 1980); GOLD730101 Hydrophobicity factor (Goldsack-Chalifoux, 1973); GOLD730102 Residue volume (Goldsack-Chalifoux, 1973); GRAR740101 Composition (Grantham, 1974); GRAR740102 Polarity (Grantham, 1974)

GRAR740103 Volume (Grantham, 1974); GUYH850101 Partition energy (Guy, 1985); HOPA770101 Hydration number (Hopfinger, 1971), Cited by Charton-Charton (1982)

HOPT810101 Hydrophilicity value (Hopp-Woods, 1981); HUTJ700101 Heat capacity (Hutchens, 1970); HUTJ700102 Absolute entropy (Hutchens, 1970); HUTJ700103 Entropy of formation (Hutchens, 1970); ISOY800101 Normalized relative frequency of alpha-helix (Isogai et al., 1980); ISOY800102 Normalized relative frequency of extended structure (Isogai et al., 1980); ISOY800103 Normalized relative frequency of bend (Isogai et al., 1980); ISOY800104 Normalized relative frequency of bend R (Isogai et al., 1980); ISOY800105 Normalized relative frequency of bend S (Isogai et al., 1980); ISOY800106 Normalized relative frequency of helix end (Isogai et al., 1980); ISOY800107 Normalized relative frequency of double bend (Isogai et al., 1980); ISOY800108 Normalized relative frequency of coil (Isogai et al., 1980); JANJ780101 Average accessible surface area (Janin et al., 1978); JANJ780102 Percentage of buried residues (Janin et al., 1978); JANJ780103 Percentage of exposed residues (Janin et al., 1978); JANJ790101 Ratio of buried and accessible molar fractions (Janin, 1979); JANJ790102 Transfer free energy (Janin, 1979); JOND750101 Hydrophobicity (Jones, 1975); JOND750102 pK (—COOH) (Jones, 1975); JOND920101 Relative frequency of occurrence (Jones et al., 1992); JOND920102 Relative mutability (Jones et al., 1992)

JUKT750101 Amino acid distribution (Jukes et al., 1975); JUNJ780101 Sequence frequency (Jungck, 1978); KANM800101 Average relative probability of helix (Kanehisa-Tsong, 1980); KANM800102 Average relative probability of beta-sheet (Kanehisa-Tsong, 1980); KANM800103 Average relative probability of inner helix (Kanehisa-Tsong, 1980); KANM800104 Average relative probability of inner beta-sheet (Kanehisa-Tsong, 1980); KARP850101 Flexibility parameter for no rigid neighbors (Karplus-Schulz, 1985); KARP850102 Flexibility parameter for one rigid neighbor (Karplus-Schulz, 1985); KARP850103 Flexibility parameter for two rigid neighbors (Karplus-Schulz, 1985); KHAG800101 The Kerr-constant increments (Khanarian-Moore, 1980); KLEP840101 Net charge (Klein et al., 1984); KRIW710101 Side chain interaction parameter (Krigbaum-Rubin, 1971); KRIW790101 Side chain interaction parameter (Krigbaum-Komoriya, 1979); KRIW790102 Fraction of site occupied by water (Krigbaum-Komoriya, 1979); KRIW790103 Side chain volume (Krigbaum-Komoriya, 1979); KYTJ820101 Hydropathy index (Kyte-Doolittle, 1982); LAWE840101 Transfer free energy, CHP/water (Lawson et al., 1984); LEVM760101 Hydrophobic parameter (Levitt, 1976); LEVM760102 Distance between C-alpha and centroid of side chain (Levitt, 1976); LEVM760103 Side chain angle theta(AAR) (Levitt, 1976); LEVM760104 Side chain torsion angle phi(AAAR) (Levitt, 1976); LEVM760105 Radius of gyration of side chain (Levitt, 1976); LEVM760106 van der Waals parameter RO (Levitt, 1976)

LEVM760107 van der Waals parameter epsilon (Levitt, 1976); LEVM780101 Normalized frequency of alpha-helix, with weights (Levitt, 1978); LEVM780102 Normalized frequency of beta-sheet, with weights (Levitt, 1978); LEVM780103 Normalized frequency of reverse turn, with weights (Levitt, 1978); LEVM780104 Normalized frequency of alpha-helix, unweighted (Levitt, 1978); LEVM780105 Normalized frequency of beta-sheet, unweighted (Levitt, 1978); LEVM780106 Normalized frequency of reverse turn, unweighted (Levitt, 1978); LEWP710101 Frequency of occurrence in beta-bends (Lewis et al., 1971); LIFS790101 Conformational preference for all beta-strands (Lifson-Sander, 1979); LIFS790102 Conformational preference for parallel beta-strands (Lifson-Sander, 1979); LIFS790103 Conformational preference for antiparallel beta-strands (Lifson-Sander, 1979); MANP780101 Average surrounding hydrophobicity (Manavalan-Ponnuswamy, 1978); MAXF760101 Normalized frequency of alpha-helix (Maxfield-Scheraga, 1976); MAXF760102 Normalized frequency of extended structure (Maxfield-Scheraga, 1976); MAXF760103 Normalized frequency of zeta R (Maxfield-Scheraga, 1976); MAXF760104 Normalized frequency of left-handed alpha-helix (Maxfield-Scheraga, 1976); MAXF760105 Normalized frequency of zeta L (Maxfield-Scheraga, 1976); MAXF760106 Normalized frequency of alpha region (Maxfield-Scheraga, 1976); MCMT640101 Refractivity (McMeekin et al., 1964), Cited by Jones (1975); MEEJ800101 Retention coefficient in HPLC, pH7.4 (Meek, 1980); MEEJ800102 Retention coefficient in HPLC, pH2.1 (Meek, 1980); MEEJ810101 Retention coefficient in NaClO4 (Meek-Rossetti, 1981); MEEJ810102 Retention coefficient in NaH2PO4 (Meek-Rossetti, 1981); MEIH800101 Average reduced distance for C-alpha (Meirovitch et al., 1980); MEIH800102 Average reduced distance for side chain (Meirovitch et al., 1980); MEIH800103 Average side chain orientation angle (Meirovitch et al., 1980); MIYS850101 Effective partition energy (Miyazawa-Jernigan, 1985); NAGK730101 Normalized frequency of alpha-helix (Nagano, 1973); NAGK730102 Normalized frequency of bata-structure (Nagano, 1973)

NAGK730103 Normalized frequency of coil (Nagano, 1973); NAKH900101 AA composition of total proteins (Nakashima et al., 1990); NAKH900102 SD of AA composition of total proteins (Nakashima et al., 1990);

NAKH900103 AA composition of mt-proteins (Nakashima et al., 1990); NAKH900104 Normalized composition of mt-proteins (Nakashima et al., 1990); NAKH900105 AA composition of mt-proteins from animal (Nakashima et al., 1990); NAKH900106 Normalized composition from animal (Nakashima et al., 1990); NAKH900107 AA composition of mt-proteins from fungi and plant (Nakashima et al., 1990); NAKH900108 Normalized composition from fungi and plant (Nakashima et al., 1990); NAKH900109 AA composition of membrane proteins (Nakashima et al., 1990); NAKH900110 Normalized composition of membrane proteins (Nakashima et al., 1990); NAKH900111 Transmembrane regions of non-mt-proteins (Nakashima et al., 1990); NAKH900112 Transmembrane regions of mt-proteins (Nakashima et al., 1990); NAKH900113 Ratio of average and computed composition (Nakashima et al., 1990); NAKH920101 AA composition of CYT of single-spanning proteins (Nakashima-Nishikawa, 1992); NAKH920102 AA composition of CYT2 of single-spanning proteins (Nakashima-Nishikawa, 1992); NAKH920103 AA composition of EXT of single-spanning proteins (Nakashima-Nishikawa, 1992); NAKH920104 AA composition of EXT2 of single-spanning proteins (Nakashima-Nishikawa, 1992); NAKH920105 AA composition of MEM of single-spanning proteins (Nakashima-Nishikawa, 1992); NAKH920106 AA composition of CYT of multi-spanning proteins (Nakashima-Nishikawa, 1992); NAKH920107 AA composition of EXT of multi-spanning proteins (Nakashima-Nishikawa, 1992); NAKH920108 AA composition of MEM of multi-spanning proteins (Nakashima-Nishikawa, 1992); NISK800101 8 A contact number (Nishikawa-Ooi, 1980); NISK860101 14 A contact number (Nishikawa-Ooi, 1986); NOZY710101 Transfer energy, organic solvent/water (Nozaki-Tanford, 1971); OOBM770101 Average non-bonded energy per atom (Oobatake-Ooi, 1977); OOBM770102 Short and medium range non-bonded energy per atom (Oobatake-Ooi, 1977); OOBM770103 Long range non-bonded energy per atom (Oobatake-Ooi, 1977)

OOBM770104 Average non-bonded energy per residue (Oobatake-Ooi, 1977); OOBM770105 Short and medium range non-bonded energy per residue (Oobatake-Ooi, 1977); OOBM850101 Optimized beta-structure-coil equilibrium constant (Oobatake et al., 1985); OOBM850102 Optimized propensity to form reverse turn (Oobatake et al., 1985); OOBM850103 Optimized transfer energy parameter (Oobatake et al., 1985); OOBM850104 Optimized average non-bonded energy per atom (Oobatake et al., 1985); OOBM850105 Optimized side chain interaction parameter (Oobatake et al., 1985); PALJ810101 Normalized frequency of alpha-helix from LG (Palau et al., 1981); PALJ810102 Normalized frequency of alpha-helix from CF (Palau et al., 1981); PALJ810103 Normalized frequency of beta-sheet from LG (Palau et al., 1981); PALJ810104 Normalized frequency of beta-sheet from CF (Palau et al., 1981); PALJ810105 Normalized frequency of turn from LG (Palau et al., 1981); PALJ810106 Normalized frequency of turn from CF (Palau et al., 1981); PALJ810107 Normalized frequency of alpha-helix in all-alpha class (Palau et al., 1981); PALJ810108 Normalized frequency of alpha-helix in alpha+beta class (Palau et al., 1981); PALJ810109 Normalized frequency of alpha-helix in alpha/beta class (Palau et al., 1981); PALJ810110 Normalized frequency of beta-sheet in all-beta class (Palau et al., 1981); PALJ810111 Normalized frequency of beta-sheet in alpha+beta class (Palau et al., 1981); PALJ810112 Normalized frequency of beta-sheet in alpha/beta class (Palau et al., 1981); PALJ810113 Normalized frequency of turn in all-alpha class (Palau et al., 1981); PALJ810114 Normalized frequency of turn in all-beta class (Palau et al., 1981); PALJ810115 Normalized frequency of turn in alpha+beta class (Palau et al., 1981); PALJ810116 Normalized frequency of turn in alpha/beta class (Palau et al., 1981); PARJ860101 HPLC parameter (Parker et al., 1986); PLIV810101 Partition coefficient (Pliska et al., 1981); PONP800101 Surrounding hydrophobicity in folded form (Ponnuswamy et al., 1980); PONP800102 Average gain in surrounding hydrophobicity (Ponnuswamy et al., 1980); PONP800103 Average gain ratio in surrounding hydrophobicity (Ponnuswamy et al., 1980); PONP800104 Surrounding hydrophobicity in alpha-helix (Ponnuswamy et al., 1980); PONP800105 Surrounding hydrophobicity in beta-sheet (Ponnuswamy et al., 1980); PONP800106 Surrounding hydrophobicity in turn (Ponnuswamy et al., 1980); PONP800107 Accessibility reduction ratio (Ponnuswamy et al., 1980); PONP800108 Average number of surrounding residues (Ponnuswamy et al., 1980); PRAM820101 Intercept in regression analysis (Prabhakaran-Ponnuswamy, 1982); PRAM820102 Slope in regression analysis×1.0E1 (Prabhakaran-Ponnuswamy, 1982); PRAM820103 Correlation coefficient in regression analysis (Prabhakaran-Ponnuswamy, 1982); PRAM900101 Hydrophobicity (Prabhakaran, 1990); PRAM900102 Relative frequency in alpha-helix (Prabhakaran, 1990); PRAM900103 Relative frequency in beta-sheet (Prabhakaran, 1990); PRAM900104 Relative frequency in reverse-turn (Prabhakaran, 1990); PTIO830101 Helix-coil equilibrium constant (Ptitsyn-Finkelstein, 1983); PTIO830102 Beta-coil equilibrium constant (Ptitsyn-Finkelstein, 1983); QIAN880101 Weights for alpha-helix at the window position of −6 (Qian-Sejnowski, 1988); QIAN880102 Weights for alpha-helix at the window position of −5 (Qian-Sejnowski, 1988); QIAN880103 Weights for alpha-helix at the window position of −4 (Qian-Sejnowski, 1988); QIAN880104 Weights for alpha-helix at the window position of −3 (Qian-Sejnowski, 1988); QIAN880105 Weights for alpha-helix at the window position of −2 (Qian-Sejnowski, 1988); QIAN880106 Weights for alpha-helix at the window position of −1 (Qian-Sejnowski, 1988); QIAN880107 Weights for alpha-helix at the window position of 0 (Qian-Sejnowski, 1988); QIAN880108 Weights for alpha-helix at the window position of 1 (Qian-Sejnowski, 1988); QIAN880109 Weights for alpha-helix at the window position of 2 (Qian-Sejnowski, 1988); QIAN880110 Weights for alpha-helix at the window position of 3 (Qian-Sejnowski, 1988); QIAN880111 Weights for alpha-helix at the window position of 4 (Qian-Sejnowski, 1988); QIAN880112 Weights for alpha-helix at the window position of 5 (Qian-Sejnowski, 1988); QIAN880113 Weights for alpha-helix at the window position of 6 (Qian-Sejnowski, 1988); QIAN880114 Weights for beta-sheet at the window position of −6 (Qian-Sejnowski, 1988); QIAN880115 Weights for beta-sheet at the window position of −5 (Qian-Sejnowski, 1988); QIAN880116 Weights for beta-sheet at the window position of −4 (Qian-Sejnowski, 1988); QIAN880117 Weights for beta-sheet at the window position of −3 (Qian-Sejnowski, 1988); QIAN880118 Weights for beta-sheet at the window position of −2 (Qian-Sejnowski, 1988); QIAN880119 Weights for beta-sheet at the window position of −1 (Qian-Sejnowski, 1988); QIAN880120 Weights for beta-sheet at the window position of 0 (Qian-Sejnowski, 1988); QIAN880121 Weights for beta-sheet at the window position of 1 (Qian-Sejnowski, 1988); QIAN880122 Weights for beta-sheet at the window position of 2 (Qian-Sejnowski, 1988); QIAN880123 Weights for beta-sheet at the window position of 3 (Qian-Sejnowski, 1988); QIAN880124 Weights for beta-sheet at the window position of 4 (Qian-Sejnowski, 1988); QIAN880125 Weights for beta-sheet at the window position of 5 (Qian-Sejnowski, 1988); QIAN880126 Weights for beta-sheet at the window position of 6 (Qian-Sejnowski, 1988); QIAN880127 Weights for coil at the window position of −6 (Qian-Sejnowski, 1988); QIAN880128 Weights for coil at the window position of −5 (Qian-Sejnowski, 1988); QIAN880129 Weights for coil at the window position of −4 (Qian-Sejnowski, 1988); QIAN880130 Weights for coil at the window position of −3 (Qian-Sejnowski, 1988); QIAN880131 Weights for coil at the window position of −2 (Qian-Sejnowski, 1988); QIAN880132 Weights for coil at the window position of −1 (Qian-Sejnowski, 1988); QIAN880133 Weights for coil at the window position of 0 (Qian-Sejnowski, 1988); QIAN880134 Weights for coil at the window position of 1 (Qian-Sejnowski, 1988); QIAN880135 Weights for coil at the window position of 2 (Qian-Sejnowski, 1988); QIAN880136 Weights for coil at the window position of 3 (Qian-Sejnowski, 1988); QIAN880137 Weights for coil at the window position of 4 (Qian-Sejnowski, 1988); QIAN880138 Weights for coil at the window position of 5 (Qian-Sejnowski, 1988); QIAN880139 Weights for coil at the window position of 6 (Qian-Sejnowski, 1988); RACS770101 Average reduced distance for C-alpha (Rackovsky-Scheraga, 1977); RACS770102 Average reduced distance for side chain (Rackovsky-Scheraga, 1977); RACS770103 Side chain orientational preference (Rackovsky-Scheraga, 1977); RACS820101 Average relative fractional occurrence in A0(i) (Rackovsky-Scheraga, 1982); RACS820102 Average relative fractional occurrence in AR(i) (Rackovsky-Scheraga, 1982); RACS820103 Average relative fractional occurrence in AL(i) (Rackovsky-Scheraga, 1982); RACS820104 Average relative fractional occurrence in EL(i) (Rackovsky-Scheraga, 1982); RACS820105 Average relative fractional occurrence in E0(i) (Rackovsky-Scheraga, 1982); RACS820106 Average relative fractional occurrence in ER(i) (Rackovsky-Scheraga, 1982); RACS820107 Average relative fractional occurrence in A0(i−1) (Rackovsky-Scheraga, 1982); RACS820108 Average relative fractional occurrence in AR(i−1) (Rackovsky-Scheraga, 1982); RACS820109 Average relative fractional occurrence in AL(i−1) (Rackovsky-Scheraga, 1982); RACS820110 Average relative fractional occurrence in EL(i−1) (Rackovsky-Scheraga, 1982); RACS820111 Average relative fractional occurrence in E0(i−1) (Rackovsky-Scheraga, 1982); RACS820112 Average relative fractional occurrence in ER(i−1) (Rackovsky-Scheraga, 1982); RACS820113 Value of theta(i) (Rackovsky-Scheraga, 1982); RACS820114 Value of theta(i−1) (Rackovsky-Scheraga, 1982); RADA880101 Transfer free energy from chx to wat (Radzicka-Wolfenden, 1988); RADA880102 Transfer free energy from oct to wat (Radzicka-Wolfenden, 1988); RADA880103 Transfer free energy from yap to chx (Radzicka-Wolfenden, 1988); RADA880104 Transfer free energy from chx to oct (Radzicka-Wolfenden, 1988); RADA880105 Transfer free energy from yap to oct (Radzicka-Wolfenden, 1988); RADA880106 Accessible surface area (Radzicka-Wolfenden, 1988); RADA880107 Energy transfer from out to in (95% buried) (Radzicka-Wolfenden, 1988); RADA880108 Mean polarity (Radzicka-Wolfenden, 1988); RICJ880101 Relative preference value at N" (Richardson-Richardson, 1988); RICJ880102 Relative preference value at N' (Richardson-Richardson, 1988); RICJ880103 Relative preference value at N-cap (Richardson-Richardson, 1988); RICJ880104 Relative preference value at N1 (Richardson-Richardson, 1988); RICJ880105 Relative preference value at N2 (Richardson-Richardson, 1988); RICJ880106 Relative preference value at N3 (Richardson-Richardson, 1988); RICJ880107 Relative preference value at N4 (Richardson-Richardson, 1988); RICJ880108 Relative preference value at N5 (Richardson-Richardson, 1988); RICJ880109 Relative preference value at Mid (Richardson-Richardson, 1988); RICJ880110 Relative preference value at C5 (Richardson-Richardson, 1988); RICJ880111 Relative preference value at C4 (Richardson-Richardson, 1988); RICJ880112 Relative preference value at C3 (Richardson-Richardson, 1988); RICJ880113 Relative preference value at C2 (Richardson-Richardson, 1988); RICJ880114 Relative preference value at C1 (Richardson-Richardson, 1988); RICJ880115 Relative preference value at C-cap (Richardson-Richardson, 1988); RICJ880116 Relative preference value at C' (Richardson-Richardson, 1988); RICJ880117 Relative preference value at C" (Richardson-Richardson, 1988); ROBB760101 Information measure for alpha-helix (Robson-Suzuki, 1976); ROBB760102 Information measure for N-terminal helix (Robson-Suzuki, 1976); ROBB760103 Information measure for middle helix (Robson-Suzuki, 1976); ROBB760104 Information measure for C-terminal helix (Robson-Suzuki, 1976); ROBB760105 Information measure for extended (Robson-Suzuki, 1976); ROBB760106 Information measure for pleated-sheet (Robson-Suzuki, 1976); ROBB760107 Information measure for extended without H-bond (Robson-Suzuki, 1976); ROBB760108 Information measure for turn (Robson-Suzuki, 1976); ROBB760109 Information measure for N-terminal turn (Robson-Suzuki, 1976); ROBB760110 Information measure for middle turn (Robson-Suzuki, 1976); ROBB760111 Information measure for C-terminal turn (Robson-Suzuki, 1976); ROBB760112 Information measure for coil (Robson-Suzuki, 1976); ROBB760113 Information measure for loop (Robson-Suzuki, 1976); ROBB790101 Hydration free energy (Robson-Osguthorpe, 1979); ROSG850101 Mean area buried on transfer (Rose et al., 1985); ROSG850102 Mean fractional area loss (Rose et al., 1985); ROSM880101 Side chain hydropathy, uncorrected for solvation (Roseman, 1988); ROSM880102 Side chain hydropathy, corrected for solvation (Roseman, 1988); ROSM880103 Loss of Side chain hydropathy by helix formation (Roseman, 1988); SIMZ760101 Transfer free energy (Simon, 1976), Cited by Charton-Charton (1982); SNEP660101 Principal component I (Sneath, 1966); SNEP660102 Principal component II (Sneath, 1966); SNEP660103 Principal component III (Sneath, 1966); SNEP660104 Principal component IV (Sneath, 1966); SUEM840101 Zimm-Bragg parameter s at 20 C (Sueki et al., 1984); SUEM840102 Zimm-Bragg parameter sigma× 1.0E4 (Sueki et al., 1984); SWER830101 Optimal matching hydrophobicity (Sweet-Eisenberg, 1983); TANS770101 Normalized frequency of alpha-helix (Tanaka-Scheraga, 1977); TANS770102 Normalized frequency of isolated helix (Tanaka-Scheraga, 1977); TANS770103 Normalized frequency of extended structure (Tanaka-Scheraga, 1977); TANS770104 Normalized frequency of chain reversal R (Tanaka-Scheraga, 1977); TANS770105 Normalized frequency of chain reversal S (Tanaka-Scheraga, 1977); TANS770106 Normalized frequency of chain reversal D (Tanaka-Scheraga, 1977); TANS770107 Normalized frequency of left-handed helix (Tanaka-Scheraga, 1977); TANS770108 Normalized frequency of zeta R (Tanaka-Scheraga, 1977); TANS770109 Normalized frequency of coil (Tanaka-Scheraga, 1977) TANS770110 Normalized frequency of chain reversal (Tanaka-Scheraga, 1977); VASM830101 Relative population of conformational state A (Vasquez et al., 1983); VASM830102 Relative population of conformational state C (Vasquez et al., 1983); VASM830103 Relative population of conformational state E (Vasquez et al., 1983); VELV850101 Electron-ion interaction potential (Veljkovic et al., 1985); VENT840101 Bitterness (Venanzi, 1984); VHEG790101 Transfer free energy to lipophilic phase (von Heijne-Blomberg, 1979); WARP780101 Average interactions per side chain atom (Warme-Morgan, 1978); WEBA780101 RF value in high salt chromatography (Weber-Lacey, 1978); WERD780101 Propensity to be buried inside (Wertz-Scheraga, 1978); WERD780102 Free energy change of epsilon(i) to epsilon (ex) (Wertz-Scheraga, 1978); WERD780103 Free energy change of alpha(Ri) to alpha(Rh) (Wertz-Scheraga, 1978); WERD780104 Free energy change of epsilon(i) to alpha (Rh) (Wertz-Scheraga, 1978); WOEC730101 Polar requirement (Woese, 1973); WOLR810101 Hydration potential (Wolfenden et al., 1981); WOLS870101 Principal property value z1 (Wold et al., 1987); WOLS870102 Principal property value z2 (Wold et al., 1987); WOLS870103 Principal property value z3 (Wold et al., 1987); YUTK870101 Unfolding Gibbs energy in water, pH7.0 (Yutani et al., 1987); YUTK870102 Unfolding Gibbs energy in water, pH9.0 (Yutani et al., 1987); YUTK870103 Activation Gibbs energy of unfolding, pH7.0 (Yutani et al., 1987); YUTK870104 Activation Gibbs energy of unfolding, pH9.0 (Yutani et al., 1987); ZASB820101 Dependence of partition coefficient on ionic strength (Zaslaysky et al., 1982); ZIMJ680101 Hydrophobicity (Zimmerman et al., 1968); ZIMJ680102 Bulkiness (Zimmerman et al., 1968); ZIMJ680103 Polarity (Zimmerman et al., 1968); ZIMJ680104 Isoelectric point (Zimmerman et al., 1968); ZIMJ680105 RF rank (Zimmerman et al., 1968); AURR980101 Normalized positional residue frequency at helix termini N4'(Aurora-Rose, 1998); AURR980102 Normalized positional residue frequency at helix termini N''' (Aurora-Rose, 1998); AURR980103 Normalized positional residue frequency at helix termini N'' (Aurora-Rose, 1998); AURR980104 Normalized positional residue frequency at helix termini N'(Aurora-Rose, 1998); AURR980105 Normalized positional residue frequency at helix termini Nc (Aurora-Rose, 1998); AURR980106 Normalized positional residue frequency at helix termini N1 (Aurora-Rose, 1998); AURR980107 Normalized positional residue frequency at helix termini N2 (Aurora-Rose, 1998); AURR980108 Normalized positional residue frequency at helix termini N3 (Aurora-Rose, 1998); AURR980109 Normalized positional residue frequency at helix termini N4 (Aurora-Rose, 1998); AURR980110 Normalized positional residue frequency at helix termini N5 (Aurora-Rose, 1998); AURR980111 Normalized positional residue frequency at helix termini C5 (Aurora-Rose, 1998); AURR980112 Normalized positional residue frequency at helix termini C4 (Aurora-Rose, 1998); AURR980113 Normalized positional residue frequency at helix termini C3 (Aurora-Rose, 1998); AURR980114 Normalized positional residue frequency at helix termini C2 (Aurora-Rose, 1998); AURR980115 Normalized positional residue frequency at helix termini C1 (Aurora-Rose, 1998); AURR980116 Normalized positional residue frequency at helix termini Cc (Aurora-Rose, 1998); AURR980117 Normalized positional residue frequency at helix termini C' (Aurora-Rose, 1998); AURR980118 Normalized positional residue frequency at helix termini C'' (Aurora-Rose, 1998); AURR980119 Normalized positional residue frequency at helix termini C''' (Aurora-Rose, 1998); AURR980120 Normalized positional residue frequency at helix termini C4' (Aurora-Rose, 1998); ONEK900101 Delta G values for the peptides extrapolated to 0 M urea (O'Neil-DeGrado, 1990); ONEK900102 Helix formation parameters (delta delta G) (O'Neil-DeGrado, 1990); VINM940101 Normalized flexibility parameters (B-values), average (Vihinen et al., 1994); VINM940102 Normalized flexibility parameters (B-values) for each residue surrounded by none rigid neighbours (Vihinen et al., 1994); VINM940103 Normalized flexibility parameters (B-values) for each residue surrounded by one rigid neighbours (Vihinen et al., 1994); VINM940104 Normalized flexibility parameters (B-values) for each residue surrounded by two rigid neighbours (Vihinen et al., 1994); MUNV940101 Free energy in alpha-helical conformation (Munoz-Serrano, 1994); MUNV940102 Free energy in alpha-helical region (Munoz-Serrano, 1994); MUNV940103 Free energy in beta-strand conformation (Munoz-Serrano, 1994); MUNV940104 Free energy in beta-strand region (Munoz-Serrano, 1994); MUNV940105 Free energy in beta-strand region (Munoz-Serrano, 1994) WIMW960101 Free energies of transfer of AcWl-X-LL peptides from bilayer interface to water (Wimley-White, 1996); KIMC930101 Thermodynamic beta sheet propensity (Kim-Berg, 1993); MONM990101 Turn propensity scale for transmembrane helices (Monne et al., 1999); BLAM930101 Alpha helix propensity of position 44 in T4 lysozyme (Blaber et al., 1993); PARS000101 p-Values of mesophilic proteins based on the distributions of B values (Parthasarathy-Murthy, 2000); PARS000102 p-Values of thermophilic proteins based on the distributions of B values (Parthasarathy-Murthy, 2000); KUMS000101 Distribution of amino acid residues in the 18 non-redundant families of thermophilic proteins (Kumar et al., 2000); KUMS000102 Distribution of amino acid residues in the 18 non-redundant families of mesophilic proteins (Kumar et al., 2000); KUMS000103 Distribution of amino acid residues in the alpha-helices in thermophilic proteins (Kumar et al., 2000); KUMS000104 Distribution of amino acid residues in the alpha-helices in mesophilic proteins (Kumar et al., 2000); TAKK010101 Side-chain contribution to protein stability (kJ/mol) (Takano-Yutani, 2001); FODM020101 Propensity of amino acids within pi-helices (Fodje-Al-Karadaghi, 2002); NADH010101 Hydropathy scale based on self-information values in the two-state model (5% accessibility) (Naderi-Manesh et al., 2001); NADH010102 Hydropathy scale based on self-information values in the two-state model (9% accessibility) (Naderi-Manesh et al., 2001); NADH010103 Hydropathy scale based on self-information values in the two-state model (16% accessibility) (Naderi-Manesh et al., 2001); NADH010104 Hydropathy scale based on self-information values in the two-state model (20% accessibility) (Naderi-Manesh et al., 2001); NADH010105 Hydropathy scale based on self-information values in the two-state model (25% accessibility) (Naderi-Manesh et al., 2001); NADH010106 Hydropathy scale based on self-information values in the two-state model (36% accessibility) (Naderi-Manesh et al., 2001); NADH010107 Hydropathy scale based on self-information values in the two-state model (50% accessibility) (Naderi-Manesh et al., 2001); MONM990201 Averaged turn propensities in a transmembrane helix (Monne et al., 1999); KOEP990101 Alpha-helix propensity derived from designed sequences (Koehl-Levitt, 1999); KOEP990102 Beta-sheet propensity derived from designed sequences (Koehl-Levitt, 1999); CEDJ970101 Composition of amino acids in extracellular proteins (percent) (Cedano et al., 1997); CEDJ970102 Composition of amino acids in anchored proteins (percent) (Cedano et al., 1997); CEDJ970103 Composition of amino acids in membrane proteins (percent) (Cedano et al., 1997); CEDJ970104 Composition of amino acids in intracellular proteins (percent) (Cedano et al., 1997); CEDJ970105 Composition of amino acids in nuclear proteins (percent) (Cedano et al., 1997); FUKS010101 Surface composition of amino acids in intracellular proteins of thermophiles (percent) (Fukuchi-Nishikawa, 2001); FUKS010102 Surface composition of amino acids in intracellular proteins of mesophiles (percent) (Fukuchi-Nishikawa, 2001); FUKS010103 Surface composition of amino acids in extracellular proteins of mesophiles (percent) (Fukuchi-Nishikawa, 2001); FUKS010104 Surface composition of amino acids in nuclear proteins (percent) (Fukuchi-Nishikawa, 2001); FUKS010105 Interior composition of amino acids in intracellular proteins of thermophiles (percent) (Fukuchi-Nishikawa, 2001); FUKS010106 Interior composition of amino acids in intracellular proteins of mesophiles (percent) (Fukuchi-Nishikawa, 2001); FUKS010107 Interior composition of amino acids in extracellular proteins of mesophiles (percent) (Fukuchi-Nishikawa, 2001); FUKS010108 Interior composition of amino acids in nuclear proteins (percent) (Fukuchi-Nishikawa, 2001); FUKS010109 Entire chain composition of amino acids in intracellular proteins of thermophiles (percent) (Fukuchi-Nishikawa, 2001); FUKS010110 Entire chain composition of amino acids in intracellular proteins of mesophiles (percent) (Fukuchi-Nishikawa, 2001); FUKS010111 Entire chain composition of amino acids in extracellular proteins of mesophiles (percent) (Fukuchi-Nishikawa, 2001); FUKS010112 Entire chain composition of amino acids in nuclear proteins (percent) (Fukuchi-Nishikawa, 2001); AVBF000101 Screening coefficients gamma, local (Avbelj, 2000); AVBF000102 Screening coefficients gamma, non-local (Avbelj, 2000); AVBF000103 Slopes tripeptide, FDPB VFF neutral (Avbelj, 2000); AVBF000104 Slopes tripeptides, LD VFF neutral (Avbelj, 2000); AVBF000105 Slopes tripeptide, FDPB VFF noside (Avbelj, 2000); AVBF000106 Slopes tripeptide FDPB VFF all (Avbelj, 2000); AVBF000107 Slopes tripeptide FDPB PARSE neutral (Avbelj, 2000); AVBF000108 Slopes dekapeptide, FDPB VFF neutral (Avbelj, 2000); AVBF000109 Slopes proteins, FDPB VFF neutral (Avbelj, 2000); YANJ020101 Side-chain conformation by gaussian evolutionary method (Yang et al., 2002); MITS020101 Amphiphilicity index (Mitaku et al., 2002); TSAJ990101 Volumes including the crystallographic waters using the ProtOr (Tsai et al., 1999); TSAJ990102 Volumes not including the crystallographic waters using the ProtOr (Tsai et al., 1999); C051940101 Electron-ion interaction potential values (Cosic, 1994); PONP930101 Hydrophobicity scales (Ponnuswamy, 1993); WILM950101 Hydrophobicity coefficient in RP-HPLC, C18 with 0.1% TFA/MeCN/H2O (Wilce et al. 1995); WILM950102 Hydrophobicity coefficient in RP-HPLC, C8 with 0.1% TFA/MeCN/H2O (Wilce et al. 1995); WILM950103 Hydrophobicity coefficient in RP-HPLC, C4 with 0.1% TFA/MeCN/H2O (Wilce et al. 1995); WILM950104 Hydrophobicity coefficient in RP-HPLC, C18 with 0.1% TFA/2-PrOH/MeCN/H2O (Wilce et al. 1995); KUHL950101 Hydrophilicity scale (Kuhn et al., 1995); GUOD860101 Retention coefficient at pH 2 (Guo et al., 1986); JURD980101 Modified Kyte-Doolittle hydrophobicity scale (Juretic et al., 1998); BASU050101 Interactivity scale obtained from the contact matrix (Bastolla et al., 2005); BASU050102 Interactivity scale obtained by maximizing the mean of correlation coefficient over single-domain globular proteins (Bastolla et al., 2005); BASU050103 Interactivity scale obtained by maximizing the mean of correlation coefficient over pairs of sequences sharing the TIM barrel fold (Bastolla et al., 2005); SUYM030101 Linker propensity index (Suyama-Ohara, 2003); PUNT030101 Knowledge-based membrane-propensity scale from 1D Helix in MPtopo databases (Punta-Maritan, 2003); PUNT030102 Knowledge-based membrane-propensity scale from 3D_Helix in MPtopo databases (Punta-Maritan, 2003); GEOR030101 Linker propensity from all dataset (George-Heringa, 2003); GEOR030102 Linker propensity from 1-linker dataset (George-Heringa, 2003); GEOR030103 Linker propensity from 2-linker dataset (George-Heringa, 2003); GEOR030104 Linker propensity from 3-linker dataset (George-Heringa, 2003); GEOR030105 Linker propensity from small dataset (linker length is less than six residues) (George-Heringa, 2003); GEOR030106 Linker propensity from medium dataset (linker length is between six and 14 residues) (George-Heringa, 2003); GEOR030107 Linker propensity from long dataset (linker length is greater than 14 residues) (George-Heringa, 2003); GEOR030108 Linker propensity from helical (annotated by DSSP) dataset (George-Heringa, 2003); GEOR030109 Linker propensity from non-helical (annotated by DSSP) dataset (George-Heringa, 2003); ZHOH040101 The stability scale from the knowledge-based atom-atom potential (Zhou-Zhou, 2004); ZHOH040102 The relative stability scale extracted from mutation experiments (Zhou-Zhou, 2004); ZHOH040103 Buriability (Zhou-Zhou, 2004); BAEK050101 Linker index (Bae et al., 2005); HARY940101 Mean volumes of residues buried in protein interiors (Harpaz et al., 1994); PONJ960101 Average volumes of residues (Pontius et al., 1996); DIGM050101 Hydrostatic pressure asymmetry index, PAI (Di Giulio, 2005); WOLR790101 Hydrophobicity index (Wolfenden et al., 1979); OLSK800101 Average internal preferences (Olsen, 1980); KIDA850101 Hydrophobicity-related index (Kidera et al., 1985); GUYH850102 Apparent partition energies calculated from Wertz-Scheraga index (Guy, 1985); GUYH850103 Apparent partition energies calculated from Robson-Osguthorpe index (Guy, 1985); GUYH850104 Apparent partition energies calculated from Janin index (Guy, 1985); GUYH850105 Apparent partition energies calculated from Chothia index (Guy, 1985); ROSM880104 Hydropathies of amino acid side chains, neutral form (Roseman, 1988); ROSM880105 Hydropathies of amino acid side chains, pi-values in pH 7.0 (Roseman, 1988); JACR890101 Weights from the IFH scale (Jacobs-White, 1989); COWR900101 Hydrophobicity index, 3.0 pH (Cowan-Whittaker, 1990) BLAS910101 Scaled side chain hydrophobicity values (Black-Mould, 1991); CASG920101 Hydrophobicity scale from native protein structures (Casari-Sippl, 1992); CORJ870101 NNEIG index (Cornette et al., 1987); CORJ870102 SWEIG index (Cornette et al., 1987); CORJ870103 PRIFT index (Cornette et al., 1987); CORJ870104 PRILS index (Cornette et al., 1987); CORJ870105 ALTFT index (Cornette et al., 1987)
CORJ870106 ALTLS index (Cornette et al., 1987); CORJ870107 TOTFT index (Cornette et al., 1987); CORJ870108 TOTLS index (Cornette et al., 1987); MIYS990101 Relative partition energies derived by the Bethe approximation (Miyazawa-Jernigan, 1999); MIYS990102 Optimized relative partition energies—method A (Miyazawa-Jernigan, 1999); MIYS990103 Optimized relative partition energies—method B (Miyazawa-Jernigan, 1999); MIYS990104 Optimized relative partition energies—method C (Miyazawa-Jernigan, 1999); MIYS990105 Optimized relative partition energies—method D (Miyazawa-Jernigan, 1999); ENGD860101

Hydrophobicity index (Engelman et al., 1986); and FASG890101 Hydrophobicity index (Fasman, 1989)

In some embodiments of the invention, degenerate oligonucleotides are used to synthesize one or more of the TN1, DH, N2, and/or H3-JH segments of the invention. In certain embodiments of the invention, the codon at or near the 5' end of the oligonucleotide encoding the H3-JH segment is a degenerate codon. Such degenerate codons may be the first codon from the 5' end, the second codon from the 5' end, the third codon from the 5' end, the fourth codon from the 5' end, the fifth codon from the 5' end, and/or any combination of the above. In some embodiments of the invention, one or more of the codons at or near the 5' and/or 3' ends of the DH segment are degenerate. Such degenerate codons may be the first codon from the 5' and/or 3' end(s), the second codon from the 5' and/or 3' end(s), the third codons from the 5' and/or 3' end(s), the fourth codon from the 5' and/or 3' end(s), the fifth codon from the 5' and/or 3' end(s), and/or any combination of the above. Degenerate codons used in each of the oligonucleotides encoding the segments may be selected for their ability to optimally recapitulate sequences in a theoretical segment pool and/or CDRH3 reference set.

In some embodiments, the invention provides methods of producing a theoretical segment pool of H3-JH segments, as described in the Examples. Theoretical segment pools generated utilizing NNN triplets, instead of or in addition to the NN doublets described in Example 5 also fall within the scope of the invention, as do synthetic libraries incorporating segments from these theoretical segment pools.

In some embodiments, the invention provides methods of producing a theoretical segment pool of DH segments, as described in the Examples. In particular, for example, the invention provides methods of producing a theoretical segment pool of DH segments described by the PYTHON program of Example 6. Example 6 describes the application of this program to produce the 68K theoretical segment pool (minimum length of DNA sequences after progressive deletions=4 bases; and minimum length of peptide sequences for inclusion in the theoretical segment pool=2). An alternative example is provided wherein the minimum length of the DNA sequences after progressive deletions was one base and the minimum length of the peptide sequence is one amino acid. It is also contemplated that other values could be used for these parameters. For example, the minimum length of the DNA sequences after progressive deletions could be set as 1, 2, 3, 4, 5, 6, 7, 8, 9, 10, 11, 12, 13, 14, or 15, and the minimum length of the peptide sequences in the theoretical segment pool could be set as 1, 2, 3, 4, or 5.

Design of CDRH3 Libraries Using the TN1, DH, N2, and H3-JH Segments

The CDRH3 libraries of the invention comprise TN1, DH, N2, and H3-JH segments. Thus, in certain embodiments of the invention, the overall design of the CDRH3 libraries can be represented by the following formula:

[TN1]-[DH]-[N2]-[H3-JH].

In certain embodiments of the invention, a synthetic CDRH3 repertoire is combined with selected VH chassis sequences and heavy chain constant regions, via homologous recombination. Therefore, in certain embodiments of the invention, it may be desirable to include DNA sequences flanking the 5' and 3' ends of the synthetic CDRH3 libraries, to facilitate homologous recombination between the synthetic CDRH3 libraries and vectors containing the selected chassis and constant regions. In certain embodiments, the vectors also contain a sequence encoding at least a portion of the non-truncated region of the IGHJ gene (i.e., FRM4-JH). Thus, a polynucleotide encoding an N-terminal sequence (e.g., CA(K/R/T)) may be added to the synthetic CDRH3 sequences, wherein the N-terminal polynucleotide is homologous with FRM3 of the chassis, while a polynucleotide encoding a C-terminal sequence (e.g., WG(Q/R/K)G) may be added to the synthetic CDRH3, wherein the C-terminal polynucleotide is homologous with FRM4-JH. Although the sequence WG(Q/R)G is presented in this exemplary embodiment, additional amino acids, C-terminal to this sequence in FRM4-JH may also be included in the polynucleotide encoding the C-terminal sequence. The purpose of the polynucleotides encoding the N-terminal and C-terminal sequences, in this case, is to facilitate homologous recombination, and one of ordinary skill in the art would recognize that these sequences may be longer or shorter than depicted below. Accordingly, in certain embodiments of the invention, the overall design of the CDRH3 repertoire, including the sequences required to facilitate homologous recombination with the selected chassis, can be represented by the following formula (regions homologous with vector underlined):

(SEQ ID NO. 8762, SEQ ID NO. 8763, and SEQ ID NO. 8764, respectively)
<u>CA[R/K/T]</u>-[TN1]-[DH]-[N2]-[H3-JH]-<u>[WG(Q/R/K)G]</u>.

In some embodiments of the invention, the CDRH3 repertoire can be represented by the following formula, which excludes the T residue presented in the schematic above:

(SEQ ID NO. 8762, SEQ ID NO. 8763, and SEQ ID NO. 8764, respectively)
<u>CA[R/K]</u>-[TN1]-[DH]-[N2]-[H3-JH]-<u>[WG(Q/R/K)G]</u>.

References describing collections of V, D, and J genes include Scaviner et al., Exp. Clin, Immunogenet., 1999, 16: 243 and Ruiz et al., Exp. Clin. Immunogenet, 1999, 16: 173, each incorporated by reference in its entirety.

Although homologous recombination is one method of producing the libraries of the invention, a person of ordinary skill in the art will readily recognize that other methods of DNA assembly, such as ligation or site-specific recombination, and/or DNA synthesis, can also be used to produce the libraries of the invention.

CDRH3 Lengths

The lengths of the segments may also be varied, for example, to produce libraries with a particular distribution of CDRH3 lengths. In one embodiment of the invention, the H3-JH segments are about 0 to about 10 amino acids in length, the DH segments are about 0 to about 12 amino acids in length, the TN1 segments are about 0 to about 4 amino acids in length, and the N2 segments are about 0 to about 4 amino acids in length. In certain embodiments, the H3-JH segments are at least about 0, 1, 2, 3, 4, 5, 6, 7, 8, 9, and/or 10 amino acids in length. In some embodiments, the DH segments are at least about 0, 1, 2, 3, 4, 5, 6, 7, 8, 9, 10, 11, and/or 12 amino acids in length. In certain embodiments, the TN1 segments are at least about 0, 1, 2, 3, or 4 amino acids in length. In some embodiments, the N2 amino acids are at least about 0, 1, 2, 3, or 4 amino acids in length. In certain embodiments of the invention, the CDRH3 is about 2 to about 35, about 2 to about 28, or about 5 to about 26 amino acids in length. In some embodiments, the CDRH3 is at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, and/or 35 amino acids in length. In some embodiments, the length of any of the segments or CDRH3s of the invention may be less than a particular number of amino acids, where the number of amino acids is defined using any one of the integers provided above for the respective segment or CDRH3. In certain embodiments of the invention, a particular numerical range is defined, using any two of the integers provided above as lower and upper boundaries of the range, inclusive or exclusive. All combinations of the integers provided, which define an upper and lower boundary, are contemplated.

Design of CDRL3 Libraries

The design of CDRL3 libraries, and light chain sequences, is described in detail in U.S. Publication Nos. 2009/0181855 and 2010/0056386, and WO/2009/036379, each of which is incorporated by reference in its entirety, and is therefore only described briefly herein. Libraries described herein are designed according to similar principles, with three important differences, namely that the libraries of the current invention contain (1) variability in CDRL1 and CDRL2; (2) variability in the framework regions; and/or (3) variability in CDRL3 that is designed to produce light chain libraries with CDRL3s that closely resemble human germline-like CDRL3 sequences, as defined above (Table 1).

A CDRL3 library of the invention may be a VKCDR3 library and/or a VλCDR3 library. In certain embodiments of the invention, patterns of occurrence of particular amino acids at defined positions within VL sequences are determined by analyzing data available in public or other databases, for example, the NCBI database (see, for example, WO/2009/036379). In certain embodiments of the invention, these sequences are compared on the basis of identity and assigned to families on the basis of the germline genes from which they are derived. The amino acid composition at each position of the sequence, in each germline family, may then be determined. This process is illustrated in the Examples provided herein.

Light Chains with Framework Variability

In some embodiments, the invention provides a library of light chain variable domains wherein the light chain variable domains are varied at one or more of framework positions 2, 4, 36, 46, 48, 49, and 66. In some embodiments, the invention provides a library of light chain variable domains comprising at least a plurality of light chain variable domains whose amino acid sequences are identical to one another except for substitutions at one or more of positions 2, 4, 36, 46, 48, 49, and 66. In certain embodiments, the invention provides a library of light chain variable domains comprising at least a plurality of light chain variable domains whose amino acid sequences are at least about 70%, 75%, 80%, 85%, 90%, 95%, 96%, 97%, 98%, 99%, and/or 99.5% to any of the light chain variable domain sequences disclosed herein, and further have substitutions at one or more of positions 2, 4, 36, 46, 48, 49, and 66. In some embodiments, the amino acids selected for inclusion in these positions are selected from amongst about the most 2, 3, 4, 5, 6, 7, 8, 9, and/or 10 most frequently occurring amino acids at the corresponding position in a reference set of light chain variable domains.

In some embodiments, the invention provides systems and methods of selecting framework positions to be varied in a light chain variable domain, comprising:

(i) obtaining a reference set of light chain sequences, wherein the reference set contains light chain sequences with VL segments selected from the group consisting of sequences found in, or encoded by, a single IGVL germline gene and/or sequences found in, or encoded by, allelic variants of the single IGVL germline gene;

(ii) determining which framework positions within the reference set have a degree of variability that is similar to the degree of variability occurring in one more CDR positions of the sequences in the reference set (e.g., the variability in a framework position is at least about 70%, 80%, 90%, or 95%, 100%, or more of the variability found in a CDR position of the sequences in the reference set);

(iii) determining the frequency of occurrence of amino acid residues for each of the framework positions identified in (ii);

(iv) synthesizing light chain variable domain encoding sequences wherein the framework positions identified in (ii) are varied to include the 2, 3, 4, 5, 6, 7, 8, 9, 10, 11, 12, 13, 14, 15, 16, 17, 18, 19, or 20 most frequently occurring amino acid residues (identified in (iii)) at the corresponding position.

One of ordinary skill in the art, reading the present disclosure will appreciate that the present invention provides analogous methods for developing framework variants of heavy chain sequences.

Light Chains with CDR1 and/or CDR2 Variability

In some embodiments, the invention provides a library of light chain variable domains wherein the light chain variable domains are varied at one or more of CDRL1 positions 28, 29, 30, 30A, 30B, 30E, 31, and 32 (Chothia-Lesk numbering scheme; Chothia and Lesk, J. Mol. Biol., 1987, 196: 901). In some embodiments, the invention provides a library of light chain variable domains wherein the light chain variable domains are varied at one or more of CDRL2 positions 50, 51, 53, and 55. In some embodiments, the amino acids selected for inclusion in these CDRL1 and/or CDRL2 positions are selected from amongst about the most 2, 3, 4, 5, 6, 7, 8, 9, 10, 11, 12, 13, 14, 15, 16, 17, 18, 19, and/or 20 most frequently occurring amino acids at the corresponding position in a reference set of light chain variable domains.

In some embodiments, the invention provides systems and methods for selecting CDRL1 and/or CDRL2 positions to be varied in a light chain variable domain, comprising:

(i) obtaining a reference set of light chain sequences, wherein the reference set contains light chain sequences with VL segments selected from the group consisting of sequences found in, or encoded by, a single IGVL germline gene and sequences found in, or encoded by, allelic variants of the single IGVL germline gene;

(ii) determining which CDRL1 and/or CDRL2 positions are variable within the reference set;

(iii) synthesizing light chain variable domain encoding sequences wherein the CDRL1 and/or CDRL2 positions identified in (ii) are varied to include the 2, 3, 4, 5, 6, 7, 8, 9, 10, 11, 12, 13, 14, 15, 16, 17, 18, 19, or 20 most frequently occurring amino acid residues at the corresponding position.

One of ordinary skill in the art, reading the present disclosure will appreciate that the present invention provides analogous methods for developing CDRH2 and/or CDRH2 variants of heavy chain sequences.

Light Chain Sequences

In some embodiments, the invention provides a light chain library comprising one or more of any of the light chain sequences provided herein, for example, the polypeptide sequences of Table 3 and/or Table 4 and/or the polynucleotide sequences of Table 5, Table 6, and/or Table 7. A person of ordinary skill in the art will recognize that not every light chain sequence provided herein is necessary to produce a functional light chain library of the invention. Therefore, in certain embodiments, a light chain library of the invention will contain a subset of the sequences described above. For example, in certain embodiments of the invention, at least about 10, 100, 200, 300, 400, 500, 600, 700, 800, 900, $10^3$, $10^4$, and/or $10^5$ of the light chain polynucleotide and/or polypeptide sequences provided herein are included in a library. In some embodiments, a library of the invention may contain less than a particular number of polynucleotide or polypeptide segments, where the number of segments is defined using any one of the integers provided above for the respective segment. In certain embodiments of the invention, a particular numerical range is defined, using any two of the integers provided above as lower and upper boundaries of the range, inclusive or exclusive. All combinations of the integers provided, which define an upper and lower boundary, are contemplated.

In certain embodiments, the invention provides light chain libraries comprising at least about 1%, 2.5%, 5%, 10%, 15%, 20%, 25%, 30%, 40%, 45%, 50%, 55%, 60%, 65%, 70%, 75%, 80%, 85%, 90%, 95%, or 99% of the sequences from any of the sets of light chain sequences provided herein. For example, the invention provides libraries comprising at least about 1%, 2.5%, 5%, 10%, 15%, 20%, 25%, 30%, 40%, 45%, 50%, 55%, 60%, 65%, 70%, 75%, 80%, 85%, 90%, 95%, or 99% of the light chain sequences provided in Table 3, Table 4, Table 5, Table 6, and/or Table 7. In some embodiments of the invention, a particular percentage range is defined, using any two of the percentages provided above as lower and upper boundaries of the range, inclusive or exclusive. All combinations of the percentages provided, which define an upper and lower boundary, are contemplated.

In some embodiments of the invention, at least about 1%, 2.5%, 5%, 10%, 15%, 20%, 25%, 30%, 40%, 45%, 50%, 55%, 60%, 65%, 70%, 75%, 80%, 85%, 90%, 95%, or 99% of the light chain sequences in a library are light chain sequences provided herein. In certain embodiments of the invention, at least about 1%, 2.5%, 5%, 10%, 15%, 20%, 25%, 30%, 40%, 45%, 50%, 55%, 60%, 65%, 70%, 75%, 80%, 85%, 90%, 95%, or 99% of the light chain sequences isolated from a light chain library (e.g., by binding to a particular antigen and/or generic ligand) are light chain sequences provided herein. In some embodiments, a light chain library of the invention may contain less than a particular percentage of light chain sequences provided herein, where the percentage of light chain sequences is defined using any one of the percentages provided above. In certain embodiments of the invention, a particular percentage range is defined, using any two of the percentages provided above as lower and upper boundaries of the range, inclusive or exclusive. All combinations of the percentages provided, which define an upper and lower boundary, are contemplated.

One of ordinary skill in the art will further recognize that given the light chain sequences provided herein, similar light chain sequences could be produced which share a designated level of overall sequence identity and/or one or more characteristic sequence elements described herein, which overall degree of sequence identity and/or characteristic sequence elements may confer common functional attributes. Those of ordinary skill in the art will be well familiar with a variety of techniques for preparing such related sequences, including the mutagenesis techniques provided herein. Therefore, each of the explicitly enumerated embodiments of the invention can also be practiced using light chain sequences that share a particular percent identity to any of the light chain sequences provided herein. For example, each of the previously described embodiments of the invention can be practiced using light chain sequences that are at least about 70%, 75%, 80%, 85%, 90%, 91%, 92%, 93%, 94%, 95%, 96%, 97%, 98%, 99%, 99.5%, or 99.9% identical to the light chain sequences provided herein. For example, in some embodiments, light chain libraries provided by the invention comprise light chain variable domains at least about 70%, 75%, 80%, 85%, 90%, 91%, 92%, 93%, 94%, 95%, 96%, 97%, 98%, 99%, 99.5%, or 99.9% identical to the light chain sequences provided herein, with substitutions in one or more of framework positions 2, 4, 36, 46, 48, 49, and 66, CDRL1 positions 28, 29, 30, 30A, 30B, 30E, 31, and 32 (Chothia-Lesk numbering scheme), and/or CDRL2 positions 50, 51, 53, and 55.

In some embodiments, the invention provides systems and methods for varying positions within the portion of CDRL3s encoded by a particular IGVL germline gene, comprising:

(i) obtaining a reference set of light chain sequences, wherein the reference set contains light chain sequences with VL segments originating from the same IGVL germline gene and/or its allelic variants;
(ii) determining which amino acids occur at each of the CDRL3 positions in the reference set that are encoded by the IGVL gene (i.e., positions 89-94, inclusive);
(iii) synthesizing light chain variable domain encoding sequences wherein two positions in each light chain variable domain encoding sequence contain degenerate codons encoding the 2, 3, 4, 5, 6, 7, 8, 9, 10, 11, 12, 13, 14, 15, 16, 17, 18, 19, or 20 most frequently occurring amino acid residues at the corresponding positions in the reference set.

As described in the examples, the degenerate codons of (iii) can be chosen to best reproduce the amino acid diversity contained in the reference set for each of the two positions varied in each light chain. Finally, while the methods and systems described above are described with respect to CDRL3, one of ordinary skill in the art will readily recognize that the same principles can be applied to CDRH1 and/or CDRH2 of the heavy chain, which are encoded entirely by the IGHV gene.

CDRL3 Lengths

In some embodiments, as an alternative or in addition to other features described herein, the present invention provides libraries in which lengths of CDRL3s may be varied. The present invention therefore provides, among other things, libraries with a particular distribution of CDRL3 lengths. Although CDRL3 libraries of lengths 8, 9, and 10 are exemplified, one of ordinary skill in the art will readily recognize that the methods described herein can be applied to produce light chains with CDRL3s of different lengths (e.g., about 5, 6, 7, 11, 12, 13, 14, 15, and/or 16) that also fall within the scope of the invention. In some embodiments, the length of any of the CDRL3s of the invention may be less than a particular number of amino acids, where the number of amino acids is defined using any one of the integers provided above. In some embodiments of the invention, a particular numerical range is defined, using any two of the integers provided above as lower and upper boundaries of the range, inclusive or exclusive. All combinations of the integers provided, which define an upper and lower boundary, are contemplated.

Synthetic Antibody Libraries

In some embodiments of the invention, provided libraries include one or more synthetic polynucleotides. In some embodiments, provided libraries may comprise synthetic polynucleotides selected from (a) heavy chain chassis polynucleotides; (b) light chain chassis polynucleotides; (c) CDR3 polynucleotides; (d) constant domain polynucleotides; and (e) combinations thereof. Those of ordinary skill in the art will appreciate that such synthetic polynucleotides may be linked to other synthetic or non-synthetic polynucleotides in provided libraries.

Synthetic polynucleotides provided herein may be prepared by any available method. For example, in some embodiments, synthetic polynucleotides can be synthesized by split pool DNA synthesis as described in Feldhaus et al., Nucleic Acids Research, 2000, 28: 534; Omstein et al., Biopolymers, 1978, 17: 2341; Brenner and Lerner, PNAS, 1992, 87: 6378, U.S. Publication Nos. 2009/0181855 and 2010/0056386, and WO/2009/036379 (each incorporated by reference in its entirety).

In some embodiments of the invention, segments representing the possible TN1, DH, N2, and JH diversity found in the human repertoire are synthesized de novo either as double-stranded DNA oligonucleotides, single-stranded DNA oligonucleotides representative of the coding strand, or single-stranded DNA oligonucleotides representative of the non-coding strand. Such sequences can then be introduced into a host cell along with an acceptor vector containing a chassis sequence and, in some cases a portion of FRM4 and a constant region. No primer-based PCR amplification from mammalian cDNA or mRNA or template-directed cloning steps from mammalian cDNA or mRNA need be employed.

Construction of Libraries by Yeast Homologous Recombination

In certain embodiments, the invention exploits the inherent ability of yeast cells to facilitate homologous recombination at high efficiency. The mechanism of homologous recombination in yeast and its applications are briefly described below (also see e.g., U.S. Pat. Nos. 6,406,863; 6,410,246; 6,410,271; 6,610,472; and 7,700,302, each of which is incorporated by reference in its entirety).

As an illustrative embodiment, homologous recombination can be carried out in, for example, *Saccharomyces cerevisiae*, which has genetic machinery designed to carry out homologous recombination with high efficiency. Exemplary *S. cerevisiae* strains include EM93, CEN.PK2, RM11-1a, YJM789, and BJ5465. This mechanism is believed to have evolved for the purpose of chromosomal repair, and is also called "gap repair" or "gap filling". By exploiting this mechanism, mutations can be introduced into specific loci of the yeast genome. For example, a vector carrying a mutant gene can contain two sequence segments that are homologous to the 5' and 3' open reading frame (ORF) sequences of a gene that is intended to be interrupted or mutated. The vector may also encode a positive selection marker, such as a nutritional enzyme allele (e.g., URA3) and/or an antibiotic resistant marker (e.g., Geneticin/G418), flanked by the two homologous DNA segments. Other selection markers and antibiotic resistance markers are known to one of ordinary skill in the art.

In some embodiments of the invention, this vector (e.g., a plasmid) is linearized and transformed into the yeast cells. Through homologous recombination between the plasmid and the yeast genome, at the two homologous recombination sites, a reciprocal exchange of the DNA content occurs between the wild type gene in the yeast genome and the mutant gene (including the selection marker gene(s)) that is flanked by the two homologous sequence segments. By selecting for the one or more selection markers, the surviving yeast cells will be those cells in which the wild-type gene has been replaced by the mutant gene (Pearson et al., Yeast, 1998, 14: 391, incorporated by reference in its entirety). This mechanism has been used to make systematic mutations in all 6,000 yeast genes, or open reading frames (ORFs), for functional genomics studies. Because the exchange is reciprocal, a similar approach has also been used successfully to clone yeast genomic DNA fragments into a plasmid vector (Iwasaki et al., Gene, 1991, 109: 81, incorporated by reference in its entirety).

By utilizing the endogenous homologous recombination machinery present in yeast, gene fragments or synthetic oligonucleotides can also be cloned into a plasmid vector without a ligation step. In this application of homologous recombination, a target gene fragment (i.e., the fragment to be inserted into a plasmid vector, e.g., a CDR3) is obtained (e.g., by oligonucleotides synthesis, PCR amplification, restriction digestion out of another vector, etc.). DNA sequences that are homologous to selected regions of the plasmid vector are added to the 5' and 3' ends of the target gene fragment. These homologous regions may be fully synthetic, or added via PCR amplification of a target gene fragment with primers that incorporate the homologous sequences. The plasmid vector may include a positive selection marker, such as a nutritional enzyme allele (e.g., URA3), or an antibiotic resistance marker (e.g., Geneticin/G418). The plasmid vector is then linearized by a unique restriction cut located in-between the regions of sequence homology shared with the target gene fragment, thereby creating an artificial gap at the cleavage site. The linearized plasmid vector and the target gene fragment flanked by sequences homologous to the plasmid vector are co-transformed into a yeast host strain. The yeast is then able to recognize the two stretches of sequence homology between the vector and target gene fragment and facilitate a reciprocal exchange of DNA content through homologous recombination at the gap. As a consequence, the target gene fragment is inserted into the vector without ligation.

The method described above has also been demonstrated to work when the target gene fragments are in the form of single stranded DNA, for example, as a circular M13 phage derived form, or as single stranded oligonucleotides (Simon and Moore, Mol. Cell Biol., 1987, 7: 2329; Ivanov et al., Genetics, 1996, 142: 693; and DeMarini et al., 2001, 30: 520, each incorporated by reference in its entirety). Thus, the form of the target that can be recombined into the gapped vector can be double stranded or single stranded, and derived from chemical synthesis, PCR, restriction digestion, or other methods.

Several factors may influence the efficiency of homologous recombination in yeast. For example, the efficiency of the gap repair is correlated with the length of the homologous sequences flanking both the linearized vector and the target gene. In certain embodiments, about 20 or more base pairs may be used for the length of the homologous sequence, and about 80 base pairs may give a near-optimized result (Hua et al., Plasmid, 1997, 38: 91; Raymond et al., Genome Res., 2002, 12: 190, each incorporated by reference in its entirety). In certain embodiments of the invention, at least about 5, 10, 15, 20, 21, 22, 23, 24, 25, 26, 27, 28, 29, 30, 31, 32, 33, 34 35, 36, 37, 38, 39, 40, 45, 50, 55, 60, 65, 70, 75, 80, 85, 90, 95, 100, 110, 120, 130, 140, 150, 160, 170, 180, 187, 190, or 200 homologous base pairs may be used to facilitate recombination. In certain embodiments, between about 20 and about 40 base pairs are utilized. In addition, the reciprocal exchange between the vector and gene fragment is strictly sequence-dependent, i.e. it does not cause a frame shift. Therefore, gap-repair cloning assures the insertion of gene fragments with both high efficiency and precision. The high efficiency makes it possible to clone two, three, or more targeted gene fragments simultaneously into the same vector in one transformation attempt (Raymond et al., Biotechniques, 1999, 26: 134, incorporated by reference in its entirety). Moreover, the nature of precision sequence conservation through homologous recombination makes it possible to clone selected genes or gene fragments into expression or fusion vectors for direct functional examination (El-Deiry et al., Nature Genetics, 1992, 1: 4549; Ishioka et al., PNAS, 1997, 94: 2449, each incorporated by reference in its entirety).

Libraries of gene fragments have also been constructed in yeast using homologous recombination. For example, a human brain cDNA library was constructed as a two-hybrid fusion library in vector pJG4-5 (Guidotti and Zervos, Yeast, 1999, 15: 715, incorporated by reference in its entirety). It has also been reported that a total of 6,000 pairs of PCR primers were used for amplification of 6,000 known yeast ORFs for a study of yeast genomic protein interactions (Hudson et al., Genome Res., 1997, 7: 1169, incorporated by reference in its entirety). In 2000, Uetz et al. conducted a comprehensive analysis-of protein-protein interactions in *Saccharomyces cerevisiae* (Uetz et al., Nature, 2000, 403: 623, incorporated by reference in its entirety). The protein-protein interaction map of the budding yeast was studied by using a comprehensive system to examine two-hybrid interactions in all possible combinations between the yeast proteins (Ito et al., PNAS, 2000, 97: 1143, incorporated by reference in its entirety), and the genomic protein linkage map of Vaccinia virus was studied using this system (McCraith et al., PNAS, 2000, 97: 4879, incorporated by reference in its entirety).

In certain embodiments of the invention, a synthetic CDR3 (heavy or light chain) may be joined by homologous recombination with a vector encoding a heavy or light chain chassis, a portion of FRM4, and a constant region, to form a full-length heavy or light chain. In certain embodiments of the invention, the homologous recombination is performed directly in yeast cells. In some embodiments, such a method comprises:

(a) transforming into yeast cells:
  (i) a linearized vector encoding a heavy or light chain chassis, a portion of FRM4, and a constant region, wherein the site of linearization is between the end of FRM3 of the chassis and the beginning of the constant region; and
  (ii) a library of CDR3 insert nucleotide sequences that are linear and double stranded, wherein each of the CDR3 insert sequences comprises a nucleotide sequence encoding CDR3 and 5'- and 3'-flanking sequences that are sufficiently homologous to the termini of the vector of (i) at the site of linearization to enable homologous recombination to occur between the vector and the library of CDR3 insert sequences; and
(b) allowing homologous recombination to occur between the vector and the CDR3 insert sequences in the transformed yeast cells, such that the CDR3 insert sequences are incorporated into the vector, to produce a vector encoding full-length heavy chain or light chain.

As specified above, CDR3 inserts may have a 5' flanking sequence and a 3' flanking sequence that are homologous to the termini of the linearized vector. When the CDR3 inserts and the linearized vectors are introduced into a host cell, for example, a yeast cell, the "gap" (the linearization site) created by linearization of the vector is filled by the CDR3 fragment insert through recombination of the homologous sequences at the 5' and 3' termini of these two linear double-stranded DNAs (i.e., the vector and the insert). Through this event of homologous recombination, libraries of circular vectors encoding full-length heavy or light chains comprising variable CDR3 inserts is generated. Particular instances of these methods are presented in the Examples.

Subsequent analysis may be carried out to determine, for example, the efficiency of homologous recombination that results in correct insertion of the CDR3 sequences into the vectors. For example, PCR amplification of the CDR3 inserts directly from selected yeast clones may reveal how many clones are recombinant. In certain embodiments, libraries with minimum of about 90% recombinant clones are utilized. In certain embodiments libraries with a minimum of about 1%, 5% 10%, 15%, 20%, 25%, 30%, 35%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, or 99% recombinant clones are utilized. The same PCR amplification of selected clones may also reveal the insert size.

To verify the sequence diversity of the inserts in the selected clones, a PCR amplification product with the correct size of insert may be "fingerprinted" with restriction enzymes known to cut or not cut within the amplified region. From a gel electrophoresis pattern, it may be determined whether the clones analyzed are of the same identity or of the distinct or diversified identity. The PCR products may also be sequenced directly to reveal the identity of inserts and the fidelity of the cloning procedure, and to prove the independence and diversity of the clones.

Expression and Screening Systems

Libraries of polynucleotides generated by any of the techniques described herein, or other suitable techniques, can be expressed and screened to identify antibodies having desired structure and/or activity. Expression of the antibodies can be carried out, for example, using cell-free extracts (and e.g., ribosome display), phage display, prokaryotic cells (e.g., bacterial display), or eukaryotic cells (e.g., yeast display). In certain embodiments of the invention, the antibody libraries are expressed in yeast.

In some embodiments, polynucleotides are engineered to serve as templates that can be expressed in a cell-free extract. Vectors and extracts as described, for example in U.S. Pat. Nos. 5,324,637; 5,492,817; 5,665,563, (each incorporated by reference in its entirety) can be used and many are commercially available. Ribosome display and other cell-free techniques for linking a polynucleotide (i.e., a genotype) to a polypeptide (i.e., a phenotype) can be used, e.g., Profusion™ (see, e.g., U.S. Pat. Nos. 6,348,315; 6,261,804; 6,258,558; and 6,214,553, each incorporated by reference in its entirety).

Alternatively or additionally, polynucleotides of the invention can be expressed in an *E. coli* expression system, such as that described by Pluckthun and Skerra. (Meth. Enzymol., 1989, 178: 476; Biotechnology, 1991, 9: 273, each incorporated by reference in its entirety). Mutant proteins can be expressed for secretion in the medium and/or in the cytoplasm of the bacteria, as described by Better and Horwitz, Meth. Enzymol., 1989, 178: 476, incorporated by reference in its entirety. In some embodiments, the single domains encoding VH and VL are each attached to the 3' end of a sequence encoding a signal sequence, such as the ompA, phoA or pelB signal sequence (Lei et al., J. Bacteriol., 1987, 169: 4379, incorporated by reference in its entirety). These gene fusions are assembled in a dicistronic construct, so that they can be expressed from a single vector, and secreted into the periplasmic space of *E. coli* where they will refold and can be recovered in active form. (Skerra et al., Biotechnology, 1991, 9: 273, incorporated by reference in its entirety). For example, antibody heavy chain genes can be concurrently expressed with antibody light chain genes to produce antibodies or antibody fragments.

In some embodiments of the invention, antibody sequences are expressed on the membrane surface of a prokaryote, e.g., *E. coli*, using a secretion signal and lipidation moiety as described, e.g., in US2004/0072740; US2003/0100023; and US2003/0036092 (each incorporated by reference in its entirety).

Higher eukaryotic cells, such as mammalian cells, for example myeloma cells (e.g., NS/0 cells), hybridoma cells, Chinese hamster ovary (CHO), and human embryonic kidney (HEK) cells, can also be used for expression of the antibodies of the invention. Typically, antibodies expressed in mammalian cells are designed to be secreted into the culture medium, or expressed on the surface of the cell. Antibody or antibody fragments can be produced, for example, as intact antibody molecules or as individual VH and VL fragments, Fab fragments, single domains, or as single chains (scFv) (Huston et al., PNAS, 1988, 85: 5879, incorporated by reference in its entirety).

Alternatively or additionally, antibodies can be expressed and screened by anchored periplasmic expression (APEx 2-hybrid surface display), as described, for example, in Jeong et al., PNAS, 2007, 104: 8247 (incorporated by reference in its entirety) or by other anchoring methods as described, for example, in Mazor et al., Nature Biotechnology, 2007, 25: 563 (incorporated by reference in its entirety).

In some embodiments of the invention, antibodies can be selected using mammalian cell display (Ho et al., PNAS, 2006, 103: 9637, incorporated by reference in its entirety).

Screening of the antibodies derived from the libraries of the invention can be carried out by any appropriate means. For example, binding activity can be evaluated by standard immunoassay and/or affinity chromatography. Screening of antibodies of the invention for catalytic function, e.g., proteolytic function can be accomplished using a standard assays, e.g., the hemoglobin plaque assay as described in U.S. Pat. No. 5,798,208 (incorporated by reference in its entirety). Determining the ability of candidate antibodies to bind therapeutic targets can be assayed in vitro using, e.g., a BIACORE instrument, which measures binding rates of an antibody to a given target or antigen based on surface plasmon resonance. In vivo assays can be conducted using any of a number of animal models and then subsequently tested, as appropriate, in humans. Cell-based biological assays are also contemplated.

One feature of the instant invention is the speed at which the antibodies of the library can be expressed and screened. In certain embodiments of the invention, the antibody library can be expressed in yeast, which have a doubling time of less than about 3, 4, 5, 6, 7, 8, 9, 10, 11, 12, 13, 14, 15, 16, 17, 18, 19, 20, 21, 22, 23, or 24 hours. In some embodiments, the doubling times are about 1 to about 3 hours, about 2 to about 4, about 3 to about 8 hours, about 3 to about 24, about 5 to about 24, about 4 to about 6 about 5 to about 22, about 6 to about 8, about 7 to about 22, about 8 to about 10 hours, about 7 to about 20, about 9 to about 20, about 9 to about 18, about 11 to about 18, about 11 to about 16, about 13 to about 16, about 16 to about 20, or about 20 to about 30 hours. In certain embodiments of the invention, an antibody library is expressed in yeast with a doubling time of about 16 to about 20 hours, about 8 to about 16 hours, or about 4 to about 8 hours. Thus, an antibody library of the instant invention can be expressed and screened in a matter of hours, as compared to previously known techniques which take several days to express and screen antibody libraries. A limiting step in the throughput of such screening processes in mammalian cells is typically the time required to iteratively regrow populations of isolated cells, which, in some cases, have doubling times greater than the doubling times of the yeast used in the current invention.

In certain embodiments of the invention, the composition of a library may be defined after one or more enrichment steps (for example by screening for antigen binding, binding to a generic ligand, or other properties). For example, a library with a composition comprising about x % sequences or libraries of the invention may be enriched to contain about 2x %, 3x %, 4x %, 5x %, 6x %, 7x %, 8x %, 9x %, 10x %, 20x %, 25x %, 40x %, 50x %, 60x % 75x %, 80x %, 90x %, 95x %,or 99x % sequences or libraries of the invention, after one or more screening steps. In some embodiments of the invention, the sequences or libraries of the invention may be enriched about 2-fold, 3-fold, 4-fold, 5-fold, 6-fold, 7-fold, 8-fold, 9-fold, 10-fold, 100-fold, 1,000-fold, or more, relative to their occurrence prior to the one or more enrichment steps. In certain embodiments of the invention, a library may contain at least a certain number of a particular type of sequence(s), such as CDRH3s, CDRL3s, heavy chains, light chains, or whole antibodies (e.g., at least about $10^3$, $10^4$, $10^5$, $10^6$, $10^7$, $10^8$, $10^9$, $10^{10}$ $10^{11}$, $10^{12}$, $10^{13}$, $10^{14}$, $10^{15}$, $10^{16}$, $10^{17}$, $10^{18}$, $10^{19}$, or $10^{20}$). In certain embodiments, these sequences may be enriched during one or more enrichment steps, to provide libraries comprising at least about $10^2$, $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, $10^{16}$, $10^{17}$, $10^{18}$, or $10^{19}$ of the respective sequence(s).

Mutagenesis Approaches for Affinity Maturation

As described above, antibody leads can be identified through a selection process that involves screening the antibodies of a library of the invention for binding to one or more antigens, or for a biological activity. Coding sequences of these antibody leads may be further mutagenized in vitro or in vivo to generate secondary libraries with diversity introduced in the context of the initial antibody leads. Such mutagenized antibody leads can then be further screened for binding to target antigens or biological activity, in vitro or in vivo, following procedures similar to those used for the selection of the initial antibody lead from the primary library. Such mutagenesis and selection of primary antibody leads effectively mimics the affinity maturation process naturally occurring in a mammal that produces antibodies with progressive increases in the affinity to an antigen.

In some embodiments of the invention, only the CDRH3 region is mutagenized. In some embodiments of the invention, the whole variable region is mutagenized. In some embodiments of the invention one or more of CDRH1, CDRH2, CDRH3, CDRL1, CDRL2, and/CDRL3 may be mutagenized. In some embodiments of the invention, "light chain shuffling" may be used as part of the affinity maturation protocol. In certain embodiments, this may involve pairing one or more heavy chains with a number of light chains, to select light chains that enhance the affinity and/or biological activity of an antibody. In certain embodiments of the invention, the number of light chains to which the one or more heavy chains can be paired is at least about 2, 5, 10, 100, $10^3$, $10^4$, $10^5$, $10^6$, $10^7$, $10^8$, $10^9$, or $10^{10}$. In certain embodiments of the invention, these light chains are encoded by plasmids. In some embodiments of the invention, the light chains may be integrated into the genome of the host cell.

Coding sequences of antibody leads may be mutagenized using any of wide variety of methods. Examples of methods of mutagenesis include, but are not limited to site-directed mutagenesis, error-prone PCR mutagenesis, cassette mutagenesis, and random PCR mutagenesis. Alternatively or additionally, oligonucleotides encoding regions with the desired mutations can be synthesized and introduced into the sequence to be mutagenized, for example, via recombination or ligation.

Site-directed mutagenesis or point mutagenesis may be used to gradually change the CDR sequences in specific regions. For example, this may be accomplished by using oligonucleotide-directed mutagenesis or PCR. For example, a short sequence of an antibody lead may be replaced with a synthetically mutagenized oligonucleotide in either the heavy chain or light chain region, or both. Such a method may not be efficient for mutagenizing large numbers of CDR sequences, but may be used for fine tuning of a particular lead to achieve higher affinity toward a specific target protein.

Cassette mutagenesis may alternatively or additionally be used to mutagenize the CDR sequences in specific regions. In a typical cassette mutagenesis, a sequence block, or a region, of a single template is replaced by a completely or partially randomized sequence. However, the maximum information content that can be obtained may be statistically limited by the number of random sequences of the oligonucleotides. Similar to point mutagenesis, this method may also be used for fine tuning of a particular lead to achieve higher affinity towards a specific target protein.

Error-prone PCR, or "poison" PCR, may be used to mutagenize the CDR sequences, for example, by following protocols described in U.S. Pat. No. 6,153,745; Caldwell and Joyce, PCR Methods and Applications, 1992, 2: 28; Leung et al., Technique, 1989, 1: 11; Shafikhani et al., Biotechniques, 1997, 23: 304; and Stemmer et al., PNAS, 1994, 91: 10747 (each of which is incorporated by reference in its entirety).

Conditions for error prone PCR may include, for example, (a) high concentrations of $Mn^{2+}$ (e.g., about 0.4 to about 0.6 mM) that efficiently induces malfunction of Taq DNA polymerase; and/or (b) a disproportionally high concentration of one nucleotide substrate (e.g., dGTP) in the PCR reaction that causes incorrect incorporation of this high concentration substrate into the template and produces mutations. Alternatively or additionally, other factors such as, the number of PCR cycles, the species of DNA polymerase used, and the length of the template, may affect the rate of misincorporation of "wrong" nucleotides into the PCR product. Commercially available kits may be utilized for the mutagenesis of the selected antibody library, such as the "Diversity PCR random mutagenesis kit" (CLONTECH™).

Primer pairs used in PCR-based mutagenesis may, in certain embodiments, include regions matched with the homologous recombination sites in the expression vectors. Such a design allows facile re-introduction of the PCR products back into the heavy or light chain chassis vectors, after mutagenesis, via homologous recombination.

Other PCR-based mutagenesis methods can also be used, alone or in conjunction with the error prone PCR described above. For example, the PCR amplified CDR segments may be digested with DNase to create nicks in the double stranded DNA. These nicks can be expanded into gaps by other exonucleases such as Bal 31. Gaps may then be filled by random sequences by using DNA Klenow polymerase at a low concentration of regular substrates dGTP, dATP, dTTP, and dCTP with one substrate (e.g., dGTP) at a disproportionately high concentration. This fill-in reaction should produce high frequency mutations in the filled gap regions. Such methods of DNase digestion may be used in conjunction with error prone PCR to create a high frequency of mutations in the desired CDR segments.

CDR or antibody segments amplified from the primary antibody leads may also be mutagenized in vivo by exploiting the inherent ability of mutation in pre-B cells. The Ig genes in pre-B cells are specifically susceptible to a high-rate of mutation. The Ig promoter and enhancer facilitate such high rate mutations in a pre-B cell environment while the pre-B cells proliferate. Accordingly, CDR gene segments may be cloned into a mammalian expression vector that contains a human Ig enhancer and promoter. Such a construct may be introduced into a pre-B cell line, such as 38B9, which allows the mutation of the VH and VL gene segments naturally in the pre-B cells (Liu and Van Ness, Mol. Immunol., 1999, 36: 461, incorporated by reference in its entirety). The mutagenized CDR segments can be amplified from the cultured pre-B cell line and re-introduced back into the chassis-containing vector(s) via, for example, homologous recombination.

In some embodiments, a CDR "hit" isolated from screening the library can be re-synthesized, for example using degenerate codons or trinucleotides, and re-cloned into the heavy or light chain vector using gap repair.

Other Variants of Polynucleotide Sequences of the Invention

In certain embodiments, the invention provides a polynucleotide that hybridizes with a polynucleotide taught herein, or that hybridizes with the complement of a polynucleotide taught herein. For example, an isolated polynucleotide that remains hybridized after hybridization and washing under low, medium, or high stringency conditions to a polynucleotide taught herein or the complement of a polynucleotide taught herein is encompassed by the present invention.

Exemplary low stringency conditions include hybridization with a buffer solution of about 30% to about 35% formamide, about 1 M NaCl, about 1% SDS (sodium dodecyl sulphate) at about 37° C., and a wash in about 1× to about 2×SSC (20×SSC=3.0 M NaCl/0.3 M trisodium citrate) at about 50° C. to about 55° C.

Exemplary moderate stringency conditions include hybridization in about 40% to about 45% formamide, about 1 M NaCl, about 1% SDS at about 37° C., and a wash in about 0.5× to about 1×SSC at abut 55° C. to about 60° C.

Exemplary high stringency conditions include hybridization in about 50% formamide, about 1 M NaCl, about 1% SDS at about 37° C., and a wash in about 0.1×SSC at about 60° C. to about 65° C.

Optionally, wash buffers may comprise about 0.1% to about 1% SDS.

The duration of hybridization is generally less than about 24 hours, usually about 4 to about 12 hours.

Sublibraries and Larger Libraries Comprising Libraries or Sub-Libraries of the Invention Libraries comprising combinations of the libraries described herein (e.g., CDRH3 and CDRL3 libraries) are encompassed by the invention. Sublibraries comprising portions of the libraries described herein are also encompassed by the invention (e.g., a CDRH3 library in a particular heavy chain chassis or a sub-set of the CDRH3 libraries, for example based on length).

Moreover, libraries containing one of the libraries or sublibraries of the invention also fall within the scope of the invention. For example, in certain embodiments of the invention, one or more libraries or sublibraries of the invention may be contained within a larger library (theoretical or physical), which may include sequences derived by other means, for example, non-human or human sequence derived by stochastic or sitewise-stochastic synthesis. In certain embodiments of the invention, at least about 1% of the sequences in a polynucleotide library may be those of the invention (e.g., CDRH3 sequences, CDRL3 sequences, VH sequences, VL sequences), regardless of the composition of the other 99% of sequences. For the purposes of illustration only, one of ordinary skill in the art would readily recognize that a library containing $10^9$ total members, where $10^7$ members are members of the libraries of the invention (i.e., 1%) would have utility, and that members of the libraries of the invention could be isolated from such a library. In some embodiments of the invention, at least about 0.001%, 0.01%, 0.1%, 2%, 5%, 10%, 20%, 30%, 40%, 50%, 60%, 70%, 80%, 81%, 82%, 83%, 84%, 85%, 86%, 87%, 88%, 89%, 90%, 91,%, 92%, 93%, 94%, 95%, 96%, 97%, 98% or 99% of the sequences in any polynucleotide library may be those of the invention, regardless of the composition of the other sequences. In some embodiments, the sequences of the invention may comprise about 0.001% to about 1%, about 1% to about 2%, about 2% to about 5%, about 5% to about 10%, about 10% to about 15%, about 15% to about 20%, about 20% to about 25%, about 25% to about 30%, about 30% to about 35%, about 35% to about 40%, about 40% to about 45%, about 45% to about 50%, about 50% to about 55%, about 55% to about 60%, about 60% to about 65%, about 65% to about 70%, about 70% to about 75%, about 75% to about 80%, about 80% to about 85%, about 85% to about 90%, about 90% to about 95%, or about 95% to about 99% of the sequences in any polynucleotide library, regardless of the composition of the other sequences. Thus, libraries more diverse than one or more libraries or sublibraries of the invention, but yet still comprising one or more libraries or sublibraries of the invention, in an amount in which the one or more libraries or sublibraries of the invention can be effectively screened and from which sequences encoded by the one or more libraries or sublibraries of the invention can be isolated, also fall within the scope of the invention.

Alternative Scaffolds

As would be evident to one of ordinary skill in the art, the CDRH3 and/or CDRL3 polypeptides provided by the invention may also be displayed on alternative scaffolds. Several such scaffolds have been shown to yield molecules with specificities and affinities that rival those of antibodies. Exemplary alternative scaffolds include those derived from fibronectin (e.g., AdNectin), the β-sandwich (e.g., iMab), lipocalin (e.g., Anticalin), EETI-II/AGRP, BPTI/LACI-D1/ITI-D2 (e.g., Kunitz domain), thioredoxin (e.g., peptide aptamer), protein A (e.g., Affibody), ankyrin repeats (e.g., DARPin), yB-crystallin/ubiquitin (e.g., Affilin), $CTLD_3$ (e.g., Tetranectin), and (LDLR-A module)$_3$ (e.g., Avimers). Additional information on alternative scaffolds is provided, for example, in Binz et al., Nat. Biotechnol., 2005 23: 1257 and Skerra, Current Opin. in Biotech., 2007 18: 295-304, each of which is incorporated by reference in its entirety.

Additional Embodiments of the Invention

Library Sizes

In some embodiments of the invention, a library comprises about $10^1$ to about $10^{20}$ different polynucleotide or polypeptide sequences (encoding or comprising e.g., antibodies, heavy chains, CDRH3s, light chains, and/or CDRL3s). In some embodiments, the libraries of the invention are designed to include at least about $10^1$, $10^2$, $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, $10^{16}$, $10^{17}$, $10^{18}$, $10^{19}$, or $10^{20}$, or more different antibody, heavy chain, CDRH3, light chain, and/or CDRL3 polynucleotide or polypeptide sequences. In some embodiments, a library of the invention may contain less than a particular number of polynucleotide or polypeptide sequences, where the number of sequences is defined using any one of the integers provided above. In certain embodiments of the invention, a particular numerical range is defined, using any two of the integers provided above as lower and upper boundaries of the range, inclusive or exclusive. All combinations of the integers provided, which define an upper and lower boundary, are contemplated.

In some embodiments, the invention provides libraries wherein a fraction of the members of the library are members produced according to the methods, systems, and compositions provided herein. One important property of the libraries of the invention is that they favorably mimic certain aspects of the human preimmune repertoire, including length diversity and sequence diversity. One or ordinary skill in the art will readily recognize that libraries provided by the invention include libraries where a subset of the members of the library are members produced according to the methods, systems, and compositions provided herein. For example, a library containing $10^8$ members wherein $10^6$ members are produced according to the methods, systems, and compositions provided herein, would contain 1% sequences produced according to the methods, systems, and compositions provided herein. One of ordinary skill in the art would recognize that one or more of the $10^6$ members could readily be isolated using screening techniques known in the art. Therefore, said libraries fall within the scope of the invention. More specifically, libraries comprising at least about 1%, 2.5%, 5%, 10%, 15%, 20%, 25%, 30%, 40%, 45%, 50%, 55%, 60%, 65%, 70%, 75%, 80%, 85%, 90%, 95%, or 99% CDRH3, CDRL3, light chain, or heavy chain, and/or full-length antibody sequences provided herein fall within the scope of the invention. Libraries comprising at least about $10^3$, $10^4$, $10^5$, $10^6$, $10^7$, $10^8$, $10^9$, $10^{10}$, $10^{11}$, $10^{12}$, $10^{13}$, $10^{14}$, $10^{15}$ CDRH3, CDRL3, light chain, heavy chain, and/or full-length antibody sequences provided herein also fall within the scope of the invention.

Human Preimmune Set

In some embodiments, the invention comprises the set of 3,571 curated human preimmune antibody sequences contained within the HPS, their corresponding CDRH3 sequences (Appendix A), and/or a representation of these CDRH3 sequences (and/or TN1, DH, N2, and/or H3-JH segments thereof) in a computer readable format. In certain embodiments, the invention comprises a method of producing a CDRH3 library, the method comprising matching candidate segments (i.e., TN1, DH, N2, and H3-JH) from a theoretical segment pool with CDRH3 sequences in the HPS and/or any other repertoire of CDRH3 sequences. In some embodiments, the invention comprises the candidate segments from the theoretical segment pools disclosed herein and/or the segments selected for inclusion in a physical library.

Embodiments

While the methods described herein demonstrate the production of theoretical segment pools of H3-JH and DH segments using a limited number of allelic variants, one of ordinary skill in the art will recognize that methods taught herein may be applied to any IGHJ and IGHD genes, including any other allelic variants and all non-human IGHJ and IGHD genes. Alternatively or additionally, methods described herein may be applied to any reference set of CDRH3 sequences, for example to extract additional TN1 and/or N2 segments. Alternatively or additionally, one of ordinary skill in the art will recognize that each of the described embodiments of the invention may be in polynucleotide or polypeptide form, within a vector, virus, or microorganism (e.g., a yeast or bacteria). Furthermore, since the invention involves synthetic libraries that are fully enumerated, certain embodiments of the invention relate to any of the embodiments described above in a computer readable format, and uses thereof.

Non-human antibody libraries also fall within the scope of the invention.

The present disclosure describes the removal of sequences containing Cys residues, N-linked glycosylation motifs, deamidation motifs, and highly hydrophobic sequences from the libraries of the invention. One of ordinary skill in the art will recognize that one or more of these criteria (i.e., not necessarily all) can be applied to remove undesirable sequences from any library of the invention. However, libraries containing one or more of these types of sequences also fall within the scope of the invention. Other criteria can also be used; those described herein are not limiting.

In certain embodiments, the invention provides libraries in which the number of times a particular sequence is repeated within the library (either theoretical, synthetic, or physical realization) is limited. For example, in some embodiments, the invention provides libraries wherein the frequency of occurrence of any of the sequences in the library (e.g., CDRH3, CDRL3, heavy chain, light chain, full-length antibody) is less than about 2, 5, 10, 15, 20, 25, 30, 35, 40, 45, 50, 55, 60, 65, 70, 75, 80, 85, 90, 95, 100, 200, 300, 400, 500, 600, 700, 800, 900, or 1000. In some embodiments, the frequency of occurrence of any of the sequences in the library is less than a multiple of the frequency of occurrence of any other sequence in the library, for examples less than about 2, 5, 10, 15, 20, 25, 30, 35, 40, 45, 50, 55, 60, 65, 70, 75, 80, 85, 90, 95, 100, 200, 300, 400, 500, 600, 700, 800, 900, or 1000 times the frequency of occurrence of any other sequence in the library.

In some embodiments, libraries are defined by the combinatorial diversity of the segments used to produce CDRH3 sequences, in particular the number of non-degenerate segment combinations that can be used to produce a particular CDRH3 sequence. In some embodiments, this metric may be calculated using, for example, a sample of about 2000, 5000, 10000, 20000, 50000, 100000, or more sequences from the CDRH3 library and "self-matching" using the segments used to generate the CDRH3 sequences of that library. In certain embodiments, the invention provides libraries wherein at least about 95%, 90%, 85%, 80%, 75%, 70%, 65%, 60%, 55%, 50%, 45%, 40%, 35%, 30%, 25%, 20%, 15%, 10%, or 5% of the CDRH3 sequences in the library may be formed by a single combination of segments.

In certain embodiments of the invention, a statistical bootstrap analysis was used to generate CDRH3 reference sets. While it may be advantageous to use this method, it is not required for every embodiment of the invention.

In some embodiments, the invention provides methods and systems of selecting polynucleotides to encode polypeptides of the invention, comprising selecting polynucleotide segments lacking (or containing) certain restriction sites individually and/or after combinatorial concatenation with other segments (e.g., see Example 9.3.7).

The exemplary libraries provided herein are not limiting and provided for exemplification only.

EXAMPLES

This invention is further illustrated by the following examples which should not be construed as limiting. The contents of all references, patents and published patent applications cited throughout this application are hereby incorporated by reference.

In general, the practice of the present invention employs, unless otherwise indicated, conventional techniques of chemistry, molecular biology, recombinant DNA technology, PCR technology, immunology (especially, e.g., antibody technology), expression systems (e.g., yeast expression, cell-free expression, phage display, ribosome display, and PROFUSION™), and any necessary cell culture that are within the skill of the art and are explained in the literature. See, e.g., Sambrook, Fritsch and Maniatis, *Molecular Cloning*: Cold Spring Harbor Laboratory Press (1989); *DNA Cloning*, Vols. 1 and 2, (D.N. Glover, Ed. 1985); *Oligonucleotide Synthesis* (M. J. Gait, Ed. 1984); *PCR Handbook Current Protocols in Nucleic Acid Chemistry*, Beaucage, Ed. John Wiley & Sons (1999) (Editor); *Oxford Handbook of Nucleic Acid Structure*, Neidle, Ed., Oxford Univ Press (1999); *PCR Protocols: A Guide to Methods and Applications*, Innis et al., Academic Press (1990); *PCR Essential Techniques: Essential Techniques*, Burke, Ed., John Wiley & Son Ltd (1996); *The PCR Technique: RT-PCR*, Siebert, Ed., Eaton Pub. Co. (1998); *Antibody Engineering Protocols* (*Methods in Molecular Biology*), 510, Paul, S., Humana Pr (1996); *Antibody Engineering: A Practical Approach* (*Practical Approach Series,* 169), McCafferty, Ed., Irl Pr (1996); *Antibodies: A Laboratory Manual*, Harlow et al., C.S.H.L. Press, Pub. (1999); *Current Protocols in Molecular Biology*, eds. Ausubel et al., John Wiley & Sons (1992); *Large-Scale Mammalian Cell Culture Technology*, Lubiniecki, A., Ed., Marcel Dekker, Pub., (1990); *Phage Display: A Laboratory Manual*, C. Barbas (Ed.), CSHL Press, (2001); *Antibody Phage Display*, P O'Brien (Ed.), Humana Press (2001); Border et al., Nature Biotechnology, 1997, 15: 553; Border et al., Methods Enzymol., 2000, 328: 430; ribosome display as described by Pluckthun et al. in U.S. Pat. No. 6,348,315, and Profusion™ as described by Szostak et al. in U.S. Pat. Nos. 6,258,558; 6,261,804; and 6,214,553; and bacterial periplasmic expression as described in US20040058403A1. Each of the references cited in this paragraph is incorporated by reference in its entirety.

Further details regarding antibody sequence analysis using Kabat conventions and programs to analyze aligned nucleotide and amino acid sequences may be found, e.g., in Johnson et al., Methods Mol. Biol., 2004, 248: 11; Johnson et al., Int. Immunol., 1998, 10: 1801; Johnson et al., Methods Mol. Biol., 1995, 51: 1; Wu et al., Proteins, 1993, 16: 1; and Martin, Proteins, 1996, 25: 130. Each of the references cited in this paragraph is incorporated by reference in its entirety.

Further details regarding antibody sequence analysis using Chothia conventions may be found, e.g., in Chothia et al., J. Mol. Biol., 1998, 278: 457; Morea et al., Biophys. Chem., 1997, 68: 9; Morea et al., J. Mol. Biol., 1998, 275: 269; Al-Lazikani et al., J. Mol. Biol., 1997, 273: 927. Bane et al., Nat. Struct. Biol., 1994, 1: 915; Chothia et al., J. Mol. Biol., 1992, 227: 799; Chothia et al., Nature, 1989, 342: 877; and Chothia et al., J. Mol. Biol., 1987, 196: 901. Further analysis of CDRH3 conformation may be found in Shirai et al., FEBS Lett., 1999, 455: 188 and Shirai et al., FEBS Lett., 1996, 399: 1. Further details regarding Chothia analysis are described, for example, in Chothia et al., Cold Spring Harb. Symp. Quant Biol., 1987, 52: 399. Each of the references cited in this paragraph is incorporated by reference in its entirety.

Further details regarding CDR contact considerations are described, for example, in MacCallum et al., J. Mol. Biol., 1996, 262: 732, incorporated by reference in its entirety.

Further details regarding the antibody sequences and databases referred to herein are found, e.g., in Tomlinson et al., J. Mol. Biol., 1992, 227: 776, VBASE2 (Retter et al., Nucleic Acids Res., 2005, 33: D671); BLAST (world wide web at ncbi.nlm.nih.gov/BLAST/); CDHIT (bioinformatics.ljcrf.edu/cd-hi/); EMBOSS (world wide web at hgmp.mrc.ac.uk/Software/EMBOSS/); PHYLIP (evolution.genetics.washington.edu/phylip.html); and FASTA (fasta.bioch.virginia.edu). Each of the references cited in this paragraph is incorporated by reference in its entirety.

Light Chain Libraries

Example 1. Light Chain Libraries with Framework and/or CDRL1 and/or CDRL2 Variability Although the diversity in antibody sequences is concentrated in the CDRs, certain residues in the framework regions can also influence antigen recognition and/or modulate affinity (Queen et al., Proc. Natl. Acad. Sci. USA, 1989, 86: 10029; Carter et al., Proc. Natl. Acad. Sci. USA, 1992, 89: 4285, each incorporated by reference in its entirety). These residues have been cataloged and used to make framework substitutions that improve antibody affinity, for example, during the process of antibody humanization (e.g., see the "Vernier" residues in Foote and Winter, J. Mol. Biol., 1992, 224: 487, incorporated by reference in its entirety). In the heavy chain, the Vernier residues include Kabat-numbered residues 2, 27-30, 47-49, 67, 69, 71, 73, 78, 93-94, and 103. In the light chain, the Vernier residues include Kabat residues 2, 4, 35-36, 46-49, 64, 66, 68-69, 71, and 98. The Vernier residue numbers are the same for kappa and lambda light chain sequences (see Table 4 in Chothia et al., J. Mol. Biol., 1985, 186: 651, which is incorporated by reference in its entirety). Additionally, framework positions at the VL-VH interface may also influence affinity. In the heavy chain, the interface residues include Kabat residues 35, 37, 39, 45, 47, 91, 93, 95, 100, and 103 (Chothia et al., J. Mol. Biol., 1985, 186: 651, incorporated by reference in its entirety). In the light chain, the interface residues include Kabat residues 34, 36, 38 44, 46, 87, 89, 91, 96, and 98.

The following procedure was used to select the framework residues to be varied and the amino acids to which they should be varied:

a. A collection of human VK light chain DNA sequences was obtained from NCBI (see Appendix A of WO/2009/036379 for GI Nos.). These sequences were classified according to the germline origin of their VK germline segment.

b. Patterns of variation at each of the Vernier and interface positions were examined as follows:

i. Equation 1 (from Makowski & Soares, Bioinformatics, 2003, 19: 483, incorporated by reference in its entirety) was used to calculate a diversity index for the Vernier positions, interface positions, CDRL1, and CDRL2.

$$d = \frac{1}{N\Sigma p_i^2} \qquad \text{Equation 1}$$

Figure 1:
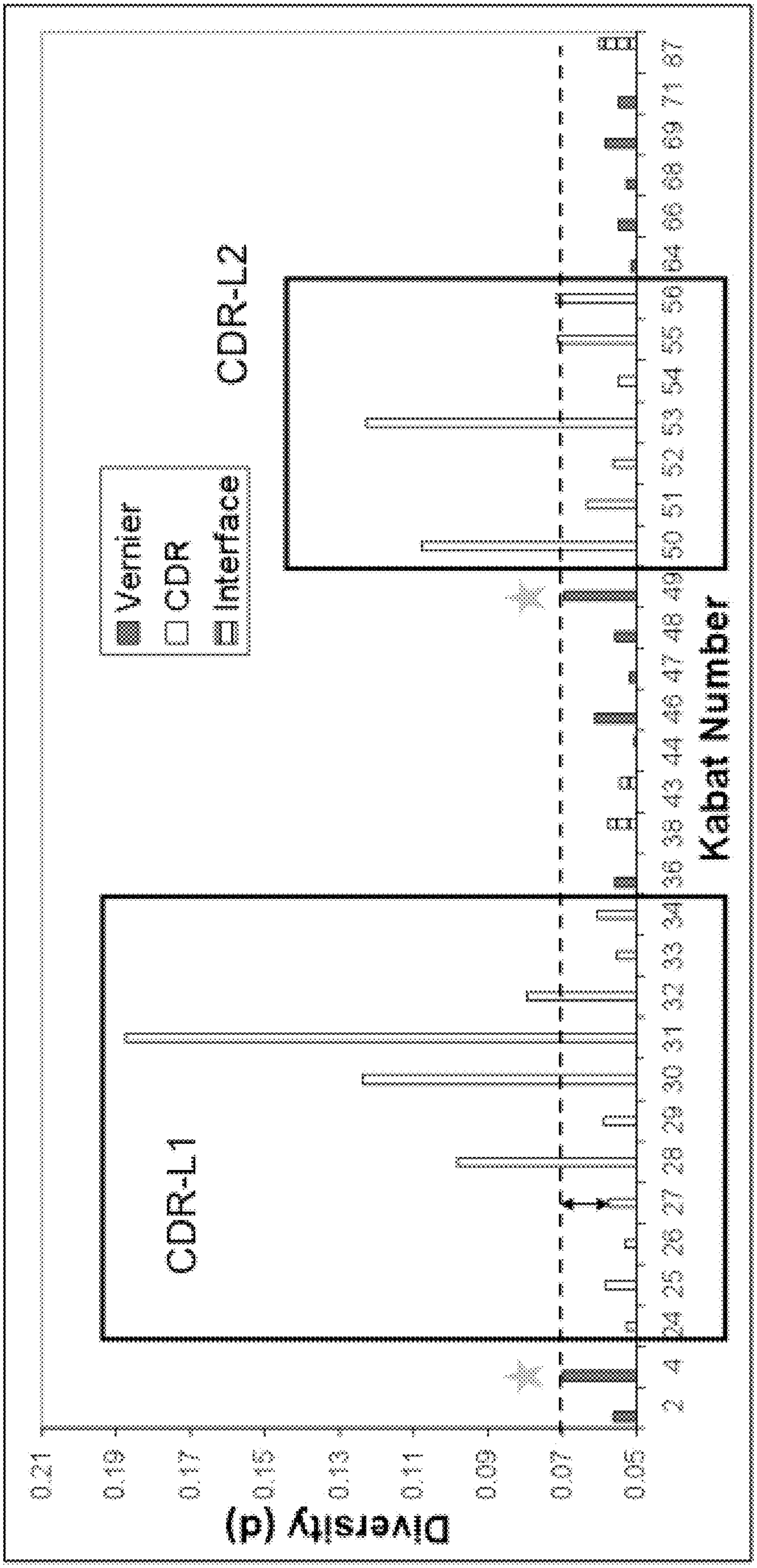
FIG. 1 shows that Vernier residues 4 and 49 (starred) in VK1-39 have a diversity index comparable to or greater than the diversity indices of the CDR positions (i.e., at or above 0.07, in this example).

Here, d is the diversity index, N is 20, the total number of amino acid types, and $p_i$ is the fraction of amino acid of type "i" at the position of interest. The sum is carried out over the 20 amino acid types. The parameter d will attain its minimum value of 0.05 or 1/20, when a single amino acid type is observed at a given position: $p_i$ is 1 for one type and zero for all the rest. Conversely, when all the amino acid types are equally probable (e.g., $p_i$ is 0.05 for all i), d will attain its maximum value of 1.0.

ii. The diversity index for each of the Vernier and interface positions were compared to the diversity index for the positions in CDRL1 and CDRL2.

iii. The interface positions were found to be relatively invariant, with d values very close to the minimum of 0.05, and were thus not altered. The Vernier residues with a diversity index comparable to or larger than that of the CDR positions (i.e., at or above 0.07 for the particular example provided in FIG. 1) were selected as candidates for variance (see FIG. 1). The amino acid residues included in these positions were selected from amongst the two to three amino acids most frequently occurring in that position in the sequences in the collection of human VK light chains, for each particular VK germline.

iv. Table 2 shows the positions selected for variance in each of nine exemplified light chain germlines. The alternative framework positions represent positions with a diversity index less than the primary framework positions, but where variability may still be incorporated to influence antigen binding.

v. The amino acid residues in the framework positions selected for variance were varied as follows (Table 3 provides the polypeptide sequences of these variants):

1. Position 2: Germline I was optionally changed to V.
2. Position 4: Germline M or L was optionally changed to L or M. In some embodiments, changes from M to L, but not the reverse, may be preferred, because M may undergo oxidation during production, processing, or storage, potentially altering the properties of the antibody.
3. Position 36: Germline Y was optionally changed to F and H.
4. Position 46: Germline L was optionally changed to V.
5. Position 48: Germline I was optionally changed to L.
6. Position 49: Germline Y was optionally changed to S, F, and H.
7. Position 66: Germline G was optionally changed to R and E.

One of ordinary skill in the art would readily recognize that the procedure outlined above could also be used to select positions to vary in Vλ germline sequences, and that libraries containing Vλ chains also fall within the scope of the invention.

In addition to the framework mutations, variability was also introduced into CDRL1 and CDRL2. This was performed by determining which residues in CDRL1 and CDRL2 were variable, within a particular germline, in the VK dataset used above and incorporating the most frequently occurring 2 to 4 variants into CDRL1 and CDRL2 in the synthetic libraries of the invention. With the exception of position 50 of CDRL2 of the VK1-5 germline, these alternatives did not arise from allelic variation. Table 3 shows the polypeptide sequences of nine light chain chassis and their framework and CDR L1/L2 variants for the currently exemplified embodiment of the invention. The amino acid residues in the CDRL1/L2 positions selected for variance were varied as follows (using the Chothia-Lesk numbering system; Chothia and Lesk, J. Mol. Biol., 1987, 196: 901):

1. Position 28: Germline S or G were optionally changed to G, A, or D.
2. Position 29: Germline V was optionally changed to I.
3. Position 30: Germline S was optionally changed to N, D, G, T, A, or R.
4. Position 30A: Germline H was optionally changed to Y
5. Position 30B: Germline S was optionally changed to R or T.
6. Position 30E: Germline Y was optionally changed to N.
7. Position 31: Germline S was optionally changed to D, R, I, N, or T.
8. Position 32: Germline Y or N were optionally changed to F, S, or D.
9. Position 50: Germline A, D, or G were optionally changed to G, S, E, K, or D.
10. Position 51: Germline G or A were optionally changed to A, S, or T.
11. Position 53: Germline S or N were optionally changed to N, H, S, K, or R.
12. Position 55: Germline E was optionally changed to A or Q.

Example 2. Light Chain Libraries with Enhanced Diversity in CDRL3

Figure 2:
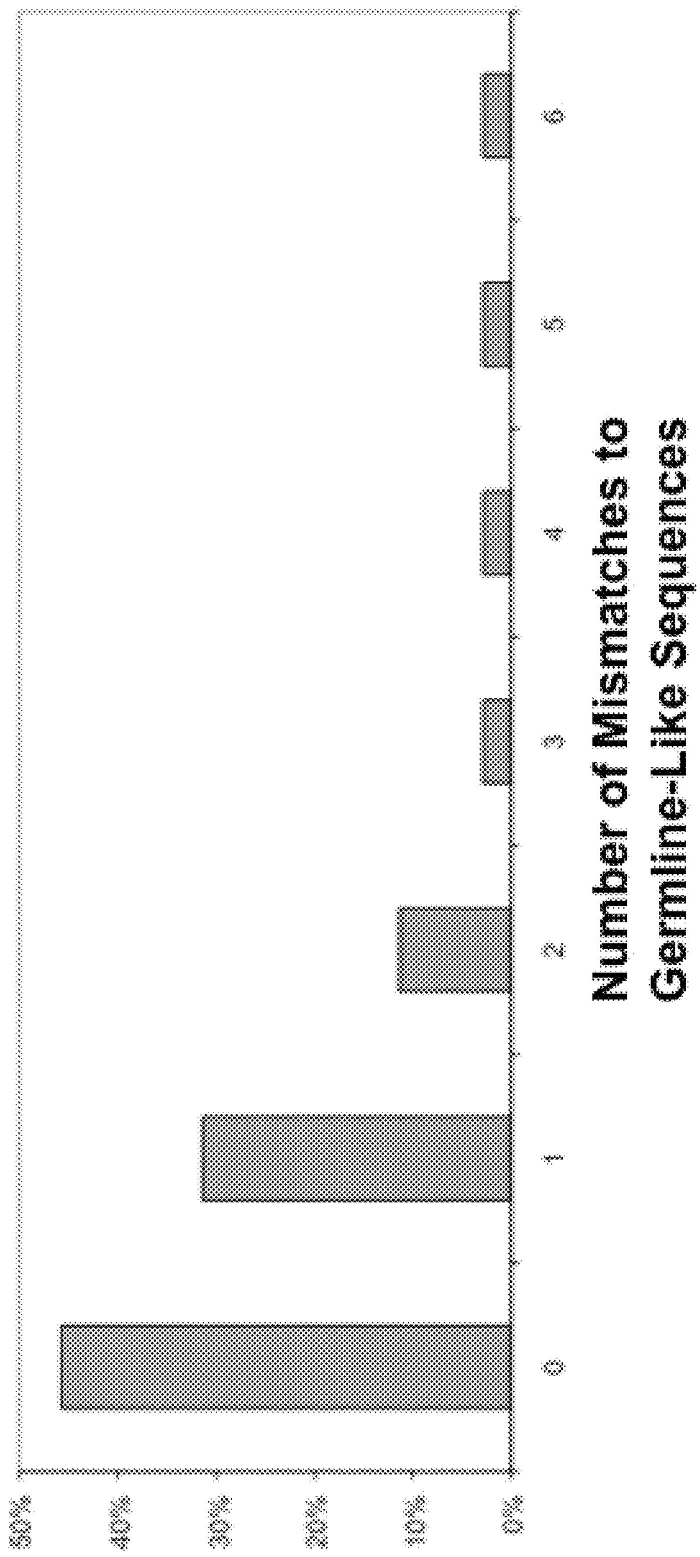
FIG. 2 shows that clinically validated CDRL3 sequences deviate little from germline-like sequences (n=35).

A variety of methods of producing light chain libraries are known in the art (e.g., see U.S. Publication Nos. 2009/0181855, 2010/0056386, and WO/2009/036379). An analysis of clinically validated antibody sequences indicated that these sequences have very little deviation from germline-like VL-JL (where "L" can be a kappa or lambda germline sequence) rearrangements prior to somatic mutation (FIG. 2). Here, a germline-like rearrangement is one where neither the V nor J portion differ from the respective germline genes and, for the purposes of this particular example, where the length of CDRL3 is restricted to 8, 9 or 10 amino acids (see U.S. Publication Nos. 2009/0181855, 2010/0056386, and WO/2009/036379). For the IGHJK1 gene, however, both WT (Trp-Thr) and RT (Arg-Thr) sequences (the first two N-terminal residues) are considered "germline-like" and so are full L3 rearrangements containing such sequences. Therefore, new light chain libraries were designed and constructed with the objectives of simultaneously (1) minimizing deviation from germline-like sequences, as defined above; and (2) generating maximal diversity. In particular, the overarching goal was to maximize the type of diversity that is indicated to be most favorable by clinically validated antibody sequences. In particular, the designed library sought to maximize the diversity of CDRL3 sequences that differ from length-matched germline sequences by two amino acids or fewer.

This was accomplished by utilizing a "jumping dimer" or "jumping trimer" approach to light chain oligonucleotide design. The jumping dimer approach involves the incorporation of degenerate codons at each of the six positions of CDRL3 encoded by the VL segment (L3-VL). At most two positions vary from germline in each individual L3-VL sequence, but the two positions do not have to be adjacent to one another. Thus, the total number of designed degenerate oligonucleotides synthesized per VL chassis is 6!/(4!2!), or fifteen (accounting for six of the most commonly occurring amino acids at the junction (position 96) between VL and JL for each kappa germline chassis (namely F, L, I, R, W, Y, and P; see U.S. Publication Nos. 2009/0181855 and 2010/0056386, and WO/2009/036379, each of which is incorporated by reference in its entirety, for more details on the junctional amino acids at position 96). The jumping trimer approach is analogous to the jumping dimer approach, but with three positions varying from germline in each individual L3-VL sequence, instead of two as in the jumping dimer. The degenerate codons selected for each position in the jumping dimer and trimer approaches were chosen to (1) to reproduce the diversity contained in the known repertoire of publicly available human VK sequences (see Appendix A of WO/2009/036379); and (2) to minimize or eliminate undesirable sequences within the CDRL3s of the resulting synthetic light chains, such as N-linked glycosylation motifs (NXS/NXT), Cys residues, stop codons, and deamidation-prone NG motifs. Table 4 shows the fifteen degenerate oligonucleotides encoding the VK1-39 CDRL3 sequences with a length of nine amino acids and F or Y as the junctional amino acid, and the corresponding degenerate polypeptide sequences. Table 5, Table 6, and Table 7 provide the oligonucleotide sequences for each of the VK sequences of the exemplary jumping dimer and trimer libraries, for CDRL3 lengths of 8, 9, and 10, respectively, and the sequences for the corresponding CDRL3s.

The number of unique CDRL3 sequences within each germline library was then enumerated and compared to the number of unique CDRL3 sequences in a different light chain library, designated "VK-v1.0" (see Example 6.2 in US Publication No. 2009/0181855), for each of the three lengths. Table 8 provides the number of unique CDRL3 sequences in each of the respective germline libraries.

Figure 3:
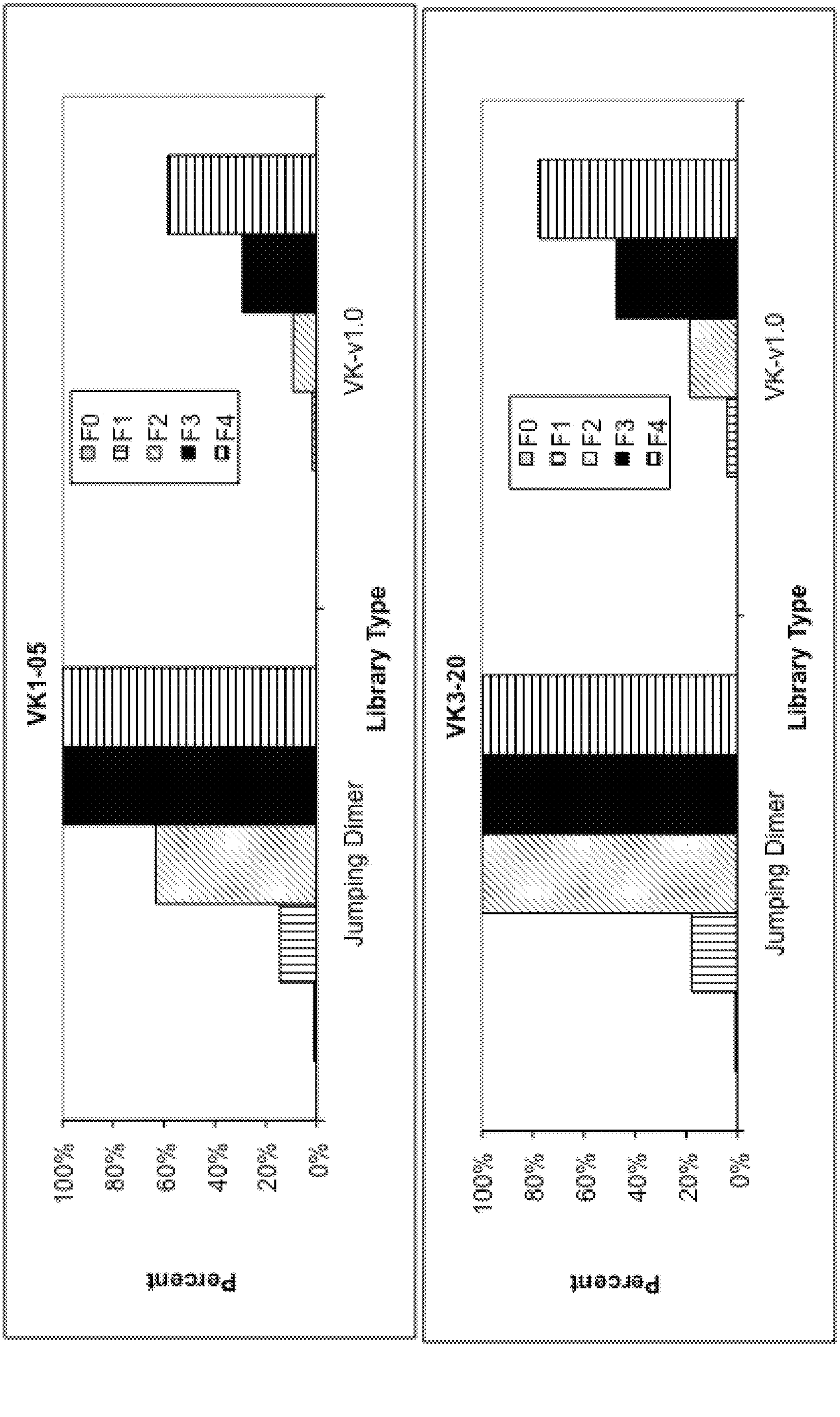
FIG. 3 shows the percent of sequences in the jumping dimer CDRL3 libraries of the invention and a previous CDRL3 library, VK-v1.0, with X or fewer mutations from germline. Here, FX is the percentage of sequences in a library with X or fewer mutations from germline.

FIG. 3 provides the percentage of sequences in the jumping dimer and VK-v1.0 libraries with CDRL3 length of nine amino acids that contain no mutations from germline-like sequences (Table 1) or 1, 2, 3, or 4 or fewer mutations from germline-like sequences. Naturally-occurring VK1-05 sequences are almost as likely to have Ser (germline amino acid type) as Pro at Kabat position 95, thus both residues (S and P) were incorporated in the synthetic libraries representing VK1-05 repertoires. However, as indicated in Table 1, only Ser was considered to be a germline-like residue at position 95 for the purposes of this analysis when the VK gene is VK1-05. The plot for VK3-20 is representative of the remaining chassis in the library for a length nine. All of the sequences in the VK1-05 library were within three amino acids of human germline sequences, and approximately 63% of the sequences were within two amino acids of human germline-like sequences. For the rest of the libraries, and as designed, 100% of the sequences were within two amino acids of human germline-like sequences; thus, over 95% of the sequences of length 9 in the jumping dimer library considered as a whole were within 2 amino acids of germline-like sequences. By comparison, only 16% of the members of the VK-v1.0 libraries of length nine amino acids are within two amino acids of the corresponding human germline-like sequences. For length 8, about 98% of the sequences in the jumping dimer libraries were within two amino acids of germline-like, versus about 19% for VK-v1.0. For length 10, more than 95% of the sequences of the jumping dimer library were within two amino acids of germline-like, versus about 8% for VK-v1.0.

In some embodiments, to concentrate the diversity in positions most likely to be solvent-exposed in the folded antibody, positions 89 and 90 (Kabat numbering) are not modified from germline—these are most often QQ, but the sequence is MQ for the VK2-28 chassis. Other VK germline genes have different sequences at positions 88-89, and the use of these genes as chassis also falls within the scope of the invention. For example, VK1-27 has QK, VK1-17 and VK1-6 both have LQ, and so on. The sequences in these positions are known in the art and can be obtained, for example, from Scaviner et al., Exp. Clin. Immunogenet., 1999, 16: 234 (see FIG. 2), which is incorporated by reference in its entirety.

CDRH3 Libraries

The following examples describe methods and compositions useful for the design and synthesis of antibody libraries with improved CDRH3 sequences in comparison to libraries known in the art. The CDRH3 sequences of the invention have enhanced diversity in comparison to libraries known in the art, while retaining the character of human sequences, improving combinatorial efficiency of the synthetic CDRH3 segments, and/or improving the matching between synthetic CDRH3 sequences and human CDRH3 sequences in one or more reference sets.

Example 3. Generating a Curated Reference Set of Human Preimmune CDRH3 Sequences A file containing approximately 84,000 human and mouse heavy chain DNA sequences was downloaded from the BLAST public resource (ftp.ncbi.nih.gov/blast/db/FASTA/; filename: igSeqNt.gz; download date: Aug. 29, 2008). Of these approximately 84,000 sequences, approximately 34,000 sequences were identified as human heavy chain sequences based on analysis of the sequence header annotation. These sequences were then filtered as follows: First, all sequences were classified, via their VH-region, according to their corresponding (closest matched) VH germline. Sequences that were of an incorrect or insufficient length, or that could not be matched due to extensive mutation, were discarded. Second, any sequences containing more than five mutations, at the DNA level, when compared to their corresponding germline VH sequence were also discarded. It was assumed, consistent with Rada and Milstein, EMBO J., 2001, 20: 4570, that mutations (or lack thereof) in the N-terminal portion of the variable region may be used as conservative surrogates for mutations (or lack thereof) in the C-terminal portion of the variable region, in particular in CDRH3. Therefore, selecting only sequences with five or fewer nucleotide mutations in VH, which is N-terminal to CDRH3 is highly likely to also select for CDRH3 sequences that are either lightly mutated or not mutated at all (i.e., having preimmune character).

After translating the remaining DNA sequences into their amino acid counterparts, the appropriate reading frame containing the heavy chain germline amino acid sequence was identified and used to identify the sequences of the CDRs, including that of the CDRH3. The list of CDRH3 sequences obtained at this point was further filtered to eliminate members that did not differ from any other sequence in the set by at least three amino acids (after matching for length). This process yielded 11,411 CDRH3 sequences, with 3,571 sequences annotated as originating from healthy adults ("Healthy Preimmune Set" or "HPS"; see Appendix A for GI Nos.) and the other 7,840 sequences annotated as originating from individuals suffering from disease, of fetal origin, or of antigen-specific origin. The methods described below were then used to deconvolute each of the sequences in the HPS into the four segments that constitute the CDRH3: (1) TN1, (2) DH, (3) N2, and (4) H3-JH.

Example 4. Method to Match Segments from a Theoretical Segment Pool to CDRH3s in a Reference Set This example describes the method used to identify the TN1, DH, N2, and H3-JH segments of the CDRH3s in the HPS. The currently exemplified approach to the design and synthesis of human CDRH3 sequences mimics the segmental V-D-J gene recombination processes by which the human immune system generates the preimmune CDRH3 repertoire. The matching method described here determines which TN1, DH, N2 and H3-JH segments have been used to produce a particular CDRH3 across a reference set of CDRH3s (e.g., the HPS). This information is then used, optionally in conjunction with other information described below (e.g., physicochemical properties), to determine which TN1, DH, N2, and H3-JH segments from a theoretical segment pool (or segments extracted from the CDRH3 sequences in the reference set, in the case of the TN1 and N2) should be included in a synthetic CDRH3 library.

The inputs to the matching method are: (1) a reference set of CDRH3 sequences (e.g., the human CDRH3 sequences in the HPS), and (2) a theoretical segment pool, containing a plurality of TN1, DH, N2 and/or H3-JH segments. Methods by which the members of the theoretical segment pool are generated are more fully described below. For each CDRH3 in the reference set, the matching method generates two outputs: (i) a list of the closest matched CDRH3 sequences that can be generated using the segments of the theoretical segment pool, and (ii) the one or more segment combinations from the theoretical segment pool that can be used to create these closest matched CDRH3 sequences.

The matching method was performed as follows: Each TN1 segment in the theoretical segment pool was aligned at its first amino acid with the first amino acid (position 95) of the CDRH3 sequence from the reference set. For each segment length, all (i.e., one or more) of the segments returning the best matches are retained, and the remaining segments are discarded. The retained TN1 segments are then concatenated with all DH segments from the theoretical segment pool, to create [TN1]-[DH] segments. These segments are then aligned as above, and all the best matches for each of the [TN1]-[DH] segments are retained. The procedure is repeated with [TN1]-[DH]-[N2] and [TN1]-[DH]-[N2]-[H3-JH] segments until the length of the CDRH3 sequence from the reference set is identically recapitulated by the segment combinations from the theoretical segment pool. All segment combinations returning the best match to the CDRH3s in the reference set are retained as the output of the matching method.

Table 9 provides an example of the output of the matching method, specifically the output for four individual sequences from the HPS, using a theoretical segment pool designated "Theoretical Segment Pool 1," or "TSP1". TSP1 contains several theoretical segment pools, namely: 212 TN1 segments (Table 10), 1,111 DH segments (Table 11), 141 N2 segments (Table 12), and 285 H3-JH segments (Table 13). The CDRH3 sequence in Test Case 1 contains an identical match in TSP1 that is reached via a unique combination of the four segments. Test Cases 2.1 and 2.2 each return an identical match, but via two distinct combinations that differ in the TN1 and DH segments. In Test Cases 3.1, 4.1, and 4.2, the closest matches are all a single amino acid away from the reference CDRH3, and can be reached via one (3.1) or two (4.1 and 4.2) combinations of segments from TSP1. This approach can be generalized to find all of the closest matches to any reference CDRH3 sequence within any theoretical segment pool and all combinations of the segments within the theoretical segment pool that can produce the reference CDRH3 sequence exactly and/or its closest matches.

Example 5. Deriving Theoretical Segment Pools of H3-JH Segments

In order to produce theoretical segment pools of H3-JH segments for consideration for inclusion in a synthetic CDRH3 library, the following method was applied to generate mutants of seven (IGHJ1-01, IGHJ2-01, IGHJ3-02, IGHJ4-02, IGHJ5-02, IGHJ6-02 and IGHJ6-03) of the twelve germline IGHJ sequences of Table 14. These seven alleles were chosen because they were among the most commonly occurring alleles in human sequences. Libraries where all sequences of Table 14 (some differing only in FRM4) are used to generate H3-JH and/or JH (i.e., H3-JH and FRM4) also fall within the scope of the invention. The method is intended to simulate the creation of junctional diversity during the V-D-J recombination process in vivo, which occurs via enzyme-mediated addition and deletion of nucleotides to the germline gene segments. The method proceeds as follows, and results in a fully enumerated theoretical segment pool of H3-JH segments:

1. A pre-treatment was applied to the IGHJ genes that contain a partial codon consisting of two nucleotide bases at their 5' terminus (IGHJ3-02, IGHJ4-02, IGHJ5-02, IGHJ6-02 and IGHJ6-03), prior to the first nucleotide encoding the translation of the JH segment that produces the well-known JH framework regions. For example, the IGHJ3-02 gene contains an AT dinucleotide sequence prior to the first nucleotide encoding the translation of the JH segment that produces the JH framework region (FIG. 4, top). All partial codons consisting of two nucleotide bases were completed, using all possible nucleotide doublets (i.e., NN) at their two most 5' positions (FIG. 4, top, second row for IGHJ3-02). More specifically, the most 5' nucleotide in the germline sequence was mutated to N and an additional N was added 5' to that nucleotide.
2. IGHJ genes IGHJ1-01 (FIG. 4, center) and IGHJ2-01 (FIG. 4, bottom) contain zero and one nucleotide base(s) at their 5' termini, prior to the first nucleotide encoding the translation of the JH segment that produces the JH framework region. For these genes, the pre-treatment described in step 1 was not performed. Instead, the 5' doublets were mutated to NN (FIG. 4, middle and bottom, second row of each). Therefore, after performing this step, each of the seven IGHJ genes enumerated above was converted to a variant with an NN doublet as its first two 5' positions.
3. The 5' codons of the sequences produced via steps 1 and 2 were then deleted, and the first two bases of the resulting DNA sequence were subsequently mutated to an NN doublet (FIG. 4, rows 3-4 for all).
4. The 5' codons of the sequences produced in step 3 were then deleted, and the first two bases of the resulting DNA sequence were subsequently mutated to an NN doublet (FIG. 4, rows 5-6 for all).
5. Each of the polynucleotide sequences generated by steps (1)-(4) were then translated, to obtain a theoretical segment pool consisting of 248 parent H3-JH polypeptide segments (Table 15) from the reading frame for each sequence that produced the JH framework region.
6. The parent H3-JH polypeptide segments were truncated at their N-termini, by removing one amino acid at a time until only the portion of the JH segment comprising FW4 remains (i.e., an H3-JH segment with a length of zero amino acids).

The methods described above resulted in the production of a theoretical segment pool of 285 H3-JH segments (Table 13).

Example 6. Deriving Theoretical Segment Pools of DH Segments

Two theoretical pools of DH segments were generated, using one or more of two translation methods, designated "Translation Method 0" (TM0), or "Translation Method 1" ("TM1"), each performed in the three forward reading frames of 27 human germline IGHD DNA sequences or segments derived therefrom (Table 16).

The 1K DH Theoretical Segment Pool (1K DH)

TM1 was used to generate the "1K DH Theoretical Segment Pool" ("1K DH"; see the 1,111 DH segments of Table 11). In TM1, IGHD sequences that had a partial codon containing two untranslated bases after translation in any of the three forward reading frames were completed to produce a full codon only if the two bases could encode only a single amino acid upon completion. For example, a DNA sequence such as TTA-GCT-CG has two full codons that would be translated to LA, and a remaining partial codon (CG) that can only encode R, as any of CGA, CGC, CGG, or CGT will encode R. Thus, applying TM1 to this sequence will yield LAR. For sequences with partial codons that could encode more than one amino acid (e.g., GA or AG), the partial codons were ignored. Applying TM1 to the 27 IGHD sequences of Table 16 generated a theoretical segment pool containing the 73 DH parent segments of Table 17 (some containing stop codons ("Z") and unpaired Cys residues). These sequences were then progressively deleted at the amino acid level, at their N- and C-termini, until only two amino acids remained. Truncated segments were discarded if they contained a stop codon, unpaired Cys residues, N-linked glycosylation motifs, or deamidation motifs. This process yielded the 1,111 DH segments of Table 11.

The 68K DH Theoretical Segment Pool (68K DH)

The 27 IGHD genes and alleles of Table 16 were progressively deleted on either or both of their 5' and 3' ends until four bases remained, yielding 5,076 unique polynucleotide sequences of four or more nucleotides. These 5,076 sequences were subjected to systematic addition of 0, 1 and/or 2 N nucleotides their 5' and/or 3' ends. The resulting sequences were translated using TM0. In TM0, only full codons are translated; partial codons (i.e., 1 or 2 bases) are ignored. This method yielded 68,374 unique DH polypeptide segments after elimination of segments with stop codons, unpaired Cys residues, Asn in the last or next to last position that can lead to N-linked glycosylation motifs, and deamidation motifs (the "68K DH Theoretical Segment Pool"). Using the IGHD genes of Table 16 as an input for the PYTHON computer code provided below will reproduce the exact theoretical segment pool of 68,374 DH segments. There are two free parameters in this program: (1) the minimum length of the DNA sequences remaining after progressive deletions (4 bases in this example), and (2) the minimum length of the peptide sequences (2 amino acids in this example) acceptable for inclusion in the theoretical segment pool. These parameters can be changed to alter the output of the program. For example, changing the first parameter to one base and the second parameter to one amino acid would lead to a larger theoretical segment pool with 68,396 unique sequences, including 18 single-amino acid segments. DH segments progressively truncated to different lengths also fall within the scope of the invention; for example those truncated to 1, 2, 3, or 4 or more amino acids, or 1, 2, 3, 4, 5, 6, 7, 8, 9, 10, or more nucleotides prior to translation.

PYTHON Computer Program to Generate 68,374 DH Segments

```
import math, sys, string
class genes:
    name = 'x'
    seq = 'x'
    progdel = set( )
class table:
    name = 'x'
    dna = 'x'
    dna_n = 20 * ['x']
    prot = 60 * ['x']
    uprot = set( )
pepcod = { 'A':0, 'C':1, 'D':2, 'E': 3, 'F': 4, 'G': 5, 'H': 6,
'I':7, 'K':8, 'L': 9, 'M': 10,
'N':11, 'P':12, 'Q':13, 'R': 14, 'S': 15, 'T': 16, 'V':17,
'W':18, 'Y': 19, 'Z': 20}
codpep = 21 * ['']
codpep[0] = 'A'
codpep[1] = 'C'
codpep[2] = 'D'
codpep[3] = 'E'
codpep[4] = 'F'
codpep[5] = 'G'
codpep[6] = 'H'
codpep[7] = 'I'
codpep[8] = 'K'
codpep[9] = 'L'
codpep[10] = 'M'
codpep[11] = 'N'
codpep[12] = 'P'
codpep[13] = 'Q'
codpep[14] = 'R'
codpep[15] = 'S'
codpep[16] = 'T'
codpep[17] = 'V'
codpep[18] = 'W'
codpep[19] = 'Y'
# Z represents a stop codon
codpep[20] = 'Z'
bases = 'ACGT'
def translate_dna(sequence):
    # Translation of input DNA sequence using standard genetic code
    # Only full codons are considered with any remaining 1 or 2 bp
    being ignored
    # Z represents a stop codon
        code = {
        'ATA':'I', 'ATC':'I', 'ATT':'I', 'ATG ':'M',
        'ACA':'T', 'ACC':'T', 'ACG':'T', 'ACT':'T',
        'AAC':'N', 'AAT':'N', 'AAA':'K', 'AAG':'K',
        'AGC':'S', 'AGT':'S', 'AGA':'R', 'AGG':'R',
        'CTA':'L', 'CTC':'L', 'CTG':'L', 'CTT':'L',
        'CCA':'P', 'CCC':'P', 'CCG':'P', 'CCT':'P',
        'CAC':'H', 'CAT':'H', 'CAA':'Q', 'CAG':'Q',
        'CGA':'R', 'CGC':'R', 'CGG':'R', 'CGT':'R',
        'GTA':'V', 'GTC':'V', 'GTG':'V', 'GTT':'V',
        'GCA':'A', 'GCC':'A', 'GCG':'A', 'GCT':'A',
        'GAC':'D', 'GAT':'D', 'GAA':'E', 'GAG':'E',
        'GGA':'G', 'GGC':'G', 'GGG':'G', 'GGT':'G',
        'TCA':'S', 'TCC':'S', 'TCG':'S', 'TCT':'S',
        'TTC':'F', 'TTT':'F', 'TTA':'L', 'TTG':'L',
        'TAC':'Y', 'TAT':'Y', 'TAA':'Z', 'TAG':'Z',
        'TGC':'C', 'TGT':'C', 'TGA':'Z', 'TGG':'W',
        )
        proteinseq = ''
        for n in range(0,1en(sequence),3):
            if code.has_key(sequence[n:n+3]) == True:
                proteinseq += code[sequence[n:n+3]]
        return proteinseq
# main body starts here
# open input and output files
in1 = open(sys.argv[1], 'r')
ou1 = open(sys.argv[2], 'w')
# read DNA sequences for input DH segments
data = in1.readlines( )
nseg = len(data)
seqs = [ genes( ) for i in range(nseg) ]
for i in range(nseg):
    line = data[i]
    words = string.split(line)
    seqs[i].name = words [0]
    seqs[i].seq = words [1]
    seqs[i].progdel = set( )
# Define here minimum length for DNA (4) and for protein (2)
minlen = 4
minp = 2
# Implement progressive base by base deletion from 5' or 3' or
both ends
alln = 0
for i in range(nseg):
    seq = seqs[i].seq
    lseq = len(seq)
    nt = ct = lseq
    for n in range(nt):
        for c in range(ct):
            nseq = seq[n:lseq-c]
            if (len(nseq) >= minlen):
                seqs[i].progdel.add(nseq)
    alln += len(seqs[i].progdel)
# Collect unique DNA sequences across all DH genes of origin
and ignore redundant ones
progdel = [table( ) for i in range(alln) ]
n = 0
for i in range(nseg):
    for kk in seqs[i].progdel:
        unix = 1
        for j in range(n):
            if (kk == progdel[j].dna):
                unix = 0
                break
        if (unix == 1):
            progdel[n].name = seqs[i].name
            progdel[n].dna = kk
            n +=1
# Add none, 1 or 2 bp on one or both ends
# extras 20 + 20 * (21) = 20 + 420 = 440
# allocate memory for all variants
for i in range (n)
    progdel[i].dna_n = 440 * ['x']
    progdel[i].prot = 441 *3 * ['x']
    progdel[i].uprot = set( )
# add 1 or 2 bases at each end of input segment
tot = 0
for i in range (n)
# Step over each unique DNA sequence
    k = 0
# One base on 5' end combined with 1 or 2 bases added to 3' end
    for 15 in range (4)
        progdel[i].dna_n[k] = bases[15] + progdel[i].dna
        k +=1
        for 13 in range(4):
            progdel[i].dna_n[k] = bases[15] + progdel[i].dna +
bases [13]
            k +=1
```

-continued

PYTHON Computer Program to Generate 68,374 DH Segments

```
        for 13 in range(4):
          for m3 in range (4):
            progdel[i].dna_n[k] = bases[15] + progdel[i].dna +
bases[13] + bases [m3]
            k +=1
# One or two bases added to 3' only in this part
    for 13 in range (4)
      progdel[i].dna_n[k] = progdel[i].dna + bases [13]
      k +=1
    for 13 in range (4)
      for m3 in range(4):
        progdel[i].dna_n[k] = progdel[i].dna + bases[13] +
bases [m3]
        k +=1
# Two bases on 5' end combined with 1 or 2 bp on 3' end
    for 15 in range (4)
      for m5 in range(4):
        progdel[i].dna_n[k] = bases[15] + bases[m5] +
progdel[i].dna
        k +=1
        for 13 in range (4):
          progdel[i].dna_n[k] = bases[15] + bases[m5] +
progdel[i].dna + bases [13]
          k +=1
        for 13 in range (4):
          for m3 in range (4)
            progdel[i].dna_n[k] = bases[15] + bases[m5] +
progdel[i].dna + bases[13] + bases[m3]
            k +=1
# Now translate in all 3 forwared reading frames
# Save unique peptide sequences
    for fr in range(3):
      piece = progdel[i].dna
      piece = piece[fr:]
      tpiece = translate_dna(piece)
      progdel[i].prot[fr] = tpiece
      progdel[i].uprot.add(tpiece)
      for k in range (440):
        piece = progdel[i].dna_n[k]
        piece = piece[fr:]
        tpiece = translate_dna(piece)
        progdel[i].uprot.add(tpiece)
        progdel[i].prot[3+440*fr +k] = tpiece
    tot += len(progdel[i].uprot)
# Collect unique sequences with no ASN at last or next to last
position, no unpaired or consecutive CYS, no stops
unset = set( )
segm = [ genes( ) for i in range(tot) ]
lux = 0
nn = 0
for i in range (n)
        k = 0
        for kk in progdel[i].uprot:
# Filter out sequences with undesired features, including
length being too short (under "minp" defined above)
                if (len(kk) < minp): continue
                if (kk[len(kk)-1] == "N" or kk[len(kk)-2] ==
"N"): continue
                if (kk.count("Z") > 0 or kk.count("CC") >0 or
kk.count("C") % 2 >0): continue
                unset.add(kk)
                lux1 = len(unset)
                if (lux1 > lux):
                    segm[nn].name = progdel[i].name + "_" +
str(nn)
                    segm[nn].seq = kk
                    nn += 1
                lux = lux1
                k += 1
# Print out unique peptide sequences that pass all the filters
for i in range (nn):
        ou1.write("%s\t%s\n" % (segm[i].name, segm[i].seq))
```

Example 7. Deriving Theoretical Segment Pools of TN1 and N2 Segments

The libraries of this example are designed to, in some instances, have a greater diversity in their TN1 and N2 segments in comparison to other libraries known in the art. The diversity of the TN1 and N2 segments was increased by using the matching method described in Example 4 to deconvolute the CDRH3 sequences in the HPS into their constituent segments (i.e., TN1, DH, N2, and H3-JH), followed by extraction of "novel" TN1 and N2 segments in the manner described below. For the purposes of the invention, "novel" TN1 and N2 segments are TN1 and N2 segments that do not appear in a theoretical segment pool that is matched to a reference set of CDRH3 sequences. Following is an example of the method used to extract novel TN1 and N2 segments from the HPS. This method can be generalized to extract novel TN1 and N2 segments from any reference set of CDRH3 sequences, using any theoretical segment pool containing TN1, DH, N2, and/or H3-JH segments.

Table 9 provides the matching results for the reference CDRH3 sequence ERTINWGWGVYAFDI (SEQ ID NO: 8760) (Test Cases 5.1-5.4) from the HPS, using Theoretical Segment Pool 1 ("TSP1"). The best matches to the reference CDRH3 are four CDRH3 sequences, each within three amino acids of the reference CDRH3 sequence. In each of these matches, the TN1, DH, N2 and H3-JH segments are of length 4, 3, 3 and 5 amino acids, respectively. Thus the reference CDRH3 can be deconvoluted into the following segments: ERTI-NWG-WGW-YAFDI (SEQ ID NO: 8761) (i.e. [TN1]-[DH]-[N2]-[H3-JH], respectively). The DH and H3-JH segments from the reference CDRH3, NWG and YAFDI (SEQ ID NO: 4540) respectively, are identically present in TSP1. However, the TN1 (ERTI) (SEQ ID NO: 8718) and N2 (WGW) segments from the reference CDRH3 are absent in TSP1 and match TSP1 segments with one or more amino acid mismatches. These "novel" TN1 and N2 segments are extracted from the reference CDRH3 and considered for inclusion prospective theoretical segment pools and/or synthetic libraries. Additional novel TN1 and N2 segments were accumulated by applying this analysis to all members of the HPS. In order to robustly identify TN1 and N2 sequences, the extraction was performed only for those CDRH3 sequences in which the DH and H3-JH segments in the reference CDRH3 and TSP1 cumulatively return no more than 3 amino acid mismatches, implying that the DH and H3-JH segments of the reference CDRH3 had been reliably assigned.

Example 8. Calculation of Segment Usage Weights

Segment usage weights were calculated for their utility in determining which segments from the theoretical segment pools (e.g., TSP1 and TSP1 plus novel TN1 and N2 segments identified as described in Example 7) should be included in a synthetic library. Segment usage weights were obtained by utilization of the matching method described above and Equation 2:

$$w(i) = \frac{1}{S_m}\sum_{j=1}^{S_m}\frac{1}{g(j)}\sum_{k=1}^{g(j)} f_i(k) \quad \text{Equation 2}$$

where, w(i): Weight for segment i. 0≤w(i)≤1.

$S_m$: Number of sequences (out of total S in the reference CDRH3 set) which contain one or more best matches with no more than m amino acid mismatches in the specified region of the reference CDRH3 sequence. Here, the mismatches are computed over the Kabat-CDRH3 region, but other fragments of the CDRH3 sequences may also be considered. A constant value of m=3 was used here, but other values may be used, or the value may depend on the length of the reference CDRH3 sequence.

g(j): Total number of degenerate segment combinations producing the best match to the reference CDRH3 sequence j.

$f_i(k)$: Fractional amino acid identity of TN1, DH, N2 or H3-JH segment in degenerate match k, relative to the corresponding sequence fragment in the reference CDRH3 sequence j. The fractional amino acid identity equals zero if the segment does not appear in match k. Other definitions off such as amino acid similarity (e.g., based on physicochemical properties of the amino acids such as hydrophobicity), instead of identity, may be also used.

The procedure for calculating segment usage weights will be further exemplified below. In each of these examples, the best match combinations from TSP1 are provided for a single CDRH3 sequence ($S_m$=1) and the degeneracy (k) and fractional mismatch (f) dependent weight calculations are explained.

Example 8.1. Segment Usage Weights for Test Case 1 in Table 9

Refer to Test Case 1 in Table 9. The CDRH3 sequence RTAHHFDY (SEQ ID NO: 3660) is identically located in TSP1 (f=1, subscripts dropped for simplicity) via a unique segment combination (g=1). Table 18 provides the usage weights for the segments corresponding to the best match from TSP1 for the CDRH3 of Test Case 1.

Example 8.2. Segment Usage Weights for Test Cases 2.1 and 2.2 in Table 9

Refer to Test Cases 2.1 and 2.2 in Table 9. The CDRH3 sequence VGIVGAASY (SEQ ID NO: 3661) may be identically located in TSP1 (f=1) via two distinct segment combinations (g=2). Table 19 provides the usage weights for the segments corresponding to the best match from TSP1 for the CDRH3 of Test Cases 2.1 and 2.2.

Example 8.3. Segment Usage Weights for Test Case 3.1 in Table 9

Refer to Test Case 3.1 in Table 9. The CDRH3 sequence DRYSGHDLGY (SEQ ID NO: 3662) may be identically located in TSP1 via a unique segment combination (g=1) with a single amino acid difference. As provided below, the TN1, N2 and H3-JH segments match the corresponding reference sequence fragments identically, while four of the five DH amino acids match identically.

```
Sequence from the HPS:
DR-YSGHD-LG-Y        (SEQ ID NO: 3662)

Nearest Neighbor in TSP1:
DR-YSGYD-LG-Y        (SEQ ID NO: 8719)
```

Thus, here $$f = 4/5 \text{ for the } DH \text{ segment; and}$$

$$= 1 \text{ for the } TN1, N2, \text{ and } H3\text{-}JH \text{ segments (Table 20).}$$

Example 8.4. Matching of Test Cases 4.1 and 4.2 in Table 9

Refer to test cases 4.1 and 4.2 in Table 9. The CDRH3 sequence GIAAADSNWLDP (SEQ ID NO: 3663) may be located in TSP1 via two distinct segment combinations (g=2), each with a single amino acid difference. As provided below, the TN1, DH and N2 segments match the corresponding reference sequence fragments identically, while five of the six H3-JH amino acids match identically.

```
Sequence from HPS:
(-)-GIAAA-D-SNWLDP       (SEQ ID NO: 3663)

Nearest Neighbor in TSP1:
(-)-GIAAA-D-SNWFDP       (SEQ ID NO: 8720)

Sequence from HPS:
G-IAAA-D-SNWLDP          (SEQ ID NO: 3663)

Nearest Neighbor in TSP1:
G-IAAA-D-SNWFDP          (SEQ ID NO: 8720)
Here, (-) represents the "empty" TN1 segment.
```

Applying Equation 2 results in the segment usage weights provided in Table 21.

Example 8.5. Calculating the Segment Usage Weights for Test Cases 1 to 4.2 of Table 9

Extending the individual calculations described above to simultaneously include all of Test Cases 1 to 4.2 of Table 9 results in the segment usage weights of Table 22.

Example 8.6. Calculating the Segment Usage Weights for Test Cases 5.1 to 5.4 of Table 9

Refer to the CDRH3 sequence ERTINWGWGVYAFDI (SEQ ID NO: 8760) and the novel TN1 and N2 segments extracted from the CDRH3 sequence, in Example 7. In this case, the novel TN1 and N2 segments (ERTI (SEQ ID NO: 8718) and WGV respectively), and the DH and H3-JH segments from TSP1 (NWG and YAFDI (SEQ ID NO: 4540) respectively) are each assigned usage weights of unity.

Figure 5:
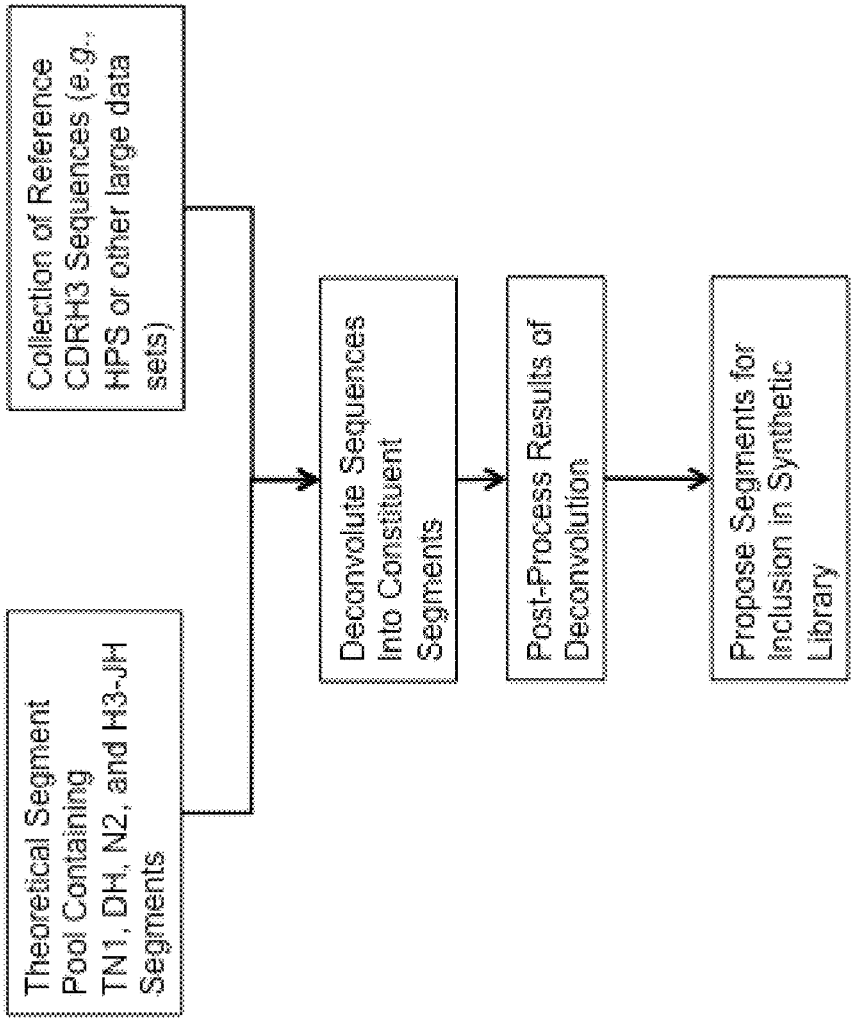
FIG. 5 shows the general schematic of an approach used to select segments from a theoretical segment pool for inclusion in a theoretical and/or synthetic library.

Example 9. Selection of TN1, DH, N2 and JH Segments for Inclusion in Synthetic Libraries FIG. 5 provides the general method used for the design of synthetic CDRH3 libraries. The method uses as input: (1) a theoretical segment pool containing TN1, DH, N2, and H3-JH segments (e.g., TSP plus novel TN1 and N2 segments); and (2) a collection of reference CDRH3 sequences (e.g., the HPS). From these inputs, a particular subset of segments from the theoretical segment pool is selected for inclusion in a physical CDRH3 library.

First, the best matches to the CDRH3s of the HPS were obtained, from within the TSP1 set, with or without the novel TN1 and N2 segments, using the matching method described above. This data was then used to compute the segment usage weights via Equation 2. Segments were prioritized for inclusion in the physical library based on their relative frequency of occurrence in the CDRH3 sequences of the HPS (as indicated by the segment usage weights), as well as other factors (more fully described below), such as hydrophobicity, alpha-helical propensity, and expressibility in yeast.

Example 9.1. Exemplary Library Design (ELD-1)

ELD-1 uses the HPS and the segments from TSP1 1 ($9.5\times10^9$ members) as inputs and produces an output of 100 TN1, 200 DH, 141 N2 and 100 H3JH segments, each from TSP1, ranked in order by their usage weights in the HPS, to produce a library with theoretical complexity of $2.82\times10^8$. The segments corresponding to ELD-1 are provided in Table 23. Note that here the combination of all of the segments (i.e., TN1, DH, N2, and H3-JH), and the individual sets of segments (i.e., TN1 only, DH only, N2 only, and H3JH only) each constitute theoretical segment pools.

Example 9.2. Exemplary Library Design 2 (ELD-2)

The inputs for this design are the HPS and the segments from TSP1 plus the novel TN1 and N2 segments extracted from the HPS (Example 7). The outputs are (1) 200 DH and 100 H3JH segments, each from TSP1; and (2) 100 TN1 and 200 N2 segments including TN1 and N2 segments originally in TSP1 and those extracted from the sequences in the HPS. Applying the method described in Example 7 to extract novel TN1 and N2 segments (i.e., those not included in TSP1) resulted in the identification of 1,710 novel TN1 segments and 1,024 novel N2 segments. The segments corresponding to ELD-2 are provided in Table 24. Note that here the combination of all of the segments (i.e., TN1, DH, N2, and H3-JH), and the individual sets of segments (i.e., TN1 only, DH only, N2 only, and H3JH only) each constitute theoretical segment pools. As in ELD-1, all segments in ELD-2 were selected for inclusion based solely on their usage weights in the HPS.

Example 9.3. Exemplary Library Design 3 (ELD-3)

The inputs for this design are identical to those for ELD-2. As in ELD-2, the outputs are (1) a set of 200 DH and 100 H3-JH segments, each from TSP1; and (2) a set of 100 TN1 and 200 N2 segments, including TN1 and N2 segments originally in TSP1 and those extracted from the sequences in the HPS (Example 7). However, the approach used for the selection of the segments for ELD-3 differs in two respects. First, selected physicochemical properties of the segments (hydrophobicity, isoelectric point, and alpha-helix propensity) were used, in addition to the segment usage weights, to prioritize segments for inclusion in the physical library. Hydrophobicity was used to de-prioritize hydrophobic DH segments that are empirically over-represented in poorly expressed antibodies isolated from yeast-based libraries. Isoelectric point and propensity for alpha-helix formation were utilized to identify segments located in regions of physicochemical property space that were relatively unexplored in CDRH3 libraries known in the art (e.g., U.S. Publication Nos. 2009/0181855 and 2010/0056386, and WO/2009/036379). Second, the segment usage weights were calculated via a bootstrap analysis of the HPS dataset. These methods are more fully described below. The segments corresponding to ELD-3 are provided in Table 25. Note that here the combination of all of the segments (i.e., TN1, DH, N2, and H3-JH), and the individual sets of segments (i.e., TN1 only, DH only, N2 only, and H3-JH only) each constitute theoretical segment pools.

Example 9.3.1. Generation of Segment Usage Weights Via Bootstrap Analysis

Bootstrap analysis (Efron & Tibshirani, *An Introduction to the Bootstrap,* 1994 Chapman Hill, N.Y.) is a widely used statistical procedure for estimating the variability of a statistic of a given sample. This estimate is based on the value of the statistic calculated for several sub-samples, equal in size to the original sample and derived from it via sampling with replacement. Members of the original sample are chosen at random to form the sub-samples, and are typically included multiple times in each sub-sample (hence, "sampling with replacement").

Here, the original sample is the HPS dataset with n=3,571 members and the statistic is the segment usage weight. One-thousand sub-samples, each with 3,571 members, were generated by randomly choosing sequences from the HPS dataset (no more than 10 repeats of a given sequence were allowed in each sub-sample). The matching method described above was then applied to each sub-sample, and the final segment usage weights were calculated as the average of the values obtained for the individual sub-samples. Average values derived via this bootstrap procedure are more robust than values calculated from the parent HPS dataset alone. Unless indicated otherwise, these average values of the 1,000 sub-samples were used in the selection of segments for ELD-3.

Example 9.3.2. Amino Acid Property Indices

The AAindex database, available online at world wide web at genome.jp/aaindex/, provides more than 500 numerical indices representing various physicochemical and biochemical properties of amino acids and pairs of amino acids. These properties include hydrophobicity, electrostatic behavior, secondary structure propensities and other characteristics, with several indices often available for a given property. The following three indices were chosen by starting with the well-understood Kyte-Doolittle hydropathy index (KYJT820101) and adding the indices most numerically de-correlated from it and each other. They thus potentially describe non-overlapping regions of amino acid property space and were used for analysis and selection of the DH and H3-JH segments for ELD-3:

1. KYTJ820101 (hydropathy index)
2. LEVM780101 (normalized frequency of alpha helix)
3. ZIMJ680104 (isoelectric point)

Figure 6:
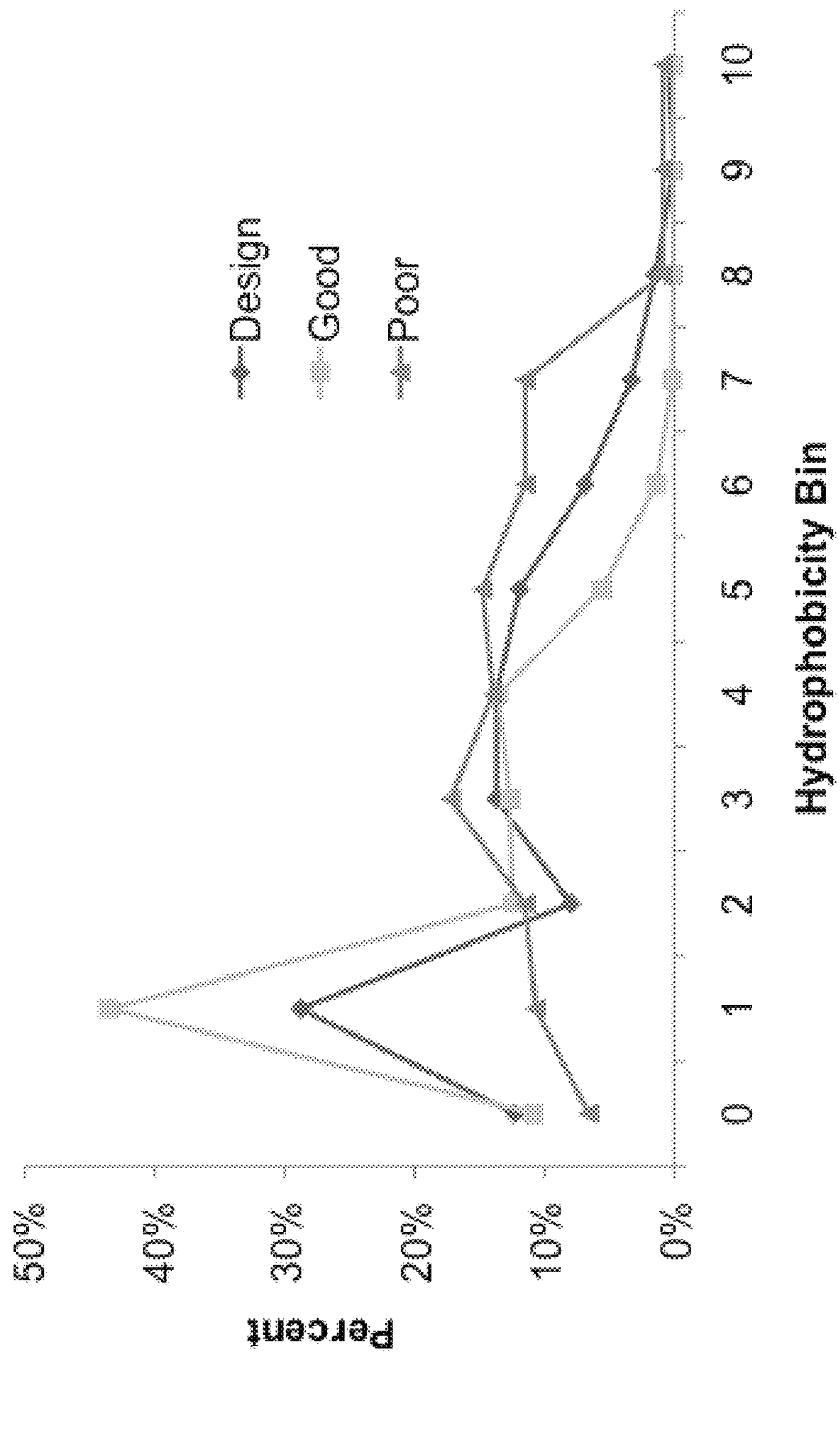
FIG. 6 shows the frequency of “Good” and “Poor” expressing CDRH3 sequences isolated from yeast-based libraries described in US 2009/0181855, and their comparison to the sequences contained in the library design described therein (“Design”), as a function of the DH segment hydrophobicity (increasing to the right).

Example 9.3.3. Hydrophobic DH Segments are Over-Represented in Poorly Expressed Antibodies Isolated from Yeast-Based Libraries Based on protein expression levels from approximately 1200 antibodies expressed in *S. cerevisiae*, antibodies were classified as either "Good" or "Poor" expressors. The CDRH3 sequence of each antibody in each category was examined to identify sequence features that correlated with the expression level. One such sequence feature is the hydrophobicity of the DH segments calculated using the KYTJ820101 index. FIG. 6 provides the frequency of "Good" and "Poor" expressors as a function of the DH segment hydrophobicity (increasing to the right). The distribution expected from the synthetic library used to isolate these antibodies is also provided as a reference ("Design"). DH segments with the highest hydrophobicity values (far right of the plot) are over-represented (relative to the expectation based on the design) among "Poor" expressors and under-represented among "Good" expressors. Similarly, hydrophilic DH segments (far left) are over-represented among "Good" expressors and under-represented among "Poor" expressors. From this data, it was inferred that the overall expressibility of the antibodies of the library may be improved by synthesizing CDRH3 sequences with fewer hydrophobic DH segments.

Example 9.3.4. Selection of the 200 DH Segments for Inclusion in ELD-3

A set of 71 DH segments from TSP1 were designated as "core" DH segments for automatic inclusion in ELD-3. These segments had the following desirable properties:

1. Fifty-three of seventy-one were present within the top 7% of DH segments rank-ordered by segment usage weights from the bootstrap analysis.
2. Eighteen of seventy-one were present within the top 7% of DH segments rank-ordered by usage weights derived from antibodies isolated from libraries expressed in *S. cerevisiae*.

The remaining 1,040 segments were designated as "non-core." To complete the set of 200 segments in ELD-3, 129 segments were chosen from the "non-core" pool of segments in the following manner:

1. Sixty-five segments were eliminated because they contain either (a) an Asn residue at the last or next-to-last position with the potential to form N-linked glycosylation motifs via combination with N2 amino acids or (b) the amino acid sequence NG, implicated in de-amidation.
2. Segments with higher than median values for the KYTJ820101 hydropathy index (median=2.9 for 1K DH) were eliminated from further consideration. In view of the known importance of Tyr for antigen recognition (Fellouse et al., PNAS, 2004, 101: 12467; and Hofstadter et al., J. Mol. Biol., 1999, 285: 805, each incorporated by reference in its entirety), segments containing at least one Tyr residue were retained unless located in the highest hydrophobicity quartile (KYTJ820101 value higher than 9.4). This eliminated 443 segments.
3. The final set of 129 segments was obtained by using an objective function that aimed to maximize the Euclidean distance, between the "core" and the remaining 443 "non-core" segments, in a multi-dimensional space defined by the following variables: (1) amino acid mismatches to nearest neighbor; and (2) values of the three physicochemical property indices.

Example 9.3.5. Selection of the 100 H3-JH Segments for Inclusion in ELD-3

One-hundred H3-JH segments were chosen for inclusion in ELD-3 in the following manner.

1. Twenty-eight H3-JH segments were selected after being experimentally validated in other libraries containing only these H3-JH segments (see U.S. Publication Nos. 2009/0181855 and 2010/0056386, and WO/2009/036379).
2. Fifty-seven segments were selected based on their presence within the top 25% of H3-JH segments rank-ordered by usage weights from the bootstrap analysis described above. These 57 H3-JH segments, plus the 28 H3-JH segments of (1) (i.e., 85 segments total) were designated as the "core" H3-JH segments, which, like the core DH segments, were automatically included in ELD-3.
4. Fifteen additional segments were chosen by using an objective function that aimed to maximize the Euclidian distance, between the "core" and the remaining 200 "non-core" segments, in a multi-dimensional space defined by the following variables: (1) amino acid mismatches to nearest neighbor; and (2) values of the three physicochemical property indices.

Example 9.3.6. Selection of 100 TN1 and 200 N2 Segments for Inclusion in ELD-3

TN1 and N2 segments were extracted from the sequences in each sub-sample of the bootstrap procedure, and the 100 TN1 and 200 N2 segments with the highest average segment usage weights were chosen for inclusion into the library, after elimination of sequences with undesirable motifs, namely Cys and Asn residues.

Example 9.3.7. Selection of Nucleotide Sequences to Encode the Segments Chosen for Inclusion in ELD-3

Each of the polypeptide segments chosen for inclusion in the library must be back translated (polypeptide to DNA) into a corresponding oligonucleotide sequence. While a large number of oligonucleotides could possibly encode each polypeptide segment, due to the degeneracy of the genetic code, certain constraints were imposed to select oligonucleotides that were more desirable. First, since ELD-3 was expressed in yeast (*S. cerevisiae*), codons that are rarely used in yeast were avoided. For example, of the six possible codons for Arg, three: CGA, CGC and CGG are used to encode yeast proteins at rates of under 10% (see, for example, Nakamura et al., Nucleic Acids Res., 2000, 28:292), and therefore those three codons were avoided to the extent possible. Second, since many antibodies are produced in Chinese Hamster Ovary (CHO) cells (after discovery e.g., in yeast), the CCG codon (encoding Pro) was also avoided, since it is rarely used by hamsters (Nakamura et al.)

A number of restriction enzymes are employed during the actual construction of the CDRH3 oligonucleotide library (see Example 10 of U.S. Pub. No. 2009/0181855). It is thus desirable to avoid the occurrence of recognition motifs for these restriction enzymes within the CDRH3 polynucleotide sequences. Codons are selected at the individual segment level to avoid introducing recognition motifs for restriction enzymes that may be used downstream. Since such motifs may also be generated by combinatorial assembly of the segments, the segment combinations are also checked and, whenever possible, codons are changed to eliminate the occurrence of such motifs. Specifically, three restriction enzymes were used during the construction of the currently exemplified CDRH3 library: BsrDI, BbsI, and AvrII. The first two are type II enzymes with non-palindromic recognition sites. The reverse strand of the oligonucleotides encoding the segments was checked explicitly for recognition sites for these two enzymes. In particular, the reverse strands were checked for the motifs GCAATG and CATTGC (for BsrDI) and GAAGAC and GTCTTC (for BbsI). The recognition motif for AvrII is palindromic so the oligonucleotides were only checked for the sequence CCTAGG. However, AvrII is used only to treat TN1 segments, and thus it is not necessary to evaluate its presence in the other segments or their combinations.

An additional constraint that was imposed to improve engineering of the polypeptide to polynucleotide conversion was avoidance of consecutive runs of 6 or more of the same type of base, as this is believed to increase errors during solid phase oligonucleotide synthesis. Therefore, DNA sequences for the segments of ELD-3 were chosen to avoid such motifs. The DNA sequences for the ELD-3 segments are included, with the respective polypeptide sequences, in Table 25. One of ordinary skill in the art will readily recognize that these methods can also be applied to any other library, any restriction sites, any number of nucleotide repeats, and/or to avoid the occurrence of any codons considered undesirable in any organism.

Example 10. Matching of ELD-3 to Human CDRH3 Datasets and Clinically Relevant Antibodies Among the objectives of the invention is to mimic the V-D-J recombination processes underlying the creation of the human CDRH3 repertoire in vivo, thereby increasing the diversity of the CDRH3 library in comparison to other libraries known in the art, while maintaining the human character of CDRH3. One measure of success is the extent to which collections of human reference CDRH3 sequences are represented identically, or via close matches (e.g., less than about 5, 4, 3, or 2 amino acid differences) in any library of the invention. We evaluated this metric using two human CDRH3 sequence reference datasets, both non-overlapping with each other and the HPS: (1) a collection of 666 human CDRH3 sequences (Lee et al., Immunogenetics, 2006, 57: 917; "Lee-666"); and (2) a collection of 3,000 human CDRH3 sequences randomly chosen from the over 200,000 sequences disclosed in Boyd et al., Science Translational Medicine, 2009, 1: 1-8 ("Boyd-3000"). The results of the random sample of the 3,000 human CDRH3 sequences from Boyd et al. was representative of the results of the same analysis as applied to all members of the Boyd et al. set (>200,000 CDRH3 sequences).

Figure 7:
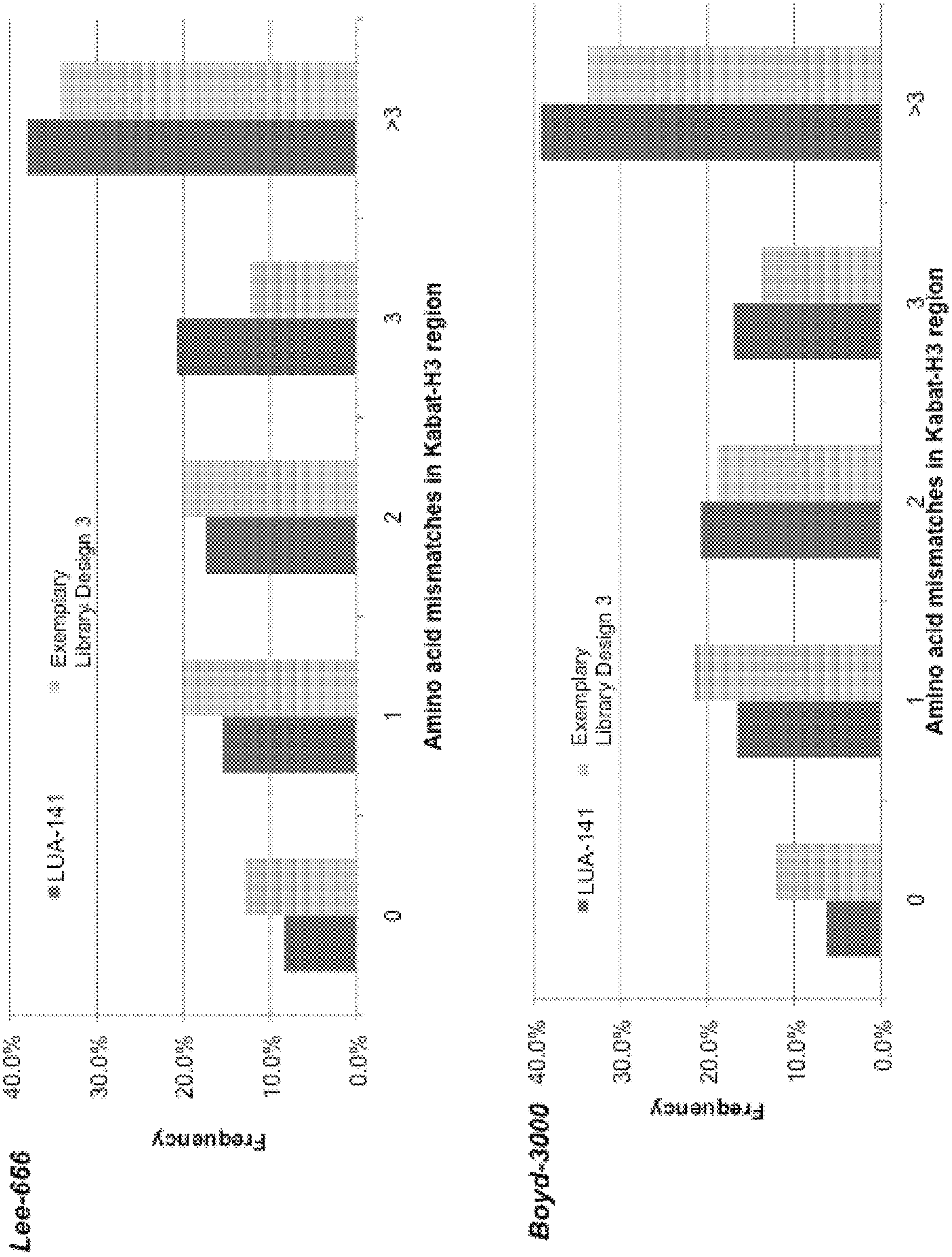
FIG. 7 shows the percentage of CDRH3 sequences in the LUA-141 library and Exemplary Library Design 3 (ELD-3)

FIG. 7 provides the percentage of CDRH3 sequences in two synthetic libraries, "LUA-141" and ELD-3, that match a sequence from the Lee-666 or Boyd-3000 sets with zero, one, two, three, or more than three amino acid mismatches. Here, "LUA-141" represents a library containing 212 TN1, 278 DH, 141 N2, and 28 H3JH (see U.S. Publication No. 2009/0181855 for details). In particular, it is notable that ELD-3 exhibits a higher percentage of sequences (12.9% and 12.1% for the Lee-666 and Boyd-3000 sets, respectively) that identically match a reference CDRH3 sequence than LUA-141 (8.4% and 6.3% for the Lee-666 and Boyd-3000 sets, respectively). It is also notable that ELD-3 exhibits a higher cumulative percentage of human CDRH3 sequences found with no more than two amino acid mismatches (54.1% and 52.5% for the Lee-666 and Boyd-3000 sets, respectively) relative to LUA-141 (41.2% and 43.7% for the Lee-666 and Boyd-3000 sets, respectively).

Another metric by which antibody libraries can be evaluated is their ability to match "clinically relevant" reference CDRH3 sequences. FIG. 8 demonstrates that ELD-3 returns better matches to clinically relevant CDRH3 sequences than the LUA-141 library. Specifically, ELD-3 matches 34 of 55 (62%) clinically validated antibodies within one amino acid, while the LUA-141 library only matches 20 of 55 (37%).

Example 11. Comparison of ELD-3 to LUA-141

ELD-3 has 73 TN1, 92 DH, 119 N2, and 28 H3-JH in common with LUA-141. Thus, 94.5% of the sequences in ELD-3 ($4.0\times10^8$ members) are different from the LUA-141 library ($2.3\times10^8$ members). FIG. 9 demonstrates that the combinatorial efficiency of the segments in ELD-3 is greater than that of the segments in LUA-141. Specifically, the ELD-3 segments are more likely to yield a unique CDRH3 than the LUA-141 library segments. This is advantageous, because it allows one to synthesize libraries with increased CDRH3 diversity using fewer segments.

FIG. 10 provides the amino acid compositions of the Kabat-CDRH3s of LUA-141, ELD-3, and Human CDRH3 sequences from the HPS.

FIG. 11 provides the Kabat-CDRH3 length distribution of LUA-141, ELD-3, and Human CDRH3 sequences from the HPS.

CDRH3 Libraries Synthesized with Degenerate Oligonucleotides

Example 12. Further Increasing CDRH3 Diversity by Utilizing Degenerate Oligonucleotides The methods described in this example extend the methods taught above, to produce CDRH3 libraries with more members than those of the libraries described above. In particular, one or two degenerate codons were introduced into the DH and or N2 polynucleotide segments, and (generally) no degenerate codon or one degenerate codon were introduced into the H3-JH segments. Segments with different numbers of degenerate codons are also contemplated; for example DH segments with 0, 1, 2, 3, 4, 5, 6, 7, 8, or more degenerate codons, and H3-JH segments with 0, 1, 2, 3, 4, 5, or more degenerate codons. This results in CDRH3 libraries containing greater than about $10^{11}$ (about $2\times10^{11}$) distinct CDRH3 amino acid sequences that closely reflect properties, such as length and composition among others, of a reference set of human CDRH3 sequences. As described below, the degenerate positions in the DH segments are usually, but not always, the very N- and/or C-terminal positions, or 5' and 3' end codons (i.e., not necessarily only the first or last base), respectively, when considering the corresponding oligonucleotide sequences. Degenerate codons were similarly used to synthesize N2 segments. Two hundred of the TN1 segments were as described in ELD-3, although libraries with degenerate TN1 segments, or with alternative choices of TN1 segment sequences, fall within the scope of the invention. An additional one hundred TN1 segments complete the set of 300 TN1 segments for this library. The amino acid and nucleotide sequences are listed in Table 26. It is also possible to use mixtures of trinucleotides instead of, or in addition to, degenerate oligonucleotides in order to allow amino acid type variation at one or more selected positions within "base" or "seed" segment sequences (defined below).

Example 13. Selection of DH Segments for Synthesis by Degenerate Oligonucleotides The segment usage weights were calculated for the 68K DH Theoretical Segment Pool by comparison to the sequences contained in Boyd et al. The DH segments with a length of three or more amino acids were ranked according to their segment usage weights (as described above), and the top 201 were designated as "seed" sequences. These seed sequences were then varied by selecting certain positions to incorporate degenerate codons. The positions selected for variance, the amino acids types to which they were varied, were determined by comparing the seed sequences to a reference set of 9,171 DH segments that were a subset of the 68K DH Theoretical Segment Pool. These 9,171 DH segments were selected because their segment usage weight in Boyd et al. was significant, meaning that the cumulative segment usage weight (Example 8) is at least 1.0.

Each of the 201 seed sequences was compared to each of the sequences in the reference set of 9,171 DH segments, and those of identical length and differing at a single position were further considered to inform possible variants of the seed. In this manner, the most variable position for each seed was identified and a set of candidate amino acid types was also identified for each position. Finally, a set of degenerate codons was considered, to identify the codon that most faithfully represented the set of candidate amino acid types for each particular position. Degenerate codons encoding stop codons, Cys residues, N-linked glycosylation motifs (i.e., NXS or NXT, where X is any amino acid type), or deamidation motifs (NG) were eliminated from consideration. This process generated 149 unique degenerate oligonucleotide sequences, which collectively encode 3,566 unique polypeptide sequences. Alternative designs generated according to the same principles were also considered, and those having a larger diversity (in terms of the number of unique polypeptide sequences) and smaller RMAX values (see below) were given preference for inclusion in the libraries of the invention. However, it is also conceivable that different criteria could be used to select DH segments from the 68K DH Theoretical Segment Pool, and that libraries including DH segments selected by these different criteria would also fall within the scope of the invention.

Because not all degenerate oligonucleotides encode an identical number of polypeptides, the latter do not occur with uniformly identical weights over the entirety of a given theoretical segment pool (i.e., TN1, DH, N2 and H3-JH) contained within a CDRH3 library of the invention. For example, an individual amino acid sequence X encoded by an oligonucleotide of total degeneracy 4 will have a "weight" of ¼, while another individual amino acid sequence, Y, encoded by an oligonucleotide of degeneracy 6 will have a weight of ⅙. Moreover, certain amino acid sequences could be encoded by more than one degenerate oligonucleotide, so their weights will be the sum of the individual contributions by each oligonucleotide. Within a given theoretical segment pool, the ratio of the weight of the most heavily weighted polypeptide to that of the least heavily weighted one, RMAX, is an important design criterion that one would ideally like to minimize. The RMAX value may be defined by length, or overall for all of the segments of any given type (i.e., all the DH segments, or all the H3-JH segments, and so on for the TN1, and/or the N2 segments). Table 27 lists the degenerate oligonucleotide sequences, while Table 28 lists the unique polypeptide sequences resulting from these oligonucleotides. These two tables include the DH dimer segments the design of which is detailed below.

Example 13.1. Selection of DH Dimer Segments

A different method was employed to design a set of degenerate oligonucleotides encoding DH dimer sequences. The method aimed to include all of the 45 dimer sequences in ELD-3 plus as many of the other 400 theoretically possible dimer sequences (i.e., 20 residues possible in each of 2 positions=20*20), minus segments containing Asn (N) residues and excessively hydrophobic dimers (i.e., any dimer combination comprising only F, I, L, M, and/or V residues). This design process ultimately yielded 35 degenerate oligonucleotide sequences encoding 213 unique peptide dimer sequences. As with the selection processes used for all of the other segments of the invention, one or ordinary skill in the art will readily recognize that other criteria could be used to select the DH dimer segments, and that libraries including these segments also fall within the scope of the invention.

Combining the DH dimer segments with the longer DH segments of Example 13, yielded the final set of DH segments of the currently exemplified library, encoded by a total of 184 oligonucleotides (35 encoding dimers and 149 encoding segments having three or more amino acids) versus the 200 oligonucleotides of ELD-3. The 184 oligonucleotides encode a total of 3,779 unique polypeptide sequences: 213 dimers and 3,566 longer segments of three amino acids or greater.

Example 14. Generation of Expanded N2 Diversity

As described above, ELD-3 contains 200 N2 segments. In the currently exemplified library, the empty N2 segment (i.e., no N2, so that the DH segments are joined directly to the H3-JH segments) and monomer N2 segments were the same as in ELD-3. However, degenerate oligonucleotides were used to generate sets of two-, three-, and four-mers that not only recapitulated all of the corresponding sequences in ELD-3 but also resulted in additional diversity. As with the DH segments, these degenerate oligonucleotides were designed to eliminate Asn (in unsuitable positions) and Cys residues, and stop codons. More specifically, Asn residues were allowed at the first position of trimers and at the first or second position of tetramers whenever the subsequent amino acid was not Gly and the next amino acid was not Ser or Thr, thus avoiding deamidation or N-linked glycosylation motifs within the candidate N2 segments. The N2 theoretical segment pool for the currently exemplified library contains one zero-mer (i.e., no N2 segment), 18 monomer, 279 dimer, 339 trimers, and 90 tetramer N2 amino acid sequences, or 727 segments in total. These amino acid sequences are encoded by 1, 18, 81, 36, and 10 oligonucleotides, respectively, for a total of 146 oligonucleotides. All but the first 19 oligonucleotides, those encoding the zero- and one-mers, are degenerate. Table 29 lists the 146 oligonucleotide sequences, while Table 30 lists the resulting 727 unique polypeptide sequences.

Example 15. Generation of Expanded H3-JH Diversity

Application of nucleotide-level progressive deletions on the 5' end of the human IGHJ polynucleotide segments down to the point where only the DNA sequence corresponding to FRM4 remained (i.e., no H3-JH remained), followed by systematic 1- or 2-bp completions on the same 5' end, resulted in 643 unique H3-JH peptide segments after translation ("643 H3-JH Set"). As done with the DH segments, it is possible to rank order each of the 643 segments by their usage weights obtained after comparison to the approximately 237,000 human sequences from Boyd et al., and the top 200 individual sequences, from those devoid of the undesired motifs described above, were chosen to provide the set of H3-JH segments for the currently exemplified library.

In an alternatively exemplified embodiment, 46 of the 200 H3-JH segments were designed with a two-fold degenerate codon in the first position (i.e., N-terminal or 5' end, respectively, at the peptide and oligonucleotide level), so that, overall, 200 oligonucleotides would encode 246 unique peptide sequences.

In yet other alternatively exemplified embodiments, further use of degenerate codons may be conceived to produce libraries encoded by 90, 100, 200 or more oligonucleotides representing up to 500 distinct polypeptide sequences. Preferably, but not necessarily, these up to 500 unique sequences could be a subset of the sequences in the 643 H3-JH reference set described above, or a subset of variants of these sequences. As exemplified above, H3-JH segments containing undesirable polypeptide motifs may be eliminated from the design. The oligonucleotide sequences for the JH segments are listed on Table 31, while the resulting unique polypeptide sequences are provided in Table 32. In Table 31, nucleotide sequences corresponding to the FRM4 region are also provided, but the "peptide length" value refers to the H3-JH portion only. For simplicity, only the H3-JH peptide sequences are included in Table 32.

Example 16. Extended Diversity Library Design (EDLD)

The TN1, DH, H3-JH, and N2 segments selected above, and provided in Tables 26 to 32, were combined to generate an Extended Diversity Library Design (EDLD) with theoretical diversity of about $2\times10^{11}$ (300 TN1×3,779 DH×727 N2×246 H3-JH). The oligonucleotides encoding the selected segments were chosen according to the principles of Example 9.3.7.

FIGS. 12-15 illustrate certain characteristics of this design indicating, for example, that about 50% of the approximately 237,000 CDRH3 sequences in Boyd et al. may be recapitulated by library sequences with either one or no mismatches (i.e., by summing the "0" and "1" bins of FIG. 12). The theoretical length distributions (FIG. 13) and amino acid compositions (FIG. 14) of these libraries also match closely the respective characteristics observed in the same set of human CDRH3 sequences. FIG. 15 shows the combinatorial efficiency of the Extended Diversity Library Design. Approximately 65% of the sequences appear only once in the design (i.e., are generated via one non-degenerate combination of segments). FIG. 8, previously presented, shows that the Extended Diversity Library Design outperforms both LUA-141 and ELD-3 in terms of matching to clinically relevant human antibody sequences.

TABLE 1

Germline-like sequences for eight of the VK chassis provided by the invention.

| Germline | Junction | Germline-Like CDRL3 Sequence | SEQ ID NO |
|---|---|---|---|
| VK1-05 | 1 | QQYNSYST | 1 |
| VK1-05 | 2 | QQYNSYFT | 2 |
| VK1-05 | 3 | QQYNSYLT | 3 |
| VK1-05 | 4 | QQYNSYIT | 4 |

TABLE 1-continued

Germline-like sequences for eight of the VK chassis provided by the invention.

| Germline | Junction | Germline-Like CDRL3 Sequence | SEQ ID NO |
|---|---|---|---|
| VK1-05 | 5 | QQYNSYRT | 5 |
| VK1-05 | 6 | QQYNSYWT | 6 |
| VK1-05 | 7 | QQYNSYYT | 7 |
| VK1-05 | 8 | QQYNSYSPT | 8 |
| VK1-05 | 9 | QQYNSYSFT | 9 |
| VK1-05 | 10 | QQYNSYSLT | 10 |
| VK1-05 | 11 | QQYNSYSIT | 11 |
| VK1-05 | 12 | QQYNSYSRT | 12 |
| VK1-05 | 13 | QQYNSYSWT | 13 |
| VK1-05 | 14 | QQYNSYSYT | 14 |
| VK1-05 | 15 | QQYNSYSPFT | 15 |
| VK1-05 | 16 | QQYNSYSPLT | 16 |
| VK1-05 | 17 | QQYNSYSPIT | 17 |
| VK1-05 | 18 | QQYNSYSPRT | 18 |
| VK1-05 | 19 | QQYNSYSPWT | 19 |
| VK1-05 | 20 | QQYNSYSPYT | 20 |
| VK1-12 | 1 | QQANSFPT | 21 |
| VK1-12 | 2 | QQANSFFT | 22 |
| VK1-12 | 3 | QQANSFLT | 23 |
| VK1-12 | 4 | QQANSFIT | 24 |
| VK1-12 | 5 | QQANSFRT | 25 |
| VK1-12 | 6 | QQANSFWT | 26 |
| VK1-12 | 7 | QQANSFYT | 27 |
| VK1-12 | 8 | QQANSFPPT | 28 |
| VK1-12 | 9 | QQANSFPFT | 29 |
| VK1-12 | 10 | QQANSFPLT | 30 |
| VK1-12 | 11 | QQANSFPIT | 31 |
| VK1-12 | 12 | QQANSFPRT | 32 |
| VK1-12 | 13 | QQANSFPWT | 33 |
| VK1-12 | 14 | QQANSFPYT | 34 |
| VK1-12 | 15 | QQANSFPPFT | 35 |
| VK1-12 | 16 | QQANSFPPLT | 36 |
| VK1-12 | 17 | QQANSFPPIT | 37 |
| VK1-12 | 18 | QQANSFPPRT | 38 |
| VK1-12 | 19 | QQANSFPPWT | 39 |
| VK1-12 | 20 | QQANSFPPYT | 40 |
| VK1-33 | 1 | QQYDNLPT | 41 |

TABLE 1-continued

Germline-like sequences for eight of the VK chassis provided by the invention.

| Germline | Junction | Germline-Like CDRL3 Sequence | SEQ ID NO |
|---|---|---|---|
| VK1-33 | 2 | QQYDNLFT | 42 |
| VK1-33 | 3 | QQYDNLLT | 43 |
| VK1-33 | 4 | QQYDNLIT | 44 |
| VK1-33 | 5 | QQYDNLRT | 45 |
| VK1-33 | 6 | QQYDNLWT | 46 |
| VK1-33 | 7 | QQYDNLYT | 47 |
| VK1-33 | 8 | QQYDNLPPT | 48 |
| VK1-33 | 9 | QQYDNLPFT | 49 |
| VK1-33 | 10 | QQYDNLPLT | 50 |
| VK1-33 | 11 | QQYDNLPIT | 51 |
| VK1-33 | 12 | QQYDNLPRT | 52 |
| VK1-33 | 13 | QQYDNLPWT | 53 |
| VK1-33 | 14 | QQYDNLPYT | 54 |
| VK1-33 | 15 | QQYDNLPPFT | 55 |
| VK1-33 | 16 | QQYDNLPPLT | 56 |
| VK1-33 | 17 | QQYDNLPPIT | 57 |
| VK1-33 | 18 | QQYDNLPPRT | 58 |
| VK1-33 | 19 | QQYDNLPPWT | 59 |
| VK1-33 | 20 | QQYDNLPPYT | 60 |
| VK1-39 | 1 | QQSYSTPT | 61 |
| VK1-39 | 2 | QQSYSTFT | 62 |
| VK1-39 | 3 | QQSYSTLT | 63 |
| VK1-39 | 4 | QQSYSTIT | 64 |
| VK1-39 | 5 | QQSYSTRT | 65 |
| VK1-39 | 6 | QQSYSTWT | 66 |
| VK1-39 | 7 | QQSYSTYT | 67 |
| VK1-39 | 8 | QQSYSTPPT | 68 |
| VK1-39 | 9 | QQSYSTPFT | 69 |
| VK1-39 | 10 | QQSYSTPLT | 70 |
| VK1-39 | 11 | QQSYSTPIT | 71 |
| VK1-39 | 12 | QQSYSTPRT | 72 |
| VK1-39 | 13 | QQSYSTPWT | 73 |
| VK1-39 | 14 | QQSYSTPYT | 74 |
| VK1-39 | 15 | QQSYSTPPFT | 75 |
| VK1-39 | 16 | QQSYSTPPLT | 76 |
| VK1-39 | 17 | QQSYSTPPIT | 77 |
| VK1-39 | 18 | QQSYSTPPRT | 78 |
| VK1-39 | 19 | QQSYSTPPWT | 79 |
| VK1-39 | 20 | QQSYSTPPYT | 80 |
| VK4-01 | 1 | QQYYSTPT | 81 |
| VK4-01 | 2 | QQYYSTFT | 82 |
| VK4-01 | 3 | QQYYSTLT | 83 |
| VK4-01 | 4 | QQYYSTIT | 84 |
| VK4-01 | 5 | QQYYSTRT | 85 |
| VK4-01 | 6 | QQYYSTWT | 86 |
| VK4-01 | 7 | QQYYSTYT | 87 |
| VK4-01 | 8 | QQYYSTPPT | 88 |
| VK4-01 | 9 | QQYYSTPFT | 89 |
| VK4-01 | 10 | QQYYSTPLT | 90 |
| VK4-01 | 11 | QQYYSTPIT | 91 |
| VK4-01 | 12 | QQYYSTPRT | 92 |
| VK4-01 | 13 | QQYYSTPWT | 93 |
| VK4-01 | 14 | QQYYSTPYT | 94 |
| VK4-01 | 15 | QQYYSTPPFT | 95 |
| VK4-01 | 16 | QQYYSTPPLT | 96 |
| VK4-01 | 17 | QQYYSTPPIT | 97 |
| VK4-01 | 18 | QQYYSTPPRT | 98 |
| VK4-01 | 19 | QQYYSTPPWT | 99 |
| VK4-01 | 20 | QQYYSTPPYT | 100 |
| VK2-28 | 1 | MQALQTPT | 101 |
| VK2-28 | 2 | MQALQTFT | 102 |
| VK2-28 | 3 | MQALQTLT | 103 |
| VK2-28 | 4 | MQALQTIT | 104 |
| VK2-28 | 5 | MQALQTRT | 105 |
| VK2-28 | 6 | MQALQTWT | 106 |
| VK2-28 | 7 | MQALQTYT | 107 |
| VK2-28 | 8 | MQALQTPPT | 108 |
| VK2-28 | 9 | MQALQTPFT | 109 |
| VK2-28 | 10 | MQALQTPLT | 110 |
| VK2-28 | 11 | MQALQTPIT | 111 |
| VK2-28 | 12 | MQALQTPRT | 112 |
| VK2-28 | 13 | MQALQTPWT | 113 |
| VK2-28 | 14 | MQALQTPYT | 114 |
| VK2-28 | 15 | MQALQTPPFT | 115 |

TABLE 1-continued

Germline-like sequences for eight of the VK chassis provided by the invention.

| Germline | Junction | Germline-Like CDRL3 Sequence | SEQ ID NO |
|---|---|---|---|
| VK2-28 | 16 | MQALQTPPLT | 116 |
| VK2-28 | 17 | MQALQTPPIT | 117 |
| VK2-28 | 18 | MQALQTPPRT | 118 |
| VK2-28 | 19 | MQALQTPPWT | 119 |
| VK2-28 | 20 | MQALQTPPYT | 120 |
| VK3-11 | 1 | QQRSNWPT | 121 |
| VK3-11 | 2 | QQRSNWFT | 122 |
| VK3-11 | 3 | QQRSNWLT | 123 |
| VK3-11 | 4 | QQRSNWIT | 124 |
| VK3-11 | 5 | QQRSNWRT | 125 |
| VK3-11 | 6 | QQRSNWWT | 126 |
| VK3-11 | 7 | QQRSNWYT | 127 |
| VK3-11 | 8 | QQRSNWPPT | 128 |
| VK3-11 | 9 | QQRSNWPFT | 129 |
| VK3-11 | 10 | QQRSNWPLT | 130 |
| VK3-11 | 11 | QQRSNWPIT | 131 |
| VK3-11 | 12 | QQRSNWPRT | 132 |
| VK3-11 | 13 | QQRSNWPWT | 133 |
| VK3-11 | 14 | QQRSNWPYT | 134 |
| VK3-11 | 15 | QQRSNWPPFT | 135 |
| VK3-11 | 16 | QQRSNWPPLT | 136 |
| VK3-11 | 17 | QQRSNWPPIT | 137 |
| VK3-11 | 18 | QQRSNWPPRT | 138 |
| VK3-11 | 19 | QQRSNWPPWT | 139 |
| VK3-11 | 20 | QQRSNWPPYT | 140 |
| VK3-15 | 1 | QQYNNWPT | 141 |
| VK3-15 | 2 | QQYNNWFT | 142 |
| VK3-15 | 3 | QQYNNWLT | 143 |
| VK3-15 | 4 | QQYNNWIT | 144 |
| VK3-15 | 5 | QQYNNWRT | 145 |
| VK3-15 | 6 | QQYNNWWT | 146 |
| VK3-15 | 7 | QQYNNWYT | 147 |
| VK3-15 | 8 | QQYNNWPPT | 148 |
| VK3-15 | 9 | QQYNNWPFT | 149 |
| VK3-15 | 10 | QQYNNWPLT | 150 |
| VK3-15 | 11 | QQYNNWPIT | 151 |
| VK3-15 | 12 | QQYNNWPRT | 152 |

TABLE 1-continued

Germline-like sequences for eight of the VK chassis provided by the invention.

| Germline | Junction | Germline-Like CDRL3 Sequence | SEQ ID NO |
|---|---|---|---|
| VK3-15 | 13 | QQYNNWPWT | 153 |
| VK3-15 | 14 | QQYNNWPYT | 154 |
| VK3-15 | 15 | QQYNNWPPFT | 155 |
| VK3-15 | 16 | QQYNNWPPLT | 156 |
| VK3-15 | 17 | QQYNNWPPIT | 157 |
| VK3-15 | 18 | QQYNNWPPRT | 158 |
| VK3-15 | 19 | QQYNNWPPWT | 159 |
| VK3-15 | 20 | QQYNNWPPYT | 160 |
| VK3-20 | 1 | QQYGSSPT | 161 |
| VK3-20 | 2 | QQYGSSFT | 162 |
| VK3-20 | 3 | QQYGSSLT | 163 |
| VK3-20 | 4 | QQYGSSIT | 164 |
| VK3-20 | 5 | QQYGSSRT | 165 |
| VK3-20 | 6 | QQYGSSWT | 166 |
| VK3-20 | 7 | QQYGSSYT | 167 |
| VK3-20 | 8 | QQYGSSPPT | 168 |
| VK3-20 | 9 | QQYGSSPFT | 169 |
| VK3-20 | 10 | QQYGSSPLT | 170 |
| VK3-20 | 11 | QQYGSSPIT | 171 |
| VK3-20 | 12 | QQYGSSPRT | 172 |
| VK3-20 | 13 | QQYGSSPWT | 173 |
| VK3-20 | 14 | QQYGSSPYT | 174 |
| VK3-20 | 15 | QQYGSSPPFT | 175 |
| VK3-20 | 16 | QQYGSSPPLT | 176 |
| VK3-20 | 17 | QQYGSSPPIT | 177 |
| VK3-20 | 18 | QQYGSSPPRT | 178 |
| VK3-20 | 19 | QQYGSSPPWT | 179 |
| VK3-20 | 20 | QQYGSSPPYT | 180 |

TABLE 2

Summary of framework variants for exemplified light chain germlines.

| Light Chain Germline | Number of Sequences Analyzed | Primary Framework Positions Selected for Variance | Alternative Framework Positions Selected for Variance |
|---|---|---|---|
| VK1-5 | 307 | 4, 49 | 46 |
| VK1-12 | 113 | 4, 49 | 46, 66 |
| VK1-33 | 188 | 4, 66 | 49 |
| VK1-39 | 656 | 4, 49 | 46 |
| VK2-28 | 275 | 46, 49 | 2, 4 |

TABLE 2-continued

Summary of framework variants for exemplified light chain germlines.

| Light Chain Germline | Number of Sequences Analyzed | Primary Framework Positions Selected for Variance | Alternative Framework Positions Selected for Variance |
|---|---|---|---|
| VK3-11 | 375 | 4, 36 | 2, 49 |
| VK3-15 | 202 | 4, 49 | 2, 48 |

TABLE 2-continued

Summary of framework variants for exemplified light chain germlines.

| Light Chain Germline | Number of Sequences Analyzed | Primary Framework Positions Selected for Variance | Alternative Framework Positions Selected for Variance |
|---|---|---|---|
| VK3-20 | 867 | 4, 49 | 2, 48 |
| VK4-1 | 368 | 4, 49 | 46, 66 |

TABLE 3

Polypeptide sequences of exemplified light chain chassis with variability in CDRL1, CDRL2, and frameworks. The Kabat numbers for segment boundaries are indicated. Here, L1 and L2 (in the "Category" column) indicate variability in CDRL1 and CDRL2, respectively, while "F" indicates a framework variant. Sequences designated with both L1 or L2 and F contain variability in both a CDR and framework region.

| Name | Chassis | Category | FRM1: 1-23 | CDR1: 24-34 | FRM2: 35-49 | CDR2: 50-56 | FRM3: 57-88 | SEQ ID NOs: |
|---|---|---|---|---|---|---|---|---|
| VK1-39 | VK1-39 | Germline | DIQMTQSPSSLSASVGDRVTITC | RASQSISSYLN | WYQQKPGKAPKLLIY | AASSLQS | GVPSRFSGSGSGTDFTLTISSLQPEDFATYYC | 181 |
| VK1-39.1 | VK1-39 | L1 | DIQMTQSPSSLSASVGDRVTITC | RASQSINSYLN | WYQQKPGKAPKLLIY | AASSLQS | GVPSRFSGSGSGTDFTLTISSLQPEDFATYYC | 182 |
| VK1-39.2 | VK1-39 | L1 | DIQMTQSPSSLSASVGDRVTITC | RASQSIDSYLN | WYQQKPGKAPKLLIY | AASSLQS | GVPSRFSGSGSGTDFTLTISSLQPEDFATYYC | 183 |
| VK1-39.3 | VK1-39 | L1 | DIQMTQSPSSLSASVGDRVTITC | RASQSISRYLN | WYQQKPGKAPKLLIY | AASSLQS | GVPSRFSGSGSGTDFTLTISSLQPEDFATYYC | 184 |
| VK1-39.6 | VK1-39 | L2 | DIQMTQSPSSLSASVGDRVTITC | RASQSISSYLN | WYQQKPGKAPKLLIY | GASSLQS | GVPSRFSGSGSGTDFTLTISSLQPEDFATYYC | 185 |
| VK1-39.7 | VK1-39 | L2 | DIQMTQSPSSLSASVGDRVTITC | RASQSISSYLN | WYQQKPGKAPKLLIY | SASSLQS | GVPSRFSGSGSGTDFTLTISSLQPEDFATYYC | 186 |
| VK1-39.8 | VK1-39 | L2 | DIQMTQSPSSLSASVGDRVTITC | RASQSISSYLN | WYQQKPGKAPKLLIY | AASNLQS | GVPSRFSGSGSGTDFTLTISSLQPEDFATYYC | 187 |
| VK1-39.10 | VK1-39 | F | DIQLTQSPSSLSASVGDRVTITC | RASQSISSYLN | WYQQKPGKAPKLLIY | AASSLQS | GVPSRFSGSGSGTDFTLTISSLQPEDFATYYC | 188 |
| VK1-39.11 | VK1-39 | FL1 | DIQLTQSPSSLSASVGDRVTITC | RASQSINSYLN | WYQQKPGKAPKLLIY | AASSLQS | GVPSRFSGSGSGTDFTLTISSLQPEDFATYYC | 189 |
| VK1-39.12 | VK1-39 | FL1 | DIQLTQSPSSLSASVGDRVTITC | RASQSIDSYLN | WYQQKPGKAPKLLIY | AASSLQS | GVPSRFSGSGSGTDFTLTISSLQPEDFATYYC | 190 |
| VK1-39.15 | VK1-39 | FL1 | DIQLTQSPSSLSASVGDRVTITC | RASQSISSFLN | WYQQKPGKAPKLLIY | AASSLQS | GVPSRFSGSGSGTDFTLTISSLQPEDFATYYC | 191 |
| VK1-39.17 | VK1-39 | FL2 | DIQLTQSPSSLSASVGDRVTITC | RASQSISSYLN | WYQQKPGKAPKLLIY | SASSLQS | GVPSRFSGSGSGTDFTLTISSLQPEDFATYYC | 192 |
| VK1-39.18 | VK1-39 | FL2 | DIQLTQSPSSLSASVGDRVTITC | RASQSISSYLN | WYQQKPGKAPKLLIY | AASNLQS | GVPSRFSGSGSGTDFTLTISSLQPEDFATYYC | 193 |

TABLE 3-continued

Polypeptide sequences of exemplified light chain chassis with variability in CDRL1, CDRL2, and frameworks. The Kabat numbers for segment boundaries are indicated. Here, L1 and L2 (in the "Category" column) indicate variability in CDRL1 and CDRL2, respectively, while "F" indicates a framework variant. Sequences designated with both L1 or L2 and F contain variability in both a CDR and framework region.

| Name | Chassis | Category | FRM1: 1-23 | CDR1: 24-34 | FRM2: 35-49 | CDR2: 50-56 | FRM3: 57-88 | SEQ ID NOs: |
|---|---|---|---|---|---|---|---|---|
| VK1-39.20 | VK1-39 | F | DIQMTQSPSSLSASVGDRVTITC | RASQSISSYLN | WYQQKPGKAPKLLIS | AASSLQS | GVPSRFSGSGSGTDFTLTISSLQPEDFATYYC | 194 |
| VK1-39.23 | VK1-39 | FL1 | DIQMTQSPSSLSASVGDRVTITC | RASQSISRYLN | WYQQKPGKAPKLLIS | AASSLQS | GVPSRFSGSGSGTDFTLTISSLQPEDFATYYC | 195 |
| VK1-39.24 | VK1-39 | FL1 | DIQMTQSPSSLSASVGDRVTITC | RASQSISIYLN | WYQQKPGKAPKLLIS | AASSLQS | GVPSRFSGSGSGTDFTLTISSLQPEDFATYYC | 196 |
| VK1-39.25 | VK1-39 | FL1 | DIQMTQSPSSLSASVGDRVTITC | RASQSISSFLN | WYQQKPGKAPKLLIS | AASSLQS | GVPSRFSGSGSGTDFTLTISSLQPEDFATYYC | 197 |
| VK1-05 | VK1-05 | Germline | DIQMTQSPSTLSASVGDRVTITC | RASQSISSWLA | WYQQKPGKAPKLLIY | DASSLES | GVPSRFSGSGSGTEFTLTISSLQPDDFATYYC | 198 |
| VK1-05.1 | VK1-05 | L1 | DIQMTQSPSTLSASVGDRVTITC | RASQGISSWLA | WYQQKPGKAPKLLIY | DASSLES | GVPSRFSGSGSGTEFTLTISSLQPDDFATYYC | 199 |
| VK1-05.5 | VK1-05 | L2 | DIQMTQSPSTLSASVGDRVTITC | RASQSISSWLA | WYQQKPGKAPKLLIY | EASSLES | GVPSRFSGSGSGTEFTLTISSLQPDDFATYYC | 200 |
| VK1-05.6 | VK1-05 | L2 | DIQMTQSPSTLSASVGDRVTITC | RASQSISSWLA | WYQQKPGKAPKLLIY | KASSLES | GVPSRFSGSGSGTEFTLTISSLQPDDFATYYC | 201 |
| VK1-05.7 | VK1-05 | L12 | DIQMTQSPSTLSASVGDRVTITC | RASQAISSWLA | WYQQKPGKAPKLLIY | KASSLES | GVPSRFSGSGSGTEFTLTISSLQPDDFATYYC | 202 |
| VK1-05.8 | VK1-05 | L12 | DIQMTQSPSTLSASVGDRVTITC | RASQSINSWLA | WYQQKPGKAPKLLIY | KASSLES | GVPSRFSGSGSGTEFTLTISSLQPDDFATYYC | 203 |
| VK1-05.9 | VK1-05 | L12 | DIQMTQSPSTLSASVGDRVTITC | RASQSIGSWLA | WYQQKPGKAPKLLIY | KASSLES | GVPSRFSGSGSGTEFTLTISSLQPDDFATYYC | 204 |
| VK1-05.10 | VK1-05 | F | DIQLTQSPSTLSASVGDRVTITC | RASQSISSWLA | WYQQKPGKAPKLLIY | DASSLES | GVPSRFSGSGSGTEFTLTISSLQPDDFATYYC | 205 |
| VK1-05.11 | VK1-05 | FL1 | DIQLTQSPSTLSASVGDRVTITC | RASQGISSWLA | WYQQKPGKAPKLLIY | DASSLES | GVPSRFSGSGSGTEFTLTISSLQPDDFATYYC | 206 |
| VK1-05.12 | VK1-05 | FL1 | DIQLTQSPSTLSASVGDRVTITC | RASQAISSWLA | WYQQKPGKAPKLLIY | DASSLES | GVPSRFSGSGSGTEFTLTISSLQPDDFATYYC | 207 |
| VK1-05.14 | VK1-05 | FL1 | DIQLTQSPSTLSASVGDRVTITC | RASQSIGSWLA | WYQQKPGKAPKLLIY | DASSLES | GVPSRFSGSGSGTEFTLTISSLQPDDFATYYC | 208 |
| VK1-05.20 | VK1-05 | F | DIQMTQSPSTLSASVGDRVTITC | RASQSISSWLA | WYQQKPGKAPKLLIS | DASSLES | GVPSRFSGSGSGTEFTLTISSLQPDDFATYYC | 209 |
| VK1-05.21 | VK1-05 | FL1 | DIQMTQSPSTLSASVGDRVTITC | RASQSINSWLA | WYQQKPGKAPKLLIS | DASSLES | GVPSRFSGSGSGTEFTLTISSLQPDDFATYYC | 210 |

TABLE 3-continued

Polypeptide sequences of exemplified light chain chassis with variability in CDRL1, CDRL2, and frameworks. The Kabat numbers for segment boundaries are indicated. Here, L1 and L2 (in the "Category" column) indicate variability in CDRL1 and CDRL2, respectively, while "F" indicates a framework variant. Sequences designated with both L1 or L2 and F contain variability in both a CDR and framework region.

| Name | Chassis | Category | FRM1: 1-23 | CDR1: 24-34 | FRM2: 35-49 | CDR2: 50-56 | FRM3: 57-88 | SEQ ID NOs: |
|---|---|---|---|---|---|---|---|---|
| VK1-05.25 | VK1-05 | FL2 | DIQLTQSPSTLSASVGDRVTITC | RASQSIGSWLA | WYQQKPGKAPKLLIY | KASSLES | GVPSRFSGSGSGTEFTLTISSLQPDDFATYYC | 211 |
| VK1-05.26 | VK1-05 | FL2 | DIQMTQSPSTLSASVGDRVTITC | RASQSISSWLA | WYQQKPGKAPKLLIS | KASSLES | GVPSRFSGSGSGTEFTLTISSLQPDDFATYYC | 212 |
| VK1-12 | VK1-12 | Germline | DIQMTQSPSSVSASVGDRVTITC | RASQGISSWLA | WYQQKPGKAPKLLIY | AASSLQS | GVPSRFSGSGSGTDFTLTISSLQPEDFATYYC | 213 |
| VK1-12.2 | VK1-12 | L1 | DIQMTQSPSSVSASVGDRVTITC | RASQGIGSWLA | WYQQKPGKAPKLLIY | AASSLQS | GVPSRFSGSGSGTDFTLTISSLQPEDFATYYC | 214 |
| VK1-12.3 | VK1-12 | L1 | DIQMTQSPSSVSASVGDRVTITC | RASQGIDSWLA | WYQQKPGKAPKLLIY | AASSLQS | GVPSRFSGSGSGTDFTLTISSLQPEDFATYYC | 215 |
| VK1-12.4 | VK1-12 | L1 | DIQMTQSPSSVSASVGDRVTITC | RASQGISRWLA | WYQQKPGKAPKLLIY | AASSLQS | GVPSRFSGSGSGTDFTLTISSLQPEDFATYYC | 216 |
| VK1-12.5 | VK1-12 | L2 | DIQMTQSPSSVSASVGDRVTITC | RASQGISSWLA | WYQQKPGKAPKLLIY | GASSLQS | GVPSRFSGSGSGTDFTLTISSLQPEDFATYYC | 217 |
| VK1-12.6 | VK1-12 | L2 | DIQMTQSPSSVSASVGDRVTITC | RASQGISSWLA | WYQQKPGKAPKLLIY | SASSLQS | GVPSRFSGSGSGTDFTLTISSLQPEDFATYYC | 218 |
| VK1-12.7 | VK1-12 | L2 | DIQMTQSPSSVSASVGDRVTITC | RASQGISSWLA | WYQQKPGKAPKLLIY | AASNLQS | GVPSRFSGSGSGTDFTLTISSLQPEDFATYYC | 219 |
| VK1-12.10 | VK1-12 | F | DIQLTQSPSSVSASVGDRVTITC | RASQGISSWLA | WYQQKPGKAPKLLIY | AASSLQS | GVPSRFSGSGSGTDFTLTISSLQPEDFATYYC | 220 |
| VK1-12.11 | VK1-12 | FL1 | DIQLTQSPSSVSASVGDRVTITC | RASQDISSWLA | WYQQKPGKAPKLLIY | AASSLQS | GVPSRFSGSGSGTDFTLTISSLQPEDFATYYC | 221 |
| VK1-12.14 | VK1-12 | FL1 | DIQLTQSPSSVSASVGDRVTITC | RASQGISRWLA | WYQQKPGKAPKLLIY | AASSLQS | GVPSRFSGSGSGTDFTLTISSLQPEDFATYYC | 222 |
| VK1-12.15 | VK1-12 | FL2 | DIQLTQSPSSVSASVGDRVTITC | RASQGISSWLA | WYQQKPGKAPKLLIY | GASSLQS | GVPSRFSGSGSGTDFTLTISSLQPEDFATYYC | 223 |
| VK1-12.16 | VK1-12 | FL2 | DIQLTQSPSSVSASVGDRVTITC | RASQGISSWLA | WYQQKPGKAPKLLIY | SASSLQS | GVPSRFSGSGSGTDFTLTISSLQPEDFATYYC | 224 |
| VK1-12.17 | VK1-12 | FL2 | DIQLTQSPSSVSASVGDRVTITC | RASQGISSWLA | WYQQKPGKAPKLLIY | AASNLQS | GVPSRFSGSGSGTDFTLTISSLQPEDFATYYC | 225 |
| VK1-12.20 | VK1-12 | F | DIQMTQSPSSVSASVGDRVTITC | RASQGISSWLA | WYQQKPGKAPKLLIS | AASSLQS | GVPSRFSGSGSGTDFTLTISSLQPEDFATYYC | 226 |
| VK1-12.21 | VK1-12 | FL1 | DIQMTQSPSSVSASVGDRVTITC | RASQDISSWLA | WYQQKPGKAPKLLIS | AASSLQS | GVPSRFSGSGSGTDFTLTISSLQPEDFATYYC | 227 |

TABLE 3-continued

Polypeptide sequences of exemplified light chain chassis with variability in CDRL1, CDRL2, and frameworks. The Kabat numbers for segment boundaries are indicated. Here, L1 and L2 (in the "Category" column) indicate variability in CDRL1 and CDRL2, respectively, while "F" indicates a framework variant. Sequences designated with both L1 or L2 and F contain variability in both a CDR and framework region.

| Name | Chassis | Category | FRM1: 1-23 | CDR1: 24-34 | FRM2: 35-49 | CDR2: 50-56 | FRM3: 57-88 | SEQ ID NOs: |
|---|---|---|---|---|---|---|---|---|
| VK1-12.23 | VK1-12 | FL1 | DIQMTQSPSSVSASVGDRVTITC | RASQGIDSWLA | WYQQKPGKAPKLLIS | AASSLQS | GVPSRFSGSGSGTDFTLTISSLQPEDFATYYC | 228 |
| VK1-12.24 | VK1-12 | FL1 | DIQMTQSPSSVSASVGDRVTITC | RASQGISRWLA | WYQQKPGKAPKLLIS | AASSLQS | GVPSRFSGSGSGTDFTLTISSLQPEDFATYYC | 229 |
| VK1-33 | VK1-33 | Germline | DIQMTQSPSSLSASVGDRVTITC | QASQDISNYLN | WYQQKPGKAPKLLIY | DASNLET | GVPSRFSGSGSGTDFTFTISSLQPEDIATYYC | 230 |
| VK1-33.1 | VK1-33 | L1 | DIQMTQSPSSLSASVGDRVTITC | QASQDITNYLN | WYQQKPGKAPKLLIY | DASNLET | GVPSRFSGSGSGTDFTFTISSLQPEDIATYYC | 231 |
| VK1-33.2 | VK1-33 | L1 | DIQMTQSPSSLSASVGDRVTITC | QASQDIANYLN | WYQQKPGKAPKLLIY | DASNLET | GVPSRFSGSGSGTDFTFTISSLQPEDIATYYC | 232 |
| VK1-33.8 | VK1-33 | L2 | DIQMTQSPSSLSASVGDRVTITC | QASQDISNYLN | WYQQKPGKAPKLLIY | DASNLAT | GVPSRFSGSGSGTDFTFTISSLQPEDIATYYC | 233 |
| VK1-33.10 | VK1-33 | F | DIQLTQSPSSLSASVGDRVTITC | QASQDISNYLN | WYQQKPGKAPKLLIY | DASNLET | GVPSRFSGSGSGTDFTFTISSLQPEDIATYYC | 234 |
| VK1-33.13 | VK1-33 | FL1 | DIQLTQSPSSLSASVGDRVTITC | QASQDISNSLN | WYQQKPGKAPKLLIY | DASNLET | GVPSRFSGSGSGTDFTFTISSLQPEDIATYYC | 235 |
| VK1-33.14 | VK1-33 | FL1 | DIQLTQSPSSLSASVGDRVTITC | QASQDISNFLN | WYQQKPGKAPKLLIY | DASNLET | GVPSRFSGSGSGTDFTFTISSLQPEDIATYYC | 236 |
| VK1-33.17 | VK1-33 | FL2 | DIQLTQSPSSLSASVGDRVTITC | QASQDISNYLN | WYQQKPGKAPKLLIY | DASNLQT | GVPSRFSGSGSGTDFTFTISSLQPEDIATYYC | 237 |
| VK1-33.20 | VK1-33 | F | DIQMTQSPSSLSASVGDRVTITC | QASQDISNYLN | WYQQKPGKAPKLLIY | DASNLET | GVPSRFSGSRSGTDFTFTISSLQPEDIATYYC | 238 |
| VK1-33.21 | VK1-33 | FL1 | DIQMTQSPSSLSASVGDRVTITC | QASQDITNYLN | WYQQKPGKAPKLLIY | DASNLET | GVPSRFSGSRSGTDFTFTISSLQPEDIATYYC | 239 |
| VK1-33.22 | VK1-33 | FL1 | DIQMTQSPSSLSASVGDRVTITC | QASQDIANYLN | WYQQKPGKAPKLLIY | DASNLET | GVPSRFSGSRSGTDFTFTISSLQPEDIATYYC | 240 |
| VK1-33.23 | VK1-33 | FL1 | DIQMTQSPSSLSASVGDRVTITC | QASQDISNSLN | WYQQKPGKAPKLLIY | DASNLET | GVPSRFSGSRSGTDFTFTISSLQPEDIATYYC | 241 |
| VK1-33.24 | VK1-33 | FL1 | DIQMTQSPSSLSASVGDRVTITC | QASQDISNFLN | WYQQKPGKAPKLLIY | DASNLET | GVPSRFSGSRSGTDFTFTISSLQPEDIATYYC | 242 |
| VK2-28 | VK2-28 | Germline | DIVMTQSPLSLPVTPGEPASISC | RSSQSLLHSNGYNYLD | WYLQKPGQSPQLLIY | LGSNRAS | GVPDRFSGSGSGTDFTLKISRVEAEDVGVYYC | 243 |
| VK2-28.1 | VK2-28 | L1 | DIVMTQSPLSLPVTPGEPASISC | RSSQSLLYSNGYNYLD | WYLQKPGQSPQLLIY | LGSNRAS | GVPDRFSGSGSGTDFTLKISRVEAEDVGVYYC | 244 |

TABLE 3-continued

Polypeptide sequences of exemplified light chain chassis with variability in CDRL1, CDRL2, and frameworks. The Kabat numbers for segment boundaries are indicated. Here, L1 and L2 (in the "Category" column) indicate variability in CDRL1 and CDRL2, respectively, while "F" indicates a framework variant. Sequences designated with both L1 or L2 and F contain variability in both a CDR and framework region.

| Name | Chassis | Category | FRM1: 1-23 | CDR1: 24-34 | FRM2: 35-49 | CDR2: 50-56 | FRM3: 57-88 | SEQ ID NOs: |
|---|---|---|---|---|---|---|---|---|
| VK2-28.2 | VK2-28 | L1 | DIVMTQSPLSLPVTPGEPASISC | RSSQSLLHRNGYNYLD | WYLQKPGQSPQLLIY | LGSNRAS | GVPDRFSGSGSGTDFTLKISRVEAEDVGVYYC | 245 |
| VK2-28.3 | VK2-28 | L1 | DIVMTQSPLSLPVTPGEPASISC | RSSQSLLHTNGYNYLD | WYLQKPGQSPQLLIY | LGSNRAS | GVPDRFSGSGSGTDFTLKISRVEAEDVGVYYC | 246 |
| VK2-28.4 | VK2-28 | L1 | DIVMTQSPLSLPVTPGEPASISC | RSSQSLLHSNGNNYLD | WYLQKPGQSPQLLIY | LGSNRAS | GVPDRFSGSGSGTDFTLKISRVEAEDVGVYYC | 247 |
| VK2-28.5 | VK2-28 | L2 | DIVMTQSPLSLPVTPGEPASISC | RSSQSLLHSNGYNYLD | WYLQKPGQSPQLLIY | LASNRAS | GVPDRFSGSGSGTDFTLKISRVEAEDVGVYYC | 248 |
| VK2-28.6 | VK2-28 | L2 | DIVMTQSPLSLPVTPGEPASISC | RSSQSLLHSNGYNYLD | WYLQKPGQSPQLLIY | LGSHRAS | GVPDRFSGSGSGTDFTLKISRVEAEDVGVYYC | 249 |
| VK2-28.10 | VK2-28 | F | DIVMTQSPLSLPVTPGEPASISC | RSSQSLLHSNGYNYLD | WYLQKPGQSPQVLIY | LGSNRAS | GVPDRFSGSGSGTDFTLKISRVEAEDVGVYYC | 250 |
| VK2-28.11 | VK2-28 | L1 | DIVMTQSPLSLPVTPGEPASISC | RSSQSLLYSNGYNYLD | WYLQKPGQSPQVLIY | LGSNRAS | GVPDRFSGSGSGTDFTLKISRVEAEDVGVYYC | 251 |
| VK2-28.15 | VK2-28 | FL2 | DIVMTQSPLSLPVTPGEPASISC | RSSQSLLHSNGYNYLD | WYLQKPGQSPQVLIY | LASNRAS | GVPDRFSGSGSGTDFTLKISRVEAEDVGVYYC | 252 |
| VK2-28.17 | VK2-28 | FL2 | DIVMTQSPLSLPVTPGEPASISC | RSSQSLLHSNGYNYLD | WYLQKPGQSPQVLIY | LGSSRAS | GVPDRFSGSGSGTDFTLKISRVEAEDVGVYYC | 253 |
| VK2-28.20 | VK2-28 | F | DIVMTQSPLSLPVTPGEPASISC | RSSQSLLHSNGYNYLD | WYLQKPGQSPQLLIF | LGSNRAS | GVPDRFSGSGSGTDFTLKISRVEAEDVGVYYC | 254 |
| VK2-28.24 | VK2-28 | FL1 | DIVMTQSPLSLPVTPGEPASISC | RSSQSLLHSNGNNYLD | WYLQKPGQSPQLLIF | LGSNRAS | GVPDRFSGSGSGTDFTLKISRVEAEDVGVYYC | 255 |
| VK3-11 | VK3-11 | Germline | EIVLTQSPATLSLSPGERATLSC | RASQSVSSYLA | WYQQKPGQAPRLLIY | DASNRAT | GIPARFSGSGSGTDFTLTISSLEPEDFAVYYC | 256 |
| VK3-11.2 | VK3-11 | L1 | EIVLTQSPATLSLSPGERATLSC | RASQSVSRYLA | WYQQKPGQAPRLLIY | DASNRAT | GIPARFSGSGSGTDFTLTISSLEPEDFAVYYC | 257 |
| VK3-11.3 | VK3-11 | L1 | EIVLTQSPATLSLSPGERATLSC | RASQSVSNYLA | WYQQKPGQAPRLLIY | DASNRAT | GIPARFSGSGSGTDFTLTISSLEPEDFAVYYC | 258 |
| VK3-11.4 | VK3-11 | L2 | EIVLTQSPATLSLSPGERATLSC | RASQSVSSYLA | WYQQKPGQAPRLLIY | DSSNRAT | GIPARFSGSGSGTDFTLTISSLEPEDFAVYYC | 259 |
| VK3-11.5 | VK3-11 | L2 | EIVLTQSPATLSLSPGERATLSC | RASQSVSSYLA | WYQQKPGQAPRLLIY | DTSNRAT | GIPARFSGSGSGTDFTLTISSLEPEDFAVYYC | 260 |
| VK3-11.6 | VK3-11 | L2 | EIVLTQSPATLSLSPGERATLSC | RASQSVSSYLA | WYQQKPGQAPRLLIY | DASKRAT | GIPARFSGSGSGTDFTLTISSLEPEDFAVYYC | 261 |

TABLE 3-continued

Polypeptide sequences of exemplified light chain chassis with variability in CDRL1, CDRL2, and frameworks. The Kabat numbers for segment boundaries are indicated. Here, L1 and L2 (in the "Category" column) indicate variability in CDRL1 and CDRL2, respectively, while "F" indicates a framework variant. Sequences designated with both L1 or L2 and F contain variability in both a CDR and framework region.

| Name | Chassis | Category | FRM1: 1-23 | CDR1: 24-34 | FRM2: 35-49 | CDR2: 50-56 | FRM3: 57-88 | SEQ ID NOs: |
|---|---|---|---|---|---|---|---|---|
| VK3-11.10 | VK3-11 | F | EIVMTQSPATLSLSPGERATLSC | RASQSVSSYLA | WYQQKPGQAPRLLIY | DASNRAT | GIPARFSGSGSGTDFTLTISSLEPEDFAVYYC | 262 |
| VK3-11.13 | VK3-11 | FL1 | EIVMTQSPATLSLSPGERATLSC | RASQSVSNYLA | WYQQKPGQAPRLLIY | DASNRAT | GIPARFSGSGSGTDFTLTISSLEPEDFAVYYC | 263 |
| VK3-11.14 | VK3-11 | FL2 | EIVMTQSPATLSLSPGERATLSC | RASQSVSSYLA | WYQQKPGQAPRLLIY | DSSNRAT | GIPARFSGSGSGTDFTLTISSLEPEDFAVYYC | 264 |
| VK3-11.15 | VK3-11 | FL2 | EIVMTQSPATLSLSPGERATLSC | RASQSVSSYLA | WYQQKPGQAPRLLIY | DTSNRAT | GIPARFSGSGSGTDFTLTISSLEPEDFAVYYC | 265 |
| VK3-11.16 | VK3-11 | FL2 | EIVMTQSPATLSLSPGERATLSC | RASQSVSSYLA | WYQQKPGQAPRLLIY | DASKRAT | GIPARFSGSGSGTDFTLTISSLEPEDFAVYYC | 266 |
| VK3-11.20 | VK3-11 | F | EIVLTQSPATLSLSPGERATLSC | RASQSVSSYLA | WFQQKPGQAPRLLIY | DASNRAT | GIPARFSGSGSGTDFTLTISSLEPEDFAVYYC | 267 |
| VK3-11.21 | VK3-11 | FL1 | EIVLTQSPATLSLSPGERATLSC | RASQSISSYLA | WFQQKPGQAPRLLIY | DASNRAT | GIPARFSGSGSGTDFTLTISSLEPEDFAVYYC | 268 |
| VK3-11.24 | VK3-11 | FL2 | EIVLTQSPATLSLSPGERATLSC | RASQSVSSYLA | WFQQKPGQAPRLLIY | DSSNRAT | GIPARFSGSGSGTDFTLTISSLEPEDFAVYYC | 269 |
| VK3-11.25 | VK3-11 | FL2 | EIVLTQSPATLSLSPGERATLSC | RASQSVSSYLA | WFQQKPGQAPRLLIY | DTSNRAT | GIPARFSGSGSGTDFTLTISSLEPEDFAVYYC | 270 |
| VK3-15 | VK3-15 | Germline | EIVMTQSPATLSVSPGERATLSC | RASQSVSSNLA | WYQQKPGQAPRLLIY | GASTRAT | GIPARFSGSGSGTEFTLTISSLQSEDFAVYYC | 271 |
| VK3-15.1 | VK3-15 | L1 | EIVMTQSPATLSVSPGERATLSC | RASQSVGSNLA | WYQQKPGQAPRLLIY | GASTRAT | GIPARFSGSGSGTEFTLTISSLQSEDFAVYYC | 272 |
| VK3-15.6 | VK3-15 | L1 | EIVMTQSPATLSVSPGERATLSC | RASQSVSSSLA | WYQQKPGQAPRLLIY | GASTRAT | GIPARFSGSGSGTEFTLTISSLQSEDFAVYYC | 273 |
| VK3-15.7 | VK3-15 | L2 | EIVMTQSPATLSVSPGERATLSC | RASQSVSSNLA | WYQQKPGQAPRLLIY | DASTRAT | GIPARFSGSGSGTEFTLTISSLQSEDFAVYYC | 274 |
| VK3-15.8 | VK3-15 | L2 | EIVMTQSPATLSVSPGERATLSC | RASQSVSSNLA | WYQQKPGQAPRLLIY | SASTRAT | GIPARFSGSGSGTEFTLTISSLQSEDFAVYYC | 275 |
| VK3-15.10 | VK3-15 | F | EIVLTQSPATLSVSPGERATLSC | RASQSVSSNLA | WYQQKPGQAPRLLIY | GASTRAT | GIPARFSGSGSGTEFTLTISSLQSEDFAVYYC | 276 |
| VK3-15.11 | VK3-15 | FL1 | EIVLTQSPATLSVSPGERATLSC | RASQSVGSNLA | WYQQKPGQAPRLLIY | GASTRAT | GIPARFSGSGSGTEFTLTISSLQSEDFAVYYC | 277 |
| VK3-15.14 | VK3-15 | FL1 | EIVLTQSPATLSVSPGERATLSC | RASQSVSTNLA | WYQQKPGQAPRLLIY | GASTRAT | GIPARFSGSGSGTEFTLTISSLQSEDFAVYYC | 278 |

TABLE 3-continued

Polypeptide sequences of exemplified light chain chassis with variability in CDRL1, CDRL2, and frameworks. The Kabat numbers for segment boundaries are indicated. Here, L1 and L2 (in the "Category" column) indicate variability in CDRL1 and CDRL2, respectively, while "F" indicates a framework variant. Sequences designated with both L1 or L2 and F contain variability in both a CDR and framework region.

| Name | Chassis | Category | FRM1: 1-23 | CDR1: 24-34 | FRM2: 35-49 | CDR2: 50-56 | FRM3: 57-88 | SEQ ID NOs: |
|---|---|---|---|---|---|---|---|---|
| VK3-15.16 | VK3-15 | FL1 | EIVLTQSPATLSVSPGERATLSC | RASQSVSSDLA | WYQQKPGQAPRLLIY | GASTRAT | GIPARFSGSGSGTEFTLTISSLQSEDFAVYYC | 279 |
| VK3-15.20 | VK3-15 | F | EIVMTQSPATLSVSPGERATLSC | RASQSVSSNLA | WYQQKPGQAPRLLIF | GASTRAT | GIPARFSGSGSGTEFTLTISSLQSEDFAVYYC | 280 |
| VK3-15.21 | VK3-15 | FL1 | EIVMTQSPATLSVSPGERATLSC | RASQSVGSNLA | WYQQKPGQAPRLLIF | GASTRAT | GIPARFSGSGSGTEFTLTISSLQSEDFAVYYC | 281 |
| VK3-15.25 | VK3-15 | FL1 | EIVMTQSPATLSVSPGERATLSC | RASQSVSSDLA | WYQQKPGQAPRLLIF | GASTRAT | GIPARFSGSGSGTEFTLTISSLQSEDFAVYYC | 282 |
| VK3-15.26 | VK3-15 | FL1 | EIVMTQSPATLSVSPGERATLSC | RASQSVSSSLA | WYQQKPGQAPRLLIF | GASTRAT | GIPARFSGSGSGTEFTLTISSLQSEDFAVYYC | 283 |
| VK3-20 | VK3-20 | Germline | EIVLTQSPGTLSLSPGERATLSC | RASQSVSSSYLA | WYQQKPGQAPRLLIY | GASSRAT | GIPDRFSGSGSGTDFTLTISRLEPEDFAVYYC | 284 |
| VK3-20.1 | VK3-20 | L1 | EIVLTQSPGTLSLSPGERATLSC | RASQSVRSSYLA | WYQQKPGQAPRLLIY | GASSRAT | GIPDRFSGSGSGTDFTLTISRLEPEDFAVYYC | 285 |
| VK3-20.4 | VK3-20 | L1 | EIVLTQSPGTLSLSPGERATLSC | RASQSVSSDYLA | WYQQKPGQAPRLLIY | GASSRAT | GIPDRFSGSGSGTDFTLTISRLEPEDFAVYYC | 286 |
| VK3-20.7 | VK3-20 | L2 | EIVLTQSPGTLSLSPGERATLSC | RASQSVSSSYLA | WYQQKPGQAPRLLIY | GASNRAT | GIPDRFSGSGSGTDFTLTISRLEPEDFAVYYC | 287 |
| VK3-20.8 | VK3-20 | L2 | EIVLTQSPGTLSLSPGERATLSC | RASQSVSSSYLA | WYQQKPGQAPRLLIY | GASRRAT | GIPDRFSGSGSGTDFTLTISRLEPEDFAVYYC | 288 |
| VK3-20.10 | VK3-20 | F | EIVMTQSPGTLSLSPGERATLSC | RASQSVSSSYLA | WYQQKPGQAPRLLIY | GASSRAT | GIPDRFSGSGSGTDFTLTISRLEPEDFAVYYC | 289 |
| VK3-20.17 | VK3-20 | FL2 | EIVMTQSPGTLSLSPGERATLSC | RASQSVSSSYLA | WYQQKPGQAPRLLIY | GASNRAT | GIPDRFSGSGSGTDFTLTISRLEPEDFAVYYC | 290 |
| VK3-20.20 | VK3-20 | F | EIVLTQSPGTLSLSPGERATLSC | RASQSVSSSYLA | WYQQKPGQAPRLLIS | GASSRAT | GIPDRFSGSGSGTDFTLTISRLEPEDFAVYYC | 291 |
| VK3-20.22 | VK3-20 | FL1 | EIVLTQSPGTLSLSPGERATLSC | RASQSVSSNYLA | WYQQKPGQAPRLLIS | GASSRAT | GIPDRFSGSGSGTDFTLTISRLEPEDFAVYYC | 292 |
| VK4-01 | VK4-01 | Germline | DIVMTQSPDSLAVSLGERATINC | KSSQSVLYSSNNKNYLA | WYQQKPGQPPKLLIY | WASTRES | GVPDRFSGSGSGTDFTLTISSLQAEDVAVYYC | 293 |
| VK4-01.1 | VK4-01 | L1 | DIVMTQSPDSLAVSLGERATINC | KSSQSLLYSSNNKNYLA | WYQQKPGQPPKLLIY | WASTRES | GVPDRFSGSGSGTDFTLTISSLQAEDVAVYYC | 294 |
| VK4-01.2 | VK4-01 | L1 | DIVMTQSPDSLAVSLGERATINC | KSSQSILYSSNNKNYLA | WYQQKPGQPPKLLIY | WASTRES | GVPDRFSGSGSGTDFTLTISSLQAEDVAVYYC | 295 |

TABLE 3-continued

Polypeptide sequences of exemplified light chain chassis with variability in CDRL1, CDRL2, and frameworks. The Kabat numbers for segment boundaries are indicated. Here, L1 and L2 (in the "Category" column) indicate variability in CDRL1 and CDRL2, respectively, while "F" indicates a framework variant. Sequences designated with both L1 or L2 and F contain variability in both a CDR and framework region.

| Name | Chassis | Cate-gory | FRM1: 1-23 | CDR1: 24-34 | FRM2: 35-49 | CDR2: 50-56 | FRM3: 57-88 | SEQ ID NOs: |
|---|---|---|---|---|---|---|---|---|
| VK4-01.3 | VK4-01 | L1 | DIVMTQSPDSLAVS LGERATINC | KSSQSVLHSS NNKNYLA | WYQQKPGQPPK LLIY | WASTRES | GVPDRFSGSGS GTDFTLTISSL QAEDVAVYYC | 296 |
| VK4-01.4 | VK4-01 | L1 | DIVMTQSPDSLAVS LGERATINC | KSSQSVLFSS NNKNYLA | WYQQKPGQPPK LLIY | WASTRES | GVPDRFSGSGS GTDFTLTISSL QAEDVAVYYC | 297 |
| VK4-01.5 | VK4-01 | L1 | DIVMTQSPDSLAVS LGERATINC | KSSQSVLYTS NNKNYLA | WYQQKPGQPPK LLIY | WASTRES | GVPDRFSGSGS GTDFTLTISSL QAEDVAVYYC | 298 |
| VK4-01.7 | VK4-01 | L2 | DIVMTQSPDSLAVS LGERATINC | KSSQSVLYSS NNKNYLA | WYQQKPGQPPK LLIY | WASSRES | GVPDRFSGSGS GTDFTLTISSL QAEDVAVYYC | 299 |
| VK4-01.10 | VK4-01 | F | DIVLTQSPDSLAVS LGERATINC | KSSQSVLYSS NNKNYLA | WYQQKPGQPPK LLIY | WASTRES | GVPDRFSGSGS GTDFTLTISSL QAEDVAVYYC | 300 |
| VK4-01.13 | VK4-01 | FL1 | DIVLTQSPDSLAVS LGERATINC | KSSQSVLHSS NNKNYLA | WYQQKPGQPPK LLIY | WASTRES | GVPDRFSGSGS GTDFTLTISSL QAEDVAVYYC | 301 |
| VK4-01.17 | VK4-01 | FL2 | DIVLTQSPDSLAVS LGERATINC | KSSQSVLYSS NNKNYLA | WYQQKPGQPPK LLIY | WASSRES | GVPDRFSGSGS GTDFTLTISSL QAEDVAVYYC | 302 |
| VK4-01.20 | VK4-01 | F | DIVMTQSPDSLAVS LGERATINC | KSSQSVLYSS NNKNYLA | WYQQKPGQPPK LLIS | WASTRES | GVPDRFSGSGS GTDFTLTISSL QAEDVAVYYC | 303 |
| VK4-01.23 | VK4-01 | FL1 | DIVMTQSPDSLAVS LGERATINC | KSSQSVLHSS NNKNYLA | WYQQKPGQPPK LLIS | WASTRES | GVPDRFSGSGS GTDFTLTISSL QAEDVAVYYC | 304 |

TABLE 4

Jumping dimer and trimer oligonucleotides for the VK1-39 sequences with CDRL3 length nine and F as the junctional amino acid. i.e., The sequences depicted below occur between YYC and FGG, to yield: YYC-[89-97]-FGG. The sequences in this table encompassed by positions "[89-97]" are disclosed as SEQ ID NOS 8721-8745, respectively, in order of appearance.

| Name | Oligo | SEQ ID NO | 89 | 90 | 91 | 92 | 93 | 94 | 95 | 96 | 97 |
|---|---|---|---|---|---|---|---|---|---|---|---|
| Jumping Dimer | | | | | | | | | | | |
| VK1-39_1 | SWMSWMAGC TACAGTACT CCTTWCACT | 305 | DEHLQV | DEHLQV | S | Y | S | T | P | FY | T |
| VK1-39_2 | SWMCAAVNA TACAGTACT CCTTWCACT | 306 | DEHLQV | Q | AEGIKLPQR TV | Y | S | T | P | FY | T |
| VK1-39_3 | SWMCAAAGC BHCAGTACT CCTTWCACT | 307 | DEHLQV | Q | S | ADFHLPS VY | S | T | P | FY | T |

TABLE 4-continued

Jumping dimer and trimer oligonucleotides for the VK1-39 sequences with CDRL3 length nine and F as the junctional amino acid. i.e., The sequences depicted below occur between YYC and FGG, to yield: YYC-[89-97]-FGG. The sequences in this table encompassed by positions "[89-97]" are disclosed as SEQ ID NOS 8721-8745, respectively, in order of appearance.

| Name | Oligo | SEQ ID NO | 89 | 90 | 91 | 92 | 93 | 94 | 95 | 96 | 97 |
|---|---|---|---|---|---|---|---|---|---|---|---|
| VK1-39_4 | SWMCAAAGC TACNHCACT CCTTWCACT | 308 | DEHLQV | Q | S | Y | ADFHILNP STVY | T | P | FY | T |
| VK1-39_5 | SWMCAAAGC TACAGTBHC CCTTWCACT | 309 | DEHLQV | Q | S | Y | S | ADFHLP PSVY | | FY | T |
| VK1-39_6 | CAGSWMVNA TACAGTACT CCTTWCACT | 310 | Q | DEHLQV | AEGIKLPQR TV | Y | S | T | P | FY | T |
| VK1-39_7 | CAGSWMAGC BHCAGTACT CCTTWCACT | 311 | Q | DEHLQV | S | ADFHLPS VY | S | T | P | FY | T |
| VK1-39_8 | CAGSWMAGC TACNHCACT CCTTWCACT | 312 | Q | DEHLQV | S | Y | ADFHILNP STVY | T | P | FY | T |
| VK1-39_9 | CAGSWMAGC TACAGTBHC CCTTWCACT | 313 | Q | DEHLQV | S | Y | S | ADFHLP PSVY | | FY | T |
| VK1-39_10 | CAGCAAVNA BHCAGTACT CCTTWCACT | 314 | Q | Q | AEGIKLPQR TV | ADFHLPS VY | S | T | P | FY | T |
| VK1-39_11 | CAGCAAVNA TACNHCACT CCTTWCACT | 315 | Q | Q | AEGIKLPQR TV | Y | ADFHILNP STVY | T | P | FY | T |
| VK1-39_12 | CAGCAAVNA TACAGTBHC CCTTWCACT | 316 | Q | Q | AEGIKLPQR TV | Y | S | ADFHLP PSVY | | FY | T |
| VK1-39_13 | CAGCAAAGC BHCNHCACT CCTTWCACT | 317 | Q | Q | S | ADFHLPS VY | ADFHILNP STVY | T | P | FY | T |
| VK1-39_14 | CAGCAAAGC BHCAGTBHC CCTTWCACT | 318 | Q | Q | S | ADFHLPS VY | S | ADFHLP PSVY | | FY | T |
| VK1-39_15 | CAGCAAAGC TACNHCBHC CCTTWCACT | 319 | Q | Q | S | Y | ADFHILNP STVY | ADFHLP PSVY | | FY | T |
| **Jumping Trimer** | | | | | | | | | | | |
| VK1-39_10_0_9 | CAGCAAVNA BHCAGTACT CCTTWCACT | 314 | Q | Q | AEGIKLPQR TV | ADFHLPS VY | S | T | P | FY | T |
| VK1-39_11_0_9 | CAGCAAVNA TACNHCACT CCTTWCACT | 315 | Q | Q | AEGIKLPQR TV | Y | ADFHILNP STVY | T | P | FY | T |
| VK1-39_12_0_9 | CAGCAAVNA TACAGTBHC CCTTWCACT | 316 | Q | Q | AEGIKLPQR TV | Y | S | ADFHLP PSVY | | FY | T |
| VK1-39_13_0_9 | CAGCAAAGC BHCNHCACT CCTTWCACT | 317 | Q | Q | S | ADFHLPS VY | ADFHILNP STVY | T | P | FY | T |

TABLE 4-continued

Jumping dimer and trimer oligonucleotides for the VK1-39 sequences with CDRL3 length nine and F as the junctional amino acid. i.e., The sequences depicted below occur between YYC and FGG, to yield: YYC-[89-97]-FGG. The sequences in this table encompassed by positions "[89-97]" are disclosed as SEQ ID NOS 8721-8745, respectively, in order of appearance.

| Name | Oligo | SEQ ID NO | 89 | 90 | 91 | 92 | 93 | 94 | 95 | 96 | 97 |
|---|---|---|---|---|---|---|---|---|---|---|---|
| VK1-39_14_0_9 | CAGCAAAGC BHCAGTBHC CCTTWCACT | 318 | Q | Q | S | ADFHLPS VY | S | ADFHLP PSVY | | FY | T |
| VK1-39_15_0_9 | CAGCAAAGC TACNHCBHC CCTTWCACT | 319 | Q | Q | S | Y | ADFHILNP STVY | ADFHLP PSVY | | FY | T |
| VK1-39_t1_0_9 | CAGCAAVNA BHCNHCACT CCTTWCACT | 320 | Q | Q | AEGIKLPQR TV | ADFHLPS VY | ADFHILNP STVY | T | P | FY | T |
| VK1-39_t2_0_9 | CAGCAAVNA BHCAGTBHC CCTTWCACT | 321 | Q | Q | AEGIKLPQR TV | ADFHLPS VY | S | ADFHLP PSVY | | FY | T |
| VK1-39_t3_0_9 | CAGCAAVNA TACNHCBHC CCTTWCACT | 322 | Q | Q | AEGIKLPQR TV | Y | ADFHILNP STVY | ADFHLP PSVY | | FY | T |
| VK1-39_t4_0_9 | CAGCAAAGC BHCNHCBHC CCTTWCACT | 323 | Q | Q | S | ADFHLPS VY | ADFHILNP STVY | ADFHLP PSVY | | FY | T |

TABLE 5

Oligonucleotide sequences for exemplary VK jumping dimer and trimer sequences with CDRL3 length 8.

| Name | Sequence of Synthesized Oligonucleotide | Portion of Oligonucleotide Corresponding to CDRL3 Proper | SEQ ID NO (Oligo) | SEQ ID NO (CDRL3 Portion) |
|---|---|---|---|---|
| Jumping Dimer | | | | |
| VK1-05 1 0 8 | CCTGATGATTTTGCAACTTATTACTGCSWMSWMTACA ATAGTTACTWCACTTTTGGCGGAGGGACCAAG | SWMSWMTACAATAGTTACTWCACT | 324 | 948 |
| VK1-05 10 0 8 | CCTGATGATTTTGCAACTTATTACTGCCAGCAGBHCV RMAGTTACTWCACTTTTGGCGGAGGGACCAAG | CAGCAGBHCVRMAGTTACTWCACT | 325 | 949 |
| VK1-05 11 0 8 | CCTGATGATTTTGCAACTTATTACTGCCAGCAGBHCA ATMBCTACTWCACTTTTGGCGGAGGGACCAAG | CAGCAGBHCAATMBCTACTWCACT | 326 | 950 |
| VK1-05 12 0 8 | CCTGATGATTTTGCAACTTATTACTGCCAGCAGBHCA ATAGTYWCTWCACTTTTGGCGGAGGGACCAAG | CAGCAGBHCAATAGTYWCTWCACT | 327 | 951 |
| VK1-05 13 0 8 | CCTGATGATTTTGCAACTTATTACTGCCAGCAGTACV RMMBCTACTWCACTTTTGGCGGAGGGACCAAG | CAGCAGTACVRMMBCTACTWCACT | 328 | 952 |
| VK1-05 14 0 8 | CCTGATGATTTTGCAACTTATTACTGCCAGCAGTACV RMAGTYWCTWCACTTTTGGCGGAGGGACCAAG | CAGCAGTACVRMAGTYWCTWCACT | 329 | 953 |
| VK1-05 15 0 8 | CCTGATGATTTTGCAACTTATTACTGCCAGCAGTACA ATMBCYWCTWCACTTTTGGCGGAGGGACCAAG | CAGCAGTACAATMBCYWCTWCACT | 330 | 954 |
| VK1-05 2 0 8 | CCTGATGATTTTGCAACTTATTACTGCSWMCAGBHCA ATAGTTACTWCACTTTTGGCGGAGGGACCAAG | SWMCAGBHCAATAGTTACTWCACT | 331 | 955 |
| VK1-05 3 0 8 | CCTGATGATTTTGCAACTTATTACTGCSWMCAGTACV RMAGTTACTWCACTTTTGGCGGAGGGACCAAG | SWMCAGTACVRMAGTTACTWCACT | 332 | 956 |

TABLE 5-continued

Oligonucleotide sequences for exemplary VK jumping dimer and trimer sequences with CDRL3 length 8.

| Name | Sequence of Synthesized Oligonucleotide | Portion of Oligonucleotide Corresponding to CDRL3 Proper | SEQ ID NO (Oligo) | SEQ ID NO (CDRL3 Portion) |
|---|---|---|---|---|
| VK1-05 4 0 8 | CCTGATGATTTTGCAACTTATTACTGCSWMCAGTACAATMBCTACTWCACTTTTGGCGGAGGGACCAAG | SWMCAGTACAATMBCTACTWCACT | 333 | 957 |
| VK1-05 5 0 8 | CCTGATGATTTTGCAACTTATTACTGCSWMCAGTACAATAGTYWCTWCACTTTTGGCGGAGGGACCAAG | SWMCAGTACAATAGTYWCTWCACT | 334 | 958 |
| VK1-05 6 0 8 | CCTGATGATTTTGCAACTTATTACTGCCAGSWMBHCAATAGTTACTWCACTTTTGGCGGAGGGACCAAG | CAGSWMBHCAATAGTTACTWCACT | 335 | 959 |
| VK1-05 7 0 8 | CCTGATGATTTTGCAACTTATTACTGCCAGSWMTACVRMAGTTACTWCACTTTTGGCGGAGGGACCAAG | CAGSWMTACVRMAGTTACTWCACT | 336 | 960 |
| VK1-05 8 0 8 | CCTGATGATTTTGCAACTTATTACTGCCAGSWMTACAATMBCTACTWCACTTTTGGCGGAGGGACCAAG | CAGSWMTACAATMBCTACTWCACT | 337 | 961 |
| VK1-05 9 0 8 | CCTGATGATTTTGCAACTTATTACTGCCAGSWMTACAATAGTYWCTWCACTTTTGGCGGAGGGACCAAG | CAGSWMTACAATAGTYWCTWCACT | 338 | 962 |
| VK1-05 1 1 8 | CCTGATGATTTTGCAACTTATTACTGCSWMSWMTACAATAGTTACMTCACTTTTGGCGGAGGGACCAAG | SWMSWMTACAATAGTTACMTCACT | 339 | 963 |
| VK1-05 10 1 8 | CCTGATGATTTTGCAACTTATTACTGCCAGCAGBHCVRMAGTTACMTCACTTTTGGCGGAGGGACCAAG | CAGCAGBHCVRMAGTTACMTCACT | 340 | 964 |
| VK1-05 11 1 8 | CCTGATGATTTTGCAACTTATTACTGCCAGCAGBHCAATMBCTACMTCACTTTTGGCGGAGGGACCAAG | CAGCAGBHCAATMBCTACMTCACT | 341 | 965 |
| VK1-05 12 1 8 | CCTGATGATTTTGCAACTTATTACTGCCAGCAGBHCAATAGTYWCMTCACTTTTGGCGGAGGGACCAAG | CAGCAGBHCAATAGTYWCMTCACT | 342 | 966 |
| VK1-05 13 1 8 | CCTGATGATTTTGCAACTTATTACTGCCAGCAGTACVRMMBCTACMTCACTTTTGGCGGAGGGACCAAG | CAGCAGTACVRMMBCTACMTCACT | 343 | 967 |
| VK1-05 14 1 8 | CCTGATGATTTTGCAACTTATTACTGCCAGCAGTACVRMAGTYWCMTCACTTTTGGCGGAGGGACCAAG | CAGCAGTACVRMAGTYWCMTCACT | 344 | 968 |
| VK1-05 15 1 8 | CCTGATGATTTTGCAACTTATTACTGCCAGCAGTACAATMBCYWCMTCACTTTTGGCGGAGGGACCAAG | CAGCAGTACAATMBCYWCMTCACT | 345 | 969 |
| VK1-05 2 1 8 | CCTGATGATTTTGCAACTTATTACTGCSWMCAGBHCAATAGTTACMTCACTTTTGGCGGAGGGACCAAG | SWMCAGBHCAATAGTTACMTCACT | 346 | 970 |
| VK1-05 3 1 8 | CCTGATGATTTTGCAACTTATTACTGCSWMCAGTACVRMAGTTACMTCACTTTTGGCGGAGGGACCAAG | SWMCAGTACVRMAGTTACMTCACT | 347 | 971 |
| VK1-05 4 1 8 | CCTGATGATTTTGCAACTTATTACTGCSWMCAGTACAATMBCTACMTCACTTTTGGCGGAGGGACCAAG | SWMCAGTACAATMBCTACMTCACT | 348 | 972 |
| VK1-05 5 1 8 | CCTGATGATTTTGCAACTTATTACTGCSWMCAGTACAATAGTYWCMTCACTTTTGGCGGAGGGACCAAG | SWMCAGTACAATAGTYWCMTCACT | 349 | 973 |
| VK1-05 6 1 8 | CCTGATGATTTTGCAACTTATTACTGCCAGSWMBHCAATAGTTACMTCACTTTTGGCGGAGGGACCAAG | CAGSWMBHCAATAGTTACMTCACT | 350 | 974 |
| VK1-05 7 1 8 | CCTGATGATTTTGCAACTTATTACTGCCAGSWMTACVRMAGTTACMTCACTTTTGGCGGAGGGACCAAG | CAGSWMTACVRMAGTTACMTCACT | 351 | 975 |
| VK1-05 8 1 8 | CCTGATGATTTTGCAACTTATTACTGCCAGSWMTACAATMBCTACMTCACTTTTGGCGGAGGGACCAAG | CAGSWMTACAATMBCTACMTCACT | 352 | 976 |
| VK1-05 9 1 8 | CCTGATGATTTTGCAACTTATTACTGCCAGSWMTACAATAGTYWCMTCACTTTTGGCGGAGGGACCAAG | CAGSWMTACAATAGTYWCMTCACT | 353 | 977 |
| VK1-05 1 2 8 | CCTGATGATTTTGCAACTTATTACTGCSWMSWMTACAATAGTTACWGGACTTTTGGCGGAGGGACCAAG | SWMSWMTACAATAGTTACWGGACT | 354 | 978 |
| VK1-05 10 2 8 | CCTGATGATTTTGCAACTTATTACTGCCAGCAGBHCVRMAGTTACWGGACTTTTGGCGGAGGGACCAAG | CAGCAGBHCVRMAGTTACWGGACT | 355 | 979 |

TABLE 5-continued

Oligonucleotide sequences for exemplary VK jumping dimer and trimer sequences with CDRL3 length 8.

| Name | Sequence of Synthesized Oligonucleotide | Portion of Oligonucleotide Corresponding to CDRL3 Proper | SEQ ID NO (Oligo) | SEQ ID NO (CDRL3 Portion) |
|---|---|---|---|---|
| VK1-05 11 2 8 | CCTGATGATTTTGCAACTTATTACTGCCAGCAGBHCAATMBCTACWGGACTTTTGGCGGAGGGACCAAG | CAGCAGBHCAATMBCTACWGGACT | 356 | 980 |
| VK1-05 12 2 8 | CCTGATGATTTTGCAACTTATTACTGCCAGCAGBHCAATAGTYWCWGGACTTTTGGCGGAGGGACCAAG | CAGCAGBHCAATAGTYWCWGGACT | 357 | 981 |
| VK1-05 13 2 8 | CCTGATGATTTTGCAACTTATTACTGCCAGCAGTACVRMMBCTACWGGACTTTTGGCGGAGGGACCAAG | CAGCAGTACVRMMBCTACWGGACT | 358 | 982 |
| VK1-05 14 2 8 | CCTGATGATTTTGCAACTTATTACTGCCAGCAGTACVRMAGTYWCWGGACTTTTGGCGGAGGGACCAAG | CAGCAGTACVRMAGTYWCWGGACT | 359 | 983 |
| VK1-05 15 2 8 | CCTGATGATTTTGCAACTTATTACTGCCAGCAGTACAATMBCYWCWGGACTTTTGGCGGAGGGACCAAG | CAGCAGTACAATMBCYWCWGGACT | 360 | 984 |
| VK1-05 2 2 8 | CCTGATGATTTTGCAACTTATTACTGCSWMCAGBHCAATAGTTACWGGACTTTTGGCGGAGGGACCAAG | SWMCAGBHCAATAGTTACWGGACT | 361 | 985 |
| VK1-05 3 2 8 | CCTGATGATTTTGCAACTTATTACTGCSWMCAGTACVRMAGTTACWGGACTTTTGGCGGAGGGACCAAG | SWMCAGTACVRMAGTTACWGGACT | 362 | 986 |
| VK1-05 4 2 8 | CCTGATGATTTTGCAACTTATTACTGCSWMCAGTACAATMBCTACWGGACTTTTGGCGGAGGGACCAAG | SWMCAGTACAATMBCTACWGGACT | 363 | 987 |
| VK1-05 5 2 8 | CCTGATGATTTTGCAACTTATTACTGCSWMCAGTACAATAGTYWCWGGACTTTTGGCGGAGGGACCAAG | SWMCAGTACAATAGTYWCWGGACT | 364 | 988 |
| VK1-05 6 2 8 | CCTGATGATTTTGCAACTTATTACTGCCAGSWMBHCAATAGTTACWGGACTTTTGGCGGAGGGACCAAG | CAGSWMBHCAATAGTTACWGGACT | 365 | 989 |
| VK1-05 7 2 8 | CCTGATGATTTTGCAACTTATTACTGCCAGSWMTACVRMAGTTACWGGACTTTTGGCGGAGGGACCAAG | CAGSWMTACVRMAGTTACWGGACT | 366 | 990 |
| VK1-05 8 2 8 | CCTGATGATTTTGCAACTTATTACTGCCAGSWMTACAATMBCTACWGGACTTTTGGCGGAGGGACCAAG | CAGSWMTACAATMBCTACWGGACT | 367 | 991 |
| VK1-05 9 2 8 | CCTGATGATTTTGCAACTTATTACTGCCAGSWMTACAATAGTYWCWGGACTTTTGGCGGAGGGACCAAG | CAGSWMTACAATAGTYWCWGGACT | 368 | 992 |
| VK1-05 1 3 8 | CCTGATGATTTTGCAACTTATTACTGCSWMSWMTACAATAGTTACCCTACTTTTGGCGGAGGGACCAAG | SWMSWMTACAATAGTTACCCTACT | 369 | 993 |
| VK1-05 10 3 8 | CCTGATGATTTTGCAACTTATTACTGCCAGCAGBHCVRMAGTTACCCTACTTTTGGCGGAGGGACCAAG | CAGCAGBHCVRMAGTTACCCTACT | 370 | 994 |
| VK1-05 11 3 8 | CCTGATGATTTTGCAACTTATTACTGCCAGCAGBHCAATMBCTACCCTACTTTTGGCGGAGGGACCAAG | CAGCAGBHCAATMBCTACCCTACT | 371 | 995 |
| VK1-05 12 3 8 | CCTGATGATTTTGCAACTTATTACTGCCAGCAGBHCAATAGTYWCCCTACTTTTGGCGGAGGGACCAAG | CAGCAGBHCAATAGTYWCCCTACT | 372 | 996 |
| VK1-05 13 3 8 | CCTGATGATTTTGCAACTTATTACTGCCAGCAGTACVRMMBCTACCCTACTTTTGGCGGAGGGACCAAG | CAGCAGTACVRMMBCTACCCTACT | 373 | 997 |
| VK1-05 14 3 8 | CCTGATGATTTTGCAACTTATTACTGCCAGCAGTACVRMAGTYWCCCTACTTTTGGCGGAGGGACCAAG | CAGCAGTACVRMAGTYWCCCTACT | 374 | 998 |
| VK1-05 15 3 8 | CCTGATGATTTTGCAACTTATTACTGCCAGCAGTACAATMBCYWCCCTACTTTTGGCGGAGGGACCAAG | CAGCAGTACAATMBCYWCCCTACT | 375 | 999 |
| VK1-05 2 3 8 | CCTGATGATTTTGCAACTTATTACTGCSWMCAGBHCAATAGTTACCCTACTTTTGGCGGAGGGACCAAG | SWMCAGBHCAATAGTTACCCTACT | 376 | 1000 |
| VK1-05 3 3 8 | CCTGATGATTTTGCAACTTATTACTGCSWMCAGTACVRMAGTTACCCTACTTTTGGCGGAGGGACCAAG | SWMCAGTACVRMAGTTACCCTACT | 377 | 1001 |
| VK1-05 4 3 8 | CCTGATGATTTTGCAACTTATTACTGCSWMCAGTACAATMBCTACCCTACTTTTGGCGGAGGGACCAAG | SWMCAGTACAATMBCTACCCTACT | 378 | 1002 |

TABLE 5-continued

Oligonucleotide sequences for exemplary VK jumping dimer and trimer sequences with CDRL3 length 8.

| Name | Sequence of Synthesized Oligonucleotide | Portion of Oligonucleotide Corresponding to CDRL3 Proper | SEQ ID NO (Oli-go) | SEQ ID NO (CDRL3 Por-tion) |
|---|---|---|---|---|
| VK1-05 5 3 8 | CCTGATGATTTTGCAACTTATTACTGCSWMCAGTACAATAGTYWCCCTACTTTTGGCGGAGGGACCAAG | SWMCAGTACAATAGTYWCCCTACT | 379 | 1003 |
| VK1-05 6 3 8 | CCTGATGATTTTGCAACTTATTACTGCCAGSWMBHCAATAGTTACCCTACTTTTGGCGGAGGGACCAAG | CAGSWMBHCAATAGTTACCCTACT | 380 | 1004 |
| VK1-05 7 3 8 | CCTGATGATTTTGCAACTTATTACTGCCAGSWMTACVRMAGTTACCCTACTTTTGGCGGAGGGACCAAG | CAGSWMTACVRMAGTTACCCTACT | 381 | 1005 |
| VK1-05 8 3 8 | CCTGATGATTTTGCAACTTATTACTGCCAGSWMTACAATMBCTACCCTACTTTTGGCGGAGGGACCAAG | CAGSWMTACAATMBCTACCCTACT | 382 | 1006 |
| VK1-05 9 3 8 | CCTGATGATTTTGCAACTTATTACTGCCAGSWMTACAATAGTYWCCCTACTTTTGGCGGAGGGACCAAG | CAGSWMTACAATAGTYWCCCTACT | 383 | 1007 |
| VK1-12 1 0 8 | CCTGAAGATTTTGCAACTTATTACTGTSWMSWMGCAAATAGTTTCTWCACTTTTGGCGGAGGGACCAAG | SWMSWMGCAAATAGTTTCTWCACT | 384 | 1008 |
| VK1-12 10 0 8 | CCTGAAGATTTTGCAACTTATTACTGTCAGCAGRNANHCAGTTTCTWCACTTTTGGCGGAGGGACCAAG | CAGCAGRNANHCAGTTTCTWCACT | 385 | 1009 |
| VK1-12 11 0 8 | CCTGAAGATTTTGCAACTTATTACTGTCAGCAGRNAAATNHCTTCTWCACTTTTGGCGGAGGGACCAAG | CAGCAGRNAAATNHCTTCTWCACT | 386 | 1010 |
| VK1-12 12 0 8 | CCTGAAGATTTTGCAACTTATTACTGTCAGCAGRNAAATAGTYWCTWCACTTTTGGCGGAGGGACCAAG | CAGCAGRNAAATAGTYWCTWCACT | 387 | 1011 |
| VK1-12 13 0 8 | CCTGAAGATTTTGCAACTTATTACTGTCAGCAGGCANHCNHCTTCTWCACTTTTGGCGGAGGGACCAAG | CAGCAGGCANHCNHCTTCTWCACT | 388 | 1012 |
| VK1-12 14 0 8 | CCTGAAGATTTTGCAACTTATTACTGTCAGCAGGCANHCAGTYWCTWCACTTTTGGCGGAGGGACCAAG | CAGCAGGCANHCAGTYWCTWCACT | 389 | 1013 |
| VK1-12 15 0 8 | CCTGAAGATTTTGCAACTTATTACTGTCAGCAGGCAAATNHCYWCTWCACTTTTGGCGGAGGGACCAAG | CAGCAGGCAAATNHCYWCTWCACT | 390 | 1014 |
| VK1-12 2 0 8 | CCTGAAGATTTTGCAACTTATTACTGTSWMCAGRNAAATAGTTTCTWCACTTTTGGCGGAGGGACCAAG | SWMCAGRNAAATAGTTTCTWCACT | 391 | 1015 |
| VK1-12 3 0 8 | CCTGAAGATTTTGCAACTTATTACTGTSWMCAGGCANHCAGTTTCTWCACTTTTGGCGGAGGGACCAAG | SWMCAGGCANHCAGTTTCTWCACT | 392 | 1016 |
| VK1-12 4 0 8 | CCTGAAGATTTTGCAACTTATTACTGTSWMCAGGCAAATNHCTTCTWCACTTTTGGCGGAGGGACCAAG | SWMCAGGCAAATNHCTTCTWCACT | 393 | 1017 |
| VK1-12 5 0 8 | CCTGAAGATTTTGCAACTTATTACTGTSWMCAGGCAAATAGTYWCTWCACTTTTGGCGGAGGGACCAAG | SWMCAGGCAAATAGTYWCTWCACT | 394 | 1018 |
| VK1-12 6 0 8 | CCTGAAGATTTTGCAACTTATTACTGTCAGSWMRNAAATAGTTTCTWCACTTTTGGCGGAGGGACCAAG | CAGSWMRNAAATAGTTTCTWCACT | 395 | 1019 |
| VK1-12 7 0 8 | CCTGAAGATTTTGCAACTTATTACTGTCAGSWMGCANHCAGTTTCTWCACTTTTGGCGGAGGGACCAAG | CAGSWMGCANHCAGTTTCTWCACT | 396 | 1020 |
| VK1-12 8 0 8 | CCTGAAGATTTTGCAACTTATTACTGTCAGSWMGCAAATNHCTTCTWCACTTTTGGCGGAGGGACCAAG | CAGSWMGCAAATNHCTTCTWCACT | 397 | 1021 |
| VK1-12 9 0 8 | CCTGAAGATTTTGCAACTTATTACTGTCAGSWMGCAAATAGTYWCTWCACTTTTGGCGGAGGGACCAAG | CAGSWMGCAAATAGTYWCTWCACT | 398 | 1022 |
| VK1-12 1 1 8 | CCTGAAGATTTTGCAACTTATTACTGTSWMSWMGCAAATAGTTTCMTCACTTTTGGCGGAGGGACCAAG | SWMSWMGCAAATAGTTTCMTCACT | 399 | 1023 |
| VK1-12 10 1 8 | CCTGAAGATTTTGCAACTTATTACTGTCAGCAGRNANHCAGTTTCMTCACTTTTGGCGGAGGGACCAAG | CAGCAGRNANHCAGTTTCMTCACT | 400 | 1024 |
| VK1-12 11 1 8 | CCTGAAGATTTTGCAACTTATTACTGTCAGCAGRNAAATNHCTTCMTCACTTTTGGCGGAGGGACCAAG | CAGCAGRNAAATNHCTTCMTCACT | 401 | 1025 |
| VK1-12 12 1 8 | CCTGAAGATTTTGCAACTTATTACTGTCAGCAGRNAAATAGTYWCMTCACTTTTGGCGGAGGGACCAAG | CAGCAGRNAAATAGTYWCMTCACT | 402 | 1026 |

TABLE 5-continued

Oligonucleotide sequences for exemplary VK jumping dimer and trimer sequences with CDRL3 length 8.

| Name | Sequence of Synthesized Oligonucleotide | Portion of Oligonucleotide Corresponding to CDRL3 Proper | SEQ ID NO (Oligo) | SEQ ID NO (CDRL3 Portion) |
|---|---|---|---|---|
| VK1-12 13 1 8 | CCTGAAGATTTTGCAACTTATTACTGTCAGCAGGCANHCNHCTTCMTCACTTTTGGCGGAGGGACCAAG | CAGCAGGCANHCNHCTTCMTCACT | 403 | 1027 |
| VK1-12 14 1 8 | CCTGAAGATTTTGCAACTTATTACTGTCAGCAGGCANHCAGTYWCMTCACTTTTGGCGGAGGGACCAAG | CAGCAGGCANHCAGTYWCMTCACT | 404 | 1028 |
| VK1-12 15 1 8 | CCTGAAGATTTTGCAACTTATTACTGTCAGCAGGCAAATNHCYWCMTCACTTTTGGCGGAGGGACCAAG | CAGCAGGCAAATNHCYWCMTCACT | 405 | 1029 |
| VK1-12 2 1 8 | CCTGAAGATTTTGCAACTTATTACTGTSWMCAGRNAAATAGTTTCMTCACTTTTGGCGGAGGGACCAAG | SWMCAGRNAAATAGTTTCMTCACT | 406 | 1030 |
| VK1-12 3 1 8 | CCTGAAGATTTTGCAACTTATTACTGTSWMCAGGCANHCAGTTTCMTCACTTTTGGCGGAGGGACCAAG | SWMCAGGCANHCAGTTTCMTCACT | 407 | 1031 |
| VK1-12 4 1 8 | CCTGAAGATTTTGCAACTTATTACTGTSWMCAGGCAAATNHCTTCMTCACTTTTGGCGGAGGGACCAAG | SWMCAGGCAAATNHCTTCMTCACT | 408 | 1032 |
| VK1-12 5 1 8 | CCTGAAGATTTTGCAACTTATTACTGTSWMCAGGCAAATAGTYWCMTCACTTTTGGCGGAGGGACCAAG | SWMCAGGCAAATAGTYWCMTCACT | 409 | 1033 |
| VK1-12 6 1 8 | CCTGAAGATTTTGCAACTTATTACTGTCAGSWMRNAAATAGTTTCMTCACTTTTGGCGGAGGGACCAAG | CAGSWMRNAAATAGTTTCMTCACT | 410 | 1034 |
| VK1-12 7 1 8 | CCTGAAGATTTTGCAACTTATTACTGTCAGSWMGCANHCAGTTTCMTCACTTTTGGCGGAGGGACCAAG | CAGSWMGCANHCAGTTTCMTCACT | 411 | 1035 |
| VK1-12 8 1 8 | CCTGAAGATTTTGCAACTTATTACTGTCAGSWMGCAAATNHCTTCMTCACTTTTGGCGGAGGGACCAAG | CAGSWMGCAAATNHCTTCMTCACT | 412 | 1036 |
| VK1-12 9 1 8 | CCTGAAGATTTTGCAACTTATTACTGTCAGSWMGCAAATAGTYWCMTCACTTTTGGCGGAGGGACCAAG | CAGSWMGCAAATAGTYWCMTCACT | 413 | 1037 |
| VK1-12 1 2 8 | CCTGAAGATTTTGCAACTTATTACTGTSWMSWMGCAAATAGTTTCWGGACTTTTGGCGGAGGGACCAAG | SWMSWMGCAAATAGTTTCWGGACT | 414 | 1038 |
| VK1-12 10 2 8 | CCTGAAGATTTTGCAACTTATTACTGTCAGCAGRNANHCAGTTTCWGGACTTTTGGCGGAGGGACCAAG | CAGCAGRNANHCAGTTTCWGGACT | 415 | 1039 |
| VK1-12 11 2 8 | CCTGAAGATTTTGCAACTTATTACTGTCAGCAGRNAAATNHCTTCWGGACTTTTGGCGGAGGGACCAAG | CAGCAGRNAAATNHCTTCWGGACT | 416 | 1040 |
| VK1-12 12 2 8 | CCTGAAGATTTTGCAACTTATTACTGTCAGCAGRNAAATAGTYWCWGGACTTTTGGCGGAGGGACCAAG | CAGCAGRNAAATAGTYWCWGGACT | 417 | 1041 |
| VK1-12 13 2 8 | CCTGAAGATTTTGCAACTTATTACTGTCAGCAGGCANHCNHCTTCWGGACTTTTGGCGGAGGGACCAAG | CAGCAGGCANHCNHCTTCWGGACT | 418 | 1042 |
| VK1-12 14 2 8 | CCTGAAGATTTTGCAACTTATTACTGTCAGCAGGCANHCAGTYWCWGGACTTTTGGCGGAGGGACCAAG | CAGCAGGCANHCAGTYWCWGGACT | 419 | 1043 |
| VK1-12 15 2 8 | CCTGAAGATTTTGCAACTTATTACTGTCAGCAGGCAAATNHCYWCWGGACTTTTGGCGGAGGGACCAAG | CAGCAGGCAAATNHCYWCWGGACT | 420 | 1044 |
| VK1-12 2 2 8 | CCTGAAGATTTTGCAACTTATTACTGTSWMCAGRNAAATAGTTTCWGGACTTTTGGCGGAGGGACCAAG | SWMCAGRNAAATAGTTTCWGGACT | 421 | 1045 |
| VK1-12 3 2 8 | CCTGAAGATTTTGCAACTTATTACTGTSWMCAGGCANHCAGTTTCWGGACTTTTGGCGGAGGGACCAAG | SWMCAGGCANHCAGTTTCWGGACT | 422 | 1046 |
| VK1-12 4 2 8 | CCTGAAGATTTTGCAACTTATTACTGTSWMCAGGCAAATNHCTTCWGGACTTTTGGCGGAGGGACCAAG | SWMCAGGCAAATNHCTTCWGGACT | 423 | 1047 |
| VK1-12 5 2 8 | CCTGAAGATTTTGCAACTTATTACTGTSWMCAGGCAAATAGTYWCWGGACTTTTGGCGGAGGGACCAAG | SWMCAGGCAAATAGTYWCWGGACT | 424 | 1048 |
| VK1-12 6 2 8 | CCTGAAGATTTTGCAACTTATTACTGTCAGSWMRNAAATAGTTTCWGGACTTTTGGCGGAGGGACCAAG | CAGSWMRNAAATAGTTTCWGGACT | 425 | 1049 |

TABLE 5-continued

Oligonucleotide sequences for exemplary VK jumping dimer and trimer sequences with CDRL3 length 8.

| Name | Sequence of Synthesized Oligonucleotide | Portion of Oligonucleotide Corresponding to CDRL3 Proper | SEQ ID NO (Oligo) | SEQ ID NO (CDRL3 Portion) |
|---|---|---|---|---|
| VK1-12 7 2 8 | CCTGAAGATTTTGCAACTTATTACTGTCAGSWMGCANHCAGTTTCWGGACTTTTGGCGGAGGGACCAAG | CAGSWMGCANHCAGTTTCWGGACT | 426 | 1050 |
| VK1-12 8 2 8 | CCTGAAGATTTTGCAACTTATTACTGTCAGSWMGCAAATNHCTTCWGGACTTTTGGCGGAGGGACCAAG | CAGSWMGCAAATNHCTTCWGGACT | 427 | 1051 |
| VK1-12 9 2 8 | CCTGAAGATTTTGCAACTTATTACTGTCAGSWMGCAAATAGTYWCWGGACTTTTGGCGGAGGGACCAAG | CAGSWMGCAAATAGTYWCWGGACT | 428 | 1052 |
| VK1-12 1 3 8 | CCTGAAGATTTTGCAACTTATTACTGTSWMSWMGCAAATAGTTTCCCTACTTTTGGCGGAGGGACCAAG | SWMSWMGCAAATAGTTTCCCTACT | 429 | 1053 |
| VK1-12 10 3 8 | CCTGAAGATTTTGCAACTTATTACTGTCAGCAGRNANHCAGTTTCCCTACTTTTGGCGGAGGGACCAAG | CAGCAGRNANHCAGTTTCCCTACT | 430 | 1054 |
| VK1-12 11 3 8 | CCTGAAGATTTTGCAACTTATTACTGTCAGCAGRNAAATNHCTTCCCTACTTTTGGCGGAGGGACCAAG | CAGCAGRNAAATNHCTTCCCTACT | 431 | 1055 |
| VK1-12 12 3 8 | CCTGAAGATTTTGCAACTTATTACTGTCAGCAGRNAAATAGTYWCCCTACTTTTGGCGGAGGGACCAAG | CAGCAGRNAAATAGTYWCCCTACT | 432 | 1056 |
| VK1-12 13 3 8 | CCTGAAGATTTTGCAACTTATTACTGTCAGCAGGCANHCNHCTTCCCTACTTTTGGCGGAGGGACCAAG | CAGCAGGCANHCNHCTTCCCTACT | 433 | 1057 |
| VK1-12 14 3 8 | CCTGAAGATTTTGCAACTTATTACTGTCAGCAGGCANHCAGTYWCCCTACTTTTGGCGGAGGGACCAAG | CAGCAGGCANHCAGTYWCCCTACT | 434 | 1058 |
| VK1-12 15 3 8 | CCTGAAGATTTTGCAACTTATTACTGTCAGCAGGCAAATNHCYWCCCTACTTTTGGCGGAGGGACCAAG | CAGCAGGCAAATNHCYWCCCTACT | 435 | 1059 |
| VK1-12 2 3 8 | CCTGAAGATTTTGCAACTTATTACTGTSWMCAGRNAAATAGTTTCCCTACTTTTGGCGGAGGGACCAAG | SWMCAGRNAAATAGTTTCCCTACT | 436 | 1060 |
| VK1-12 3 3 8 | CCTGAAGATTTTGCAACTTATTACTGTSWMCAGGCANHCAGTTTCCCTACTTTTGGCGGAGGGACCAAG | SWMCAGGCANHCAGTTTCCCTACT | 437 | 1061 |
| VK1-12 4 3 8 | CCTGAAGATTTTGCAACTTATTACTGTSWMCAGGCAAATNHCTTCCCTACTTTTGGCGGAGGGACCAAG | SWMCAGGCAAATNHCTTCCCTACT | 438 | 1062 |
| VK1-12 5 3 8 | CCTGAAGATTTTGCAACTTATTACTGTSWMCAGGCAAATAGTYWCCCTACTTTTGGCGGAGGGACCAAG | SWMCAGGCAAATAGTYWCCCTACT | 439 | 1063 |
| VK1-12 6 3 8 | CCTGAAGATTTTGCAACTTATTACTGTCAGSWMRNAAATAGTTTCCCTACTTTTGGCGGAGGGACCAAG | CAGSWMRNAAATAGTTTCCCTACT | 440 | 1064 |
| VK1-12 7 3 8 | CCTGAAGATTTTGCAACTTATTACTGTCAGSWMGCANHCAGTTTCCCTACTTTTGGCGGAGGGACCAAG | CAGSWMGCANHCAGTTTCCCTACT | 441 | 1065 |
| VK1-12 8 3 8 | CCTGAAGATTTTGCAACTTATTACTGTCAGSWMGCAAATNHCTTCCCTACTTTTGGCGGAGGGACCAAG | CAGSWMGCAAATNHCTTCCCTACT | 442 | 1066 |
| VK1-12 9 3 8 | CCTGAAGATTTTGCAACTTATTACTGTCAGSWMGCAAATAGTYWCCCTACTTTTGGCGGAGGGACCAAG | CAGSWMGCAAATAGTYWCCCTACT | 443 | 1067 |
| VK1-33 1 0 8 | CCTGAAGATATTGCAACATATTACTGTSWMSWMTACGATAATCTCTWCACTTTTGGCGGAGGGACCAAG | SWMSWMTACGATAATCTCTWCACT | 444 | 1068 |
| VK1-33 10 0 8 | CCTGAAGATATTGCAACATATTACTGTCAGCAGBHCNHCAATCTCTWCACTTTTGGCGGAGGGACCAAG | CAGCAGBHCNHCAATCTCTWCACT | 445 | 1069 |
| VK1-33 11 0 8 | CCTGAAGATATTGCAACATATTACTGTCAGCAGBHCGATNHCCTCTWCACTTTTGGCGGAGGGACCAAG | CAGCAGBHCGATNHCCTCTWCACT | 446 | 1070 |
| VK1-33 12 0 8 | CCTGAAGATATTGCAACATATTACTGTCAGCAGBHCGATAATYWCTWCACTTTTGGCGGAGGGACCAAG | CAGCAGBHCGATAATYWCTWCACT | 447 | 1071 |
| VK1-33 13 0 8 | CCTGAAGATATTGCAACATATTACTGTCAGCAGTACNHCNHCCTCTWCACTTTTGGCGGAGGGACCAAG | CAGCAGTACNHCNHCCTCTWCACT | 448 | 1072 |
| VK1-33 14 0 8 | CCTGAAGATATTGCAACATATTACTGTCAGCAGTACNHCAATYWCTWCACTTTTGGCGGAGGGACCAAG | CAGCAGTACNHCAATYWCTWCACT | 449 | 1073 |

TABLE 5-continued

Oligonucleotide sequences for exemplary VK jumping dimer and trimer sequences with CDRL3 length 8.

| Name | Sequence of Synthesized Oligonucleotide | Portion of Oligonucleotide Corresponding to CDRL3 Proper | SEQ ID NO (Oligo) | SEQ ID NO (CDRL3 Portion) |
|---|---|---|---|---|
| VK1-33 15 0 8 | CCTGAAGATATTGCAACATATTACTGTCAGCAGTACGATNHCYWCTWCACTTTTGGCGGAGGGACCAAG | CAGCAGTACGATNHCYWCTWCACT | 450 | 1074 |
| VK1-33 2 0 8 | CCTGAAGATATTGCAACATATTACTGTSWMCAGBHCGATAATCTCTWCACTTTTGGCGGAGGGACCAAG | SWMCAGBHCGATAATCTCTWCACT | 451 | 1075 |
| VK1-33 3 0 8 | CCTGAAGATATTGCAACATATTACTGTSWMCAGTACNHCAATCTCTWCACTTTTGGCGGAGGGACCAAG | SWMCAGTACNHCAATCTCTWCACT | 452 | 1076 |
| VK1-33 4 0 8 | CCTGAAGATATTGCAACATATTACTGTSWMCAGTACGATNHCCTCTWCACTTTTGGCGGAGGGACCAAG | SWMCAGTACGATNHCCTCTWCACT | 453 | 1077 |
| VK1-33 5 0 8 | CCTGAAGATATTGCAACATATTACTGTSWMCAGTACGATAATYWCTWCACTTTTGGCGGAGGGACCAAG | SWMCAGTACGATAATYWCTWCACT | 454 | 1078 |
| VK1-33 6 0 8 | CCTGAAGATATTGCAACATATTACTGTCAGSWMBHCGATAATCTCTWCACTTTTGGCGGAGGGACCAAG | CAGSWMBHCGATAATCTCTWCACT | 455 | 1079 |
| VK1-33 7 0 8 | CCTGAAGATATTGCAACATATTACTGTCAGSWMTACNHCAATCTCTWCACTTTTGGCGGAGGGACCAAG | CAGSWMTACNHCAATCTCTWCACT | 456 | 1080 |
| VK1-33 8 0 8 | CCTGAAGATATTGCAACATATTACTGTCAGSWMTACGATNHCCTCTWCACTTTTGGCGGAGGGACCAAG | CAGSWMTACGATNHCCTCTWCACT | 457 | 1081 |
| VK1-33 9 0 8 | CCTGAAGATATTGCAACATATTACTGTCAGSWMTACGATAATYWCTWCACTTTTGGCGGAGGGACCAAG | CAGSWMTACGATAATYWCTWCACT | 458 | 1082 |
| VK1-33 1 1 8 | CCTGAAGATATTGCAACATATTACTGTSWMSWMTACGATAATCTCMTCACTTTTGGCGGAGGGACCAAG | SWMSWMTACGATAATCTCMTCACT | 459 | 1083 |
| VK1-33 10 1 8 | CCTGAAGATATTGCAACATATTACTGTCAGCAGBHCNHCAATCTCMTCACTTTTGGCGGAGGGACCAAG | CAGCAGBHCNHCAATCTCMTCACT | 460 | 1084 |
| VK1-33 11 1 8 | CCTGAAGATATTGCAACATATTACTGTCAGCAGBHCGATNHCCTCMTCACTTTTGGCGGAGGGACCAAG | CAGCAGBHCGATNHCCTCMTCACT | 461 | 1085 |
| VK1-33 12 1 8 | CCTGAAGATATTGCAACATATTACTGTCAGCAGBHCGATAATYWCMTCACTTTTGGCGGAGGGACCAAG | CAGCAGBHCGATAATYWCMTCACT | 462 | 1086 |
| VK1-33 13 1 8 | CCTGAAGATATTGCAACATATTACTGTCAGCAGTACNHCNHCCTCMTCACTTTTGGCGGAGGGACCAAG | CAGCAGTACNHCNHCCTCMTCACT | 463 | 1087 |
| VK1-33 14 1 8 | CCTGAAGATATTGCAACATATTACTGTCAGCAGTACNHCAATYWCMTCACTTTTGGCGGAGGGACCAAG | CAGCAGTACNHCAATYWCMTCACT | 464 | 1088 |
| VK1-33 15 1 8 | CCTGAAGATATTGCAACATATTACTGTCAGCAGTACGATNHCYWCMTCACTTTTGGCGGAGGGACCAAG | CAGCAGTACGATNHCYWCMTCACT | 465 | 1089 |
| VK1-33 2 1 8 | CCTGAAGATATTGCAACATATTACTGTSWMCAGBHCGATAATCTCMTCACTTTTGGCGGAGGGACCAAG | SWMCAGBHCGATAATCTCMTCACT | 466 | 1090 |
| VK1-33 3 1 8 | CCTGAAGATATTGCAACATATTACTGTSWMCAGTACNHCAATCTCMTCACTTTTGGCGGAGGGACCAAG | SWMCAGTACNHCAATCTCMTCACT | 467 | 1091 |
| VK1-33 4 1 8 | CCTGAAGATATTGCAACATATTACTGTSWMCAGTACGATNHCCTCMTCACTTTTGGCGGAGGGACCAAG | SWMCAGTACGATNHCCTCMTCACT | 468 | 1092 |
| VK1-33 5 1 8 | CCTGAAGATATTGCAACATATTACTGTSWMCAGTACGATAATYWCMTCACTTTTGGCGGAGGGACCAAG | SWMCAGTACGATAATYWCMTCACT | 469 | 1093 |
| VK1-33 6 1 8 | CCTGAAGATATTGCAACATATTACTGTCAGSWMBHCGATAATCTCMTCACTTTTGGCGGAGGGACCAAG | CAGSWMBHCGATAATCTCMTCACT | 470 | 1094 |
| VK1-33 7 1 8 | CCTGAAGATATTGCAACATATTACTGTCAGSWMTACNHCAATCTCMTCACTTTTGGCGGAGGGACCAAG | CAGSWMTACNHCAATCTCMTCACT | 471 | 1095 |

TABLE 5-continued

Oligonucleotide sequences for exemplary VK jumping dimer and trimer sequences with CDRL3 length 8.

| Name | Sequence of Synthesized Oligonucleotide | Portion of Oligonucleotide Corresponding to CDRL3 Proper | SEQ ID NO (Oligo) | SEQ ID NO (CDRL3 Portion) |
|---|---|---|---|---|
| VK1-33 8 1 8 | CCTGAAGATATTGCAACATATTACTGTCAGSWMTACGATNHCCTCMTCACTTTTGGCGGAGGGACCAAG | CAGSWMTACGATNHCCTCMTCACT | 472 | 1096 |
| VK1-33 9 1 8 | CCTGAAGATATTGCAACATATTACTGTCAGSWMTACGATAATYWCMTCACTTTTGGCGGAGGGACCAAG | CAGSWMTACGATAATYWCMTCACT | 473 | 1097 |
| VK1-33 1 2 8 | CCTGAAGATATTGCAACATATTACTGTSWMSWMTACGATAATCTCWGGACTTTTGGCGGAGGGACCAAG | SWMSWMTACGATAATCTCWGGACT | 474 | 1098 |
| VK1-33 10 2 8 | CCTGAAGATATTGCAACATATTACTGTCAGCAGBHCNHCAATCTCWGGACTTTTGGCGGAGGGACCAAG | CAGCAGBHCNHCAATCTCWGGACT | 475 | 1099 |
| VK1-33 11 2 8 | CCTGAAGATATTGCAACATATTACTGTCAGCAGBHCGATNHCCTCWGGACTTTTGGCGGAGGGACCAAG | CAGCAGBHCGATNHCCTCWGGACT | 476 | 1100 |
| VK1-33 12 2 8 | CCTGAAGATATTGCAACATATTACTGTCAGCAGBHCGATAATYWCWGGACTTTTGGCGGAGGGACCAAG | CAGCAGBHCGATAATYWCWGGACT | 477 | 1101 |
| VK1-33 13 2 8 | CCTGAAGATATTGCAACATATTACTGTCAGCAGTACNHCNHCCTCWGGACTTTTGGCGGAGGGACCAAG | CAGCAGTACNHCNHCCTCWGGACT | 478 | 1102 |
| VK1-33 14 2 8 | CCTGAAGATATTGCAACATATTACTGTCAGCAGTACNHCAATYWCWGGACTTTTGGCGGAGGGACCAAG | CAGCAGTACNHCAATYWCWGGACT | 479 | 1103 |
| VK1-33 15 2 8 | CCTGAAGATATTGCAACATATTACTGTCAGCAGTACGATNHCYWCWGGACTTTTGGCGGAGGGACCAAG | CAGCAGTACGATNHCYWCWGGACT | 480 | 1104 |
| VK1-33 2 2 8 | CCTGAAGATATTGCAACATATTACTGTSWMCAGBHCGATAATCTCWGGACTTTTGGCGGAGGGACCAAG | SWMCAGBHCGATAATCTCWGGACT | 481 | 1105 |
| VK1-33 3 2 8 | CCTGAAGATATTGCAACATATTACTGTSWMCAGTACNHCAATCTCWGGACTTTTGGCGGAGGGACCAAG | SWMCAGTACNHCAATCTCWGGACT | 482 | 1106 |
| VK1-33 4 2 8 | CCTGAAGATATTGCAACATATTACTGTSWMCAGTACGATNHCCTCWGGACTTTTGGCGGAGGGACCAAG | SWMCAGTACGATNHCCTCWGGACT | 483 | 1107 |
| VK1-33 5 2 8 | CCTGAAGATATTGCAACATATTACTGTSWMCAGTACGATAATYWCWGGACTTTTGGCGGAGGGACCAAG | SWMCAGTACGATAATYWCWGGACT | 484 | 1108 |
| VK1-33 6 2 8 | CCTGAAGATATTGCAACATATTACTGTCAGSWMBHCGATAATCTCWGGACTTTTGGCGGAGGGACCAAG | CAGSWMBHCGATAATCTCWGGACT | 485 | 1109 |
| VK1-33 7 2 8 | CCTGAAGATATTGCAACATATTACTGTCAGSWMTACNHCAATCTCWGGACTTTTGGCGGAGGGACCAAG | CAGSWMTACNHCAATCTCWGGACT | 486 | 1110 |
| VK1-33 8 2 8 | CCTGAAGATATTGCAACATATTACTGTCAGSWMTACGATNHCCTCWGGACTTTTGGCGGAGGGACCAAG | CAGSWMTACGATNHCCTCWGGACT | 487 | 1111 |
| VK1-33 9 2 8 | CCTGAAGATATTGCAACATATTACTGTCAGSWMTACGATAATYWCWGGACTTTTGGCGGAGGGACCAAG | CAGSWMTACGATAATYWCWGGACT | 488 | 1112 |
| VK1-33 1 3 8 | CCTGAAGATATTGCAACATATTACTGTSWMSWMTACGATAATCTCCCTACTTTTGGCGGAGGGACCAAG | SWMSWMTACGATAATCTCCCTACT | 489 | 1113 |
| VK1-33 10 3 8 | CCTGAAGATATTGCAACATATTACTGTCAGCAGBHCNHCAATCTCCCTACTTTTGGCGGAGGGACCAAG | CAGCAGBHCNHCAATCTCCCTACT | 490 | 1114 |
| VK1-33 11 3 8 | CCTGAAGATATTGCAACATATTACTGTCAGCAGBHCGATNHCCTCCCTACTTTTGGCGGAGGGACCAAG | CAGCAGBHCGATNHCCTCCCTACT | 491 | 1115 |
| VK1-33 12 3 8 | CCTGAAGATATTGCAACATATTACTGTCAGCAGBHCGATAATYWCCCTACTTTTGGCGGAGGGACCAAG | CAGCAGBHCGATAATYWCCCTACT | 492 | 1116 |
| VK1-33 13 3 8 | CCTGAAGATATTGCAACATATTACTGTCAGCAGTACNHCNHCCTCCCTACTTTTGGCGGAGGGACCAAG | CAGCAGTACNHCNHCCTCCCTACT | 493 | 1117 |
| VK1-33 14 3 8 | CCTGAAGATATTGCAACATATTACTGTCAGCAGTACNHCAATYWCCCTACTTTTGGCGGAGGGACCAAG | CAGCAGTACNHCAATYWCCCTACT | 494 | 1118 |
| VK1-33 15 3 8 | CCTGAAGATATTGCAACATATTACTGTCAGCAGTACGATNHCYWCCCTACTTTTGGCGGAGGGACCAAG | CAGCAGTACGATNHCYWCCCTACT | 495 | 1119 |

TABLE 5-continued

Oligonucleotide sequences for exemplary VK jumping dimer and trimer sequences with CDRL3 length 8.

| Name | Sequence of Synthesized Oligonucleotide | Portion of Oligonucleotide Corresponding to CDRL3 Proper | SEQ ID NO (Oli-go) | SEQ ID NO (CDRL3 Por-tion) |
|---|---|---|---|---|
| VK1-33 2 3 8 | CCTGAAGATATTGCAACATATTACTGTSWMCAGBHCGATAATCTCCCTACTTTTGGCGGAGGGACCAAG | SWMCAGBHCGATAATCTCCCTACT | 496 | 1120 |
| VK1-33 3 3 8 | CCTGAAGATATTGCAACATATTACTGTSWMCAGTACNHCAATCTCCCTACTTTTGGCGGAGGGACCAAG | SWMCAGTACNHCAATCTCCCTACT | 497 | 1121 |
| VK1-33 4 3 8 | CCTGAAGATATTGCAACATATTACTGTSWMCAGTACGATNHCCTCCCTACTTTTGGCGGAGGGACCAAG | SWMCAGTACGATNHCCTCCCTACT | 498 | 1122 |
| VK1-33 5 3 8 | CCTGAAGATATTGCAACATATTACTGTSWMCAGTACGATAATYWCCCTACTTTTGGCGGAGGGACCAAG | SWMCAGTACGATAATYWCCCTACT | 499 | 1123 |
| VK1-33 6 3 8 | CCTGAAGATATTGCAACATATTACTGTCAGSWMBHCGATAATCTCCCTACTTTTGGCGGAGGGACCAAG | CAGSWMBHCGATAATCTCCCTACT | 500 | 1124 |
| VK1-33 7 3 8 | CCTGAAGATATTGCAACATATTACTGTCAGSWMTACNHCAATCTCCCTACTTTTGGCGGAGGGACCAAG | CAGSWMTACNHCAATCTCCCTACT | 501 | 1125 |
| VK1-33 8 3 8 | CCTGAAGATATTGCAACATATTACTGTCAGSWMTACGATNHCCTCCCTACTTTTGGCGGAGGGACCAAG | CAGSWMTACGATNHCCTCCCTACT | 502 | 1126 |
| VK1-33 9 3 8 | CCTGAAGATATTGCAACATATTACTGTCAGSWMTACGATAATYWCCCTACTTTTGGCGGAGGGACCAAG | CAGSWMTACGATAATYWCCCTACT | 503 | 1127 |
| VK1-39 1 0 8 | CCTGAAGATTTTGCAACTTACTACTGTSWMSWMAGCTACAGTACTTWCACTTTTGGCGGAGGGACCAAG | SWMSWMAGCTACAGTACTTWCACT | 504 | 1128 |
| VK1-39 10 0 8 | CCTGAAGATTTTGCAACTTACTACTGTCAGCAAVNABHCAGTACTTWCACTTTTGGCGGAGGGACCAAG | CAGCAAVNABHCAGTACTTWCACT | 505 | 1129 |
| VK1-39 11 0 8 | CCTGAAGATTTTGCAACTTACTACTGTCAGCAAVNATACNHCACTTWCACTTTTGGCGGAGGGACCAAG | CAGCAAVNATACNHCACTTWCACT | 506 | 1130 |
| VK1-39 12 0 8 | CCTGAAGATTTTGCAACTTACTACTGTCAGCAAVNATACAGTBHCTWCACTTTTGGCGGAGGGACCAAG | CAGCAAVNATACAGTBHCTWCACT | 507 | 1131 |
| VK1-39 13 0 8 | CCTGAAGATTTTGCAACTTACTACTGTCAGCAAAGCBHCNHCACTTWCACTTTTGGCGGAGGGACCAAG | CAGCAAAGCBHCNHCACTTWCACT | 508 | 1132 |
| VK1-39 14 0 8 | CCTGAAGATTTTGCAACTTACTACTGTCAGCAAAGCBHCAGTBHCTWCACTTTTGGCGGAGGGACCAAG | CAGCAAAGCBHCAGTBHCTWCACT | 509 | 1133 |
| VK1-39 15 0 8 | CCTGAAGATTTTGCAACTTACTACTGTCAGCAAAGCTACNHCBHCTWCACTTTTGGCGGAGGGACCAAG | CAGCAAAGCTACNHCBHCTWCACT | 510 | 1134 |
| VK1-39 2 0 8 | CCTGAAGATTTTGCAACTTACTACTGTSWMCAAVNATACAGTACTTWCACTTTTGGCGGAGGGACCAAG | SWMCAAVNATACAGTACTTWCACT | 511 | 1135 |
| VK1-39 3 0 8 | CCTGAAGATTTTGCAACTTACTACTGTSWMCAAAGCBHCAGTACTTWCACTTTTGGCGGAGGGACCAAG | SWMCAAAGCBHCAGTACTTWCACT | 512 | 1136 |
| VK1-39 4 0 8 | CCTGAAGATTTTGCAACTTACTACTGTSWMCAAAGCTACNHCACTTWCACTTTTGGCGGAGGGACCAAG | SWMCAAAGCTACNHCACTTWCACT | 513 | 1137 |
| VK1-39 5 0 8 | CCTGAAGATTTTGCAACTTACTACTGTSWMCAAAGCTACAGTBHCTWCACTTTTGGCGGAGGGACCAAG | SWMCAAAGCTACAGTBHCTWCACT | 514 | 1138 |
| VK1-39 6 0 8 | CCTGAAGATTTTGCAACTTACTACTGTCAGSWMVNATACAGTACTTWCACTTTTGGCGGAGGGACCAAG | CAGSWMVNATACAGTACTTWCACT | 515 | 1139 |
| VK1-39 7 0 8 | CCTGAAGATTTTGCAACTTACTACTGTCAGSWMAGCBHCAGTACTTWCACTTTTGGCGGAGGGACCAAG | CAGSWMAGCBHCAGTACTTWCACT | 516 | 1140 |
| VK1-39 8 0 8 | CCTGAAGATTTTGCAACTTACTACTGTCAGSWMAGCTACNHCACTTWCACTTTTGGCGGAGGGACCAAG | CAGSWMAGCTACNHCACTTWCACT | 517 | 1141 |
| VK1-39 9 0 8 | CCTGAAGATTTTGCAACTTACTACTGTCAGSWMAGCTACAGTBHCTWCACTTTTGGCGGAGGGACCAAG | CAGSWMAGCTACAGTBHCTWCACT | 518 | 1142 |

TABLE 5-continued

Oligonucleotide sequences for exemplary VK jumping dimer and trimer sequences with CDRL3 length 8.

| Name | Sequence of Synthesized Oligonucleotide | Portion of Oligonucleotide Corresponding to CDRL3 Proper | SEQ ID NO (Oli-go) | SEQ ID NO (CDRL3 Por-tion) |
|---|---|---|---|---|
| VK1-39 1 1 8 | CCTGAAGATTTTGCAACTTACTACTGTSWMSWMAGCTACAGTACTMTCACTTTTGGCGGAGGGACCAAG | SWMSWMAGCTACAGTACTMTCACT | 519 | 1143 |
| VK1-39 10 1 8 | CCTGAAGATTTTGCAACTTACTACTGTCAGCAAVNABHCAGTACTMTCACTTTTGGCGGAGGGACCAAG | CAGCAAVNABHCAGTACTMTCACT | 520 | 1144 |
| VK1-39 11 1 8 | CCTGAAGATTTTGCAACTTACTACTGTCAGCAAVNATACNHCACTMTCACTTTTGGCGGAGGGACCAAG | CAGCAAVNATACNHCACTMTCACT | 521 | 1145 |
| VK1-39 12 1 8 | CCTGAAGATTTTGCAACTTACTACTGTCAGCAAVNATACAGTBHCMTCACTTTTGGCGGAGGGACCAAG | CAGCAAVNATACAGTBHCMTCACT | 522 | 1146 |
| VK1-39 13 1 8 | CCTGAAGATTTTGCAACTTACTACTGTCAGCAAAGCBHCNHCACTMTCACTTTTGGCGGAGGGACCAAG | CAGCAAAGCBHCNHCACTMTCACT | 523 | 1147 |
| VK1-39 14 1 8 | CCTGAAGATTTTGCAACTTACTACTGTCAGCAAAGCBHCAGTBHCMTCACTTTTGGCGGAGGGACCAAG | CAGCAAAGCBHCAGTBHCMTCACT | 524 | 1148 |
| VK1-39 15 1 8 | CCTGAAGATTTTGCAACTTACTACTGTCAGCAAAGCTACNHCBHCMTCACTTTTGGCGGAGGGACCAAG | CAGCAAAGCTACNHCBHCMTCACT | 525 | 1149 |
| VK1-39 2 1 8 | CCTGAAGATTTTGCAACTTACTACTGTSWMCAAVNATACAGTACTMTCACTTTTGGCGGAGGGACCAAG | SWMCAAVNATACAGTACTMTCACT | 526 | 1150 |
| VK1-39 3 1 8 | CCTGAAGATTTTGCAACTTACTACTGTSWMCAAAGCBHCAGTACTMTCACTTTTGGCGGAGGGACCAAG | SWMCAAAGCBHCAGTACTMTCACT | 527 | 1151 |
| VK1-39 4 1 8 | CCTGAAGATTTTGCAACTTACTACTGTSWMCAAAGCTACNHCACTMTCACTTTTGGCGGAGGGACCAAG | SWMCAAAGCTACNHCACTMTCACT | 528 | 1152 |
| VK1-39 5 1 8 | CCTGAAGATTTTGCAACTTACTACTGTSWMCAAAGCTACAGTBHCMTCACTTTTGGCGGAGGGACCAAG | SWMCAAAGCTACAGTBHCMTCACT | 529 | 1153 |
| VK1-39 6 1 8 | CCTGAAGATTTTGCAACTTACTACTGTCAGSWMVNATACAGTACTMTCACTTTTGGCGGAGGGACCAAG | CAGSWMVNATACAGTACTMTCACT | 530 | 1154 |
| VK1-39 7 1 8 | CCTGAAGATTTTGCAACTTACTACTGTCAGSWMAGCBHCAGTACTMTCACTTTTGGCGGAGGGACCAAG | CAGSWMAGCBHCAGTACTMTCACT | 531 | 1155 |
| VK1-39 8 1 8 | CCTGAAGATTTTGCAACTTACTACTGTCAGSWMAGCTACNHCACTMTCACTTTTGGCGGAGGGACCAAG | CAGSWMAGCTACNHCACTMTCACT | 532 | 1156 |
| VK1-39 9 1 8 | CCTGAAGATTTTGCAACTTACTACTGTCAGSWMAGCTACAGTBHCMTCACTTTTGGCGGAGGGACCAAG | CAGSWMAGCTACAGTBHCMTCACT | 533 | 1157 |
| VK1-39 1 2 8 | CCTGAAGATTTTGCAACTTACTACTGTSWMSWMAGCTACAGTACTWGGACTTTTGGCGGAGGGACCAAG | SWMSWMAGCTACAGTACTWGGACT | 534 | 1158 |
| VK1-39 10 2 8 | CCTGAAGATTTTGCAACTTACTACTGTCAGCAAVNABHCAGTACTWGGACTTTTGGCGGAGGGACCAAG | CAGCAAVNABHCAGTACTWGGACT | 535 | 1159 |
| VK1-39 11 2 8 | CCTGAAGATTTTGCAACTTACTACTGTCAGCAAVNATACNHCACTWGGACTTTTGGCGGAGGGACCAAG | CAGCAAVNATACNHCACTWGGACT | 536 | 1160 |
| VK1-39 12 2 8 | CCTGAAGATTTTGCAACTTACTACTGTCAGCAAVNATACAGTBHCWGGACTTTTGGCGGAGGGACCAAG | CAGCAAVNATACAGTBHCWGGACT | 537 | 1161 |
| VK1-39 13 2 8 | CCTGAAGATTTTGCAACTTACTACTGTCAGCAAAGCBHCNHCACTWGGACTTTTGGCGGAGGGACCAAG | CAGCAAAGCBHCNHCACTWGGACT | 538 | 1162 |
| VK1-39 14 2 8 | CCTGAAGATTTTGCAACTTACTACTGTCAGCAAAGCBHCAGTBHCWGGACTTTTGGCGGAGGGACCAAG | CAGCAAAGCBHCAGTBHCWGGACT | 539 | 1163 |
| VK1-39 15 2 8 | CCTGAAGATTTTGCAACTTACTACTGTCAGCAAAGCTACNHCBHCWGGACTTTTGGCGGAGGGACCAAG | CAGCAAAGCTACNHCBHCWGGACT | 540 | 1164 |
| VK1-39 2 2 8 | CCTGAAGATTTTGCAACTTACTACTGTSWMCAAVNATACAGTACTWGGACTTTTGGCGGAGGGACCAAG | SWMCAAVNATACAGTACTWGGACT | 541 | 1165 |
| VK1-39 3 2 8 | CCTGAAGATTTTGCAACTTACTACTGTSWMCAAAGCBHCAGTACTWGGACTTTTGGCGGAGGGACCAAG | SWMCAAAGCBHCAGTACTWGGACT | 542 | 1166 |

TABLE 5-continued

Oligonucleotide sequences for exemplary VK jumping dimer and trimer sequences with CDRL3 length 8.

| Name | Sequence of Synthesized Oligonucleotide | Portion of Oligonucleotide Corresponding to CDRL3 Proper | SEQ ID NO (Oli-go) | SEQ ID NO (CDRL3 Por-tion) |
|---|---|---|---|---|
| VK1-39 4 2 8 | CCTGAAGATTTTGCAACTTACTACTGTSWMCAAAGCTACNHCACTWGGACTTTTGGCGGAGGGACCAAG | SWMCAAAGCTACNHCACTWGGACT | 543 | 1167 |
| VK1-39 5 2 8 | CCTGAAGATTTTGCAACTTACTACTGTSWMCAAAGCTACAGTBHCWGGACTTTTGGCGGAGGGACCAAG | SWMCAAAGCTACAGTBHCWGGACT | 544 | 1168 |
| VK1-39 6 2 8 | CCTGAAGATTTTGCAACTTACTACTGTCAGSWMVNATACAGTACTWGGACTTTTGGCGGAGGGACCAAG | CAGSWMVNATACAGTACTWGGACT | 545 | 1169 |
| VK1-39 7 2 8 | CCTGAAGATTTTGCAACTTACTACTGTCAGSWMAGCBHCAGTACTWGGACTTTTGGCGGAGGGACCAAG | CAGSWMAGCBHCAGTACTWGGACT | 546 | 1170 |
| VK1-39 8 2 8 | CCTGAAGATTTTGCAACTTACTACTGTCAGSWMAGCTACNHCACTWGGACTTTTGGCGGAGGGACCAAG | CAGSWMAGCTACNHCACTWGGACT | 547 | 1171 |
| VK1-39 9 2 8 | CCTGAAGATTTTGCAACTTACTACTGTCAGSWMAGCTACAGTBHCWGGACTTTTGGCGGAGGGACCAAG | CAGSWMAGCTACAGTBHCWGGACT | 548 | 1172 |
| VK1-39 1 3 8 | CCTGAAGATTTTGCAACTTACTACTGTSWMSWMAGCTACAGTACTCCTACTTTTGGCGGAGGGACCAAG | SWMSWMAGCTACAGTACTCCTACT | 549 | 1173 |
| VK1-39 10 3 8 | CCTGAAGATTTTGCAACTTACTACTGTCAGCAAVNABHCAGTACTCCTACTTTTGGCGGAGGGACCAAG | CAGCAAVNABHCAGTACTCCTACT | 550 | 1174 |
| VK1-39 11 3 8 | CCTGAAGATTTTGCAACTTACTACTGTCAGCAAVNATACNHCACTCCTACTTTTGGCGGAGGGACCAAG | CAGCAAVNATACNHCACTCCTACT | 551 | 1175 |
| VK1-39 12 3 8 | CCTGAAGATTTTGCAACTTACTACTGTCAGCAAVNATACAGTBHCCCTACTTTTGGCGGAGGGACCAAG | CAGCAAVNATACAGTBHCCCTACT | 552 | 1176 |
| VK1-39 13 3 8 | CCTGAAGATTTTGCAACTTACTACTGTCAGCAAAGCBHCNHCACTCCTACTTTTGGCGGAGGGACCAAG | CAGCAAAGCBHCNHCACTCCTACT | 553 | 1177 |
| VK1-39 14 3 8 | CCTGAAGATTTTGCAACTTACTACTGTCAGCAAAGCBHCAGTBHCCCTACTTTTGGCGGAGGGACCAAG | CAGCAAAGCBHCAGTBHCCCTACT | 554 | 1178 |
| VK1-39 15 3 8 | CCTGAAGATTTTGCAACTTACTACTGTCAGCAAAGCTACNHCBHCCCTACTTTTGGCGGAGGGACCAAG | CAGCAAAGCTACNHCBHCCCTACT | 555 | 1179 |
| VK1-39 2 3 8 | CCTGAAGATTTTGCAACTTACTACTGTSWMCAAVNATACAGTACTCCTACTTTTGGCGGAGGGACCAAG | SWMCAAVNATACAGTACTCCTACT | 556 | 1180 |
| VK1-39 3 3 8 | CCTGAAGATTTTGCAACTTACTACTGTSWMCAAAGCBHCAGTACTCCTACTTTTGGCGGAGGGACCAAG | SWMCAAAGCBHCAGTACTCCTACT | 557 | 1181 |
| VK1-39 4 3 8 | CCTGAAGATTTTGCAACTTACTACTGTSWMCAAAGCTACNHCACTCCTACTTTTGGCGGAGGGACCAAG | SWMCAAAGCTACNHCACTCCTACT | 558 | 1182 |
| VK1-39 5 3 8 | CCTGAAGATTTTGCAACTTACTACTGTSWMCAAAGCTACAGTBHCCCTACTTTTGGCGGAGGGACCAAG | SWMCAAAGCTACAGTBHCCCTACT | 559 | 1183 |
| VK1-39 6 3 8 | CCTGAAGATTTTGCAACTTACTACTGTCAGSWMVNATACAGTACTCCTACTTTTGGCGGAGGGACCAAG | CAGSWMVNATACAGTACTCCTACT | 560 | 1184 |
| VK1-39 7 3 8 | CCTGAAGATTTTGCAACTTACTACTGTCAGSWMAGCBHCAGTACTCCTACTTTTGGCGGAGGGACCAAG | CAGSWMAGCBHCAGTACTCCTACT | 561 | 1185 |
| VK1-39 8 3 8 | CCTGAAGATTTTGCAACTTACTACTGTCAGSWMAGCTACNHCACTCCTACTTTTGGCGGAGGGACCAAG | CAGSWMAGCTACNHCACTCCTACT | 562 | 1186 |
| VK1-39 9 3 8 | CCTGAAGATTTTGCAACTTACTACTGTCAGSWMAGCTACAGTBHCCCTACTTTTGGCGGAGGGACCAAG | CAGSWMAGCTACAGTBHCCCTACT | 563 | 1187 |
| VK2-28 1 0 8 | GCTGAGGATGTTGGGGTTTATTACTGCDTSSWMGCACTCCAGACTTWCACTTTTGGCGGAGGGACCAAG | DTSSWMGCACTCCAGACTTWCACT | 564 | 1188 |
| VK2-28 10 0 8 | GCTGAGGATGTTGGGGTTTATTACTGCATGCAGVNAMNACAGACTTWCACTTTTGGCGGAGGGACCAAG | ATGCAGVNAMNACAGACTTWCACT | 565 | 1189 |

TABLE 5-continued

Oligonucleotide sequences for exemplary VK jumping dimer and trimer sequences with CDRL3 length 8.

| Name | Sequence of Synthesized Oligonucleotide | Portion of Oligonucleotide Corresponding to CDRL3 Proper | SEQ ID NO (Oli-go) | SEQ ID NO (CDRL3 Por-tion) |
|---|---|---|---|---|
| VK2-28 11 0 8 | GCTGAGGATGTTGGGGTTTATTACTGCATGCAGVNACTCSRMACTTWCACTTTTGGCGGAGGGACCAAG | ATGCAGVNACTCSRMACTTWCACT | 566 | 1190 |
| VK2-28 12 0 8 | GCTGAGGATGTTGGGGTTTATTACTGCATGCAGVNACTCCAGVBCTWCACTTTTGGCGGAGGGACCAAG | ATGCAGVNACTCCAGVBCTWCACT | 567 | 1191 |
| VK2-28 13 0 8 | GCTGAGGATGTTGGGGTTTATTACTGCATGCAGGCAMNASRMACTTWCACTTTTGGCGGAGGGACCAAG | ATGCAGGCAMNASRMACTTWCACT | 568 | 1192 |
| VK2-28 14 0 8 | GCTGAGGATGTTGGGGTTTATTACTGCATGCAGGCAMNACAGVBCTWCACTTTTGGCGGAGGGACCAAG | ATGCAGGCAMNACAGVBCTWCACT | 569 | 1193 |
| VK2-28 15 0 8 | GCTGAGGATGTTGGGGTTTATTACTGCATGCAGGCACTCSRMVBCTWCACTTTTGGCGGAGGGACCAAG | ATGCAGGCACTCSRMVBCTWCACT | 570 | 1194 |
| VK2-28 2 0 8 | GCTGAGGATGTTGGGGTTTATTACTGCDTSCAGVNACTCCAGACTTWCACTTTTGGCGGAGGGACCAAG | DTSCAGVNACTCCAGACTTWCACT | 571 | 1195 |
| VK2-28 3 0 8 | GCTGAGGATGTTGGGGTTTATTACTGCDTSCAGGCAMNACAGACTTWCACTTTTGGCGGAGGGACCAAG | DTSCAGGCAMNACAGACTTWCACT | 572 | 1196 |
| VK2-28 4 0 8 | GCTGAGGATGTTGGGGTTTATTACTGCDTSCAGGCACTCSRMACTTWCACTTTTGGCGGAGGGACCAAG | DTSCAGGCACTCSRMACTTWCACT | 573 | 1197 |
| VK2-28 5 0 8 | GCTGAGGATGTTGGGGTTTATTACTGCDTSCAGGCACTCCAGVBCTWCACTTTTGGCGGAGGGACCAAG | DTSCAGGCACTCCAGVBCTWCACT | 574 | 1198 |
| VK2-28 6 0 8 | GCTGAGGATGTTGGGGTTTATTACTGCATGSWMVNACTCCAGACTTWCACTTTTGGCGGAGGGACCAAG | ATGSWMVNACTCCAGACTTWCACT | 575 | 1199 |
| VK2-28 7 0 8 | GCTGAGGATGTTGGGGTTTATTACTGCATGSWMGCAMNACAGACTTWCACTTTTGGCGGAGGGACCAAG | ATGSWMGCAMNACAGACTTWCACT | 576 | 1200 |
| VK2-28 8 0 8 | GCTGAGGATGTTGGGGTTTATTACTGCATGSWMGCACTCSRMACTTWCACTTTTGGCGGAGGGACCAAG | ATGSWMGCACTCSRMACTTWCACT | 577 | 1201 |
| VK2-28 9 0 8 | GCTGAGGATGTTGGGGTTTATTACTGCATGSWMGCACTCCAGVBCTWCACTTTTGGCGGAGGGACCAAG | ATGSWMGCACTCCAGVBCTWCACT | 578 | 1202 |
| VK2-28 1 1 8 | GCTGAGGATGTTGGGGTTTATTACTGCDTSSWMGCACTCCAGACTMTCACTTTTGGCGGAGGGACCAAG | DTSSWMGCACTCCAGACTMTCACT | 579 | 1203 |
| VK2-28 10 1 8 | GCTGAGGATGTTGGGGTTTATTACTGCATGCAGVNAMNACAGACTMTCACTTTTGGCGGAGGGACCAAG | ATGCAGVNAMNACAGACTMTCACT | 580 | 1204 |
| VK2-28 11 1 8 | GCTGAGGATGTTGGGGTTTATTACTGCATGCAGVNACTCSRMACTMTCACTTTTGGCGGAGGGACCAAG | ATGCAGVNACTCSRMACTMTCACT | 581 | 1205 |
| VK2-28 12 1 8 | GCTGAGGATGTTGGGGTTTATTACTGCATGCAGVNACTCCAGVBCMTCACTTTTGGCGGAGGGACCAAG | ATGCAGVNACTCCAGVBCMTCACT | 582 | 1206 |
| VK2-28 13 1 8 | GCTGAGGATGTTGGGGTTTATTACTGCATGCAGGCAMNASRMACTMTCACTTTTGGCGGAGGGACCAAG | ATGCAGGCAMNASRMACTMTCACT | 583 | 1207 |
| VK2-28 14 1 8 | GCTGAGGATGTTGGGGTTTATTACTGCATGCAGGCAMNACAGVBCMTCACTTTTGGCGGAGGGACCAAG | ATGCAGGCAMNACAGVBCMTCACT | 584 | 1208 |
| VK2-28 15 1 8 | GCTGAGGATGTTGGGGTTTATTACTGCATGCAGGCACTCSRMVBCMTCACTTTTGGCGGAGGGACCAAG | ATGCAGGCACTCSRMVBCMTCACT | 585 | 1209 |
| VK2-28 2 1 8 | GCTGAGGATGTTGGGGTTTATTACTGCDTSCAGVNACTCCAGACTMTCACTTTTGGCGGAGGGACCAAG | DTSCAGVNACTCCAGACTMTCACT | 586 | 1210 |
| VK2-28 3 1 8 | GCTGAGGATGTTGGGGTTTATTACTGCDTSCAGGCAMNACAGACTMTCACTTTTGGCGGAGGGACCAAG | DTSCAGGCAMNACAGACTMTCACT | 587 | 1211 |
| VK2-28 4 1 8 | GCTGAGGATGTTGGGGTTTATTACTGCDTSCAGGCACTCSRMACTMTCACTTTTGGCGGAGGGACCAAG | DTSCAGGCACTCSRMACTMTCACT | 588 | 1212 |
| VK2-28 5 1 8 | GCTGAGGATGTTGGGGTTTATTACTGCDTSCAGGCACTCCAGVBCMTCACTTTTGGCGGAGGGACCAAG | DTSCAGGCACTCCAGVBCMTCACT | 589 | 1213 |

TABLE 5-continued

Oligonucleotide sequences for exemplary VK jumping dimer and trimer sequences with CDRL3 length 8.

| Name | Sequence of Synthesized Oligonucleotide | Portion of Oligonucleotide Corresponding to CDRL3 Proper | SEQ ID NO (Oligo) | SEQ ID NO (CDRL3 Portion) |
|---|---|---|---|---|
| VK2-28 6 1 8 | GCTGAGGATGTTGGGGTTTATTACTGCATGSWMVNACTCCAGACTMTCACTTTTGGCGGAGGGACCAAG | ATGSWMVNACTCCAGACTMTCACT | 590 | 1214 |
| VK2-28 7 1 8 | GCTGAGGATGTTGGGGTTTATTACTGCATGSWMGCAMNACAGACTMTCACTTTTGGCGGAGGGACCAAG | ATGSWMGCAMNACAGACTMTCACT | 591 | 1215 |
| VK2-28 8 1 8 | GCTGAGGATGTTGGGGTTTATTACTGCATGSWMGCACTCSRMACTMTCACTTTTGGCGGAGGGACCAAG | ATGSWMGCACTCSRMACTMTCACT | 592 | 1216 |
| VK2-28 9 1 8 | GCTGAGGATGTTGGGGTTTATTACTGCATGSWMGCACTCCAGVBCMTCACTTTTGGCGGAGGGACCAAG | ATGSWMGCACTCCAGVBCMTCACT | 593 | 1217 |
| VK2-28 1 2 8 | GCTGAGGATGTTGGGGTTTATTACTGCDTSSWMGCACTCCAGACTWGGACTTTTGGCGGAGGGACCAAG | DTSSWMGCACTCCAGACTWGGACT | 594 | 1218 |
| VK2-28 10 2 8 | GCTGAGGATGTTGGGGTTTATTACTGCATGCAGVNAMNACAGACTWGGACTTTTGGCGGAGGGACCAAG | ATGCAGVNAMNACAGACTWGGACT | 595 | 1219 |
| VK2-28 11 2 8 | GCTGAGGATGTTGGGGTTTATTACTGCATGCAGVNACTCSRMACTWGGACTTTTGGCGGAGGGACCAAG | ATGCAGVNACTCSRMACTWGGACT | 596 | 1220 |
| VK2-28 12 2 8 | GCTGAGGATGTTGGGGTTTATTACTGCATGCAGVNACTCCAGVBCWGGACTTTTGGCGGAGGGACCAAG | ATGCAGVNACTCCAGVBCWGGACT | 597 | 1221 |
| VK2-28 13 2 8 | GCTGAGGATGTTGGGGTTTATTACTGCATGCAGGCAMNASRMACTWGGACTTTTGGCGGAGGGACCAAG | ATGCAGGCAMNASRMACTWGGACT | 598 | 1222 |
| VK2-28 14 2 8 | GCTGAGGATGTTGGGGTTTATTACTGCATGCAGGCAMNACAGVBCWGGACTTTTGGCGGAGGGACCAAG | ATGCAGGCAMNACAGVBCWGGACT | 599 | 1223 |
| VK2-28 15 2 8 | GCTGAGGATGTTGGGGTTTATTACTGCATGCAGGCACTCSRMVBCWGGACTTTTGGCGGAGGGACCAAG | ATGCAGGCACTCSRMVBCWGGACT | 600 | 1224 |
| VK2-28 2 2 8 | GCTGAGGATGTTGGGGTTTATTACTGCDTSCAGVNACTCCAGACTWGGACTTTTGGCGGAGGGACCAAG | DTSCAGVNACTCCAGACTWGGACT | 601 | 1225 |
| VK2-28 3 2 8 | GCTGAGGATGTTGGGGTTTATTACTGCDTSCAGGCAMNACAGACTWGGACTTTTGGCGGAGGGACCAAG | DTSCAGGCAMNACAGACTWGGACT | 602 | 1226 |
| VK2-28 4 2 8 | GCTGAGGATGTTGGGGTTTATTACTGCDTSCAGGCACTCSRMACTWGGACTTTTGGCGGAGGGACCAAG | DTSCAGGCACTCSRMACTWGGACT | 603 | 1227 |
| VK2-28 5 2 8 | GCTGAGGATGTTGGGGTTTATTACTGCDTSCAGGCACTCCAGVBCWGGACTTTTGGCGGAGGGACCAAG | DTSCAGGCACTCCAGVBCWGGACT | 604 | 1228 |
| VK2-28 6 2 8 | GCTGAGGATGTTGGGGTTTATTACTGCATGSWMVNACTCCAGACTWGGACTTTTGGCGGAGGGACCAAG | ATGSWMVNACTCCAGACTWGGACT | 605 | 1229 |
| VK2-28 7 2 8 | GCTGAGGATGTTGGGGTTTATTACTGCATGSWMGCAMNACAGACTWGGACTTTTGGCGGAGGGACCAAG | ATGSWMGCAMNACAGACTWGGACT | 606 | 1230 |
| VK2-28 8 2 8 | GCTGAGGATGTTGGGGTTTATTACTGCATGSWMGCACTCSRMACTWGGACTTTTGGCGGAGGGACCAAG | ATGSWMGCACTCSRMACTWGGACT | 607 | 1231 |
| VK2-28 9 2 8 | GCTGAGGATGTTGGGGTTTATTACTGCATGSWMGCACTCCAGVBCWGGACTTTTGGCGGAGGGACCAAG | ATGSWMGCACTCCAGVBCWGGACT | 608 | 1232 |
| VK2-28 1 3 8 | GCTGAGGATGTTGGGGTTTATTACTGCDTSSWMGCACTCCAGACTCCTACTTTTGGCGGAGGGACCAAG | DTSSWMGCACTCCAGACTCCTACT | 609 | 1233 |
| VK2-28 10 3 8 | GCTGAGGATGTTGGGGTTTATTACTGCATGCAGVNAMNACAGACTCCTACTTTTGGCGGAGGGACCAAG | ATGCAGVNAMNACAGACTCCTACT | 610 | 1234 |
| VK2-28 11 3 8 | GCTGAGGATGTTGGGGTTTATTACTGCATGCAGVNACTCSRMACTCCTACTTTTGGCGGAGGGACCAAG | ATGCAGVNACTCSRMACTCCTACT | 611 | 1235 |
| VK2-28 12 3 8 | GCTGAGGATGTTGGGGTTTATTACTGCATGCAGVNACTCCAGVBCCCTACTTTTGGCGGAGGGACCAAG | ATGCAGVNACTCCAGVBCCCTACT | 612 | 1236 |

TABLE 5-continued

Oligonucleotide sequences for exemplary VK jumping dimer and trimer sequences with CDRL3 length 8.

| Name | Sequence of Synthesized Oligonucleotide | Portion of Oligonucleotide Corresponding to CDRL3 Proper | SEQ ID NO (Oli-go) | SEQ ID NO (CDRL3 Por-tion) |
|---|---|---|---|---|
| VK2-28 13 3 8 | GCTGAGGATGTTGGGGTTTATTACTGCATGCAGGCAMNASRMACTCCTACTTTTGGCGGAGGGACCAAG | ATGCAGGCAMNASRMACTCCTACT | 613 | 1237 |
| VK2-28 14 3 8 | GCTGAGGATGTTGGGGTTTATTACTGCATGCAGGCAMNACAGVBCCCTACTTTTGGCGGAGGGACCAAG | ATGCAGGCAMNACAGVBCCCTACT | 614 | 1238 |
| VK2-28 15 3 8 | GCTGAGGATGTTGGGGTTTATTACTGCATGCAGGCACTCSRMVBCCCTACTTTTGGCGGAGGGACCAAG | ATGCAGGCACTCSRMVBCCCTACT | 615 | 1239 |
| VK2-28 2 3 8 | GCTGAGGATGTTGGGGTTTATTACTGCDTSCAGVNACTCCAGACTCCTACTTTTGGCGGAGGGACCAAG | DTSCAGVNACTCCAGACTCCTACT | 616 | 1240 |
| VK2-28 3 3 8 | GCTGAGGATGTTGGGGTTTATTACTGCDTSCAGGCAMNACAGACTCCTACTTTTGGCGGAGGGACCAAG | DTSCAGGCAMNACAGACTCCTACT | 617 | 1241 |
| VK2-28 4 3 8 | GCTGAGGATGTTGGGGTTTATTACTGCDTSCAGGCACTCSRMACTCCTACTTTTGGCGGAGGGACCAAG | DTSCAGGCACTCSRMACTCCTACT | 618 | 1242 |
| VK2-28 5 3 8 | GCTGAGGATGTTGGGGTTTATTACTGCDTSCAGGCACTCCAGVBCCCTACTTTTGGCGGAGGGACCAAG | DTSCAGGCACTCCAGVBCCCTACT | 619 | 1243 |
| VK2-28 6 3 8 | GCTGAGGATGTTGGGGTTTATTACTGCATGSWMVNACTCCAGACTCCTACTTTTGGCGGAGGGACCAAG | ATGSWMVNACTCCAGACTCCTACT | 620 | 1244 |
| VK2-28 7 3 8 | GCTGAGGATGTTGGGGTTTATTACTGCATGSWMGCAMNACAGACTCCTACTTTTGGCGGAGGGACCAAG | ATGSWMGCAMNACAGACTCCTACT | 621 | 1245 |
| VK2-28 8 3 8 | GCTGAGGATGTTGGGGTTTATTACTGCATGSWMGCACTCSRMACTCCTACTTTTGGCGGAGGGACCAAG | ATGSWMGCACTCSRMACTCCTACT | 622 | 1246 |
| VK2-28 9 3 8 | GCTGAGGATGTTGGGGTTTATTACTGCATGSWMGCACTCCAGVBCCCTACTTTTGGCGGAGGGACCAAG | ATGSWMGCACTCCAGVBCCCTACT | 623 | 1247 |
| VK3-11 1 0 8 | CCTGAAGATTTTGCAGTTTATTACTGTSWMSWMAGAAGTAATTGGTWCACTTTTGGCGGAGGGACCAAG | SWMSWMAGAAGTAATTGGTWCACT | 624 | 1248 |
| VK3-11 10 0 8 | CCTGAAGATTTTGCAGTTTATTACTGTCAGCAGBHCNHCAATTGGTWCACTTTTGGCGGAGGGACCAAG | CAGCAGBHCNHCAATTGGTWCACT | 625 | 1249 |
| VK3-11 11 0 8 | CCTGAAGATTTTGCAGTTTATTACTGTCAGCAGBHCAGTNHCTGGTWCACTTTTGGCGGAGGGACCAAG | CAGCAGBHCAGTNHCTGGTWCACT | 626 | 1250 |
| VK3-11 12 0 8 | CCTGAAGATTTTGCAGTTTATTACTGTCAGCAGBHCAGTAATYWCTWCACTTTTGGCGGAGGGACCAAG | CAGCAGBHCAGTAATYWCTWCACT | 627 | 1251 |
| VK3-11 13 0 8 | CCTGAAGATTTTGCAGTTTATTACTGTCAGCAGAGANHCNHCTGGTWCACTTTTGGCGGAGGGACCAAG | CAGCAGAGANHCNHCTGGTWCACT | 628 | 1252 |
| VK3-11 14 0 8 | CCTGAAGATTTTGCAGTTTATTACTGTCAGCAGAGANHCAATYWCTWCACTTTTGGCGGAGGGACCAAG | CAGCAGAGANHCAATYWCTWCACT | 629 | 1253 |
| VK3-11 15 0 8 | CCTGAAGATTTTGCAGTTTATTACTGTCAGCAGAGAAGTNHCYWCTWCACTTTTGGCGGAGGGACCAAG | CAGCAGAGAAGTNHCYWCTWCACT | 630 | 1254 |
| VK3-11 2 0 8 | CCTGAAGATTTTGCAGTTTATTACTGTSWMCAGBHCAGTAATTGGTWCACTTTTGGCGGAGGGACCAAG | SWMCAGBHCAGTAATTGGTWCACT | 631 | 1255 |
| VK3-11 3 0 8 | CCTGAAGATTTTGCAGTTTATTACTGTSWMCAGAGANHCAATTGGTWCACTTTTGGCGGAGGGACCAAG | SWMCAGAGANHCAATTGGTWCACT | 632 | 1256 |
| VK3-11 4 0 8 | CCTGAAGATTTTGCAGTTTATTACTGTSWMCAGAGAAGTNHCTGGTWCACTTTTGGCGGAGGGACCAAG | SWMCAGAGAAGTNHCTGGTWCACT | 633 | 1257 |
| VK3-11 5 0 8 | CCTGAAGATTTTGCAGTTTATTACTGTSWMCAGAGAAGTAATYWCTWCACTTTTGGCGGAGGGACCAAG | SWMCAGAGAAGTAATYWCTWCACT | 634 | 1258 |
| VK3-11 6 0 8 | CCTGAAGATTTTGCAGTTTATTACTGTCAGSWMBHCAGTAATTGGTWCACTTTTGGCGGAGGGACCAAG | CAGSWMBHCAGTAATTGGTWCACT | 635 | 1259 |
| VK3-11 7 0 8 | CCTGAAGATTTTGCAGTTTATTACTGTCAGSWMAGANHCAATTGGTWCACTTTTGGCGGAGGGACCAAG | CAGSWMAGANHCAATTGGTWCACT | 636 | 1260 |

TABLE 5-continued

Oligonucleotide sequences for exemplary VK jumping dimer and trimer sequences with CDRL3 length 8.

| Name | Sequence of Synthesized Oligonucleotide | Portion of Oligonucleotide Corresponding to CDRL3 Proper | SEQ ID NO (Oligo) | SEQ ID NO (CDRL3 Portion) |
|---|---|---|---|---|
| VK3-11 8 0 8 | CCTGAAGATTTTGCAGTTTATTACTGTCAGSWMAGAAGTNHCTGGTWCACTTTTGGCGGAGGGACCAAG | CAGSWMAGAAGTNHCTGGTWCACT | 637 | 1261 |
| VK3-11 9 0 8 | CCTGAAGATTTTGCAGTTTATTACTGTCAGSWMAGAAGTAATYWCTWCACTTTTGGCGGAGGGACCAAG | CAGSWMAGAAGTAATYWCTWCACT | 638 | 1262 |
| VK3-11 1 1 8 | CCTGAAGATTTTGCAGTTTATTACTGTSWMSWMAGAAGTAATTGGMTCACTTTTGGCGGAGGGACCAAG | SWMSWMAGAAGTAATTGGMTCACT | 639 | 1263 |
| VK3-11 10 1 8 | CCTGAAGATTTTGCAGTTTATTACTGTCAGCAGBHCNHCAATTGGMTCACTTTTGGCGGAGGGACCAAG | CAGCAGBHCNHCAATTGGMTCACT | 640 | 1264 |
| VK3-11 11 1 8 | CCTGAAGATTTTGCAGTTTATTACTGTCAGCAGBHCAGTNHCTGGMTCACTTTTGGCGGAGGGACCAAG | CAGCAGBHCAGTNHCTGGMTCACT | 641 | 1265 |
| VK3-11 12 1 8 | CCTGAAGATTTTGCAGTTTATTACTGTCAGCAGBHCAGTAATYWCMTCACTTTTGGCGGAGGGACCAAG | CAGCAGBHCAGTAATYWCMTCACT | 642 | 1266 |
| VK3-11 13 1 8 | CCTGAAGATTTTGCAGTTTATTACTGTCAGCAGAGANHCNHCTGGMTCACTTTTGGCGGAGGGACCAAG | CAGCAGAGANHCNHCTGGMTCACT | 643 | 1267 |
| VK3-11 14 1 8 | CCTGAAGATTTTGCAGTTTATTACTGTCAGCAGAGANHCAATYWCMTCACTTTTGGCGGAGGGACCAAG | CAGCAGAGANHCAATYWCMTCACT | 644 | 1268 |
| VK3-11 15 1 8 | CCTGAAGATTTTGCAGTTTATTACTGTCAGCAGAGAAGTNHCYWCMTCACTTTTGGCGGAGGGACCAAG | CAGCAGAGAAGTNHCYWCMTCACT | 645 | 1269 |
| VK3-11 2 1 8 | CCTGAAGATTTTGCAGTTTATTACTGTSWMCAGBHCAGTAATTGGMTCACTTTTGGCGGAGGGACCAAG | SWMCAGBHCAGTAATTGGMTCACT | 646 | 1270 |
| VK3-11 3 1 8 | CCTGAAGATTTTGCAGTTTATTACTGTSWMCAGAGANHCAATTGGMTCACTTTTGGCGGAGGGACCAAG | SWMCAGAGANHCAATTGGMTCACT | 647 | 1271 |
| VK3-11 4 1 8 | CCTGAAGATTTTGCAGTTTATTACTGTSWMCAGAGAAGTNHCTGGMTCACTTTTGGCGGAGGGACCAAG | SWMCAGAGAAGTNHCTGGMTCACT | 648 | 1272 |
| VK3-11 5 1 8 | CCTGAAGATTTTGCAGTTTATTACTGTSWMCAGAGAAGTAATYWCMTCACTTTTGGCGGAGGGACCAAG | SWMCAGAGAAGTAATYWCMTCACT | 649 | 1273 |
| VK3-11 6 1 8 | CCTGAAGATTTTGCAGTTTATTACTGTCAGSWMBHCAGTAATTGGMTCACTTTTGGCGGAGGGACCAAG | CAGSWMBHCAGTAATTGGMTCACT | 650 | 1274 |
| VK3-11 7 1 8 | CCTGAAGATTTTGCAGTTTATTACTGTCAGSWMAGANHCAATTGGMTCACTTTTGGCGGAGGGACCAAG | CAGSWMAGANHCAATTGGMTCACT | 651 | 1275 |
| VK3-11 8 1 8 | CCTGAAGATTTTGCAGTTTATTACTGTCAGSWMAGAAGTNHCTGGMTCACTTTTGGCGGAGGGACCAAG | CAGSWMAGAAGTNHCTGGMTCACT | 652 | 1276 |
| VK3-11 9 1 8 | CCTGAAGATTTTGCAGTTTATTACTGTCAGSWMAGAAGTAATYWCMTCACTTTTGGCGGAGGGACCAAG | CAGSWMAGAAGTAATYWCMTCACT | 653 | 1277 |
| VK3-11 1 2 8 | CCTGAAGATTTTGCAGTTTATTACTGTSWMSWMAGAAGTAATTGGWGGACTTTTGGCGGAGGGACCAAG | SWMSWMAGAAGTAATTGGWGGACT | 654 | 1278 |
| VK3-11 10 2 8 | CCTGAAGATTTTGCAGTTTATTACTGTCAGCAGBHCNHCAATTGGWGGACTTTTGGCGGAGGGACCAAG | CAGCAGBHCNHCAATTGGWGGACT | 655 | 1279 |
| VK3-11 11 2 8 | CCTGAAGATTTTGCAGTTTATTACTGTCAGCAGBHCAGTNHCTGGWGGACTTTTGGCGGAGGGACCAAG | CAGCAGBHCAGTNHCTGGWGGACT | 656 | 1280 |
| VK3-11 12 2 8 | CCTGAAGATTTTGCAGTTTATTACTGTCAGCAGBHCAGTAATYWCWGGACTTTTGGCGGAGGGACCAAG | CAGCAGBHCAGTAATYWCWGGACT | 657 | 1281 |
| VK3-11 13 2 8 | CCTGAAGATTTTGCAGTTTATTACTGTCAGCAGAGANHCNHCTGGWGGACTTTTGGCGGAGGGACCAAG | CAGCAGAGANHCNHCTGGWGGACT | 658 | 1282 |
| VK3-11 14 2 8 | CCTGAAGATTTTGCAGTTTATTACTGTCAGCAGAGANHCAATYWCWGGACTTTTGGCGGAGGGACCAAG | CAGCAGAGANHCAATYWCWGGACT | 659 | 1283 |

TABLE 5-continued

Oligonucleotide sequences for exemplary VK jumping dimer and trimer sequences with CDRL3 length 8.

| Name | Sequence of Synthesized Oligonucleotide | Portion of Oligonucleotide Corresponding to CDRL3 Proper | SEQ ID NO (Oligo) | SEQ ID NO (CDRL3 Portion) |
|---|---|---|---|---|
| VK3-11 15 2 8 | CCTGAAGATTTTGCAGTTTATTACTGTCAGCAGAGAAGTNHCYWCWGGACTTTTGGCGGAGGGACCAAG | CAGCAGAGAAGTNHCYWCWGGACT | 660 | 1284 |
| VK3-11 2 2 8 | CCTGAAGATTTTGCAGTTTATTACTGTSWMCAGBHCAGTAATTGGWGGACTTTTGGCGGAGGGACCAAG | SWMCAGBHCAGTAATTGGWGGACT | 661 | 1285 |
| VK3-11 3 2 8 | CCTGAAGATTTTGCAGTTTATTACTGTSWMCAGAGANHCAATTGGWGGACTTTTGGCGGAGGGACCAAG | SWMCAGAGANHCAATTGGWGGACT | 662 | 1286 |
| VK3-11 4 2 8 | CCTGAAGATTTTGCAGTTTATTACTGTSWMCAGAGAAGTNHCTGGWGGACTTTTGGCGGAGGGACCAAG | SWMCAGAGAAGTNHCTGGWGGACT | 663 | 1287 |
| VK3-11 5 2 8 | CCTGAAGATTTTGCAGTTTATTACTGTSWMCAGAGAAGTAATYWCWGGACTTTTGGCGGAGGGACCAAG | SWMCAGAGAAGTAATYWCWGGACT | 664 | 1288 |
| VK3-11 6 2 8 | CCTGAAGATTTTGCAGTTTATTACTGTCAGSWMBHCAGTAATTGGWGGACTTTTGGCGGAGGGACCAAG | CAGSWMBHCAGTAATTGGWGGACT | 665 | 1289 |
| VK3-11 7 2 8 | CCTGAAGATTTTGCAGTTTATTACTGTCAGSWMAGANHCAATTGGWGGACTTTTGGCGGAGGGACCAAG | CAGSWMAGANHCAATTGGWGGACT | 666 | 1290 |
| VK3-11 8 2 8 | CCTGAAGATTTTGCAGTTTATTACTGTCAGSWMAGAAGTNHCTGGWGGACTTTTGGCGGAGGGACCAAG | CAGSWMAGAAGTNHCTGGWGGACT | 667 | 1291 |
| VK3-11 9 2 8 | CCTGAAGATTTTGCAGTTTATTACTGTCAGSWMAGAAGTAATYWCWGGACTTTTGGCGGAGGGACCAAG | CAGSWMAGAAGTAATYWCWGGACT | 668 | 1292 |
| VK3-11 1 3 8 | CCTGAAGATTTTGCAGTTTATTACTGTSWMSWMAGAAGTAATTGGCCTACTTTTGGCGGAGGGACCAAG | SWMSWMAGAAGTAATTGGCCTACT | 669 | 1293 |
| VK3-11 10 3 8 | CCTGAAGATTTTGCAGTTTATTACTGTCAGCAGBHCNHCAATTGGCCTACTTTTGGCGGAGGGACCAAG | CAGCAGBHCNHCAATTGGCCTACT | 670 | 1294 |
| VK3-11 11 3 8 | CCTGAAGATTTTGCAGTTTATTACTGTCAGCAGBHCAGTNHCTGGCCTACTTTTGGCGGAGGGACCAAG | CAGCAGBHCAGTNHCTGGCCTACT | 671 | 1295 |
| VK3-11 12 3 8 | CCTGAAGATTTTGCAGTTTATTACTGTCAGCAGBHCAGTAATYWCCCTACTTTTGGCGGAGGGACCAAG | CAGCAGBHCAGTAATYWCCCTACT | 672 | 1296 |
| VK3-11 13 3 8 | CCTGAAGATTTTGCAGTTTATTACTGTCAGCAGAGANHCNHCTGGCCTACTTTTGGCGGAGGGACCAAG | CAGCAGAGANHCNHCTGGCCTACT | 673 | 1297 |
| VK3-11 14 3 8 | CCTGAAGATTTTGCAGTTTATTACTGTCAGCAGAGANHCAATYWCCCTACTTTTGGCGGAGGGACCAAG | CAGCAGAGANHCAATYWCCCTACT | 674 | 1298 |
| VK3-11 15 3 8 | CCTGAAGATTTTGCAGTTTATTACTGTCAGCAGAGAAGTNHCYWCCCTACTTTTGGCGGAGGGACCAAG | CAGCAGAGAAGTNHCYWCCCTACT | 675 | 1299 |
| VK3-11 2 3 8 | CCTGAAGATTTTGCAGTTTATTACTGTSWMCAGBHCAGTAATTGGCCTACTTTTGGCGGAGGGACCAAG | SWMCAGBHCAGTAATTGGCCTACT | 676 | 1300 |
| VK3-11 3 3 8 | CCTGAAGATTTTGCAGTTTATTACTGTSWMCAGAGANHCAATTGGCCTACTTTTGGCGGAGGGACCAAG | SWMCAGAGANHCAATTGGCCTACT | 677 | 1301 |
| VK3-11 4 3 8 | CCTGAAGATTTTGCAGTTTATTACTGTSWMCAGAGAAGTNHCTGGCCTACTTTTGGCGGAGGGACCAAG | SWMCAGAGAAGTNHCTGGCCTACT | 678 | 1302 |
| VK3-11 5 3 8 | CCTGAAGATTTTGCAGTTTATTACTGTSWMCAGAGAAGTAATYWCCCTACTTTTGGCGGAGGGACCAAG | SWMCAGAGAAGTAATYWCCCTACT | 679 | 1303 |
| VK3-11 6 3 8 | CCTGAAGATTTTGCAGTTTATTACTGTCAGSWMBHCAGTAATTGGCCTACTTTTGGCGGAGGGACCAAG | CAGSWMBHCAGTAATTGGCCTACT | 680 | 1304 |
| VK3-11 7 3 8 | CCTGAAGATTTTGCAGTTTATTACTGTCAGSWMAGANHCAATTGGCCTACTTTTGGCGGAGGGACCAAG | CAGSWMAGANHCAATTGGCCTACT | 681 | 1305 |
| VK3-11 8 3 8 | CCTGAAGATTTTGCAGTTTATTACTGTCAGSWMAGAAGTNHCTGGCCTACTTTTGGCGGAGGGACCAAG | CAGSWMAGAAGTNHCTGGCCTACT | 682 | 1306 |
| VK3-11 9 3 8 | CCTGAAGATTTTGCAGTTTATTACTGTCAGSWMAGAAGTAATYWCCCTACTTTTGGCGGAGGGACCAAG | CAGSWMAGAAGTAATYWCCCTACT | 683 | 1307 |

TABLE 5-continued

Oligonucleotide sequences for exemplary VK jumping dimer and trimer sequences with CDRL3 length 8.

| Name | Sequence of Synthesized Oligonucleotide | Portion of Oligonucleotide Corresponding to CDRL3 Proper | SEQ ID NO (Oligo) | SEQ ID NO (CDRL3 Portion) |
|---|---|---|---|---|
| VK3-15 1 0 8 | CAGTCTGAAGATTTTGCAGTTTATTACTGTSWMSWMTACAATAATTGGTWCACTTTTGGCGGAGGGACCAAG | SWMSWMTACAATAATTGGTWCACT | 684 | 1308 |
| VK3-15 10 0 8 | CAGTCTGAAGATTTTGCAGTTTATTACTGTCAGCAGBHCNHCAATTGGTWCACTTTTGGCGGAGGGACCAAG | CAGCAGBHCNHCAATTGGTWCACT | 685 | 1249 |
| VK3-15 11 0 8 | CAGTCTGAAGATTTTGCAGTTTATTACTGTCAGCAGBHCAATNHCTGGTWCACTTTTGGCGGAGGGACCAAG | CAGCAGBHCAATNHCTGGTWCACT | 686 | 1309 |
| VK3-15 12 0 8 | CAGTCTGAAGATTTTGCAGTTTATTACTGTCAGCAGBHCAATAATYWCTWCACTTTTGGCGGAGGGACCAAG | CAGCAGBHCAATAATYWCTWCACT | 687 | 1310 |
| VK3-15 13 0 8 | CAGTCTGAAGATTTTGCAGTTTATTACTGTCAGCAGTACNHCNHCTGGTWCACTTTTGGCGGAGGGACCAAG | CAGCAGTACNHCNHCTGGTWCACT | 688 | 1311 |
| VK3-15 14 0 8 | CAGTCTGAAGATTTTGCAGTTTATTACTGTCAGCAGTACNHCAATYWCTWCACTTTTGGCGGAGGGACCAAG | CAGCAGTACNHCAATYWCTWCACT | 689 | 1073 |
| VK3-15 15 0 8 | CAGTCTGAAGATTTTGCAGTTTATTACTGTCAGCAGTACAATNHCYWCTWCACTTTTGGCGGAGGGACCAAG | CAGCAGTACAATNHCYWCTWCACT | 690 | 1312 |
| VK3-15 2 0 8 | CAGTCTGAAGATTTTGCAGTTTATTACTGTSWMCAGBHCAATAATTGGTWCACTTTTGGCGGAGGGACCAAG | SWMCAGBHCAATAATTGGTWCACT | 691 | 1313 |
| VK3-15 3 0 8 | CAGTCTGAAGATTTTGCAGTTTATTACTGTSWMCAGTACNHCAATTGGTWCACTTTTGGCGGAGGGACCAAG | SWMCAGTACNHCAATTGGTWCACT | 692 | 1314 |
| VK3-15 4 0 8 | CAGTCTGAAGATTTTGCAGTTTATTACTGTSWMCAGTACAATNHCTGGTWCACTTTTGGCGGAGGGACCAAG | SWMCAGTACAATNHCTGGTWCACT | 693 | 1315 |
| VK3-15 5 0 8 | CAGTCTGAAGATTTTGCAGTTTATTACTGTSWMCAGTACAATAATYWCTWCACTTTTGGCGGAGGGACCAAG | SWMCAGTACAATAATYWCTWCACT | 694 | 1316 |
| VK3-15 6 0 8 | CAGTCTGAAGATTTTGCAGTTTATTACTGTCAGSWMBHCAATAATTGGTWCACTTTTGGCGGAGGGACCAAG | CAGSWMBHCAATAATTGGTWCACT | 695 | 1317 |
| VK3-15 7 0 8 | CAGTCTGAAGATTTTGCAGTTTATTACTGTCAGSWMTACNHCAATTGGTWCACTTTTGGCGGAGGGACCAAG | CAGSWMTACNHCAATTGGTWCACT | 696 | 1318 |
| VK3-15 8 0 8 | CAGTCTGAAGATTTTGCAGTTTATTACTGTCAGSWMTACAATNHCTGGTWCACTTTTGGCGGAGGGACCAAG | CAGSWMTACAATNHCTGGTWCACT | 697 | 1319 |
| VK3-15 9 0 8 | CAGTCTGAAGATTTTGCAGTTTATTACTGTCAGSWMTACAATAATYWCTWCACTTTTGGCGGAGGGACCAAG | CAGSWMTACAATAATYWCTWCACT | 698 | 1320 |
| VK3-15 1 1 8 | CAGTCTGAAGATTTTGCAGTTTATTACTGTSWMSWMTACAATAATTGGMTCACTTTTGGCGGAGGGACCAAG | SWMSWMTACAATAATTGGMTCACT | 699 | 1321 |
| VK3-15 10 1 8 | CAGTCTGAAGATTTTGCAGTTTATTACTGTCAGCAGBHCNHCAATTGGMTCACTTTTGGCGGAGGGACCAAG | CAGCAGBHCNHCAATTGGMTCACT | 700 | 1264 |
| VK3-15 11 1 8 | CAGTCTGAAGATTTTGCAGTTTATTACTGTCAGCAGBHCAATNHCTGGMTCACTTTTGGCGGAGGGACCAAG | CAGCAGBHCAATNHCTGGMTCACT | 701 | 1322 |
| VK3-15 12 1 8 | CAGTCTGAAGATTTTGCAGTTTATTACTGTCAGCAGBHCAATAATYWCMTCACTTTTGGCGGAGGGACCAAG | CAGCAGBHCAATAATYWCMTCACT | 702 | 1323 |
| VK3-15 13 1 8 | CAGTCTGAAGATTTTGCAGTTTATTACTGTCAGCAGTACNHCNHCTGGMTCACTTTTGGCGGAGGGACCAAG | CAGCAGTACNHCNHCTGGMTCACT | 703 | 1324 |
| VK3-15 14 1 8 | CAGTCTGAAGATTTTGCAGTTTATTACTGTCAGCAGTACNHCAATYWCMTCACTTTTGGCGGAGGGACCAAG | CAGCAGTACNHCAATYWCMTCACT | 704 | 1088 |
| VK3-15 15 1 8 | CAGTCTGAAGATTTTGCAGTTTATTACTGTCAGCAGTACAATNHCYWCMTCACTTTTGGCGGAGGGACCAAG | CAGCAGTACAATNHCYWCMTCACT | 705 | 1325 |
| VK3-15 2 1 8 | CAGTCTGAAGATTTTGCAGTTTATTACTGTSWMCAGBHCAATAATTGGMTCACTTTTGGCGGAGGGACCAAG | SWMCAGBHCAATAATTGGMTCACT | 706 | 1326 |

TABLE 5-continued

Oligonucleotide sequences for exemplary VK jumping dimer and trimer sequences with CDRL3 length 8.

| Name | Sequence of Synthesized Oligonucleotide | Portion of Oligonucleotide Corresponding to CDRL3 Proper | SEQ ID NO (Oligo) | SEQ ID NO (CDRL3 Portion) |
|---|---|---|---|---|
| VK3-15 3 1 8 | CAGTCTGAAGATTTTGCAGTTTATTACTGTSWMCAGTACNHCAATTGGMTCACTTTTGGCGGAGGGACCAAG | SWMCAGTACNHCAATTGGMTCACT | 707 | 1327 |
| VK3-15 4 1 8 | CAGTCTGAAGATTTTGCAGTTTATTACTGTSWMCAGTACAATNHCTGGMTCACTTTTGGCGGAGGGACCAAG | SWMCAGTACAATNHCTGGMTCACT | 708 | 1328 |
| VK3-15 5 1 8 | CAGTCTGAAGATTTTGCAGTTTATTACTGTSWMCAGTACAATAATYWCMTCACTTTTGGCGGAGGGACCAAG | SWMCAGTACAATAATYWCMTCACT | 709 | 1329 |
| VK3-15 6 1 8 | CAGTCTGAAGATTTTGCAGTTTATTACTGTCAGSWMBHCAATAATTGGMTCACTTTTGGCGGAGGGACCAAG | CAGSWMBHCAATAATTGGMTCACT | 710 | 1330 |
| VK3-15 7 1 8 | CAGTCTGAAGATTTTGCAGTTTATTACTGTCAGSWMTACNHCAATTGGMTCACTTTTGGCGGAGGGACCAAG | CAGSWMTACNHCAATTGGMTCACT | 711 | 1331 |
| VK3-15 8 1 8 | CAGTCTGAAGATTTTGCAGTTTATTACTGTCAGSWMTACAATNHCTGGMTCACTTTTGGCGGAGGGACCAAG | CAGSWMTACAATNHCTGGMTCACT | 712 | 1332 |
| VK3-15 9 1 8 | CAGTCTGAAGATTTTGCAGTTTATTACTGTCAGSWMTACAATAATYWCMTCACTTTTGGCGGAGGGACCAAG | CAGSWMTACAATAATYWCMTCACT | 713 | 1333 |
| VK3-15 1 2 8 | CAGTCTGAAGATTTTGCAGTTTATTACTGTSWMSWMTACAATAATTGGWGGACTTTTGGCGGAGGGACCAAG | SWMSWMTACAATAATTGGWGGACT | 714 | 1334 |
| VK3-15 10 2 8 | CAGTCTGAAGATTTTGCAGTTTATTACTGTCAGCAGBHCNHCAATTGGWGGACTTTTGGCGGAGGGACCAAG | CAGCAGBHCNHCAATTGGWGGACT | 715 | 1279 |
| VK3-15 11 2 8 | CAGTCTGAAGATTTTGCAGTTTATTACTGTCAGCAGBHCAATNHCTGGWGGACTTTTGGCGGAGGGACCAAG | CAGCAGBHCAATNHCTGGWGGACT | 716 | 1335 |
| VK3-15 12 2 8 | CAGTCTGAAGATTTTGCAGTTTATTACTGTCAGCAGBHCAATAATYWCWGGACTTTTGGCGGAGGGACCAAG | CAGCAGBHCAATAATYWCWGGACT | 717 | 1336 |
| VK3-15 13 2 8 | CAGTCTGAAGATTTTGCAGTTTATTACTGTCAGCAGTACNHCNHCTGGWGGACTTTTGGCGGAGGGACCAAG | CAGCAGTACNHCNHCTGGWGGACT | 718 | 1337 |
| VK3-15 14 2 8 | CAGTCTGAAGATTTTGCAGTTTATTACTGTCAGCAGTACNHCAATYWCWGGACTTTTGGCGGAGGGACCAAG | CAGCAGTACNHCAATYWCWGGACT | 719 | 1103 |
| VK3-15 15 2 8 | CAGTCTGAAGATTTTGCAGTTTATTACTGTCAGCAGTACAATNHCYWCWGGACTTTTGGCGGAGGGACCAAG | CAGCAGTACAATNHCYWCWGGACT | 720 | 1338 |
| VK3-15 2 2 8 | CAGTCTGAAGATTTTGCAGTTTATTACTGTSWMCAGBHCAATAATTGGWGGACTTTTGGCGGAGGGACCAAG | SWMCAGBHCAATAATTGGWGGACT | 721 | 1339 |
| VK3-15 3 2 8 | CAGTCTGAAGATTTTGCAGTTTATTACTGTSWMCAGTACNHCAATTGGWGGACTTTTGGCGGAGGGACCAAG | SWMCAGTACNHCAATTGGWGGACT | 722 | 1340 |
| VK3-15 4 2 8 | CAGTCTGAAGATTTTGCAGTTTATTACTGTSWMCAGTACAATNHCTGGWGGACTTTTGGCGGAGGGACCAAG | SWMCAGTACAATNHCTGGWGGACT | 723 | 1341 |
| VK3-15 5 2 8 | CAGTCTGAAGATTTTGCAGTTTATTACTGTSWMCAGTACAATAATYWCWGGACTTTTGGCGGAGGGACCAAG | SWMCAGTACAATAATYWCWGGACT | 724 | 1342 |
| VK3-15 6 2 8 | CAGTCTGAAGATTTTGCAGTTTATTACTGTCAGSWMBHCAATAATTGGWGGACTTTTGGCGGAGGGACCAAG | CAGSWMBHCAATAATTGGWGGACT | 725 | 1343 |
| VK3-15 7 2 8 | CAGTCTGAAGATTTTGCAGTTTATTACTGTCAGSWMTACNHCAATTGGWGGACTTTTGGCGGAGGGACCAAG | CAGSWMTACNHCAATTGGWGGACT | 726 | 1344 |
| VK3-15 8 2 8 | CAGTCTGAAGATTTTGCAGTTTATTACTGTCAGSWMTACAATNHCTGGWGGACTTTTGGCGGAGGGACCAAG | CAGSWMTACAATNHCTGGWGGACT | 727 | 1345 |
| VK3-15 9 2 8 | CAGTCTGAAGATTTTGCAGTTTATTACTGTCAGSWMTACAATAATYWCWGGACTTTTGGCGGAGGGACCAAG | CAGSWMTACAATAATYWCWGGACT | 728 | 1346 |
| VK3-15 1 3 8 | CAGTCTGAAGATTTTGCAGTTTATTACTGTSWMSWMTACAATAATTGGCCTACTTTTGGCGGAGGGACCAAG | SWMSWMTACAATAATTGGCCTACT | 729 | 1347 |
| VK3-15 10 3 8 | CAGTCTGAAGATTTTGCAGTTTATTACTGTCAGCAGBHCNHCAATTGGCCTACTTTTGGCGGAGGGACCAAG | CAGCAGBHCNHCAATTGGCCTACT | 730 | 1294 |

TABLE 5-continued

Oligonucleotide sequences for exemplary VK jumping dimer and trimer sequences with CDRL3 length 8.

| Name | Sequence of Synthesized Oligonucleotide | Portion of Oligonucleotide Corresponding to CDRL3 Proper | SEQ ID NO (Oligo) | SEQ ID NO (CDRL3 Portion) |
|---|---|---|---|---|
| VK3-15 11 3 8 | CAGTCTGAAGATTTTGCAGTTTATTACTGTCAGCAGBHCAATNHCTGGCCTACTTTTGGCGGAGGGACCAAG | CAGCAGBHCAATNHCTGGCCTACT | 731 | 1348 |
| VK3-15 12 3 8 | CAGTCTGAAGATTTTGCAGTTTATTACTGTCAGCAGBHCAATAATYWCCCTACTTTTGGCGGAGGGACCAAG | CAGCAGBHCAATAATYWCCCTACT | 732 | 1349 |
| VK3-15 13 3 8 | CAGTCTGAAGATTTTGCAGTTTATTACTGTCAGCAGTACNHCNHCTGGCCTACTTTTGGCGGAGGGACCAAG | CAGCAGTACNHCNHCTGGCCTACT | 733 | 1350 |
| VK3-15 14 3 8 | CAGTCTGAAGATTTTGCAGTTTATTACTGTCAGCAGTACNHCAATYWCCCTACTTTTGGCGGAGGGACCAAG | CAGCAGTACNHCAATYWCCCTACT | 734 | 1118 |
| VK3-15 15 3 8 | CAGTCTGAAGATTTTGCAGTTTATTACTGTCAGCAGTACAATNHCYWCCCTACTTTTGGCGGAGGGACCAAG | CAGCAGTACAATNHCYWCCCTACT | 735 | 1351 |
| VK3-15 2 3 8 | CAGTCTGAAGATTTTGCAGTTTATTACTGTSWMCAGBHCAATAATTGGCCTACTTTTGGCGGAGGGACCAAG | SWMCAGBHCAATAATTGGCCTACT | 736 | 1352 |
| VK3-15 3 3 8 | CAGTCTGAAGATTTTGCAGTTTATTACTGTSWMCAGTACNHCAATTGGCCTACTTTTGGCGGAGGGACCAAG | SWMCAGTACNHCAATTGGCCTACT | 737 | 1353 |
| VK3-15 4 3 8 | CAGTCTGAAGATTTTGCAGTTTATTACTGTSWMCAGTACAATNHCTGGCCTACTTTTGGCGGAGGGACCAAG | SWMCAGTACAATNHCTGGCCTACT | 738 | 1354 |
| VK3-15 5 3 8 | CAGTCTGAAGATTTTGCAGTTTATTACTGTSWMCAGTACAATAATYWCCCTACTTTTGGCGGAGGGACCAAG | SWMCAGTACAATAATYWCCCTACT | 739 | 1355 |
| VK3-15 6 3 8 | CAGTCTGAAGATTTTGCAGTTTATTACTGTCAGSWMBHCAATAATTGGCCTACTTTTGGCGGAGGGACCAAG | CAGSWMBHCAATAATTGGCCTACT | 740 | 1356 |
| VK3-15 7 3 8 | CAGTCTGAAGATTTTGCAGTTTATTACTGTCAGSWMTACNHCAATTGGCCTACTTTTGGCGGAGGGACCAAG | CAGSWMTACNHCAATTGGCCTACT | 741 | 1357 |
| VK3-15 8 3 8 | CAGTCTGAAGATTTTGCAGTTTATTACTGTCAGSWMTACAATNHCTGGCCTACTTTTGGCGGAGGGACCAAG | CAGSWMTACAATNHCTGGCCTACT | 742 | 1358 |
| VK3-15 9 3 8 | CAGTCTGAAGATTTTGCAGTTTATTACTGTCAGSWMTACAATAATYWCCCTACTTTTGGCGGAGGGACCAAG | CAGSWMTACAATAATYWCCCTACT | 743 | 1359 |
| VK3-20 1 0 8 | CCTGAAGATTTTGCAGTGTATTACTGTSWMSWMTACGGAAGTAGTTWCACTTTTGGCGGAGGGACCAAG | SWMSWMTACGGAAGTAGTTWCACT | 744 | 1360 |
| VK3-20 10 0 8 | CCTGAAGATTTTGCAGTGTATTACTGTCAGCAGBHCBHCAGTAGTTWCACTTTTGGCGGAGGGACCAAG | CAGCAGBHCBHCAGTAGTTWCACT | 745 | 1361 |
| VK3-20 11 0 8 | CCTGAAGATTTTGCAGTGTATTACTGTCAGCAGBHCGGAVNCAGTTWCACTTTTGGCGGAGGGACCAAG | CAGCAGBHCGGAVNCAGTTWCACT | 746 | 1362 |
| VK3-20 12 0 8 | CCTGAAGATTTTGCAGTGTATTACTGTCAGCAGBHCGGAAGTBHCTWCACTTTTGGCGGAGGGACCAAG | CAGCAGBHCGGAAGTBHCTWCACT | 747 | 1363 |
| VK3-20 13 0 8 | CCTGAAGATTTTGCAGTGTATTACTGTCAGCAGTACBHCVNCAGTTWCACTTTTGGCGGAGGGACCAAG | CAGCAGTACBHCVNCAGTTWCACT | 748 | 1364 |
| VK3-20 14 0 8 | CCTGAAGATTTTGCAGTGTATTACTGTCAGCAGTACBHCAGTBHCTWCACTTTTGGCGGAGGGACCAAG | CAGCAGTACBHCAGTBHCTWCACT | 749 | 1365 |
| VK3-20 15 0 8 | CCTGAAGATTTTGCAGTGTATTACTGTCAGCAGTACGGAVNCBHCTWCACTTTTGGCGGAGGGACCAAG | CAGCAGTACGGAVNCBHCTWCACT | 750 | 1366 |
| VK3-20 2 0 8 | CCTGAAGATTTTGCAGTGTATTACTGTSWMCAGBHCGGAAGTAGTTWCACTTTTGGCGGAGGGACCAAG | SWMCAGBHCGGAAGTAGTTWCACT | 751 | 1367 |
| VK3-20 3 0 8 | CCTGAAGATTTTGCAGTGTATTACTGTSWMCAGTACBHCAGTAGTTWCACTTTTGGCGGAGGGACCAAG | SWMCAGTACBHCAGTAGTTWCACT | 752 | 1368 |
| VK3-20 4 0 8 | CCTGAAGATTTTGCAGTGTATTACTGTSWMCAGTACGGAVNCAGTTWCACTTTTGGCGGAGGGACCAAG | SWMCAGTACGGAVNCAGTTWCACT | 753 | 1369 |

TABLE 5-continued

Oligonucleotide sequences for exemplary VK jumping dimer and trimer sequences with CDRL3 length 8.

| Name | Sequence of Synthesized Oligonucleotide | Portion of Oligonucleotide Corresponding to CDRL3 Proper | SEQ ID NO (Oligo) | SEQ ID NO (CDRL3 Portion) |
|---|---|---|---|---|
| VK3-20 5 0 8 | CCTGAAGATTTTGCAGTGTATTACTGTSWMCAGTACGGAAGTBHCTWCACTTTTGGCGGAGGGACCAAG | SWMCAGTACGGAAGTBHCTWCACT | 754 | 1370 |
| VK3-20 6 0 8 | CCTGAAGATTTTGCAGTGTATTACTGTCAGSWMBHCGGAAGTAGTTWCACTTTTGGCGGAGGGACCAAG | CAGSWMBHCGGAAGTAGTTWCACT | 755 | 1371 |
| VK3-20 7 0 8 | CCTGAAGATTTTGCAGTGTATTACTGTCAGSWMTACBHCAGTAGTTWCACTTTTGGCGGAGGGACCAAG | CAGSWMTACBHCAGTAGTTWCACT | 756 | 1372 |
| VK3-20 8 0 8 | CCTGAAGATTTTGCAGTGTATTACTGTCAGSWMTACGGAVNCAGTTWCACTTTTGGCGGAGGGACCAAG | CAGSWMTACGGAVNCAGTTWCACT | 757 | 1373 |
| VK3-20 9 0 8 | CCTGAAGATTTTGCAGTGTATTACTGTCAGSWMTACGGAAGTBHCTWCACTTTTGGCGGAGGGACCAAG | CAGSWMTACGGAAGTBHCTWCACT | 758 | 1374 |
| VK3-20 1 1 8 | CCTGAAGATTTTGCAGTGTATTACTGTSWMSWMTACGGAAGTAGTMTCACTTTTGGCGGAGGGACCAAG | SWMSWMTACGGAAGTAGTMTCACT | 759 | 1375 |
| VK3-20 10 1 8 | CCTGAAGATTTTGCAGTGTATTACTGTCAGCAGBHCBHCAGTAGTMTCACTTTTGGCGGAGGGACCAAG | CAGCAGBHCBHCAGTAGTMTCACT | 760 | 1376 |
| VK3-20 11 1 8 | CCTGAAGATTTTGCAGTGTATTACTGTCAGCAGBHCGGAVNCAGTMTCACTTTTGGCGGAGGGACCAAG | CAGCAGBHCGGAVNCAGTMTCACT | 761 | 1377 |
| VK3-20 12 1 8 | CCTGAAGATTTTGCAGTGTATTACTGTCAGCAGBHCGGAAGTBHCMTCACTTTTGGCGGAGGGACCAAG | CAGCAGBHCGGAAGTBHCMTCACT | 762 | 1378 |
| VK3-20 13 1 8 | CCTGAAGATTTTGCAGTGTATTACTGTCAGCAGTACBHCVNCAGTMTCACTTTTGGCGGAGGGACCAAG | CAGCAGTACBHCVNCAGTMTCACT | 763 | 1379 |
| VK3-20 14 1 8 | CCTGAAGATTTTGCAGTGTATTACTGTCAGCAGTACBHCAGTBHCMTCACTTTTGGCGGAGGGACCAAG | CAGCAGTACBHCAGTBHCMTCACT | 764 | 1380 |
| VK3-20 15 1 8 | CCTGAAGATTTTGCAGTGTATTACTGTCAGCAGTACGGAVNCBHCMTCACTTTTGGCGGAGGGACCAAG | CAGCAGTACGGAVNCBHCMTCACT | 765 | 1381 |
| VK3-20 2 1 8 | CCTGAAGATTTTGCAGTGTATTACTGTSWMCAGBHCGGAAGTAGTMTCACTTTTGGCGGAGGGACCAAG | SWMCAGBHCGGAAGTAGTMTCACT | 766 | 1382 |
| VK3-20 3 1 8 | CCTGAAGATTTTGCAGTGTATTACTGTSWMCAGTACBHCAGTAGTMTCACTTTTGGCGGAGGGACCAAG | SWMCAGTACBHCAGTAGTMTCACT | 767 | 1383 |
| VK3-20 4 1 8 | CCTGAAGATTTTGCAGTGTATTACTGTSWMCAGTACGGAVNCAGTMTCACTTTTGGCGGAGGGACCAAG | SWMCAGTACGGAVNCAGTMTCACT | 768 | 1384 |
| VK3-20 5 1 8 | CCTGAAGATTTTGCAGTGTATTACTGTSWMCAGTACGGAAGTBHCMTCACTTTTGGCGGAGGGACCAAG | SWMCAGTACGGAAGTBHCMTCACT | 769 | 1385 |
| VK3-20 6 1 8 | CCTGAAGATTTTGCAGTGTATTACTGTCAGSWMBHCGGAAGTAGTMTCACTTTTGGCGGAGGGACCAAG | CAGSWMBHCGGAAGTAGTMTCACT | 770 | 1386 |
| VK3-20 7 1 8 | CCTGAAGATTTTGCAGTGTATTACTGTCAGSWMTACBHCAGTAGTMTCACTTTTGGCGGAGGGACCAAG | CAGSWMTACBHCAGTAGTMTCACT | 771 | 1387 |
| VK3-20 8 1 8 | CCTGAAGATTTTGCAGTGTATTACTGTCAGSWMTACGGAVNCAGTMTCACTTTTGGCGGAGGGACCAAG | CAGSWMTACGGAVNCAGTMTCACT | 772 | 1388 |
| VK3-20 9 1 8 | CCTGAAGATTTTGCAGTGTATTACTGTCAGSWMTACGGAAGTBHCMTCACTTTTGGCGGAGGGACCAAG | CAGSWMTACGGAAGTBHCMTCACT | 773 | 1389 |
| VK3-20 1 2 8 | CCTGAAGATTTTGCAGTGTATTACTGTSWMSWMTACGGAAGTAGTWGGACTTTTGGCGGAGGGACCAAG | SWMSWMTACGGAAGTAGTWGGACT | 774 | 1390 |
| VK3-20 10 2 8 | CCTGAAGATTTTGCAGTGTATTACTGTCAGCAGBHCBHCAGTAGTWGGACTTTTGGCGGAGGGACCAAG | CAGCAGBHCBHCAGTAGTWGGACT | 775 | 1391 |
| VK3-20 11 2 8 | CCTGAAGATTTTGCAGTGTATTACTGTCAGCAGBHCGGAVNCAGTWGGACTTTTGGCGGAGGGACCAAG | CAGCAGBHCGGAVNCAGTWGGACT | 776 | 1392 |
| VK3-20 12 2 8 | CCTGAAGATTTTGCAGTGTATTACTGTCAGCAGBHCGGAAGTBHCWGGACTTTTGGCGGAGGGACCAAG | CAGCAGBHCGGAAGTBHCWGGACT | 777 | 1393 |

TABLE 5-continued

Oligonucleotide sequences for exemplary VK jumping dimer and trimer sequences with CDRL3 length 8.

| Name | Sequence of Synthesized Oligonucleotide | Portion of Oligonucleotide Corresponding to CDRL3 Proper | SEQ ID NO (Oligo) | SEQ ID NO (CDRL3 Portion) |
|---|---|---|---|---|
| VK3-20 13 2 8 | CCTGAAGATTTTGCAGTGTATTACTGTCAGCAGTACBHCVNCAGTWGGACTTTTGGCGGAGGGACCAAG | CAGCAGTACBHCVNCAGTWGGACT | 778 | 1394 |
| VK3-20 14 2 8 | CCTGAAGATTTTGCAGTGTATTACTGTCAGCAGTACBHCAGTBHCWGGACTTTTGGCGGAGGGACCAAG | CAGCAGTACBHCAGTBHCWGGACT | 779 | 1395 |
| VK3-20 15 2 8 | CCTGAAGATTTTGCAGTGTATTACTGTCAGCAGTACGGAVNCBHCWGGACTTTTGGCGGAGGGACCAAG | CAGCAGTACGGAVNCBHCWGGACT | 780 | 1396 |
| VK3-20 2 2 8 | CCTGAAGATTTTGCAGTGTATTACTGTSWMCAGBHCGGAAGTAGTWGGACTTTTGGCGGAGGGACCAAG | SWMCAGBHCGGAAGTAGTWGGACT | 781 | 1397 |
| VK3-20 3 2 8 | CCTGAAGATTTTGCAGTGTATTACTGTSWMCAGTACBHCAGTAGTWGGACTTTTGGCGGAGGGACCAAG | SWMCAGTACBHCAGTAGTWGGACT | 782 | 1398 |
| VK3-20 4 2 8 | CCTGAAGATTTTGCAGTGTATTACTGTSWMCAGTACGGAVNCAGTWGGACTTTTGGCGGAGGGACCAAG | SWMCAGTACGGAVNCAGTWGGACT | 783 | 1399 |
| VK3-20 5 2 8 | CCTGAAGATTTTGCAGTGTATTACTGTSWMCAGTACGGAAGTBHCWGGACTTTTGGCGGAGGGACCAAG | SWMCAGTACGGAAGTBHCWGGACT | 784 | 1400 |
| VK3-20 6 2 8 | CCTGAAGATTTTGCAGTGTATTACTGTCAGSWMBHCGGAAGTAGTWGGACTTTTGGCGGAGGGACCAAG | CAGSWMBHCGGAAGTAGTWGGACT | 785 | 1401 |
| VK3-20 7 2 8 | CCTGAAGATTTTGCAGTGTATTACTGTCAGSWMTACBHCAGTAGTWGGACTTTTGGCGGAGGGACCAAG | CAGSWMTACBHCAGTAGTWGGACT | 786 | 1402 |
| VK3-20 8 2 8 | CCTGAAGATTTTGCAGTGTATTACTGTCAGSWMTACGGAVNCAGTWGGACTTTTGGCGGAGGGACCAAG | CAGSWMTACGGAVNCAGTWGGACT | 787 | 1403 |
| VK3-20 9 2 8 | CCTGAAGATTTTGCAGTGTATTACTGTCAGSWMTACGGAAGTBHCWGGACTTTTGGCGGAGGGACCAAG | CAGSWMTACGGAAGTBHCWGGACT | 788 | 1404 |
| VK3-20 1 3 8 | CCTGAAGATTTTGCAGTGTATTACTGTSWMSWMTACGGAAGTAGTCCTACTTTTGGCGGAGGGACCAAG | SWMSWMTACGGAAGTAGTCCTACT | 789 | 1405 |
| VK3-20 10 3 8 | CCTGAAGATTTTGCAGTGTATTACTGTCAGCAGBHCBHCAGTAGTCCTACTTTTGGCGGAGGGACCAAG | CAGCAGBHCBHCAGTAGTCCTACT | 790 | 1406 |
| VK3-20 11 3 8 | CCTGAAGATTTTGCAGTGTATTACTGTCAGCAGBHCGGAVNCAGTCCTACTTTTGGCGGAGGGACCAAG | CAGCAGBHCGGAVNCAGTCCTACT | 791 | 1407 |
| VK3-20 12 3 8 | CCTGAAGATTTTGCAGTGTATTACTGTCAGCAGBHCGGAAGTBHCCCTACTTTTGGCGGAGGGACCAAG | CAGCAGBHCGGAAGTBHCCCTACT | 792 | 1408 |
| VK3-20 13 3 8 | CCTGAAGATTTTGCAGTGTATTACTGTCAGCAGTACBHCVNCAGTCCTACTTTTGGCGGAGGGACCAAG | CAGCAGTACBHCVNCAGTCCTACT | 793 | 1409 |
| VK3-20 14 3 8 | CCTGAAGATTTTGCAGTGTATTACTGTCAGCAGTACBHCAGTBHCCCTACTTTTGGCGGAGGGACCAAG | CAGCAGTACBHCAGTBHCCCTACT | 794 | 1410 |
| VK3-20 15 3 8 | CCTGAAGATTTTGCAGTGTATTACTGTCAGCAGTACGGAVNCBHCCCTACTTTTGGCGGAGGGACCAAG | CAGCAGTACGGAVNCBHCCCTACT | 795 | 1411 |
| VK3-20 2 3 8 | CCTGAAGATTTTGCAGTGTATTACTGTSWMCAGBHCGGAAGTAGTCCTACTTTTGGCGGAGGGACCAAG | SWMCAGBHCGGAAGTAGTCCTACT | 796 | 1412 |
| VK3-20 3 3 8 | CCTGAAGATTTTGCAGTGTATTACTGTSWMCAGTACBHCAGTAGTCCTACTTTTGGCGGAGGGACCAAG | SWMCAGTACBHCAGTAGTCCTACT | 797 | 1413 |
| VK3-20 4 3 8 | CCTGAAGATTTTGCAGTGTATTACTGTSWMCAGTACGGAVNCAGTCCTACTTTTGGCGGAGGGACCAAG | SWMCAGTACGGAVNCAGTCCTACT | 798 | 1414 |
| VK3-20 5 3 8 | CCTGAAGATTTTGCAGTGTATTACTGTSWMCAGTACGGAAGTBHCCCTACTTTTGGCGGAGGGACCAAG | SWMCAGTACGGAAGTBHCCCTACT | 799 | 1415 |
| VK3-20 6 3 8 | CCTGAAGATTTTGCAGTGTATTACTGTCAGSWMBHCGGAAGTAGTCCTACTTTTGGCGGAGGGACCAAG | CAGSWMBHCGGAAGTAGTCCTACT | 800 | 1416 |

TABLE 5-continued

Oligonucleotide sequences for exemplary VK jumping dimer and trimer sequences with CDRL3 length 8.

| Name | Sequence of Synthesized Oligonucleotide | Portion of Oligonucleotide Corresponding to CDRL3 Proper | SEQ ID NO (Oligo) | SEQ ID NO (CDRL3 Portion) |
|---|---|---|---|---|
| VK3-20 7 3 8 | CCTGAAGATTTTGCAGTGTATTACTGTCAGSWMTACBHCAGTAGTCCTACTTTTGGCGGAGGGACCAAG | CAGSWMTACBHCAGTAGTCCTACT | 801 | 1417 |
| VK3-20 8 3 8 | CCTGAAGATTTTGCAGTGTATTACTGTCAGSWMTACGGAVNCAGTCCTACTTTTGGCGGAGGGACCAAG | CAGSWMTACGGAVNCAGTCCTACT | 802 | 1418 |
| VK3-20 9 3 8 | CCTGAAGATTTTGCAGTGTATTACTGTCAGSWMTACGGAAGTBHCCCTACTTTTGGCGGAGGGACCAAG | CAGSWMTACGGAAGTBHCCCTACT | 803 | 1419 |
| Jumping Trimer | | | | |
| VK1-05 t1 0 8 | CCTGATGATTTTGCAACTTATTACTGCCAGCAGBHCVRMMBCTACTWCACTTTTGGCGGAGGGACCAAG | CAGCAGBHCVRMMBCTACTWCACT | 804 | 1420 |
| VK1-05 t1 1 8 | CCTGATGATTTTGCAACTTATTACTGCCAGCAGBHCVRMMBCTACMTCACTTTTGGCGGAGGGACCAAG | CAGCAGBHCVRMMBCTACMTCACT | 805 | 1421 |
| VK1-05 t1 2 8 | CCTGATGATTTTGCAACTTATTACTGCCAGCAGBHCVRMMBCTACWGGACTTTTGGCGGAGGGACCAAG | CAGCAGBHCVRMMBCTACWGGACT | 806 | 1422 |
| VK1-05 t1 3 8 | CCTGATGATTTTGCAACTTATTACTGCCAGCAGBHCVRMMBCTACYCTACTTTTGGCGGAGGGACCAAG | CAGCAGBHCVRMMBCTACYCTACT | 807 | 1423 |
| VK1-05 t2 0 8 | CCTGATGATTTTGCAACTTATTACTGCCAGCAGBHCAATMBCYWCTWCACTTTTGGCGGAGGGACCAAG | CAGCAGBHCAATMBCYWCTWCACT | 808 | 1424 |
| VK1-05 t2 1 8 | CCTGATGATTTTGCAACTTATTACTGCCAGCAGBHCAATMBCYWCMTCACTTTTGGCGGAGGGACCAAG | CAGCAGBHCAATMBCYWCMTCACT | 809 | 1425 |
| VK1-05 t2 2 8 | CCTGATGATTTTGCAACTTATTACTGCCAGCAGBHCAATMBCYWCWGGACTTTTGGCGGAGGGACCAAG | CAGCAGBHCAATMBCYWCWGGACT | 810 | 1426 |
| VK1-05 t2 3 8 | CCTGATGATTTTGCAACTTATTACTGCCAGCAGBHCAATMBCYWCYCTACTTTTGGCGGAGGGACCAAG | CAGCAGBHCAATMBCYWCYCTACT | 811 | 1427 |
| VK1-05 t3 0 8 | CCTGATGATTTTGCAACTTATTACTGCCAGCAGBHCVRMAGTYWCTWCACTTTTGGCGGAGGGACCAAG | CAGCAGBHCVRMAGTYWCTWCACT | 812 | 1428 |
| VK1-05 t3 1 8 | CCTGATGATTTTGCAACTTATTACTGCCAGCAGBHCVRMAGTYWCMTCACTTTTGGCGGAGGGACCAAG | CAGCAGBHCVRMAGTYWCMTCACT | 813 | 1429 |
| VK1-05 t3 2 8 | CCTGATGATTTTGCAACTTATTACTGCCAGCAGBHCVRMAGTYWCWGGACTTTTGGCGGAGGGACCAAG | CAGCAGBHCVRMAGTYWCWGGACT | 814 | 1430 |
| VK1-05 t3 3 8 | CCTGATGATTTTGCAACTTATTACTGCCAGCAGBHCVRMAGTYWCYCTACTTTTGGCGGAGGGACCAAG | CAGCAGBHCVRMAGTYWCYCTACT | 815 | 1431 |
| VK1-05 t4 0 8 | CCTGATGATTTTGCAACTTATTACTGCCAGCAGTACVRMMBCYWCTWCACTTTTGGCGGAGGGACCAAG | CAGCAGTACVRMMBCYWCTWCACT | 816 | 1432 |
| VK1-05 t4 1 8 | CCTGATGATTTTGCAACTTATTACTGCCAGCAGTACVRMMBCYWCMTCACTTTTGGCGGAGGGACCAAG | CAGCAGTACVRMMBCYWCMTCACT | 817 | 1433 |
| VK1-05 t4 2 8 | CCTGATGATTTTGCAACTTATTACTGCCAGCAGTACVRMMBCYWCWGGACTTTTGGCGGAGGGACCAAG | CAGCAGTACVRMMBCYWCWGGACT | 818 | 1434 |
| VK1-05 t4 3 8 | CCTGATGATTTTGCAACTTATTACTGCCAGCAGTACVRMMBCYWCYCTACTTTTGGCGGAGGGACCAAG | CAGCAGTACVRMMBCYWCYCTACT | 819 | 1435 |
| VK1-12 t1 0 8 | CCTGAAGATTTTGCAACTTATTACTGTCAGCAGRNANHCNHCTTCTWCACTTTTGGCGGAGGGACCAAG | CAGCAGRNANHCNHCTTCTWCACT | 820 | 1436 |
| VK1-12 t1 1 8 | CCTGAAGATTTTGCAACTTATTACTGTCAGCAGRNANHCNHCTTCMTCACTTTTGGCGGAGGGACCAAG | CAGCAGRNANHCNHCTTCMTCACT | 821 | 1437 |
| VK1-12 t1 2 8 | CCTGAAGATTTTGCAACTTATTACTGTCAGCAGRNANHCNHCTTCWGGACTTTTGGCGGAGGGACCAAG | CAGCAGRNANHCNHCTTCWGGACT | 822 | 1438 |
| VK1-12 t1 3 8 | CCTGAAGATTTTGCAACTTATTACTGTCAGCAGRNANHCNHCTTCCCTACTTTTGGCGGAGGGACCAAG | CAGCAGRNANHCNHCTTCCCTACT | 823 | 1439 |

TABLE 5-continued

Oligonucleotide sequences for exemplary VK jumping dimer and trimer sequences with CDRL3 length 8.

| Name | Sequence of Synthesized Oligonucleotide | Portion of Oligonucleotide Corresponding to CDRL3 Proper | SEQ ID NO (Oligo) | SEQ ID NO (CDRL3 Portion) |
|---|---|---|---|---|
| VK1-12 t2 0 8 | CCTGAAGATTTTGCAACTTATTACTGTCAGCAGRNANHCAGTYWCTWCACTTTTGGCGGAGGGACCAAG | CAGCAGRNANHCAGTYWCTWCACT | 824 | 1440 |
| VK1-12 t2 1 8 | CCTGAAGATTTTGCAACTTATTACTGTCAGCAGRNANHCAGTYWCMTCACTTTTGGCGGAGGGACCAAG | CAGCAGRNANHCAGTYWCMTCACT | 825 | 1441 |
| VK1-12 t2 2 8 | CCTGAAGATTTTGCAACTTATTACTGTCAGCAGRNANHCAGTYWCWGGACTTTTGGCGGAGGGACCAAG | CAGCAGRNANHCAGTYWCWGGACT | 826 | 1442 |
| VK1-12 t2 3 8 | CCTGAAGATTTTGCAACTTATTACTGTCAGCAGRNANHCAGTYWCCCTACTTTTGGCGGAGGGACCAAG | CAGCAGRNANHCAGTYWCCCTACT | 827 | 1443 |
| VK1-12 t3 0 8 | CCTGAAGATTTTGCAACTTATTACTGTCAGCAGRNAAATNHCYWCTWCACTTTTGGCGGAGGGACCAAG | CAGCAGRNAAATNHCYWCTWCACT | 828 | 1444 |
| VK1-12 t3 1 8 | CCTGAAGATTTTGCAACTTATTACTGTCAGCAGRNAAATNHCYWCMTCACTTTTGGCGGAGGGACCAAG | CAGCAGRNAAATNHCYWCMTCACT | 829 | 1445 |
| VK1-12 t3 2 8 | CCTGAAGATTTTGCAACTTATTACTGTCAGCAGRNAAATNHCYWCWGGACTTTTGGCGGAGGGACCAAG | CAGCAGRNAAATNHCYWCWGGACT | 830 | 1446 |
| VK1-12 t3 3 8 | CCTGAAGATTTTGCAACTTATTACTGTCAGCAGRNAAATNHCYWCCCTACTTTTGGCGGAGGGACCAAG | CAGCAGRNAAATNHCYWCCCTACT | 831 | 1447 |
| VK1-12 t4 0 8 | CCTGAAGATTTTGCAACTTATTACTGTCAGCAGGCANHCNHCYWCTWCACTTTTGGCGGAGGGACCAAG | CAGCAGGCANHCNHCYWCTWCACT | 832 | 1448 |
| VK1-12 t4 1 8 | CCTGAAGATTTTGCAACTTATTACTGTCAGCAGGCANHCNHCYWCMTCACTTTTGGCGGAGGGACCAAG | CAGCAGGCANHCNHCYWCMTCACT | 833 | 1449 |
| VK1-12 t4 2 8 | CCTGAAGATTTTGCAACTTATTACTGTCAGCAGGCANHCNHCYWCWGGACTTTTGGCGGAGGGACCAAG | CAGCAGGCANHCNHCYWCWGGACT | 834 | 1450 |
| VK1-12 t4 3 8 | CCTGAAGATTTTGCAACTTATTACTGTCAGCAGGCANHCNHCYWCCCTACTTTTGGCGGAGGGACCAAG | CAGCAGGCANHCNHCYWCCCTACT | 835 | 1451 |
| VK1-33 t1 0 8 | CCTGAAGATATTGCAACATATTACTGTCAGCAGBHCNHCNHCCTCTWCACTTTTGGCGGAGGGACCAAG | CAGCAGBHCNHCNHCCTCTWCACT | 836 | 1452 |
| VK1-33 t1 1 8 | CCTGAAGATATTGCAACATATTACTGTCAGCAGBHCNHCNHCCTCMTCACTTTTGGCGGAGGGACCAAG | CAGCAGBHCNHCNHCCTCMTCACT | 837 | 1453 |
| VK1-33 t1 2 8 | CCTGAAGATATTGCAACATATTACTGTCAGCAGBHCNHCNHCCTCWGGACTTTTGGCGGAGGGACCAAG | CAGCAGBHCNHCNHCCTCWGGACT | 838 | 1454 |
| VK1-33 t1 3 8 | CCTGAAGATATTGCAACATATTACTGTCAGCAGBHCNHCNHCCTCCCTACTTTTGGCGGAGGGACCAAG | CAGCAGBHCNHCNHCCTCCCTACT | 839 | 1455 |
| VK1-33 t2 0 8 | CCTGAAGATATTGCAACATATTACTGTCAGCAGBHCNHCAATYWCTWCACTTTTGGCGGAGGGACCAAG | CAGCAGBHCNHCAATYWCTWCACT | 840 | 1456 |
| VK1-33 t2 1 8 | CCTGAAGATATTGCAACATATTACTGTCAGCAGBHCNHCAATYWCMTCACTTTTGGCGGAGGGACCAAG | CAGCAGBHCNHCAATYWCMTCACT | 841 | 1457 |
| VK1-33 t2 2 8 | CCTGAAGATATTGCAACATATTACTGTCAGCAGBHCNHCAATYWCWGGACTTTTGGCGGAGGGACCAAG | CAGCAGBHCNHCAATYWCWGGACT | 842 | 1458 |
| VK1-33 t2 3 8 | CCTGAAGATATTGCAACATATTACTGTCAGCAGBHCNHCAATYWCCCTACTTTTGGCGGAGGGACCAAG | CAGCAGBHCNHCAATYWCCCTACT | 843 | 1459 |
| VK1-33 t3 0 8 | CCTGAAGATATTGCAACATATTACTGTCAGCAGBHCGATNHCYWCTWCACTTTTGGCGGAGGGACCAAG | CAGCAGBHCGATNHCYWCTWCACT | 844 | 1460 |
| VK1-33 t3 1 8 | CCTGAAGATATTGCAACATATTACTGTCAGCAGBHCGATNHCYWCMTCACTTTTGGCGGAGGGACCAAG | CAGCAGBHCGATNHCYWCMTCACT | 845 | 1461 |
| VK1-33 t3 2 8 | CCTGAAGATATTGCAACATATTACTGTCAGCAGBHCGATNHCYWCWGGACTTTTGGCGGAGGGACCAAG | CAGCAGBHCGATNHCYWCWGGACT | 846 | 1462 |
| VK1-33 t3 3 8 | CCTGAAGATATTGCAACATATTACTGTCAGCAGBHCGATNHCYWCCCTACTTTTGGCGGAGGGACCAAG | CAGCAGBHCGATNHCYWCCCTACT | 847 | 1463 |

TABLE 5-continued

Oligonucleotide sequences for exemplary VK jumping dimer and trimer sequences with CDRL3 length 8.

| Name | Sequence of Synthesized Oligonucleotide | Portion of Oligonucleotide Corresponding to CDRL3 Proper | SEQ ID NO (Oligo) | SEQ ID NO (CDRL3 Portion) |
|---|---|---|---|---|
| VK1-33 t4 0 8 | CCTGAAGATATTGCAACATATTACTGTCAGCAGTACNHCNHCYWCTWCACTTTTGGCGGAGGGACCAAG | CAGCAGTACNHCNHCYWCTWCACT | 848 | 1464 |
| VK1-33 t4 1 8 | CCTGAAGATATTGCAACATATTACTGTCAGCAGTACNHCNHCYWCMTCACTTTTGGCGGAGGGACCAAG | CAGCAGTACNHCNHCYWCMTCACT | 849 | 1465 |
| VK1-33 t4 2 8 | CCTGAAGATATTGCAACATATTACTGTCAGCAGTACNHCNHCYWCWGGACTTTTGGCGGAGGGACCAAG | CAGCAGTACNHCNHCYWCWGGACT | 850 | 1466 |
| VK1-33 t4 3 8 | CCTGAAGATATTGCAACATATTACTGTCAGCAGTACNHCNHCYWCCCTACTTTTGGCGGAGGGACCAAG | CAGCAGTACNHCNHCYWCCCTACT | 851 | 1467 |
| VK1-39 t1 0 8 | CCTGAAGATTTTGCAACTTACTACTGTCAGCAAVNABHCNHCACTTWCACTTTTGGCGGAGGGACCAAG | CAGCAAVNABHCNHCACTTWCACT | 852 | 1468 |
| VK1-39 t1 1 8 | CCTGAAGATTTTGCAACTTACTACTGTCAGCAAVNABHCNHCACTMTCACTTTTGGCGGAGGGACCAAG | CAGCAAVNABHCNHCACTMTCACT | 853 | 1469 |
| VK1-39 t1 2 8 | CCTGAAGATTTTGCAACTTACTACTGTCAGCAAVNABHCNHCACTWGGACTTTTGGCGGAGGGACCAAG | CAGCAAVNABHCNHCACTWGGACT | 854 | 1470 |
| VK1-39 t1 3 8 | CCTGAAGATTTTGCAACTTACTACTGTCAGCAAVNABHCNHCACTCCTACTTTTGGCGGAGGGACCAAG | CAGCAAVNABHCNHCACTCCTACT | 855 | 1471 |
| VK1-39 t2 0 8 | CCTGAAGATTTTGCAACTTACTACTGTCAGCAAVNABHCAGTBHCTWCACTTTTGGCGGAGGGACCAAG | CAGCAAVNABHCAGTBHCTWCACT | 856 | 1472 |
| VK1-39 t2 1 8 | CCTGAAGATTTTGCAACTTACTACTGTCAGCAAVNABHCAGTBHCMTCACTTTTGGCGGAGGGACCAAG | CAGCAAVNABHCAGTBHCMTCACT | 857 | 1473 |
| VK1-39 t2 2 8 | CCTGAAGATTTTGCAACTTACTACTGTCAGCAAVNABHCAGTBHCWGGACTTTTGGCGGAGGGACCAAG | CAGCAAVNABHCAGTBHCWGGACT | 858 | 1474 |
| VK1-39 t2 3 8 | CCTGAAGATTTTGCAACTTACTACTGTCAGCAAVNABHCAGTBHCCCTACTTTTGGCGGAGGGACCAAG | CAGCAAVNABHCAGTBHCCCTACT | 859 | 1475 |
| VK1-39 t3 0 8 | CCTGAAGATTTTGCAACTTACTACTGTCAGCAAVNATACNHCBHCTWCACTTTTGGCGGAGGGACCAAG | CAGCAAVNATACNHCBHCTWCACT | 860 | 1476 |
| VK1-39 t3 1 8 | CCTGAAGATTTTGCAACTTACTACTGTCAGCAAVNATACNHCBHCMTCACTTTTGGCGGAGGGACCAAG | CAGCAAVNATACNHCBHCMTCACT | 861 | 1477 |
| VK1-39 t3 2 8 | CCTGAAGATTTTGCAACTTACTACTGTCAGCAAVNATACNHCBHCWGGACTTTTGGCGGAGGGACCAAG | CAGCAAVNATACNHCBHCWGGACT | 862 | 1478 |
| VK1-39 t3 3 8 | CCTGAAGATTTTGCAACTTACTACTGTCAGCAAVNATACNHCBHCCCTACTTTTGGCGGAGGGACCAAG | CAGCAAVNATACNHCBHCCCTACT | 863 | 1479 |
| VK1-39 t4 0 8 | CCTGAAGATTTTGCAACTTACTACTGTCAGCAAAGCBHCNHCBHCTWCACTTTTGGCGGAGGGACCAAG | CAGCAAAGCBHCNHCBHCTWCACT | 864 | 1480 |
| VK1-39 t4 1 8 | CCTGAAGATTTTGCAACTTACTACTGTCAGCAAAGCBHCNHCBHCMTCACTTTTGGCGGAGGGACCAAG | CAGCAAAGCBHCNHCBHCMTCACT | 865 | 1481 |
| VK1-39 t4 2 8 | CCTGAAGATTTTGCAACTTACTACTGTCAGCAAAGCBHCNHCBHCWGGACTTTTGGCGGAGGGACCAAG | CAGCAAAGCBHCNHCBHCWGGACT | 866 | 1482 |
| VK1-39 t4 3 8 | CCTGAAGATTTTGCAACTTACTACTGTCAGCAAAGCBHCNHCBHCCCTACTTTTGGCGGAGGGACCAAG | CAGCAAAGCBHCNHCBHCCCTACT | 867 | 1483 |
| VK2-28 t1 0 8 | GCTGAGGATGTTGGGGTTTATTACTGCATGCAGVNAMNASRMACTTWCACTTTTGGCGGAGGGACCAAG | ATGCAGVNAMNASRMACTTWCACT | 868 | 1484 |
| VK2-28 t1 1 8 | GCTGAGGATGTTGGGGTTTATTACTGCATGCAGVNAMNASRMACTMTCACTTTTGGCGGAGGGACCAAG | ATGCAGVNAMNASRMACTMTCACT | 869 | 1485 |
| VK2-28 t1 2 8 | GCTGAGGATGTTGGGGTTTATTACTGCATGCAGVNAMNASRMACTWGGACTTTTGGCGGAGGGACCAAG | ATGCAGVNAMNASRMACTWGGACT | 870 | 1486 |

TABLE 5-continued

Oligonucleotide sequences for exemplary VK jumping dimer and trimer sequences with CDRL3 length 8.

| Name | Sequence of Synthesized Oligonucleotide | Portion of Oligonucleotide Corresponding to CDRL3 Proper | SEQ ID NO (Oli-go) | SEQ ID NO (CDRL3 Por-tion) |
|---|---|---|---|---|
| VK2-28 t1 3 8 | GCTGAGGATGTTGGGGTTTATTACTGCATGCAGVNAMNASRMACTCCTACTTTTGGCGGAGGGACCAAG | ATGCAGVNAMNASRMACTCCTACT | 871 | 1487 |
| VK2-28 t2 0 8 | GCTGAGGATGTTGGGGTTTATTACTGCATGCAGVNAMNACAGVBCTWCACTTTTGGCGGAGGGACCAAG | ATGCAGVNAMNACAGVBCTWCACT | 872 | 1488 |
| VK2-28 t2 1 8 | GCTGAGGATGTTGGGGTTTATTACTGCATGCAGVNAMNACAGVBCMTCACTTTTGGCGGAGGGACCAAG | ATGCAGVNAMNACAGVBCMTCACT | 873 | 1489 |
| VK2-28 t2 2 8 | GCTGAGGATGTTGGGGTTTATTACTGCATGCAGVNAMNACAGVBCWGGACTTTTGGCGGAGGGACCAAG | ATGCAGVNAMNACAGVBCWGGACT | 874 | 1490 |
| VK2-28 t2 3 8 | GCTGAGGATGTTGGGGTTTATTACTGCATGCAGVNAMNACAGVBCCCTACTTTTGGCGGAGGGACCAAG | ATGCAGVNAMNACAGVBCCCTACT | 875 | 1491 |
| VK2-28 t3 0 8 | GCTGAGGATGTTGGGGTTTATTACTGCATGCAGVNACTCSRMVBCTWCACTTTTGGCGGAGGGACCAAG | ATGCAGVNACTCSRMVBCTWCACT | 876 | 1492 |
| VK2-28 t3 1 8 | GCTGAGGATGTTGGGGTTTATTACTGCATGCAGVNACTCSRMVBCMTCACTTTTGGCGGAGGGACCAAG | ATGCAGVNACTCSRMVBCMTCACT | 877 | 1493 |
| VK2-28 t3 2 8 | GCTGAGGATGTTGGGGTTTATTACTGCATGCAGVNACTCSRMVBCWGGACTTTTGGCGGAGGGACCAAG | ATGCAGVNACTCSRMVBCWGGACT | 878 | 1494 |
| VK2-28 t3 3 8 | GCTGAGGATGTTGGGGTTTATTACTGCATGCAGVNACTCSRMVBCCCTACTTTTGGCGGAGGGACCAAG | ATGCAGVNACTCSRMVBCCCTACT | 879 | 1495 |
| VK2-28 t4 0 8 | GCTGAGGATGTTGGGGTTTATTACTGCATGCAGGCAMNASRMVBCTWCACTTTTGGCGGAGGGACCAAG | ATGCAGGCAMNASRMVBCTWCACT | 880 | 1496 |
| VK2-28 t4 1 8 | GCTGAGGATGTTGGGGTTTATTACTGCATGCAGGCAMNASRMVBCMTCACTTTTGGCGGAGGGACCAAG | ATGCAGGCAMNASRMVBCMTCACT | 881 | 1497 |
| VK2-28 t4 2 8 | GCTGAGGATGTTGGGGTTTATTACTGCATGCAGGCAMNASRMVBCWGGACTTTTGGCGGAGGGACCAAG | ATGCAGGCAMNASRMVBCWGGACT | 882 | 1498 |
| VK2-28 t4 3 8 | GCTGAGGATGTTGGGGTTTATTACTGCATGCAGGCAMNASRMVBCCCTACTTTTGGCGGAGGGACCAAG | ATGCAGGCAMNASRMVBCCCTACT | 883 | 1499 |
| VK3-11 t1 0 8 | CCTGAAGATTTTGCAGTTTATTACTGTCAGCAGBHCNHCNHCTGGTWCACTTTTGGCGGAGGGACCAAG | CAGCAGBHCNHCNHCTGGTWCACT | 884 | 1500 |
| VK3-11 t1 1 8 | CCTGAAGATTTTGCAGTTTATTACTGTCAGCAGBHCNHCNHCTGGMTCACTTTTGGCGGAGGGACCAAG | CAGCAGBHCNHCNHCTGGMTCACT | 885 | 1501 |
| VK3-11 t1 2 8 | CCTGAAGATTTTGCAGTTTATTACTGTCAGCAGBHCNHCNHCTGGWGGACTTTTGGCGGAGGGACCAAG | CAGCAGBHCNHCNHCTGGWGGACT | 886 | 1502 |
| VK3-11 t1 3 8 | CCTGAAGATTTTGCAGTTTATTACTGTCAGCAGBHCNHCNHCTGGCCTACTTTTGGCGGAGGGACCAAG | CAGCAGBHCNHCNHCTGGCCTACT | 887 | 1503 |
| VK3-11 t2 0 8 | CCTGAAGATTTTGCAGTTTATTACTGTCAGCAGBHCNHCAATYWCTWCACTTTTGGCGGAGGGACCAAG | CAGCAGBHCNHCAATYWCTWCACT | 888 | 1456 |
| VK3-11 t2 1 8 | CCTGAAGATTTTGCAGTTTATTACTGTCAGCAGBHCNHCAATYWCMTCACTTTTGGCGGAGGGACCAAG | CAGCAGBHCNHCAATYWCMTCACT | 889 | 1457 |
| VK3-11 t2 2 8 | CCTGAAGATTTTGCAGTTTATTACTGTCAGCAGBHCNHCAATYWCWGGACTTTTGGCGGAGGGACCAAG | CAGCAGBHCNHCAATYWCWGGACT | 890 | 1458 |
| VK3-11 t2 3 8 | CCTGAAGATTTTGCAGTTTATTACTGTCAGCAGBHCNHCAATYWCCCTACTTTTGGCGGAGGGACCAAG | CAGCAGBHCNHCAATYWCCCTACT | 891 | 1459 |
| VK3-11 t3 0 8 | CCTGAAGATTTTGCAGTTTATTACTGTCAGCAGBHCAGTNHCYWCTWCACTTTTGGCGGAGGGACCAAG | CAGCAGBHCAGTNHCYWCTWCACT | 892 | 1504 |
| VK3-11 t3 1 8 | CCTGAAGATTTTGCAGTTTATTACTGTCAGCAGBHCAGTNHCYWCMTCACTTTTGGCGGAGGGACCAAG | CAGCAGBHCAGTNHCYWCMTCACT | 893 | 1505 |
| VK3-11 t3 2 8 | CCTGAAGATTTTGCAGTTTATTACTGTCAGCAGBHCAGTNHCYWCWGGACTTTTGGCGGAGGGACCAAG | CAGCAGBHCAGTNHCYWCWGGACT | 894 | 1506 |

TABLE 5-continued

Oligonucleotide sequences for exemplary VK jumping dimer and trimer sequences with CDRL3 length 8.

| Name | Sequence of Synthesized Oligonucleotide | Portion of Oligonucleotide Corresponding to CDRL3 Proper | SEQ ID NO (Oligo) | SEQ ID NO (CDRL3 Portion) |
|---|---|---|---|---|
| VK3-11 t3 3 8 | CCTGAAGATTTTGCAGTTTATTACTGTCAGCAGBHCAGTNHCYWCCCTACTTTTGGCGGAGGGACCAAG | CAGCAGBHCAGTNHCYWCCCTACT | 895 | 1507 |
| VK3-11 t4 0 8 | CCTGAAGATTTTGCAGTTTATTACTGTCAGCAGAGANHCNHCYWCTWCACTTTTGGCGGAGGGACCAAG | CAGCAGAGANHCNHCYWCTWCACT | 896 | 1508 |
| VK3-11 t4 1 8 | CCTGAAGATTTTGCAGTTTATTACTGTCAGCAGAGANHCNHCYWCMTCACTTTTGGCGGAGGGACCAAG | CAGCAGAGANHCNHCYWCMTCACT | 897 | 1509 |
| VK3-11 t4 2 8 | CCTGAAGATTTTGCAGTTTATTACTGTCAGCAGAGANHCNHCYWCWGGACTTTTGGCGGAGGGACCAAG | CAGCAGAGANHCNHCYWCWGGACT | 898 | 1510 |
| VK3-11 t4 3 8 | CCTGAAGATTTTGCAGTTTATTACTGTCAGCAGAGANHCNHCYWCCCTACTTTTGGCGGAGGGACCAAG | CAGCAGAGANHCNHCYWCCCTACT | 899 | 1511 |
| VK3-15 t1 0 8 | CAGTCTGAAGATTTTGCAGTTTATTACTGTCAGCAGBHCNHCNHCTGGTWCACTTTTGGCGGAGGGACCAAG | CAGCAGBHCNHCNHCTGGTWCACT | 900 | 1500 |
| VK3-15 t1 1 8 | CAGTCTGAAGATTTTGCAGTTTATTACTGTCAGCAGBHCNHCNHCTGGMTCACTTTTGGCGGAGGGACCAAG | CAGCAGBHCNHCNHCTGGMTCACT | 901 | 1501 |
| VK3-15 t1 2 8 | CAGTCTGAAGATTTTGCAGTTTATTACTGTCAGCAGBHCNHCNHCTGGWGGACTTTTGGCGGAGGGACCAAG | CAGCAGBHCNHCNHCTGGWGGACT | 902 | 1502 |
| VK3-15 t1 3 8 | CAGTCTGAAGATTTTGCAGTTTATTACTGTCAGCAGBHCNHCNHCTGGCCTACTTTTGGCGGAGGGACCAAG | CAGCAGBHCNHCNHCTGGCCTACT | 903 | 1503 |
| VK3-15 t2 0 8 | CAGTCTGAAGATTTTGCAGTTTATTACTGTCAGCAGBHCNHCAATYWCTWCACTTTTGGCGGAGGGACCAAG | CAGCAGBHCNHCAATYWCTWCACT | 904 | 1456 |
| VK3-15 t2 1 8 | CAGTCTGAAGATTTTGCAGTTTATTACTGTCAGCAGBHCNHCAATYWCMTCACTTTTGGCGGAGGGACCAAG | CAGCAGBHCNHCAATYWCMTCACT | 905 | 1457 |
| VK3-15 t2 2 8 | CAGTCTGAAGATTTTGCAGTTTATTACTGTCAGCAGBHCNHCAATYWCWGGACTTTTGGCGGAGGGACCAAG | CAGCAGBHCNHCAATYWCWGGACT | 906 | 1458 |
| VK3-15 t2 3 8 | CAGTCTGAAGATTTTGCAGTTTATTACTGTCAGCAGBHCNHCAATYWCCCTACTTTTGGCGGAGGGACCAAG | CAGCAGBHCNHCAATYWCCCTACT | 907 | 1459 |
| VK3-15 t3 0 8 | CAGTCTGAAGATTTTGCAGTTTATTACTGTCAGCAGBHCAATNHCYWCTWCACTTTTGGCGGAGGGACCAAG | CAGCAGBHCAATNHCYWCTWCACT | 908 | 1512 |
| VK3-15 t3 1 8 | CAGTCTGAAGATTTTGCAGTTTATTACTGTCAGCAGBHCAATNHCYWCMTCACTTTTGGCGGAGGGACCAAG | CAGCAGBHCAATNHCYWCMTCACT | 909 | 1513 |
| VK3-15 t3 2 8 | CAGTCTGAAGATTTTGCAGTTTATTACTGTCAGCAGBHCAATNHCYWCWGGACTTTTGGCGGAGGGACCAAG | CAGCAGBHCAATNHCYWCWGGACT | 910 | 1514 |
| VK3-15 t3 3 8 | CAGTCTGAAGATTTTGCAGTTTATTACTGTCAGCAGBHCAATNHCYWCCCTACTTTTGGCGGAGGGACCAAG | CAGCAGBHCAATNHCYWCCCTACT | 911 | 1515 |
| VK3-15 t4 0 8 | CAGTCTGAAGATTTTGCAGTTTATTACTGTCAGCAGTACNHCNHCYWCTWCACTTTTGGCGGAGGGACCAAG | CAGCAGTACNHCNHCYWCTWCACT | 912 | 1464 |
| VK3-15 t4 1 8 | CAGTCTGAAGATTTTGCAGTTTATTACTGTCAGCAGTACNHCNHCYWCMTCACTTTTGGCGGAGGGACCAAG | CAGCAGTACNHCNHCYWCMTCACT | 913 | 1465 |
| VK3-15 t4 2 8 | CAGTCTGAAGATTTTGCAGTTTATTACTGTCAGCAGTACNHCNHCYWCWGGACTTTTGGCGGAGGGACCAAG | CAGCAGTACNHCNHCYWCWGGACT | 914 | 1466 |
| VK3-15 t4 3 8 | CAGTCTGAAGATTTTGCAGTTTATTACTGTCAGCAGTACNHCNHCYWCCCTACTTTTGGCGGAGGGACCAAG | CAGCAGTACNHCNHCYWCCCTACT | 915 | 1467 |
| VK3-20 t1 0 8 | CCTGAAGATTTTGCAGTGTATTACTGTCAGCAGBHCBHCVNCAGTTWCACTTTTGGCGGAGGGACCAAG | CAGCAGBHCBHCVNCAGTTWCACT | 916 | 1516 |
| VK3-20 t1 1 8 | CCTGAAGATTTTGCAGTGTATTACTGTCAGCAGBHCBHCVNCAGTMTCACTTTTGGCGGAGGGACCAAG | CAGCAGBHCBHCVNCAGTMTCACT | 917 | 1517 |

TABLE 5-continued

Oligonucleotide sequences for exemplary VK jumping dimer and trimer sequences with CDRL3 length 8.

| Name | Sequence of Synthesized Oligonucleotide | Portion of Oligonucleotide Corresponding to CDRL3 Proper | SEQ ID NO (Oligo) | SEQ ID NO (CDRL3 Portion) |
|---|---|---|---|---|
| VK3-20 t1 2 8 | CCTGAAGATTTTGCAGTGTATTACTGTCAGCAGBHCBHCVNCAGTWGGACTTTTGGCGGAGGGACCAAG | CAGCAGBHCBHCVNCAGTWGGACT | 918 | 1518 |
| VK3-20 t1 3 8 | CCTGAAGATTTTGCAGTGTATTACTGTCAGCAGBHCBHCVNCAGTCCTACTTTTGGCGGAGGGACCAAG | CAGCAGBHCBHCVNCAGTCCTACT | 919 | 1519 |
| VK3-20 t2 0 8 | CCTGAAGATTTTGCAGTGTATTACTGTCAGCAGBHCBHCAGTBHCTWCACTTTTGGCGGAGGGACCAAG | CAGCAGBHCBHCAGTBHCTWCACT | 920 | 1520 |
| VK3-20 t2 1 8 | CCTGAAGATTTTGCAGTGTATTACTGTCAGCAGBHCBHCAGTBHCMTCACTTTTGGCGGAGGGACCAAG | CAGCAGBHCBHCAGTBHCMTCACT | 921 | 1521 |
| VK3-20 t2 2 8 | CCTGAAGATTTTGCAGTGTATTACTGTCAGCAGBHCBHCAGTBHCWGGACTTTTGGCGGAGGGACCAAG | CAGCAGBHCBHCAGTBHCWGGACT | 922 | 1522 |
| VK3-20 t2 3 8 | CCTGAAGATTTTGCAGTGTATTACTGTCAGCAGBHCBHCAGTBHCCCTACTTTTGGCGGAGGGACCAAG | CAGCAGBHCBHCAGTBHCCCTACT | 923 | 1523 |
| VK3-20 t3 0 8 | CCTGAAGATTTTGCAGTGTATTACTGTCAGCAGBHCGGAVNCBHCTWCACTTTTGGCGGAGGGACCAAG | CAGCAGBHCGGAVNCBHCTWCACT | 924 | 1524 |
| VK3-20 t3 1 8 | CCTGAAGATTTTGCAGTGTATTACTGTCAGCAGBHCGGAVNCBHCMTCACTTTTGGCGGAGGGACCAAG | CAGCAGBHCGGAVNCBHCMTCACT | 925 | 1525 |
| VK3-20 t3 2 8 | CCTGAAGATTTTGCAGTGTATTACTGTCAGCAGBHCGGAVNCBHCWGGACTTTTGGCGGAGGGACCAAG | CAGCAGBHCGGAVNCBHCWGGACT | 926 | 1526 |
| VK3-20 t3 3 8 | CCTGAAGATTTTGCAGTGTATTACTGTCAGCAGBHCGGAVNCBHCCCTACTTTTGGCGGAGGGACCAAG | CAGCAGBHCGGAVNCBHCCCTACT | 927 | 1527 |
| VK3-20 t4 0 8 | CCTGAAGATTTTGCAGTGTATTACTGTCAGCAGTACBHCVNCBHCTWCACTTTTGGCGGAGGGACCAAG | CAGCAGTACBHCVNCBHCTWCACT | 928 | 1528 |
| VK3-20 t4 1 8 | CCTGAAGATTTTGCAGTGTATTACTGTCAGCAGTACBHCVNCBHCMTCACTTTTGGCGGAGGGACCAAG | CAGCAGTACBHCVNCBHCMTCACT | 929 | 1529 |
| VK3-20 t4 2 8 | CCTGAAGATTTTGCAGTGTATTACTGTCAGCAGTACBHCVNCBHCWGGACTTTTGGCGGAGGGACCAAG | CAGCAGTACBHCVNCBHCWGGACT | 930 | 1530 |
| VK3-20 t4 3 8 | CCTGAAGATTTTGCAGTGTATTACTGTCAGCAGTACBHCVNCBHCCCTACTTTTGGCGGAGGGACCAAG | CAGCAGTACBHCVNCBHCCCTACT | 931 | 1531 |
| VK4-01 t1 0 8 | GCTGAAGATGTGGCAGTTTATTACTGTCAGCAGBHCBHCNHCACTTWCACTTTTGGCGGAGGGACCAAG | CAGCAGBHCBHCNHCACTTWCACT | 932 | 1532 |
| VK4-01 t1 1 8 | GCTGAAGATGTGGCAGTTTATTACTGTCAGCAGBHCBHCNHCACTMTCACTTTTGGCGGAGGGACCAAG | CAGCAGBHCBHCNHCACTMTCACT | 933 | 1533 |
| VK4-01 t1 2 8 | GCTGAAGATGTGGCAGTTTATTACTGTCAGCAGBHCBHCNHCACTWGGACTTTTGGCGGAGGGACCAAG | CAGCAGBHCBHCNHCACTWGGACT | 934 | 1534 |
| VK4-01 t1 3 8 | GCTGAAGATGTGGCAGTTTATTACTGTCAGCAGBHCBHCNHCACTCCTACTTTTGGCGGAGGGACCAAG | CAGCAGBHCBHCNHCACTCCTACT | 935 | 1535 |
| VK4-01 t2 0 8 | GCTGAAGATGTGGCAGTTTATTACTGTCAGCAGBHCBHCAGTBHCTWCACTTTTGGCGGAGGGACCAAG | CAGCAGBHCBHCAGTBHCTWCACT | 936 | 1520 |
| VK4-01 t2 1 8 | GCTGAAGATGTGGCAGTTTATTACTGTCAGCAGBHCBHCAGTBHCMTCACTTTTGGCGGAGGGACCAAG | CAGCAGBHCBHCAGTBHCMTCACT | 937 | 1521 |
| VK4-01 t2 2 8 | GCTGAAGATGTGGCAGTTTATTACTGTCAGCAGBHCBHCAGTBHCWGGACTTTTGGCGGAGGGACCAAG | CAGCAGBHCBHCAGTBHCWGGACT | 938 | 1522 |
| VK4-01 t2 3 8 | GCTGAAGATGTGGCAGTTTATTACTGTCAGCAGBHCBHCAGTBHCCCTACTTTTGGCGGAGGGACCAAG | CAGCAGBHCBHCAGTBHCCCTACT | 939 | 1523 |
| VK4-01 t3 0 8 | GCTGAAGATGTGGCAGTTTATTACTGTCAGCAGBHCTACNHCBHCTWCACTTTTGGCGGAGGGACCAAG | CAGCAGBHCTACNHCBHCTWCACT | 940 | 1536 |
| VK4-01 t3 1 8 | GCTGAAGATGTGGCAGTTTATTACTGTCAGCAGBHCTACNHCBHCMTCACTTTTGGCGGAGGGACCAAG | CAGCAGBHCTACNHCBHCMTCACT | 941 | 1537 |

TABLE 5-continued

Oligonucleotide sequences for exemplary VK jumping dimer and trimer sequences with CDRL3 length 8.

| Name | Sequence of Synthesized Oligonucleotide | Portion of Oligonucleotide Corresponding to CDRL3 Proper | SEQ ID NO (Oli-go) | SEQ ID NO (CDRL3 Por-tion) |
|---|---|---|---|---|
| VK4-01 t3 2 8 | GCTGAAGATGTGGCAGTTTATTACTGTCAGCAGBHCT ACNHCBHCWGGACTTTTGGCGGAGGGACCAAG | CAGCAGBHCTACNHCBHCWGGACT | 942 | 1538 |
| VK4-01 t3 3 8 | GCTGAAGATGTGGCAGTTTATTACTGTCAGCAGBHCT ACNHCBHCCCTACTTTTGGCGGAGGGACCAAG | CAGCAGBHCTACNHCBHCCCTACT | 943 | 1539 |
| VK4-01 t4 0 8 | GCTGAAGATGTGGCAGTTTATTACTGTCAGCAGTACB HCNHCBHCTWCACTTTTGGCGGAGGGACCAAG | CAGCAGTACBHCNHCBHCTWCACT | 944 | 1540 |
| VK4-01 t4 1 8 | GCTGAAGATGTGGCAGTTTATTACTGTCAGCAGTACB HCNHCBHCMTCACTTTTGGCGGAGGGACCAAG | CAGCAGTACBHCNHCBHCMTCACT | 945 | 1541 |
| VK4-01 t4 2 8 | GCTGAAGATGTGGCAGTTTATTACTGTCAGCAGTACB HCNHCBHCWGGACTTTTGGCGGAGGGACCAAG | CAGCAGTACBHCNHCBHCWGGACT | 946 | 1542 |
| VK4-01 t4 3 8 | GCTGAAGATGTGGCAGTTTATTACTGTCAGCAGTACB HCNHCBHCCCTACTTTTGGCGGAGGGACCAAG | CAGCAGTACBHCNHCBHCCCTACT | 947 | 1543 |

TABLE 6

Oligonucleotide sequences for exemplary VK jumping dimer and trimer sequences with CDRL3 length 9.

| Name | Sequence of Synthesized Oligonucleotide | Portion of Oligonucleotide Corresponding to CDRL3 Proper | SEQ ID NO (Oli-go) | SEQ ID NO (CDRL3 Por-tion) |
|---|---|---|---|---|
| | | Jumping Dimer | | |
| VK1-05 1 0 9 | CCTGATGATTTTGCAACTTATTACTGCSWMSWMTACAATAG TTACYCTTWCACTTTTGGCGGAGGGACCAAG | SWMSWMTACAATAGTTACYCTT WCACT | 1544 | 2168 |
| VK1-05 10 0 9 | CCTGATGATTTTGCAACTTATTACTGCCAGCAGBHCVRMAG TTACYCTTWCACTTTTGGCGGAGGGACCAAG | CAGCAGBHCVRMAGTTACYCTT WCACT | 1545 | 2169 |
| VK1-05 11 0 9 | CCTGATGATTTTGCAACTTATTACTGCCAGCAGBHCAATMB CTACYCTTWCACTTTTGGCGGAGGGACCAAG | CAGCAGBHCAATMECTACYCTT WCACT | 1546 | 2170 |
| VK1-05 12 0 9 | CCTGATGATTTTGCAACTTATTACTGCCAGCAGBHCAATAG TYWCYCTTWCACTTTTGGCGGAGGGACCAAG | CAGCAGBHCAATAGTYWCYCTT WCACT | 1547 | 2171 |
| VK1-05 13 0 9 | CCTGATGATTTTGCAACTTATTACTGCCAGCAGTACVRMMB CTACYCTTWCACTTTTGGCGGAGGGACCAAG | CAGCAGTACVRMMBCTACYCTT WCACT | 1548 | 2172 |
| VK1-05 14 0 9 | CCTGATGATTTTGCAACTTATTACTGCCAGCAGTACVRMAG TYWCYCTTWCACTTTTGGCGGAGGGACCAAG | CAGCAGTACVRMAGTYWCYCTT WCACT | 1549 | 2173 |
| VK1-05 15 0 9 | CCTGATGATTTTGCAACTTATTACTGCCAGCAGTACAATMB CYWCYCTTWCACTTTTGGCGGAGGGACCAAG | CAGCAGTACAATMBCYWCYCTT WCACT | 1550 | 2174 |
| VK1-05 2 0 9 | CCTGATGATTTTGCAACTTATTACTGCSWMCAGBHCAATAG TTACYCTTWCACTTTTGGCGGAGGGACCAAG | SWMCAGBHCAATAGTTACYCTT WCACT | 1551 | 2175 |
| VK1-05 3 0 9 | CCTGATGATTTTGCAACTTATTACTGCSWMCAGTACVRMAG TTACYCTTWCACTTTTGGCGGAGGGACCAAG | SWMCAGTACVRMAGTTACYCTT WCACT | 1552 | 2176 |
| VK1-05 4 0 9 | CCTGATGATTTTGCAACTTATTACTGCSWMCAGTACAATMB CTACYCTTWCACTTTTGGCGGAGGGACCAAG | SWMCAGTACAATMBCTACYCTT WCACT | 1553 | 2177 |
| VK1-05 5 0 9 | CCTGATGATTTTGCAACTTATTACTGCSWMCAGTACAATAG TYWCYCTTWCACTTTTGGCGGAGGGACCAAG | SWMCAGTACAATAGTYWCYCTT WCACT | 1554 | 2178 |
| VK1-05 6 0 9 | CCTGATGATTTTGCAACTTATTACTGCCAGSWMBHCAATAG TTACYCTTWCACTTTTGGCGGAGGGACCAAG | CAGSWMBHCAATAGTTACYCTT WCACT | 1555 | 2179 |

TABLE 6 -continued

Oligonucleotide sequences for exemplary VK jumping dimer and trimer sequences with CDRL3 length 9.

| Name | Sequence of Synthesized Oligonucleotide | Portion of Oligonucleotide Corresponding to CDRL3 Proper | SEQ ID NO (Oligo) | SEQ ID NO (CDRL3 Portion) |
|---|---|---|---|---|
| VK1-05 7 0 9 | CCTGATGATTTTGCAACTTATTACTGCCAGSWMTACVRMAGTTACYCTTWCACTTTTGGCGGAGGGACCAAG | CAGSWMTACVRMAGTTACYCTTWCACT | 1556 | 2180 |
| VK1-05 8 0 9 | CCTGATGATTTTGCAACTTATTACTGCCAGSWMTACAATMBCTACYCTTWCACTTTTGGCGGAGGGACCAAG | CAGSWMTACAATMBCTACYCTTWCACT | 1557 | 2181 |
| VK1-05 9 0 9 | CCTGATGATTTTGCAACTTATTACTGCCAGSWMTACAATAGTYWCYCTTWCACTTTTGGCGGAGGGACCAAG | CAGSWMTACAATAGTYWCYCTTWCACT | 1558 | 2182 |
| VK1-05 1 1 9 | CCTGATGATTTTGCAACTTATTACTGCSWMSWMTACAATAGTTACYCTMTCACTTTTGGCGGAGGGACCAAG | SWMSWMTACAATAGTTACYCTMTCACT | 1559 | 2183 |
| VK1-05 10 1 9 | CCTGATGATTTTGCAACTTATTACTGCCAGCAGBHCVRMAGTTACYCTMTCACTTTTGGCGGAGGGACCAAG | CAGCAGBHCVRMAGTTACYCTMTCACT | 1560 | 2184 |
| VK1-05 11 1 9 | CCTGATGATTTTGCAACTTATTACTGCCAGCAGBHCAATMBCTACYCTMTCACTTTTGGCGGAGGGACCAAG | CAGCAGBHCAATMECTACYCTMTCACT | 1561 | 2185 |
| VK1-05 12 1 9 | CCTGATGATTTTGCAACTTATTACTGCCAGCAGBHCAATAGTYWCYCTMTCACTTTTGGCGGAGGGACCAAG | CAGCAGBHCAATAGTYWCYCTMTCACT | 1562 | 2186 |
| VK1-05 13 1 9 | CCTGATGATTTTGCAACTTATTACTGCCAGCAGTACVRMMBCTACYCTMTCACTTTTGGCGGAGGGACCAAG | CAGCAGTACVRMMBCTACYCTMTCACT | 1563 | 2187 |
| VK1-05 14 1 9 | CCTGATGATTTTGCAACTTATTACTGCCAGCAGTACVRMAGTYWCYCTMTCACTTTTGGCGGAGGGACCAAG | CAGCAGTACVRMAGTYWCYCTMTCACT | 1564 | 2188 |
| VK1-05 15 1 9 | CCTGATGATTTTGCAACTTATTACTGCCAGCAGTACAATMBCYWCYCTMTCACTTTTGGCGGAGGGACCAAG | CAGCAGTACAATMBCYWCYCTMTCACT | 1565 | 2189 |
| VK1-05 2 1 9 | CCTGATGATTTTGCAACTTATTACTGCSWMCAGBHCAATAGTTACYCTMTCACTTTTGGCGGAGGGACCAAG | SWMCAGBHCAATAGTTACYCTMTCACT | 1566 | 2190 |
| VK1-05 3 1 9 | CCTGATGATTTTGCAACTTATTACTGCSWMCAGTACVRMAGTTACYCTMTCACTTTTGGCGGAGGGACCAAG | SWMCAGTACVRMAGTTACYCTMTCACT | 1567 | 2191 |
| VK1-05 4 1 9 | CCTGATGATTTTGCAACTTATTACTGCSWMCAGTACAATMBCTACYCTMTCACTTTTGGCGGAGGGACCAAG | SWMCAGTACAATMBCTACYCTMTCACT | 1568 | 2192 |
| VK1-05 5 1 9 | CCTGATGATTTTGCAACTTATTACTGCSWMCAGTACAATAGTYWCYCTMTCACTTTTGGCGGAGGGACCAAG | SWMCAGTACAATAGTYWCYCTMTCACT | 1569 | 2193 |
| VK1-05 6 1 9 | CCTGATGATTTTGCAACTTATTACTGCCAGSWMBHCAATAGTTACYCTMTCACTTTTGGCGGAGGGACCAAG | CAGSWMBHCAATAGTTACYCTMTCACT | 1570 | 2194 |
| VK1-05 7 1 9 | CCTGATGATTTTGCAACTTATTACTGCCAGSWMTACVRMAGTTACYCTMTCACTTTTGGCGGAGGGACCAAG | CAGSWMTACVRMAGTTACYCTMTCACT | 1571 | 2195 |
| VK1-05 8 1 9 | CCTGATGATTTTGCAACTTATTACTGCCAGSWMTACAATMBCTACYCTMTCACTTTTGGCGGAGGGACCAAG | CAGSWMTACAATMBCTACYCTMTCACT | 1572 | 2196 |
| VK1-05 9 1 9 | CCTGATGATTTTGCAACTTATTACTGCCAGSWMTACAATAGTYWCYCTMTCACTTTTGGCGGAGGGACCAAG | CAGSWMTACAATAGTYWCYCTMTCACT | 1573 | 2197 |
| VK1-05 1 2 9 | CCTGATGATTTTGCAACTTATTACTGCSWMSWMTACAATAGTTACYCTWGGACTTTTGGCGGAGGGACCAAG | SWMSWMTACAATAGTTACYCTWGGACT | 1574 | 2198 |
| VK1-05 10 2 9 | CCTGATGATTTTGCAACTTATTACTGCCAGCAGBHCVRMAGTTACYCTWGGACTTTTGGCGGAGGGACCAAG | CAGCAGBHCVRMAGTTACYCTWGGACT | 1575 | 2199 |
| VK1-05 11 2 9 | CCTGATGATTTTGCAACTTATTACTGCCAGCAGBHCAATMBCTACYCTWGGACTTTTGGCGGAGGGACCAAG | CAGCAGBHCAATMECTACYCTWGGACT | 1576 | 2200 |
| VK1-05 12 2 9 | CCTGATGATTTTGCAACTTATTACTGCCAGCAGBHCAATAGTYWCYCTWGGACTTTTGGCGGAGGGACCAAG | CAGCAGBHCAATAGTYWCYCTWGGACT | 1577 | 2201 |
| VK1-05 13 2 9 | CCTGATGATTTTGCAACTTATTACTGCCAGCAGTACVRMMBCTACYCTWGGACTTTTGGCGGAGGGACCAAG | CAGCAGTACVRMMBCTACYCTWGGACT | 1578 | 2202 |
| VK1-05 14 2 9 | CCTGATGATTTTGCAACTTATTACTGCCAGCAGTACVRMAGTYWCYCTWGGACTTTTGGCGGAGGGACCAAG | CAGCAGTACVRMAGTYWCYCTWGGACT | 1579 | 2203 |

TABLE 6 -continued

Oligonucleotide sequences for exemplary VK jumping dimer and trimer sequences with CDRL3 length 9.

| Name | Sequence of Synthesized Oligonucleotide | Portion of Oligonucleotide Corresponding to CDRL3 Proper | SEQ ID NO (Oligo) | SEQ ID NO (CDRL3 Portion) |
|---|---|---|---|---|
| VK1-05 15 2 9 | CCTGATGATTTTGCAACTTATTACTGCCAGCAGTACAATMBCYWCYCTWGGACTTTTGGCGGAGGGACCAAG | CAGCAGTACAATMBCYWCYCTWGGACT | 1580 | 2204 |
| VK1-05 2 2 9 | CCTGATGATTTTGCAACTTATTACTGCSWMCAGBHCAATAGTTACYCTWGGACTTTTGGCGGAGGGACCAAG | SWMCAGBHCAATAGTTACYCTWGGACT | 1581 | 2205 |
| VK1-05 3 2 9 | CCTGATGATTTTGCAACTTATTACTGCSWMCAGTACVRMAGTTACYCTWGGACTTTTGGCGGAGGGACCAAG | SWMCAGTACVRMAGTTACYCTWGGACT | 1582 | 2206 |
| VK1-05 4 2 9 | CCTGATGATTTTGCAACTTATTACTGCSWMCAGTACAATMBCTACYCTWGGACTTTTGGCGGAGGGACCAAG | SWMCAGTACAATMBCTACYCTWGGACT | 1583 | 2207 |
| VK1-05 5 2 9 | CCTGATGATTTTGCAACTTATTACTGCSWMCAGTACAATAGTYWCYCTWGGACTTTTGGCGGAGGGACCAAG | SWMCAGTACAATAGTYWCYCTWGGACT | 1584 | 2208 |
| VK1-05 6 2 9 | CCTGATGATTTTGCAACTTATTACTGCCAGSWMBHCAATAGTTACYCTWGGACTTTTGGCGGAGGGACCAAG | CAGSWMBHCAATAGTTACYCTWGGACT | 1585 | 2209 |
| VK1-05 7 2 9 | CCTGATGATTTTGCAACTTATTACTGCCAGSWMTACVRMAGTTACYCTWGGACTTTTGGCGGAGGGACCAAG | CAGSWMTACVRMAGTTACYCTWGGACT | 1586 | 2210 |
| VK1-05 8 2 9 | CCTGATGATTTTGCAACTTATTACTGCCAGSWMTACAATMBCTACYCTWGGACTTTTGGCGGAGGGACCAAG | CAGSWMTACAATMBCTACYCTWGGACT | 1587 | 2211 |
| VK1-05 9 2 9 | CCTGATGATTTTGCAACTTATTACTGCCAGSWMTACAATAGTYWCYCTWGGACTTTTGGCGGAGGGACCAAG | CAGSWMTACAATAGTYWCYCTWGGACT | 1588 | 2212 |
| VK1-05 1 3 9 | CCTGATGATTTTGCAACTTATTACTGCSWMSWMTACAATAGTTACYCTCCTACTTTTGGCGGAGGGACCAAG | SWMSWMTACAATAGTTACYCTCCTACT | 1589 | 2213 |
| VK1-05 10 3 9 | CCTGATGATTTTGCAACTTATTACTGCCAGCAGBHCVRMAGTTACYCTCCTACTTTTGGCGGAGGGACCAAG | CAGCAGBHCVRMAGTTACYCTCCTACT | 1590 | 2214 |
| VK1-05 11 3 9 | CCTGATGATTTTGCAACTTATTACTGCCAGCAGBHCAATMBCTACYCTCCTACTTTTGGCGGAGGGACCAAG | CAGCAGBHCAATMECTACYCTCCTACT | 1591 | 2215 |
| VK1-05 12 3 9 | CCTGATGATTTTGCAACTTATTACTGCCAGCAGBHCAATAGTYWCYCTCCTACTTTTGGCGGAGGGACCAAG | CAGCAGBHCAATAGTYWCYCTCCTACT | 1592 | 2216 |
| VK1-05 13 3 9 | CCTGATGATTTTGCAACTTATTACTGCCAGCAGTACVRMMBCTACYCTCCTACTTTTGGCGGAGGGACCAAG | CAGCAGTACVRMMBCTACYCTCCTACT | 1593 | 2217 |
| VK1-05 14 3 9 | CCTGATGATTTTGCAACTTATTACTGCCAGCAGTACVRMAGTYWCYCTCCTACTTTTGGCGGAGGGACCAAG | CAGCAGTACVRMAGTYWCYCTCCTACT | 1594 | 2218 |
| VK1-05 15 3 9 | CCTGATGATTTTGCAACTTATTACTGCCAGCAGTACAATMBCYWCYCTCCTACTTTTGGCGGAGGGACCAAG | CAGCAGTACAATMBCYWCYCTCCTACT | 1595 | 2219 |
| VK1-05 2 3 9 | CCTGATGATTTTGCAACTTATTACTGCSWMCAGBHCAATAGTTACYCTCCTACTTTTGGCGGAGGGACCAAG | SWMCAGBHCAATAGTTACYCTCCTACT | 1596 | 2220 |
| VK1-05 3 3 9 | CCTGATGATTTTGCAACTTATTACTGCSWMCAGTACVRMAGTTACYCTCCTACTTTTGGCGGAGGGACCAAG | SWMCAGTACVRMAGTTACYCTCCTACT | 1597 | 2221 |
| VK1-05 4 3 9 | CCTGATGATTTTGCAACTTATTACTGCSWMCAGTACAATMBCTACYCTCCTACTTTTGGCGGAGGGACCAAG | SWMCAGTACAATMBCTACYCTCCTACT | 1598 | 2222 |
| VK1-05 5 3 9 | CCTGATGATTTTGCAACTTATTACTGCSWMCAGTACAATAGTYWCYCTCCTACTTTTGGCGGAGGGACCAAG | SWMCAGTACAATAGTYWCYCTCCTACT | 1599 | 2223 |
| VK1-05 6 3 9 | CCTGATGATTTTGCAACTTATTACTGCCAGSWMBHCAATAGTTACYCTCCTACTTTTGGCGGAGGGACCAAG | CAGSWMBHCAATAGTTACYCTCCTACT | 1600 | 2224 |
| VK1-05 7 3 9 | CCTGATGATTTTGCAACTTATTACTGCCAGSWMTACVRMAGTTACYCTCCTACTTTTGGCGGAGGGACCAAG | CAGSWMTACVRMAGTTACYCTCCTACT | 1601 | 2225 |
| VK1-05 8 3 9 | CCTGATGATTTTGCAACTTATTACTGCCAGSWMTACAATMBCTACYCTCCTACTTTTGGCGGAGGGACCAAG | CAGSWMTACAATMBCTACYCTCCTACT | 1602 | 2226 |

TABLE 6 -continued

Oligonucleotide sequences for exemplary VK jumping dimer and trimer sequences with CDRL3 length 9.

| Name | Sequence of Synthesized Oligonucleotide | Portion of Oligonucleotide Corresponding to CDRL3 Proper | SEQ ID NO (Oligo) | SEQ ID NO (CDRL3 Portion) |
|---|---|---|---|---|
| VK1-05 9 3 9 | CCTGATGATTTTGCAACTTATTACTGCCAGSWMTACAATAGTYWCYCTCCTACTTTTGGCGGAGGGACCAAG | CAGSWMTACAATAGTYWCYCTCCTACT | 1603 | 2227 |
| VK1-12 1 0 9 | CCTGAAGATTTTGCAACTTATTACTGTSWMSWMGCAAATAGTTTCCCTTWCACTTTTGGCGGAGGGACCAAG | SWMSWMGCAAATAGTTTCCCTTWCACT | 1604 | 2228 |
| VK1-12 10 0 9 | CCTGAAGATTTTGCAACTTATTACTGTCAGCAGRNANHCAGTTTCCCTTWCACTTTTGGCGGAGGGACCAAG | CAGCAGRNANHCAGTTTCCCTTWCACT | 1605 | 2229 |
| VK1-12 11 0 9 | CCTGAAGATTTTGCAACTTATTACTGTCAGCAGRNAAATNHCTTCCCTTWCACTTTTGGCGGAGGGACCAAG | CAGCAGRNAAATNHCTTCCCTTWCACT | 1606 | 2230 |
| VK1-12 12 0 9 | CCTGAAGATTTTGCAACTTATTACTGTCAGCAGRNAAATAGTYWCCCTTWCACTTTTGGCGGAGGGACCAAG | CAGCAGRNAAATAGTYWCCCTTWCACT | 1607 | 2231 |
| VK1-12 13 0 9 | CCTGAAGATTTTGCAACTTATTACTGTCAGCAGGCANHCNHCTTCCCTTWCACTTTTGGCGGAGGGACCAAG | CAGCAGGCANHCNHCTTCCCTTWCACT | 1608 | 2232 |
| VK1-12 14 0 9 | CCTGAAGATTTTGCAACTTATTACTGTCAGCAGGCANHCAGTYWCCCTTWCACTTTTGGCGGAGGGACCAAG | CAGCAGGCANHCAGTYWCCCTTWCACT | 1609 | 2233 |
| VK1-12 15 0 9 | CCTGAAGATTTTGCAACTTATTACTGTCAGCAGGCAAATNHCYWCCCTTWCACTTTTGGCGGAGGGACCAAG | CAGCAGGCAAATNHCYWCCCTTWCACT | 1610 | 2234 |
| VK1-12 2 0 9 | CCTGAAGATTTTGCAACTTATTACTGTSWMCAGRNAAATAGTTTCCCTTWCACTTTTGGCGGAGGGACCAAG | SWMCAGRNAAATAGTTTCCCTTWCACT | 1611 | 2235 |
| VK1-12 3 0 9 | CCTGAAGATTTTGCAACTTATTACTGTSWMCAGGCANHCAGTTTCCCTTWCACTTTTGGCGGAGGGACCAAG | SWMCAGGCANHCAGTTTCCCTTWCACT | 1612 | 2236 |
| VK1-12 4 0 9 | CCTGAAGATTTTGCAACTTATTACTGTSWMCAGGCAAATNHCTTCCCTTWCACTTTTGGCGGAGGGACCAAG | SWMCAGGCAAATNHCTTCCCTTWCACT | 1613 | 2237 |
| VK1-12 5 0 9 | CCTGAAGATTTTGCAACTTATTACTGTSWMCAGGCAAATAGTYWCCCTTWCACTTTTGGCGGAGGGACCAAG | SWMCAGGCAAATAGTYWCCCTTWCACT | 1614 | 2238 |
| VK1-12 6 0 9 | CCTGAAGATTTTGCAACTTATTACTGTCAGSWMRNAAATAGTTTCCCTTWCACTTTTGGCGGAGGGACCAAG | CAGSWMRNAAATAGTTTCCCTTWCACT | 1615 | 2239 |
| VK1-12 7 0 9 | CCTGAAGATTTTGCAACTTATTACTGTCAGSWMGCANHCAGTTTCCCTTWCACTTTTGGCGGAGGGACCAAG | CAGSWMGCANHCAGTTTCCCTTWCACT | 1616 | 2240 |
| VK1-12 8 0 9 | CCTGAAGATTTTGCAACTTATTACTGTCAGSWMGCAAATNHCTTCCCTTWCACTTTTGGCGGAGGGACCAAG | CAGSWMGCAAATNHCTTCCCTTWCACT | 1617 | 2241 |
| VK1-12 9 0 9 | CCTGAAGATTTTGCAACTTATTACTGTCAGSWMGCAAATAGTYWCCCTTWCACTTTTGGCGGAGGGACCAAG | CAGSWMGCAAATAGTYWCCCTTWCACT | 1618 | 2242 |
| VK1-12 1 1 9 | CCTGAAGATTTTGCAACTTATTACTGTSWMSWMGCAAATAGTTTCCCTMTCACTTTTGGCGGAGGGACCAAG | SWMSWMGCAAATAGTTTCCCTMTCACT | 1619 | 2243 |
| VK1-12 10 1 9 | CCTGAAGATTTTGCAACTTATTACTGTCAGCAGRNANHCAGTTTCCCTMTCACTTTTGGCGGAGGGACCAAG | CAGCAGRNANHCAGTTTCCCTMTCACT | 1620 | 2244 |
| VK1-12 11 1 9 | CCTGAAGATTTTGCAACTTATTACTGTCAGCAGRNAAATNHCTTCCCTMTCACTTTTGGCGGAGGGACCAAG | CAGCAGRNAAATNHCTTCCCTMTCACT | 1621 | 2245 |
| VK1-12 12 1 9 | CCTGAAGATTTTGCAACTTATTACTGTCAGCAGRNAAATAGTYWCCCTMTCACTTTTGGCGGAGGGACCAAG | CAGCAGRNAAATAGTYWCCCTMTCACT | 1622 | 2246 |
| VK1-12 13 1 9 | CCTGAAGATTTTGCAACTTATTACTGTCAGCAGGCANHCNHCTTCCCTMTCACTTTTGGCGGAGGGACCAAG | CAGCAGGCANHCNHCTTCCCTMTCACT | 1623 | 2247 |
| VK1-12 14 1 9 | CCTGAAGATTTTGCAACTTATTACTGTCAGCAGGCANHCAGTYWCCCTMTCACTTTTGGCGGAGGGACCAAG | CAGCAGGCANHCAGTYWCCCTMTCACT | 1624 | 2248 |
| VK1-12 15 1 9 | CCTGAAGATTTTGCAACTTATTACTGTCAGCAGGCAAATNHCYWCCCTMTCACTTTTGGCGGAGGGACCAAG | CAGCAGGCAAATNHCYWCCCTMTCACT | 1625 | 2249 |
| VK1-12 2 1 9 | CCTGAAGATTTTGCAACTTATTACTGTSWMCAGRNAAATAGTTTCCCTMTCACTTTTGGCGGAGGGACCAAG | SWMCAGRNAAATAGTTTCCCTMTCACT | 1626 | 2250 |

TABLE 6 -continued

Oligonucleotide sequences for exemplary VK jumping dimer and trimer sequences with CDRL3 length 9.

| Name | Sequence of Synthesized Oligonucleotide | Portion of Oligonucleotide Corresponding to CDRL3 Proper | SEQ ID NO (Oli-go) | SEQ ID NO (CDRL3 Por-tion) |
|---|---|---|---|---|
| VK1-12 3 1 9 | CCTGAAGATTTTGCAACTTATTACTGTSWMCAGGCANHCAG TTTCCCTMTCACTTTTGGCGGAGGGACCAAG | SWMCAGGCANHCAGTTTCCCTM TCACT | 1627 | 2251 |
| VK1-12 4 1 9 | CCTGAAGATTTTGCAACTTATTACTGTSWMCAGGCAAATNH CTTCCCTMTCACTTTTGGCGGAGGGACCAAG | SWMCAGGCAAATNHCTTCCCTM TCACT | 1628 | 2252 |
| VK1-12 5 1 9 | CCTGAAGATTTTGCAACTTATTACTGTSWMCAGGCAAATAG TYWCCCTMTCACTTTTGGCGGAGGGACCAAG | SWMCAGGCAAATAGTYWCCCTM TCACT | 1629 | 2253 |
| VK1-12 6 1 9 | CCTGAAGATTTTGCAACTTATTACTGTCAGSWMRNAAATAG TTTCCCTMTCACTTTTGGCGGAGGGACCAAG | CAGSWMRNAAATAGTTTCCCTM TCACT | 1630 | 2254 |
| VK1-12 7 1 9 | CCTGAAGATTTTGCAACTTATTACTGTCAGSWMGCANHCAG TTTCCCTMTCACTTTTGGCGGAGGGACCAAG | CAGSWMGCANHCAGTTTCCCTM TCACT | 1631 | 2255 |
| VK1-12 8 1 9 | CCTGAAGATTTTGCAACTTATTACTGTCAGSWMGCAAATNH CTTCCCTMTCACTTTTGGCGGAGGGACCAAG | CAGSWMGCAAATNHCTTCCCTM TCACT | 1632 | 2256 |
| VK1-12 9 1 9 | CCTGAAGATTTTGCAACTTATTACTGTCAGSWMGCAAATAG TYWCCCTMTCACTTTTGGCGGAGGGACCAAG | CAGSWMGCAAATAGTYWCCCTM TCACT | 1633 | 2257 |
| VK1-12 1 2 9 | CCTGAAGATTTTGCAACTTATTACTGTSWMSWMGCAAATAG TTTCCCTWGGACTTTTGGCGGAGGGACCAAG | SWMSWMGCAAATAGTTTCCCTW GGACT | 1634 | 2258 |
| VK1-12 10 2 9 | CCTGAAGATTTTGCAACTTATTACTGTCAGCAGRNANHCAG TTTCCCTWGGACTTTTGGCGGAGGGACCAAG | CAGCAGRNANHCAGTTTCCCTW GGACT | 1635 | 2259 |
| VK1-12 11 2 9 | CCTGAAGATTTTGCAACTTATTACTGTCAGCAGRNAAATNH CTTCCCTWGGACTTTTGGCGGAGGGACCAAG | CAGCAGRNAAATNHCTTCCCTW GGACT | 1636 | 2260 |
| VK1-12 12 2 9 | CCTGAAGATTTTGCAACTTATTACTGTCAGCAGRNAAATAG TYWCCCTWGGACTTTTGGCGGAGGGACCAAG | CAGCAGRNAAATAGTYWCCCTW GGACT | 1637 | 2261 |
| VK1-12 13 2 9 | CCTGAAGATTTTGCAACTTATTACTGTCAGCAGGCANHCNH CTTCCCTWGGACTTTTGGCGGAGGGACCAAG | CAGCAGGCANHCNHCTTCCCTW GGACT | 1638 | 2262 |
| VK1-12 14 2 9 | CCTGAAGATTTTGCAACTTATTACTGTCAGCAGGCANHCAG TYWCCCTWGGACTTTTGGCGGAGGGACCAAG | CAGCAGGCANHCAGTYWCCCTW GGACT | 1639 | 2263 |
| VK1-12 15 2 9 | CCTGAAGATTTTGCAACTTATTACTGTCAGCAGGCAAATNH CYWCCCTWGGACTTTTGGCGGAGGGACCAAG | CAGCAGGCAAATNHCYWCCCTW GGACT | 1640 | 2264 |
| VK1-12 2 2 9 | CCTGAAGATTTTGCAACTTATTACTGTSWMCAGRNAAATAG TTTCCCTWGGACTTTTGGCGGAGGGACCAAG | SWMCAGRNAAATAGTTTCCCTW GGACT | 1641 | 2265 |
| VK1-12 3 2 9 | CCTGAAGATTTTGCAACTTATTACTGTSWMCAGGCANHCAG TTTCCCTWGGACTTTTGGCGGAGGGACCAAG | SWMCAGGCANHCAGTTTCCCTW GGACT | 1642 | 2266 |
| VK1-12 4 2 9 | CCTGAAGATTTTGCAACTTATTACTGTSWMCAGGCAAATNH CTTCCCTWGGACTTTTGGCGGAGGGACCAAG | SWMCAGGCAAATNHCTTCCCTW GGACT | 1643 | 2267 |
| VK1-12 5 2 9 | CCTGAAGATTTTGCAACTTATTACTGTSWMCAGGCAAATAG TYWCCCTWGGACTTTTGGCGGAGGGACCAAG | SWMCAGGCAAATAGTYWCCCTW GGACT | 1644 | 2268 |
| VK1-12 6 2 9 | CCTGAAGATTTTGCAACTTATTACTGTCAGSWMRNAAATAG TTTCCCTWGGACTTTTGGCGGAGGGACCAAG | CAGSWMRNAAATAGTTTCCCTW GGACT | 1645 | 2269 |
| VK1-12 7 2 9 | CCTGAAGATTTTGCAACTTATTACTGTCAGSWMGCANHCAG TTTCCCTWGGACTTTTGGCGGAGGGACCAAG | CAGSWMGCANHCAGTTTCCCTW GGACT | 1646 | 2270 |
| VK1-12 8 2 9 | CCTGAAGATTTTGCAACTTATTACTGTCAGSWMGCAAATNH CTTCCCTWGGACTTTTGGCGGAGGGACCAAG | CAGSWMGCAAATNHCTTCCCTW GGACT | 1647 | 2271 |
| VK1-12 9 2 9 | CCTGAAGATTTTGCAACTTATTACTGTCAGSWMGCAAATAG TYWCCCTWGGACTTTTGGCGGAGGGACCAAG | CAGSWMGCAAATAGTYWCCCTW GGACT | 1648 | 2272 |
| VK1-12 1 3 9 | CCTGAAGATTTTGCAACTTATTACTGTSWMSWMGCAAATAG TTTCCCTCCTACTTTTGGCGGAGGGACCAAG | SWMSWMGCAAATAGTTTCCCTC CTACT | 1649 | 2273 |

TABLE 6 -continued

Oligonucleotide sequences for exemplary VK jumping dimer and trimer sequences with CDRL3 length 9.

| Name | Sequence of Synthesized Oligonucleotide | Portion of Oligonucleotide Corresponding to CDRL3 Proper | SEQ ID NO (Oligo) | SEQ ID NO (CDRL3 Portion) |
|---|---|---|---|---|
| VK1-12 10 3 9 | CCTGAAGATTTTGCAACTTATTACTGTCAGCAGRNANHCAGTTTCCCTCCTACTTTTGGCGGAGGGACCAAG | CAGCAGRNANHCAGTTTCCCTCCTACT | 1650 | 2274 |
| VK1-12 11 3 9 | CCTGAAGATTTTGCAACTTATTACTGTCAGCAGRNAAATNHCTTCCCTCCTACTTTTGGCGGAGGGACCAAG | CAGCAGRNAAATNHCTTCCCTCCTACT | 1651 | 2275 |
| VK1-12 12 3 9 | CCTGAAGATTTTGCAACTTATTACTGTCAGCAGRNAAATAGTYWCCCTCCTACTTTTGGCGGAGGGACCAAG | CAGCAGRNAAATAGTYWCCCTCCTACT | 1652 | 2276 |
| VK1-12 13 3 9 | CCTGAAGATTTTGCAACTTATTACTGTCAGCAGGCANHCNHCTTCCCTCCTACTTTTGGCGGAGGGACCAAG | CAGCAGGCANHCNHCTTCCCTCCTACT | 1653 | 2277 |
| VK1-12 14 3 9 | CCTGAAGATTTTGCAACTTATTACTGTCAGCAGGCANHCAGTYWCCCTCCTACTTTTGGCGGAGGGACCAAG | CAGCAGGCANHCAGTYWCCCTCCTACT | 1654 | 2278 |
| VK1-12 15 3 9 | CCTGAAGATTTTGCAACTTATTACTGTCAGCAGGCAAATNHCYWCCCTCCTACTTTTGGCGGAGGGACCAAG | CAGCAGGCAAATNHCYWCCCTCCTACT | 1655 | 2279 |
| VK1-12 2 3 9 | CCTGAAGATTTTGCAACTTATTACTGTSWMCAGRNAAATAGTTTCCCTCCTACTTTTGGCGGAGGGACCAAG | SWMCAGRNAAATAGTTTCCCTCCTACT | 1656 | 2280 |
| VK1-12 3 3 9 | CCTGAAGATTTTGCAACTTATTACTGTSWMCAGGCANHCAGTTTCCCTCCTACTTTTGGCGGAGGGACCAAG | SWMCAGGCANHCAGTTTCCCTCCTACT | 1657 | 2281 |
| VK1-12 4 3 9 | CCTGAAGATTTTGCAACTTATTACTGTSWMCAGGCAAATNHCTTCCCTCCTACTTTTGGCGGAGGGACCAAG | SWMCAGGCAAATNHCTTCCCTCCTACT | 1658 | 2282 |
| VK1-12 5 3 9 | CCTGAAGATTTTGCAACTTATTACTGTSWMCAGGCAAATAGTYWCCCTCCTACTTTTGGCGGAGGGACCAAG | SWMCAGGCAAATAGTYWCCCTCCTACT | 1659 | 2283 |
| VK1-12 6 3 9 | CCTGAAGATTTTGCAACTTATTACTGTCAGSWMRNAAATAGTTTCCCTCCTACTTTTGGCGGAGGGACCAAG | CAGSWMRNAAATAGTTTCCCTCCTACT | 1660 | 2284 |
| VK1-12 7 3 9 | CCTGAAGATTTTGCAACTTATTACTGTCAGSWMGCANHCAGTTTCCCTCCTACTTTTGGCGGAGGGACCAAG | CAGSWMGCANHCAGTTTCCCTCCTACT | 1661 | 2285 |
| VK1-12 8 3 9 | CCTGAAGATTTTGCAACTTATTACTGTCAGSWMGCAAATNHCTTCCCTCCTACTTTTGGCGGAGGGACCAAG | CAGSWMGCAAATNHCTTCCCTCCTACT | 1662 | 2286 |
| VK1-12 9 3 9 | CCTGAAGATTTTGCAACTTATTACTGTCAGSWMGCAAATAGTYWCCCTCCTACTTTTGGCGGAGGGACCAAG | CAGSWMGCAAATAGTYWCCCTCCTACT | 1663 | 2287 |
| VK1-33 1 0 9 | CCTGAAGATATTGCAACATATTACTGTSWMSWMTACGATAATCTCCCTTWCACTTTTGGCGGAGGGACCAAG | SWMSWMTACGATAATCTCCCTTWCACT | 1664 | 2288 |
| VK1-33 10 0 9 | CCTGAAGATATTGCAACATATTACTGTCAGCAGBHCNHCAATCTCCCTTWCACTTTTGGCGGAGGGACCAAG | CAGCAGBHCNHCAATCTCCCTTWCACT | 1665 | 2289 |
| VK1-33 11 0 9 | CCTGAAGATATTGCAACATATTACTGTCAGCAGBHCGATNHCCTCCCTTWCACTTTTGGCGGAGGGACCAAG | CAGCAGBHCGATNHCCTCCCTTWCACT | 1666 | 2290 |
| VK1-33 12 0 9 | CCTGAAGATATTGCAACATATTACTGTCAGCAGBHCGATAATYWCCCTTWCACTTTTGGCGGAGGGACCAAG | CAGCAGBHCGATAATYWCCCTTWCACT | 1667 | 2291 |
| VK1-33 13 0 9 | CCTGAAGATATTGCAACATATTACTGTCAGCAGTACNHCNHCCTCCCTTWCACTTTTGGCGGAGGGACCAAG | CAGCAGTACNHCNHCCTCCCTTWCACT | 1668 | 2292 |
| VK1-33 14 0 9 | CCTGAAGATATTGCAACATATTACTGTCAGCAGTACNHCAATYWCCCTTWCACTTTTGGCGGAGGGACCAAG | CAGCAGTACNHCAATYWCCCTTWCACT | 1669 | 2293 |
| VK1-33 15 0 9 | CCTGAAGATATTGCAACATATTACTGTCAGCAGTACGATNHCYWCCCTTWCACTTTTGGCGGAGGGACCAAG | CAGCAGTACGATNHCYWCCCTTWCACT | 1670 | 2294 |
| VK1-33 2 0 9 | CCTGAAGATATTGCAACATATTACTGTSWMCAGBHCGATAATCTCCCTTWCACTTTTGGCGGAGGGACCAAG | SWMCAGBHCGATAATCTCCCTTWCACT | 1671 | 2295 |
| VK1-33 3 0 9 | CCTGAAGATATTGCAACATATTACTGTSWMCAGTACNHCAATCTCCCTTWCACTTTTGGCGGAGGGACCAAG | SWMCAGTACNHCAATCTCCCTTWCACT | 1672 | 2296 |
| VK1-33 4 0 9 | CCTGAAGATATTGCAACATATTACTGTSWMCAGTACGATNHCCTCCCTTWCACTTTTGGCGGAGGGACCAAG | SWMCAGTACGATNHCCTCCCTTWCACT | 1673 | 2297 |

TABLE 6 -continued

Oligonucleotide sequences for exemplary VK jumping dimer and trimer sequences with CDRL3 length 9.

| Name | Sequence of Synthesized Oligonucleotide | Portion of Oligonucleotide Corresponding to CDRL3 Proper | SEQ ID NO (Oligo) | SEQ ID NO (CDRL3 Portion) |
|---|---|---|---|---|
| VK1-33 5 0 9 | CCTGAAGATATTGCAACATATTACTGTSWMCAGTACGATAATYWCCCTTWCACTTTTGGCGGAGGGACCAAG | SWMCAGTACGATAATYWCCCTTWCACT | 1674 | 2298 |
| VK1-33 6 0 9 | CCTGAAGATATTGCAACATATTACTGTCAGSWMBHCGATAATCTCCCTTWCACTTTTGGCGGAGGGACCAAG | CAGSWMBHCGATAATCTCCCTTWCACT | 1675 | 2299 |
| VK1-33 7 0 9 | CCTGAAGATATTGCAACATATTACTGTCAGSWMTACNHCAATCTCCCTTWCACTTTTGGCGGAGGGACCAAG | CAGSWMTACNHCAATCTCCCTTWCACT | 1676 | 2300 |
| VK1-33 8 0 9 | CCTGAAGATATTGCAACATATTACTGTCAGSWMTACGATNHCCTCCCTTWCACTTTTGGCGGAGGGACCAAG | CAGSWMTACGATNHCCTCCCTTWCACT | 1677 | 2301 |
| VK1-33 9 0 9 | CCTGAAGATATTGCAACATATTACTGTCAGSWMTACGATAATYWCCCTTWCACTTTTGGCGGAGGGACCAAG | CAGSWMTACGATAATYWCCCTTWCACT | 1678 | 2302 |
| VK1-33 1 1 9 | CCTGAAGATATTGCAACATATTACTGTSWMSWMTACGATAATCTCCCTMTCACTTTTGGCGGAGGGACCAAG | SWMSWMTACGATAATCTCCCTMTCACT | 1679 | 2303 |
| VK1-33 10 1 9 | CCTGAAGATATTGCAACATATTACTGTCAGCAGBHCNHCAATCTCCCTMTCACTTTTGGCGGAGGGACCAAG | CAGCAGBHCNHCAATCTCCCTMTCACT | 1680 | 2304 |
| VK1-33 11 1 9 | CCTGAAGATATTGCAACATATTACTGTCAGCAGBHCGATNHCCTCCCTMTCACTTTTGGCGGAGGGACCAAG | CAGCAGBHCGATNHCCTCCCTMTCACT | 1681 | 2305 |
| VK1-33 12 1 9 | CCTGAAGATATTGCAACATATTACTGTCAGCAGBHCGATAATYWCCCTMTCACTTTTGGCGGAGGGACCAAG | CAGCAGBHCGATAATYWCCCTMTCACT | 1682 | 2306 |
| VK1-33 13 1 9 | CCTGAAGATATTGCAACATATTACTGTCAGCAGTACNHCNHCCTCCCTMTCACTTTTGGCGGAGGGACCAAG | CAGCAGTACNHCNHCCTCCCTMTCACT | 1683 | 2307 |
| VK1-33 14 1 9 | CCTGAAGATATTGCAACATATTACTGTCAGCAGTACNHCAATYWCCCTMTCACTTTTGGCGGAGGGACCAAG | CAGCAGTACNHCAATYWCCCTMTCACT | 1684 | 2308 |
| VK1-33 15 1 9 | CCTGAAGATATTGCAACATATTACTGTCAGCAGTACGATNHCYWCCCTMTCACTTTTGGCGGAGGGACCAAG | CAGCAGTACGATNHCYWCCCTMTCACT | 1685 | 2309 |
| VK1-33 2 1 9 | CCTGAAGATATTGCAACATATTACTGTSWMCAGBHCGATAATCTCCCTMTCACTTTTGGCGGAGGGACCAAG | SWMCAGBHCGATAATCTCCCTMTCACT | 1686 | 2310 |
| VK1-33 3 1 9 | CCTGAAGATATTGCAACATATTACTGTSWMCAGTACNHCAATCTCCCTMTCACTTTTGGCGGAGGGACCAAG | SWMCAGTACNHCAATCTCCCTMTCACT | 1687 | 2311 |
| VK1-33 4 1 9 | CCTGAAGATATTGCAACATATTACTGTSWMCAGTACGATNHCCTCCCTMTCACTTTTGGCGGAGGGACCAAG | SWMCAGTACGATNHCCTCCCTMTCACT | 1688 | 2312 |
| VK1-33 5 1 9 | CCTGAAGATATTGCAACATATTACTGTSWMCAGTACGATAATYWCCCTMTCACTTTTGGCGGAGGGACCAAG | SWMCAGTACGATAATYWCCCTMTCACT | 1689 | 2313 |
| VK1-33 6 1 9 | CCTGAAGATATTGCAACATATTACTGTCAGSWMBHCGATAATCTCCCTMTCACTTTTGGCGGAGGGACCAAG | CAGSWMBHCGATAATCTCCCTMTCACT | 1690 | 2314 |
| VK1-33 7 1 9 | CCTGAAGATATTGCAACATATTACTGTCAGSWMTACNHCAATCTCCCTMTCACTTTTGGCGGAGGGACCAAG | CAGSWMTACNHCAATCTCCCTMTCACT | 1691 | 2315 |
| VK1-33 8 1 9 | CCTGAAGATATTGCAACATATTACTGTCAGSWMTACGATNHCCTCCCTMTCACTTTTGGCGGAGGGACCAAG | CAGSWMTACGATNHCCTCCCTMTCACT | 1692 | 2316 |
| VK1-33 9 1 9 | CCTGAAGATATTGCAACATATTACTGTCAGSWMTACGATAATYWCCCTMTCACTTTTGGCGGAGGGACCAAG | CAGSWMTACGATAATYWCCCTMTCACT | 1693 | 2317 |
| VK1-33 1 2 9 | CCTGAAGATATTGCAACATATTACTGTSWMSWMTACGATAATCTCCCTWGGACTTTTGGCGGAGGGACCAAG | SWMSWMTACGATAATCTCCCTWGGACT | 1694 | 2318 |
| VK1-33 10 2 9 | CCTGAAGATATTGCAACATATTACTGTCAGCAGBHCNHCAATCTCCCTWGGACTTTTGGCGGAGGGACCAAG | CAGCAGBHCNHCAATCTCCCTWGGACT | 1695 | 2319 |
| VK1-33 11 2 9 | CCTGAAGATATTGCAACATATTACTGTCAGCAGBHCGATNHCCTCCCTWGGACTTTTGGCGGAGGGACCAAG | CAGCAGBHCGATNHCCTCCCTWGGACT | 1696 | 2320 |

TABLE 6 -continued

Oligonucleotide sequences for exemplary VK jumping dimer and trimer sequences with CDRL3 length 9.

| Name | Sequence of Synthesized Oligonucleotide | Portion of Oligonucleotide Corresponding to CDRL3 Proper | SEQ ID NO (Oli-go) | SEQ ID NO (CDRL3 Por-tion) |
|---|---|---|---|---|
| VK1-33 12 2 9 | CCTGAAGATATTGCAACATATTACTGTCAGCAGBHCGATAATYWCCCTWGGACTTTTGGCGGAGGGACCAAG | CAGCAGBHCGATAATYWCCCTWGGACT | 1697 | 2321 |
| VK1-33 13 2 9 | CCTGAAGATATTGCAACATATTACTGTCAGCAGTACNHCNHCCTCCCTWGGACTTTTGGCGGAGGGACCAAG | CAGCAGTACNHCNHCCTCCCTWGGACT | 1698 | 2322 |
| VK1-33 14 2 9 | CCTGAAGATATTGCAACATATTACTGTCAGCAGTACNHCAATYWCCCTWGGACTTTTGGCGGAGGGACCAAG | CAGCAGTACNHCAATYWCCCTWGGACT | 1699 | 2323 |
| VK1-33 15 2 9 | CCTGAAGATATTGCAACATATTACTGTCAGCAGTACGATNHCYWCCCTWGGACTTTTGGCGGAGGGACCAAG | CAGCAGTACGATNHCYWCCCTWGGACT | 1700 | 2324 |
| VK1-33 2 2 9 | CCTGAAGATATTGCAACATATTACTGTSWMCAGBHCGATAATCTCCCTWGGACTTTTGGCGGAGGGACCAAG | SWMCAGBHCGATAATCTCCCTWGGACT | 1701 | 2325 |
| VK1-33 3 2 9 | CCTGAAGATATTGCAACATATTACTGTSWMCAGTACNHCAATCTCCCTWGGACTTTTGGCGGAGGGACCAAG | SWMCAGTACNHCAATCTCCCTWGGACT | 1702 | 2326 |
| VK1-33 4 2 9 | CCTGAAGATATTGCAACATATTACTGTSWMCAGTACGATNHCCTCCCTWGGACTTTTGGCGGAGGGACCAAG | SWMCAGTACGATNHCCTCCCTWGGACT | 1703 | 2327 |
| VK1-33 5 2 9 | CCTGAAGATATTGCAACATATTACTGTSWMCAGTACGATAATYWCCCTWGGACTTTTGGCGGAGGGACCAAG | SWMCAGTACGATAATYWCCCTWGGACT | 1704 | 2328 |
| VK1-33 6 2 9 | CCTGAAGATATTGCAACATATTACTGTCAGSWMBHCGATAATCTCCCTWGGACTTTTGGCGGAGGGACCAAG | CAGSWMBHCGATAATCTCCCTWGGACT | 1705 | 2329 |
| VK1-33 7 2 9 | CCTGAAGATATTGCAACATATTACTGTCAGSWMTACNHCAATCTCCCTWGGACTTTTGGCGGAGGGACCAAG | CAGSWMTACNHCAATCTCCCTWGGACT | 1706 | 2330 |
| VK1-33 8 2 9 | CCTGAAGATATTGCAACATATTACTGTCAGSWMTACGATNHCCTCCCTWGGACTTTTGGCGGAGGGACCAAG | CAGSWMTACGATNHCCTCCCTWGGACT | 1707 | 2331 |
| VK1-33 9 2 9 | CCTGAAGATATTGCAACATATTACTGTCAGSWMTACGATAATYWCCCTWGGACTTTTGGCGGAGGGACCAAG | CAGSWMTACGATAATYWCCCTWGGACT | 1708 | 2332 |
| VK1-33 1 3 9 | CCTGAAGATATTGCAACATATTACTGTSWMSWMTACGATAATCTCCCTCCTACTTTTGGCGGAGGGACCAAG | SWMSWMTACGATAATCTCCCTCCTACT | 1709 | 2333 |
| VK1-33 10 3 9 | CCTGAAGATATTGCAACATATTACTGTCAGCAGBHCNHCAATCTCCCTCCTACTTTTGGCGGAGGGACCAAG | CAGCAGBHCNHCAATCTCCCTCCTACT | 1710 | 2334 |
| VK1-33 11 3 9 | CCTGAAGATATTGCAACATATTACTGTCAGCAGBHCGATNHCCTCCCTCCTACTTTTGGCGGAGGGACCAAG | CAGCAGBHCGATNHCCTCCCTCCTACT | 1711 | 2335 |
| VK1-33 12 3 9 | CCTGAAGATATTGCAACATATTACTGTCAGCAGBHCGATAATYWCCCTCCTACTTTTGGCGGAGGGACCAAG | CAGCAGBHCGATAATYWCCCTCCTACT | 1712 | 2336 |
| VK1-33 13 3 9 | CCTGAAGATATTGCAACATATTACTGTCAGCAGTACNHCNHCCTCCCTCCTACTTTTGGCGGAGGGACCAAG | CAGCAGTACNHCNHCCTCCCTCCTACT | 1713 | 2337 |
| VK1-33 14 3 9 | CCTGAAGATATTGCAACATATTACTGTCAGCAGTACNHCAATYWCCCTCCTACTTTTGGCGGAGGGACCAAG | CAGCAGTACNHCAATYWCCCTCCTACT | 1714 | 2338 |
| VK1-33 15 3 9 | CCTGAAGATATTGCAACATATTACTGTCAGCAGTACGATNHCYWCCCTCCTACTTTTGGCGGAGGGACCAAG | CAGCAGTACGATNHCYWCCCTCCTACT | 1715 | 2339 |
| VK1-33 2 3 9 | CCTGAAGATATTGCAACATATTACTGTSWMCAGBHCGATAATCTCCCTCCTACTTTTGGCGGAGGGACCAAG | SWMCAGBHCGATAATCTCCCTCCTACT | 1716 | 2340 |
| VK1-33 3 3 9 | CCTGAAGATATTGCAACATATTACTGTSWMCAGTACNHCAATCTCCCTCCTACTTTTGGCGGAGGGACCAAG | SWMCAGTACNHCAATCTCCCTCCTACT | 1717 | 2341 |
| VK1-33 43 9 | CCTGAAGATATTGCAACATATTACTGTSWMCAGTACGATNHCCTCCCTCCTACTTTTGGCGGAGGGACCAAG | SWMCAGTACGATNHCCTCCCTCCTACT | 1718 | 2342 |
| VK1-33 5 3 9 | CCTGAAGATATTGCAACATATTACTGTSWMCAGTACGATAATYWCCCTCCTACTTTTGGCGGAGGGACCAAG | SWMCAGTACGATAATYWCCCTCCTACT | 1719 | 2343 |
| VK1-33 6 3 9 | CCTGAAGATATTGCAACATATTACTGTCAGSWMBHCGATAATCTCCCTCCTACTTTTGGCGGAGGGACCAAG | CAGSWMBHCGATAATCTCCCTCCTACT | 1720 | 2344 |

TABLE 6 -continued

Oligonucleotide sequences for exemplary VK jumping dimer and trimer sequences with CDRL3 length 9.

| Name | Sequence of Synthesized Oligonucleotide | Portion of Oligonucleotide Corresponding to CDRL3 Proper | SEQ ID NO (Oli-go) | SEQ ID NO (CDRL3 Por-tion) |
|---|---|---|---|---|
| VK1-33 7 3 9 | CCTGAAGATATTGCAACATATTACTGTCAGSWMTACNHCAA TCTCCCTCCTACTTTTGGCGGAGGGACCAAG | CAGSWMTACNHCAATCTCCCTC CTACT | 1721 | 2345 |
| VK1-33 8 3 9 | CCTGAAGATATTGCAACATATTACTGTCAGSWMTACGATNH CCTCCCTCCTACTTTTGGCGGAGGGACCAAG | CAGSWMTACGATNHCCTCCCTC CTACT | 1722 | 2346 |
| VK1-33 9 3 9 | CCTGAAGATATTGCAACATATTACTGTCAGSWMTACGATAA TYWCCCTCCTACTTTTGGCGGAGGGACCAAG | CAGSWMTACGATAATYWCCCTC CTACT | 1723 | 2347 |
| VK1-39 1 0 9 | CCTGAAGATTTTGCAACTTACTACTGTSWMSWMAGCTACAG TACTCCTTWCACTTTTGGCGGAGGGACCAAG | SWMSWMAGCTACAGTACTCCTT WCACT | 1724 | 305 |
| VK1-39 10 0 9 | CCTGAAGATTTTGCAACTTACTACTGTCAGCAAVNABHCAG TACTCCTTWCACTTTTGGCGGAGGGACCAAG | CAGCAAVNABHCAGTACTCCTT WCACT | 1725 | 314 |
| VK1-39 11 0 9 | CCTGAAGATTTTGCAACTTACTACTGTCAGCAAVNATACNH CACTCCTTWCACTTTTGGCGGAGGGACCAAG | CAGCAAVNATACNHCACTCCTT WCACT | 1726 | 315 |
| VK1-391 2 0 9 | CCTGAAGATTTTGCAACTTACTACTGTCAGCAAVNATACAG TBHCCCTTWCACTTTTGGCGGAGGGACCAAG | CAGCAAVNATACAGTBHCCCTT WCACT | 1727 | 316 |
| VK1-39 13 0 9 | CCTGAAGATTTTGCAACTTACTACTGTCAGCAAAGCBHCNH CACTCCTTWCACTTTTGGCGGAGGGACCAAG | CAGCAAAGCBHCNHCACTCCTT WCACT | 1728 | 317 |
| VK1-39 14 0 9 | CCTGAAGATTTTGCAACTTACTACTGTCAGCAAAGCBHCAG TBHCCCTTWCACTTTTGGCGGAGGGACCAAG | CAGCAAAGCBHCAGTBHCCCTT WCACT | 1729 | 318 |
| VK1-39 15 0 9 | CCTGAAGATTTTGCAACTTACTACTGTCAGCAAAGCTACNH CBHCCCTTWCACTTTTGGCGGAGGGACCAAG | CAGCAAAGCTACNHCBHCCCTT WCACT | 1730 | 319 |
| VK1-39 2 0 9 | CCTGAAGATTTTGCAACTTACTACTGTSWMCAAVNATACAG TACTCCTTWCACTTTTGGCGGAGGGACCAAG | SWMCAAVNATACAGTACTCCTT WCACT | 1731 | 306 |
| VK1-39 3 0 9 | CCTGAAGATTTTGCAACTTACTACTGTSWMCAAAGCBHCAG TACTCCTTWCACTTTTGGCGGAGGGACCAAG | SWMCAAAGCBHCAGTACTCCTT WCACT | 1732 | 307 |
| VK1-39 4 0 9 | CCTGAAGATTTTGCAACTTACTACTGTSWMCAAAGCTACNH CACTCCTTWCACTTTTGGCGGAGGGACCAAG | SWMCAAAGCTACNHCACTCCTT WCACT | 1733 | 308 |
| VK1-39 5 0 9 | CCTGAAGATTTTGCAACTTACTACTGTSWMCAAAGCTACAG TBHCCCTTWCACTTTTGGCGGAGGGACCAAG | SWMCAAAGCTACAGTBHCCCTT WCACT | 1734 | 309 |
| VK1-39 6 0 9 | CCTGAAGATTTTGCAACTTACTACTGTCAGSWMVNATACAG TACTCCTTWCACTTTTGGCGGAGGGACCAAG | CAGSWMVNATACAGTACTCCTT WCACT | 1735 | 310 |
| VK1-39 7 0 9 | CCTGAAGATTTTGCAACTTACTACTGTCAGSWMAGCBHCAG TACTCCTTWCACTTTTGGCGGAGGGACCAAG | CAGSWMAGCBHCAGTACTCCTT WCACT | 1736 | 311 |
| VK1-39 8 0 9 | CCTGAAGATTTTGCAACTTACTACTGTCAGSWMAGCTACNH CACTCCTTWCACTTTTGGCGGAGGGACCAAG | CAGSWMAGCTACNHCACTCCTT WCACT | 1737 | 312 |
| VK1-39 9 0 9 | CCTGAAGATTTTGCAACTTACTACTGTCAGSWMAGCTACAG TBHCCCTTWCACTTTTGGCGGAGGGACCAAG | CAGSWMAGCTACAGTBHCCCTT WCACT | 1738 | 313 |
| VK1-39 1 1 9 | CCTGAAGATTTTGCAACTTACTACTGTSWMSWMAGCTACAG TACTCCTMTCACTTTTGGCGGAGGGACCAAG | SWMSWMAGCTACAGTACTCCTM TCACT | 1739 | 2348 |
| VK1-39 10 1 9 | CCTGAAGATTTTGCAACTTACTACTGTCAGCAAVNABHCAG TACTCCTMTCACTTTTGGCGGAGGGACCAAG | CAGCAAVNABHCAGTACTCCTM TCACT | 1740 | 2349 |
| VK1-39 11 1 9 | CCTGAAGATTTTGCAACTTACTACTGTCAGCAAVNATACNH CACTCCTMTCACTTTTGGCGGAGGGACCAAG | CAGCAAVNATACNHCACTCCTM TCACT | 1741 | 2350 |
| VK1-39 12 1 9 | CCTGAAGATTTTGCAACTTACTACTGTCAGCAAVNATACAG TBHCCCTMTCACTTTTGGCGGAGGGACCAAG | CAGCAAVNATACAGTBHCCCTM TCACT | 1742 | 2351 |
| VK1-39 13 1 9 | CCTGAAGATTTTGCAACTTACTACTGTCAGCAAAGCBHCNH CACTCCTMTCACTTTTGGCGGAGGGACCAAG | CAGCAAAGCBHCNHCACTCCTM TCACT | 1743 | 2352 |

TABLE 6 -continued

Oligonucleotide sequences for exemplary VK jumping dimer and trimer sequences with CDRL3 length 9.

| Name | Sequence of Synthesized Oligonucleotide | Portion of Oligonucleotide Corresponding to CDRL3 Proper | SEQ ID NO (Oligo) | SEQ ID NO (CDRL3 Portion) |
|---|---|---|---|---|
| VK1-39 14 1 9 | CCTGAAGATTTTGCAACTTACTACTGTCAGCAAAGCBHCAGTBHCCCTMTCACTTTTGGCGGAGGGACCAAG | CAGCAAAGCBHCAGTBHCCCTMTCACT | 1744 | 2353 |
| VK1-39 15 1 9 | CCTGAAGATTTTGCAACTTACTACTGTCAGCAAAGCTACNHCBHCCCTMTCACTTTTGGCGGAGGGACCAAG | CAGCAAAGCTACNHCBHCCCTMTCACT | 1745 | 2354 |
| VK1-39 2 1 9 | CCTGAAGATTTTGCAACTTACTACTGTSWMCAAVNATACAGTACTCCTMTCACTTTTGGCGGAGGGACCAAG | SWMCAAVNATACAGTACTCCTMTCACT | 1746 | 2355 |
| VK1-39 3 1 9 | CCTGAAGATTTTGCAACTTACTACTGTSWMCAAAGCBHCAGTACTCCTMTCACTTTTGGCGGAGGGACCAAG | SWMCAAAGCBHCAGTACTCCTMTCACT | 1747 | 2356 |
| VK1-39 4 1 9 | CCTGAAGATTTTGCAACTTACTACTGTSWMCAAAGCTACNHCACTCCTMTCACTTTTGGCGGAGGGACCAAG | SWMCAAAGCTACNHCACTCCTMTCACT | 1748 | 2357 |
| VK1-39 5 1 9 | CCTGAAGATTTTGCAACTTACTACTGTSWMCAAAGCTACAGTBHCCCTMTCACTTTTGGCGGAGGGACCAAG | SWMCAAAGCTACAGTBHCCCTMTCACT | 1749 | 2358 |
| VK1-39 6 1 9 | CCTGAAGATTTTGCAACTTACTACTGTCAGSWMVNATACAGTACTCCTMTCACTTTTGGCGGAGGGACCAAG | CAGSWMVNATACAGTACTCCTMTCACT | 1750 | 2359 |
| VK1-39 7 1 9 | CCTGAAGATTTTGCAACTTACTACTGTCAGSWMAGCBHCAGTACTCCTMTCACTTTTGGCGGAGGGACCAAG | CAGSWMAGCBHCAGTACTCCTMTCACT | 1751 | 2360 |
| VK1-39 8 1 9 | CCTGAAGATTTTGCAACTTACTACTGTCAGSWMAGCTACNHCACTCCTMTCACTTTTGGCGGAGGGACCAAG | CAGSWMAGCTACNHCACTCCTMTCACT | 1752 | 2361 |
| VK1-39 9 1 9 | CCTGAAGATTTTGCAACTTACTACTGTCAGSWMAGCTACAGTBHCCCTMTCACTTTTGGCGGAGGGACCAAG | CAGSWMAGCTACAGTBHCCCTMTCACT | 1753 | 2362 |
| VK1-39 1 2 9 | CCTGAAGATTTTGCAACTTACTACTGTSWMSWMAGCTACAGTACTCCTWGGACTTTTGGCGGAGGGACCAAG | SWMSWMAGCTACAGTACTCCTWGGACT | 1754 | 2363 |
| VK1-39 10 2 9 | CCTGAAGATTTTGCAACTTACTACTGTCAGCAAVNABHCAGTACTCCTWGGACTTTTGGCGGAGGGACCAAG | CAGCAAVNABHCAGTACTCCTWGGACT | 1755 | 2364 |
| VK1-39 11 2 9 | CCTGAAGATTTTGCAACTTACTACTGTCAGCAAVNATACNHCACTCCTWGGACTTTTGGCGGAGGGACCAAG | CAGCAAVNATACNHCACTCCTWGGACT | 1756 | 2365 |
| VK1-39 12 2 9 | CCTGAAGATTTTGCAACTTACTACTGTCAGCAAVNATACAGTBHCCCTWGGACTTTTGGCGGAGGGACCAAG | CAGCAAVNATACAGTBHCCCTWGGACT | 1757 | 2366 |
| VK1-39 13 2 9 | CCTGAAGATTTTGCAACTTACTACTGTCAGCAAAGCBHCNHCACTCCTWGGACTTTTGGCGGAGGGACCAAG | CAGCAAAGCBHCNHCACTCCTWGGACT | 1758 | 2367 |
| VK1-39 14 2 9 | CCTGAAGATTTTGCAACTTACTACTGTCAGCAAAGCBHCAGTBHCCCTWGGACTTTTGGCGGAGGGACCAAG | CAGCAAAGCBHCAGTBHCCCTWGGACT | 1759 | 2368 |
| VK1-39 15 2 9 | CCTGAAGATTTTGCAACTTACTACTGTCAGCAAAGCTACNHCBHCCCTWGGACTTTTGGCGGAGGGACCAAG | CAGCAAAGCTACNHCBHCCCTWGGACT | 1760 | 2369 |
| VK1-39 2 2 9 | CCTGAAGATTTTGCAACTTACTACTGTSWMCAAVNATACAGTACTCCTWGGACTTTTGGCGGAGGGACCAAG | SWMCAAVNATACAGTACTCCTWGGACT | 1761 | 2370 |
| VK1-39 3 2 9 | CCTGAAGATTTTGCAACTTACTACTGTSWMCAAAGCBHCAGTACTCCTWGGACTTTTGGCGGAGGGACCAAG | SWMCAAAGCBHCAGTACTCCTWGGACT | 1762 | 2371 |
| VK1-39 4 2 9 | CCTGAAGATTTTGCAACTTACTACTGTSWMCAAAGCTACNHCACTCCTWGGACTTTTGGCGGAGGGACCAAG | SWMCAAAGCTACNHCACTCCTWGGACT | 1763 | 2372 |
| VK1-39 5 2 9 | CCTGAAGATTTTGCAACTTACTACTGTSWMCAAAGCTACAGTBHCCCTWGGACTTTTGGCGGAGGGACCAAG | SWMCAAAGCTACAGTBHCCCTWGGACT | 1764 | 2373 |
| VK1-39 6 2 9 | CCTGAAGATTTTGCAACTTACTACTGTCAGSWMVNATACAGTACTCCTWGGACTTTTGGCGGAGGGACCAAG | CAGSWMVNATACAGTACTCCTWGGACT | 1765 | 2374 |
| VK1-39 7 2 9 | CCTGAAGATTTTGCAACTTACTACTGTCAGSWMAGCBHCAGTACTCCTWGGACTTTTGGCGGAGGGACCAAG | CAGSWMAGCBHCAGTACTCCTWGGACT | 1766 | 2375 |
| VK1-39 8 2 9 | CCTGAAGATTTTGCAACTTACTACTGTCAGSWMAGCTACNHCACTCCTWGGACTTTTGGCGGAGGGACCAAG | CAGSWMAGCTACNHCACTCCTWGGACT | 1767 | 2376 |

TABLE 6 -continued

| Name | Sequence of Synthesized Oligonucleotide | Portion of Oligonucleotide Corresponding to CDRL3 Proper | SEQ ID NO (Oligo) | SEQ ID NO (CDRL3 Portion) |
|---|---|---|---|---|
| Oligonucleotide sequences for exemplary VK jumping dimer and trimer sequences with CDRL3 length 9. | | | | |
| VK1-39 9 2 9 | CCTGAAGATTTTGCAACTTACTACTGTCAGSWMAGCTACAGTBHCCCTWGGACTTTTGGCGGAGGGACCAAG | CAGSWMAGCTACAGTBHCCCTWGGACT | 1768 | 2377 |
| VK1-39 1 3 9 | CCTGAAGATTTTGCAACTTACTACTGTSWMSWMAGCTACAGTACTCCTCCTACTTTTGGCGGAGGGACCAAG | SWMSWMAGCTACAGTACTCCTCCTACT | 1769 | 2378 |
| VK1-39 10 3 9 | CCTGAAGATTTTGCAACTTACTACTGTCAGCAAVNABHCAGTACTCCTCCTACTTTTGGCGGAGGGACCAAG | CAGCAAVNABHCAGTACTCCTCCTACT | 1770 | 2379 |
| VK1-39 11 3 9 | CCTGAAGATTTTGCAACTTACTACTGTCAGCAAVNATACNHCACTCCTCCTACTTTTGGCGGAGGGACCAAG | CAGCAAVNATACNHCACTCCTCCTACT | 1771 | 2380 |
| VK1-39 12 3 9 | CCTGAAGATTTTGCAACTTACTACTGTCAGCAAVNATACAGTBHCCCTCCTACTTTTGGCGGAGGGACCAAG | CAGCAAVNATACAGTBHCCCTCCTACT | 1772 | 2381 |
| VK1-39 13 3 9 | CCTGAAGATTTTGCAACTTACTACTGTCAGCAAAGCBHCNHCACTCCTCCTACTTTTGGCGGAGGGACCAAG | CAGCAAAGCBHCNHCACTCCTCCTACT | 1773 | 2382 |
| VK1-39 14 3 9 | CCTGAAGATTTTGCAACTTACTACTGTCAGCAAAGCBHCAGTBHCCCTCCTACTTTTGGCGGAGGGACCAAG | CAGCAAAGCBHCAGTBHCCCTCCTACT | 1774 | 2383 |
| VK1-39 15 3 9 | CCTGAAGATTTTGCAACTTACTACTGTCAGCAAAGCTACNHCBHCCCTCCTACTTTTGGCGGAGGGACCAAG | CAGCAAAGCTACNHCBHCCCTCCTACT | 1775 | 2384 |
| VK1-39 2 3 9 | CCTGAAGATTTTGCAACTTACTACTGTSWMCAAVNATACAGTACTCCTCCTACTTTTGGCGGAGGGACCAAG | SWMCAAVNATACAGTACTCCTCCTACT | 1776 | 2385 |
| VK1-39 3 3 9 | CCTGAAGATTTTGCAACTTACTACTGTSWMCAAAGCBHCAGTACTCCTCCTACTTTTGGCGGAGGGACCAAG | SWMCAAAGCBHCAGTACTCCTCCTACT | 1777 | 2386 |
| VK1-39 4 3 9 | CCTGAAGATTTTGCAACTTACTACTGTSWMCAAAGCTACNHCACTCCTCCTACTTTTGGCGGAGGGACCAAG | SWMCAAAGCTACNHCACTCCTCCTACT | 1778 | 2387 |
| VK1-39 5 3 9 | CCTGAAGATTTTGCAACTTACTACTGTSWMCAAAGCTACAGTBHCCCTCCTACTTTTGGCGGAGGGACCAAG | SWMCAAAGCTACAGTBHCCCTCCTACT | 1779 | 2388 |
| VK1-39 6 3 9 | CCTGAAGATTTTGCAACTTACTACTGTCAGSWMVNATACAGTACTCCTCCTACTTTTGGCGGAGGGACCAAG | CAGSWMVNATACAGTACTCCTCCTACT | 1780 | 2389 |
| VK1-39 7 3 9 | CCTGAAGATTTTGCAACTTACTACTGTCAGSWMAGCBHCAGTACTCCTCCTACTTTTGGCGGAGGGACCAAG | CAGSWMAGCBHCAGTACTCCTCCTACT | 1781 | 2390 |
| VK1-39 8 3 9 | CCTGAAGATTTTGCAACTTACTACTGTCAGSWMAGCTACNHCACTCCTCCTACTTTTGGCGGAGGGACCAAG | CAGSWMAGCTACNHCACTCCTCCTACT | 1782 | 2391 |
| VK1-39 9 3 9 | CCTGAAGATTTTGCAACTTACTACTGTCAGSWMAGCTACAGTBHCCCTCCTACTTTTGGCGGAGGGACCAAG | CAGSWMAGCTACAGTBHCCCTCCTACT | 1783 | 2392 |
| VK2-28 1 0 9 | GCTGAGGATGTTGGGGTTTATTACTGCDTSSWMGCACTCCAGACTCCTTWCACTTTTGGCGGAGGGACCAAG | DTSSWMGCACTCCAGACTCCTTWCACT | 1784 | 2393 |
| VK2-28 10 0 9 | GCTGAGGATGTTGGGGTTTATTACTGCATGCAGVNAMNACAGACTCCTTWCACTTTTGGCGGAGGGACCAAG | ATGCAGVNAMNACAGACTCCTTWCACT | 1785 | 2394 |
| VK2-28 11 0 9 | GCTGAGGATGTTGGGGTTTATTACTGCATGCAGVNACTCSRMACTCCTTWCACTTTTGGCGGAGGGACCAAG | ATGCAGVNACTCSRMACTCCTTWCACT | 1786 | 2395 |
| VK2-28 12 0 9 | GCTGAGGATGTTGGGGTTTATTACTGCATGCAGVNACTCCAGVBCCCTTWCACTTTTGGCGGAGGGACCAAG | ATGCAGVNACTCCAGVBCCCTTWCACT | 1787 | 2396 |
| VK2-28 13 0 9 | GCTGAGGATGTTGGGGTTTATTACTGCATGCAGGCAMNASRMACTCCTTWCACTTTTGGCGGAGGGACCAAG | ATGCAGGCAMNASRMACTCCTTWCACT | 1788 | 2397 |
| VK2-28 14 0 9 | GCTGAGGATGTTGGGGTTTATTACTGCATGCAGGCAMNACAGVBCCCTTWCACTTTTGGCGGAGGGACCAAG | ATGCAGGCAMNACAGVBCCCTTWCACT | 1789 | 2398 |
| VK2-28 15 0 9 | GCTGAGGATGTTGGGGTTTATTACTGCATGCAGGCACTCSRMVBCCCTTWCACTTTTGGCGGAGGGACCAAG | ATGCAGGCACTCSRMVBCCCTTWCACT | 1790 | 2399 |

TABLE 6 -continued

Oligonucleotide sequences for exemplary VK jumping dimer and trimer sequences with CDRL3 length 9.

| Name | Sequence of Synthesized Oligonucleotide | Portion of Oligonucleotide Corresponding to CDRL3 Proper | SEQ ID NO (Oligo) | SEQ ID NO (CDRL3 Portion) |
|---|---|---|---|---|
| VK2-28 2 0 9 | GCTGAGGATGTTGGGGTTTATTACTGCDTSCAGVNACTCCAGACTCCTTWCACTTTTGGCGGAGGGACCAAG | DTSCAGVNACTCCAGACTCCTTWCACT | 1791 | 2400 |
| VK2-28 3 0 9 | GCTGAGGATGTTGGGGTTTATTACTGCDTSCAGGCAMNACAGACTCCTTWCACTTTTGGCGGAGGGACCAAG | DTSCAGGCAMNACAGACTCCTTWCACT | 1792 | 2401 |
| VK2-28 4 0 9 | GCTGAGGATGTTGGGGTTTATTACTGCDTSCAGGCACTCSRMACTCCTTWCACTTTTGGCGGAGGGACCAAG | DTSCAGGCACTCSRMACTCCTTWCACT | 1793 | 2402 |
| VK2-28 5 0 9 | GCTGAGGATGTTGGGGTTTATTACTGCDTSCAGGCACTCCAGVBCCCTTWCACTTTTGGCGGAGGGACCAAG | DTSCAGGCACTCCAGVBCCCTTWCACT | 1794 | 2403 |
| VK2-28 6 0 9 | GCTGAGGATGTTGGGGTTTATTACTGCATGSWMVNACTCCAGACTCCTTWCACTTTTGGCGGAGGGACCAAG | ATGSWMVNACTCCAGACTCCTTWCACT | 1795 | 2404 |
| VK2-28 7 0 9 | GCTGAGGATGTTGGGGTTTATTACTGCATGSWMGCAMNACAGACTCCTTWCACTTTTGGCGGAGGGACCAAG | ATGSWMGCAMNACAGACTCCTTWCACT | 1796 | 2405 |
| VK2-28 8 0 9 | GCTGAGGATGTTGGGGTTTATTACTGCATGSWMGCACTCSRMACTCCTTWCACTTTTGGCGGAGGGACCAAG | ATGSWMGCACTCSRMACTCCTTWCACT | 1797 | 2406 |
| VK2-28 9 0 9 | GCTGAGGATGTTGGGGTTTATTACTGCATGSWMGCACTCCAGVBCCCTTWCACTTTTGGCGGAGGGACCAAG | ATGSWMGCACTCCAGVBCCCTTWCACT | 1798 | 2407 |
| VK2-28 1 1 9 | GCTGAGGATGTTGGGGTTTATTACTGCDTSSWMGCACTCCAGACTCCTMTCACTTTTGGCGGAGGGACCAAG | DTSSWMGCACTCCAGACTCCTMTCACT | 1799 | 2408 |
| VK2-28 10 1 9 | GCTGAGGATGTTGGGGTTTATTACTGCATGCAGVNAMNACAGACTCCTMTCACTTTTGGCGGAGGGACCAAG | ATGCAGVNAMNACAGACTCCTMTCACT | 1800 | 2409 |
| VK2-28 11 1 9 | GCTGAGGATGTTGGGGTTTATTACTGCATGCAGVNACTCSRMACTCCTMTCACTTTTGGCGGAGGGACCAAG | ATGCAGVNACTCSRMACTCCTMTCACT | 1801 | 2410 |
| VK2-28 12 1 9 | GCTGAGGATGTTGGGGTTTATTACTGCATGCAGVNACTCCAGVBCCCTMTCACTTTTGGCGGAGGGACCAAG | ATGCAGVNACTCCAGVBCCCTMTCACT | 1802 | 2411 |
| VK2-28 13 1 9 | GCTGAGGATGTTGGGGTTTATTACTGCATGCAGGCAMNASRMACTCCTMTCACTTTTGGCGGAGGGACCAAG | ATGCAGGCAMNASRMACTCCTMTCACT | 1803 | 2412 |
| VK2-28 14 1 9 | GCTGAGGATGTTGGGGTTTATTACTGCATGCAGGCAMNACAGVBCCCTMTCACTTTTGGCGGAGGGACCAAG | ATGCAGGCAMNACAGVBCCCTMTCACT | 1804 | 2413 |
| VK2-28 15 1 9 | GCTGAGGATGTTGGGGTTTATTACTGCATGCAGGCACTCSRMVBCCCTMTCACTTTTGGCGGAGGGACCAAG | ATGCAGGCACTCSRMVBCCCTMTCACT | 1805 | 2414 |
| VK2-28 2 1 9 | GCTGAGGATGTTGGGGTTTATTACTGCDTSCAGVNACTCCAGACTCCTMTCACTTTTGGCGGAGGGACCAAG | DTSCAGVNACTCCAGACTCCTMTCACT | 1806 | 2415 |
| VK2-28 3 1 9 | GCTGAGGATGTTGGGGTTTATTACTGCDTSCAGGCAMNACAGACTCCTMTCACTTTTGGCGGAGGGACCAAG | DTSCAGGCAMNACAGACTCCTMTCACT | 1807 | 2416 |
| VK2-28 4 1 9 | GCTGAGGATGTTGGGGTTTATTACTGCDTSCAGGCACTCSRMACTCCTMTCACTTTTGGCGGAGGGACCAAG | DTSCAGGCACTCSRMACTCCTMTCACT | 1808 | 2417 |
| VK2-28 5 1 9 | GCTGAGGATGTTGGGGTTTATTACTGCDTSCAGGCACTCCAGVBCCCTMTCACTTTTGGCGGAGGGACCAAG | DTSCAGGCACTCCAGVBCCCTMTCACT | 1809 | 2418 |
| VK2-28 6 1 9 | GCTGAGGATGTTGGGGTTTATTACTGCATGSWMVNACTCCAGACTCCTMTCACTTTTGGCGGAGGGACCAAG | ATGSWMVNACTCCAGACTCCTMTCACT | 1810 | 2419 |
| VK2-28 7 1 9 | GCTGAGGATGTTGGGGTTTATTACTGCATGSWMGCAMNACAGACTCCTMTCACTTTTGGCGGAGGGACCAAG | ATGSWMGCAMNACAGACTCCTMTCACT | 1811 | 2420 |
| VK2-28 8 1 9 | GCTGAGGATGTTGGGGTTTATTACTGCATGSWMGCACTCSRMACTCCTMTCACTTTTGGCGGAGGGACCAAG | ATGSWMGCACTCSRMACTCCTMTCACT | 1812 | 2421 |
| VK2-28 9 1 9 | GCTGAGGATGTTGGGGTTTATTACTGCATGSWMGCACTCCAGVBCCCTMTCACTTTTGGCGGAGGGACCAAG | ATGSWMGCACTCCAGVBCCCTMTCACT | 1813 | 2422 |
| VK2-28 1 2 9 | GCTGAGGATGTTGGGGTTTATTACTGCDTSSWMGCACTCCAGACTCCTWGGACTTTTGGCGGAGGGACCAAG | DTSSWMGCACTCCAGACTCCTWGGACT | 1814 | 2423 |

TABLE 6 -continued

Oligonucleotide sequences for exemplary VK jumping dimer and trimer sequences with CDRL3 length 9.

| Name | Sequence of Synthesized Oligonucleotide | Portion of Oligonucleotide Corresponding to CDRL3 Proper | SEQ ID NO (Oligo) | SEQ ID NO (CDRL3 Portion) |
|---|---|---|---|---|
| VK2-28 10 2 9 | GCTGAGGATGTTGGGGTTTATTACTGCATGCAGVNAMNACAGACTCCTWGGACTTTTGGCGGAGGGACCAAG | ATGCAGVNAMNACAGACTCCTWGGACT | 1815 | 2424 |
| VK2-28 11 2 9 | GCTGAGGATGTTGGGGTTTATTACTGCATGCAGVNACTCSRMACTCCTWGGACTTTTGGCGGAGGGACCAAG | ATGCAGVNACTCSRMACTCCTWGGACT | 1816 | 2425 |
| VK2-28 12 2 9 | GCTGAGGATGTTGGGGTTTATTACTGCATGCAGVNACTCCAGVBCCCTWGGACTTTTGGCGGAGGGACCAAG | ATGCAGVNACTCCAGVBCCCTWGGACT | 1817 | 2426 |
| VK2-28 13 2 9 | GCTGAGGATGTTGGGGTTTATTACTGCATGCAGGCAMNASRMACTCCTWGGACTTTTGGCGGAGGGACCAAG | ATGCAGGCAMNASRMACTCCTWGGACT | 1818 | 2427 |
| VK2-28 14 2 9 | GCTGAGGATGTTGGGGTTTATTACTGCATGCAGGCAMNACAGVBCCCTWGGACTTTTGGCGGAGGGACCAAG | ATGCAGGCAMNACAGVBCCCTWGGACT | 1819 | 2428 |
| VK2-28 15 2 9 | GCTGAGGATGTTGGGGTTTATTACTGCATGCAGGCACTCSRMVBCCCTWGGACTTTTGGCGGAGGGACCAAG | ATGCAGGCACTCSRMVBCCCTWGGACT | 1820 | 2429 |
| VK2-28 2 2 9 | GCTGAGGATGTTGGGGTTTATTACTGCDTSCAGVNACTCCAGACTCCTWGGACTTTTGGCGGAGGGACCAAG | DTSCAGVNACTCCAGACTCCTWGGACT | 1821 | 2430 |
| VK2-28 3 2 9 | GCTGAGGATGTTGGGGTTTATTACTGCDTSCAGGCAMNACAGACTCCTWGGACTTTTGGCGGAGGGACCAAG | DTSCAGGCAMNACAGACTCCTWGGACT | 1822 | 2431 |
| VK2-28 4 2 9 | GCTGAGGATGTTGGGGTTTATTACTGCDTSCAGGCACTCSRMACTCCTWGGACTTTTGGCGGAGGGACCAAG | DTSCAGGCACTCSRMACTCCTWGGACT | 1823 | 2432 |
| VK2-28 5 2 9 | GCTGAGGATGTTGGGGTTTATTACTGCDTSCAGGCACTCCAGVBCCCTWGGACTTTTGGCGGAGGGACCAAG | DTSCAGGCACTCCAGVBCCCTWGGACT | 1824 | 2433 |
| VK2-28 6 2 9 | GCTGAGGATGTTGGGGTTTATTACTGCATGSWMVNACTCCAGACTCCTWGGACTTTTGGCGGAGGGACCAAG | ATGSWMVNACTCCAGACTCCTWGGACT | 1825 | 2434 |
| VK2-28 7 2 9 | GCTGAGGATGTTGGGGTTTATTACTGCATGSWMGCAMNACAGACTCCTWGGACTTTTGGCGGAGGGACCAAG | ATGSWMGCAMNACAGACTCCTWGGACT | 1826 | 2435 |
| VK2-28 8 2 9 | GCTGAGGATGTTGGGGTTTATTACTGCATGSWMGCACTCSRMACTCCTWGGACTTTTGGCGGAGGGACCAAG | ATGSWMGCACTCSRMACTCCTWGGACT | 1827 | 2436 |
| VK2-28 9 2 9 | GCTGAGGATGTTGGGGTTTATTACTGCATGSWMGCACTCCAGVBCCCTWGGACTTTTGGCGGAGGGACCAAG | ATGSWMGCACTCCAGVBCCCTWGGACT | 1828 | 2437 |
| VK2-28 1 3 9 | GCTGAGGATGTTGGGGTTTATTACTGCDTSSWMGCACTCCAGACTCCTCCTACTTTTGGCGGAGGGACCAAG | DTSSWMGCACTCCAGACTCCTCCTACT | 1829 | 2438 |
| VK2-28 10 3 9 | GCTGAGGATGTTGGGGTTTATTACTGCATGCAGVNAMNACAGACTCCTCCTACTTTTGGCGGAGGGACCAAG | ATGCAGVNAMNACAGACTCCTCCTACT | 1830 | 2439 |
| VK2-28 11 3 9 | GCTGAGGATGTTGGGGTTTATTACTGCATGCAGVNACTCSRMACTCCTCCTACTTTTGGCGGAGGGACCAAG | ATGCAGVNACTCSRMACTCCTCCTACT | 1831 | 2440 |
| VK2-28 12 3 9 | GCTGAGGATGTTGGGGTTTATTACTGCATGCAGVNACTCCAGVBCCCTCCTACTTTTGGCGGAGGGACCAAG | ATGCAGVNACTCCAGVBCCCTCCTACT | 1832 | 2441 |
| VK2-28 13 3 9 | GCTGAGGATGTTGGGGTTTATTACTGCATGCAGGCAMNASRMACTCCTCCTACTTTTGGCGGAGGGACCAAG | ATGCAGGCAMNASRMACTCCTCCTACT | 1833 | 2442 |
| VK2-28 14 3 9 | GCTGAGGATGTTGGGGTTTATTACTGCATGCAGGCAMNACAGVBCCCTCCTACTTTTGGCGGAGGGACCAAG | ATGCAGGCAMNACAGVBCCCTCCTACT | 1834 | 2443 |
| VK2-28 15 3 9 | GCTGAGGATGTTGGGGTTTATTACTGCATGCAGGCACTCSRMVBCCCTCCTACTTTTGGCGGAGGGACCAAG | ATGCAGGCACTCSRMVBCCCTCCTACT | 1835 | 2444 |
| VK2-28 2 3 9 | GCTGAGGATGTTGGGGTTTATTACTGCDTSCAGVNACTCCAGACTCCTCCTACTTTTGGCGGAGGGACCAAG | DTSCAGVNACTCCAGACTCCTCCTACT | 1836 | 2445 |
| VK2-28 3 3 9 | GCTGAGGATGTTGGGGTTTATTACTGCDTSCAGGCAMNACAGACTCCTCCTACTTTTGGCGGAGGGACCAAG | DTSCAGGCAMNACAGACTCCTCCTACT | 1837 | 2446 |

TABLE 6 -continued

Oligonucleotide sequences for exemplary VK jumping dimer and trimer sequences with CDRL3 length 9.

| Name | Sequence of Synthesized Oligonucleotide | Portion of Oligonucleotide Corresponding to CDRL3 Proper | SEQ ID NO (Oli-go) | SEQ ID NO (CDRL3 Por-tion) |
|---|---|---|---|---|
| VK2-28 4 3 9 | GCTGAGGATGTTGGGGTTTATTACTGCDTSCAGGCACTCSRMACTCCTCCTACTTTTGGCGGAGGGACCAAG | DTSCAGGCACTCSRMACTCCTCCTACT | 1838 | 2447 |
| VK2-28 5 3 9 | GCTGAGGATGTTGGGGTTTATTACTGCDTSCAGGCACTCCAGVBCCCTCCTACTTTTGGCGGAGGGACCAAG | DTSCAGGCACTCCAGVBCCCTCCTACT | 1839 | 2448 |
| VK2-28 6 3 9 | GCTGAGGATGTTGGGGTTTATTACTGCATGSWMVNACTCCAGACTCCTCCTACTTTTGGCGGAGGGACCAAG | ATGSWMVNACTCCAGACTCCTCCTACT | 1840 | 2449 |
| VK2-28 7 3 9 | GCTGAGGATGTTGGGGTTTATTACTGCATGSWMGCAMNACAGACTCCTCCTACTTTTGGCGGAGGGACCAAG | ATGSWMGCAMNACAGACTCCTCCTACT | 1841 | 2450 |
| VK2-28 8 3 9 | GCTGAGGATGTTGGGGTTTATTACTGCATGSWMGCACTCSRMACTCCTCCTACTTTTGGCGGAGGGACCAAG | ATGSWMGCACTCSRMACTCCTCCTACT | 1842 | 2451 |
| VK2-28 9 3 9 | GCTGAGGATGTTGGGGTTTATTACTGCATGSWMGCACTCCAGVBCCCTCCTACTTTTGGCGGAGGGACCAAG | ATGSWMGCACTCCAGVBCCCTCCTACT | 1843 | 2452 |
| VK3-11 1 0 9 | CCTGAAGATTTTGCAGTTTATTACTGTSWMSWMAGAAGTAATTGGCCTTWCACTTTTGGCGGAGGGACCAAG | SWMSWMAGAAGTAATTGGCCTTWCACT | 1844 | 2453 |
| VK3-11 10 0 9 | CCTGAAGATTTTGCAGTTTATTACTGTCAGCAGBHCNHCAATTGGCCTTWCACTTTTGGCGGAGGGACCAAG | CAGCAGBHCNHCAATTGGCCTTWCACT | 1845 | 2454 |
| VK3-11 11 0 9 | CCTGAAGATTTTGCAGTTTATTACTGTCAGCAGBHCAGTNHCTGGCCTTWCACTTTTGGCGGAGGGACCAAG | CAGCAGBHCAGTNHCTGGCCTTWCACT | 1846 | 2455 |
| VK3-11 12 0 9 | CCTGAAGATTTTGCAGTTTATTACTGTCAGCAGBHCAGTAATYWCCCTTWCACTTTTGGCGGAGGGACCAAG | CAGCAGBHCAGTAATYWCCCTTWCACT | 1847 | 2456 |
| VK3-11 13 0 9 | CCTGAAGATTTTGCAGTTTATTACTGTCAGCAGAGANHCNHCTGGCCTTWCACTTTTGGCGGAGGGACCAAG | CAGCAGAGANHCNHCTGGCCTTWCACT | 1848 | 2457 |
| VK3-11 14 0 9 | CCTGAAGATTTTGCAGTTTATTACTGTCAGCAGAGANHCAATYWCCCTTWCACTTTTGGCGGAGGGACCAAG | CAGCAGAGANHCAATYWCCCTTWCACT | 1849 | 2458 |
| VK3-11 15 0 9 | CCTGAAGATTTTGCAGTTTATTACTGTCAGCAGAGAAGTNHCYWCCCTTWCACTTTTGGCGGAGGGACCAAG | CAGCAGAGAAGTNHCYWCCCTTWCACT | 1850 | 2459 |
| VK3-11 2 0 9 | CCTGAAGATTTTGCAGTTTATTACTGTSWMCAGBHCAGTAATTGGCCTTWCACTTTTGGCGGAGGGACCAAG | SWMCAGBHCAGTAATTGGCCTTWCACT | 1851 | 2460 |
| VK3-11 3 0 9 | CCTGAAGATTTTGCAGTTTATTACTGTSWMCAGAGANHCAATTGGCCTTWCACTTTTGGCGGAGGGACCAAG | SWMCAGAGANHCAATTGGCCTTWCACT | 1852 | 2461 |
| VK3-11 4 0 9 | CCTGAAGATTTTGCAGTTTATTACTGTSWMCAGAGAAGTNHCTGGCCTTWCACTTTTGGCGGAGGGACCAAG | SWMCAGAGAAGTNHCTGGCCTTWCACT | 1853 | 2462 |
| VK3-11 5 0 9 | CCTGAAGATTTTGCAGTTTATTACTGTSWMCAGAGAAGTAATYWCCCTTWCACTTTTGGCGGAGGGACCAAG | SWMCAGAGAAGTAATYWCCCTTWCACT | 1854 | 2463 |
| VK3-1 16 0 9 | CCTGAAGATTTTGCAGTTTATTACTGTCAGSWMBHCAGTAATTGGCCTTWCACTTTTGGCGGAGGGACCAAG | CAGSWMBHCAGTAATTGGCCTTWCACT | 1855 | 2464 |
| VK3-11 7 0 9 | CCTGAAGATTTTGCAGTTTATTACTGTCAGSWMAGANHCAATTGGCCTTWCACTTTTGGCGGAGGGACCAAG | CAGSWMAGANHCAATTGGCCTTWCACT | 1856 | 2465 |
| VK3-11 8 0 9 | CCTGAAGATTTTGCAGTTTATTACTGTCAGSWMAGAAGTNHCTGGCCTTWCACTTTTGGCGGAGGGACCAAG | CAGSWMAGAAGTNHCTGGCCTTWCACT | 1857 | 2466 |
| VK3-11 9 0 9 | CCTGAAGATTTTGCAGTTTATTACTGTCAGSWMAGAAGTAATYWCCCTTWCACTTTTGGCGGAGGGACCAAG | CAGSWMAGAAGTAATYWCCCTTWCACT | 1858 | 2467 |
| VK3-11 1 1 9 | CCTGAAGATTTTGCAGTTTATTACTGTSWMSWMAGAAGTAATTGGCCTMTCACTTTTGGCGGAGGGACCAAG | SWMSWMAGAAGTAATTGGCCTMTCACT | 1859 | 2468 |
| VK3-11 10 1 9 | CCTGAAGATTTTGCAGTTTATTACTGTCAGCAGBHCNHCAATTGGCCTMTCACTTTTGGCGGAGGGACCAAG | CAGCAGBHCNHCAATTGGCCTMTCACT | 1860 | 2469 |
| VK3-11 11 1 9 | CCTGAAGATTTTGCAGTTTATTACTGTCAGCAGBHCAGTNHCTGGCCTMTCACTTTTGGCGGAGGGACCAAG | CAGCAGBHCAGTNHCTGGCCTMTCACT | 1861 | 2470 |

TABLE 6 -continued

Oligonucleotide sequences for exemplary VK jumping dimer and trimer sequences with CDRL3 length 9.

| Name | Sequence of Synthesized Oligonucleotide | Portion of Oligonucleotide Corresponding to CDRL3 Proper | SEQ ID NO (Oli-go) | SEQ ID NO (CDRL3 Por-tion) |
|---|---|---|---|---|
| VK3-11 12 1 9 | CCTGAAGATTTTGCAGTTTATTACTGTCAGCAGBHCAGTAATYWCCCTMTCACTTTTGGCGGAGGGACCAAG | CAGCAGBHCAGTAATYWCCCTMTCACT | 1862 | 2471 |
| VK3-11 13 1 9 | CCTGAAGATTTTGCAGTTTATTACTGTCAGCAGAGANHCNHCTGGCCTMTCACTTTTGGCGGAGGGACCAAG | CAGCAGAGANHCNHCTGGCCTMTCACT | 1863 | 2472 |
| VK3-11 14 1 9 | CCTGAAGATTTTGCAGTTTATTACTGTCAGCAGAGANHCAATYWCCCTMTCACTTTTGGCGGAGGGACCAAG | CAGCAGAGANHCAATYWCCCTMTCACT | 1864 | 2473 |
| VK3-11 15 1 9 | CCTGAAGATTTTGCAGTTTATTACTGTCAGCAGAGAAGTNHCYWCCCTMTCACTTTTGGCGGAGGGACCAAG | CAGCAGAGAAGTNHCYWCCCTMTCACT | 1865 | 2474 |
| VK3-11 2 1 9 | CCTGAAGATTTTGCAGTTTATTACTGTSWMCAGBHCAGTAATTGGCCTMTCACTTTTGGCGGAGGGACCAAG | SWMCAGBHCAGTAATTGGCCTMTCACT | 1866 | 2475 |
| VK3-11 3 1 9 | CCTGAAGATTTTGCAGTTTATTACTGTSWMCAGAGANHCAATTGGCCTMTCACTTTTGGCGGAGGGACCAAG | SWMCAGAGANHCAATTGGCCTMTCACT | 1867 | 2476 |
| VK3-11 4 1 9 | CCTGAAGATTTTGCAGTTTATTACTGTSWMCAGAGAAGTNHCTGGCCTMTCACTTTTGGCGGAGGGACCAAG | SWMCAGAGAAGTNHCTGGCCTMTCACT | 1868 | 2477 |
| VK3-11 5 1 9 | CCTGAAGATTTTGCAGTTTATTACTGTSWMCAGAGAAGTAATYWCCCTMTCACTTTTGGCGGAGGGACCAAG | SWMCAGAGAAGTAATYWCCCTMTCACT | 1869 | 2478 |
| VK3-11 6 1 9 | CCTGAAGATTTTGCAGTTTATTACTGTCAGSWMBHCAGTAATTGGCCTMTCACTTTTGGCGGAGGGACCAAG | CAGSWMBHCAGTAATTGGCCTMTCACT | 1870 | 2479 |
| VK3-11 7 1 9 | CCTGAAGATTTTGCAGTTTATTACTGTCAGSWMAGANHCAATTGGCCTMTCACTTTTGGCGGAGGGACCAAG | CAGSWMAGANHCAATTGGCCTMTCACT | 1871 | 2480 |
| VK3-11 8 1 9 | CCTGAAGATTTTGCAGTTTATTACTGTCAGSWMAGAAGTNHCTGGCCTMTCACTTTTGGCGGAGGGACCAAG | CAGSWMAGAAGTNHCTGGCCTMTCACT | 1872 | 2481 |
| VK3-11 9 1 9 | CCTGAAGATTTTGCAGTTTATTACTGTCAGSWMAGAAGTAATYWCCCTMTCACTTTTGGCGGAGGGACCAAG | CAGSWMAGAAGTAATYWCCCTMTCACT | 1873 | 2482 |
| VK3-11 1 2 9 | CCTGAAGATTTTGCAGTTTATTACTGTSWMSWMAGAAGTAATTGGCCTWGGACTTTTGGCGGAGGGACCAAG | SWMSWMAGAAGTAATTGGCCTWGGACT | 1874 | 2483 |
| VK3-11 10 2 9 | CCTGAAGATTTTGCAGTTTATTACTGTCAGCAGBHCNHCAATTGGCCTWGGACTTTTGGCGGAGGGACCAAG | CAGCAGBHCNHCAATTGGCCTWGGACT | 1875 | 2484 |
| VK3-11 11 2 9 | CCTGAAGATTTTGCAGTTTATTACTGTCAGCAGBHCAGTNHCTGGCCTWGGACTTTTGGCGGAGGGACCAAG | CAGCAGBHCAGTNHCTGGCCTWGGACT | 1876 | 2485 |
| VK3-11 12 2 9 | CCTGAAGATTTTGCAGTTTATTACTGTCAGCAGBHCAGTAATYWCCCTWGGACTTTTGGCGGAGGGACCAAG | CAGCAGBHCAGTAATYWCCCTWGGACT | 1877 | 2486 |
| VK3-11 13 2 9 | CCTGAAGATTTTGCAGTTTATTACTGTCAGCAGAGANHCNHCTGGCCTWGGACTTTTGGCGGAGGGACCAAG | CAGCAGAGANHCNHCTGGCCTWGGACT | 1878 | 2487 |
| VK3-11 14 2 9 | CCTGAAGATTTTGCAGTTTATTACTGTCAGCAGAGANHCAATYWCCCTWGGACTTTTGGCGGAGGGACCAAG | CAGCAGAGANHCAATYWCCCTWGGACT | 1879 | 2488 |
| VK3-11 15 2 9 | CCTGAAGATTTTGCAGTTTATTACTGTCAGCAGAGAAGTNHCYWCCCTWGGACTTTTGGCGGAGGGACCAAG | CAGCAGAGAAGTNHCYWCCCTWGGACT | 1880 | 2489 |
| VK3-11 2 2 9 | CCTGAAGATTTTGCAGTTTATTACTGTSWMCAGBHCAGTAATTGGCCTWGGACTTTTGGCGGAGGGACCAAG | SWMCAGBHCAGTAATTGGCCTWGGACT | 1881 | 2490 |
| VK3-11 3 2 9 | CCTGAAGATTTTGCAGTTTATTACTGTSWMCAGAGANHCAATTGGCCTWGGACTTTTGGCGGAGGGACCAAG | SWMCAGAGANHCAATTGGCCTWGGACT | 1882 | 2491 |
| VK3-11 4 2 9 | CCTGAAGATTTTGCAGTTTATTACTGTSWMCAGAGAAGTNHCTGGCCTWGGACTTTTGGCGGAGGGACCAAG | SWMCAGAGAAGTNHCTGGCCTWGGACT | 1883 | 2492 |
| VK3-11 5 2 9 | CCTGAAGATTTTGCAGTTTATTACTGTSWMCAGAGAAGTAATYWCCCTWGGACTTTTGGCGGAGGGACCAAG | SWMCAGAGAAGTAATYWCCCTWGGACT | 1884 | 2493 |

TABLE 6 -continued

Oligonucleotide sequences for exemplary VK jumping dimer and trimer sequences with CDRL3 length 9.

| Name | Sequence of Synthesized Oligonucleotide | Portion of Oligonucleotide Corresponding to CDRL3 Proper | SEQ ID NO (Oligo) | SEQ ID NO (CDRL3 Portion) |
|---|---|---|---|---|
| VK3-11 6 2 9 | CCTGAAGATTTTGCAGTTTATTACTGTCAGSWMBHCAGTAATTGGCCTWGGACTTTTGGCGGAGGGACCAAG | CAGSWMBHCAGTAATTGGCCTWGGACT | 1885 | 2494 |
| VK3-11 7 2 9 | CCTGAAGATTTTGCAGTTTATTACTGTCAGSWMAGANHCAATTGGCCTWGGACTTTTGGCGGAGGGACCAAG | CAGSWMAGANHCAATTGGCCTWGGACT | 1886 | 2495 |
| VK3-11 8 2 9 | CCTGAAGATTTTGCAGTTTATTACTGTCAGSWMAGAAGTNHCTGGCCTWGGACTTTTGGCGGAGGGACCAAG | CAGSWMAGAAGTNHCTGGCCTWGGACT | 1887 | 2496 |
| VK3-11 9 2 9 | CCTGAAGATTTTGCAGTTTATTACTGTCAGSWMAGAAGTAATYWCCCTWGGACTTTTGGCGGAGGGACCAAG | CAGSWMAGAAGTAATYWCCCTWGGACT | 1888 | 2497 |
| VK3-11 1 3 9 | CCTGAAGATTTTGCAGTTTATTACTGTSWMSWMAGAAGTAATTGGCCTCCTACTTTTGGCGGAGGGACCAAG | SWMSWMAGAAGTAATTGGCCTCCTACT | 1889 | 2498 |
| VK3-11 10 3 9 | CCTGAAGATTTTGCAGTTTATTACTGTCAGCAGBHCNHCAATTGGCCTCCTACTTTTGGCGGAGGGACCAAG | CAGCAGBHCNHCAATTGGCCTCCTACT | 1890 | 2499 |
| VK3-11 11 3 9 | CCTGAAGATTTTGCAGTTTATTACTGTCAGCAGBHCAGTNHCTGGCCTCCTACTTTTGGCGGAGGGACCAAG | CAGCAGBHCAGTNHCTGGCCTCCTACT | 1891 | 2500 |
| VK3-11 12 3 9 | CCTGAAGATTTTGCAGTTTATTACTGTCAGCAGBHCAGTAATYWCCCTCCTACTTTTGGCGGAGGGACCAAG | CAGCAGBHCAGTAATYWCCCTCCTACT | 1892 | 2501 |
| VK3-11 13 3 9 | CCTGAAGATTTTGCAGTTTATTACTGTCAGCAGAGANHCNHCTGGCCTCCTACTTTTGGCGGAGGGACCAAG | CAGCAGAGANHCNHCTGGCCTCCTACT | 1893 | 2502 |
| VK3-11 14 3 9 | CCTGAAGATTTTGCAGTTTATTACTGTCAGCAGAGANHCAATYWCCCTCCTACTTTTGGCGGAGGGACCAAG | CAGCAGAGANHCAATYWCCCTCCTACT | 1894 | 2503 |
| VK3-11 15 3 9 | CCTGAAGATTTTGCAGTTTATTACTGTCAGCAGAGAAGTNHCYWCCCTCCTACTTTTGGCGGAGGGACCAAG | CAGCAGAGAAGTNHCYWCCCTCCTACT | 1895 | 2504 |
| VK3-11 2 3 9 | CCTGAAGATTTTGCAGTTTATTACTGTSWMCAGBHCAGTAATTGGCCTCCTACTTTTGGCGGAGGGACCAAG | SWMCAGBHCAGTAATTGGCCTCCTACT | 1896 | 2505 |
| VK3-11 3 3 9 | CCTGAAGATTTTGCAGTTTATTACTGTSWMCAGAGANHCAATTGGCCTCCTACTTTTGGCGGAGGGACCAAG | SWMCAGAGANHCAATTGGCCTCCTACT | 1897 | 2506 |
| VK3-11 4 3 9 | CCTGAAGATTTTGCAGTTTATTACTGTSWMCAGAGAAGTNHCTGGCCTCCTACTTTTGGCGGAGGGACCAAG | SWMCAGAGAAGTNHCTGGCCTCCTACT | 1898 | 2507 |
| VK3-1 15 3 9 | CCTGAAGATTTTGCAGTTTATTACTGTSWMCAGAGAAGTAATYWCCCTCCTACTTTTGGCGGAGGGACCAAG | SWMCAGAGAAGTAATYWCCCTCCTACT | 1899 | 2508 |
| VK3-11 6 3 9 | CCTGAAGATTTTGCAGTTTATTACTGTCAGSWMBHCAGTAATTGGCCTCCTACTTTTGGCGGAGGGACCAAG | CAGSWMBHCAGTAATTGGCCTCCTACT | 1900 | 2509 |
| VK3-11 7 3 9 | CCTGAAGATTTTGCAGTTTATTACTGTCAGSWMAGANHCAATTGGCCTCCTACTTTTGGCGGAGGGACCAAG | CAGSWMAGANHCAATTGGCCTCCTACT | 1901 | 2510 |
| VK3-11 8 3 9 | CCTGAAGATTTTGCAGTTTATTACTGTCAGSWMAGAAGTNHCTGGCCTCCTACTTTTGGCGGAGGGACCAAG | CAGSWMAGAAGTNHCTGGCCTCCTACT | 1902 | 2511 |
| VK3-11 9 3 9 | CCTGAAGATTTTGCAGTTTATTACTGTCAGSWMAGAAGTAATYWCCCTCCTACTTTTGGCGGAGGGACCAAG | CAGSWMAGAAGTAATYWCCCTCCTACT | 1903 | 2512 |
| VK3-15 1 0 9 | CAGTCTGAAGATTTTGCAGTTTATTACTGTSWMSWMTACAATAATTGGCCTTWCACTTTTGGCGGAGGGACCAAG | SWMSWMTACAATAATTGGCCTTWCACT | 1904 | 2513 |
| VK3-15 10 0 9 | CAGTCTGAAGATTTTGCAGTTTATTACTGTCAGCAGBHCNHCAATTGGCCTTWCACTTTTGGCGGAGGGACCAAG | CAGCAGBHCNHCAATTGGCCTTWCACT | 1905 | 2454 |
| VK3-15 11 0 9 | CAGTCTGAAGATTTTGCAGTTTATTACTGTCAGCAGBHCAATNHCTGGCCTTWCACTTTTGGCGGAGGGACCAAG | CAGCAGBHCAATNHCTGGCCTTWCACT | 1906 | 2514 |
| VK3-15 12 0 9 | CAGTCTGAAGATTTTGCAGTTTATTACTGTCAGCAGBHCAATAATYWCCCTTWCACTTTTGGCGGAGGGACCAAG | CAGCAGBHCAATAATYWCCCTTWCACT | 1907 | 2515 |
| VK3-15 13 0 9 | CAGTCTGAAGATTTTGCAGTTTATTACTGTCAGCAGTACNHCNHCTGGCCTTWCACTTTTGGCGGAGGGACCAAG | CAGCAGTACNHCNHCTGGCCTTWCACT | 1908 | 2516 |

TABLE 6 -continued

Oligonucleotide sequences for exemplary VK jumping dimer and trimer sequences with CDRL3 length 9.

| Name | Sequence of Synthesized Oligonucleotide | Portion of Oligonucleotide Corresponding to CDRL3 Proper | SEQ ID NO (Oligo) | SEQ ID NO (CDRL3 Portion) |
|---|---|---|---|---|
| VK3-15 14 0 9 | CAGTCTGAAGATTTTGCAGTTTATTACTGTCAGCAGTACNHCAATYWCCCTTWCACTTTTGGCGGAGGGACCAAG | CAGCAGTACNHCAATYWCCCTTWCACT | 1909 | 2293 |
| VK3-15 15 0 9 | CAGTCTGAAGATTTTGCAGTTTATTACTGTCAGCAGTACAATNHCYWCCCTTWCACTTTTGGCGGAGGGACCAAG | CAGCAGTACAATNHCYWCCCTTWCACT | 1910 | 2517 |
| VK3-15 2 0 9 | CAGTCTGAAGATTTTGCAGTTTATTACTGTSWMCAGBHCAATAATTGGCCTTWCACTTTTGGCGGAGGGACCAAG | SWMCAGBHCAATAATTGGCCTTWCACT | 1911 | 2518 |
| VK3-15 3 0 9 | CAGTCTGAAGATTTTGCAGTTTATTACTGTSWMCAGTACNHCAATTGGCCTTWCACTTTTGGCGGAGGGACCAAG | SWMCAGTACNHCAATTGGCCTTWCACT | 1912 | 2519 |
| VK3-15 4 0 9 | CAGTCTGAAGATTTTGCAGTTTATTACTGTSWMCAGTACAATNHCTGGCCTTWCACTTTTGGCGGAGGGACCAAG | SWMCAGTACAATNHCTGGCCTTWCACT | 1913 | 2520 |
| VK3-15 5 0 9 | CAGTCTGAAGATTTTGCAGTTTATTACTGTSWMCAGTACAATAATYWCCCTTWCACTTTTGGCGGAGGGACCAAG | SWMCAGTACAATAATYWCCCTTWCACT | 1914 | 2521 |
| VK3-15 6 0 9 | CAGTCTGAAGATTTTGCAGTTTATTACTGTCAGSWMBHCAATAATTGGCCTTWCACTTTTGGCGGAGGGACCAAG | CAGSWMBHCAATAATTGGCCTTWCACT | 1915 | 2522 |
| VK3-15 7 0 9 | CAGTCTGAAGATTTTGCAGTTTATTACTGTCAGSWMTACNHCAATTGGCCTTWCACTTTTGGCGGAGGGACCAAG | CAGSWMTACNHCAATTGGCCTTWCACT | 1916 | 2523 |
| VK3-15 8 0 9 | CAGTCTGAAGATTTTGCAGTTTATTACTGTCAGSWMTACAATNHCTGGCCTTWCACTTTTGGCGGAGGGACCAAG | CAGSWMTACAATNHCTGGCCTTWCACT | 1917 | 2524 |
| VK3-15 9 0 9 | CAGTCTGAAGATTTTGCAGTTTATTACTGTCAGSWMTACAATAATYWCCCTTWCACTTTTGGCGGAGGGACCAAG | CAGSWMTACAATAATYWCCCTTWCACT | 1918 | 2525 |
| VK3-15 1 1 9 | CAGTCTGAAGATTTTGCAGTTTATTACTGTSWMSWMTACAATAATTGGCCTMTCACTTTTGGCGGAGGGACCAAG | SWMSWMTACAATAATTGGCCTMTCACT | 1919 | 2526 |
| VK3-15 10 1 9 | CAGTCTGAAGATTTTGCAGTTTATTACTGTCAGCAGBHCNHCAATTGGCCTMTCACTTTTGGCGGAGGGACCAAG | CAGCAGBHCNHCAATTGGCCTMTCACT | 1920 | 2469 |
| VK3-15 11 1 9 | CAGTCTGAAGATTTTGCAGTTTATTACTGTCAGCAGBHCAATNHCTGGCCTMTCACTTTTGGCGGAGGGACCAAG | CAGCAGBHCAATNHCTGGCCTMTCACT | 1921 | 2527 |
| VK3-15 12 1 9 | CAGTCTGAAGATTTTGCAGTTTATTACTGTCAGCAGBHCAATAATYWCCCTMTCACTTTTGGCGGAGGGACCAAG | CAGCAGBHCAATAATYWCCCTMTCACT | 1922 | 2528 |
| VK3-15 13 1 9 | CAGTCTGAAGATTTTGCAGTTTATTACTGTCAGCAGTACNHCNHCTGGCCTMTCACTTTTGGCGGAGGGACCAAG | CAGCAGTACNHCNHCTGGCCTMTCACT | 1923 | 2529 |
| VK3-15 14 1 9 | CAGTCTGAAGATTTTGCAGTTTATTACTGTCAGCAGTACNHCAATYWCCCTMTCACTTTTGGCGGAGGGACCAAG | CAGCAGTACNHCAATYWCCCTMTCACT | 1924 | 2308 |
| VK3-15 15 1 9 | CAGTCTGAAGATTTTGCAGTTTATTACTGTCAGCAGTACAATNHCYWCCCTMTCACTTTTGGCGGAGGGACCAAG | CAGCAGTACAATNHCYWCCCTMTCACT | 1925 | 2530 |
| VK3-15 2 1 9 | CAGTCTGAAGATTTTGCAGTTTATTACTGTSWMCAGBHCAATAATTGGCCTMTCACTTTTGGCGGAGGGACCAAG | SWMCAGBHCAATAATTGGCCTMTCACT | 1926 | 2531 |
| VK3-15 3 1 9 | CAGTCTGAAGATTTTGCAGTTTATTACTGTSWMCAGTACNHCAATTGGCCTMTCACTTTTGGCGGAGGGACCAAG | SWMCAGTACNHCAATTGGCCTMTCACT | 1927 | 2532 |
| VK3-15 4 1 9 | CAGTCTGAAGATTTTGCAGTTTATTACTGTSWMCAGTACAATNHCTGGCCTMTCACTTTTGGCGGAGGGACCAAG | SWMCAGTACAATNHCTGGCCTMTCACT | 1928 | 2533 |
| VK3-15 5 1 9 | CAGTCTGAAGATTTTGCAGTTTATTACTGTSWMCAGTACAATAATYWCCCTMTCACTTTTGGCGGAGGGACCAAG | SWMCAGTACAATAATYWCCCTMTCACT | 1929 | 2534 |
| VK3-15 6 1 9 | CAGTCTGAAGATTTTGCAGTTTATTACTGTCAGSWMBHCAATAATTGGCCTMTCACTTTTGGCGGAGGGACCAAG | CAGSWMBHCAATAATTGGCCTMTCACT | 1930 | 2535 |
| VK3-15 7 1 9 | CAGTCTGAAGATTTTGCAGTTTATTACTGTCAGSWMTACNHCAATTGGCCTMTCACTTTTGGCGGAGGGACCAAG | CAGSWMTACNHCAATTGGCCTMTCACT | 1931 | 2536 |

TABLE 6 -continued

Oligonucleotide sequences for exemplary VK jumping dimer and trimer sequences with CDRL3 length 9.

| Name | Sequence of Synthesized Oligonucleotide | Portion of Oligonucleotide Corresponding to CDRL3 Proper | SEQ ID NO (Oli-go) | SEQ ID NO (CDRL3 Por-tion) |
|---|---|---|---|---|
| VK3-15 8 1 9 | CAGTCTGAAGATTTTGCAGTTTATTACTGTCAGSWMTACAATNHCTGGCCTMTCACTTTTGGCGGAGGGACCAAG | CAGSWMTACAATNHCTGGCCTMTCACT | 1932 | 2537 |
| VK3-15 9 1 9 | CAGTCTGAAGATTTTGCAGTTTATTACTGTCAGSWMTACAATAATYWCCCTMTCACTTTTGGCGGAGGGACCAAG | CAGSWMTACAATAATYWCCCTMTCACT | 1933 | 2538 |
| VK3-15 1 2 9 | CAGTCTGAAGATTTTGCAGTTTATTACTGTSWMSWMTACAATAATTGGCCTWGGACTTTTGGCGGAGGGACCAAG | SWMSWMTACAATAATTGGCCTWGGACT | 1934 | 2539 |
| VK3-15 10 2 9 | CAGTCTGAAGATTTTGCAGTTTATTACTGTCAGCAGBHCNHCAATTGGCCTWGGACTTTTGGCGGAGGGACCAAG | CAGCAGBHCNHCAATTGGCCTWGGACT | 1935 | 2484 |
| VK3-15 11 2 9 | CAGTCTGAAGATTTTGCAGTTTATTACTGTCAGCAGBHCAATNHCTGGCCTWGGACTTTTGGCGGAGGGACCAAG | CAGCAGBHCAATNHCTGGCCTWGGACT | 1936 | 2540 |
| VK3-15 12 2 9 | CAGTCTGAAGATTTTGCAGTTTATTACTGTCAGCAGBHCAATAATYWCCCTWGGACTTTTGGCGGAGGGACCAAG | CAGCAGBHCAATAATYWCCCTWGGACT | 1937 | 2541 |
| VK3-15 13 2 9 | CAGTCTGAAGATTTTGCAGTTTATTACTGTCAGCAGTACNHCNHCTGGCCTWGGACTTTTGGCGGAGGGACCAAG | CAGCAGTACNHCNHCTGGCCTWGGACT | 1938 | 2542 |
| VK3-15 14 2 9 | CAGTCTGAAGATTTTGCAGTTTATTACTGTCAGCAGTACNHCAATYWCCCTWGGACTTTTGGCGGAGGGACCAAG | CAGCAGTACNHCAATYWCCCTWGGACT | 1939 | 2323 |
| VK3-15 15 2 9 | CAGTCTGAAGATTTTGCAGTTTATTACTGTCAGCAGTACAATNHCYWCCCTWGGACTTTTGGCGGAGGGACCAAG | CAGCAGTACAATNHCYWCCCTWGGACT | 1940 | 2543 |
| VK3-15 2 2 9 | CAGTCTGAAGATTTTGCAGTTTATTACTGTSWMCAGBHCAATAATTGGCCTWGGACTTTTGGCGGAGGGACCAAG | SWMCAGBHCAATAATTGGCCTWGGACT | 1941 | 2544 |
| VK3-15 3 2 9 | CAGTCTGAAGATTTTGCAGTTTATTACTGTSWMCAGTACNHCAATTGGCCTWGGACTTTTGGCGGAGGGACCAAG | SWMCAGTACNHCAATTGGCCTWGGACT | 1942 | 2545 |
| VK3-15 4 2 9 | CAGTCTGAAGATTTTGCAGTTTATTACTGTSWMCAGTACAATNHCTGGCCTWGGACTTTTGGCGGAGGGACCAAG | SWMCAGTACAATNHCTGGCCTWGGACT | 1943 | 2546 |
| VK3-15 5 2 9 | CAGTCTGAAGATTTTGCAGTTTATTACTGTSWMCAGTACAATAATYWCCCTWGGACTTTTGGCGGAGGGACCAAG | SWMCAGTACAATAATYWCCCTWGGACT | 1944 | 2547 |
| VK3-15 6 2 9 | CAGTCTGAAGATTTTGCAGTTTATTACTGTCAGSWMBHCAATAATTGGCCTWGGACTTTTGGCGGAGGGACCAAG | CAGSWMBHCAATAATTGGCCTWGGACT | 1945 | 2548 |
| VK3-15 7 2 9 | CAGTCTGAAGATTTTGCAGTTTATTACTGTCAGSWMTACNHCAATTGGCCTWGGACTTTTGGCGGAGGGACCAAG | CAGSWMTACNHCAATTGGCCTWGGACT | 1946 | 2549 |
| VK3-15 8 2 9 | CAGTCTGAAGATTTTGCAGTTTATTACTGTCAGSWMTACAATNHCTGGCCTWGGACTTTTGGCGGAGGGACCAAG | CAGSWMTACAATNHCTGGCCTWGGACT | 1947 | 2550 |
| VK3-15 9 2 9 | CAGTCTGAAGATTTTGCAGTTTATTACTGTCAGSWMTACAATAATYWCCCTWGGACTTTTGGCGGAGGGACCAAG | CAGSWMTACAATAATYWCCCTWGGACT | 1948 | 2551 |
| VK3-15 1 3 9 | CAGTCTGAAGATTTTGCAGTTTATTACTGTSWMSWMTACAATAATTGGCCTCCTACTTTTGGCGGAGGGACCAAG | SWMSWMTACAATAATTGGCCTCCTACT | 1949 | 2552 |
| VK3-15 10 3 9 | CAGTCTGAAGATTTTGCAGTTTATTACTGTCAGCAGBHCNHCAATTGGCCTCCTACTTTTGGCGGAGGGACCAAG | CAGCAGBHCNHCAATTGGCCTCCTACT | 1950 | 2499 |
| VK3-15 11 3 9 | CAGTCTGAAGATTTTGCAGTTTATTACTGTCAGCAGBHCAATNHCTGGCCTCCTACTTTTGGCGGAGGGACCAAG | CAGCAGBHCAATNHCTGGCCTCCTACT | 1951 | 2553 |
| VK3-15 12 3 9 | CAGTCTGAAGATTTTGCAGTTTATTACTGTCAGCAGBHCAATAATYWCCCTCCTACTTTTGGCGGAGGGACCAAG | CAGCAGBHCAATAATYWCCCTCCTACT | 1952 | 2554 |
| VK3-15 13 3 9 | CAGTCTGAAGATTTTGCAGTTTATTACTGTCAGCAGTACNHCNHCTGGCCTCCTACTTTTGGCGGAGGGACCAAG | CAGCAGTACNHCNHCTGGCCTCCTACT | 1953 | 2555 |
| VK3-15 14 3 9 | CAGTCTGAAGATTTTGCAGTTTATTACTGTCAGCAGTACNHCAATYWCCCTCCTACTTTTGGCGGAGGGACCAAG | CAGCAGTACNHCAATYWCCCTCCTACT | 1954 | 2338 |
| VK3-15 15 3 9 | CAGTCTGAAGATTTTGCAGTTTATTACTGTCAGCAGTACAATNHCYWCCCTCCTACTTTTGGCGGAGGGACCAAG | CAGCAGTACAATNHCYWCCCTCCTACT | 1955 | 2556 |

TABLE 6 -continued

Oligonucleotide sequences for exemplary VK jumping dimer and trimer sequences with CDRL3 length 9.

| Name | Sequence of Synthesized Oligonucleotide | Portion of Oligonucleotide Corresponding to CDRL3 Proper | SEQ ID NO (Oligo) | SEQ ID NO (CDRL3 Portion) |
|---|---|---|---|---|
| VK3-15 2 3 9 | CAGTCTGAAGATTTTGCAGTTTATTACTGTSWMCAGBHCAA TAATTGGCCTCCTACTTTTGGCGGAGGGACCAAG | SWMCAGBHCAATAATTGGCCTC CTACT | 1956 | 2557 |
| VK3-15 3 3 9 | CAGTCTGAAGATTTTGCAGTTTATTACTGTSWMCAGTACNH CAATTGGCCTCCTACTTTTGGCGGAGGGACCAAG | SWMCAGTACNHCAATTGGCCTC CTACT | 1957 | 2558 |
| VK3-15 4 3 9 | CAGTCTGAAGATTTTGCAGTTTATTACTGTSWMCAGTACAA TNHCTGGCCTCCTACTTTTGGCGGAGGGACCAAG | SWMCAGTACAATNHCTGGCCTC CTACT | 1958 | 2559 |
| VK3-15 5 3 9 | CAGTCTGAAGATTTTGCAGTTTATTACTGTSWMCAGTACAA TAATYWCCCTCCTACTTTTGGCGGAGGGACCAAG | SWMCAGTACAATAATYWCCCTC CTACT | 1959 | 2560 |
| VK3-15 6 3 9 | CAGTCTGAAGATTTTGCAGTTTATTACTGTCAGSWMBHCAA TAATTGGCCTCCTACTTTTGGCGGAGGGACCAAG | CAGSWMBHCAATAATTGGCCTC CTACT | 1960 | 2561 |
| VK3-15 7 3 9 | CAGTCTGAAGATTTTGCAGTTTATTACTGTCAGSWMTACNH CAATTGGCCTCCTACTTTTGGCGGAGGGACCAAG | CAGSWMTACNHCAATTGGCCTC CTACT | 1961 | 2562 |
| VK3-15 8 3 9 | CAGTCTGAAGATTTTGCAGTTTATTACTGTCAGSWMTACAA TNHCTGGCCTCCTACTTTTGGCGGAGGGACCAAG | CAGSWMTACAATNHCTGGCCTC CTACT | 1962 | 2563 |
| VK3-15 9 3 9 | CAGTCTGAAGATTTTGCAGTTTATTACTGTCAGSWMTACAA TAATYWCCCTCCTACTTTTGGCGGAGGGACCAAG | CAGSWMTACAATAATYWCCCTC CTACT | 1963 | 2564 |
| VK3-20 1 0 9 | CCTGAAGATTTTGCAGTGTATTACTGTSWMSWMTACGGAAG TAGTCCTTWCACTTTTGGCGGAGGGACCAAG | SWMSWMTACGGAAGTAGTCCTT WCACT | 1964 | 2565 |
| VK3-20 10 0 9 | CCTGAAGATTTTGCAGTGTATTACTGTCAGCAGBHCBHCAG TAGTCCTTWCACTTTTGGCGGAGGGACCAAG | CAGCAGBHCBHCAGTAGTCCTT WCACT | 1965 | 2566 |
| VK3-20 11 0 9 | CCTGAAGATTTTGCAGTGTATTACTGTCAGCAGBHCGGAVN CAGTCCTTWCACTTTTGGCGGAGGGACCAAG | CAGCAGBHCGGAVNCAGTCCTT WCACT | 1966 | 2567 |
| VK3-20 12 0 9 | CCTGAAGATTTTGCAGTGTATTACTGTCAGCAGBHCGGAAG TBHCCCTTWCACTTTTGGCGGAGGGACCAAG | CAGCAGBHCGGAAGTBHCCCTT WCACT | 1967 | 2568 |
| VK3-20 13 0 9 | CCTGAAGATTTTGCAGTGTATTACTGTCAGCAGTACBHCVN CAGTCCTTWCACTTTTGGCGGAGGGACCAAG | CAGCAGTACBHCVNCAGTCCTT WCACT | 1968 | 2569 |
| VK3-20 14 0 9 | CCTGAAGATTTTGCAGTGTATTACTGTCAGCAGTACBHCAG TBHCCCTTWCACTTTTGGCGGAGGGACCAAG | CAGCAGTACBHCAGTBHCCCTT WCACT | 1969 | 2570 |
| VK3-20 15 0 9 | CCTGAAGATTTTGCAGTGTATTACTGTCAGCAGTACGGAVN CBHCCCTTWCACTTTTGGCGGAGGGACCAAG | CAGCAGTACGGAVNCBHCCCTT WCACT | 1970 | 2571 |
| VK3-20 2 0 9 | CCTGAAGATTTTGCAGTGTATTACTGTSWMCAGBHCGGAAG TAGTCCTTWCACTTTTGGCGGAGGGACCAAG | SWMCAGBHCGGAAGTAGTCCTT WCACT | 1971 | 2572 |
| VK3-20 3 0 9 | CCTGAAGATTTTGCAGTGTATTACTGTSWMCAGTACBHCAG TAGTCCTTWCACTTTTGGCGGAGGGACCAAG | SWMCAGTACBHCAGTAGTCCTT WCACT | 1972 | 2573 |
| VK3-20 4 0 9 | CCTGAAGATTTTGCAGTGTATTACTGTSWMCAGTACGGAVN CAGTCCTTWCACTTTTGGCGGAGGGACCAAG | SWMCAGTACGGAVNCAGTCCTT WCACT | 1973 | 2574 |
| VK3-20 5 0 9 | CCTGAAGATTTTGCAGTGTATTACTGTSWMCAGTACGGAAG TBHCCCTTWCACTTTTGGCGGAGGGACCAAG | SWMCAGTACGGAAGTBHCCCTT WCACT | 1974 | 2575 |
| VK3-20 6 0 9 | CCTGAAGATTTTGCAGTGTATTACTGTCAGSWMBHCGGAAG TAGTCCTTWCACTTTTGGCGGAGGGACCAAG | CAGSWMBHCGGAAGTAGTCCTT WCACT | 1975 | 2576 |
| VK3-20 7 0 9 | CCTGAAGATTTTGCAGTGTATTACTGTCAGSWMTACBHCAG TAGTCCTTWCACTTTTGGCGGAGGGACCAAG | CAGSWMTACBHCAGTAGTCCTT WCACT | 1976 | 2577 |
| VK3-20 8 0 9 | CCTGAAGATTTTGCAGTGTATTACTGTCAGSWMTACGGAVN CAGTCCTTWCACTTTTGGCGGAGGGACCAAG | CAGSWMTACGGAVNCAGTCCTT WCACT | 1977 | 2578 |
| VK3-20 9 0 9 | CCTGAAGATTTTGCAGTGTATTACTGTCAGSWMTACGGAAG TBHCCCTTWCACTTTTGGCGGAGGGACCAAG | CAGSWMTACGGAAGTBHCCCTT WCACT | 1978 | 2579 |

TABLE 6 -continued

Oligonucleotide sequences for exemplary VK jumping dimer and trimer sequences with CDRL3 length 9.

| Name | Sequence of Synthesized Oligonucleotide | Portion of Oligonucleotide Corresponding to CDRL3 Proper | SEQ ID NO (Oligo) | SEQ ID NO (CDRL3 Portion) |
|---|---|---|---|---|
| VK3-20 1 1 9 | CCTGAAGATTTTGCAGTGTATTACTGTSWMSWMTACGGAAGTAGTCCTMTCACTTTTGGCGGAGGGACCAAG | SWMSWMTACGGAAGTAGTCCTMTCACT | 1979 | 2580 |
| VK3-20 10 1 9 | CCTGAAGATTTTGCAGTGTATTACTGTCAGCAGBHCBHCAGTAGTCCTMTCACTTTTGGCGGAGGGACCAAG | CAGCAGBHCBHCAGTAGTCCTMTCACT | 1980 | 2581 |
| VK3-20 11 1 9 | CCTGAAGATTTTGCAGTGTATTACTGTCAGCAGBHCGGAVNCAGTCCTMTCACTTTTGGCGGAGGGACCAAG | CAGCAGBHCGGAVNCAGTCCTMTCACT | 1981 | 2582 |
| VK3-20 12 1 9 | CCTGAAGATTTTGCAGTGTATTACTGTCAGCAGBHCGGAAGTBHCCCTMTCACTTTTGGCGGAGGGACCAAG | CAGCAGBHCGGAAGTBHCCCTMTCACT | 1982 | 2583 |
| VK3-20 13 1 9 | CCTGAAGATTTTGCAGTGTATTACTGTCAGCAGTACBHCVNCAGTCCTMTCACTTTTGGCGGAGGGACCAAG | CAGCAGTACBHCVNCAGTCCTMTCACT | 1983 | 2584 |
| VK3-20 14 1 9 | CCTGAAGATTTTGCAGTGTATTACTGTCAGCAGTACBHCAGTBHCCCTMTCACTTTTGGCGGAGGGACCAAG | CAGCAGTACBHCAGTBHCCCTMTCACT | 1984 | 2585 |
| VK3-20 15 1 9 | CCTGAAGATTTTGCAGTGTATTACTGTCAGCAGTACGGAVNCBHCCCTMTCACTTTTGGCGGAGGGACCAAG | CAGCAGTACGGAVNCBHCCCTMTCACT | 1985 | 2586 |
| VK3-20 2 1 9 | CCTGAAGATTTTGCAGTGTATTACTGTSWMCAGBHCGGAAGTAGTCCTMTCACTTTTGGCGGAGGGACCAAG | SWMCAGBHCGGAAGTAGTCCTMTCACT | 1986 | 2587 |
| VK3-20 3 1 9 | CCTGAAGATTTTGCAGTGTATTACTGTSWMCAGTACBHCAGTAGTCCTMTCACTTTTGGCGGAGGGACCAAG | SWMCAGTACBHCAGTAGTCCTMTCACT | 1987 | 2588 |
| VK3-20 4 1 9 | CCTGAAGATTTTGCAGTGTATTACTGTSWMCAGTACGGAVNCAGTCCTMTCACTTTTGGCGGAGGGACCAAG | SWMCAGTACGGAVNCAGTCCTMTCACT | 1988 | 2589 |
| VK3-20 5 1 9 | CCTGAAGATTTTGCAGTGTATTACTGTSWMCAGTACGGAAGTBHCCCTMTCACTTTTGGCGGAGGGACCAAG | SWMCAGTACGGAAGTBHCCCTMTCACT | 1989 | 2590 |
| VK3-20 6 1 9 | CCTGAAGATTTTGCAGTGTATTACTGTCAGSWMBHCGGAAGTAGTCCTMTCACTTTTGGCGGAGGGACCAAG | CAGSWMBHCGGAAGTAGTCCTMTCACT | 1990 | 2591 |
| VK3-20 7 1 9 | CCTGAAGATTTTGCAGTGTATTACTGTCAGSWMTACBHCAGTAGTCCTMTCACTTTTGGCGGAGGGACCAAG | CAGSWMTACBHCAGTAGTCCTMTCACT | 1991 | 2592 |
| VK3-20 8 1 9 | CCTGAAGATTTTGCAGTGTATTACTGTCAGSWMTACGGAVNCAGTCCTMTCACTTTTGGCGGAGGGACCAAG | CAGSWMTACGGAVNCAGTCCTMTCACT | 1992 | 2593 |
| VK3-20 9 1 9 | CCTGAAGATTTTGCAGTGTATTACTGTCAGSWMTACGGAAGTBHCCCTMTCACTTTTGGCGGAGGGACCAAG | CAGSWMTACGGAAGTBHCCCTMTCACT | 1993 | 2594 |
| VK3-20 1 2 9 | CCTGAAGATTTTGCAGTGTATTACTGTSWMSWMTACGGAAGTAGTCCTWGGACTTTTGGCGGAGGGACCAAG | SWMSWMTACGGAAGTAGTCCTWGGACT | 1994 | 2595 |
| VK3-20 10 2 9 | CCTGAAGATTTTGCAGTGTATTACTGTCAGCAGBHCBHCAGTAGTCCTWGGACTTTTGGCGGAGGGACCAAG | CAGCAGBHCBHCAGTAGTCCTWGGACT | 1995 | 2596 |
| VK3-20 11 2 9 | CCTGAAGATTTTGCAGTGTATTACTGTCAGCAGBHCGGAVNCAGTCCTWGGACTTTTGGCGGAGGGACCAAG | CAGCAGBHCGGAVNCAGTCCTWGGACT | 1996 | 2597 |
| VK3-20 12 2 9 | CCTGAAGATTTTGCAGTGTATTACTGTCAGCAGBHCGGAAGTBHCCCTWGGACTTTTGGCGGAGGGACCAAG | CAGCAGBHCGGAAGTBHCCCTWGGACT | 1997 | 2598 |
| VK3-20 13 2 9 | CCTGAAGATTTTGCAGTGTATTACTGTCAGCAGTACBHCVNCAGTCCTWGGACTTTTGGCGGAGGGACCAAG | CAGCAGTACBHCVNCAGTCCTWGGACT | 1998 | 2599 |
| VK3-20 14 2 9 | CCTGAAGATTTTGCAGTGTATTACTGTCAGCAGTACBHCAGTBHCCCTWGGACTTTTGGCGGAGGGACCAAG | CAGCAGTACBHCAGTBHCCCTWGGACT | 1999 | 2600 |
| VK3-20 15 2 9 | CCTGAAGATTTTGCAGTGTATTACTGTCAGCAGTACGGAVNCBHCCCTWGGACTTTTGGCGGAGGGACCAAG | CAGCAGTACGGAVNCBHCCCTWGGACT | 2000 | 2601 |
| VK3-20 2 2 9 | CCTGAAGATTTTGCAGTGTATTACTGTSWMCAGBHCGGAAGTAGTCCTWGGACTTTTGGCGGAGGGACCAAG | SWMCAGBHCGGAAGTAGTCCTWGGACT | 2001 | 2602 |
| VK3-20 3 2 9 | CCTGAAGATTTTGCAGTGTATTACTGTSWMCAGTACBHCAGTAGTCCTWGGACTTTTGGCGGAGGGACCAAG | SWMCAGTACBHCAGTAGTCCTWGGACT | 2002 | 2603 |

TABLE 6 -continued

Oligonucleotide sequences for exemplary VK jumping dimer and trimer sequences with CDRL3 length 9.

| Name | Sequence of Synthesized Oligonucleotide | Portion of Oligonucleotide Corresponding to CDRL3 Proper | SEQ ID NO (Oli-go) | SEQ ID NO (CDRL3 Por-tion) |
|---|---|---|---|---|
| VK3-20 4 2 9 | CCTGAAGATTTTGCAGTGTATTACTGTSWMCAGTACGGAVN CAGTCCTWGGACTTTTGGCGGAGGGACCAAG | SWMCAGTACGGAVNCAGTCCTW GGACT | 2003 | 2604 |
| VK3-20 5 2 9 | CCTGAAGATTTTGCAGTGTATTACTGTSWMCAGTACGGAAG TBHCCCTWGGACTTTTGGCGGAGGGACCAAG | SWMCAGTACGGAAGTBHCCCTW GGACT | 2004 | 2605 |
| VK3-20 6 2 9 | CCTGAAGATTTTGCAGTGTATTACTGTCAGSWMBHCGGAAG TAGTCCTWGGACTTTTGGCGGAGGGACCAAG | CAGSWMBHCGGAAGTAGTCCTW GGACT | 2005 | 2606 |
| VK3-20 7 2 9 | CCTGAAGATTTTGCAGTGTATTACTGTCAGSWMTACBHCAG TAGTCCTWGGACTTTTGGCGGAGGGACCAAG | CAGSWMTACBHCAGTAGTCCTW GGACT | 2006 | 2607 |
| VK3-20 8 2 9 | CCTGAAGATTTTGCAGTGTATTACTGTCAGSWMTACGGAVN CAGTCCTWGGACTTTTGGCGGAGGGACCAAG | CAGSWMTACGGAVNCAGTCCTW GGACT | 2007 | 2608 |
| VK3-20 9 2 9 | CCTGAAGATTTTGCAGTGTATTACTGTCAGSWMTACGGAAG TBHCCCTWGGACTTTTGGCGGAGGGACCAAG | CAGSWMTACGGAAGTBHCCCTW GGACT | 2008 | 2609 |
| VK3-20 1 3 9 | CCTGAAGATTTTGCAGTGTATTACTGTSWMSWMTACGGAAG TAGTCCTCCTACTTTTGGCGGAGGGACCAAG | SWMSWMTACGGAAGTAGTCCTC CTACT | 2009 | 2610 |
| VK3-20 10 3 9 | CCTGAAGATTTTGCAGTGTATTACTGTCAGCAGBHCBHCAG TAGTCCTCCTACTTTTGGCGGAGGGACCAAG | CAGCAGBHCBHCAGTAGTCCTC CTACT | 2010 | 2611 |
| VK3-20 11 3 9 | CCTGAAGATTTTGCAGTGTATTACTGTCAGCAGBHCGGAVN CAGTCCTCCTACTTTTGGCGGAGGGACCAAG | CAGCAGBHCGGAVNCAGTCCTC CTACT | 2011 | 2612 |
| VK3-20 12 3 9 | CCTGAAGATTTTGCAGTGTATTACTGTCAGCAGBHCGGAAG TBHCCCTCCTACTTTTGGCGGAGGGACCAAG | CAGCAGBHCGGAAGTBHCCCTC CTACT | 2012 | 2613 |
| VK3-20 13 3 9 | CCTGAAGATTTTGCAGTGTATTACTGTCAGCAGTACBHCVN CAGTCCTCCTACTTTTGGCGGAGGGACCAAG | CAGCAGTACBHCVNCAGTCCTC CTACT | 2013 | 2614 |
| VK3-20 14 3 9 | CCTGAAGATTTTGCAGTGTATTACTGTCAGCAGTACBHCAG TBHCCCTCCTACTTTTGGCGGAGGGACCAAG | CAGCAGTACBHCAGTBHCCCTC CTACT | 2014 | 2615 |
| VK3-20 15 3 9 | CCTGAAGATTTTGCAGTGTATTACTGTCAGCAGTACGGAVN CBHCCCTCCTACTTTTGGCGGAGGGACCAAG | CAGCAGTACGGAVNCBHCCCTC CTACT | 2015 | 2616 |
| VK3-20 2 3 9 | CCTGAAGATTTTGCAGTGTATTACTGTSWMCAGBHCGGAAG TAGTCCTCCTACTTTTGGCGGAGGGACCAAG | SWMCAGBHCGGAAGTAGTCCTC CTACT | 2016 | 2617 |
| VK3-20 3 3 9 | CCTGAAGATTTTGCAGTGTATTACTGTSWMCAGTACBHCAG TAGTCCTCCTACTTTTGGCGGAGGGACCAAG | SWMCAGTACBHCAGTAGTCCTC CTACT | 2017 | 2618 |
| VK3-20 4 3 9 | CCTGAAGATTTTGCAGTGTATTACTGTSWMCAGTACGGAVN CAGTCCTCCTACTTTTGGCGGAGGGACCAAG | SWMCAGTACGGAVNCAGTCCTC CTACT | 2018 | 2619 |
| VK3-20 5 3 9 | CCTGAAGATTTTGCAGTGTATTACTGTSWMCAGTACGGAAG TBHCCCTCCTACTTTTGGCGGAGGGACCAAG | SWMCAGTACGGAAGTBHCCCTC CTACT | 2019 | 2620 |
| VK3-20 6 3 9 | CCTGAAGATTTTGCAGTGTATTACTGTCAGSWMBHCGGAAG TAGTCCTCCTACTTTTGGCGGAGGGACCAAG | CAGSWMBHCGGAAGTAGTCCTC CTACT | 2020 | 2621 |
| VK3-20 7 3 9 | CCTGAAGATTTTGCAGTGTATTACTGTCAGSWMTACBHCAG TAGTCCTCCTACTTTTGGCGGAGGGACCAAG | CAGSWMTACBHCAGTAGTCCTC CTACT | 2021 | 2622 |
| VK3-20 8 3 9 | CCTGAAGATTTTGCAGTGTATTACTGTCAGSWMTACGGAVN CAGTCCTCCTACTTTTGGCGGAGGGACCAAG | CAGSWMTACGGAVNCAGTCCTC CTACT | 2022 | 2623 |
| VK3-20 9 3 9 | CCTGAAGATTTTGCAGTGTATTACTGTCAGSWMTACGGAAG TBHCCCTCCTACTTTTGGCGGAGGGACCAAG | CAGSWMTACGGAAGTBHCCCTC CTACT | 2023 | 2624 |
| Jumping Trimer | | | | |
| VK1-05_t1_0_9 | CCTGATGATTTTGCAACTTATTACTGCCAGCAGBHCVRMMBCTAC YCTTWCACTTTTGGCGGAGGGACCAAG | CAGCAGBHCVRMMBCTACYCTTWC ACT | 2024 | 2625 |
| VK1-05_t1_1_9 | CCTGATGATTTTGCAACTTATTACTGCCAGCAGBHCVRMMBCTAC YCTMTCACTTTTGGCGGAGGGACCAAG | CAGCAGBHCVRMMBCTACYCTMTC ACT | 2025 | 2626 |

TABLE 6 -continued

Oligonucleotide sequences for exemplary VK jumping dimer and trimer sequences with CDRL3 length 9.

| Name | Sequence of Synthesized Oligonucleotide | Portion of Oligonucleotide Corresponding to CDRL3 Proper | SEQ ID NO (Oli-go) | SEQ ID NO (CDRL3 Por-tion) |
|---|---|---|---|---|
| VK1-05_t1_2_9 | CCTGATGATTTTGCAACTTATTACTGCCAGCAGBHCVRMMBCTACYCTWGGACTTTTGGCGGAGGGACCAAG | CAGCAGBHCVRMMBCTACYCTWGGACT | 2026 | 2627 |
| VK1-05_t1_3_9 | CCTGATGATTTTGCAACTTATTACTGCCAGCAGBHCVRMMBCTACYCTCCTACTTTTGGCGGAGGGACCAAG | CAGCAGBHCVRMMBCTACYCTCCTACT | 2027 | 2628 |
| VK1-05_t2_0_9 | CCTGATGATTTTGCAACTTATTACTGCCAGCAGBHCAATMBCYWCYCTTWCACTTTTGGCGGAGGGACCAAG | CAGCAGBHCAATMBCYWCYCTTWCACT | 2028 | 2629 |
| VK1-05_t2_1_9 | CCTGATGATTTTGCAACTTATTACTGCCAGCAGBHCAATMBCYWCYCTMTCACTTTTGGCGGAGGGACCAAG | CAGCAGBHCAATMBCYWCYCTMTCACT | 2029 | 2630 |
| VK1-05_t2_2_9 | CCTGATGATTTTGCAACTTATTACTGCCAGCAGBHCAATMBCYWCYCTWGGACTTTTGGCGGAGGGACCAAG | CAGCAGBHCAATMBCYWCYCTWGGACT | 2030 | 2631 |
| VK1-05_t2_3_9 | CCTGATGATTTTGCAACTTATTACTGCCAGCAGBHCAATMBCYWCYCTCCTACTTTTGGCGGAGGGACCAAG | CAGCAGBHCAATMBCYWCYCTCCTACT | 2031 | 2632 |
| VK1-05_t3_0_9 | CCTGATGATTTTGCAACTTATTACTGCCAGCAGBHCVRMAGTYWCYCTTWCACTTTTGGCGGAGGGACCAAG | CAGCAGBHCVRMAGTYWCYCTTWCACT | 2032 | 2633 |
| VK1-05_t3_1_9 | CCTGATGATTTTGCAACTTATTACTGCCAGCAGBHCVRMAGTYWCYCTMTCACTTTTGGCGGAGGGACCAAG | CAGCAGBHCVRMAGTYWCYCTMTCACT | 2033 | 2634 |
| VK1-05_t3_2_9 | CCTGATGATTTTGCAACTTATTACTGCCAGCAGBHCVRMAGTYWCYCTWGGACTTTTGGCGGAGGGACCAAG | CAGCAGBHCVRMAGTYWCYCTWGGACT | 2034 | 2635 |
| VK1-05_t3_3_9 | CCTGATGATTTTGCAACTTATTACTGCCAGCAGBHCVRMAGTYWCYCTCCTACTTTTGGCGGAGGGACCAAG | CAGCAGBHCVRMAGTYWCYCTCCTACT | 2035 | 2636 |
| VK1-05_t4_0_9 | CCTGATGATTTTGCAACTTATTACTGCCAGCAGTACVRMMBCYWCYCTTWCACTTTTGGCGGAGGGACCAAG | CAGCAGTACVRMMBCYWCYCTTWCACT | 2036 | 2637 |
| VK1-05_t4_1_9 | CCTGATGATTTTGCAACTTATTACTGCCAGCAGTACVRMMBCYWCYCTMTCACTTTTGGCGGAGGGACCAAG | CAGCAGTACVRMMBCYWCYCTMTCACT | 2037 | 2638 |
| VK1-05_t4_2_9 | CCTGATGATTTTGCAACTTATTACTGCCAGCAGTACVRMMBCYWCYCTWGGACTTTTGGCGGAGGGACCAAG | CAGCAGTACVRMMBCYWCYCTWGGACT | 2038 | 2639 |
| VK1-05_t4_3_9 | CCTGATGATTTTGCAACTTATTACTGCCAGCAGTACVRMMBCYWCYCTCCTACTTTTGGCGGAGGGACCAAG | CAGCAGTACVRMMBCYWCYCTCCTACT | 2039 | 2640 |
| VK1-12 t1_0_9 | CCTGAAGATTTTGCAACTTATTACTGTCAGCAGRNANHCNHCTTCCCTTWCACTTTTGGCGGAGGGACCAAG | CAGCAGRNANHCNHCTTCCCTTWCACT | 2040 | 2641 |
| VK1-12 t1_1_9 | CCTGAAGATTTTGCAACTTATTACTGTCAGCAGRNANHCNHCTTCCCTMTCACTTTTGGCGGAGGGACCAAG | CAGCAGRNANHCNHCTTCCCTMTCACT | 2041 | 2642 |
| VK1-12 t1_2_9 | CCTGAAGATTTTGCAACTTATTACTGTCAGCAGRNANHCNHCTTCCCTWGGACTTTTGGCGGAGGGACCAAG | CAGCAGRNANHCNHCTTCCCTWGGACT | 2042 | 2643 |
| VK1-12 t1_3_9 | CCTGAAGATTTTGCAACTTATTACTGTCAGCAGRNANHCNHCTTCCCTCCTACTTTTGGCGGAGGGACCAAG | CAGCAGRNANHCNHCTTCCCTCCTACT | 2043 | 2644 |
| VK1-12 t2_0_9 | CCTGAAGATTTTGCAACTTATTACTGTCAGCAGRNANHCAGCWC CCTTWCACTTTTGGCGGAGGGACCAAG | CAGCAGRNANHCAGTYWCCCTTWCACT | 2044 | 2645 |
| VK1-12 t2_1_9 | CCTGAAGATTTTGCAACTTATTACTGTCAGCAGRNANHCAGTYWCCCTMTCACTTTTGGCGGAGGGACCAAG | CAGCAGRNANHCAGTYWCCCTMTCACT | 2045 | 2646 |
| VK1-12 t2_2_9 | CCTGAAGATTTTGCAACTTATTACTGTCAGCAGRNANHCAGTYWCCCTWGGACTTTTGGCGGAGGGACCAAG | CAGCAGRNANHCAGTYWCCCTWGGACT | 2046 | 2647 |
| VK1-12 t2_3_9 | CCTGAAGATTTTGCAACTTATTACTGTCAGCAGRNANHCAGTYWCCCTCCTACTTTTGGCGGAGGGACCAAG | CAGCAGRNANHCAGTYWCCCTCCTACT | 2047 | 2648 |
| VK1-12 t3_0_9 | CCTGAAGATTTTGCAACTTATTACTGTCAGCAGRNAAATNHCYWCCCTTWCACTTTTGGCGGAGGGACCAAG | CAGCAGRNAAATNHCYWCCCTTWCACT | 2048 | 2649 |

TABLE 6 -continued

Oligonucleotide sequences for exemplary VK jumping dimer and trimer sequences with CDRL3 length 9.

| Name | Sequence of Synthesized Oligonucleotide | Portion of Oligonucleotide Corresponding to CDRL3 Proper | SEQ ID NO (Oli-go) | SEQ ID NO (CDRL3 Por-tion) |
|---|---|---|---|---|
| VK1-12 t3_1_9 | CCTGAAGATTTTGCAACTTATTACTGTCAGCAGRNAAATNHCYWCCCTMTCCCTMTCACTTTTGGCGGAGGGACCAAG | CAGCAGRNAAATNHCYWCCCTMTCACT | 2049 | 2650 |
| VK1-12 t3_2_9 | CCTGAAGATTTTGCAACTTATTACTGTCAGCAGRNAAATNHCYWCCCTWGGCCTWGGACTTTTGGCGGAGGGACCAAG | CAGCAGRNAAATNHCYWCCCTWGGACT | 2050 | 2651 |
| VK1-12 t3_3_9 | CCTGAAGATTTTGCAACTTATTACTGTCAGCAGRNAAATNHCYWCCCTCCTCCTCCTACTTTTGGCGGAGGGACCAAG | CAGCAGRNAAATNHCYWCCCTCCTACT | 2051 | 2652 |
| VK1-12 t4_0_9 | CCTGAAGATTTTGCAACTTATTACTGTCAGCAGGCANHCNHCYWCCCTTWCCCTTWCACTTTTGGCGGAGGGACCAAG | CAGCAGGCANHCNHCYWCCCTTWCACT | 2052 | 2653 |
| VK1-12 t4_1_9 | CCTGAAGATTTTGCAACTTATTACTGTCAGCAGGCANHCNHCYWCCCTMTCCCTMTCACTTTTGGCGGAGGGACCAAG | CAGCAGGCANHCNHCYWCCCTMTCACT | 2053 | 2654 |
| VK1-12 t4_2_9 | CCTGAAGATTTTGCAACTTATTACTGTCAGCAGGCANHCNHCYWCCCTWGGCCTWGGACTTTTGGCGGAGGGACCAAG | CAGCAGGCANHCNHCYWCCCTWGGACT | 2054 | 2655 |
| VK1-12 t4_3_9 | CCTGAAGATTTTGCAACTTATTACTGTCAGCAGGCANHCNHCYWCCCTCCTCCTCCTACTTTTGGCGGAGGGACCAAG | CAGCAGGCANHCNHCYWCCCTCCTACT | 2055 | 2656 |
| VK1-33 t1_0_9 | CCTGAAGATATTGCAACATATTACTGTCAGCAGBHCNHCNHCCTCCCTTWCCCTTWCACTTTTGGCGGAGGGACCAAG | CAGCAGBHCNHCNHCCTCCCTTWCACT | 2056 | 2657 |
| VK1-33 t1_1_9 | CCTGAAGATATTGCAACATATTACTGTCAGCAGBHCNHCNHCCTCCCTMTCCCTMTCACTTTTGGCGGAGGGACCAAG | CAGCAGBHCNHCNHCCTCCCTMTCACT | 2057 | 2658 |
| VK1-33 t1_2_9 | CCTGAAGATATTGCAACATATTACTGTCAGCAGBHCNHCNHCCTCCCTWGGCCTWGGACTTTTGGCGGAGGGACCAAG | CAGCAGBHCNHCNHCCTCCCTWGGACT | 2058 | 2659 |
| VK1-33 t1_3_9 | CCTGAAGATATTGCAACATATTACTGTCAGCAGBHCNHCNHCCTCCCTCCTCCTCCTACTTTTGGCGGAGGGACCAAG | CAGCAGBHCNHCNHCCTCCCTCCTACT | 2059 | 2660 |
| VK1-33_t2_0_9 | CCTGAAGATATTGCAACATATTACTGTCAGCAGBHCNHCAATYWCCCTTWCCCTTWCACTTTTGGCGGAGGGACCAAG | CAGCAGBHCNHCAATYWCCCTTWCACT | 2060 | 2661 |
| VK1-33_t2_1_9 | CCTGAAGATATTGCAACATATTACTGTCAGCAGBHCNHCAATYWCCCTMTCCCTMTCACTTTTGGCGGAGGGACCAAG | CAGCAGBHCNHCAATYWCCCTMTCACT | 2061 | 2662 |
| VK1-33_t2_2_9 | CCTGAAGATATTGCAACATATTACTGTCAGCAGBHCNHCAATYWCCCTWGGCCTWGGACTTTTGGCGGAGGGACCAAG | CAGCAGBHCNHCAATYWCCCTWGGACT | 2062 | 2663 |
| VK1-33_t2_3_9 | CCTGAAGATATTGCAACATATTACTGTCAGCAGBHCNHCAATYWCCCTCCTCCTCCTACTTTTGGCGGAGGGACCAAG | CAGCAGBHCNHCAATYWCCCTCCTACT | 2063 | 2664 |
| VK1-33_t3_0_9 | CCTGAAGATATTGCAACATATTACTGTCAGCAGBHCGATNHCYWCCCTTWCCCTTWCACTTTTGGCGGAGGGACCAAG | CAGCAGBHCGATNHCYWCCCTTWCACT | 2064 | 2665 |
| VK1-33_t3_1_9 | CCTGAAGATATTGCAACATATTACTGTCAGCAGBHCGATNHCYWCCCTMTCCCTMTCACTTTTGGCGGAGGGACCAAG | CAGCAGBHCGATNHCYWCCCTMTCACT | 2065 | 2666 |
| VK1-33_t3_2_9 | CCTGAAGATATTGCAACATATTACTGTCAGCAGBHCGATNHCYWCCCTWGGCCTWGGACTTTTGGCGGAGGGACCAAG | CAGCAGBHCGATNHCYWCCCTWGGACT | 2066 | 2667 |
| VK1-33_t3_3_9 | CCTGAAGATATTGCAACATATTACTGTCAGCAGBHCGATNHCYWCCCTCCTCCTCCTACTTTTGGCGGAGGGACCAAG | CAGCAGBHCGATNHCYWCCCTCCTACT | 2067 | 2668 |
| VK1-33_t4_0_9 | CCTGAAGATATTGCAACATATTACTGTCAGCAGTACNHCNHCYWCCCTTWCCCTTWCACTTTTGGCGGAGGGACCAAG | CAGCAGTACNHCNHCYWCCCTTWCACT | 2068 | 2669 |
| VK1-33_t4_1_9 | CCTGAAGATATTGCAACATATTACTGTCAGCAGTACNHCNHCYWCCCTMTCCCTMTCACTTTTGGCGGAGGGACCAAG | CAGCAGTACNHCNHCYWCCCTMTCACT | 2069 | 2670 |
| VK1-33_t4_2_9 | CCTGAAGATATTGCAACATATTACTGTCAGCAGTACNHCNHCYWCCCTWGGCCTWGGACTTTTGGCGGAGGGACCAAG | CAGCAGTACNHCNHCYWCCCTWGGACT | 2070 | 2671 |
| VK1-33_t4_3_9 | CCTGAAGATATTGCAACATATTACTGTCAGCAGTACNHCNHCYWCCCTCCTCCTCCTACTTTTGGCGGAGGGACCAAG | CAGCAGTACNHCNHCYWCCCTCCTACT | 2071 | 2672 |
| VK1-39_t1_0_9 | CCTGAAGATTTTGCAACTTACTACTGTCAGCAAVNABHCNHCACTCCTTWCCCTTWCACTTTTGGCGGAGGGACCAAG | CAGCAAVNABHCNHCACTCCTTWCACT | 2072 | 320 |

TABLE 6 -continued

Oligonucleotide sequences for exemplary VK jumping dimer and trimer sequences with CDRL3 length 9.

| Name | Sequence of Synthesized Oligonucleotide | Portion of Oligonucleotide Corresponding to CDRL3 Proper | SEQ ID NO (Oligo) | SEQ ID NO (CDRL3 Portion) |
|---|---|---|---|---|
| VK1-39_t1_1_9 | CCTGAAGATTTTGCAACTTACTACTGTCAGCAAVNABHCNHCACTCCTMTCCCTMTCACTTTTGGCGGAGGGACCAAG | CAGCAAVNABHCNHCACTCCTMTCACT | 2073 | 2673 |
| VK1-39_t1_2_9 | CCTGAAGATTTTGCAACTTACTACTGTCAGCAAVNABHCNHCACTCCTWGGCCTWGGACTTTTGGCGGAGGGACCAAG | CAGCAAVNABHCNHCACTCCTWGGACT | 2074 | 2674 |
| VK1-39_t1_3_9 | CCTGAAGATTTTGCAACTTACTACTGTCAGCAAVNABHCNHCACTCCTCCTCCTCCTACTTTTGGCGGAGGGACCAAG | CAGCAAVNABHCNHCACTCCTCCTACT | 2075 | 2675 |
| VK1-39_t2_0_9 | CCTGAAGATTTTGCAACTTACTACTGTCAGCAAVNABHCAGTBHCCCTTWCCCTTWCACTTTTGGCGGAGGGACCAAG | CAGCAAVNABHCAGTBHCCCTTWCACT | 2076 | 321 |
| VK1-39_t2_1_9 | CCTGAAGATTTTGCAACTTACTACTGTCAGCAAVNABHCAGTBHCCCTMTCCCTMTCACTTTTGGCGGAGGGACCAAG | CAGCAAVNABHCAGTBHCCCTMTCACT | 2077 | 2676 |
| VK1-39_t2_2_9 | CCTGAAGATTTTGCAACTTACTACTGTCAGCAAVNABHCAGTBHCCCTWGGCCTWGGACTTTTGGCGGAGGGACCAAG | CAGCAAVNABHCAGTBHCCCTWGGACT | 2078 | 2677 |
| VK1-39_t2_3_9 | CCTGAAGATTTTGCAACTTACTACTGTCAGCAAVNABHCAGTBHCCCTCCTCCTCCTACTTTTGGCGGAGGGACCAAG | CAGCAAVNABHCAGTBHCCCTCCTACT | 2079 | 2678 |
| VK1-39_t3_0_9 | CCTGAAGATTTTGCAACTTACTACTGTCAGCAAVNATACNHCBHCCCTTWCCCTTWCACTTTTGGCGGAGGGACCAAG | CAGCAAVNATACNHCBHCCCTTWCACT | 2080 | 322 |
| VK1-39_t3_1_9 | CCTGAAGATTTTGCAACTTACTACTGTCAGCAAVNATACNHCBHCCCTMTCCCTMTCACTTTTGGCGGAGGGACCAAG | CAGCAAVNATACNHCBHCCCTMTCACT | 2081 | 2679 |
| VK1-39_t3_2_9 | CCTGAAGATTTTGCAACTTACTACTGTCAGCAAVNATACNHCBHCCCTWGGCCTWGGACTTTTGGCGGAGGGACCAAG | CAGCAAVNATACNHCBHCCCTWGGACT | 2082 | 2680 |
| VK1-39_t3_3_9 | CCTGAAGATTTTGCAACTTACTACTGTCAGCAAVNATACNHCBHCCCTCCTCCTCCTACTTTTGGCGGAGGGACCAAG | CAGCAAVNATACNHCBHCCCTCCTACT | 2083 | 2681 |
| VK1-39_t4_0_9 | CCTGAAGATTTTGCAACTTACTACTGTCAGCAAAGCBHCNHCBHCCCTTWCCCTTWCACTTTTGGCGGAGGGACCAAG | CAGCAAAGCBHCNHCBHCCCTTWCACT | 2084 | 323 |
| VK1-39_t4_1_9 | CCTGAAGATTTTGCAACTTACTACTGTCAGCAAAGCBHCNHCBHCCCTMTCCCTMTCACTTTTGGCGGAGGGACCAAG | CAGCAAAGCBHCNHCBHCCCTMTCACT | 2085 | 2682 |
| VK1-39_t4_2_9 | CCTGAAGATTTTGCAACTTACTACTGTCAGCAAAGCBHCNHCBHCCCTWGGCCTWGGACTTTTGGCGGAGGGACCAAG | CAGCAAAGCBHCNHCBHCCCTWGGACT | 2086 | 2683 |
| VK1-39_t4_3_9 | CCTGAAGATTTTGCAACTTACTACTGTCAGCAAAGCBHCNHCBHCCCTCCTCCTCCTACTTTTGGCGGAGGGACCAAG | CAGCAAAGCBHCNHCBHCCCTCCTACT | 2087 | 2684 |
| VK2-28_t1_0_9 | GCTGAGGATGTTGGGGTTTATTACTGCATGCAGVNAMNASRMACTCCTTWCCCTTWCACTTTTGGCGGAGGGACCAAG | ATGCAGVNAMNASRMACTCCTTWCACT | 2088 | 2685 |
| VK2-28_t1_1_9 | GCTGAGGATGTTGGGGTTTATTACTGCATGCAGVNAMNASRMACTCCTMTCCCTMTCACTTTTGGCGGAGGGACCAAG | ATGCAGVNAMNASRMACTCCTMTCACT | 2089 | 2686 |
| VK2-28_t1_2_9 | GCTGAGGATGTTGGGGTTTATTACTGCATGCAGVNAMNASRMACTCCTWGGCCTWGGACTTTTGGCGGAGGGACCAAG | ATGCAGVNAMNASRMACTCCTWGGACT | 2090 | 2687 |
| VK2-28_t1_3_9 | GCTGAGGATGTTGGGGTTTATTACTGCATGCAGVNAMNASRMACTCCTCCTCCTCCTACTTTTGGCGGAGGGACCAAG | ATGCAGVNAMNASRMACTCCTCCTACT | 2091 | 2688 |
| VK2-28_t2_0_9 | GCTGAGGATGTTGGGGTTTATTACTGCATGCAGVNAMNACAGVBCCCTTWCCCTTWCACTTTTGGCGGAGGGACCAAG | ATGCAGVNAMNACAGVBCCCTTWCACT | 2092 | 2689 |
| VK2-28_t2_1_9 | GCTGAGGATGTTGGGGTTTATTACTGCATGCAGVNAMNACAGVBCCCTMTCCCTMTCACTTTTGGCGGAGGGACCAAG | ATGCAGVNAMNACAGVBCCCTMTCACT | 2093 | 2690 |
| VK2-28_t2_2_9 | GCTGAGGATGTTGGGGTTTATTACTGCATGCAGVNAMNACAGVBCCCTWGGCCTWGGACTTTTGGCGGAGGGACCAAG | ATGCAGVNAMNACAGVBCCCTWGGACT | 2094 | 2691 |
| VK2-28_t2_3_9 | GCTGAGGATGTTGGGGTTTATTACTGCATGCAGVNAMNACAGVBCCCTCCTCCTCCTACTTTTGGCGGAGGGACCAAG | ATGCAGVNAMNACAGVBCCCTCCTACT | 2095 | 2692 |

TABLE 6 -continued

Oligonucleotide sequences for exemplary VK jumping dimer and trimer sequences with CDRL3 length 9.

| Name | Sequence of Synthesized Oligonucleotide | Portion of Oligonucleotide Corresponding to CDRL3 Proper | SEQ ID NO (Oli-go) | SEQ ID NO (CDRL3 Por-tion) |
|---|---|---|---|---|
| VK2-28_t3_0_9 | GCTGAGGATGTTGGGGTTTATTACTGCATGCAGVNACTCSRMVBCCCTTWCCCTTWCACTTTTGGCGGAGGGACCAAG | ATGCAGVNACTCSRMVBCCCTTWCACT | 2096 | 2693 |
| VK2-28_t3_1_9 | GCTGAGGATGTTGGGGTTTATTACTGCATGCAGVNACTCSRMVBCCCTMTCCCTMTCACTTTTGGCGGAGGGACCAAG | ATGCAGVNACTCSRMVBCCCTMTCACT | 2097 | 2694 |
| VK2-28_t3_2_9 | GCTGAGGATGTTGGGGTTTATTACTGCATGCAGVNACTCSRMVBCCCTWGGCCTWGGACTTTTGGCGGAGGGACCAAG | ATGCAGVNACTCSRMVBCCCTWGGACT | 2098 | 2695 |
| VK2-28_t3_3_9 | GCTGAGGATGTTGGGGTTTATTACTGCATGCAGVNACTCSRMVBCCCTCCTCCTCCTACTTTTGGCGGAGGGACCAAG | ATGCAGVNACTCSRMVBCCCTCCTACT | 2099 | 2696 |
| VK2-28_t4_0_9 | GCTGAGGATGTTGGGGTTTATTACTGCATGCAGGCAMNASRMVBCCCTTWCCCTTWCACTTTTGGCGGAGGGACCAAG | ATGCAGGCAMNASRMVBCCCTTWCACT | 2100 | 2697 |
| VK2-28_t4_1_9 | GCTGAGGATGTTGGGGTTTATTACTGCATGCAGGCAMNASRMVBCCCTMTCCCTMTCACTTTTGGCGGAGGGACCAAG | ATGCAGGCAMNASRMVBCCCTMTCACT | 2101 | 2698 |
| VK2-28_t4_2_9 | GCTGAGGATGTTGGGGTTTATTACTGCATGCAGGCAMNASRMVBCCCTWGGCCTWGGACTTTTGGCGGAGGGACCAAG | ATGCAGGCAMNASRMVBCCCTWGGACT | 2102 | 2699 |
| VK2-28_t4_3_9 | GCTGAGGATGTTGGGGTTTATTACTGCATGCAGGCAMNASRMVBCCCTCCTCCTCCTACTTTTGGCGGAGGGACCAAG | ATGCAGGCAMNASRMVBCCCTCCTACT | 2103 | 2700 |
| VK3-11_t1_0_9 | CCTGAAGATTTTGCAGTTTATTACTGTCAGCAGBHCNHCNHCTGGCCTTWCCCTTWCACTTTTGGCGGAGGGACCAAG | GGCAGCAGBHCNHCNHCTGGCCTTWCACT | 2104 | 2701 |
| VK3-11_t1_1_9 | CCTGAAGATTTTGCAGTTTATTACTGTCAGCAGBHCNHCNHCTGGCCTMTCCCTMTCACTTTTGGCGGAGGGACCAAG | GGCAGCAGBHCNHCNHCTGGCCTMTCACT | 2105 | 2702 |
| VK3-11_t1_2_9 | CCTGAAGATTTTGCAGTTTATTACTGTCAGCAGBHCNHCNHCTGGCCTWGGCCTWGGACTTTTGGCGGAGGGACCAAG | GGCAGCAGBHCNHCNHCTGGCCTWGGACT | 2106 | 2703 |
| VK3-11_t1_3_9 | CCTGAAGATTTTGCAGTTTATTACTGTCAGCAGBHCNHCNHCTGGCCTCCTCCTCCTACTTTTGGCGGAGGGACCAAG | GGCAGCAGBHCNHCNHCTGGCCTCCTACT | 2107 | 2704 |
| VK3-11_t2_0_9 | CCTGAAGATTTTGCAGTTTATTACTGTCAGCAGBHCNHCAATYWCCCTTWCCCTTWCACTTTTGGCGGAGGGACCAAG | CCAGCAGBHCNHCAATYWCCCTTWCACT | 2108 | 2661 |
| VK3-11_t2_1_9 | CCTGAAGATTTTGCAGTTTATTACTGTCAGCAGBHCNHCAATYWCCCTMTCCCTMTCACTTTTGGCGGAGGGACCAAG | CCAGCAGBHCNHCAATYWCCCTMTCACT | 2109 | 2662 |
| VK3-11_t2_2_9 | CCTGAAGATTTTGCAGTTTATTACTGTCAGCAGBHCNHCAATYWCCCTWGGCCTWGGACTTTTGGCGGAGGGACCAAG | CCAGCAGBHCNHCAATYWCCCTWGGACT | 2110 | 2663 |
| VK3-11_t2_3_9 | CCTGAAGATTTTGCAGTTTATTACTGTCAGCAGBHCNHCAATYWCCCTCCTCCTCCTACTTTTGGCGGAGGGACCAAG | CCAGCAGBHCNHCAATYWCCCTCCTACT | 2111 | 2664 |
| VK3-11_t3_0_9 | CCTGAAGATTTTGCAGTTTATTACTGTCAGCAGBHCAGTNHCYWCCCTTWCCCTTWCACTTTTGGCGGAGGGACCAAG | CCAGCAGBHCAGTNHCYWCCCTTWCACT | 2112 | 2705 |
| VK3-11_t3_1_9 | CCTGAAGATTTTGCAGTTTATTACTGTCAGCAGBHCAGTNHCYWCCCTMTCCCTMTCACTTTTGGCGGAGGGACCAAG | CCAGCAGBHCAGTNHCYWCCCTMTCACT | 2113 | 2706 |
| VK3-11_t3_2_9 | CCTGAAGATTTTGCAGTTTATTACTGTCAGCAGBHCAGTNHCYWCCCTWGGCCTWGGACTTTTGGCGGAGGGACCAAG | CCAGCAGBHCAGTNHCYWCCCTWGGACT | 2114 | 2707 |
| VK3-11_t3_3_9 | CCTGAAGATTTTGCAGTTTATTACTGTCAGCAGBHCAGTNHCYWCCCTCCTCCTCCTACTTTTGGCGGAGGGACCAAG | CCAGCAGBHCAGTNHCYWCCCTCCTACT | 2115 | 2708 |
| VK3-11_t4_0_9 | CCTGAAGATTTTGCAGTTTATTACTGTCAGCAGAGANHCNHCYWCCCTTWCCCTTWCACTTTTGGCGGAGGGACCAAG | CCAGCAGAGANHCNHCYWCCCTTWCACT | 2116 | 2709 |
| VK3-11_t4_1_9 | CCTGAAGATTTTGCAGTTTATTACTGTCAGCAGAGANHCNHCYWCCCTMTCCCTMTCACTTTTGGCGGAGGGACCAAG | CCAGCAGAGANHCNHCYWCCCTMTCACT | 2117 | 2710 |
| VK3-11_t4_2_9 | CCTGAAGATTTTGCAGTTTATTACTGTCAGCAGAGANHCNHCYWCCCTWGGCCTWGGACTTTTGGCGGAGGGACCAAG | CCAGCAGAGANHCNHCYWCCCTWGGACT | 2118 | 2711 |
| VK3-11_t4_3_9 | CCTGAAGATTTTGCAGTTTATTACTGTCAGCAGAGANHCNHCYWCCCTCCTCCTCCTACTTTTGGCGGAGGGACCAAG | CCAGCAGAGANHCNHCYWCCCTCCTACT | 2119 | 2712 |

TABLE 6 -continued

Oligonucleotide sequences for exemplary VK jumping dimer and trimer sequences with CDRL3 length 9.

| Name | Sequence of Synthesized Oligonucleotide | Portion of Oligonucleotide Corresponding to CDRL3 Proper | SEQ ID NO (Oligo) | SEQ ID NO (CDRL3 Portion) |
|---|---|---|---|---|
| VK3-15_t1_0_9 | CAGTCTGAAGATTTTGCAGTTTATTACTGTCAGCAGBHCNHCNHCCAGCAGBHCNHCNHCTGGCCTTWCTGGCCTTWCACTTTTGGCGGAGGGACCAAG | CAGCAGBHCNHCNHCTGGCCTTWCACT | 2120 | 2701 |
| VK3-15_t1_1_9 | CAGTCTGAAGATTTTGCAGTTTATTACTGTCAGCAGBHCNHCNHCCAGCAGBHCNHCNHCTGGCCTMTCTGGCCTMTCACTTTTGGCGGAGGGACCAAG | CAGCAGBHCNHCNHCTGGCCTMTCACT | 2121 | 2702 |
| VK3-15_t1_2_9 | CAGTCTGAAGATTTTGCAGTTTATTACTGTCAGCAGBHCNHCNHCCAGCAGBHCNHCNHCTGGCCTWGGTGGCCTWGGACTTTTGGCGGAGGGACCAAG | CAGCAGBHCNHCNHCTGGCCTWGGACT | 2122 | 2703 |
| VK3-15_t1_3_9 | CAGTCTGAAGATTTTGCAGTTTATTACTGTCAGCAGBHCNHCNHCCAGCAGBHCNHCNHCTGGCCTCCTTGGCCTCCTACTTTTGGCGGAGGGACCAAG | CAGCAGBHCNHCNHCTGGCCTCCTACT | 2123 | 2704 |
| VK3-15_t2_0_9 | CAGTCTGAAGATTTTGCAGTTTATTACTGTCAGCAGBHCNHCAATCAGCAGBHCNHCAATYWCCCTTWCYWCCCTTWCACTTTTGGCGGAGGGACCAAG | CAGCAGBHCNHCAATYWCCCTTWCACT | 2124 | 2661 |
| VK3-15_t2_1_9 | CAGTCTGAAGATTTTGCAGTTTATTACTGTCAGCAGBHCNHCAATCAGCAGBHCNHCAATYWCCCTMTCYWCCCTMTCACTTTTGGCGGAGGGACCAAG | CAGCAGBHCNHCAATYWCCCTMTCACT | 2125 | 2662 |
| VK3-15_t2_2_9 | CAGTCTGAAGATTTTGCAGTTTATTACTGTCAGCAGBHCNHCAATCAGCAGBHCNHCAATYWCCCTWGGYWCCCTWGGACTTTTGGCGGAGGGACCAAG | CAGCAGBHCNHCAATYWCCCTWGGACT | 2126 | 2663 |
| VK3-15_t2_3_9 | CAGTCTGAAGATTTTGCAGTTTATTACTGTCAGCAGBHCNHCAATCAGCAGBHCNHCAATYWCCCTCCTYWCCCTCCTACTTTTGGCGGAGGGACCAAG | CAGCAGBHCNHCAATYWCCCTCCTACT | 2127 | 2664 |
| VK3-15_t3_0_9 | CAGTCTGAAGATTTTGCAGTTTATTACTGTCAGCAGBHCAATNHCCAGCAGBHCAATNHCYWCCCTTWCYWCCCTTWCACTTTTGGCGGAGGGACCAAG | CAGCAGBHCAATNHCYWCCCTTWCACT | 2128 | 2713 |
| VK3-15_t3_1_9 | CAGTCTGAAGATTTTGCAGTTTATTACTGTCAGCAGBHCAATNHCCAGCAGBHCAATNHCYWCCCTMTCYWCCCTMTCACTTTTGGCGGAGGGACCAAG | CAGCAGBHCAATNHCYWCCCTMTCACT | 2129 | 2714 |
| VK3-15_t3_2_9 | CAGTCTGAAGATTTTGCAGTTTATTACTGTCAGCAGBHCAATNHCCAGCAGBHCAATNHCYWCCCTWGGYWCCCTWGGACTTTTGGCGGAGGGACCAAG | CAGCAGBHCAATNHCYWCCCTWGGACT | 2130 | 2715 |
| VK3-15_t3_3_9 | CAGTCTGAAGATTTTGCAGTTTATTACTGTCAGCAGBHCAATNHCCAGCAGBHCAATNHCYWCCCTCCTYWCCCTCCTACTTTTGGCGGAGGGACCAAG | CAGCAGBHCAATNHCYWCCCTCCTACT | 2131 | 2716 |
| VK3-15_t4_0_9 | CAGTCTGAAGATTTTGCAGTTTATTACTGTCAGCAGTACNHCNHCCAGCAGTACNHCNHCYWCCCTTWCYWCCCTTWCACTTTTGGCGGAGGGACCAAG | CAGCAGTACNHCNHCYWCCCTTWCACT | 2132 | 2669 |
| VK3-15_t4_1_9 | CAGTCTGAAGATTTTGCAGTTTATTACTGTCAGCAGTACNHCNHCCAGCAGTACNHCNHCYWCCCTMTCYWCCCTMTCACTTTTGGCGGAGGGACCAAG | CAGCAGTACNHCNHCYWCCCTMTCACT | 2133 | 2670 |
| VK3-15_t4_2_9 | CAGTCTGAAGATTTTGCAGTTTATTACTGTCAGCAGTACNHCNHCCAGCAGTACNHCNHCYWCCCTWGGYWCCCTWGGACTTTTGGCGGAGGGACCAAG | CAGCAGTACNHCNHCYWCCCTWGGACT | 2134 | 2671 |
| VK3-15_t4_3_9 | CAGTCTGAAGATTTTGCAGTTTATTACTGTCAGCAGTACNHCNHCCAGCAGTACNHCNHCYWCCCTCCTYWCCCTCCTACTTTTGGCGGAGGGACCAAG | CAGCAGTACNHCNHCYWCCCTCCTACT | 2135 | 2672 |
| VK3-20_t1_0_9 | CCTGAAGATTTTGCAGTGTATTACTGTCAGCAGBHCBHCVNCAGTCAGCAGBHCBHCVNCAGTCCTTWCCCTTWCACTTTTGGCGGAGGGACCAAG | CAGCAGBHCBHCVNCAGTCCTTWCACT | 2136 | 2717 |
| VK3-20_t1_1_9 | CCTGAAGATTTTGCAGTGTATTACTGTCAGCAGBHCBHCVNCAGTCAGCAGBHCBHCVNCAGTCCTMTCCCTMTCACTTTTGGCGGAGGGACCAAG | CAGCAGBHCBHCVNCAGTCCTMTCACT | 2137 | 2718 |
| VK3-20_t1_2_9 | CCTGAAGATTTTGCAGTGTATTACTGTCAGCAGBHCBHCVNCAGTCAGCAGBHCBHCVNCAGTCCTWGGCCTWGGACTTTTGGCGGAGGGACCAAG | CAGCAGBHCBHCVNCAGTCCTWGGACT | 2138 | 2719 |
| VK3-20_t1_3_9 | CCTGAAGATTTTGCAGTGTATTACTGTCAGCAGBHCBHCVNCAGTCAGCAGBHCBHCVNCAGTCCTCCTCCTCCTACTTTTGGCGGAGGGACCAAG | CAGCAGBHCBHCVNCAGTCCTCCTACT | 2139 | 2720 |
| VK3-20_t2_0_9 | CCTGAAGATTTTGCAGTGTATTACTGTCAGCAGBHCBHCAGTBHCCAGCAGBHCBHCAGTBHCCCTTWCCCTTWCACTTTTGGCGGAGGGACCAAG | CAGCAGBHCBHCAGTBHCCCTTWCACT | 2140 | 2721 |
| VK3-20_t2_1_9 | CCTGAAGATTTTGCAGTGTATTACTGTCAGCAGBHCBHCAGTBHCCAGCAGBHCBHCAGTBHCCCTMTCCCTMTCACTTTTGGCGGAGGGACCAAG | CAGCAGBHCBHCAGTBHCCCTMTCACT | 2141 | 2722 |
| VK3-20_t2_2_9 | CCTGAAGATTTTGCAGTGTATTACTGTCAGCAGBHCBHCAGTBHCCAGCAGBHCBHCAGTBHCCCTWGGCCTWGGACTTTTGGCGGAGGGACCAAG | CAGCAGBHCBHCAGTBHCCCTWGGACT | 2142 | 2723 |

TABLE 6 -continued

Oligonucleotide sequences for exemplary VK jumping dimer and trimer sequences with CDRL3 length 9.

| Name | Sequence of Synthesized Oligonucleotide | Portion of Oligonucleotide Corresponding to CDRL3 Proper | SEQ ID NO (Oli-go) | SEQ ID NO (CDRL3 Por-tion) |
|---|---|---|---|---|
| VK3-20_ t2_3_9 | CCTGAAGATTTTGCAGTGTATTACTGTCAGCAGBHCBHCAGTBHCCAGCAGBHCBHCAGTBHCCCTCCT CCTCCTACTTTTGGCGGAGGGACCAAG | ACT | 2143 | 2724 |
| VK3-20_ t3_0_9 | CCTGAAGATTTTGCAGTGTATTACTGTCAGCAGBHCGGAVNCBHCCAGCAGBHCGGAVNCBHCCCTTWC CCTTWCACTTTTGGCGGAGGGACCAAG | ACT | 2144 | 2725 |
| VK3-20_ t3_1_9 | CCTGAAGATTTTGCAGTGTATTACTGTCAGCAGBHCGGAVNCBHCCAGCAGBHCGGAVNCBHCCCTMTC CCTMTCACTTTTGGCGGAGGGACCAAG | ACT | 2145 | 2726 |
| VK3-20_ t3_2_9 | CCTGAAGATTTTGCAGTGTATTACTGTCAGCAGBHCGGAVNCBHCCAGCAGBHCGGAVNCBHCCCTWGG CCTWGGACTTTTGGCGGAGGGACCAAG | ACT | 2146 | 2727 |
| VK3-20_ t3_3_9 | CCTGAAGATTTTGCAGTGTATTACTGTCAGCAGBHCGGAVNCBHCCAGCAGBHCGGAVNCBHCCCTCCT CCTCCTACTTTTGGCGGAGGGACCAAG | ACT | 2147 | 2728 |
| VK3-20_ t4_0_9 | CCTGAAGATTTTGCAGTGTATTACTGTCAGCAGTACBHCVNCBHCCAGCAGTACBHCVNCBHCCCTTWC CCTTWCACTTTTGGCGGAGGGACCAAG | ACT | 2148 | 2729 |
| VK3-20_ t4_1_9 | CCTGAAGATTTTGCAGTGTATTACTGTCAGCAGTACBHCVNCBHCCAGCAGTACBHCVNCBHCCCTMTC CCTMTCACTTTTGGCGGAGGGACCAAG | ACT | 2149 | 2730 |
| VK3-20_ t4_2_9 | CCTGAAGATTTTGCAGTGTATTACTGTCAGCAGTACBHCVNCBHCCAGCAGTACBHCVNCBHCCCTWGG CCTWGGACTTTTGGCGGAGGGACCAAG | ACT | 2150 | 2731 |
| VK3-20_ t4_3_9 | CCTGAAGATTTTGCAGTGTATTACTGTCAGCAGTACBHCVNCBHCCAGCAGTACBHCVNCBHCCCTCCT CCTCCTACTTTTGGCGGAGGGACCAAG | ACT | 2151 | 2732 |
| VK4-01_ t1_0_9 | GCTGAAGATGTGGCAGTTTATTACTGTCAGCAGBHCBHCNHCACTCAGCAGBHCBHCNHCACTCCTTWC CCTTWCACTTTTGGCGGAGGGACCAAG | ACT | 2152 | 2733 |
| VK4-01_ t1_1_9 | GCTGAAGATGTGGCAGTTTATTACTGTCAGCAGBHCBHCNHCACTCAGCAGBHCBHCNHCACTCCTMTC CCTMTCACTTTTGGCGGAGGGACCAAG | ACT | 2153 | 2734 |
| VK4-01_ t1_2_9 | GCTGAAGATGTGGCAGTTTATTACTGTCAGCAGBHCBHCNHCACTCAGCAGBHCBHCNHCACTCCTWGG CCTWGGACTTTTGGCGGAGGGACCAAG | ACT | 2154 | 2735 |
| VK4-01_ t1_3_9 | GCTGAAGATGTGGCAGTTTATTACTGTCAGCAGBHCBHCNHCACTCAGCAGBHCBHCNHCACTCCTCCT CCTCCTACTTTTGGCGGAGGGACCAAG | ACT | 2155 | 2736 |
| VK4-01_ t2_0_9 | GCTGAAGATGTGGCAGTTTATTACTGTCAGCAGBHCBHCAGTBHCCAGCAGBHCBHCAGTBHCCCTTWC CCTTWCACTTTTGGCGGAGGGACCAAG | ACT | 2156 | 2721 |
| VK4-01_ t2_1_9 | GCTGAAGATGTGGCAGTTTATTACTGTCAGCAGBHCBHCAGTBHCCAGCAGBHCBHCAGTBHCCCTMTC CCTMTCACTTTTGGCGGAGGGACCAAG | ACT | 2157 | 2722 |
| VK4-01_ t2_2_9 | GCTGAAGATGTGGCAGTTTATTACTGTCAGCAGBHCBHCAGTBHCCAGCAGBHCBHCAGTBHCCCTWGG CCTWGGACTTTTGGCGGAGGGACCAAG | ACT | 2158 | 2723 |
| VK4-01_ t2_3_9 | GCTGAAGATGTGGCAGTTTATTACTGTCAGCAGBHCBHCAGTBHCCAGCAGBHCBHCAGTBHCCCTCCT CCTCCTACTTTTGGCGGAGGGACCAAG | ACT | 2159 | 2724 |
| VK4-01_ t3_0_9 | GCTGAAGATGTGGCAGTTTATTACTGTCAGCAGBHCTACNHCBHCCAGCAGBHCTACNHCBHCCCTTWC CCTTWCACTTTTGGCGGAGGGACCAAG | ACT | 2160 | 2737 |
| VK4-01_ t3_1_9 | GCTGAAGATGTGGCAGTTTATTACTGTCAGCAGBHCTACNHCBHCCAGCAGBHCTACNHCBHCCCTMTC CCTMTCACTTTTGGCGGAGGGACCAAG | ACT | 2161 | 2738 |
| VK4-01_ t3_2_9 | GCTGAAGATGTGGCAGTTTATTACTGTCAGCAGBHCTACNHCBHCCAGCAGBHCTACNHCBHCCCTWGG CCTWGGACTTTTGGCGGAGGGACCAAG | ACT | 2162 | 2739 |
| VK4-01_ t3_3_9 | GCTGAAGATGTGGCAGTTTATTACTGTCAGCAGBHCTACNHCBHCCAGCAGBHCTACNHCBHCCCTCCT CCTCCTACTTTTGGCGGAGGGACCAAG | ACT | 2163 | 2740 |
| VK4-01_ t4_0_9 | GCTGAAGATGTGGCAGTTTATTACTGTCAGCAGTACBHCNHCBHCCAGCAGTACBHCNHCBHCCCTTWC CCTTWCACTTTTGGCGGAGGGACCAAG | ACT | 2164 | 2741 |
| VK4-01_ t4_1_9 | GCTGAAGATGTGGCAGTTTATTACTGTCAGCAGTACBHCNHCBHCCAGCAGTACBHCNHCBHCCCTMTC CCTMTCACTTTTGGCGGAGGGACCAAG | ACT | 2165 | 2742 |
| VK4-01_ t4_2_9 | GCTGAAGATGTGGCAGTTTATTACTGTCAGCAGTACBHCNHCBHCCAGCAGTACBHCNHCBHCCCTWGG CCTWGGACTTTTGGCGGAGGGACCAAG | ACT | 2166 | 2743 |

TABLE 6 -continued

| Oligonucleotide sequences for exemplary VK jumping dimer and trimer sequences with CDRL3 length 9. | | | | |
|---|---|---|---|---|
| Name | Sequence of Synthesized Oligonucleotide | Portion of Oligonucleotide Corresponding to CDRL3 Proper | SEQ ID NO (Oligo) | SEQ ID NO (CDRL3 Portion) |
| VK4-01_ t4_3_9 | GCTGAAGATGTGGCAGTTTATTACTGTCAGCAGTACBHCNHCBHCCAGCAGTACBHCNHCBHCCCTCCT CCTCCTACTTTTGGCGGAGGGACCAAG | ACT | 2167 | 2744 |

TABLE 7

| Oligonucleotide sequences for exemplary VK jumping dimer and trimer sequences with CDRL3 length 10. | | | | |
|---|---|---|---|---|
| Name | Sequence of Synthesized Oligonucleotide | Portion of Oligonucleotide Corresponding to CDRL3 Proper | SEQ ID NO (Oligo) | SEQ ID NO (CDRL3 Portion) |
| Jumping Dimer | | | | |
| VK1-05 1 0 10 | CCTGATGATTTTGCAACTTATTACTGCSWMSWMTACAATAG TTACYCTCCTTWCACTTTTGGCGGAGGGACCAAG | SWMSWMTACAATAGTTACYC TCCTTWCACT | 2745 | 3213 |
| VK1-05 10 0 10 | CCTGATGATTTTGCAACTTATTACTGCCAGCAGBHCVRMAG TTACYCTCCTTWCACTTTTGGCGGAGGGACCAAG | CAGCAGBHCVRMAGTTACYC TCCTTWCACT | 2746 | 3214 |
| VK1-05 11 0 10 | CCTGATGATTTTGCAACTTATTACTGCCAGCAGBHCAATMB CTACYCTCCTTWCACTTTTGGCGGAGGGACCAAG | CAGCAGBHCAATMECTACYC TCCTTWCACT | 2747 | 3215 |
| VK1-05 12 0 10 | CCTGATGATTTTGCAACTTATTACTGCCAGCAGBHCAATAG TYWCYCTCCTTWCACTTTTGGCGGAGGGACCAAG | CAGCAGBHCAATAGTYWCYC TCCTTWCACT | 2748 | 3216 |
| VK1-05 13 0 10 | CCTGATGATTTTGCAACTTATTACTGCCAGCAGTACVRMMB CTACYCTCCTTWCACTTTTGGCGGAGGGACCAAG | CAGCAGTACVRMMBCTACYC TCCTTWCACT | 2749 | 3217 |
| VK1-05 14 0 10 | CCTGATGATTTTGCAACTTATTACTGCCAGCAGTACVRMAG TYWCYCTCCTTWCACTTTTGGCGGAGGGACCAAG | CAGCAGTACVRMAGTYWCYC TCCTTWCACT | 2750 | 3218 |
| VK1-05 15 0 10 | CCTGATGATTTTGCAACTTATTACTGCCAGCAGTACAATMB CYWCYCTCCTTWCACTTTTGGCGGAGGGACCAAG | CAGCAGTACAATMBCYWCYC TCCTTWCACT | 2751 | 3219 |
| VK1-05 2 0 10 | CCTGATGATTTTGCAACTTATTACTGCSWMCAGBHCAATAG TTACYCTCCTTWCACTTTTGGCGGAGGGACCAAG | SWMCAGBHCAATAGTTACYC TCCTTWCACT | 2752 | 3220 |
| VK1-05 3 0 10 | CCTGATGATTTTGCAACTTATTACTGCSWMCAGTACVRMAG TTACYCTCCTTWCACTTTTGGCGGAGGGACCAAG | SWMCAGTACVRMAGTTACYC TCCTTWCACT | 2753 | 3221 |
| VK1-05 4 0 10 | CCTGATGATTTTGCAACTTATTACTGCSWMCAGTACAATMB CTACYCTCCTTWCACTTTTGGCGGAGGGACCAAG | SWMCAGTACAATMBCTACYC TCCTTWCACT | 2754 | 3222 |
| VK1-05 5 0 10 | CCTGATGATTTTGCAACTTATTACTGCSWMCAGTACAATAG TYWCYCTCCTTWCACTTTTGGCGGAGGGACCAAG | SWMCAGTACAATAGTYWCYC TCCTTWCACT | 2755 | 3223 |
| VK1-05 6 0 10 | CCTGATGATTTTGCAACTTATTACTGCCAGSWMBHCAATAG TTACYCTCCTTWCACTTTTGGCGGAGGGACCAAG | CAGSWMBHCAATAGTTACYC TCCTTWCACT | 2756 | 3224 |
| VK1-05 7 0 10 | CCTGATGATTTTGCAACTTATTACTGCCAGSWMTACVRMAG TTACYCTCCTTWCACTTTTGGCGGAGGGACCAAG | CAGSWMTACVRMAGTTACYC TCCTTWCACT | 2757 | 3225 |
| VK1-05 8 0 10 | CCTGATGATTTTGCAACTTATTACTGCCAGSWMTACAATMB CTACYCTCCTTWCACTTTTGGCGGAGGGACCAAG | CAGSWMTACAATMBCTACYC TCCTTWCACT | 2758 | 3226 |
| VK1-05 9 0 10 | CCTGATGATTTTGCAACTTATTACTGCCAGSWMTACAATAG TYWCYCTCCTTWCACTTTTGGCGGAGGGACCAAG | CAGSWMTACAATAGTYWCYC TCCTTWCACT | 2759 | 3227 |
| VK1-05 1 1 10 | CCTGATGATTTTGCAACTTATTACTGCSWMSWMTACAATAG TTACYCTCCTMTCACTTTTGGCGGAGGGACCAAG | SWMSWMTACAATAGTTACYC TCCTMTCACT | 2760 | 3228 |
| VK1-05 10 1 10 | CCTGATGATTTTGCAACTTATTACTGCCAGCAGBHCVRMAG TTACYCTCCTMTCACTTTTGGCGGAGGGACCAAG | CAGCAGBHCVRMAGTTACYC TCCTMTCACT | 2761 | 3229 |

TABLE 7-continued

Oligonucleotide sequences for exemplary VK jumping dimer and trimer sequences with CDRL3 length 10.

| Name | Sequence of Synthesized Oligonucleotide | Portion of Oligonucleotide Corresponding to CDRL3 Proper | SEQ ID NO (Oligo) | SEQ ID NO (CDRL3 Portion) |
|---|---|---|---|---|
| VK1-05 11 1 10 | CCTGATGATTTTGCAACTTATTACTGCCAGCAGBHCAATMB CTACYCTCCTMTCACTTTTGGCGGAGGGACCAAG | CAGCAGBHCAATMECTACYC TCCTMTCACT | 2762 | 3230 |
| VK1-05 12 1 10 | CCTGATGATTTTGCAACTTATTACTGCCAGCAGBHCAATAG TYWCYCTCCTMTCACTTTTGGCGGAGGGACCAAG | CAGCAGBHCAATAGTYWCYC TCCTMTCACT | 2763 | 3231 |
| VK1-05 13 1 10 | CCTGATGATTTTGCAACTTATTACTGCCAGCAGTACVRMMB CTACYCTCCTMTCACTTTTGGCGGAGGGACCAAG | CAGCAGTACVRMMBCTACYC TCCTMTCACT | 2764 | 3232 |
| VK1-05 14 1 10 | CCTGATGATTTTGCAACTTATTACTGCCAGCAGTACVRMAG TYWCYCTCCTMTCACTTTTGGCGGAGGGACCAAG | CAGCAGTACVRMAGTYWCYC TCCTMTCACT | 2765 | 3233 |
| VK1-05 15 1 10 | CCTGATGATTTTGCAACTTATTACTGCCAGCAGTACAATMB CYWCYCTCCTMTCACTTTTGGCGGAGGGACCAAG | CAGCAGTACAATMBCYWCYC TCCTMTCACT | 2766 | 3234 |
| VK1-05 2 1 10 | CCTGATGATTTTGCAACTTATTACTGCSWMCAGBHCAATAG TTACYCTCCTMTCACTTTTGGCGGAGGGACCAAG | SWMCAGBHCAATAGTTACYC TCCTMTCACT | 2767 | 3235 |
| VK1-05 3 1 10 | CCTGATGATTTTGCAACTTATTACTGCSWMCAGTACVRMAG TTACYCTCCTMTCACTTTTGGCGGAGGGACCAAG | SWMCAGTACVRMAGTTACYC TCCTMTCACT | 2768 | 3236 |
| VK1-05 4 1 10 | CCTGATGATTTTGCAACTTATTACTGCSWMCAGTACAATMB CTACYCTCCTMTCACTTTTGGCGGAGGGACCAAG | SWMCAGTACAATMBCTACYC TCCTMTCACT | 2769 | 3237 |
| VK1-05 5 1 10 | CCTGATGATTTTGCAACTTATTACTGCSWMCAGTACAATAG TYWCYCTCCTMTCACTTTTGGCGGAGGGACCAAG | SWMCAGTACAATAGTYWCYC TCCTMTCACT | 2770 | 3238 |
| VK1-05 6 1 10 | CCTGATGATTTTGCAACTTATTACTGCCAGSWMBHCAATAG TTACYCTCCTMTCACTTTTGGCGGAGGGACCAAG | CAGSWMBHCAATAGTTACYC TCCTMTCACT | 2771 | 3239 |
| VK1-05 7 1 10 | CCTGATGATTTTGCAACTTATTACTGCCAGSWMTACVRMAG TTACYCTCCTMTCACTTTTGGCGGAGGGACCAAG | CAGSWMTACVRMAGTTACYC TCCTMTCACT | 2772 | 3240 |
| VK1-05 8 1 10 | CCTGATGATTTTGCAACTTATTACTGCCAGSWMTACAATMB CTACYCTCCTMTCACTTTTGGCGGAGGGACCAAG | CAGSWMTACAATMBCTACYC TCCTMTCACT | 2773 | 3241 |
| VK1-05 9 1 10 | CCTGATGATTTTGCAACTTATTACTGCCAGSWMTACAATAG TYWCYCTCCTMTCACTTTTGGCGGAGGGACCAAG | CAGSWMTACAATAGTYWCYC TCCTMTCACT | 2774 | 3242 |
| VK1-05 1 2 10 | CCTGATGATTTTGCAACTTATTACTGCSWMSWMTACAATAG TTACYCTCCTWGGACTTTTGGCGGAGGGACCAAG | SWMSWMTACAATAGTTACYC TCCTWGGACT | 2775 | 3243 |
| VK1-05 10 2 10 | CCTGATGATTTTGCAACTTATTACTGCCAGCAGBHCVRMAG TTACYCTCCTWGGACTTTTGGCGGAGGGACCAAG | CAGCAGBHCVRMAGTTACYC TCCTWGGACT | 2776 | 3244 |
| VK1-05 11 2 10 | CCTGATGATTTTGCAACTTATTACTGCCAGCAGBHCAATMB CTACYCTCCTWGGACTTTTGGCGGAGGGACCAAG | CAGCAGBHCAATMECTACYC TCCTWGGACT | 2777 | 3245 |
| VK1-05 12 2 10 | CCTGATGATTTTGCAACTTATTACTGCCAGCAGBHCAATAG TYWCYCTCCTWGGACTTTTGGCGGAGGGACCAAG | CAGCAGBHCAATAGTYWCYC TCCTWGGACT | 2778 | 3246 |
| VK1-05 13 2 10 | CCTGATGATTTTGCAACTTATTACTGCCAGCAGTACVRMMB CTACYCTCCTWGGACTTTTGGCGGAGGGACCAAG | CAGCAGTACVRMMBCTACYC TCCTWGGACT | 2779 | 3247 |
| VK1-05 14 2 10 | CCTGATGATTTTGCAACTTATTACTGCCAGCAGTACVRMAG TYWCYCTCCTWGGACTTTTGGCGGAGGGACCAAG | CAGCAGTACVRMAGTYWCYC TCCTWGGACT | 2780 | 3248 |
| VK1-05 15 2 10 | CCTGATGATTTTGCAACTTATTACTGCCAGCAGTACAATMB CYWCYCTCCTWGGACTTTTGGCGGAGGGACCAAG | CAGCAGTACAATMBCYWCYC TCCTWGGACT | 2781 | 3249 |
| VK1-05 2 2 10 | CCTGATGATTTTGCAACTTATTACTGCSWMCAGBHCAATAG TTACYCTCCTWGGACTTTTGGCGGAGGGACCAAG | SWMCAGBHCAATAGTTACYC TCCTWGGACT | 2782 | 3250 |
| VK1-05 3 2 10 | CCTGATGATTTTGCAACTTATTACTGCSWMCAGTACVRMAG TTACYCTCCTWGGACTTTTGGCGGAGGGACCAAG | SWMCAGTACVRMAGTTACYC TCCTWGGACT | 2783 | 3251 |
| VK1-05 4 2 10 | CCTGATGATTTTGCAACTTATTACTGCSWMCAGTACAATMB CTACYCTCCTWGGACTTTTGGCGGAGGGACCAAG | SWMCAGTACAATMBCTACYC TCCTWGGACT | 2784 | 3252 |
| VK1-05 5 2 10 | CCTGATGATTTTGCAACTTATTACTGCSWMCAGTACAATAG TYWCYCTCCTWGGACTTTTGGCGGAGGGACCAAG | SWMCAGTACAATAGTYWCYC TCCTWGGACT | 2785 | 3253 |

TABLE 7-continued

Oligonucleotide sequences for exemplary VK jumping dimer and trimer sequences with CDRL3 length 10.

| Name | Sequence of Synthesized Oligonucleotide | Portion of Oligonucleotide Corresponding to CDRL3 Proper | SEQ ID NO (Oligo) | SEQ ID NO (CDRL3 Portion) |
|---|---|---|---|---|
| VK1-05 6 2 10 | CCTGATGATTTTGCAACTTATTACTGCCAGSWMBHCAATAG TTACYCTCCTWGGACTTTTGGCGGAGGGACCAAG | CAGSWMBHCAATAGTTACYC TCCTWGGACT | 2786 | 3254 |
| VK1-05 7 2 10 | CCTGATGATTTTGCAACTTATTACTGCCAGSWMTACVRMAG TTACYCTCCTWGGACTTTTGGCGGAGGGACCAAG | CAGSWMTACVRMAGTTACYC TCCTWGGACT | 2787 | 3255 |
| VK1-05 8 2 10 | CCTGATGATTTTGCAACTTATTACTGCCAGSWMTACAATMB CTACYCTCCTWGGACTTTTGGCGGAGGGACCAAG | CAGSWMTACAATMBCTACYC TCCTWGGACT | 2788 | 3256 |
| VK1-05 9 2 10 | CCTGATGATTTTGCAACTTATTACTGCCAGSWMTACAATAG TYWCYCTCCTWGGACTTTTGGCGGAGGGACCAAG | CAGSWMTACAATAGTYWCYC TCCTWGGACT | 2789 | 3257 |
| VK1-12 1 0 10 | CCTGAAGATTTTGCAACTTATTACTGTSWMSWMGCAAATAG TTTCCCTCCTTWCACTTTTGGCGGAGGGACCAAG | SWMSWMGCAAATAGTTTCCC TCCTTWCACT | 2790 | 3258 |
| VK1-12 10 0 10 | CCTGAAGATTTTGCAACTTATTACTGTCAGCAGRNANHCAG TTTCCCTCCTTWCACTTTTGGCGGAGGGACCAAG | CAGCAGRNANHCAGTTTCCC TCCTTWCACT | 2791 | 3259 |
| VK1-12 11 0 10 | CCTGAAGATTTTGCAACTTATTACTGTCAGCAGRNAAATNH CTTCCCTCCTTWCACTTTTGGCGGAGGGACCAAG | CAGCAGRNAAATNHCTTCCC TCCTTWCACT | 2792 | 3260 |
| VK1-12 12 0 10 | CCTGAAGATTTTGCAACTTATTACTGTCAGCAGRNAAATAG TYWCCCTCCTTWCACTTTTGGCGGAGGGACCAAG | CAGCAGRNAAATAGTYWCCC TCCTTWCACT | 2793 | 3261 |
| VK1-12 13 0 10 | CCTGAAGATTTTGCAACTTATTACTGTCAGCAGGCANHCNH CTTCCCTCCTTWCACTTTTGGCGGAGGGACCAAG | CAGCAGGCANHCNHCTTCCC TCCTTWCACT | 2794 | 3262 |
| VK1-12 14 0 10 | CCTGAAGATTTTGCAACTTATTACTGTCAGCAGGCANHCAG TYWCCCTCCTTWCACTTTTGGCGGAGGGACCAAG | CAGCAGGCANHCAGTYWCCC TCCTTWCACT | 2795 | 3263 |
| VK1-12 15 0 10 | CCTGAAGATTTTGCAACTTATTACTGTCAGCAGGCAAATNH CYWCCCTCCTTWCACTTTTGGCGGAGGGACCAAG | CAGCAGGCAAATNHCYWCCC TCCTTWCACT | 2796 | 3264 |
| VK1-12 2 0 10 | CCTGAAGATTTTGCAACTTATTACTGTSWMCAGRNAAATAG TTTCCCTCCTTWCACTTTTGGCGGAGGGACCAAG | SWMCAGRNAAATAGTTTCCC TCCTTWCACT | 2797 | 3265 |
| VK1-12 3 0 10 | CCTGAAGATTTTGCAACTTATTACTGTSWMCAGGCANHCAG TTTCCCTCCTTWCACTTTTGGCGGAGGGACCAAG | SWMCAGGCANHCAGTTTCCC TCCTTWCACT | 2798 | 3266 |
| VK1-12 4 0 10 | CCTGAAGATTTTGCAACTTATTACTGTSWMCAGGCAAATNH CTTCCCTCCTTWCACTTTTGGCGGAGGGACCAAG | SWMCAGGCAAATNHCTTCCC TCCTTWCACT | 2799 | 3267 |
| VK1-12 5 0 10 | CCTGAAGATTTTGCAACTTATTACTGTSWMCAGGCAAATAG TYWCCCTCCTTWCACTTTTGGCGGAGGGACCAAG | SWMCAGGCAAATAGTYWCCC TCCTTWCACT | 2800 | 3268 |
| VK1-12 6 0 10 | CCTGAAGATTTTGCAACTTATTACTGTCAGSWMRNAAATAG TTTCCCTCCTTWCACTTTTGGCGGAGGGACCAAG | CAGSWMRNAAATAGTTTCCC TCCTTWCACT | 2801 | 3269 |
| VK1-12 7 0 10 | CCTGAAGATTTTGCAACTTATTACTGTCAGSWMGCANHCAG TTTCCCTCCTTWCACTTTTGGCGGAGGGACCAAG | CAGSWMGCANHCAGTTTCCC TCCTTWCACT | 2802 | 3270 |
| VK1-12 8 0 10 | CCTGAAGATTTTGCAACTTATTACTGTCAGSWMGCAAATNH CTTCCCTCCTTWCACTTTTGGCGGAGGGACCAAG | CAGSWMGCAAATNHCTTCCC TCCTTWCACT | 2803 | 3271 |
| VK1-12 9 0 10 | CCTGAAGATTTTGCAACTTATTACTGTCAGSWMGCAAATAG TYWCCCTCCTTWCACTTTTGGCGGAGGGACCAAG | CAGSWMGCAAATAGTYWCCC TCCTTWCACT | 2804 | 3272 |
| VK1-12 1 1 10 | CCTGAAGATTTTGCAACTTATTACTGTSWMSWMGCAAATAG TTTCCCTCCTMTCACTTTTGGCGGAGGGACCAAG | SWMSWMGCAAATAGTTTCCC TCCTMTCACT | 2805 | 3273 |
| VK1-12 10 1 10 | CCTGAAGATTTTGCAACTTATTACTGTCAGCAGRNANHCAG TTTCCCTCCTMTCACTTTTGGCGGAGGGACCAAG | CAGCAGRNANHCAGTTTCCC TCCTMTCACT | 2806 | 3274 |
| VK1-12 11 1 10 | CCTGAAGATTTTGCAACTTATTACTGTCAGCAGRNAAATNH CTTCCCTCCTMTCACTTTTGGCGGAGGGACCAAG | CAGCAGRNAAATNHCTTCCC TCCTMTCACT | 2807 | 3275 |
| VK1-12 12 1 10 | CCTGAAGATTTTGCAACTTATTACTGTCAGCAGRNAAATAG TYWCCCTCCTMTCACTTTTGGCGGAGGGACCAAG | CAGCAGRNAAATAGTYWCCC TCCTMTCACT | 2808 | 3276 |
| VK1-12 13 1 10 | CCTGAAGATTTTGCAACTTATTACTGTCAGCAGGCANHCNH CTTCCCTCCTMTCACTTTTGGCGGAGGGACCAAG | CAGCAGGCANHCNHCTTCCC TCCTMTCACT | 2809 | 3277 |

TABLE 7-continued

Oligonucleotide sequences for exemplary VK jumping dimer and trimer sequences with CDRL3 length 10.

| Name | Sequence of Synthesized Oligonucleotide | Portion of Oligonucleotide Corresponding to CDRL3 Proper | SEQ ID NO (Oligo) | SEQ ID NO (CDRL3 Portion) |
|---|---|---|---|---|
| VK1-12 14 1 10 | CCTGAAGATTTTGCAACTTATTACTGTCAGCAGGCANHCAG TYWCCCTCCTMTCACTTTTGGCGGAGGGACCAAG | CAGCAGGCANHCAGTYWCCC TCCTMTCACT | 2810 | 3278 |
| VK1-12 15 1 10 | CCTGAAGATTTTGCAACTTATTACTGTCAGCAGGCAAATNH CYWCCCTCCTMTCACTTTTGGCGGAGGGACCAAG | CAGCAGGCAAATNHCYWCCC TCCTMTCACT | 2811 | 3279 |
| VK1-12 2 1 10 | CCTGAAGATTTTGCAACTTATTACTGTSWMCAGRNAAATAG TTTCCCTCCTMTCACTTTTGGCGGAGGGACCAAG | SWMCAGRNAAATAGTTTCCC TCCTMTCACT | 2812 | 3280 |
| VK1-12 3 1 10 | CCTGAAGATTTTGCAACTTATTACTGTSWMCAGGCANHCAG TTTCCCTCCTMTCACTTTTGGCGGAGGGACCAAG | SWMCAGGCANHCAGTTTCCC TCCTMTCACT | 2813 | 3281 |
| VK1-12 4 1 10 | CCTGAAGATTTTGCAACTTATTACTGTSWMCAGGCAAATNH CTTCCCTCCTMTCACTTTTGGCGGAGGGACCAAG | SWMCAGGCAAATNHCTTCCC TCCTMTCACT | 2814 | 3282 |
| VK1-12 5 1 10 | CCTGAAGATTTTGCAACTTATTACTGTSWMCAGGCAAATAG TYWCCCTCCTMTCACTTTTGGCGGAGGGACCAAG | SWMCAGGCAAATAGTYWCCC TCCTMTCACT | 2815 | 3283 |
| VK1-12 6 1 10 | CCTGAAGATTTTGCAACTTATTACTGTCAGSWMRNAAATAG TTTCCCTCCTMTCACTTTTGGCGGAGGGACCAAG | CAGSWMRNAAATAGTTTCCC TCCTMTCACT | 2816 | 3284 |
| VK1-12 7 1 10 | CCTGAAGATTTTGCAACTTATTACTGTCAGSWMGCANHCAG TTTCCCTCCTMTCACTTTTGGCGGAGGGACCAAG | CAGSWMGCANHCAGTTTCCC TCCTMTCACT | 2817 | 3285 |
| VK1-12 8 1 10 | CCTGAAGATTTTGCAACTTATTACTGTCAGSWMGCAAATNH CTTCCCTCCTMTCACTTTTGGCGGAGGGACCAAG | CAGSWMGCAAATNHCTTCCC TCCTMTCACT | 2818 | 3286 |
| VK1-12 9 1 10 | CCTGAAGATTTTGCAACTTATTACTGTCAGSWMGCAAATAG TYWCCCTCCTMTCACTTTTGGCGGAGGGACCAAG | CAGSWMGCAAATAGTYWCCC TCCTMTCACT | 2819 | 3287 |
| VK1-12 1 2 10 | CCTGAAGATTTTGCAACTTATTACTGTSWMSWMGCAAATAG TTTCCCTCCTWGGACTTTTGGCGGAGGGACCAAG | SWMSWMGCAAATAGTTTCCC TCCTWGGACT | 2820 | 3288 |
| VK1-12 10 2 10 | CCTGAAGATTTTGCAACTTATTACTGTCAGCAGRNANHCAG TTTCCCTCCTWGGACTTTTGGCGGAGGGACCAAG | CAGCAGRNANHCAGTTTCCC TCCTWGGACT | 2821 | 3289 |
| VK1-12 11 2 10 | CCTGAAGATTTTGCAACTTATTACTGTCAGCAGRNAAATNH CTTCCCTCCTWGGACTTTTGGCGGAGGGACCAAG | CAGCAGRNAAATNHCTTCCC TCCTWGGACT | 2822 | 3290 |
| VK1-12 12 2 10 | CCTGAAGATTTTGCAACTTATTACTGTCAGCAGRNAAATAG TYWCCCTCCTWGGACTTTTGGCGGAGGGACCAAG | CAGCAGRNAAATAGTYWCCC TCCTWGGACT | 2823 | 3291 |
| VK1-12 13 2 10 | CCTGAAGATTTTGCAACTTATTACTGTCAGCAGGCANHCNH CTTCCCTCCTWGGACTTTTGGCGGAGGGACCAAG | CAGCAGGCANHCNHCTTCCC TCCTWGGACT | 2824 | 3292 |
| VK1-12 14 2 10 | CCTGAAGATTTTGCAACTTATTACTGTCAGCAGGCANHCAG TYWCCCTCCTWGGACTTTTGGCGGAGGGACCAAG | CAGCAGGCANHCAGTYWCCC TCCTWGGACT | 2825 | 3293 |
| VK1-12 15 2 10 | CCTGAAGATTTTGCAACTTATTACTGTCAGCAGGCAAATNH CYWCCCTCCTWGGACTTTTGGCGGAGGGACCAAG | CAGCAGGCAAATNHCYWCCC TCCTWGGACT | 2826 | 3294 |
| VK1-12 2 2 10 | CCTGAAGATTTTGCAACTTATTACTGTSWMCAGRNAAATAG TTTCCCTCCTWGGACTTTTGGCGGAGGGACCAAG | SWMCAGRNAAATAGTTTCCC TCCTWGGACT | 2827 | 3295 |
| VK1-12 3 2 10 | CCTGAAGATTTTGCAACTTATTACTGTSWMCAGGCANHCAG TTTCCCTCCTWGGACTTTTGGCGGAGGGACCAAG | SWMCAGGCANHCAGTTTCCC TCCTWGGACT | 2828 | 3296 |
| VK1-12 4 2 10 | CCTGAAGATTTTGCAACTTATTACTGTSWMCAGGCAAATNH CTTCCCTCCTWGGACTTTTGGCGGAGGGACCAAG | SWMCAGGCAAATNHCTTCCC TCCTWGGACT | 2829 | 3297 |
| VK1-12 5 2 10 | CCTGAAGATTTTGCAACTTATTACTGTSWMCAGGCAAATAG TYWCCCTCCTWGGACTTTTGGCGGAGGGACCAAG | SWMCAGGCAAATAGTYWCCC TCCTWGGACT | 2830 | 3298 |
| VK1-12 6 2 10 | CCTGAAGATTTTGCAACTTATTACTGTCAGSWMRNAAATAG TTTCCCTCCTWGGACTTTTGGCGGAGGGACCAAG | CAGSWMRNAAATAGTTTCCC TCCTWGGACT | 2831 | 3299 |
| VK1-12 7 2 10 | CCTGAAGATTTTGCAACTTATTACTGTCAGSWMGCANHCAG TTTCCCTCCTWGGACTTTTGGCGGAGGGACCAAG | CAGSWMGCANHCAGTTTCCC TCCTWGGACT | 2832 | 3300 |
| VK1-12 8 2 10 | CCTGAAGATTTTGCAACTTATTACTGTCAGSWMGCAAATNH CTTCCCTCCTWGGACTTTTGGCGGAGGGACCAAG | CAGSWMGCAAATNHCTTCCC TCCTWGGACT | 2833 | 3301 |

TABLE 7-continued

Oligonucleotide sequences for exemplary VK jumping dimer and trimer sequences with CDRL3 length 10.

| Name | Sequence of Synthesized Oligonucleotide | Portion of Oligonucleotide Corresponding to CDRL3 Proper | SEQ ID NO (Oligo) | SEQ ID NO (CDRL3 Portion) |
|---|---|---|---|---|
| VK1-12 9 2 10 | CCTGAAGATTTTGCAACTTATTACTGTCAGSWMGCAAATAG TYWCCCTCCTWGGACTTTTGGCGGAGGGACCAAG | CAGSWMGCAAATAGTYWCCC TCCTWGGACT | 2834 | 3302 |
| VK1-33 1 0 10 | CCTGAAGATATTGCAACATATTACTGTSWMSWMTACGATAA TCTCCCTCCTTWCACTTTTGGCGGAGGGACCAAG | SWMSWMTACGATAATCTCCC TCCTTWCACT | 2835 | 3303 |
| VK1-33 10 0 10 | CCTGAAGATATTGCAACATATTACTGTCAGCAGBHCNHCAA TCTCCCTCCTTWCACTTTTGGCGGAGGGACCAAG | CAGCAGBHCNHCAATCTCCC TCCTTWCACT | 2836 | 3304 |
| VK1-33 11 0 10 | CCTGAAGATATTGCAACATATTACTGTCAGCAGBHCGATNH CCTCCCTCCTTWCACTTTTGGCGGAGGGACCAAG | CAGCAGBHCGATNHCCTCCC TCCTTWCACT | 2837 | 3305 |
| VK1-33 12 0 10 | CCTGAAGATATTGCAACATATTACTGTCAGCAGBHCGATAA TYWCCCTCCTTWCACTTTTGGCGGAGGGACCAAG | CAGCAGBHCGATAATYWCCC TCCTTWCACT | 2838 | 3306 |
| VK1-33 13 0 10 | CCTGAAGATATTGCAACATATTACTGTCAGCAGTACNHCNH CCTCCCTCCTTWCACTTTTGGCGGAGGGACCAAG | CAGCAGTACNHCNHCCTCCC TCCTTWCACT | 2839 | 3307 |
| VK1-33 14 0 10 | CCTGAAGATATTGCAACATATTACTGTCAGCAGTACNHCAA TYWCCCTCCTTWCACTTTTGGCGGAGGGACCAAG | CAGCAGTACNHCAATYWCCC TCCTTWCACT | 2840 | 3308 |
| VK1-33 15 0 10 | CCTGAAGATATTGCAACATATTACTGTCAGCAGTACGATNH CYWCCCTCCTTWCACTTTTGGCGGAGGGACCAAG | CAGCAGTACGATNHCYWCCC TCCTTWCACT | 2841 | 3309 |
| VK1-33 2 0 10 | CCTGAAGATATTGCAACATATTACTGTSWMCAGBHCGATAA TCTCCCTCCTTWCACTTTTGGCGGAGGGACCAAG | SWMCAGBHCGATAATCTCCC TCCTTWCACT | 2842 | 3310 |
| VK1-33 3 0 10 | CCTGAAGATATTGCAACATATTACTGTSWMCAGTACNHCAA TCTCCCTCCTTWCACTTTTGGCGGAGGGACCAAG | SWMCAGTACNHCAATCTCCC TCCTTWCACT | 2843 | 3311 |
| VK1-33 4 0 10 | CCTGAAGATATTGCAACATATTACTGTSWMCAGTACGATNH CCTCCCTCCTTWCACTTTTGGCGGAGGGACCAAG | SWMCAGTACGATNHCCTCCC TCCTTWCACT | 2844 | 3312 |
| VK1-33 5 0 10 | CCTGAAGATATTGCAACATATTACTGTSWMCAGTACGATAA TYWCCCTCCTTWCACTTTTGGCGGAGGGACCAAG | SWMCAGTACGATAATYWCCC TCCTTWCACT | 2845 | 3313 |
| VK1-33 6 0 10 | CCTGAAGATATTGCAACATATTACTGTCAGSWMBHCGATAA TCTCCCTCCTTWCACTTTTGGCGGAGGGACCAAG | CAGSWMBHCGATAATCTCCC TCCTTWCACT | 2846 | 3314 |
| VK1-33 7 0 10 | CCTGAAGATATTGCAACATATTACTGTCAGSWMTACNHCAA TCTCCCTCCTTWCACTTTTGGCGGAGGGACCAAG | CAGSWMTACNHCAATCTCCC TCCTTWCACT | 2847 | 3315 |
| VK1-33 8 0 10 | CCTGAAGATATTGCAACATATTACTGTCAGSWMTACGATNH CCTCCCTCCTTWCACTTTTGGCGGAGGGACCAAG | CAGSWMTACGATNHCCTCCC TCCTTWCACT | 2848 | 3316 |
| VK1-33 9 0 10 | CCTGAAGATATTGCAACATATTACTGTCAGSWMTACGATAA TYWCCCTCCTTWCACTTTTGGCGGAGGGACCAAG | CAGSWMTACGATAATYWCCC TCCTTWCACT | 2849 | 3317 |
| VK1-33 1 1 10 | CCTGAAGATATTGCAACATATTACTGTSWMSWMTACGATAA TCTCCCTCCTMTCACTTTTGGCGGAGGGACCAAG | SWMSWMTACGATAATCTCCC TCCTMTCACT | 2850 | 3318 |
| VK1-33 10 1 10 | CCTGAAGATATTGCAACATATTACTGTCAGCAGBHCNHCAA TCTCCCTCCTMTCACTTTTGGCGGAGGGACCAAG | CAGCAGBHCNHCAATCTCCC TCCTMTCACT | 2851 | 3319 |
| VK1-33 11 1 10 | CCTGAAGATATTGCAACATATTACTGTCAGCAGBHCGATNH CCTCCCTCCTMTCACTTTTGGCGGAGGGACCAAG | CAGCAGBHCGATNHCCTCCC TCCTMTCACT | 2852 | 3320 |
| VK1-33 12 1 10 | CCTGAAGATATTGCAACATATTACTGTCAGCAGBHCGATAA TYWCCCTCCTMTCACTTTTGGCGGAGGGACCAAG | CAGCAGBHCGATAATYWCCC TCCTMTCACT | 2853 | 3321 |
| VK1-33 13 1 10 | CCTGAAGATATTGCAACATATTACTGTCAGCAGTACNHCNH CCTCCCTCCTMTCACTTTTGGCGGAGGGACCAAG | CAGCAGTACNHCNHCCTCCC TCCTMTCACT | 2854 | 3322 |
| VK1-33 14 1 10 | CCTGAAGATATTGCAACATATTACTGTCAGCAGTACNHCAA TYWCCCTCCTMTCACTTTTGGCGGAGGGACCAAG | CAGCAGTACNHCAATYWCCC TCCTMTCACT | 2855 | 3323 |
| VK1-33 15 1 10 | CCTGAAGATATTGCAACATATTACTGTCAGCAGTACGATNH CYWCCCTCCTMTCACTTTTGGCGGAGGGACCAAG | CAGCAGTACGATNHCYWCCC TCCTMTCACT | 2856 | 3324 |
| VK1-33 2 1 10 | CCTGAAGATATTGCAACATATTACTGTSWMCAGBHCGATAA TCTCCCTCCTMTCACTTTTGGCGGAGGGACCAAG | SWMCAGBHCGATAATCTCCC TCCTMTCACT | 2857 | 3325 |

TABLE 7-continued

Oligonucleotide sequences for exemplary VK jumping dimer and trimer sequences with CDRL3 length 10.

| Name | Sequence of Synthesized Oligonucleotide | Portion of Oligonucleotide Corresponding to CDRL3 Proper | SEQ ID NO (Oligo) | SEQ ID NO (CDRL3 Portion) |
|---|---|---|---|---|
| VK1-33 3 1 10 | CCTGAAGATATTGCAACATATTACTGTSWMCAGTACNHCAA TCTCCCTCCTMTCACTTTTGGCGGAGGGACCAAG | SWMCAGTACNHCAATCTCCC TCCTMTCACT | 2858 | 3326 |
| VK1-33 4 1 10 | CCTGAAGATATTGCAACATATTACTGTSWMCAGTACGATNH CCTCCCTCCTMTCACTTTTGGCGGAGGGACCAAG | SWMCAGTACGATNHCCTCCC TCCTMTCACT | 2859 | 3327 |
| VK1-33 5 1 10 | CCTGAAGATATTGCAACATATTACTGTSWMCAGTACGATAA TYWCCCTCCTMTCACTTTTGGCGGAGGGACCAAG | SWMCAGTACGATAATYWCCC TCCTMTCACT | 2860 | 3328 |
| VK1-33 6 1 10 | CCTGAAGATATTGCAACATATTACTGTCAGSWMBHCGATAA TCTCCCTCCTMTCACTTTTGGCGGAGGGACCAAG | CAGSWMBHCGATAATCTCCC TCCTMTCACT | 2861 | 3329 |
| VK1-33 7 1 10 | CCTGAAGATATTGCAACATATTACTGTCAGSWMTACNHCAA TCTCCCTCCTMTCACTTTTGGCGGAGGGACCAAG | CAGSWMTACNHCAATCTCCC TCCTMTCACT | 2862 | 3330 |
| VK1-33 8 1 10 | CCTGAAGATATTGCAACATATTACTGTCAGSWMTACGATNH CCTCCCTCCTMTCACTTTTGGCGGAGGGACCAAG | CAGSWMTACGATNHCCTCCC TCCTMTCACT | 2863 | 3331 |
| VK1-33 9 1 10 | CCTGAAGATATTGCAACATATTACTGTCAGSWMTACGATAA TYWCCCTCCTMTCACTTTTGGCGGAGGGACCAAG | CAGSWMTACGATAATYWCCC TCCTMTCACT | 2864 | 3332 |
| VK1-33 1 2 10 | CCTGAAGATATTGCAACATATTACTGTSWMSWMTACGATAA TCTCCCTCCTWGGACTTTTGGCGGAGGGACCAAG | SWMSWMTACGATAATCTCCC TCCTWGGACT | 2865 | 3333 |
| VK1-33 10 2 10 | CCTGAAGATATTGCAACATATTACTGTCAGCAGBHCNHCAA TCTCCCTCCTWGGACTTTTGGCGGAGGGACCAAG | CAGCAGBHCNHCAATCTCCC TCCTWGGACT | 2866 | 3334 |
| VK1-33 11 2 10 | CCTGAAGATATTGCAACATATTACTGTCAGCAGBHCGATNH CCTCCCTCCTWGGACTTTTGGCGGAGGGACCAAG | CAGCAGBHCGATNHCCTCCC TCCTWGGACT | 2867 | 3335 |
| VK1-33 12 2 10 | CCTGAAGATATTGCAACATATTACTGTCAGCAGBHCGATAA TYWCCCTCCTWGGACTTTTGGCGGAGGGACCAAG | CAGCAGBHCGATAATYWCCC TCCTWGGACT | 2868 | 3336 |
| VK1-33 13 2 10 | CCTGAAGATATTGCAACATATTACTGTCAGCAGTACNHCNH CCTCCCTCCTWGGACTTTTGGCGGAGGGACCAAG | CAGCAGTACNHCNHCCTCCC TCCTWGGACT | 2869 | 3337 |
| VK1-33 14 2 10 | CCTGAAGATATTGCAACATATTACTGTCAGCAGTACNHCAA TYWCCCTCCTWGGACTTTTGGCGGAGGGACCAAG | CAGCAGTACNHCAATYWCCC TCCTWGGACT | 2870 | 3338 |
| VK1-33 15 2 10 | CCTGAAGATATTGCAACATATTACTGTCAGCAGTACGATNH CYWCCCTCCTWGGACTTTTGGCGGAGGGACCAAG | CAGCAGTACGATNHCYWCCC TCCTWGGACT | 2871 | 3339 |
| VK1-33 2 2 10 | CCTGAAGATATTGCAACATATTACTGTSWMCAGBHCGATAA TCTCCCTCCTWGGACTTTTGGCGGAGGGACCAAG | SWMCAGBHCGATAATCTCCC TCCTWGGACT | 2872 | 3340 |
| VK1-33 3 2 10 | CCTGAAGATATTGCAACATATTACTGTSWMCAGTACNHCAA TCTCCCTCCTWGGACTTTTGGCGGAGGGACCAAG | SWMCAGTACNHCAATCTCCC TCCTWGGACT | 2873 | 3341 |
| VK1-33 4 2 10 | CCTGAAGATATTGCAACATATTACTGTSWMCAGTACGATNH CCTCCCTCCTWGGACTTTTGGCGGAGGGACCAAG | SWMCAGTACGATNHCCTCCC TCCTWGGACT | 2874 | 3342 |
| VK1-33 5 2 10 | CCTGAAGATATTGCAACATATTACTGTSWMCAGTACGATAA TYWCCCTCCTWGGACTTTTGGCGGAGGGACCAAG | SWMCAGTACGATAATYWCCC TCCTWGGACT | 2875 | 3343 |
| VK1-33 6 2 10 | CCTGAAGATATTGCAACATATTACTGTCAGSWMBHCGATAA TCTCCCTCCTWGGACTTTTGGCGGAGGGACCAAG | CAGSWMBHCGATAATCTCCC TCCTWGGACT | 2876 | 3344 |
| VK1-33 7 2 10 | CCTGAAGATATTGCAACATATTACTGTCAGSWMTACNHCAA TCTCCCTCCTWGGACTTTTGGCGGAGGGACCAAG | CAGSWMTACNHCAATCTCCC TCCTWGGACT | 2877 | 3345 |
| VK1-33 8 2 10 | CCTGAAGATATTGCAACATATTACTGTCAGSWMTACGATNH CCTCCCTCCTWGGACTTTTGGCGGAGGGACCAAG | CAGSWMTACGATNHCCTCCC TCCTWGGACT | 2878 | 3346 |
| VK1-33 9 2 10 | CCTGAAGATATTGCAACATATTACTGTCAGSWMTACGATAA TYWCCCTCCTWGGACTTTTGGCGGAGGGACCAAG | CAGSWMTACGATAATYWCCC TCCTWGGACT | 2879 | 3347 |
| VK1-39 1 0 10 | CCTGAAGATTTTGCAACTTACTACTGTSWMSWMAGCTACAG TACTCCTCCTTWCACTTTTGGCGGAGGGACCAAG | SWMSWMAGCTACAGTACTCC TCCTTWCACT | 2880 | 3348 |
| VK1-39 10 0 10 | CCTGAAGATTTTGCAACTTACTACTGTCAGCAAVNABHCAG TACTCCTCCTTWCACTTTTGGCGGAGGGACCAAG | CAGCAAVNABHCAGTACTCC TCCTTWCACT | 2881 | 3349 |

TABLE 7-continued

Oligonucleotide sequences for exemplary VK jumping dimer and trimer sequences with CDRL3 length 10.

| Name | Sequence of Synthesized Oligonucleotide | Portion of Oligonucleotide Corresponding to CDRL3 Proper | SEQ ID NO (Oligo) | SEQ ID NO (CDRL3 Portion) |
|---|---|---|---|---|
| VK1-39 11 0 10 | CCTGAAGATTTTGCAACTTACTACTGTCAGCAAVNATACNH CACTCCTCCTTWCACTTTTGGCGGAGGGACCAAG | CAGCAAVNATACNHCACTCC TCCTTWCACT | 2882 | 3350 |
| VK1-39 12 0 10 | CCTGAAGATTTTGCAACTTACTACTGTCAGCAAVNATACAG TBHCCCTCCTTWCACTTTTGGCGGAGGGACCAAG | CAGCAAVNATACAGTBHCCC TCCTTWCACT | 2883 | 3351 |
| VK1-39 13 0 10 | CCTGAAGATTTTGCAACTTACTACTGTCAGCAAAGCBHCNH CACTCCTCCTTWCACTTTTGGCGGAGGGACCAAG | CAGCAAAGCBHCNHCACTCC TCCTTWCACT | 2884 | 3352 |
| VK1-39 14 0 10 | CCTGAAGATTTTGCAACTTACTACTGTCAGCAAAGCBHCAG TBHCCCTCCTTWCACTTTTGGCGGAGGGACCAAG | CAGCAAAGCBHCAGTBHCCC TCCTTWCACT | 2885 | 3353 |
| VK1-39 15 0 10 | CCTGAAGATTTTGCAACTTACTACTGTCAGCAAAGCTACNH CBHCCCTCCTTWCACTTTTGGCGGAGGGACCAAG | CAGCAAAGCTACNHCBHCCC TCCTTWCACT | 2886 | 3354 |
| VK1-39 2 0 10 | CCTGAAGATTTTGCAACTTACTACTGTSWMCAAVNATACAG TACTCCTCCTTWCACTTTTGGCGGAGGGACCAAG | SWMCAAVNATACAGTACTCC TCCTTWCACT | 2887 | 3355 |
| VK1-39 3 0 10 | CCTGAAGATTTTGCAACTTACTACTGTSWMCAAAGCBHCAG TACTCCTCCTTWCACTTTTGGCGGAGGGACCAAG | SWMCAAAGCBHCAGTACTCC TCCTTWCACT | 2888 | 3356 |
| VK1-39 4 0 10 | CCTGAAGATTTTGCAACTTACTACTGTSWMCAAAGCTACNH CACTCCTCCTTWCACTTTTGGCGGAGGGACCAAG | SWMCAAAGCTACNHCACTCC TCCTTWCACT | 2889 | 3357 |
| VK1-39 5 0 10 | CCTGAAGATTTTGCAACTTACTACTGTSWMCAAAGCTACAG TBHCCCTCCTTWCACTTTTGGCGGAGGGACCAAG | SWMCAAAGCTACAGTBHCCC TCCTTWCACT | 2890 | 3358 |
| VK1-39 6 0 10 | CCTGAAGATTTTGCAACTTACTACTGTCAGSWMVNATACAG TACTCCTCCTTWCACTTTTGGCGGAGGGACCAAG | CAGSWMVNATACAGTACTCC TCCTTWCACT | 2891 | 3359 |
| VK1-39 7 0 10 | CCTGAAGATTTTGCAACTTACTACTGTCAGSWMAGCBHCAG TACTCCTCCTTWCACTTTTGGCGGAGGGACCAAG | CAGSWMAGCBHCAGTACTCC TCCTTWCACT | 2892 | 3360 |
| VK1-39 8 0 10 | CCTGAAGATTTTGCAACTTACTACTGTCAGSWMAGCTACNH CACTCCTCCTTWCACTTTTGGCGGAGGGACCAAG | CAGSWMAGCTACNHCACTCC TCCTTWCACT | 2893 | 3361 |
| VK1-39 9 0 10 | CCTGAAGATTTTGCAACTTACTACTGTCAGSWMAGCTACAG TBHCCCTCCTTWCACTTTTGGCGGAGGGACCAAG | CAGSWMAGCTACAGTBHCCC TCCTTWCACT | 2894 | 3362 |
| VK1-39 1 1 10 | CCTGAAGATTTTGCAACTTACTACTGTSWMSWMAGCTACAG TACTCCTCCTMTCACTTTTGGCGGAGGGACCAAG | SWMSWMAGCTACAGTACTCC TCCTMTCACT | 2895 | 3363 |
| VK1-39 10 1 10 | CCTGAAGATTTTGCAACTTACTACTGTCAGCAAVNABHCAG TACTCCTCCTMTCACTTTTGGCGGAGGGACCAAG | CAGCAAVNABHCAGTACTCC TCCTMTCACT | 2896 | 3364 |
| VK1-39 11 1 10 | CCTGAAGATTTTGCAACTTACTACTGTCAGCAAVNATACNH CACTCCTCCTMTCACTTTTGGCGGAGGGACCAAG | CAGCAAVNATACNHCACTCC TCCTMTCACT | 2897 | 3365 |
| VK1-39 12 1 10 | CCTGAAGATTTTGCAACTTACTACTGTCAGCAAVNATACAG TBHCCCTCCTMTCACTTTTGGCGGAGGGACCAAG | CAGCAAVNATACAGTBHCCC TCCTMTCACT | 2898 | 3366 |
| VK1-39 13 1 10 | CCTGAAGATTTTGCAACTTACTACTGTCAGCAAAGCBHCNH CACTCCTCCTMTCACTTTTGGCGGAGGGACCAAG | CAGCAAAGCBHCNHCACTCC TCCTMTCACT | 2899 | 3367 |
| VK1-39 14 1 10 | CCTGAAGATTTTGCAACTTACTACTGTCAGCAAAGCBHCAG TBHCCCTCCTMTCACTTTTGGCGGAGGGACCAAG | CAGCAAAGCBHCAGTBHCCC TCCTMTCACT | 2900 | 3368 |
| VK1-39 15 1 10 | CCTGAAGATTTTGCAACTTACTACTGTCAGCAAAGCTACNH CBHCCCTCCTMTCACTTTTGGCGGAGGGACCAAG | CAGCAAAGCTACNHCBHCCC TCCTMTCACT | 2901 | 3369 |
| VK1-39 2 1 10 | CCTGAAGATTTTGCAACTTACTACTGTSWMCAAVNATACAG TACTCCTCCTMTCACTTTTGGCGGAGGGACCAAG | SWMCAAVNATACAGTACTCC TCCTMTCACT | 2902 | 3370 |
| VK1-39 3 1 10 | CCTGAAGATTTTGCAACTTACTACTGTSWMCAAAGCBHCAG TACTCCTCCTMTCACTTTTGGCGGAGGGACCAAG | SWMCAAAGCBHCAGTACTCC TCCTMTCACT | 2903 | 3371 |
| VK1-39 4 1 10 | CCTGAAGATTTTGCAACTTACTACTGTSWMCAAAGCTACNH CACTCCTCCTMTCACTTTTGGCGGAGGGACCAAG | SWMCAAAGCTACNHCACTCC TCCTMTCACT | 2904 | 3372 |
| VK1-39 5 1 10 | CCTGAAGATTTTGCAACTTACTACTGTSWMCAAAGCTACAG TBHCCCTCCTMTCACTTTTGGCGGAGGGACCAAG | SWMCAAAGCTACAGTBHCCC TCCTMTCACT | 2905 | 3373 |

TABLE 7-continued

Oligonucleotide sequences for exemplary VK jumping dimer and trimer sequences with CDRL3 length 10.

| Name | Sequence of Synthesized Oligonucleotide | Portion of Oligonucleotide Corresponding to CDRL3 Proper | SEQ ID NO (Oligo) | SEQ ID NO (CDRL3 Portion) |
|---|---|---|---|---|
| VK1-39 6 1 10 | CCTGAAGATTTTGCAACTTACTACTGTCAGSWMVNATACAG TACTCCTCCTMTCACTTTTGGCGGAGGGACCAAG | CAGSWMVNATACAGTACTCC TCCTMTCACT | 2906 | 3374 |
| VK1-39 7 1 10 | CCTGAAGATTTTGCAACTTACTACTGTCAGSWMAGCBHCAG TACTCCTCCTMTCACTTTTGGCGGAGGGACCAAG | CAGSWMAGCBHCAGTACTCC TCCTMTCACT | 2907 | 3375 |
| VK1-39 8 1 10 | CCTGAAGATTTTGCAACTTACTACTGTCAGSWMAGCTACNH CACTCCTCCTMTCACTTTTGGCGGAGGGACCAAG | CAGSWMAGCTACNHCACTCC TCCTMTCACT | 2908 | 3376 |
| VK1-39 9 1 10 | CCTGAAGATTTTGCAACTTACTACTGTCAGSWMAGCTACAG TBHCCCTCCTMTCACTTTTGGCGGAGGGACCAAG | CAGSWMAGCTACAGTBHCCC TCCTMTCACT | 2909 | 3377 |
| VK1-39 1 2 10 | CCTGAAGATTTTGCAACTTACTACTGTSWMSWMAGCTACAG TACTCCTCCTWGGACTTTTGGCGGAGGGACCAAG | SWMSWMAGCTACAGTACTCC TCCTWGGACT | 2910 | 3378 |
| VK1-39 10 2 10 | CCTGAAGATTTTGCAACTTACTACTGTCAGCAAVNABHCAG TACTCCTCCTWGGACTTTTGGCGGAGGGACCAAG | CAGCAAVNABHCAGTACTCC TCCTWGGACT | 2911 | 3379 |
| VK1-39 11 2 10 | CCTGAAGATTTTGCAACTTACTACTGTCAGCAAVNATACNH CACTCCTCCTWGGACTTTTGGCGGAGGGACCAAG | CAGCAAVNATACNHCACTCC TCCTWGGACT | 2912 | 3380 |
| VK1-39 12 2 10 | CCTGAAGATTTTGCAACTTACTACTGTCAGCAAVNATACAG TBHCCCTCCTWGGACTTTTGGCGGAGGGACCAAG | CAGCAAVNATACAGTBHCCC TCCTWGGACT | 2913 | 3381 |
| VK1-39 13 2 10 | CCTGAAGATTTTGCAACTTACTACTGTCAGCAAAGCBHCNH CACTCCTCCTWGGACTTTTGGCGGAGGGACCAAG | CAGCAAAGCBHCNHCACTCC TCCTWGGACT | 2914 | 3382 |
| VK1-39 14 2 10 | CCTGAAGATTTTGCAACTTACTACTGTCAGCAAAGCBHCAG TBHCCCTCCTWGGACTTTTGGCGGAGGGACCAAG | CAGCAAAGCBHCAGTBHCCC TCCTWGGACT | 2915 | 3383 |
| VK1-39 15 2 10 | CCTGAAGATTTTGCAACTTACTACTGTCAGCAAAGCTACNH CBHCCCTCCTWGGACTTTTGGCGGAGGGACCAAG | CAGCAAAGCTACNHCBHCCC TCCTWGGACT | 2916 | 3384 |
| VK1-39 2 2 10 | CCTGAAGATTTTGCAACTTACTACTGTSWMCAAVNATACAG TACTCCTCCTWGGACTTTTGGCGGAGGGACCAAG | SWMCAAVNATACAGTACTCC TCCTWGGACT | 2917 | 3385 |
| VK1-39 3 2 10 | CCTGAAGATTTTGCAACTTACTACTGTSWMCAAAGCBHCAG TACTCCTCCTWGGACTTTTGGCGGAGGGACCAAG | SWMCAAAGCBHCAGTACTCC TCCTWGGACT | 2918 | 3386 |
| VK1-39 4 2 10 | CCTGAAGATTTTGCAACTTACTACTGTSWMCAAAGCTACNH CACTCCTCCTWGGACTTTTGGCGGAGGGACCAAG | SWMCAAAGCTACNHCACTCC TCCTWGGACT | 2919 | 3387 |
| VK1-39 5 2 10 | CCTGAAGATTTTGCAACTTACTACTGTSWMCAAAGCTACAG TBHCCCTCCTWGGACTTTTGGCGGAGGGACCAAG | SWMCAAAGCTACAGTBHCCC TCCTWGGACT | 2920 | 3388 |
| VK1-39 6 2 10 | CCTGAAGATTTTGCAACTTACTACTGTCAGSWMVNATACAG TACTCCTCCTWGGACTTTTGGCGGAGGGACCAAG | CAGSWMVNATACAGTACTCC TCCTWGGACT | 2921 | 3389 |
| VK1-39 7 2 10 | CCTGAAGATTTTGCAACTTACTACTGTCAGSWMAGCBHCAG TACTCCTCCTWGGACTTTTGGCGGAGGGACCAAG | CAGSWMAGCBHCAGTACTCC TCCTWGGACT | 2922 | 3390 |
| VK1-39 8 2 10 | CCTGAAGATTTTGCAACTTACTACTGTCAGSWMAGCTACNH CACTCCTCCTWGGACTTTTGGCGGAGGGACCAAG | CAGSWMAGCTACNHCACTCC TCCTWGGACT | 2923 | 3391 |
| VK1-39 9 2 10 | CCTGAAGATTTTGCAACTTACTACTGTCAGSWMAGCTACAG TBHCCCTCCTWGGACTTTTGGCGGAGGGACCAAG | CAGSWMAGCTACAGTBHCCC TCCTWGGACT | 2924 | 3392 |
| VK2-28 1 0 10 | GCTGAGGATGTTGGGGTTTATTACTGCDTSSWMGCACTCCA GACTCCTCCTTWCACTTTTGGCGGAGGGACCAAG | DTSSWMGCACTCCAGACTCC TCCTTWCACT | 2925 | 3393 |
| VK2-28 10 0 10 | GCTGAGGATGTTGGGGTTTATTACTGCATGCAGVNAMNACA GACTCCTCCTTWCACTTTTGGCGGAGGGACCAAG | ATGCAGVNAMNACAGACTCC TCCTTWCACT | 2926 | 3394 |
| VK2-28 11 0 10 | GCTGAGGATGTTGGGGTTTATTACTGCATGCAGVNACTCSR MACTCCTCCTTWCACTTTTGGCGGAGGGACCAAG | ATGCAGVNACTCSRMACTCC TCCTTWCACT | 2927 | 3395 |
| VK2-28 12 0 10 | GCTGAGGATGTTGGGGTTTATTACTGCATGCAGVNACTCCA GVBCCCTCCTTWCACTTTTGGCGGAGGGACCAAG | ATGCAGVNACTCCAGVBCCC TCCTTWCACT | 2928 | 3396 |
| VK2-28 13 0 10 | GCTGAGGATGTTGGGGTTTATTACTGCATGCAGGCAMNASR MACTCCTCCTTWCACTTTTGGCGGAGGGACCAAG | ATGCAGGCAMNASRMACTCC TCCTTWCACT | 2929 | 3397 |

TABLE 7-continued

Oligonucleotide sequences for exemplary VK jumping dimer and trimer sequences with CDRL3 length 10.

| Name | Sequence of Synthesized Oligonucleotide | Portion of Oligonucleotide Corresponding to CDRL3 Proper | SEQ ID NO (Oligo) | SEQ ID NO (CDRL3 Portion) |
|---|---|---|---|---|
| VK2-28 14 0 10 | GCTGAGGATGTTGGGGTTTATTACTGCATGCAGGCAMNACA GVBCCCTCCTTWCACTTTTGGCGGAGGGACCAAG | ATGCAGGCAMNACAGVBCCC TCCTTWCACT | 2930 | 3398 |
| VK2-28 15 0 10 | GCTGAGGATGTTGGGGTTTATTACTGCATGCAGGCACTCSR MVBCCCTCCTTWCACTTTTGGCGGAGGGACCAAG | ATGCAGGCACTCSRMVBCCC TCCTTWCACT | 2931 | 3399 |
| VK2-28 2 0 10 | GCTGAGGATGTTGGGGTTTATTACTGCDTSCAGVNACTCCA GACTCCTCCTTWCACTTTTGGCGGAGGGACCAAG | DTSCAGVNACTCCAGACTCC TCCTTWCACT | 2932 | 3400 |
| VK2-28 3 0 10 | GCTGAGGATGTTGGGGTTTATTACTGCDTSCAGGCAMNACA GACTCCTCCTTWCACTTTTGGCGGAGGGACCAAG | DTSCAGGCAMNACAGACTCC TCCTTWCACT | 2933 | 3401 |
| VK2-28 4 0 10 | GCTGAGGATGTTGGGGTTTATTACTGCDTSCAGGCACTCSR MACTCCTCCTTWCACTTTTGGCGGAGGGACCAAG | DTSCAGGCACTCSRMACTCC TCCTTWCACT | 2934 | 3402 |
| VK2-28 5 0 10 | GCTGAGGATGTTGGGGTTTATTACTGCDTSCAGGCACTCCA GVBCCCTCCTTWCACTTTTGGCGGAGGGACCAAG | DTSCAGGCACTCCAGVBCCC TCCTTWCACT | 2935 | 3403 |
| VK2-28 6 0 10 | GCTGAGGATGTTGGGGTTTATTACTGCATGSWMVNACTCCA GACTCCTCCTTWCACTTTTGGCGGAGGGACCAAG | ATGSWMVNACTCCAGACTCC TCCTTWCACT | 2936 | 3404 |
| VK2-28 7 0 10 | GCTGAGGATGTTGGGGTTTATTACTGCATGSWMGCAMNACA GACTCCTCCTTWCACTTTTGGCGGAGGGACCAAG | ATGSWMGCAMNACAGACTCC TCCTTWCACT | 2937 | 3405 |
| VK2-28 8 0 10 | GCTGAGGATGTTGGGGTTTATTACTGCATGSWMGCACTCSR MACTCCTCCTTWCACTTTTGGCGGAGGGACCAAG | ATGSWMGCACTCSRMACTCC TCCTTWCACT | 2938 | 3406 |
| VK2-28 9 0 10 | GCTGAGGATGTTGGGGTTTATTACTGCATGSWMGCACTCCA GVBCCCTCCTTWCACTTTTGGCGGAGGGACCAAG | ATGSWMGCACTCCAGVBCCC TCCTTWCACT | 2939 | 3407 |
| VK2-28 1 1 10 | GCTGAGGATGTTGGGGTTTATTACTGCDTSSWMGCACTCCA GACTCCTCCTMTCACTTTTGGCGGAGGGACCAAG | DTSSWMGCACTCCAGACTCC TCCTMTCACT | 2940 | 3408 |
| VK2-28 10 1 10 | GCTGAGGATGTTGGGGTTTATTACTGCATGCAGVNAMNACA GACTCCTCCTMTCACTTTTGGCGGAGGGACCAAG | ATGCAGVNAMNACAGACTCC TCCTMTCACT | 2941 | 3409 |
| VK2-28 11 1 10 | GCTGAGGATGTTGGGGTTTATTACTGCATGCAGVNACTCSR MACTCCTCCTMTCACTTTTGGCGGAGGGACCAAG | ATGCAGVNACTCSRMACTCC TCCTMTCACT | 2942 | 3410 |
| VK2-28 12 1 10 | GCTGAGGATGTTGGGGTTTATTACTGCATGCAGVNACTCCA GVBCCCTCCTMTCACTTTTGGCGGAGGGACCAAG | ATGCAGVNACTCCAGVBCCC TCCTMTCACT | 2943 | 3411 |
| VK2-28 13 1 10 | GCTGAGGATGTTGGGGTTTATTACTGCATGCAGGCAMNASR MACTCCTCCTMTCACTTTTGGCGGAGGGACCAAG | ATGCAGGCAMNASRMACTCC TCCTMTCACT | 2944 | 3412 |
| VK2-28 14 1 10 | GCTGAGGATGTTGGGGTTTATTACTGCATGCAGGCAMNACA GVBCCCTCCTMTCACTTTTGGCGGAGGGACCAAG | ATGCAGGCAMNACAGVBCCC TCCTMTCACT | 2945 | 3413 |
| VK2-28 15 1 10 | GCTGAGGATGTTGGGGTTTATTACTGCATGCAGGCACTCSR MVBCCCTCCTMTCACTTTTGGCGGAGGGACCAAG | ATGCAGGCACTCSRMVBCCC TCCTMTCACT | 2946 | 3414 |
| VK2-28 2 1 10 | GCTGAGGATGTTGGGGTTTATTACTGCDTSCAGVNACTCCA GACTCCTCCTMTCACTTTTGGCGGAGGGACCAAG | DTSCAGVNACTCCAGACTCC TCCTMTCACT | 2947 | 3415 |
| VK2-28 3 1 10 | GCTGAGGATGTTGGGGTTTATTACTGCDTSCAGGCAMNACA GACTCCTCCTMTCACTTTTGGCGGAGGGACCAAG | DTSCAGGCAMNACAGACTCC TCCTMTCACT | 2948 | 3416 |
| VK2-28 4 1 10 | GCTGAGGATGTTGGGGTTTATTACTGCDTSCAGGCACTCSR MACTCCTCCTMTCACTTTTGGCGGAGGGACCAAG | DTSCAGGCACTCSRMACTCC TCCTMTCACT | 2949 | 3417 |
| VK2-28 5 1 10 | GCTGAGGATGTTGGGGTTTATTACTGCDTSCAGGCACTCCA GVBCCCTCCTMTCACTTTTGGCGGAGGGACCAAG | DTSCAGGCACTCCAGVBCCC TCCTMTCACT | 2950 | 3418 |
| VK2-28 6 1 10 | GCTGAGGATGTTGGGGTTTATTACTGCATGSWMVNACTCCA GACTCCTCCTMTCACTTTTGGCGGAGGGACCAAG | ATGSWMVNACTCCAGACTCC TCCTMTCACT | 2951 | 3419 |
| VK2-28 7 1 10 | GCTGAGGATGTTGGGGTTTATTACTGCATGSWMGCAMNACA GACTCCTCCTMTCACTTTTGGCGGAGGGACCAAG | ATGSWMGCAMNACAGACTCC TCCTMTCACT | 2952 | 3420 |
| VK2-28 8 1 10 | GCTGAGGATGTTGGGGTTTATTACTGCATGSWMGCACTCSR MACTCCTCCTMTCACTTTTGGCGGAGGGACCAAG | ATGSWMGCACTCSRMACTCC TCCTMTCACT | 2953 | 3421 |

TABLE 7-continued

Oligonucleotide sequences for exemplary VK jumping dimer and trimer sequences with CDRL3 length 10.

| Name | Sequence of Synthesized Oligonucleotide | Portion of Oligonucleotide Corresponding to CDRL3 Proper | SEQ ID NO (Oligo) | SEQ ID NO (CDRL3 Portion) |
|---|---|---|---|---|
| VK2-28 9 1 10 | GCTGAGGATGTTGGGGTTTATTACTGCATGSWMGCACTCCA GVBCCCTCCTMTCACTTTTGGCGGAGGGACCAAG | ATGSWMGCACTCCAGVBCCC TCCTMTCACT | 2954 | 3422 |
| VK2-28 1 2 10 | GCTGAGGATGTTGGGGTTTATTACTGCDTSSWMGCACTCCA GACTCCTCCTWGGACTTTTGGCGGAGGGACCAAG | DTSSWMGCACTCCAGACTCC TCCTWGGACT | 2955 | 3423 |
| VK2-28 10 2 10 | GCTGAGGATGTTGGGGTTTATTACTGCATGCAGVNAMNACA GACTCCTCCTWGGACTTTTGGCGGAGGGACCAAG | ATGCAGVNAMNACAGACTCC TCCTWGGACT | 2956 | 3424 |
| VK2-28 11 2 10 | GCTGAGGATGTTGGGGTTTATTACTGCATGCAGVNACTCSR MACTCCTCCTWGGACTTTTGGCGGAGGGACCAAG | ATGCAGVNACTCSRMACTCC TCCTWGGACT | 2957 | 3425 |
| VK2-28 12 2 10 | GCTGAGGATGTTGGGGTTTATTACTGCATGCAGVNACTCCA GVBCCCTCCTWGGACTTTTGGCGGAGGGACCAAG | ATGCAGVNACTCCAGVBCCC TCCTWGGACT | 2958 | 3426 |
| VK2-28 13 2 10 | GCTGAGGATGTTGGGGTTTATTACTGCATGCAGGCAMNASR MACTCCTCCTWGGACTTTTGGCGGAGGGACCAAG | ATGCAGGCAMNASRMACTCC TCCTWGGACT | 2959 | 3427 |
| VK2-28 14 2 10 | GCTGAGGATGTTGGGGTTTATTACTGCATGCAGGCAMNACA GVBCCCTCCTWGGACTTTTGGCGGAGGGACCAAG | ATGCAGGCAMNACAGVBCCC TCCTWGGACT | 2960 | 3428 |
| VK2-28 15 2 10 | GCTGAGGATGTTGGGGTTTATTACTGCATGCAGGCACTCSR MVBCCCTCCTWGGACTTTTGGCGGAGGGACCAAG | ATGCAGGCACTCSRMVBCCC TCCTWGGACT | 2961 | 3429 |
| VK2-28 2 2 10 | GCTGAGGATGTTGGGGTTTATTACTGCDTSCAGVNACTCCA GACTCCTCCTWGGACTTTTGGCGGAGGGACCAAG | DTSCAGVNACTCCAGACTCC TCCTWGGACT | 2962 | 3430 |
| VK2-28 3 2 10 | GCTGAGGATGTTGGGGTTTATTACTGCDTSCAGGCAMNACA GACTCCTCCTWGGACTTTTGGCGGAGGGACCAAG | DTSCAGGCAMNACAGACTCC TCCTWGGACT | 2963 | 3431 |
| VK2-28 4 2 10 | GCTGAGGATGTTGGGGTTTATTACTGCDTSCAGGCACTCSR MACTCCTCCTWGGACTTTTGGCGGAGGGACCAAG | DTSCAGGCACTCSRMACTCC TCCTWGGACT | 2964 | 3432 |
| VK2-28 5 2 10 | GCTGAGGATGTTGGGGTTTATTACTGCDTSCAGGCACTCCA GVBCCCTCCTWGGACTTTTGGCGGAGGGACCAAG | DTSCAGGCACTCCAGVBCCC TCCTWGGACT | 2965 | 3433 |
| VK2-28 6 2 10 | GCTGAGGATGTTGGGGTTTATTACTGCATGSWMVNACTCCA GACTCCTCCTWGGACTTTTGGCGGAGGGACCAAG | ATGSWMVNACTCCAGACTCC TCCTWGGACT | 2966 | 3434 |
| VK2-28 7 2 10 | GCTGAGGATGTTGGGGTTTATTACTGCATGSWMGCAMNACA GACTCCTCCTWGGACTTTTGGCGGAGGGACCAAG | ATGSWMGCAMNACAGACTCC TCCTWGGACT | 2967 | 3435 |
| VK2-28 8 2 10 | GCTGAGGATGTTGGGGTTTATTACTGCATGSWMGCACTCSR MACTCCTCCTWGGACTTTTGGCGGAGGGACCAAG | ATGSWMGCACTCSRMACTCC TCCTWGGACT | 2968 | 3436 |
| VK2-28 9 2 10 | GCTGAGGATGTTGGGGTTTATTACTGCATGSWMGCACTCCA GVBCCCTCCTWGGACTTTTGGCGGAGGGACCAAG | ATGSWMGCACTCCAGVBCCC TCCTWGGACT | 2969 | 3437 |
| VK3-11 1 0 10 | CCTGAAGATTTTGCAGTTTATTACTGTSWMSWMAGAAGTAA TTGGCCTCCTTWCACTTTTGGCGGAGGGACCAAG | SWMSWMAGAAGTAATTGGCC TCCTTWCACT | 2970 | 3438 |
| VK3-11 10 0 10 | CCTGAAGATTTTGCAGTTTATTACTGTCAGCAGBHCNHCAA TTGGCCTCCTTWCACTTTTGGCGGAGGGACCAAG | CAGCAGBHCNHCAATTGGCC TCCTTWCACT | 2971 | 3439 |
| VK3-11 11 0 10 | CCTGAAGATTTTGCAGTTTATTACTGTCAGCAGBHCAGTNH CTGGCCTCCTTWCACTTTTGGCGGAGGGACCAAG | CAGCAGBHCAGTNHCTGGCC TCCTTWCACT | 2972 | 3440 |
| VK3-11 12 0 10 | CCTGAAGATTTTGCAGTTTATTACTGTCAGCAGBHCAGTAA TYWCCCTCCTTWCACTTTTGGCGGAGGGACCAAG | CAGCAGBHCAGTAATYWCCC TCCTTWCACT | 2973 | 3441 |
| VK3-11 13 0 10 | CCTGAAGATTTTGCAGTTTATTACTGTCAGCAGAGANHCNH CTGGCCTCCTTWCACTTTTGGCGGAGGGACCAAG | CAGCAGAGANHCNHCTGGCC TCCTTWCACT | 2974 | 3442 |
| VK3-11 14 0 10 | CCTGAAGATTTTGCAGTTTATTACTGTCAGCAGAGANHCAA TYWCCCTCCTTWCACTTTTGGCGGAGGGACCAAG | CAGCAGAGANHCAATYWCCC TCCTTWCACT | 2975 | 3443 |
| VK3-11 15 0 10 | CCTGAAGATTTTGCAGTTTATTACTGTCAGCAGAGAAGTNH CYWCCCTCCTTWCACTTTTGGCGGAGGGACCAAG | CAGCAGAGAAGTNHCYWCCC TCCTTWCACT | 2976 | 3444 |
| VK3-11 2 0 10 | CCTGAAGATTTTGCAGTTTATTACTGTSWMCAGBHCAGTAA TTGGCCTCCTTWCACTTTTGGCGGAGGGACCAAG | SWMCAGBHCAGTAATTGGCC TCCTTWCACT | 2977 | 3445 |

TABLE 7-continued

Oligonucleotide sequences for exemplary VK jumping dimer and trimer sequences with CDRL3 length 10.

| Name | Sequence of Synthesized Oligonucleotide | Portion of Oligonucleotide Corresponding to CDRL3 Proper | SEQ ID NO (Oligo) | SEQ ID NO (CDRL3 Portion) |
|---|---|---|---|---|
| VK3-11 3 0 10 | CCTGAAGATTTTGCAGTTTATTACTGTSWMCAGAGANHCAA TTGGCCTCCTTWCACTTTTGGCGGAGGGACCAAG | SWMCAGAGANHCAATTGGCC TCCTTWCACT | 2978 | 3446 |
| VK3-11 4 0 10 | CCTGAAGATTTTGCAGTTTATTACTGTSWMCAGAGAAGTNH CTGGCCTCCTTWCACTTTTGGCGGAGGGACCAAG | SWMCAGAGAAGTNHCTGGCC TCCTTWCACT | 2979 | 3447 |
| VK3-11 5 0 10 | CCTGAAGATTTTGCAGTTTATTACTGTSWMCAGAGAAGTAA TYWCCCTCCTTWCACTTTTGGCGGAGGGACCAAG | SWMCAGAGAAGTAATYWCCC TCCTTWCACT | 2980 | 3448 |
| VK3-11 6 0 10 | CCTGAAGATTTTGCAGTTTATTACTGTCAGSWMBHCAGTAA TTGGCCTCCTTWCACTTTTGGCGGAGGGACCAAG | CAGSWMBHCAGTAATTGGCC TCCTTWCACT | 2981 | 3449 |
| VK3-11 7 0 10 | CCTGAAGATTTTGCAGTTTATTACTGTCAGSWMAGANHCAA TTGGCCTCCTTWCACTTTTGGCGGAGGGACCAAG | CAGSWMAGANHCAATTGGCC TCCTTWCACT | 2982 | 3450 |
| VK3-11 8 0 10 | CCTGAAGATTTTGCAGTTTATTACTGTCAGSWMAGAAGTNH CTGGCCTCCTTWCACTTTTGGCGGAGGGACCAAG | CAGSWMAGAAGTNHCTGGCC TCCTTWCACT | 2983 | 3451 |
| VK3-11 9 0 10 | CCTGAAGATTTTGCAGTTTATTACTGTCAGSWMAGAAGTAA TYWCCCTCCTTWCACTTTTGGCGGAGGGACCAAG | CAGSWMAGAAGTAATYWCCC TCCTTWCACT | 2984 | 3452 |
| VK3-11 1 1 10 | CCTGAAGATTTTGCAGTTTATTACTGTSWMSWMAGAAGTAA TTGGCCTCCTMTCACTTTTGGCGGAGGGACCAAG | SWMSWMAGAAGTAATTGGCC TCCTMTCACT | 2985 | 3453 |
| VK3-11 10 1 10 | CCTGAAGATTTTGCAGTTTATTACTGTCAGCAGBHCNHCAA TTGGCCTCCTMTCACTTTTGGCGGAGGGACCAAG | CAGCAGBHCNHCAATTGGCC TCCTMTCACT | 2986 | 3454 |
| VK3-11 11 1 10 | CCTGAAGATTTTGCAGTTTATTACTGTCAGCAGBHCAGTNH CTGGCCTCCTMTCACTTTTGGCGGAGGGACCAAG | CAGCAGBHCAGTNHCTGGCC TCCTMTCACT | 2987 | 3455 |
| VK3-11 12 1 10 | CCTGAAGATTTTGCAGTTTATTACTGTCAGCAGBHCAGTAA TYWCCCTCCTMTCACTTTTGGCGGAGGGACCAAG | CAGCAGBHCAGTAATYWCCC TCCTMTCACT | 2988 | 3456 |
| VK3-11 13 1 10 | CCTGAAGATTTTGCAGTTTATTACTGTCAGCAGAGANHCNH CTGGCCTCCTMTCACTTTTGGCGGAGGGACCAAG | CAGCAGAGANHCNHCTGGCC TCCTMTCACT | 2989 | 3457 |
| VK3-11 14 1 10 | CCTGAAGATTTTGCAGTTTATTACTGTCAGCAGAGANHCAA TYWCCCTCCTMTCACTTTTGGCGGAGGGACCAAG | CAGCAGAGANHCAATYWCCC TCCTMTCACT | 2990 | 3458 |
| VK3-11 15 1 10 | CCTGAAGATTTTGCAGTTTATTACTGTCAGCAGAGAAGTNH CYWCCCTCCTMTCACTTTTGGCGGAGGGACCAAG | CAGCAGAGAAGTNHCYWCCC TCCTMTCACT | 2991 | 3459 |
| VK3-11 2 1 10 | CCTGAAGATTTTGCAGTTTATTACTGTSWMCAGBHCAGTAA TTGGCCTCCTMTCACTTTTGGCGGAGGGACCAAG | SWMCAGBHCAGTAATTGGCC TCCTMTCACT | 2992 | 3460 |
| VK3-11 3 1 10 | CCTGAAGATTTTGCAGTTTATTACTGTSWMCAGAGANHCAA TTGGCCTCCTMTCACTTTTGGCGGAGGGACCAAG | SWMCAGAGANHCAATTGGCC TCCTMTCACT | 2993 | 3461 |
| VK3-11 4 1 10 | CCTGAAGATTTTGCAGTTTATTACTGTSWMCAGAGAAGTNH CTGGCCTCCTMTCACTTTTGGCGGAGGGACCAAG | SWMCAGAGAAGTNHCTGGCC TCCTMTCACT | 2994 | 3462 |
| VK3-11 5 1 10 | CCTGAAGATTTTGCAGTTTATTACTGTSWMCAGAGAAGTAA TYWCCCTCCTMTCACTTTTGGCGGAGGGACCAAG | SWMCAGAGAAGTAATYWCCC TCCTMTCACT | 2995 | 3463 |
| VK3-11 6 1 10 | CCTGAAGATTTTGCAGTTTATTACTGTCAGSWMBHCAGTAA TTGGCCTCCTMTCACTTTTGGCGGAGGGACCAAG | CAGSWMBHCAGTAATTGGCC TCCTMTCACT | 2996 | 3464 |
| VK3-11 7 1 10 | CCTGAAGATTTTGCAGTTTATTACTGTCAGSWMAGANHCAA TTGGCCTCCTMTCACTTTTGGCGGAGGGACCAAG | CAGSWMAGANHCAATTGGCC TCCTMTCACT | 2997 | 3465 |
| VK3-11 8 1 10 | CCTGAAGATTTTGCAGTTTATTACTGTCAGSWMAGAAGTNH CTGGCCTCCTMTCACTTTTGGCGGAGGGACCAAG | CAGSWMAGAAGTNHCTGGCC TCCTMTCACT | 2998 | 3466 |
| VK3-11 9 1 10 | CCTGAAGATTTTGCAGTTTATTACTGTCAGSWMAGAAGTAA TYWCCCTCCTMTCACTTTTGGCGGAGGGACCAAG | CAGSWMAGAAGTAATYWCCC TCCTMTCACT | 2999 | 3467 |
| VK3-11 1 2 10 | CCTGAAGATTTTGCAGTTTATTACTGTSWMSWMAGAAGTAA TTGGCCTCCTWGGACTTTTGGCGGAGGGACCAAG | SWMSWMAGAAGTAATTGGCC TCCTWGGACT | 3000 | 3468 |
| VK3-11 10 2 10 | CCTGAAGATTTTGCAGTTTATTACTGTCAGCAGBHCNHCAA TTGGCCTCCTWGGACTTTTGGCGGAGGGACCAAG | CAGCAGBHCNHCAATTGGCC TCCTWGGACT | 3001 | 3469 |

TABLE 7-continued

Oligonucleotide sequences for exemplary VK jumping dimer and trimer sequences with CDRL3 length 10.

| Name | Sequence of Synthesized Oligonucleotide | Portion of Oligonucleotide Corresponding to CDRL3 Proper | SEQ ID NO (Oligo) | SEQ ID NO (CDRL3 Portion) |
|---|---|---|---|---|
| VK3-11 11 2 10 | CCTGAAGATTTTGCAGTTTATTACTGTCAGCAGBHCAGTNH CTGGCCTCCTWGGACTTTTGGCGGAGGGACCAAG | CAGCAGBHCAGTNHCTGGCC TCCTWGGACT | 3002 | 3470 |
| VK3-11 12 2 10 | CCTGAAGATTTTGCAGTTTATTACTGTCAGCAGBHCAGTAA TYWCCCTCCTWGGACTTTTGGCGGAGGGACCAAG | CAGCAGBHCAGTAATYWCCC TCCTWGGACT | 3003 | 3471 |
| VK3-11 13 2 10 | CCTGAAGATTTTGCAGTTTATTACTGTCAGCAGAGANHCNH CTGGCCTCCTWGGACTTTTGGCGGAGGGACCAAG | CAGCAGAGANHCNHCTGGCC TCCTWGGACT | 3004 | 3472 |
| VK3-11 14 2 10 | CCTGAAGATTTTGCAGTTTATTACTGTCAGCAGAGANHCAA TYWCCCTCCTWGGACTTTTGGCGGAGGGACCAAG | CAGCAGAGANHCAATYWCCC TCCTWGGACT | 3005 | 3473 |
| VK3-11 15 2 10 | CCTGAAGATTTTGCAGTTTATTACTGTCAGCAGAGAAGTNH CYWCCCTCCTWGGACTTTTGGCGGAGGGACCAAG | CAGCAGAGAAGTNHCYWCCC TCCTWGGACT | 3006 | 3474 |
| VK3-11 2 2 10 | CCTGAAGATTTTGCAGTTTATTACTGTSWMCAGBHCAGTAA TTGGCCTCCTWGGACTTTTGGCGGAGGGACCAAG | SWMCAGBHCAGTAATTGGCC TCCTWGGACT | 3007 | 3475 |
| VK3-11 3 2 10 | CCTGAAGATTTTGCAGTTTATTACTGTSWMCAGAGANHCAA TTGGCCTCCTWGGACTTTTGGCGGAGGGACCAAG | SWMCAGAGANHCAATTGGCC TCCTWGGACT | 3008 | 3476 |
| VK3-11 4 2 10 | CCTGAAGATTTTGCAGTTTATTACTGTSWMCAGAGAAGTNH CTGGCCTCCTWGGACTTTTGGCGGAGGGACCAAG | SWMCAGAGAAGTNHCTGGCC TCCTWGGACT | 3009 | 3477 |
| VK3-11 5 2 10 | CCTGAAGATTTTGCAGTTTATTACTGTSWMCAGAGAAGTAA TYWCCCTCCTWGGACTTTTGGCGGAGGGACCAAG | SWMCAGAGAAGTAATYWCCC TCCTWGGACT | 3010 | 3478 |
| VK3-11 6 2 10 | CCTGAAGATTTTGCAGTTTATTACTGTCAGSWMBHCAGTAA TTGGCCTCCTWGGACTTTTGGCGGAGGGACCAAG | CAGSWMBHCAGTAATTGGCC TCCTWGGACT | 3011 | 3479 |
| VK3-11 7 2 10 | CCTGAAGATTTTGCAGTTTATTACTGTCAGSWMAGANHCAA TTGGCCTCCTWGGACTTTTGGCGGAGGGACCAAG | CAGSWMAGANHCAATTGGCC TCCTWGGACT | 3012 | 3480 |
| VK3-11 8 2 10 | CCTGAAGATTTTGCAGTTTATTACTGTCAGSWMAGAAGTNH CTGGCCTCCTWGGACTTTTGGCGGAGGGACCAAG | CAGSWMAGAAGTNHCTGGCC TCCTWGGACT | 3013 | 3481 |
| VK3-11 9 2 10 | CCTGAAGATTTTGCAGTTTATTACTGTCAGSWMAGAAGTAA TYWCCCTCCTWGGACTTTTGGCGGAGGGACCAAG | CAGSWMAGAAGTAATYWCCC TCCTWGGACT | 3014 | 3482 |
| VK3-15 1 0 10 | CAGTCTGAAGATTTTGCAGTTTATTACTGTSWMSWMTACAA TAATTGGCCTCCTTWCACTTTTGGCGGAGGGACCAAG | SWMSWMTACAATAATTGGCC TCCTTWCACT | 3015 | 3483 |
| VK3-15 10 0 10 | CAGTCTGAAGATTTTGCAGTTTATTACTGTCAGCAGBHCNH CAATTGGCCTCCTTWCACTTTTGGCGGAGGGACCAAG | CAGCAGBHCNHCAATTGGCC TCCTTWCACT | 3016 | 3439 |
| VK3-15 11 0 10 | CAGTCTGAAGATTTTGCAGTTTATTACTGTCAGCAGBHCAA TNHCTGGCCTCCTTWCACTTTTGGCGGAGGGACCAAG | CAGCAGBHCAATNHCTGGCC TCCTTWCACT | 3017 | 3484 |
| VK3-15 12 0 10 | CAGTCTGAAGATTTTGCAGTTTATTACTGTCAGCAGBHCAA TAATYWCCCTCCTTWCACTTTTGGCGGAGGGACCAAG | CAGCAGBHCAATAATYWCCC TCCTTWCACT | 3018 | 3485 |
| VK3-15 13 0 10 | CAGTCTGAAGATTTTGCAGTTTATTACTGTCAGCAGTACNH CNHCTGGCCTCCTTWCACTTTTGGCGGAGGGACCAAG | CAGCAGTACNHCNHCTGGCC TCCTTWCACT | 3019 | 3486 |
| VK3-15 14 0 10 | CAGTCTGAAGATTTTGCAGTTTATTACTGTCAGCAGTACNH CAATYWCCCTCCTTWCACTTTTGGCGGAGGGACCAAG | CAGCAGTACNHCAATYWCCC TCCTTWCACT | 3020 | 3308 |
| VK3-15 15 0 10 | CAGTCTGAAGATTTTGCAGTTTATTACTGTCAGCAGTACAA TNHCYWCCCTCCTTWCACTTTTGGCGGAGGGACCAAG | CAGCAGTACAATNHCYWCCC TCCTTWCACT | 3021 | 3487 |
| VK3-15 2 0 10 | CAGTCTGAAGATTTTGCAGTTTATTACTGTSWMCAGBHCAA TAATTGGCCTCCTTWCACTTTTGGCGGAGGGACCAAG | SWMCAGBHCAATAATTGGCC TCCTTWCACT | 3022 | 3488 |
| VK3-15 3 0 10 | CAGTCTGAAGATTTTGCAGTTTATTACTGTSWMCAGTACNH CAATTGGCCTCCTTWCACTTTTGGCGGAGGGACCAAG | SWMCAGTACNHCAATTGGCC TCCTTWCACT | 3023 | 3489 |
| VK3-15 4 0 10 | CAGTCTGAAGATTTTGCAGTTTATTACTGTSWMCAGTACAA TNHCTGGCCTCCTTWCACTTTTGGCGGAGGGACCAAG | SWMCAGTACAATNHCTGGCC TCCTTWCACT | 3024 | 3490 |
| VK3-15 5 0 10 | CAGTCTGAAGATTTTGCAGTTTATTACTGTSWMCAGTACAA TAATYWCCCTCCTTWCACTTTTGGCGGAGGGACCAAG | SWMCAGTACAATAATYWCCC TCCTTWCACT | 3025 | 3491 |

TABLE 7-continued

Oligonucleotide sequences for exemplary VK jumping dimer and trimer sequences with CDRL3 length 10.

| Name | Sequence of Synthesized Oligonucleotide | Portion of Oligonucleotide Corresponding to CDRL3 Proper | SEQ ID NO (Oligo) | SEQ ID NO (CDRL3 Portion) |
|---|---|---|---|---|
| VK3-15 6 0 10 | CAGTCTGAAGATTTTGCAGTTTATTACTGTCAGSWMBHCAATAATTGGCCTCCTTWCACTTTTGGCGGAGGGACCAAG | CAGSWMBHCAATAATTGGCCTCCTTWCACT | 3026 | 3492 |
| VK3-15 7 0 10 | CAGTCTGAAGATTTTGCAGTTTATTACTGTCAGSWMTACNHCAATTGGCCTCCTTWCACTTTTGGCGGAGGGACCAAG | CAGSWMTACNHCAATTGGCCTCCTTWCACT | 3027 | 3493 |
| VK3-15 8 0 10 | CAGTCTGAAGATTTTGCAGTTTATTACTGTCAGSWMTACAATNHCTGGCCTCCTTWCACTTTTGGCGGAGGGACCAAG | CAGSWMTACAATNHCTGGCCTCCTTWCACT | 3028 | 3494 |
| VK3-15 9 0 10 | CAGTCTGAAGATTTTGCAGTTTATTACTGTCAGSWMTACAATAATYWCCCTCCTTWCACTTTTGGCGGAGGGACCAAG | CAGSWMTACAATAATYWCCCTCCTTWCACT | 3029 | 3495 |
| VK3-15 1 1 10 | CAGTCTGAAGATTTTGCAGTTTATTACTGTSWMSWMTACAATAATTGGCCTCCTMTCACTTTTGGCGGAGGGACCAAG | SWMSWMTACAATAATTGGCCTCCTMTCACT | 3030 | 3496 |
| VK3-15 10 1 10 | CAGTCTGAAGATTTTGCAGTTTATTACTGTCAGCAGBHCNHCAATTGGCCTCCTMTCACTTTTGGCGGAGGGACCAAG | CAGCAGBHCNHCAATTGGCCTCCTMTCACT | 3031 | 3454 |
| VK3-15 11 1 10 | CAGTCTGAAGATTTTGCAGTTTATTACTGTCAGCAGBHCAATNHCTGGCCTCCTMTCACTTTTGGCGGAGGGACCAAG | CAGCAGBHCAATNHCTGGCCTCCTMTCACT | 3032 | 3497 |
| VK3-15 12 1 10 | CAGTCTGAAGATTTTGCAGTTTATTACTGTCAGCAGBHCAATAATYWCCCTCCTMTCACTTTTGGCGGAGGGACCAAG | CAGCAGBHCAATAATYWCCCTCCTMTCACT | 3033 | 3498 |
| VK3-15 13 1 10 | CAGTCTGAAGATTTTGCAGTTTATTACTGTCAGCAGTACNHCNHCTGGCCTCCTMTCACTTTTGGCGGAGGGACCAAG | CAGCAGTACNHCNHCTGGCCTCCTMTCACT | 3034 | 3499 |
| VK3-15 14 1 10 | CAGTCTGAAGATTTTGCAGTTTATTACTGTCAGCAGTACNHCAATYWCCCTCCTMTCACTTTTGGCGGAGGGACCAAG | CAGCAGTACNHCAATYWCCCTCCTMTCACT | 3035 | 3323 |
| VK3-15 15 1 10 | CAGTCTGAAGATTTTGCAGTTTATTACTGTCAGCAGTACAATNHCYWCCCTCCTMTCACTTTTGGCGGAGGGACCAAG | CAGCAGTACAATNHCYWCCCTCCTMTCACT | 3036 | 3500 |
| VK3-15 2 1 10 | CAGTCTGAAGATTTTGCAGTTTATTACTGTSWMCAGBHCAATAATTGGCCTCCTMTCACTTTTGGCGGAGGGACCAAG | SWMCAGBHCAATAATTGGCCTCCTMTCACT | 3037 | 3501 |
| VK3-15 3 1 10 | CAGTCTGAAGATTTTGCAGTTTATTACTGTSWMCAGTACNHCAATTGGCCTCCTMTCACTTTTGGCGGAGGGACCAAG | SWMCAGTACNHCAATTGGCCTCCTMTCACT | 3038 | 3502 |
| VK3-15 4 1 10 | CAGTCTGAAGATTTTGCAGTTTATTACTGTSWMCAGTACAATNHCTGGCCTCCTMTCACTTTTGGCGGAGGGACCAAG | SWMCAGTACAATNHCTGGCCTCCTMTCACT | 3039 | 3503 |
| VK3-15 5 1 10 | CAGTCTGAAGATTTTGCAGTTTATTACTGTSWMCAGTACAATAATYWCCCTCCTMTCACTTTTGGCGGAGGGACCAAG | SWMCAGTACAATAATYWCCCTCCTMTCACT | 3040 | 3504 |
| VK3-15 6 1 10 | CAGTCTGAAGATTTTGCAGTTTATTACTGTCAGSWMBHCAATAATTGGCCTCCTMTCACTTTTGGCGGAGGGACCAAG | CAGSWMBHCAATAATTGGCCTCCTMTCACT | 3041 | 3505 |
| VK3-15 7 1 10 | CAGTCTGAAGATTTTGCAGTTTATTACTGTCAGSWMTACNHCAATTGGCCTCCTMTCACTTTTGGCGGAGGGACCAAG | CAGSWMTACNHCAATTGGCCTCCTMTCACT | 3042 | 3506 |
| VK3-15 8 1 10 | CAGTCTGAAGATTTTGCAGTTTATTACTGTCAGSWMTACAATNHCTGGCCTCCTMTCACTTTTGGCGGAGGGACCAAG | CAGSWMTACAATNHCTGGCCTCCTMTCACT | 3043 | 3507 |
| VK3-15 9 1 10 | CAGTCTGAAGATTTTGCAGTTTATTACTGTCAGSWMTACAATAATYWCCCTCCTMTCACTTTTGGCGGAGGGACCAAG | CAGSWMTACAATAATYWCCCTCCTMTCACT | 3044 | 3508 |
| VK3-15 1 2 10 | CAGTCTGAAGATTTTGCAGTTTATTACTGTSWMSWMTACAATAATTGGCCTCCTWGGACTTTTGGCGGAGGGACCAAG | SWMSWMTACAATAATTGGCCTCCTWGGACT | 3045 | 3509 |
| VK3-15 10 2 10 | CAGTCTGAAGATTTTGCAGTTTATTACTGTCAGCAGBHCNHCAATTGGCCTCCTWGGACTTTTGGCGGAGGGACCAAG | CAGCAGBHCNHCAATTGGCCTCCTWGGACT | 3046 | 3469 |
| VK3-15 11 2 10 | CAGTCTGAAGATTTTGCAGTTTATTACTGTCAGCAGBHCAATNHCTGGCCTCCTWGGACTTTTGGCGGAGGGACCAAG | CAGCAGBHCAATNHCTGGCCTCCTWGGACT | 3047 | 3510 |
| VK3-15 12 2 10 | CAGTCTGAAGATTTTGCAGTTTATTACTGTCAGCAGBHCAATAATYWCCCTCCTWGGACTTTTGGCGGAGGGACCAAG | CAGCAGBHCAATAATYWCCCTCCTWGGACT | 3048 | 3511 |
| VK3-15 13 2 10 | CAGTCTGAAGATTTTGCAGTTTATTACTGTCAGCAGTACNHCNHCTGGCCTCCTWGGACTTTTGGCGGAGGGACCAAG | CAGCAGTACNHCNHCTGGCCTCCTWGGACT | 3049 | 3512 |

TABLE 7-continued

Oligonucleotide sequences for exemplary VK jumping dimer and trimer sequences with CDRL3 length 10.

| Name | Sequence of Synthesized Oligonucleotide | Portion of Oligonucleotide Corresponding to CDRL3 Proper | SEQ ID NO (Oligo) | SEQ ID NO (CDRL3 Portion) |
|---|---|---|---|---|
| VK3-15 14 2 10 | CAGTCTGAAGATTTTGCAGTTTATTACTGTCAGCAGTACNH CAATYWCCCTCCTWGGACTTTTGGCGGAGGGACCAAG | CAGCAGTACNHCAATYWCCC TCCTWGGACT | 3050 | 3338 |
| VK3-15 15 2 10 | CAGTCTGAAGATTTTGCAGTTTATTACTGTCAGCAGTACAA TNHCYWCCCTCCTWGGACTTTTGGCGGAGGGACCAAG | CAGCAGTACAATNHCYWCCC TCCTWGGACT | 3051 | 3513 |
| VK3-15 2 2 10 | CAGTCTGAAGATTTTGCAGTTTATTACTGTSWMCAGBHCAA TAATTGGCCTCCTWGGACTTTTGGCGGAGGGACCAAG | SWMCAGBHCAATAATTGGCC TCCTWGGACT | 3052 | 3514 |
| VK3-15 3 2 10 | CAGTCTGAAGATTTTGCAGTTTATTACTGTSWMCAGTACNH CAATTGGCCTCCTWGGACTTTTGGCGGAGGGACCAAG | SWMCAGTACNHCAATTGGCC TCCTWGGACT | 3053 | 3515 |
| VK3-15 4 2 10 | CAGTCTGAAGATTTTGCAGTTTATTACTGTSWMCAGTACAA TNHCTGGCCTCCTWGGACTTTTGGCGGAGGGACCAAG | SWMCAGTACAATNHCTGGCC TCCTWGGACT | 3054 | 3516 |
| VK3-15 5 2 10 | CAGTCTGAAGATTTTGCAGTTTATTACTGTSWMCAGTACAA TAATYWCCCTCCTWGGACTTTTGGCGGAGGGACCAAG | SWMCAGTACAATAATYWCCC TCCTWGGACT | 3055 | 3517 |
| VK3-15 6 2 10 | CAGTCTGAAGATTTTGCAGTTTATTACTGTCAGSWMBHCAA TAATTGGCCTCCTWGGACTTTTGGCGGAGGGACCAAG | CAGSWMBHCAATAATTGGCC TCCTWGGACT | 3056 | 3518 |
| VK3-15 7 2 10 | CAGTCTGAAGATTTTGCAGTTTATTACTGTCAGSWMTACNH CAATTGGCCTCCTWGGACTTTTGGCGGAGGGACCAAG | CAGSWMTACNHCAATTGGCC TCCTWGGACT | 3057 | 3519 |
| VK3-15 8 2 10 | CAGTCTGAAGATTTTGCAGTTTATTACTGTCAGSWMTACAA TNHCTGGCCTCCTWGGACTTTTGGCGGAGGGACCAAG | CAGSWMTACAATNHCTGGCC TCCTWGGACT | 3058 | 3520 |
| VK3-15 9 2 10 | CAGTCTGAAGATTTTGCAGTTTATTACTGTCAGSWMTACAA TAATYWCCCTCCTWGGACTTTTGGCGGAGGGACCAAG | CAGSWMTACAATAATYWCCC TCCTWGGACT | 3059 | 3521 |
| VK3-20 1 0 10 | CCTGAAGATTTTGCAGTGTATTACTGTSWMSWMTACGGAAG TAGTCCTCCTTWCACTTTTGGCGGAGGGACCAAG | SWMSWMTACGGAAGTAGTCC TCCTTWCACT | 3060 | 3522 |
| VK3-20 10 0 10 | CCTGAAGATTTTGCAGTGTATTACTGTCAGCAGBHCBHCAG TAGTCCTCCTTWCACTTTTGGCGGAGGGACCAAG | CAGCAGBHCBHCAGTAGTCC TCCTTWCACT | 3061 | 3523 |
| VK3-20 11 0 10 | CCTGAAGATTTTGCAGTGTATTACTGTCAGCAGBHCGGAVN CAGTCCTCCTTWCACTTTTGGCGGAGGGACCAAG | CAGCAGBHCGGAVNCAGTCC TCCTTWCACT | 3062 | 3524 |
| VK3-20 12 0 10 | CCTGAAGATTTTGCAGTGTATTACTGTCAGCAGBHCGGAAG TBHCCCTCCTTWCACTTTTGGCGGAGGGACCAAG | CAGCAGBHCGGAAGTBHCCC TCCTTWCACT | 3063 | 3525 |
| VK3-20 13 0 10 | CCTGAAGATTTTGCAGTGTATTACTGTCAGCAGTACBHCVN CAGTCCTCCTTWCACTTTTGGCGGAGGGACCAAG | CAGCAGTACBHCVNCAGTCC TCCTTWCACT | 3064 | 3526 |
| VK3-20 14 0 10 | CCTGAAGATTTTGCAGTGTATTACTGTCAGCAGTACBHCAG TBHCCCTCCTTWCACTTTTGGCGGAGGGACCAAG | CAGCAGTACBHCAGTBHCCC TCCTTWCACT | 3065 | 3527 |
| VK3-20 15 0 10 | CCTGAAGATTTTGCAGTGTATTACTGTCAGCAGTACGGAVN CBHCCCTCCTTWCACTTTTGGCGGAGGGACCAAG | CAGCAGTACGGAVNCBHCCC TCCTTWCACT | 3066 | 3528 |
| VK3-20 2 0 10 | CCTGAAGATTTTGCAGTGTATTACTGTSWMCAGBHCGGAAG TAGTCCTCCTTWCACTTTTGGCGGAGGGACCAAG | SWMCAGBHCGGAAGTAGTCC TCCTTWCACT | 3067 | 3529 |
| VK3-20 3 0 10 | CCTGAAGATTTTGCAGTGTATTACTGTSWMCAGTACBHCAG TAGTCCTCCTTWCACTTTTGGCGGAGGGACCAAG | SWMCAGTACBHCAGTAGTCC TCCTTWCACT | 3068 | 3530 |
| VK3-20 4 0 10 | CCTGAAGATTTTGCAGTGTATTACTGTSWMCAGTACGGAVN CAGTCCTCCTTWCACTTTTGGCGGAGGGACCAAG | SWMCAGTACGGAVNCAGTCC TCCTTWCACT | 3069 | 3531 |
| VK3-20 5 0 10 | CCTGAAGATTTTGCAGTGTATTACTGTSWMCAGTACGGAAG TBHCCCTCCTTWCACTTTTGGCGGAGGGACCAAG | SWMCAGTACGGAAGTBHCCC TCCTTWCACT | 3070 | 3532 |
| VK3-20 6 0 10 | CCTGAAGATTTTGCAGTGTATTACTGTCAGSWMBHCGGAAG TAGTCCTCCTTWCACTTTTGGCGGAGGGACCAAG | CAGSWMBHCGGAAGTAGTCC TCCTTWCACT | 3071 | 3533 |
| VK3-20 7 0 10 | CCTGAAGATTTTGCAGTGTATTACTGTCAGSWMTACBHCAG TAGTCCTCCTTWCACTTTTGGCGGAGGGACCAAG | CAGSWMTACBHCAGTAGTCC TCCTTWCACT | 3072 | 3534 |
| VK3-20 8 0 10 | CCTGAAGATTTTGCAGTGTATTACTGTCAGSWMTACGGAVN CAGTCCTCCTTWCACTTTTGGCGGAGGGACCAAG | CAGSWMTACGGAVNCAGTCC TCCTTWCACT | 3073 | 3535 |

TABLE 7-continued

Oligonucleotide sequences for exemplary VK jumping dimer and trimer sequences with CDRL3 length 10.

| Name | Sequence of Synthesized Oligonucleotide | Portion of Oligonucleotide Corresponding to CDRL3 Proper | SEQ ID NO (Oligo) | SEQ ID NO (CDRL3 Portion) |
|---|---|---|---|---|
| VK3-20 9 0 10 | CCTGAAGATTTTGCAGTGTATTACTGTCAGSWMTACGGAAG TBHCCCTCCTTWCACTTTTGGCGGAGGGACCAAG | CAGSWMTACGGAAGTBHCCC TCCTTWCACT | 3074 | 3536 |
| VK3-20 1 1 10 | CCTGAAGATTTTGCAGTGTATTACTGTSWMSWMTACGGAAG TAGTCCTCCTMTCACTTTTGGCGGAGGGACCAAG | SWMSWMTACGGAAGTAGTCC TCCTMTCACT | 3075 | 3537 |
| VK3-20 10 1 10 | CCTGAAGATTTTGCAGTGTATTACTGTCAGCAGBHCBHCAG TAGTCCTCCTMTCACTTTTGGCGGAGGGACCAAG | CAGCAGBHCBHCAGTAGTCC TCCTMTCACT | 3076 | 3538 |
| VK3-20 11 1 10 | CCTGAAGATTTTGCAGTGTATTACTGTCAGCAGBHCGGAVN CAGTCCTCCTMTCACTTTTGGCGGAGGGACCAAG | CAGCAGBHCGGAVNCAGTCC TCCTMTCACT | 3077 | 3539 |
| VK3-20 12 1 10 | CCTGAAGATTTTGCAGTGTATTACTGTCAGCAGBHCGGAAG TBHCCCTCCTMTCACTTTTGGCGGAGGGACCAAG | CAGCAGBHCGGAAGTBHCCC TCCTMTCACT | 3078 | 3540 |
| VK3-20 13 1 10 | CCTGAAGATTTTGCAGTGTATTACTGTCAGCAGTACBHCVN CAGTCCTCCTMTCACTTTTGGCGGAGGGACCAAG | CAGCAGTACBHCVNCAGTCC TCCTMTCACT | 3079 | 3541 |
| VK3-20 14 1 10 | CCTGAAGATTTTGCAGTGTATTACTGTCAGCAGTACBHCAG TBHCCCTCCTMTCACTTTTGGCGGAGGGACCAAG | CAGCAGTACBHCAGTBHCCC TCCTMTCACT | 3080 | 3542 |
| VK3-20 15 1 10 | CCTGAAGATTTTGCAGTGTATTACTGTCAGCAGTACGGAVN CBHCCCTCCTMTCACTTTTGGCGGAGGGACCAAG | CAGCAGTACGGAVNCBHCCC TCCTMTCACT | 3081 | 3543 |
| VK3-20 2 1 10 | CCTGAAGATTTTGCAGTGTATTACTGTSWMCAGBHCGGAAG TAGTCCTCCTMTCACTTTTGGCGGAGGGACCAAG | SWMCAGBHCGGAAGTAGTCC TCCTMTCACT | 3082 | 3544 |
| VK3-20 3 1 10 | CCTGAAGATTTTGCAGTGTATTACTGTSWMCAGTACBHCAG TAGTCCTCCTMTCACTTTTGGCGGAGGGACCAAG | SWMCAGTACBHCAGTAGTCC TCCTMTCACT | 3083 | 3545 |
| VK3-20 4 1 10 | CCTGAAGATTTTGCAGTGTATTACTGTSWMCAGTACGGAVN CAGTCCTCCTMTCACTTTTGGCGGAGGGACCAAG | SWMCAGTACGGAVNCAGTCC TCCTMTCACT | 3084 | 3546 |
| VK3-20 5 1 10 | CCTGAAGATTTTGCAGTGTATTACTGTSWMCAGTACGGAAG TBHCCCTCCTMTCACTTTTGGCGGAGGGACCAAG | SWMCAGTACGGAAGTBHCCC TCCTMTCACT | 3085 | 3547 |
| VK3-20 6 1 10 | CCTGAAGATTTTGCAGTGTATTACTGTCAGSWMBHCGGAAG TAGTCCTCCTMTCACTTTTGGCGGAGGGACCAAG | CAGSWMBHCGGAAGTAGTCC TCCTMTCACT | 3086 | 3548 |
| VK3-20 7 1 10 | CCTGAAGATTTTGCAGTGTATTACTGTCAGSWMTACBHCAG TAGTCCTCCTMTCACTTTTGGCGGAGGGACCAAG | CAGSWMTACBHCAGTAGTCC TCCTMTCACT | 3087 | 3549 |
| VK3-20 8 1 10 | CCTGAAGATTTTGCAGTGTATTACTGTCAGSWMTACGGAVN CAGTCCTCCTMTCACTTTTGGCGGAGGGACCAAG | CAGSWMTACGGAVNCAGTCC TCCTMTCACT | 3088 | 3550 |
| VK3-20 9 1 10 | CCTGAAGATTTTGCAGTGTATTACTGTCAGSWMTACGGAAG TBHCCCTCCTMTCACTTTTGGCGGAGGGACCAAG | CAGSWMTACGGAAGTBHCCC TCCTMTCACT | 3089 | 3551 |
| VK3-20 1 2 10 | CCTGAAGATTTTGCAGTGTATTACTGTSWMSWMTACGGAAG TAGTCCTCCTWGGACTTTTGGCGGAGGGACCAAG | SWMSWMTACGGAAGTAGTCC TCCTWGGACT | 3090 | 3552 |
| VK3-20 10 2 10 | CCTGAAGATTTTGCAGTGTATTACTGTCAGCAGBHCBHCAG TAGTCCTCCTWGGACTTTTGGCGGAGGGACCAAG | CAGCAGBHCBHCAGTAGTCC TCCTWGGACT | 3091 | 3553 |
| VK3-20 11 2 10 | CCTGAAGATTTTGCAGTGTATTACTGTCAGCAGBHCGGAVN CAGTCCTCCTWGGACTTTTGGCGGAGGGACCAAG | CAGCAGBHCGGAVNCAGTCC TCCTWGGACT | 3092 | 3554 |
| VK3-20 12 2 10 | CCTGAAGATTTTGCAGTGTATTACTGTCAGCAGBHCGGAAG TBHCCCTCCTWGGACTTTTGGCGGAGGGACCAAG | CAGCAGBHCGGAAGTBHCCC TCCTWGGACT | 3093 | 3555 |
| VK3-20 13 2 10 | CCTGAAGATTTTGCAGTGTATTACTGTCAGCAGTACBHCVN CAGTCCTCCTWGGACTTTTGGCGGAGGGACCAAG | CAGCAGTACBHCVNCAGTCC TCCTWGGACT | 3094 | 3556 |
| VK3-20 14 2 10 | CCTGAAGATTTTGCAGTGTATTACTGTCAGCAGTACBHCAG TBHCCCTCCTWGGACTTTTGGCGGAGGGACCAAG | CAGCAGTACBHCAGTBHCCC TCCTWGGACT | 3095 | 3557 |
| VK3-20 15 2 10 | CCTGAAGATTTTGCAGTGTATTACTGTCAGCAGTACGGAVN CBHCCCTCCTWGGACTTTTGGCGGAGGGACCAAG | CAGCAGTACGGAVNCBHCCC TCCTWGGACT | 3096 | 3558 |
| VK3-20 2 2 10 | CCTGAAGATTTTGCAGTGTATTACTGTSWMCAGBHCGGAAG TAGTCCTCCTWGGACTTTTGGCGGAGGGACCAAG | SWMCAGBHCGGAAGTAGTCC TCCTWGGACT | 3097 | 3559 |

TABLE 7-continued

Oligonucleotide sequences for exemplary VK jumping dimer and trimer sequences with CDRL3 length 10.

| Name | Sequence of Synthesized Oligonucleotide | Portion of Oligonucleotide Corresponding to CDRL3 Proper | SEQ ID NO (Oligo) | SEQ ID NO (CDRL3 Portion) |
|---|---|---|---|---|
| VK3-20 3 2 10 | CCTGAAGATTTTGCAGTGTATTACTGTSWMCAGTACBHCAG TAGTCCTCCTWGGACTTTTGGCGGAGGGACCAAG | SWMCAGTACBHCAGTAGTCC TCCTWGGACT | 3098 | 3560 |
| VK3-20 4 2 10 | CCTGAAGATTTTGCAGTGTATTACTGTSWMCAGTACGGAVN CAGTCCTCCTWGGACTTTTGGCGGAGGGACCAAG | SWMCAGTACGGAVNCAGTCC TCCTWGGACT | 3099 | 3561 |
| VK3-20 5 2 10 | CCTGAAGATTTTGCAGTGTATTACTGTSWMCAGTACGGAAG TBHCCCTCCTWGGACTTTTGGCGGAGGGACCAAG | SWMCAGTACGGAAGTBHCCC TCCTWGGACT | 3100 | 3562 |
| VK3-20 6 2 10 | CCTGAAGATTTTGCAGTGTATTACTGTCAGSWMBHCGGAAG TAGTCCTCCTWGGACTTTTGGCGGAGGGACCAAG | CAGSWMBHCGGAAGTAGTCC TCCTWGGACT | 3101 | 3563 |
| VK3-20 7 2 10 | CCTGAAGATTTTGCAGTGTATTACTGTCAGSWMTACBHCAG TAGTCCTCCTWGGACTTTTGGCGGAGGGACCAAG | CAGSWMTACBHCAGTAGTCC TCCTWGGACT | 3102 | 3564 |
| VK3-20 8 2 10 | CCTGAAGATTTTGCAGTGTATTACTGTCAGSWMTACGGAVN CAGTCCTCCTWGGACTTTTGGCGGAGGGACCAAG | CAGSWMTACGGAVNCAGTCC TCCTWGGACT | 3103 | 3565 |
| VK3-20 9 2 10 | CCTGAAGATTTTGCAGTGTATTACTGTCAGSWMTACGGAAG TBHCCCTCCTWGGACTTTTGGCGGAGGGACCAAG | CAGSWMTACGGAAGTBHCCC TCCTWGGACT | 3104 | 3566 |
| | | Jumping Trimer | | |
| VK1-05_t1_0_10 | CCTGATGATTTTGCAACTTATTACTGCCAGCAGBHCVRMMB CTACYCTCCTTWCACTTTTGGCGGAGGGACCAAG | CAGCAGBHCVRMMBCTACYCTCC TTWCACT | 3105 | 3567 |
| VK1-05_t1_1_10 | CCTGATGATTTTGCAACTTATTACTGCCAGCAGBHCVRMMB CTACYCTCCTMTCACTTTTGGCGGAGGGACCAAG | CAGCAGBHCVRMMBCTACYCTCC TMTCACT | 3106 | 3568 |
| VK1-05_t1_2_10 | CCTGATGATTTTGCAACTTATTACTGCCAGCAGBHCVRMMB CTACYCTCCTWGGACTTTTGGCGGAGGGACCAAG | CAGCAGBHCVRMMBCTACYCTCC TWGGACT | 3107 | 3569 |
| VK1-05_t2_0_10 | CCTGATGATTTTGCAACTTATTACTGCCAGCAGBHCAATMB CYWCYCTCCTTWCACTTTTGGCGGAGGGACCAAG | CAGCAGBHCAATMBCYWCYCTCC TTWCACT | 3108 | 3570 |
| VK1-05_t2_1_10 | CCTGATGATTTTGCAACTTATTACTGCCAGCAGBHCAATMB CYWCYCTCCTMTCACTTTTGGCGGAGGGACCAAG | CAGCAGBHCAATMBCYWCYCTCC TMTCACT | 3109 | 3571 |
| VK1-05_t2_2_10 | CCTGATGATTTTGCAACTTATTACTGCCAGCAGBHCAATMB CYWCYCTCCTWGGACTTTTGGCGGAGGGACCAAG | CAGCAGBHCAATMBCYWCYCTCC TWGGACT | 3110 | 3572 |
| VK1-05_t3_0_10 | CCTGATGATTTTGCAACTTATTACTGCCAGCAGBHCVRMAG TYWCYCTCCTTWCACTTTTGGCGGAGGGACCAAG | CAGCAGBHCVRMAGTYWCYCTCC TTWCACT | 3111 | 3573 |
| VK1-05_t3_1_10 | CCTGATGATTTTGCAACTTATTACTGCCAGCAGBHCVRMAG TYWCYCTCCTMTCACTTTTGGCGGAGGGACCAAG | CAGCAGBHCVRMAGTYWCYCTCC TMTCACT | 3112 | 3574 |
| VK1-05_t3_2_10 | CCTGATGATTTTGCAACTTATTACTGCCAGCAGBHCVRMAG TYWCYCTCCTWGGACTTTTGGCGGAGGGACCAAG | CAGCAGBHCVRMAGTYWCYCTCC TWGGACT | 3113 | 3575 |
| VK1-05_t4_0_10 | CCTGATGATTTTGCAACTTATTACTGCCAGCAGTACVRMMB CYWCYCTCCTTWCACTTTTGGCGGAGGGACCAAG | CAGCAGTACVRMMBCYWCYCTCC TTWCACT | 3114 | 3576 |
| VK1-05_t4_1_10 | CCTGATGATTTTGCAACTTATTACTGCCAGCAGTACVRMMB CYWCYCTCCTMTCACTTTTGGCGGAGGGACCAAG | CAGCAGTACVRMMBCYWCYCTCC TMTCACT | 3115 | 3577 |
| VK1-05_t4_2_10 | CCTGATGATTTTGCAACTTATTACTGCCAGCAGTACVRMMB CYWCYCTCCTWGGACTTTTGGCGGAGGGACCAAG | CAGCAGTACVRMMBCYWCYCTCC TWGGACT | 3116 | 3578 |
| VK1-12_t1_0_10 | CCTGAAGATTTTGCAACTTATTACTGTCAGCAGRNANHCNH CTTCCCTCCTTWCACTTTTGGCGGAGGGACCAAG | CAGCAGRNANHCNHCTTCCCTCC TTWCACT | 3117 | 3579 |
| VK1-12_t1_1_10 | CCTGAAGATTTTGCAACTTATTACTGTCAGCAGRNANHCNH CTTCCCTCCTMTCACTTTTGGCGGAGGGACCAAG | CAGCAGRNANHCNHCTTCCCTCC TMTCACT | 3118 | 3580 |
| VK1-12_t1_2_10 | CCTGAAGATTTTGCAACTTATTACTGTCAGCAGRNANHCNH CTTCCCTCCTWGGACTTTTGGCGGAGGGACCAAG | CAGCAGRNANHCNHCTTCCCTCC TWGGACT | 3119 | 3581 |
| VK1-12_t2_0_10 | CCTGAAGATTTTGCAACTTATTACTGTCAGCAGRNANHCAG TYWCCCTCCTTWCACTTTTGGCGGAGGGACCAAG | CAGCAGRNANHCAGTYWCCCTCC TTWCACT | 3120 | 3582 |

TABLE 7-continued

Oligonucleotide sequences for exemplary VK jumping dimer and trimer sequences with CDRL3 length 10.

| Name | Sequence of Synthesized Oligonucleotide | Portion of Oligonucleotide Corresponding to CDRL3 Proper | SEQ ID NO (Oligo) | SEQ ID NO (CDRL3 Portion) |
|---|---|---|---|---|
| VK1-12_t2_1_10 | CCTGAAGATTTTGCAACTTATTACTGTCAGCAGRNANHCAG TYWCCCTCCTMTCACTTTTGGCGGAGGGACCAAG | CAGCAGRNANHCAGTYWCCCTCC TMTCACT | 3121 | 3583 |
| VK1-12_t2_2_10 | CCTGAAGATTTTGCAACTTATTACTGTCAGCAGRNANHCA GTYWCCCTCCTWGGACTTTTGGCGGAGGGACCAAG | CAGCAGRNANHCAGTYWCCCTCC TWGGACT | 3122 | 3584 |
| VK1-12_t3_0_10 | CCTGAAGATTTTGCAACTTATTACTGTCAGCAGRNAAATNH CYWCCCTCCTTWCACTTTTGGCGGAGGGACCAAG | CAGCAGRNAAATNHCYWCCCTCC TTWCACT | 3123 | 3585 |
| VK1-12_t3_1_10 | CCTGAAGATTTTGCAACTTATTACTGTCAGCAGRNAAATNH CYWCCCTCCTMTCACTTTTGGCGGAGGGACCAAG | CAGCAGRNAAATNHCYWCCCTCC TMTCACT | 3124 | 3586 |
| VK1-12_t3_2_10 | CCTGAAGATTTTGCAACTTATTACTGTCAGCAGRNAAATNH CYWCCCTCCTWGGACTTTTGGCGGAGGGACCAAG | CAGCAGRNAAATNHCYWCCCTCC TWGGACT | 3125 | 3587 |
| VK1-12_t4_0_10 | CCTGAAGATTTTGCAACTTATTACTGTCAGCAGGCANHCNH CYWCCCTCCTTWCACTTTTGGCGGAGGGACCAAG | CAGCAGGCANHCNHCYWCCCTCC TTWCACT | 3126 | 3588 |
| VK1-12_t4_1_10 | CCTGAAGATTTTGCAACTTATTACTGTCAGCAGGCANHCNH CYWCCCTCCTMTCACTTTTGGCGGAGGGACCAAG | CAGCAGGCANHCNHCYWCCCTCC TMTCACT | 3127 | 3589 |
| VK1-12_t4_2_10 | CCTGAAGATTTTGCAACTTATTACTGTCAGCAGGCANHCNH CYWCCCTCCTWGGACTTTTGGCGGAGGGACCAAG | CAGCAGGCANHCNHCYWCCCTCC TWGGACT | 3128 | 3590 |
| VK1-33_t1_0_10 | CCTGAAGATATTGCAACATATTACTGTCAGCAGBHCNHCNH CCTCCCTCCTTWCACTTTTGGCGGAGGGACCAAG | CAGCAGBHCNHCNHCCTCCCTCC TTWCACT | 3129 | 3591 |
| VK1-33_t1_1_10 | CCTGAAGATATTGCAACATATTACTGTCAGCAGBHCNHCNH CCTCCCTCCTMTCACTTTTGGCGGAGGGACCAAG | CAGCAGBHCNHCNHCCTCCCTCC TMTCACT | 3130 | 3592 |
| VK1-33_t1_2_10 | CCTGAAGATATTGCAACATATTACTGTCAGCAGBHCNHCNH CCTCCCTCCTWGGACTTTTGGCGGAGGGACCAAG | CAGCAGBHCNHCNHCCTCCCTCC TWGGACT | 3131 | 3593 |
| VK1-33_t2_0_10 | CCTGAAGATATTGCAACATATTACTGTCAGCAGBHCNHCAA TYWCCCTCCTTWCACTTTTGGCGGAGGGACCAAG | CAGCAGBHCNHCAATYWCCCTCC TTWCACT | 3132 | 3594 |
| VK1-33_t2_1_10 | CCTGAAGATATTGCAACATATTACTGTCAGCAGBHCNHCAA TYWCCCTCCTMTCACTTTTGGCGGAGGGACCAAG | CAGCAGBHCNHCAATYWCCCTCC TMTCACT | 3133 | 3595 |
| VK1-33_t2_2_10 | CCTGAAGATATTGCAACATATTACTGTCAGCAGBHCNHCAA TYWCCCTCCTWGGACTTTTGGCGGAGGGACCAAG | CAGCAGBHCNHCAATYWCCCTCC TWGGACT | 3134 | 3596 |
| VK1-33_t3_0_10 | CCTGAAGATATTGCAACATATTACTGTCAGCAGBHCGATNH CYWCCCTCCTTWCACTTTTGGCGGAGGGACCAAG | CAGCAGBHCGATNHCYWCCCTCC TTWCACT | 3135 | 3597 |
| VK1-33_t3_1_10 | CCTGAAGATATTGCAACATATTACTGTCAGCAGBHCGATNH CYWCCCTCCTMTCACTTTTGGCGGAGGGACCAAG | CAGCAGBHCGATNHCYWCCCTCC TMTCACT | 3136 | 3598 |
| VK1-33_t3_2_10 | CCTGAAGATATTGCAACATATTACTGTCAGCAGBHCGATNH CYWCCCTCCTWGGACTTTTGGCGGAGGGACCAAG | CAGCAGBHCGATNHCYWCCCTCC TWGGACT | 3137 | 3599 |
| VK1-33_t4_0_10 | CCTGAAGATATTGCAACATATTACTGTCAGCAGTACNHCNH CYWCCCTCCTTWCACTTTTGGCGGAGGGACCAAG | CAGCAGTACNHCNHCYWCCCTCC TTWCACT | 3138 | 3600 |
| VK1-33_t4_1_10 | CCTGAAGATATTGCAACATATTACTGTCAGCAGTACNHCNH CYWCCCTCCTMTCACTTTTGGCGGAGGGACCAAG | CAGCAGTACNHCNHCYWCCCTCC TMTCACT | 3139 | 3601 |
| VK1-33_t4_2_10 | CCTGAAGATATTGCAACATATTACTGTCAGCAGTACNHCNH CYWCCCTCCTWGGACTTTTGGCGGAGGGACCAAG | CAGCAGTACNHCNHCYWCCCTCC TWGGACT | 3140 | 3602 |
| VK1-39_t1_0_10 | CCTGAAGATTTTGCAACTTACTACTGTCAGCAAVNABHCNH CACTCCTCCTTWCACTTTTGGCGGAGGGACCAAG | CAGCAAVNABHCNHCACTCCTCC TTWCACT | 3141 | 3603 |
| VK1-39_t1_1_10 | CCTGAAGATTTTGCAACTTACTACTGTCAGCAAVNABHCNH CACTCCTCCTMTCACTTTTGGCGGAGGGACCAAG | CAGCAAVNABHCNHCACTCCTCC TMTCACT | 3142 | 3604 |
| VK1-39_t1_2_10 | CCTGAAGATTTTGCAACTTACTACTGTCAGCAAVNABHCNH CACTCCTCCTWGGACTTTTGGCGGAGGGACCAAG | CAGCAAVNABHCNHCACTCCTCC TWGGACT | 3143 | 3605 |
| VK1-39_t2_0_10 | CCTGAAGATTTTGCAACTTACTACTGTCAGCAAVNABHCAG TBHCCCTCCTTWCACTTTTGGCGGAGGGACCAAG | CAGCAAVNABHCAGTBHCCCTCC TTWCACT | 3144 | 3606 |

TABLE 7-continued

Oligonucleotide sequences for exemplary VK jumping dimer and trimer sequences with CDRL3 length 10.

| Name | Sequence of Synthesized Oligonucleotide | Portion of Oligonucleotide Corresponding to CDRL3 Proper | SEQ ID NO (Oligo) | SEQ ID NO (CDRL3 Portion) |
|---|---|---|---|---|
| VK1-39_t2_1_10 | CCTGAAGATTTTGCAACTTACTACTGTCAGCAAVNABHCAG TBHCCCTCCTMTCACTTTTGGCGGAGGGACCAAG | CAGCAAVNABHCAGTBHCCCTCC TMTCACT | 3145 | 3607 |
| VK1-39_t2_2_10 | CCTGAAGATTTTGCAACTTACTACTGTCAGCAAVNABHCAG TBHCCCTCCTWGGACTTTTGGCGGAGGGACCAAG | CAGCAAVNABHCAGTBHCCCTCC TWGGACT | 3146 | 3608 |
| VK1-39_t3_0_10 | CCTGAAGATTTTGCAACTTACTACTGTCAGCAAVNATACNH CBHCCCTCCTTWCACTTTTGGCGGAGGGACCAAG | CAGCAAVNATACNHCBHCCCTCC TTWCACT | 3147 | 3609 |
| VK1-39_t3_1_10 | CCTGAAGATTTTGCAACTTACTACTGTCAGCAAVNATACNH CBHCCCTCCTMTCACTTTTGGCGGAGGGACCAAG | CAGCAAVNATACNHCBHCCCTCC TMTCACT | 3148 | 3610 |
| VK1-39_t3_2_10 | CCTGAAGATTTTGCAACTTACTACTGTCAGCAAVNATACNH CBHCCCTCCTWGGACTTTTGGCGGAGGGACCAAG | CAGCAAVNATACNHCBHCCCTCC TWGGACT | 3149 | 3611 |
| VK1-39_t4_0_10 | CCTGAAGATTTTGCAACTTACTACTGTCAGCAAAGCBHCNH CBHCCCTCCTTWCACTTTTGGCGGAGGGACCAAG | CAGCAAAGCBHCNHCBHCCCTCC TTWCACT | 3150 | 3612 |
| VK1-39_t4_1_10 | CCTGAAGATTTTGCAACTTACTACTGTCAGCAAAGCBHCNH CBHCCCTCCTMTCACTTTTGGCGGAGGGACCAAG | CAGCAAAGCBHCNHCBHCCCTCC TMTCACT | 3151 | 3613 |
| VK1-39_t4_2_10 | CCTGAAGATTTTGCAACTTACTACTGTCAGCAAAGCBHCNH CBHCCCTCCTWGGACTTTTGGCGGAGGGACCAAG | CAGCAAAGCBHCNHCBHCCCTCC TWGGACT | 3152 | 3614 |
| VK2-28_t1_0_10 | GCTGAGGATGTTGGGGTTTATTACTGCATGCAGVNAMNASR MACTCCTCCTTWCACTTTTGGCGGAGGGACCAAG | ATGCAGVNAMNASRMACTCCTCC TTWCACT | 3153 | 3615 |
| VK2-28_t1_1_10 | GCTGAGGATGTTGGGGTTTATTACTGCATGCAGVNAMNASR MACTCCTCCTMTCACTTTTGGCGGAGGGACCAAG | ATGCAGVNAMNASRMACTCCTCC TMTCACT | 3154 | 3616 |
| VK2-28_t1_2_10 | GCTGAGGATGTTGGGGTTTATTACTGCATGCAGVNAMNASR MACTCCTCCTWGGACTTTTGGCGGAGGGACCAAG | ATGCAGVNAMNASRMACTCCTCC TWGGACT | 3155 | 3617 |
| VK2-28_t2_0_10 | GCTGAGGATGTTGGGGTTTATTACTGCATGCAGVNAMNACA GVBCCCTCCTTWCACTTTTGGCGGAGGGACCAAG | ATGCAGVNAMNACAGVBCCCTCC TTWCACT | 3156 | 3618 |
| VK2-28_t2_1_10 | GCTGAGGATGTTGGGGTTTATTACTGCATGCAGVNAMNACA GVBCCCTCCTMTCACTTTTGGCGGAGGGACCAAG | ATGCAGVNAMNACAGVBCCCTCC TMTCACT | 3157 | 3619 |
| VK2-28_t2_2_10 | GCTGAGGATGTTGGGGTTTATTACTGCATGCAGVNAMNACA GVBCCCTCCTWGGACTTTTGGCGGAGGGACCAAG | ATGCAGVNAMNACAGVBCCCTCC TWGGACT | 3158 | 3620 |
| VK2-28_t3_0_10 | GCTGAGGATGTTGGGGTTTATTACTGCATGCAGVNACTCSR MVBCCCTCCTTWCACTTTTGGCGGAGGGACCAAG | ATGCAGVNACTCSRMVBCCCTCC TTWCACT | 3159 | 3621 |
| VK2-28_t3_1_10 | GCTGAGGATGTTGGGGTTTATTACTGCATGCAGVNACTCSR MVBCCCTCCTMTCACTTTTGGCGGAGGGACCAAG | ATGCAGVNACTCSRMVBCCCTCC TMTCACT | 3160 | 3622 |
| VK2-28_t3_2_10 | GCTGAGGATGTTGGGGTTTATTACTGCATGCAGVNACTCSR MVBCCCTCCTWGGACTTTTGGCGGAGGGACCAAG | ATGCAGVNACTCSRMVBCCCTCC TWGGACT | 3161 | 3623 |
| VK2-28_t4_0_10 | GCTGAGGATGTTGGGGTTTATTACTGCATGCAGGCAMNASR MVBCCCTCCTTWCACTTTTGGCGGAGGGACCAAG | ATGCAGGCAMNASRMVBCCCTCC TTWCACT | 3162 | 3624 |
| VK2-28_t4_1_10 | GCTGAGGATGTTGGGGTTTATTACTGCATGCAGGCAMNASR MVBCCCTCCTMTCACTTTTGGCGGAGGGACCAAG | ATGCAGGCAMNASRMVBCCCTCC TMTCACT | 3163 | 3625 |
| VK2-28_t4_2_10 | GCTGAGGATGTTGGGGTTTATTACTGCATGCAGGCAMNASR MVBCCCTCCTWGGACTTTTGGCGGAGGGACCAAG | ATGCAGGCAMNASRMVBCCCTCC TWGGACT | 3164 | 3626 |
| VK3-11_t1_0_10 | CCTGAAGATTTTGCAGTTTATTACTGTCAGCAGBHCNHCNH CTGGCCTCCTTWCACTTTTGGCGGAGGGACCAAG | CAGCAGBHCNHCNHCTGGCCTCC TTWCACT | 3165 | 3627 |
| VK3-11_t1_1_10 | CCTGAAGATTTTGCAGTTTATTACTGTCAGCAGBHCNHCNH CTGGCCTCCTMTCACTTTTGGCGGAGGGACCAAG | CAGCAGBHCNHCNHCTGGCCTCC TMTCACT | 3166 | 3628 |
| VK3-11_t1_2_10 | CCTGAAGATTTTGCAGTTTATTACTGTCAGCAGBHCNHCNH CTGGCCTCCTWGGACTTTTGGCGGAGGGACCAAG | CAGCAGBHCNHCNHCTGGCCTCC TWGGACT | 3167 | 3629 |
| VK3-11_t2_0_10 | CCTGAAGATTTTGCAGTTTATTACTGTCAGCAGBHCNHCAA TYWCCCTCCTTWCACTTTTGGCGGAGGGACCAAG | CAGCAGBHCNHCAATYWCCCTCC TTWCACT | 3168 | 3594 |

TABLE 7-continued

Oligonucleotide sequences for exemplary VK jumping dimer and trimer sequences with CDRL3 length 10.

| Name | Sequence of Synthesized Oligonucleotide | Portion of Oligonucleotide Corresponding to CDRL3 Proper | SEQ ID NO (Oligo) | SEQ ID NO (CDRL3 Portion) |
|---|---|---|---|---|
| VK3-11_t2_1_10 | CCTGAAGATTTTGCAGTTTATTACTGTCAGCAGBHCNHCAA TYWCCCTCCTMTCACTTTTGGCGGAGGGACCAAG | CAGCAGBHCNHCAATYWCCCTCC TMTCACT | 3169 | 3595 |
| VK3-11_t2_2_10 | CCTGAAGATTTTGCAGTTTATTACTGTCAGCAGBHCNHCAA TYWCCCTCCTWGGACTTTTGGCGGAGGGACCAAG | CAGCAGBHCNHCAATYWCCCTCC TWGGACT | 3170 | 3596 |
| VK3-11_t3_0_10 | CCTGAAGATTTTGCAGTTTATTACTGTCAGCAGBHCAGTNH CYWCCCTCCTTWCACTTTTGGCGGAGGGACCAAG | CAGCAGBHCAGTNHCYWCCCTCC TTWCACT | 3171 | 3630 |
| VK3-11_t3_1_10 | CCTGAAGATTTTGCAGTTTATTACTGTCAGCAGBHCAGTNH CYWCCCTCCTMTCACTTTTGGCGGAGGGACCAAG | CAGCAGBHCAGTNHCYWCCCTCC TMTCACT | 3172 | 3631 |
| VK3-11_t3_2_10 | CCTGAAGATTTTGCAGTTTATTACTGTCAGCAGBHCAGTNH CYWCCCTCCTWGGACTTTTGGCGGAGGGACCAAG | CAGCAGBHCAGTNHCYWCCCTCC TWGGACT | 3173 | 3632 |
| VK3-11_t4_0_10 | CCTGAAGATTTTGCAGTTTATTACTGTCAGCAGAGANHCNH CYWCCCTCCTTWCACTTTTGGCGGAGGGACCAAG | CAGCAGAGANHCNHCYWCCCTCC TTWCACT | 3174 | 3633 |
| VK3-11_t4_1_10 | CCTGAAGATTTTGCAGTTTATTACTGTCAGCAGAGANHCNH CYWCCCTCCTMTCACTTTTGGCGGAGGGACCAAG | CAGCAGAGANHCNHCYWCCCTCC TMTCACT | 3175 | 3634 |
| VK3-11_t4_2_10 | CCTGAAGATTTTGCAGTTTATTACTGTCAGCAGAGANHCNH CYWCCCTCCTWGGACTTTTGGCGGAGGGACCAAG | CAGCAGAGANHCNHCYWCCCTCC TWGGACT | 3176 | 3635 |
| VK3-15_t1_0_10 | CAGTCTGAAGATTTTGCAGTTTATTACTGTCAGCAGBHCNH CNHCTGGCCTCCTTWCACTTTTGGCGGAGGGACCAAG | CAGCAGBHCNHCNHCTGGCCTCC TTWCACT | 3177 | 3627 |
| VK3-15_t1_1_10 | CAGTCTGAAGATTTTGCAGTTTATTACTGTCAGCAGBHCNH CNHCTGGCCTCCTMTCACTTTTGGCGGAGGGACCAAG | CAGCAGBHCNHCNHCTGGCCTCC TMTCACT | 3178 | 3628 |
| VK3-15_t1_2_10 | CAGTCTGAAGATTTTGCAGTTTATTACTGTCAGCAGBHCNH CNHCTGGCCTCCTWGGACTTTTGGCGGAGGGACCAAG | CAGCAGBHCNHCNHCTGGCCTCC TWGGACT | 3179 | 3629 |
| VK3-15_t2_0_10 | CAGTCTGAAGATTTTGCAGTTTATTACTGTCAGCAGBHCNH CAATYWCCCTCCTTWCACTTTTGGCGGAGGGACCAAG | CAGCAGBHCNHCAATYWCCCTCC TTWCACT | 3180 | 3594 |
| VK3-15_t2_1_10 | CAGTCTGAAGATTTTGCAGTTTATTACTGTCAGCAGBHCNH CAATYWCCCTCCTMTCACTTTTGGCGGAGGGACCAAG | CAGCAGBHCNHCAATYWCCCTCC TMTCACT | 3181 | 3595 |
| VK3-15_t2_2_10 | CAGTCTGAAGATTTTGCAGTTTATTACTGTCAGCAGBHCNH CAATYWCCCTCCTWGGACTTTTGGCGGAGGGACCAAG | CAGCAGBHCNHCAATYWCCCTCC TWGGACT | 3182 | 3596 |
| VK3-15_t3_0_10 | CAGTCTGAAGATTTTGCAGTTTATTACTGTCAGCAGBHCAA TNHCYWCCCTCCTTWCACTTTTGGCGGAGGGACCAAG | CAGCAGBHCAATNHCYWCCCTCC TTWCACT | 3183 | 3636 |
| VK3-15_t3_1_10 | CAGTCTGAAGATTTTGCAGTTTATTACTGTCAGCAGBHCAA TNHCYWCCCTCCTMTCACTTTTGGCGGAGGGACCAAG | CAGCAGBHCAATNHCYWCCCTCC TMTCACT | 3184 | 3637 |
| VK3-15_t3_2_10 | CAGTCTGAAGATTTTGCAGTTTATTACTGTCAGCAGBHCAA TNHCYWCCCTCCTWGGACTTTTGGCGGAGGGACCAAG | CAGCAGBHCAATNHCYWCCCTCC TWGGACT | 3185 | 3638 |
| VK3-15_t4_0_10 | CAGTCTGAAGATTTTGCAGTTTATTACTGTCAGCAGTACNH CNHCYWCCCTCCTTWCACTTTTGGCGGAGGGACCAAG | CAGCAGTACNHCNHCYWCCCTCC TTWCACT | 3186 | 3600 |
| VK3-15_t4_1_10 | CAGTCTGAAGATTTTGCAGTTTATTACTGTCAGCAGTACNH CNHCYWCCCTCCTMTCACTTTTGGCGGAGGGACCAAG | CAGCAGTACNHCNHCYWCCCTCC TMTCACT | 3187 | 3601 |
| VK3-15_t4_2_10 | CAGTCTGAAGATTTTGCAGTTTATTACTGTCAGCAGTACNH CNHCYWCCCTCCTWGGACTTTTGGCGGAGGGACCAAG | CAGCAGTACNHCNHCYWCCCTCC TWGGACT | 3188 | 3602 |
| VK3-20_t1_0_10 | CCTGAAGATTTTGCAGTGTATTACTGTCAGCAGBHCBHCVN CAGTCCTCCTTWCACTTTTGGCGGAGGGACCAAG | CAGCAGBHCBHCVNCAGTCCTCC TTWCACT | 3189 | 3639 |
| VK3-20_t1_1_10 | CCTGAAGATTTTGCAGTGTATTACTGTCAGCAGBHCBHCVN CAGTCCTCCTMTCACTTTTGGCGGAGGGACCAAG | CAGCAGBHCBHCVNCAGTCCTCC TMTCACT | 3190 | 3640 |
| VK3-20_t1_2_10 | CCTGAAGATTTTGCAGTGTATTACTGTCAGCAGBHCBHCVN CAGTCCTCCTWGGACTTTTGGCGGAGGGACCAAG | CAGCAGBHCBHCVNCAGTCCTCC TWGGACT | 3191 | 3641 |
| VK3-20_t2_0_10 | CCTGAAGATTTTGCAGTGTATTACTGTCAGCAGBHCBHCAG TBHCCCTCCTTWCACTTTTGGCGGAGGGACCAAG | CAGCAGBHCBHCAGTBHCCCTCC TTWCACT | 3192 | 3642 |

TABLE 7-continued

Oligonucleotide sequences for exemplary VK jumping dimer and trimer sequences with CDRL3 length 10.

| Name | Sequence of Synthesized Oligonucleotide | Portion of Oligonucleotide Corresponding to CDRL3 Proper | SEQ ID NO (Oligo) | SEQ ID NO (CDRL3 Portion) |
|---|---|---|---|---|
| VK3-20_t2_1_10 | CCTGAAGATTTTGCAGTGTATTACTGTCAGCAGBHCBHCAG TBHCCCTCCTMTCACTTTTGGCGGAGGGACCAAG | CAGCAGBHCBHCAGTBHCCCTCC TMTCACT | 3193 | 3643 |
| VK3-20_t2_2_10 | CCTGAAGATTTTGCAGTGTATTACTGTCAGCAGBHCBHCAG TBHCCCTCCTWGGACTTTTGGCGGAGGGACCAAG | CAGCAGBHCBHCAGTBHCCCTCC TWGGACT | 3194 | 3644 |
| VK3-20_t3_0_10 | CCTGAAGATTTTGCAGTGTATTACTGTCAGCAGBHCGGAVN CBHCCCTCCTTWCACTTTTGGCGGAGGGACCAAG | CAGCAGBHCGGAVNCBHCCCTCC TTWCACT | 3195 | 3645 |
| VK3-20_t3_1_10 | CCTGAAGATTTTGCAGTGTATTACTGTCAGCAGBHCGGAVN CBHCCCTCCTMTCACTTTTGGCGGAGGGACCAAG | CAGCAGBHCGGAVNCBHCCCTCC TMTCACT | 3196 | 3646 |
| VK3-20_t3_2_10 | CCTGAAGATTTTGCAGTGTATTACTGTCAGCAGBHCGGAVN CBHCCCTCCTWGGACTTTTGGCGGAGGGACCAAG | CAGCAGBHCGGAVNCBHCCCTCC TWGGACT | 3197 | 3647 |
| VK3-20_t4_0_10 | CCTGAAGATTTTGCAGTGTATTACTGTCAGCAGTACBHCVN CBHCCCTCCTTWCACTTTTGGCGGAGGGACCAAG | CAGCAGTACBHCVNCBHCCCTCC TTWCACT | 3198 | 3648 |
| VK3-20_t4_1_10 | CCTGAAGATTTTGCAGTGTATTACTGTCAGCAGTACBHCVN CBHCCCTCCTMTCACTTTTGGCGGAGGGACCAAG | CAGCAGTACBHCVNCBHCCCTCC TMTCACT | 3199 | 3649 |
| VK3-20_t4_2_10 | CCTGAAGATTTTGCAGTGTATTACTGTCAGCAGTACBHCVN CBHCCCTCCTWGGACTTTTGGCGGAGGGACCAAG | CAGCAGTACBHCVNCBHCCCTCC TWGGACT | 3200 | 3650 |
| VK4-01_t1_0_10 | GCTGAAGATGTGGCAGTTTATTACTGTCAGCAGBHCBHCNH CACTCCTCCTTWCACTTTTGGCGGAGGGACCAAG | CAGCAGBHCBHCNHCACTCCTCC TTWCACT | 3201 | 3651 |
| VK4-01_t1_1_10 | GCTGAAGATGTGGCAGTTTATTACTGTCAGCAGBHCBHCNH CACTCCTCCTMTCACTTTTGGCGGAGGGACCAAG | CAGCAGBHCBHCNHCACTCCTCC TMTCACT | 3202 | 3652 |
| VK4-01_t1_2_10 | GCTGAAGATGTGGCAGTTTATTACTGTCAGCAGBHCBHCNH CACTCCTCCTWGGACTTTTGGCGGAGGGACCAAG | CAGCAGBHCBHCNHCACTCCTCC TWGGACT | 3203 | 3653 |
| VK4-01_t2_0_10 | GCTGAAGATGTGGCAGTTTATTACTGTCAGCAGBHCBHCAG TBHCCCTCCTTWCACTTTTGGCGGAGGGACCAAG | CAGCAGBHCBHCAGTBHCCCTCC TTWCACT | 3204 | 3642 |
| VK4-01_t2_1_10 | GCTGAAGATGTGGCAGTTTATTACTGTCAGCAGBHCBHCAG TBHCCCTCCTMTCACTTTTGGCGGAGGGACCAAG | CAGCAGBHCBHCAGTBHCCCTCC TMTCACT | 3205 | 3643 |
| VK4-01_t2_2_10 | GCTGAAGATGTGGCAGTTTATTACTGTCAGCAGBHCBHCAG TBHCCCTCCTWGGACTTTTGGCGGAGGGACCAAG | CAGCAGBHCBHCAGTBHCCCTCC TWGGACT | 3206 | 3644 |
| VK4-01_t3_0_10 | GCTGAAGATGTGGCAGTTTATTACTGTCAGCAGBHCTACNH CBHCCCTCCTTWCACTTTTGGCGGAGGGACCAAG | CAGCAGBHCTACNHCBHCCCTCC TTWCACT | 3207 | 3654 |
| VK4-01_t3_1_10 | GCTGAAGATGTGGCAGTTTATTACTGTCAGCAGBHCTACNH CBHCCCTCCTMTCACTTTTGGCGGAGGGACCAAG | CAGCAGBHCTACNHCBHCCCTCC TMTCACT | 3208 | 3655 |
| VK4-01_t3_2_10 | GCTGAAGATGTGGCAGTTTATTACTGTCAGCAGBHCTACNH CBHCCCTCCTWGGACTTTTGGCGGAGGGACCAAG | CAGCAGBHCTACNHCBHCCCTCC TWGGACT | 3209 | 3656 |
| VK4-01_t4_0_10 | GCTGAAGATGTGGCAGTTTATTACTGTCAGCAGTACBHCNH CBHCCCTCCTTWCACTTTTGGCGGAGGGACCAAG | CAGCAGTACBHCNHCBHCCCTCC TTWCACT | 3210 | 3657 |
| VK4-01_t4_1_10 | GCTGAAGATGTGGCAGTTTATTACTGTCAGCAGTACBHCNH CBHCCCTCCTMTCACTTTTGGCGGAGGGACCAAG | CAGCAGTACBHCNHCBHCCCTCC TMTCACT | 3211 | 3658 |
| VK4-01_t4_2_10 | GCTGAAGATGTGGCAGTTTATTACTGTCAGCAGTACBHCNH CBHCCCTCCTWGGACTTTTGGCGGAGGGACCAAG | CAGCAGTACBHCNHCBHCCCTCC TWGGACT | 3212 | 3659 |

TABLE 8

Number of unique CDRL3 amino acid sequences in exemplary jumping dimer ("JD") and jumping trimer ("JT") VK libraries and comparison to VK-v1.0.

| | L = 8 aa | | L = 9 aa | | L = 10 aa | |
|---|---|---|---|---|---|---|
| Jumping Dimer | | | | | | |
| Germline | JD | VK-v1.0 | JD | VK-v1.0 | JD | VK-v1.0 |
| VK1-05 | 3549 | 3072 | 7098 | 6144 | 6084 | 13824 |
| VK1-12 | 5250 | 2016 | 5250 | 2016 | 4500 | 5184 |
| VK1-33 | 5502 | 4032 | 5502 | 4032 | 4716 | 10368 |
| VK1-39 | 7224 | 3024 | 7224 | 3024 | 6192 | 7776 |
| VK2-28 | 4396 | 2016 | 4396 | 2016 | 3768 | 5184 |
| VK3-11 | 6048 | 2352 | 6048 | 2016 | 5184 | 6048 |
| VK3-15 | 5789 | 2016 | 5789 | 2352 | 4962 | 5184 |
| VK3-20 | 6405 | 2016 | 6671 | 2016 | 5490 | 5184 |
| VK4-01 | NPE* | 2016 | 6405 | 2592 | NPE* | 5184 |
| Total | $4.42*10^4$ | $2.26*10^4$ | $5.44*10^4$ | $2.62*10^4$ | $4.09*10^4$ | $6.39*10^4$ |
| Jumping Trimer | | | | | | |
| Germline | JT | VK-v1.0 | JT | VK-v1.0 | JT | VK-v1.0 |
| VK1-05 | 7872 | 3072 | 13776 | 6144 | 11808 | 13824 |
| VK1-12 | 14469 | 2016 | 14469 | 2016 | 12402 | 5184 |
| VK1-33 | 15960 | 4032 | 15960 | 4032 | 13680 | 10368 |
| VK1-39 | 28980 | 3024 | 28980 | 3024 | 24840 | 7776 |
| VK2-28 | 12306 | 2016 | 12306 | 2016 | 10548 | 5184 |
| VK3-11 | 18900 | 2352 | 18900 | 2016 | 16200 | 6048 |
| VK3-15 | 18256 | 2016 | 18256 | 2352 | 15648 | 5184 |
| VK3-20 | 23688 | 2016 | 23688 | 2016 | 20304 | 5184 |
| VK4-01 | 23688 | 2016 | 23688 | 2592 | 20304 | 5184 |
| Total | $1.64*10^5$ | $2.26*10^4$ | $1.70*10^5$ | $2.62*10^4$ | $1.46*10^5$ | $6.39*10^4$ |

*Not Presently Exemplified. However, given the teachings of the specification, a person of ordinary skill in the art could readily produce a library of such lengths, and these lengths are included within the scope of the invention.

TABLE 10

Theoretical segment pool of 212 TN1 sequences contained in Theoretical Segment Pool 1 (TSP1).

| TN1 Segment Name | Amino Acid Sequence | TN1 Segment Name | Amino Acid Sequence | SEQ ID NO |
|---|---|---|---|---|
| P000 | — | P107 | PT | n/a |
| P001 | E | P108 | EPT | n/a |
| P002 | D | P109 | DPT | n/a |
| P003 | G | P110 | GPT | n/a |
| P004 | EG | P111 | PV | n/a |
| P005 | DG | P112 | EPV | n/a |
| P006 | GG | P113 | DPV | n/a |
| P007 | R | P114 | GPV | n/a |
| P008 | ER | P115 | RP | n/a |
| P009 | DR | P116 | ERP | n/a |
| P010 | GR | P117 | DRP | n/a |
| P011 | S | P118 | GRP | n/a |
| P012 | ES | P119 | SP | n/a |
| P013 | DS | P120 | ESP | n/a |
| P014 | GS | P121 | DSP | n/a |
| P015 | P | P122 | GSP | n/a |

TABLE 9

Matching output for exemplary CDRH3 sequences from the HPS and TSP1. Amino acid mismatches in the theoretical design are indicated in bold.

| Test Case | CDRH3 Sequence from HPS | SEQ ID NO | Mis-matches | TN1 | SEQ ID NO | DH | SEQ ID NO | N2 | H3-JH | SEQ ID NO |
|---|---|---|---|---|---|---|---|---|---|---|
| 1 | RTAHHFDY | 3660 | 0 | R | | TA | | H | HFDY | 4582 |
| 2.1 | VGIVGAASY | 3661 | 0 | V | | GIVGA | 3751 | AS | Y | |
| 2.2 | VGIVGAASY | 3661 | 0 | VG | | IVGA | 3755 | AS | Y | |
| 3.1 | DRYSGHDLGY | 3662 | 1 | DR | | YSG**Y**D | 4389 | LG | Y | |
| 4.1 | GIAAADSNWLDP | 3663 | 1 | — | | GIAAA | 4448 | D | SNW**F**DP | 4600 |
| 4.2 | GIAAADSNWLDP | 3663 | 1 | — | | IAAA | 4452 | D | SNW**F**DP | 4600 |
| 5.1 | ERTINWGWGGVYAFDI | 3664 | 3 | **EGTG** | 3707 | NWG | | **G**GV | YAFDI | 4540 |
| 5.2 | ERTINWGWGGVYAFDI | 3664 | 3 | **EGTG** | 3707 | NWG | | WG**T** | YAFDI | 4540 |
| 5.3 | ERTINWGWGGVYAFDI | 3664 | 3 | ER**GG** | 3719 | NWG | | **G**GV | YAFDI | 4540 |
| 5.4 | ERTINWGWGGVYAFDI | 3664 | 3 | ER**GG** | 3719 | NWG | | WG**T** | YAFDI | 4540 |

TABLE 10-continued

Theoretical segment pool of 212 TN1 sequences contained in Theoretical Segment Pool 1 (TSP1).

| TN1 Segment Name | Amino Acid Sequence | TN1 Segment Name | Amino Acid Sequence | SEQ ID NO |
|---|---|---|---|---|
| P016 | EP | P123 | LP | n/a |
| P017 | DP | P124 | ELP | n/a |
| P018 | GP | P125 | DLP | n/a |
| P019 | L | P126 | GLP | n/a |
| P020 | EL | P127 | AP | n/a |
| P021 | DL | P128 | EAP | n/a |
| P022 | GL | P129 | DAP | n/a |
| P023 | A | P130 | GAP | n/a |
| P024 | EA | P131 | TP | n/a |
| P025 | DA | P132 | ETP | n/a |
| P026 | GA | P133 | DTP | n/a |
| P027 | T | P134 | GTP | n/a |
| P028 | ET | P135 | VP | n/a |
| P029 | DT | P136 | EVP | n/a |
| P030 | GT | P137 | DVP | n/a |
| P031 | V | P138 | GVP | n/a |
| P032 | EV | P139 | AGG | n/a |
| P033 | DV | P140 | EAGG | 3665 |
| P034 | GV | P141 | DAGG | 3666 |
| P035 | EGG | P142 | GAGG | 3667 |
| P036 | DGG | P143 | EGAG | 3668 |
| P037 | GGG | P144 | DGAG | 3669 |
| P038 | EGR | P145 | GGAG | 3670 |
| P039 | DGR | P146 | EGGA | 3671 |
| P040 | GGR | P147 | DGGA | 3672 |
| P041 | EGS | P148 | GGGA | 3673 |
| P042 | DGS | P149 | EGGG | 3674 |
| P043 | GGS | P150 | DGGG | 3675 |
| P044 | EGP | P151 | GGGG | 3676 |
| P045 | DGP | P152 | EGGL | 3677 |
| P046 | GGP | P153 | DGGL | 3678 |
| P047 | EGL | P154 | GGGL | 3679 |
| P048 | DGL | P155 | EGGP | 3680 |
| P049 | GGL | P156 | DGGP | 3681 |
| P050 | EGA | P157 | GGGP | 3682 |
| P051 | DGA | P158 | EGGR | 3683 |
| P052 | GGA | P159 | DGGR | 3684 |

TABLE 10-continued

Theoretical segment pool of 212 TN1 sequences contained in Theoretical Segment Pool 1 (TSP1).

| TN1 Segment Name | Amino Acid Sequence | TN1 Segment Name | Amino Acid Sequence | SEQ ID NO |
|---|---|---|---|---|
| P053 | EGT | P160 | GGGR | 3685 |
| P054 | DGT | P161 | EGGS | 3686 |
| P055 | GGT | P162 | DGGS | 3687 |
| P056 | EGV | P163 | GGGS | 3688 |
| P057 | DGV | P164 | EGGT | 3689 |
| P058 | GGV | P165 | DGGT | 3690 |
| P059 | RG | P166 | GGGT | 3691 |
| P060 | ERG | P167 | EGGV | 3692 |
| P061 | DRG | P168 | DGGV | 3693 |
| P062 | GRG | P169 | GGGV | 3694 |
| P063 | SG | P170 | EGLG | 3695 |
| P064 | ESG | P171 | DGLG | 3696 |
| P065 | DSG | P172 | GGLG | 3697 |
| P066 | GSG | P173 | EGPG | 3698 |
| P067 | PG | P174 | DGPG | 3699 |
| P068 | EPG | P175 | GGPG | 3700 |
| P069 | DPG | P176 | EGRG | 3701 |
| P070 | GPG | P177 | DGRG | 3702 |
| P071 | LG | P178 | GGRG | 3703 |
| P072 | ELG | P179 | EGSG | 3704 |
| P073 | DLG | P180 | DGSG | 3705 |
| P074 | GLG | P181 | GGSG | 3706 |
| P075 | AG | P182 | EGTG | 3707 |
| P076 | EAG | P183 | DGTG | 3708 |
| P077 | DAG | P184 | GGTG | 3709 |
| P078 | GAG | P185 | EGVG | 3710 |
| P079 | TG | P186 | DGVG | 3711 |
| P080 | ETG | P187 | GGVG | 3712 |
| P081 | DTG | P188 | LGG | n/a |
| P082 | GTG | P189 | ELGG | 3713 |
| P083 | VG | P190 | DLGG | 3714 |
| P084 | EVG | P191 | GLGG | 3715 |
| P085 | DVG | P192 | PGG | n/a |
| P086 | GVG | P193 | EPGG | 3716 |
| P087 | PR | P194 | DPGG | 3717 |
| P088 | EPR | P195 | GPGG | 3718 |

TABLE 10-continued

Theoretical segment pool of 212 TN1 sequences contained in Theoretical Segment Pool 1 (TSP1).

| TN1 Segment Name | Amino Acid Sequence | TN1 Segment Name | Amino Acid Sequence | SEQ ID NO |
|---|---|---|---|---|
| P089 | DPR | P196 | RGG | n/a |
| P090 | GPR | P197 | ERGG | 3719 |
| P091 | PS | P198 | DRGG | 3720 |
| P092 | EPS | P199 | GRGG | 3721 |
| P093 | DPS | P200 | SGG | n/a |
| P094 | GPS | P201 | ESGG | 3722 |
| P095 | PP | P202 | DSGG | 3723 |
| P096 | EPP | P203 | GSGG | 3724 |
| P097 | DPP | P204 | TGG | n/a |
| P098 | GPP | P205 | ETGG | 3725 |
| P099 | PL | P206 | DTGG | 3726 |
| P100 | EPL | P207 | GTGG | 3727 |
| P101 | DPL | P208 | VGG | n/a |
| P102 | GPL | P209 | EVGG | 3728 |
| P103 | PA | P210 | DVGG | 3729 |
| P104 | EPA | P211 | GVGG | 3730 |
| P105 | DPA | | | |
| P106 | GPA | | | |

TABLE 11

1K DH Theoretical Segment Pool sequences (1,111 DH segments).

| DH Segment Name | Amino Acid Sequence | SEQ ID NO | DH Segment Name | Amino Acid Sequence | SEQ ID NO |
|---|---|---|---|---|---|
| DHUNIV 001 | GTTGTT | 3731 | DHUNIV 557 | YDYV | 4107 |
| DHUNIV 002 | GTTGT | 3732 | DHUNIV 558 | DYVW | 4108 |
| DHUNIV 003 | TTGTT | 3733 | DHUNIV 559 | YVWG | 4109 |
| DHUNIV 004 | GTTG | 3734 | DHUNIV 560 | VWGS | 4110 |
| DHUNIV 005 | TTGT | 3735 | DHUNIV 561 | WGSY | 4111 |
| DHUNIV 006 | TGTT | 3736 | DHUNIV 562 | GSYA | 4112 |
| DHUNIV 007 | GTT | n/a | DHUNIV 563 | SYAY | 4113 |
| DHUNIV 008 | TTG | n/a | DHUNIV 564 | YAYT | 4114 |
| DHUNIV 009 | TGT | n/a | DHUNIV 565 | YYD | n/a |
| DHUNIV 010 | GT | n/a | DHUNIV 566 | YDY | n/a |
| DHUNIV 011 | TT | n/a | DHUNIV 567 | DYV | n/a |
| DHUNIV 012 | TG | n/a | DHUNIV 568 | YVW | n/a |
| DHUNIV 013 | VQLER | 3737 | DHUNIV 569 | VWG | n/a |
| DHUNIV 014 | VQLE | 3738 | DHUNIV 570 | WGS | n/a |
| DHUNIV 015 | QLER | 3739 | DHUNIV 571 | SYA | n/a |
| DHUNIV 016 | VQL | n/a | DHUNIV 572 | YAY | n/a |
| DHUNIV 017 | QLE | n/a | DHUNIV 573 | AYT | n/a |
| DHUNIV 018 | LER | n/a | DHUNIV 574 | YD | n/a |
| DHUNIV 019 | VQ | n/a | DHUNIV 575 | DY | n/a |
| DHUNIV 020 | QL | n/a | DHUNIV 576 | YV | n/a |
| DHUNIV 021 | LE | n/a | DHUNIV 577 | VW | n/a |
| DHUNIV 022 | ER | n/a | DHUNIV 578 | WG | n/a |
| DHUNIV 023 | YNWND | 3740 | DHUNIV 579 | IMITFGGVMLIP | 4115 |

TABLE 11-continued

1K DH Theoretical Segment Pool sequences (1,111 DH segments).

| DH Segment Name | Amino Acid Sequence | SEQ ID NO | DH Segment Name | Amino Acid Sequence | SEQ ID NO |
|---|---|---|---|---|---|
| DHUNIV 024 | YNWN | 3741 | DHUNIV 580 | IMITFGGVMLI | 4116 |
| DHUNIV 025 | NWND | 3742 | DHUNIV 581 | MITFGGVMLIP | 4117 |
| DHUNIV 026 | YNW | n/a | DHUNIV 582 | IMITFGGVML | 4118 |
| DHUNIV 027 | NWN | n/a | DHUNIV 583 | MITFGGVMLI | 4119 |
| DHUNIV 028 | WND | n/a | DHUNIV 584 | ITFGGVMLIP | 4120 |
| DHUNIV 029 | YN | n/a | DHUNIV 585 | IMITFGGVM | 4121 |
| DHUNIV 030 | NW | n/a | DHUNIV 586 | MITFGGVML | 4122 |
| DHUNIV 031 | WN | n/a | DHUNIV 587 | ITFGGVMLI | 4123 |
| DHUNIV 032 | ND | n/a | DHUNIV 588 | TFGGVMLIP | 4124 |
| DHUNIV 033 | GITGTT | 3743 | DHUNIV 589 | IMITFGGV | 4125 |
| DHUNIV 034 | GITGT | 3744 | DHUNIV 590 | MITFGGVM | 4126 |
| DHUNIV 035 | ITGTT | 3745 | DHUNIV 591 | ITFGGVML | 4127 |
| DHUNIV 036 | GITG | 3746 | DHUNIV 592 | TFGGVMLI | 4128 |
| DHUNIV 037 | ITGT | 3747 | DHUNIV 593 | FGGVMLIP | 4129 |
| DHUNIV 038 | GIT | n/a | DHUNIV 594 | IMITFGG | 4130 |
| DHUNIV 039 | ITG | n/a | DHUNIV 595 | MITFGGV | 4131 |
| DHUNIV 040 | GI | n/a | DHUNIV 596 | ITFGGVM | 4132 |
| DHUNIV 041 | IT | n/a | DHUNIV 597 | TFGGVML | 4133 |
| DHUNIV 042 | GIVGATT | 3748 | DHUNIV 598 | FGGVMLI | 4134 |
| DHUNIV 043 | GIVGAT | 3749 | DHUNIV 599 | GGVMLIP | 4135 |
| DHUNIV 044 | IVGATT | 3750 | DHUNIV 600 | IMITFG | 4136 |
| DHUNIV 045 | GIVGA | 3751 | DHUNIV 601 | MITFGG | 4137 |
| DHUNIV 046 | IVGAT | 3752 | DHUNIV 602 | ITFGGV | 4138 |
| DHUNIV 047 | VGATT | 3753 | DHUNIV 603 | TFGGVM | 4139 |
| DHUNIV 048 | GIVG | 3754 | DHUNIV 604 | FGGVML | 4140 |
| DHUNIV 049 | IVGA | 3755 | DHUNIV 605 | GGVMLI | 4141 |
| DHUNIV 050 | VGAT | 3756 | DHUNIV 606 | GVMLIP | 4142 |
| DHUNIV 051 | GATT | 3757 | DHUNIV 607 | IMITF | 4143 |
| DHUNIV 052 | GIV | n/a | DHUNIV 608 | MITFG | 4144 |
| DHUNIV 053 | IVG | n/a | DHUNIV 609 | ITFGG | 4145 |
| DHUNIV 054 | VGA | n/a | DHUNIV 610 | TFGGV | 4146 |
| DHUNIV 055 | GAT | n/a | DHUNIV 611 | FGGVM | 4147 |
| DHUNIV 056 | ATT | n/a | DHUNIV 612 | GGVML | 4148 |
| DHUNIV 057 | IV | n/a | DHUNIV 613 | GVMLI | 4149 |
| DHUNIV 058 | VG | n/a | DHUNIV 614 | VMLIP | 4150 |
| DHUNIV 059 | GA | n/a | DHUNIV 615 | IMIT | 4151 |
| DHUNIV 060 | AT | n/a | DHUNIV 616 | MITF | 4152 |

TABLE 11-continued

1K DH Theoretical Segment Pool sequences (1,111 DH segments).

| DH Segment Name | Amino Acid Sequence | SEQ ID NO | DH Segment Name | Amino Acid Sequence | SEQ ID NO |
|---|---|---|---|---|---|
| DHUNIV 061 | WELL | 3758 | DHUNIV 617 | ITFG | 4153 |
| DHUNIV 062 | WEL | n/a | DHUNIV 618 | TFGG | 4154 |
| DHUNIV 063 | ELL | n/a | DHUNIV 619 | FGGV | 4155 |
| DHUNIV 064 | WE | n/a | DHUNIV 620 | GGVM | 4156 |
| DHUNIV 065 | EL | n/a | DHUNIV 621 | GVML | 4157 |
| DHUNIV 066 | LL | n/a | DHUNIV 622 | VMLI | 4158 |
| DHUNIV 067 | YSGSYY | 3759 | DHUNIV 623 | MLIP | 4159 |
| DHUNIV 068 | YSGSY | 3760 | DHUNIV 624 | IMI | n/a |
| DHUNIV 069 | SGSYY | 3761 | DHUNIV 625 | MIT | n/a |
| DHUNIV 070 | YSGS | 3762 | DHUNIV 626 | ITF | n/a |
| DHUNIV 071 | SGSY | 3763 | DHUNIV 627 | TFG | n/a |
| DHUNIV 072 | GSYY | 3764 | DHUNIV 628 | FGG | n/a |
| DHUNIV 073 | YSG | n/a | DHUNIV 629 | GGV | n/a |
| DHUNIV 074 | SGS | n/a | DHUNIV 630 | GVM | n/a |
| DHUNIV 075 | GSY | n/a | DHUNIV 631 | VML | n/a |
| DHUNIV 076 | SYY | n/a | DHUNIV 632 | MLI | n/a |
| DHUNIV 077 | YS | n/a | DHUNIV 633 | LIP | n/a |
| DHUNIV 078 | SG | n/a | DHUNIV 634 | IM | n/a |
| DHUNIV 079 | GS | n/a | DHUNIV 635 | MI | n/a |
| DHUNIV 080 | SY | n/a | DHUNIV 636 | TF | n/a |
| DHUNIV 081 | YY | n/a | DHUNIV 637 | VM | n/a |
| DHUNIV 082 | LEL | n/a | DHUNIV 638 | LI | n/a |
| DHUNIV 083 | YNWNY | 3765 | DHUNIV 639 | WLLL | 4160 |
| DHUNIV 084 | NWNY | 3766 | DHUNIV 640 | WLL | n/a |
| DHUNIV 085 | WNY | n/a | DHUNIV 641 | WL | n/a |
| DHUNIV 086 | NY | n/a | DHUNIV 642 | YYYDSSGYYY | 4161 |
| DHUNIV 087 | RIL | n/a | DHUNIV 643 | YYYDSSGYY | 4162 |
| DHUNIV 088 | LLL | n/a | DHUNIV 644 | YYDSSGYYY | 4163 |
| DHUNIV 089 | RI | n/a | DHUNIV 645 | YYYDSSGY | 4164 |
| DHUNIV 090 | IL | n/a | DHUNIV 646 | YYDSSGYY | 4165 |
| DHUNIV 091 | WW | n/a | DHUNIV 647 | YDSSGYYY | 4166 |
| DHUNIV 092 | GYCSGGSCYS | 3767 | DHUNIV 648 | YYYDSSG | 4167 |
| DHUNIV 093 | GYCSGGSCY | 3768 | DHUNIV 649 | YYDSSGY | 4168 |
| DHUNIV 094 | YCSGGSCYS | 3769 | DHUNIV 650 | YDSSGYY | 4169 |
| DHUNIV 095 | GYCSGGSC | 3770 | DHUNIV 651 | DSSGYYY | 4170 |
| DHUNIV 096 | YCSGGSCY | 3771 | DHUNIV 652 | YYYDSS | 4171 |
| DHUNIV 097 | CSGGSCYS | 3772 | DHUNIV 653 | YYDSSG | 4172 |
| DHUNIV 098 | YCSGGSC | 3773 | DHUNIV 654 | YDSSGY | 4173 |

TABLE 11-continued

1K DH Theoretical Segment Pool sequences (1,111 DH segments).

| DH Segment Name | Amino Acid Sequence | SEQ ID NO | DH Segment Name | Amino Acid Sequence | SEQ ID NO |
|---|---|---|---|---|---|
| DHUNIV 099 | CSGGSCY | 3774 | DHUNIV 655 | DSSGYY | 4174 |
| DHUNIV 100 | CSGGSC | 3775 | DHUNIV 656 | SSGYYY | 4175 |
| DHUNIV 101 | SGGS | 3776 | DHUNIV 657 | YYYDS | 4176 |
| DHUNIV 102 | SGG | n/a | DHUNIV 658 | YYDSS | 4177 |
| DHUNIV 103 | GGS | n/a | DHUNIV 659 | YDSSG | 4178 |
| DHUNIV 104 | GY | n/a | DHUNIV 660 | DSSGY | 4179 |
| DHUNIV 105 | GG | n/a | DHUNIV 661 | SSGYY | 4180 |
| DHUNIV 106 | DIVVVVAATP | 3777 | DHUNIV 662 | SGYYY | 4181 |
| DHUNIV 107 | DIVVVVAAT | 3778 | DHUNIV 663 | YYYD | 4182 |
| DHUNIV 108 | IVVVVAATP | 3779 | DHUNIV 664 | YYDS | 4183 |
| DHUNIV 109 | DIVVVVAA | 3780 | DHUNIV 665 | YDSS | 4184 |
| DHUNIV 110 | IVVVVAAT | 3781 | DHUNIV 666 | DSSG | 4185 |
| DHUNIV 111 | VVVVAATP | 3782 | DHUNIV 667 | SSGY | 4186 |
| DHUNIV 112 | DIVVVVA | 3783 | DHUNIV 668 | SGYY | 4187 |
| DHUNIV 113 | IVVVVAA | 3784 | DHUNIV 669 | GYYY | 4188 |
| DHUNIV 114 | VVVVAAT | 3785 | DHUNIV 670 | YDS | n/a |
| DHUNIV 115 | VVVAATP | 3786 | DHUNIV 671 | DSS | n/a |
| DHUNIV 116 | DIVVVV | 3787 | DHUNIV 672 | SSG | n/a |
| DHUNIV 117 | IVVVVA | 3788 | DHUNIV 673 | SGY | n/a |
| DHUNIV 118 | VVVVAA | 3789 | DHUNIV 674 | GYY | n/a |
| DHUNIV 119 | VVVAAT | 3790 | DHUNIV 675 | DS | n/a |
| DHUNIV 120 | VVAATP | 3791 | DHUNIV 676 | ITMIVVVITT | 4189 |
| DHUNIV 121 | DIVVV | 3792 | DHUNIV 677 | ITMIVVVIT | 4190 |
| DHUNIV 122 | IVVVV | 3793 | DHUNIV 678 | TMIVVVITT | 4191 |
| DHUNIV 123 | VVVVA | 3794 | DHUNIV 679 | ITMIVVVI | 4192 |
| DHUNIV 124 | VVVAA | 3795 | DHUNIV 680 | TMIVVVIT | 4193 |
| DHUNIV 125 | VVAAT | 3796 | DHUNIV 681 | MIVVVITT | 4194 |
| DHUNIV 126 | VAATP | 3797 | DHUNIV 682 | ITMIVVV | 4195 |
| DHUNIV 127 | DIVV | 3798 | DHUNIV 683 | TMIVVVI | 4196 |
| DHUNIV 128 | IVVV | 3799 | DHUNIV 684 | MIVVVIT | 4197 |
| DHUNIV 129 | VVVV | 3800 | DHUNIV 685 | IVVVITT | 4198 |
| DHUNIV 130 | VVVA | 3801 | DHUNIV 686 | ITMIVV | 4199 |
| DHUNIV 131 | VVAA | 3802 | DHUNIV 687 | TMIVVV | 4200 |
| DHUNIV 132 | VAAT | 3803 | DHUNIV 688 | MIVVVI | 4201 |
| DHUNIV 133 | AATP | 3804 | DHUNIV 689 | IVVVIT | 4202 |
| DHUNIV 134 | DIV | n/a | DHUNIV 690 | VVVITT | 4203 |
| DHUNIV 135 | IVV | n/a | DHUNIV 691 | ITMIV | 4204 |

TABLE 11-continued

1K DH Theoretical Segment Pool sequences (1,111 DH segments).

| DH Segment Name | Amino Acid Sequence | SEQ ID NO | DH Segment Name | Amino Acid Sequence | SEQ ID NO |
|---|---|---|---|---|---|
| DHUNIV 136 | VVV | n/a | DHUNIV 692 | TMIVV | 4205 |
| DHUNIV 137 | VVA | n/a | DHUNIV 693 | MIVVV | 4206 |
| DHUNIV 138 | VAA | n/a | DHUNIV 694 | VVVIT | 4207 |
| DHUNIV 139 | AAT | n/a | DHUNIV 695 | VVITT | 4208 |
| DHUNIV 140 | ATP | n/a | DHUNIV 696 | ITMI | 4209 |
| DHUNIV 141 | DI | n/a | DHUNIV 697 | TMIV | 4210 |
| DHUNIV 142 | VV | n/a | DHUNIV 698 | MIVV | 4211 |
| DHUNIV 143 | VA | n/a | DHUNIV 699 | VVIT | 4212 |
| DHUNIV 144 | AA | n/a | DHUNIV 700 | VITT | 4213 |
| DHUNIV 145 | TP | n/a | DHUNIV 701 | TMI | n/a |
| DHUNIV 146 | YQLL | 3805 | DHUNIV 702 | MIV | n/a |
| DHUNIV 147 | YQL | n/a | DHUNIV 703 | VIT | n/a |
| DHUNIV 148 | QT | n/a | DHUNIV 704 | ITT | n/a |
| DHUNIV 149 | YQ | n/a | DHUNIV 705 | VLRFLEWLLY | 4214 |
| DHUNIV 150 | GYCSSTSCYA | 3806 | DHUNIV 706 | VLRFLEWLL | 4215 |
| DHUNIV 151 | GYCSSTSCY | 3807 | DHUNIV 707 | LRFLEWLLY | 4216 |
| DHUNIV 152 | YCSSTSCYA | 3808 | DHUNIV 708 | VLRFLEWL | 4217 |
| DHUNIV 153 | GYCSSTSC | 3809 | DHUNIV 709 | LRFLEWLL | 4218 |
| DHUNIV 154 | YCSSTSCY | 3810 | DHUNIV 710 | RFLEWLLY | 4219 |
| DHUNIV 155 | CSSTSCYA | 3811 | DHUNIV 711 | VLRFLEW | 4220 |
| DHUNIV 156 | YCSSTSC | 3812 | DHUNIV 712 | LRFLEWL | 4221 |
| DHUNIV 157 | CSSTSCY | 3813 | DHUNIV 713 | RFLEWLL | 4222 |
| DHUNIV 158 | CSSTSC | 3814 | DHUNIV 714 | FLEWLLY | 4223 |
| DHUNIV 159 | SSTS | 3815 | DHUNIV 715 | VLRFLE | 4224 |
| DHUNIV 160 | SST | n/a | DHUNIV 716 | LRFLEW | 4225 |
| DHUNIV 161 | STS | n/a | DHUNIV 717 | RFLEWL | 4226 |
| DHUNIV 162 | SS | n/a | DHUNIV 718 | FLEWLL | 4227 |
| DHUNIV 163 | ST | n/a | DHUNIV 719 | LEWLLY | 4228 |
| DHUNIV 164 | TS | n/a | DHUNIV 720 | VLRFL | 4229 |
| DHUNIV 165 | YA | n/a | DHUNIV 721 | LRFLE | 4230 |
| DHUNIV 166 | DIVVVPAAMP | 3816 | DHUNIV 722 | RFLEW | 4231 |
| DHUNIV 167 | DIVVVPAAM | 3817 | DHUNIV 723 | FLEWL | 4232 |
| DHUNIV 168 | IVVVPAAMP | 3818 | DHUNIV 724 | LEWLL | 4233 |
| DHUNIV 169 | DIVVVPAA | 3819 | DHUNIV 725 | EWLLY | 4234 |
| DHUNIV 170 | IVVVPAAM | 3820 | DHUNIV 726 | VLRF | 4235 |
| DHUNIV 171 | VVVPAAMP | 3821 | DHUNIV 727 | LRFL | 4236 |
| DHUNIV 172 | DIVVVPA | 3822 | DHUNIV 728 | RFLE | 4237 |
| DHUNIV 173 | IVVVPAA | 3823 | DHUNIV 729 | FLEW | 4238 |

TABLE 11-continued

1K DH Theoretical Segment Pool sequences (1,111 DH segments).

| DH Segment Name | Amino Acid Sequence | SEQ ID NO | DH Segment Name | Amino Acid Sequence | SEQ ID NO |
|---|---|---|---|---|---|
| DHUNIV 174 | VVVPAAM | 3824 | DHUNIV 730 | LEWL | 4239 |
| DHUNIV 175 | VVPAAMP | 3825 | DHUNIV 731 | EWLL | 4240 |
| DHUNIV 176 | DIVVVP | 3826 | DHUNIV 732 | WLLY | 4241 |
| DHUNIV 177 | IVVVPA | 3827 | DHUNIV 733 | VLR | n/a |
| DHUNIV 178 | VVVPAA | 3828 | DHUNIV 734 | LRF | n/a |
| DHUNIV 179 | VVPAAM | 3829 | DHUNIV 735 | RFL | n/a |
| DHUNIV 180 | VPAAMP | 3830 | DHUNIV 736 | FLE | n/a |
| DHUNIV 181 | IVVVP | 3831 | DHUNIV 737 | LEW | n/a |
| DHUNIV 182 | VVVPA | 3832 | DHUNIV 738 | EWL | n/a |
| DHUNIV 183 | VVPAA | 3833 | DHUNIV 739 | RF | n/a |
| DHUNIV 184 | VPAAM | 3834 | DHUNIV 740 | FL | n/a |
| DHUNIV 185 | PAAMP | 3835 | DHUNIV 741 | EW | n/a |
| DHUNIV 186 | VVVP | 3836 | DHUNIV 742 | YYDFWSGYYT | 4242 |
| DHUNIV 187 | VVPA | 3837 | DHUNIV 743 | YYDFWSGYY | 4243 |
| DHUNIV 188 | VPAA | 3838 | DHUNIV 744 | YDFWSGYYT | 4244 |
| DHUNIV 189 | PAAM | 3839 | DHUNIV 745 | YYDFWSGY | 4245 |
| DHUNIV 190 | AAMP | 3840 | DHUNIV 746 | YDFWSGYY | 4246 |
| DHUNIV 191 | VVP | n/a | DHUNIV 747 | DFWSGYYT | 4247 |
| DHUNIV 192 | VPA | n/a | DHUNIV 748 | YYDFWSG | 4248 |
| DHUNIV 193 | PAA | n/a | DHUNIV 749 | YDFWSGY | 4249 |
| DHUNIV 194 | AAM | n/a | DHUNIV 750 | DFWSGYY | 4250 |
| DHUNIV 195 | AMP | n/a | DHUNIV 751 | FWSGYYT | 4251 |
| DHUNIV 196 | VP | n/a | DHUNIV 752 | YYDFWS | 4252 |
| DHUNIV 197 | PA | n/a | DHUNIV 753 | YDFWSG | 4253 |
| DHUNIV 198 | AM | n/a | DHUNIV 754 | DFWSGY | 4254 |
| DHUNIV 199 | MP | n/a | DHUNIV 755 | FWSGYY | 4255 |
| DHUNIV 200 | YQLLY | 3841 | DHUNIV 756 | WSGYYT | 4256 |
| DHUNIV 201 | QLLY | 3842 | DHUNIV 757 | YYDFW | 4257 |
| DHUNIV 202 | LLY | n/a | DHUNIV 758 | YDFWS | 4258 |
| DHUNIV 203 | LY | n/a | DHUNIV 759 | DFWSG | 4259 |
| DHUNIV 204 | GYCSSTSCYT | 3843 | DHUNIV 760 | FWSGY | 4260 |
| DHUNIV 205 | YCSSTSCYT | 3844 | DHUNIV 761 | WSGYY | 4261 |
| DHUNIV 206 | CSSTSCYT | 3845 | DHUNIV 762 | SGYYT | 4262 |
| DHUNIV 207 | YT | n/a | DHUNIV 763 | YYDF | 4263 |
| DHUNIV 208 | DIVVVPAAIP | 3846 | DHUNIV 764 | YDFW | 4264 |
| DHUNIV 209 | DIVVVPAAI | 3847 | DHUNIV 765 | DFWS | 4265 |
| DHUNIV 210 | IVVVPAAIP | 3848 | DHUNIV 766 | FWSG | 4266 |

TABLE 11-continued

1K DH Theoretical Segment Pool sequences (1,111 DH segments).

| DH Segment Name | Amino Acid Sequence | SEQ ID NO | DH Segment Name | Amino Acid Sequence | SEQ ID NO |
|---|---|---|---|---|---|
| DHUNIV 211 | IVVVPAAI | 3849 | DHUNIV 767 | WSGY | 4267 |
| DHUNIV 212 | VVVPAAIP | 3850 | DHUNIV 768 | GYYT | 4268 |
| DHUNIV 213 | VVVPAAI | 3851 | DHUNIV 769 | YDF | n/a |
| DHUNIV 214 | VVPAAIP | 3852 | DHUNIV 770 | DFW | n/a |
| DHUNIV 215 | VVPAAI | 3853 | DHUNIV 771 | FWS | n/a |
| DHUNIV 216 | VPAAIP | 3854 | DHUNIV 772 | WSG | n/a |
| DHUNIV 217 | VPAAI | 3855 | DHUNIV 773 | YYT | n/a |
| DHUNIV 218 | PAAIP | 3856 | DHUNIV 774 | DF | n/a |
| DHUNIV 219 | PAAI | 3857 | DHUNIV 775 | FW | n/a |
| DHUNIV 220 | AAIP | 3858 | DHUNIV 776 | WS | n/a |
| DHUNIV 221 | AAI | n/a | DHUNIV 777 | ITIFGVVIIP | 4269 |
| DHUNIV 222 | AIP | n/a | DHUNIV 778 | ITIFGVVII | 4270 |
| DHUNIV 223 | Al | n/a | DHUNIV 779 | TIFGVVIIP | 4271 |
| DHUNIV 224 | IP | n/a | DHUNIV 780 | ITIFGVVI | 4272 |
| DHUNIV 225 | WIL | n/a | DHUNIV 781 | TIFGVVII | 4273 |
| DHUNIV 226 | WI | n/a | DHUNIV 782 | IFGVVIIP | 4274 |
| DHUNIV 227 | SILWW | 3859 | DHUNIV 783 | ITIFGVV | 4275 |
| DHUNIV 228 | SILW | 3860 | DHUNIV 784 | TIFGVVI | 4276 |
| DHUNIV 229 | ILWW | 3861 | DHUNIV 785 | IFGVVII | 4277 |
| DHUNIV 230 | SIL | n/a | DHUNIV 786 | FGVVIIP | 4278 |
| DHUNIV 231 | ILW | n/a | DHUNIV 787 | ITIFGV | 4279 |
| DHUNIV 232 | LWW | n/a | DHUNIV 788 | TIFGVV | 4280 |
| DHUNIV 233 | LLF | n/a | DHUNIV 789 | IFGVVI | 4281 |
| DHUNIV 234 | SI | n/a | DHUNIV 790 | FGVVII | 4282 |
| DHUNIV 235 | LW | n/a | DHUNIV 791 | GVVIIP | 4283 |
| DHUNIV 236 | LF | n/a | DHUNIV 792 | ITIFG | 4284 |
| DHUNIV 237 | AYCGGDCYS | 3862 | DHUNIV 793 | TIFGV | 4285 |
| DHUNIV 238 | AYCGGDCY | 3863 | DHUNIV 794 | IFGVV | 4286 |
| DHUNIV 239 | YCGGDCYS | 3864 | DHUNIV 795 | FGVVI | 4287 |
| DHUNIV 240 | AYCGGDC | 3865 | DHUNIV 796 | GVVII | 4288 |
| DHUNIV 241 | YCGGDCY | 3866 | DHUNIV 797 | VVIIP | 4289 |
| DHUNIV 242 | CGGDCYS | 3867 | DHUNIV 798 | ITIF | 4290 |
| DHUNIV 243 | YCGGDC | 3868 | DHUNIV 799 | TIFG | 4291 |
| DHUNIV 244 | CGGDCY | 3869 | DHUNIV 800 | IFGV | 4292 |
| DHUNIV 245 | CGGDC | 3870 | DHUNIV 801 | FGVV | 4293 |
| DHUNIV 246 | GGD | n/a | DHUNIV 802 | GVVI | 4294 |
| DHUNIV 247 | AY | n/a | DHUNIV 803 | VVII | 4295 |
| DHUNIV 248 | GD | n/a | DHUNIV 804 | VIIP | 4296 |

TABLE 11-continued

1K DH Theoretical Segment Pool sequences (1,111 DH segments).

| DH Segment Name | Amino Acid Sequence | SEQ ID NO | DH Segment Name | Amino Acid Sequence | SEQ ID NO |
|---|---|---|---|---|---|
| DHUNIV 249 | HIVVVIAIP | 3871 | DHUNIV 805 | ITI | n/a |
| DHUNIV 250 | HIVVVIAI | 3872 | DHUNIV 806 | TIF | n/a |
| DHUNIV 251 | IVVVIAIP | 3873 | DHUNIV 807 | IFG | n/a |
| DHUNIV 252 | HIVVVIA | 3874 | DHUNIV 808 | FGV | n/a |
| DHUNIV 253 | IVVVIAI | 3875 | DHUNIV 809 | GVV | n/a |
| DHUNIV 254 | VVVIAIP | 3876 | DHUNIV 810 | IIP | n/a |
| DHUNIV 255 | HIVVVI | 3877 | DHUNIV 811 | TI | n/a |
| DHUNIV 256 | IVVVIA | 3878 | DHUNIV 812 | IF | n/a |
| DHUNIV 257 | VVVIAI | 3879 | DHUNIV 813 | VLRYFDWLL | 4297 |
| DHUNIV 258 | VVIAIP | 3880 | DHUNIV 814 | VLRYFDWL | 4298 |
| DHUNIV 259 | HIVVV | 3881 | DHUNIV 815 | LRYFDWLL | 4299 |
| DHUNIV 260 | IVVVI | 3882 | DHUNIV 816 | VLRYFDW | 4300 |
| DHUNIV 261 | VVVIA | 3883 | DHUNIV 817 | LRYFDWL | 4301 |
| DHUNIV 262 | VVIAI | 3884 | DHUNIV 818 | RYFDWLL | 4302 |
| DHUNIV 263 | VIAIP | 3885 | DHUNIV 819 | VLRYFD | 4303 |
| DHUNIV 264 | HIVV | 3886 | DHUNIV 820 | LRYFDW | 4304 |
| DHUNIV 265 | VVVI | 3887 | DHUNIV 821 | RYFDWL | 4305 |
| DHUNIV 266 | VVIA | 3888 | DHUNIV 822 | YFDWLL | 4306 |
| DHUNIV 267 | VIAI | 3889 | DHUNIV 823 | VLRYF | 4307 |
| DHUNIV 268 | IAIP | 3890 | DHUNIV 824 | LRYFD | 4308 |
| DHUNIV 269 | HIV | n/a | DHUNIV 825 | RYFDW | 4309 |
| DHUNIV 270 | VVI | n/a | DHUNIV 826 | YFDWL | 4310 |
| DHUNIV 271 | VIA | n/a | DHUNIV 827 | FDWLL | 4311 |
| DHUNIV 272 | IAI | n/a | DHUNIV 828 | VLRY | 4312 |
| DHUNIV 273 | HI | n/a | DHUNIV 829 | LRYF | 4313 |
| DHUNIV 274 | VI | n/a | DHUNIV 830 | RYFD | 4314 |
| DHUNIV 275 | IA | n/a | DHUNIV 831 | YFDW | 4315 |
| DHUNIV 276 | HIVVVTAIP | 3891 | DHUNIV 832 | FDWL | 4316 |
| DHUNIV 277 | HIVVVTAI | 3892 | DHUNIV 833 | DWLL | 4317 |
| DHUNIV 278 | IVVVTAIP | 3893 | DHUNIV 834 | LRY | n/a |
| DHUNIV 279 | HIVVVTA | 3894 | DHUNIV 835 | RYF | n/a |
| DHUNIV 280 | IVVVTAI | 3895 | DHUNIV 836 | YFD | n/a |
| DHUNIV 281 | VVVTAIP | 3896 | DHUNIV 837 | FDW | n/a |
| DHUNIV 282 | HIVVVT | 3897 | DHUNIV 838 | DWL | n/a |
| DHUNIV 283 | IVVVTA | 3898 | DHUNIV 839 | RY | n/a |
| DHUNIV 284 | VVVTAI | 3899 | DHUNIV 840 | YF | n/a |
| DHUNIV 285 | VVTAIP | 3900 | DHUNIV 841 | FD | n/a |

TABLE 11-continued

1K DH Theoretical Segment Pool sequences (1,111 DH segments).

| DH Segment Name | Amino Acid Sequence | SEQ ID NO | DH Segment Name | Amino Acid Sequence | SEQ ID NO |
|---|---|---|---|---|---|
| DHUNIV 286 | IVVVT | 3901 | DHUNIV 842 | DW | n/a |
| DHUNIV 287 | VVVTA | 3902 | DHUNIV 843 | YYDILTGYYN | 4318 |
| DHUNIV 288 | VVTAI | 3903 | DHUNIV 844 | YYDILTGYY | 4319 |
| DHUNIV 289 | VTAIP | 3904 | DHUNIV 845 | YDILTGYYN | 4320 |
| DHUNIV 290 | VVVT | 3905 | DHUNIV 846 | YYDILTGY | 4321 |
| DHUNIV 291 | VVTA | 3906 | DHUNIV 847 | YDILTGYY | 4322 |
| DHUNIV 292 | VTAI | 3907 | DHUNIV 848 | DILTGYYN | 4323 |
| DHUNIV 293 | TAIP | 3908 | DHUNIV 849 | YYDILTG | 4324 |
| DHUNIV 294 | VVT | n/a | DHUNIV 850 | YDILTGY | 4325 |
| DHUNIV 295 | VTA | n/a | DHUNIV 851 | DILTGYY | 4326 |
| DHUNIV 296 | TAI | n/a | DHUNIV 852 | ILTGYYN | 4327 |
| DHUNIV 297 | VT | n/a | DHUNIV 853 | YYDILT | 4328 |
| DHUNIV 298 | TA | n/a | DHUNIV 854 | YDILTG | 4329 |
| DHUNIV 299 | RILY | 3909 | DHUNIV 855 | DILTGY | 4330 |
| DHUNIV 300 | ILY | n/a | DHUNIV 856 | ILTGYY | 4331 |
| DHUNIV 301 | MLY | n/a | DHUNIV 857 | LTGYYN | 4332 |
| DHUNIV 302 | ML | n/a | DHUNIV 858 | YYDIL | 4333 |
| DHUNIV 303 | GYCTNGVCYT | 3910 | DHUNIV 859 | YDILT | 4334 |
| DHUNIV 304 | GYCTNGVCY | 3911 | DHUNIV 860 | DILTG | 4335 |
| DHUNIV 305 | YCTNGVCYT | 3912 | DHUNIV 861 | ILTGY | 4336 |
| DHUNIV 306 | GYCTNGVC | 3913 | DHUNIV 862 | LTGYY | 4337 |
| DHUNIV 307 | YCTNGVCY | 3914 | DHUNIV 863 | TGYYN | 4338 |
| DHUNIV 308 | CTNGVCYT | 3915 | DHUNIV 864 | YYDI | 4339 |
| DHUNIV 309 | YCTNGVC | 3916 | DHUNIV 865 | YDIL | 4340 |
| DHUNIV 310 | CTNGVCY | 3917 | DHUNIV 866 | DILT | 4341 |
| DHUNIV 311 | CTNGVC | 3918 | DHUNIV 867 | ILTG | 4342 |
| DHUNIV 312 | TNGV | 3919 | DHUNIV 868 | LTGY | 4343 |
| DHUNIV 313 | TNG | n/a | DHUNIV 869 | TGYY | 4344 |
| DHUNIV 314 | NGV | n/a | DHUNIV 870 | GYYN | 4345 |
| DHUNIV 315 | TN | n/a | DHUNIV 871 | YDI | n/a |
| DHUNIV 316 | NG | n/a | DHUNIV 872 | DIL | n/a |
| DHUNIV 317 | GV | n/a | DHUNIV 873 | ILT | n/a |
| DHUNIV 318 | DIVLMVYAIP | 3920 | DHUNIV 874 | LTG | n/a |
| DHUNIV 319 | DIVLMVYAI | 3921 | DHUNIV 875 | TGY | n/a |
| DHUNIV 320 | IVLMVYAIP | 3922 | DHUNIV 876 | LT | n/a |
| DHUNIV 321 | DIVLMVYA | 3923 | DHUNIV 877 | LVIIT | 4346 |
| DHUNIV 322 | IVLMVYAI | 3924 | DHUNIV 878 | LVII | 4347 |
| DHUNIV 323 | VLMVYAIP | 3925 | DHUNIV 879 | LVI | n/a |

TABLE 11-continued

| 1K DH Theoretical Segment Pool sequences (1,111 DH segments). | | | | | |
|---|---|---|---|---|---|
| DH Segment Name | Amino Acid Sequence | SEQ ID NO | DH Segment Name | Amino Acid Sequence | SEQ ID NO |
| DHUNIV 324 | DIVLMVY | 3926 | DHUNIV 880 | LV | n/a |
| DHUNIV 325 | IVLMVYA | 3927 | DHUNIV 881 | DYGDY | 4348 |
| DHUNIV 326 | VLMVYAI | 3928 | DHUNIV 882 | DYGD | 4349 |
| DHUNIV 327 | LMVYAIP | 3929 | DHUNIV 883 | YGDY | 4350 |
| DHUNIV 328 | DIVLMV | 3930 | DHUNIV 884 | DYG | n/a |
| DHUNIV 329 | IVLMVY | 3931 | DHUNIV 885 | YGD | n/a |
| DHUNIV 330 | VLMVYA | 3932 | DHUNIV 886 | GDY | n/a |
| DHUNIV 331 | LMVYAI | 3933 | DHUNIV 887 | TTVTT | 4351 |
| DHUNIV 332 | MVYAIP | 3934 | DHUNIV 888 | TTVT | 4352 |
| DHUNIV 333 | DIVLM | 3935 | DHUNIV 889 | TVTT | 4353 |
| DHUNIV 334 | IVLMV | 3936 | DHUNIV 890 | TTV | n/a |
| DHUNIV 335 | VLMVY | 3937 | DHUNIV 891 | TVT | n/a |
| DHUNIV 336 | LMVYA | 3938 | DHUNIV 892 | VTT | n/a |
| DHUNIV 337 | MVYAI | 3939 | DHUNIV 893 | TV | n/a |
| DHUNIV 338 | VYAIP | 3940 | DHUNIV 894 | LRW | n/a |
| DHUNIV 339 | DIVL | 3941 | DHUNIV 895 | RW | n/a |
| DHUNIV 340 | IVLM | 3942 | DHUNIV 896 | DYGGNS | 4354 |
| DHUNIV 341 | VLMV | 3943 | DHUNIV 897 | DYGGN | 4355 |
| DHUNIV 342 | LMVY | 3944 | DHUNIV 898 | YGGNS | 4356 |
| DHUNIV 343 | MVYA | 3945 | DHUNIV 899 | DYGG | 4357 |
| DHUNIV 344 | VYAI | 3946 | DHUNIV 900 | YGGN | 4358 |
| DHUNIV 345 | YAIP | 3947 | DHUNIV 901 | GGNS | 4359 |
| DHUNIV 346 | IVL | n/a | DHUNIV 902 | YGG | n/a |
| DHUNIV 347 | VLM | n/a | DHUNIV 903 | GGN | n/a |
| DHUNIV 348 | LMV | n/a | DHUNIV 904 | GNS | n/a |
| DHUNIV 349 | MVY | n/a | DHUNIV 905 | GN | n/a |
| DHUNIV 350 | VYA | n/a | DHUNIV 906 | NS | n/a |
| DHUNIV 351 | YAI | n/a | DHUNIV 907 | TTVVTP | 4360 |
| DHUNIV 352 | VL | n/a | DHUNIV 908 | TTVVT | 4361 |
| DHUNIV 353 | LM | n/a | DHUNIV 909 | TVVTP | 4362 |
| DHUNIV 354 | MV | n/a | DHUNIV 910 | TTVV | 4363 |
| DHUNIV 355 | VY | n/a | DHUNIV 911 | TVVT | 4364 |
| DHUNIV 356 | VLLWFGELL | 3948 | DHUNIV 912 | VVTP | 4365 |
| DHUNIV 357 | VLLWFGEL | 3949 | DHUNIV 913 | TVV | n/a |
| DHUNIV 358 | LLWFGELL | 3950 | DHUNIV 914 | VTP | n/a |
| DHUNIV 359 | VLLWFGE | 3951 | DHUNIV 915 | LQ | n/a |
| DHUNIV 360 | LLWFGEL | 3952 | DHUNIV 916 | DYSNY | 4366 |

TABLE 11-continued

1K DH Theoretical Segment Pool sequences (1,111 DH segments).

| DH Segment Name | Amino Acid Sequence | SEQ ID NO | DH Segment Name | Amino Acid Sequence | SEQ ID NO |
|---|---|---|---|---|---|
| DHUNIV 361 | LWFGELL | 3953 | DHUNIV 917 | DYSN | 4367 |
| DHUNIV 362 | VLLWFG | 3954 | DHUNIV 918 | YSNY | 4368 |
| DHUNIV 363 | LLWFGE | 3955 | DHUNIV 919 | DYS | n/a |
| DHUNIV 364 | LWFGEL | 3956 | DHUNIV 920 | YSN | n/a |
| DHUNIV 365 | WFGELL | 3957 | DHUNIV 921 | SNY | n/a |
| DHUNIV 366 | VLLWF | 3958 | DHUNIV 922 | SN | n/a |
| DHUNIV 367 | LLWFG | 3959 | DHUNIV 923 | VDIVATIT | 4369 |
| DHUNIV 368 | LWFGE | 3960 | DHUNIV 924 | VDIVATI | 4370 |
| DHUNIV 369 | WFGEL | 3961 | DHUNIV 925 | DIVATIT | 4371 |
| DHUNIV 370 | FGELL | 3962 | DHUNIV 926 | VDIVAT | 4372 |
| DHUNIV 371 | VLLW | 3963 | DHUNIV 927 | DIVATI | 4373 |
| DHUNIV 372 | LLWF | 3964 | DHUNIV 928 | IVATIT | 4374 |
| DHUNIV 373 | LWFG | 3965 | DHUNIV 929 | VDIVA | 4375 |
| DHUNIV 374 | WFGE | 3966 | DHUNIV 930 | DIVAT | 4376 |
| DHUNIV 375 | FGEL | 3967 | DHUNIV 931 | IVATI | 4377 |
| DHUNIV 376 | GELL | 3968 | DHUNIV 932 | VATIT | 4378 |
| DHUNIV 377 | VLL | n/a | DHUNIV 933 | VDIV | 4379 |
| DHUNIV 378 | LLW | n/a | DHUNIV 934 | DIVA | 4380 |
| DHUNIV 379 | LWF | n/a | DHUNIV 935 | IVAT | 4381 |
| DHUNIV 380 | WFG | n/a | DHUNIV 936 | VATI | 4382 |
| DHUNIV 381 | FGE | n/a | DHUNIV 937 | ATIT | 4383 |
| DHUNIV 382 | GEL | n/a | DHUNIV 938 | VDI | n/a |
| DHUNIV 383 | WF | n/a | DHUNIV 939 | IVA | n/a |
| DHUNIV 384 | FG | n/a | DHUNIV 940 | VAT | n/a |
| DHUNIV 385 | GE | n/a | DHUNIV 941 | ATI | n/a |
| DHUNIV 386 | YYYGSGSYYN | 3969 | DHUNIV 942 | TIT | n/a |
| DHUNIV 387 | YYYGSGSYY | 3970 | DHUNIV 943 | VD | n/a |
| DHUNIV 388 | YYGSGSYYN | 3971 | DHUNIV 944 | WLRL | 4384 |
| DHUNIV 389 | YYYGSGSY | 3972 | DHUNIV 945 | WLR | n/a |
| DHUNIV 390 | YYGSGSYY | 3973 | DHUNIV 946 | GYSGYDY | 4385 |
| DHUNIV 391 | YGSGSYYN | 3974 | DHUNIV 947 | GYSGYD | 4386 |
| DHUNIV 392 | YYYGSGS | 3975 | DHUNIV 948 | YSGYDY | 4387 |
| DHUNIV 393 | YYGSGSY | 3976 | DHUNIV 949 | GYSGY | 4388 |
| DHUNIV 394 | YGSGSYY | 3977 | DHUNIV 950 | YSGYD | 4389 |
| DHUNIV 395 | GSGSYYN | 3978 | DHUNIV 951 | SGYDY | 4390 |
| DHUNIV 396 | YYYGSG | 3979 | DHUNIV 952 | GYSG | 4391 |
| DHUNIV 397 | YYGSGS | 3980 | DHUNIV 953 | YSGY | 4392 |
| DHUNIV 398 | YGSGSY | 3981 | DHUNIV 954 | SGYD | 4393 |

TABLE 11-continued

1K DH Theoretical Segment Pool sequences (1,111 DH segments).

| DH Segment Name | Amino Acid Sequence | SEQ ID NO | DH Segment Name | Amino Acid Sequence | SEQ ID NO |
|---|---|---|---|---|---|
| DHUNIV 399 | GSGSYY | 3982 | DHUNIV 955 | GYDY | 4394 |
| DHUNIV 400 | SGSYYN | 3983 | DHUNIV 956 | GYS | n/a |
| DHUNIV 401 | YYYGS | 3984 | DHUNIV 957 | GYD | n/a |
| DHUNIV 402 | YYGSG | 3985 | DHUNIV 958 | VEMATIT | 4395 |
| DHUNIV 403 | YGSGS | 3986 | DHUNIV 959 | VEMATI | 4396 |
| DHUNIV 404 | GSGSY | 3987 | DHUNIV 960 | EMATIT | 4397 |
| DHUNIV 405 | GSYYN | 3988 | DHUNIV 961 | VEMAT | 4398 |
| DHUNIV 406 | YYYG | 3989 | DHUNIV 962 | EMATI | 4399 |
| DHUNIV 407 | YYGS | 3990 | DHUNIV 963 | MATIT | 4400 |
| DHUNIV 408 | YGSG | 3991 | DHUNIV 964 | VEMA | 4401 |
| DHUNIV 409 | GSGS | 3992 | DHUNIV 965 | EMAT | 4402 |
| DHUNIV 410 | SYYN | 3993 | DHUNIV 966 | MATI | 4403 |
| DHUNIV 411 | YYY | n/a | DHUNIV 967 | VEM | n/a |
| DHUNIV 412 | YYG | n/a | DHUNIV 968 | EMA | n/a |
| DHUNIV 413 | YGS | n/a | DHUNIV 969 | MAT | n/a |
| DHUNIV 414 | GSG | n/a | DHUNIV 970 | VE | n/a |
| DHUNIV 415 | YYN | n/a | DHUNIV 971 | EM | n/a |
| DHUNIV 416 | YG | n/a | DHUNIV 972 | MA | n/a |
| DHUNIV 417 | ITMVRGVIIT | 3994 | DHUNIV 973 | RWLQL | 4404 |
| DHUNIV 418 | ITMVRGVII | 3995 | DHUNIV 974 | RWLQ | 4405 |
| DHUNIV 419 | TMVRGVIIT | 3996 | DHUNIV 975 | WLQL | 4406 |
| DHUNIV 420 | ITMVRGVI | 3997 | DHUNIV 976 | RWL | n/a |
| DHUNIV 421 | TMVRGVII | 3998 | DHUNIV 977 | WLQ | n/a |
| DHUNIV 422 | MVRGVIIT | 3999 | DHUNIV 978 | LQL | n/a |
| DHUNIV 423 | ITMVRGV | 4000 | DHUNIV 979 | RDGYNY | 4407 |
| DHUNIV 424 | TMVRGVI | 4001 | DHUNIV 980 | RDGYN | 4408 |
| DHUNIV 425 | MVRGVII | 4002 | DHUNIV 981 | DGYNY | 4409 |
| DHUNIV 426 | VRGVIIT | 4003 | DHUNIV 982 | RDGY | 4410 |
| DHUNIV 427 | ITMVRG | 4004 | DHUNIV 983 | DGYN | 4411 |
| DHUNIV 428 | TMVRGV | 4005 | DHUNIV 984 | GYNY | 4412 |
| DHUNIV 429 | MVRGVI | 4006 | DHUNIV 985 | RDG | n/a |
| DHUNIV 430 | VRGVII | 4007 | DHUNIV 986 | DGY | n/a |
| DHUNIV 431 | RGVIIT | 4008 | DHUNIV 987 | GYN | n/a |
| DHUNIV 432 | ITMVR | 4009 | DHUNIV 988 | YNY | n/a |
| DHUNIV 433 | TMVRG | 4010 | DHUNIV 989 | RD | n/a |
| DHUNIV 434 | MVRGV | 4011 | DHUNIV 990 | DG | n/a |
| DHUNIV 435 | VRGVI | 4012 | DHUNIV 991 | VDTAMVT | 4413 |

TABLE 11-continued

1K DH Theoretical Segment Pool sequences (1,111 DH segments).

| DH Segment Name | Amino Acid Sequence | SEQ ID NO | DH Segment Name | Amino Acid Sequence | SEQ ID NO |
|---|---|---|---|---|---|
| DHUNIV 436 | RGVII | 4013 | DHUNIV 992 | VDTAMV | 4414 |
| DHUNIV 437 | GVIIT | 4014 | DHUNIV 993 | DTAMVT | 4415 |
| DHUNIV 438 | ITMV | 4015 | DHUNIV 994 | VDTAM | 4416 |
| DHUNIV 439 | TMVR | 4016 | DHUNIV 995 | DTAMV | 4417 |
| DHUNIV 440 | MVRG | 4017 | DHUNIV 996 | TAMVT | 4418 |
| DHUNIV 441 | VRGV | 4018 | DHUNIV 997 | VDTA | 4419 |
| DHUNIV 442 | RGVI | 4019 | DHUNIV 998 | DTAM | 4420 |
| DHUNIV 443 | GVII | 4020 | DHUNIV 999 | TAMV | 4421 |
| DHUNIV 444 | VIIT | 4021 | DHUNIV 1000 | AMVT | 4422 |
| DHUNIV 445 | ITM | n/a | DHUNIV 1001 | VDT | n/a |
| DHUNIV 446 | TMV | n/a | DHUNIV 1002 | DTA | n/a |
| DHUNIV 447 | MVR | n/a | DHUNIV 1003 | TAM | n/a |
| DHUNIV 448 | VRG | n/a | DHUNIV 1004 | AMV | n/a |
| DHUNIV 449 | RGV | n/a | DHUNIV 1005 | MVT | n/a |
| DHUNIV 450 | GVI | n/a | DHUNIV 1006 | DT | n/a |
| DHUNIV 451 | VII | n/a | DHUNIV 1007 | WIQLWL | 4423 |
| DHUNIV 452 | IIT | n/a | DHUNIV 1008 | WIQLW | 4424 |
| DHUNIV 453 | TM | n/a | DHUNIV 1009 | IQLWL | 4425 |
| DHUNIV 454 | VR | n/a | DHUNIV 1010 | WIQL | 4426 |
| DHUNIV 455 | RG | n/a | DHUNIV 1011 | IQLW | 4427 |
| DHUNIV 456 | II | n/a | DHUNIV 1012 | QLWL | 4428 |
| DHUNIV 457 | VLLWFRELL | 4022 | DHUNIV 1013 | WIQ | n/a |
| DHUNIV 458 | VLLWFREL | 4023 | DHUNIV 1014 | IQL | n/a |
| DHUNIV 459 | LLWFRELL | 4024 | DHUNIV 1015 | QLW | n/a |
| DHUNIV 460 | VLLWFRE | 4025 | DHUNIV 1016 | LWL | n/a |
| DHUNIV 461 | LLWFREL | 4026 | DHUNIV 1017 | IQ | n/a |
| DHUNIV 462 | LWFRELL | 4027 | DHUNIV 1018 | GYSYGY | 4429 |
| DHUNIV 463 | VLLWFR | 4028 | DHUNIV 1019 | GYSYG | 4430 |
| DHUNIV 464 | LLWFRE | 4029 | DHUNIV 1020 | YSYGY | 4431 |
| DHUNIV 465 | LWFREL | 4030 | DHUNIV 1021 | GYSY | 4432 |
| DHUNIV 466 | WFRELL | 4031 | DHUNIV 1022 | YSYG | 4433 |
| DHUNIV 467 | LLWFR | 4032 | DHUNIV 1023 | SYGY | 4434 |
| DHUNIV 468 | LWFRE | 4033 | DHUNIV 1024 | YSY | n/a |
| DHUNIV 469 | WFREL | 4034 | DHUNIV 1025 | SYG | n/a |
| DHUNIV 470 | FRELL | 4035 | DHUNIV 1026 | YGY | n/a |
| DHUNIV 471 | LWFR | 4036 | DHUNIV 1027 | GYSSSWY | 4435 |
| DHUNIV 472 | WFRE | 4037 | DHUNIV 1028 | GYSSSW | 4436 |
| DHUNIV 473 | FREL | 4038 | DHUNIV 1029 | YSSSWY | 4437 |

TABLE 11-continued

1K DH Theoretical Segment Pool sequences (1,111 DH segments).

| DH Segment Name | Amino Acid Sequence | SEQ ID NO | DH Segment Name | Amino Acid Sequence | SEQ ID NO |
|---|---|---|---|---|---|
| DHUNIV 474 | RELL | 4039 | DHUNIV 1030 | GYSSS | 4438 |
| DHUNIV 475 | WFR | n/a | DHUNIV 1031 | YSSSW | 4439 |
| DHUNIV 476 | FRE | n/a | DHUNIV 1032 | SSSWY | 4440 |
| DHUNIV 477 | REL | n/a | DHUNIV 1033 | GYSS | 4441 |
| DHUNIV 478 | FR | n/a | DHUNIV 1034 | YSSS | 4442 |
| DHUNIV 479 | RE | n/a | DHUNIV 1035 | SSSW | 4443 |
| DHUNIV 480 | ITMVQGVIIT | 4040 | DHUNIV 1036 | SSWY | 4444 |
| DHUNIV 481 | ITMVQGVII | 4041 | DHUNIV 1037 | YSS | n/a |
| DHUNIV 482 | TMVQGVIIT | 4042 | DHUNIV 1038 | SSS | n/a |
| DHUNIV 483 | ITMVQGVI | 4043 | DHUNIV 1039 | SSW | n/a |
| DHUNIV 484 | TMVQGVII | 4044 | DHUNIV 1040 | SWY | n/a |
| DHUNIV 485 | MVQGVIIT | 4045 | DHUNIV 1041 | SW | n/a |
| DHUNIV 486 | ITMVQGV | 4046 | DHUNIV 1042 | WY | n/a |
| DHUNIV 487 | TMVQGVI | 4047 | DHUNIV 1043 | GIAAAGT | 4445 |
| DHUNIV 488 | MVQGVII | 4048 | DHUNIV 1044 | GIAAAG | 4446 |
| DHUNIV 489 | VQGVIIT | 4049 | DHUNIV 1045 | IAAAGT | 4447 |
| DHUNIV 490 | ITMVQG | 4050 | DHUNIV 1046 | GIAAA | 4448 |
| DHUNIV 491 | TMVQGV | 4051 | DHUNIV 1047 | IAAAG | 4449 |
| DHUNIV 492 | MVQGVI | 4052 | DHUNIV 1048 | AAAGT | 4450 |
| DHUNIV 493 | VQGVII | 4053 | DHUNIV 1049 | GIAA | 4451 |
| DHUNIV 494 | QGVIIT | 4054 | DHUNIV 1050 | IAAA | 4452 |
| DHUNIV 495 | ITMVQ | 4055 | DHUNIV 1051 | AAAG | 4453 |
| DHUNIV 496 | TMVQG | 4056 | DHUNIV 1052 | AAGT | 4454 |
| DHUNIV 497 | MVQGV | 4057 | DHUNIV 1053 | GIA | n/a |
| DHUNIV 498 | VQGVI | 4058 | DHUNIV 1054 | IAA | n/a |
| DHUNIV 499 | QGVII | 4059 | DHUNIV 1055 | AAA | n/a |
| DHUNIV 500 | TMVQ | 4060 | DHUNIV 1056 | AAG | n/a |
| DHUNIV 501 | MVQG | 4061 | DHUNIV 1057 | AGT | n/a |
| DHUNIV 502 | VQGV | 4062 | DHUNIV 1058 | AG | n/a |
| DHUNIV 503 | QGVI | 4063 | DHUNIV 1059 | QQLV | 4455 |
| DHUNIV 504 | MVQ | n/a | DHUNIV 1060 | QQL | n/a |
| DHUNIV 505 | VQG | n/a | DHUNIV 1061 | QLV | n/a |
| DHUNIV 506 | QGV | n/a | DHUNIV 1062 | QQ | n/a |
| DHUNIV 507 | QG | n/a | DHUNIV 1063 | GYSSGWY | 4456 |
| DHUNIV 508 | LRLGEL | 4064 | DHUNIV 1064 | GYSSGW | 4457 |
| DHUNIV 509 | LRLGE | 4065 | DHUNIV 1065 | YSSGWY | 4458 |
| DHUNIV 510 | RLGEL | 4066 | DHUNIV 1066 | GYSSG | 4459 |

TABLE 11-continued

| 1K DH Theoretical Segment Pool sequences (1,111 DH segments). | | | | | |
|---|---|---|---|---|---|
| DH Segment Name | Amino Acid Sequence | SEQ ID NO | DH Segment Name | Amino Acid Sequence | SEQ ID NO |
| DHUNIV 511 | LRLG | 4067 | DHUNIV 1067 | YSSGW | 4460 |
| DHUNIV 512 | RLGE | 4068 | DHUNIV 1068 | SSGWY | 4461 |
| DHUNIV 513 | LGEL | 4069 | DHUNIV 1069 | YSSG | 4462 |
| DHUNIV 514 | LRL | n/a | DHUNIV 1070 | SSGW | 4463 |
| DHUNIV 515 | RLG | n/a | DHUNIV 1071 | SGWY | 4464 |
| DHUNIV 516 | LGE | n/a | DHUNIV 1072 | SGW | n/a |
| DHUNIV 517 | LR | n/a | DHUNIV 1073 | GWY | n/a |
| DHUNIV 518 | RL | n/a | DHUNIV 1074 | GW | n/a |
| DHUNIV 519 | LG | n/a | DHUNIV 1075 | GIAVAGT | 4465 |
| DHUNIV 520 | YYDYVWGSYAYT | 4070 | DHUNIV 1076 | GIAVAG | 4466 |
| DHUNIV 521 | YYDYVWGSYAY | 4071 | DHUNIV 1077 | IAVAGT | 4467 |
| DHUNIV 522 | YDYVWGSYAYT | 4072 | DHUNIV 1078 | GIAVA | 4468 |
| DHUNIV 523 | YYDYVWGSYA | 4073 | DHUNIV 1079 | IAVAG | 4469 |
| DHUNIV 524 | YDYVWGSYAY | 4074 | DHUNIV 1080 | AVAGT | 4470 |
| DHUNIV 525 | DYVWGSYAYT | 4075 | DHUNIV 1081 | GIAV | 4471 |
| DHUNIV 526 | YYDYVWGSY | 4076 | DHUNIV 1082 | IAVA | 4472 |
| DHUNIV 527 | YDYVWGSYA | 4077 | DHUNIV 1083 | AVAG | 4473 |
| DHUNIV 528 | DYVWGSYAY | 4078 | DHUNIV 1084 | VAGT | 4474 |
| DHUNIV 529 | YVWGSYAYT | 4079 | DHUNIV 1085 | IAV | n/a |
| DHUNIV 530 | YYDYVWGS | 4080 | DHUNIV 1086 | AVA | n/a |
| DHUNIV 531 | YDYVWGSY | 4081 | DHUNIV 1087 | VAG | n/a |
| DHUNIV 532 | DYVWGSYA | 4082 | DHUNIV 1088 | AV | n/a |
| DHUNIV 533 | YVWGSYAY | 4083 | DHUNIV 1089 | QWLV | 4475 |
| DHUNIV 534 | VWGSYAYT | 4084 | DHUNIV 1090 | QWL | n/a |
| DHUNIV 535 | YYDYVWG | 4085 | DHUNIV 1091 | WLV | n/a |
| DHUNIV 536 | YDYVWGS | 4086 | DHUNIV 1092 | QW | n/a |
| DHUNIV 537 | DYVWGSY | 4087 | DHUNIV 1093 | EYSSSS | 4476 |
| DHUNIV 538 | YVWGSYA | 4088 | DHUNIV 1094 | EYSSS | 4477 |
| DHUNIV 539 | VWGSYAY | 4089 | DHUNIV 1095 | YSSSS | 4478 |
| DHUNIV 540 | WGSYAYT | 4090 | DHUNIV 1096 | EYSS | 4479 |
| DHUNIV 541 | YYDYVW | 4091 | DHUNIV 1097 | SSSS | 4480 |
| DHUNIV 542 | YDYVWG | 4092 | DHUNIV 1098 | EYS | n/a |
| DHUNIV 543 | DYVWGS | 4093 | DHUNIV 1099 | EY | n/a |
| DHUNIV 544 | YVWGSY | 4094 | DHUNIV 1100 | SIAARP | 4481 |
| DHUNIV 545 | VWGSYA | 4095 | DHUNIV 1101 | SIAAR | 4482 |
| DHUNIV 546 | WGSYAY | 4096 | DHUNIV 1102 | IAARP | 4483 |
| DHUNIV 547 | GSYAYT | 4097 | DHUNIV 1103 | SIAA | 4484 |
| DHUNIV 548 | YYDYV | 4098 | DHUNIV 1104 | IAAR | 4485 |

TABLE 11-continued

| 1K DH Theoretical Segment Pool sequences (1,111 DH segments). | | | | | |
|---|---|---|---|---|---|
| DH Segment Name | Amino Acid Sequence | SEQ ID NO | DH Segment Name | Amino Acid Sequence | SEQ ID NO |
| DHUNIV 549 | YDYVW | 4099 | DHUNIV 1105 | AARP | 4486 |
| DHUNIV 550 | DYVWG | 4100 | DHUNIV 1106 | SIA | n/a |
| DHUNIV 551 | YVWGS | 4101 | DHUNIV 1107 | AAR | n/a |
| DHUNIV 552 | VWGSY | 4102 | DHUNIV 1108 | ARP | n/a |
| DHUNIV 553 | WGSYA | 4103 | DHUNIV 1109 | AR | n/a |
| DHUNIV 554 | GSYAY | 4104 | DHUNIV 1110 | RP | n/a |
| DHUNIV 555 | SYAYT | 4105 | DHUNIV 1111 | NWG | n/a |
| DHUNIV556 | YYDY | 4106 | | | |

TABLE 12

| Theoretical segment pool of 141 N2 segments in Theoretical Segment Pool 1 (TSP1). | | |
|---|---|---|
| Segment Type | Sequences | Number |
| "Zero" | (no addition) V segment joins directly to D segment | 1 |
| Monomers | G, P, R, A, S, L, T, V, D, E, F, H, I, K, M, Q, W, Y | 18 |
| Dimers | GG, GP, GR, GA, GS, GL, GT, GV, PG, RG, AG, SG, LG, TG, VG, PP, PR, PA, PS, PL, PT, PV, RP, AP, SP, LP, TP, VP, AR, AS, AT, AY, DL, DT, EA, EK, FH, FS, HL, HW, IS, KV, LD, LE, LR, LS, LT, NR, NT, QE, QL, QT, RA, RD, RE, RF, RH, RL, RR, RS, RV, SA, SD, SE, SF, SI, SK, SL, SQ, SR, SS, ST, SV, TA, TR, TS, TT, TW, VD, VS, WS, YS | 82 |
| Trimers | GGG, GPG, GRG, GAG, GSG, GLG, GTG, GVG, PGG, RGG, AGG, SGG, LGG, TGG, VGG, GGP, GGR, GGA, GGS, GGL, GGT, GGV, AAE, AYH, DTL, EKR, ISR, NTP, PKS, PRP, PTA, PTQ, REL, RPL, SAA, SAL, SGL, SSE, TGL, WGT | 40 |

TABLE 13

| Theoretical segment pool of 285 H3-JH segments. | | |
|---|---|---|
| H3-JH Segment Name | Amino Acid Sequence | SEQ ID NO |
| JHUNIV 001 | TEYFQH | 4487 |
| JHUNIV 002 | EYFQH | 4488 |
| JHUNIV 003 | YFQH | 4489 |
| JHUNIV 004 | FQH | n/a |
| JHUNIV 005 | QH | n/a |
| JHUNIV 006 | H | n/a |
| JHUNIV 007 | | n/a |

TABLE 13-continued

| Theoretical segment pool of 285 H3-JH segments. | | |
|---|---|---|
| H3-JH Segment Name | Amino Acid Sequence | SEQ ID NO |
| JHUNIV 008 | SEYFQH | 4490 |
| JHUNIV 009 | PEYFQH | 4491 |
| JHUNIV 010 | FEYFQH | 4492 |
| JHUNIV 011 | HEYFQH | 4493 |
| JHUNIV 012 | REYFQH | 4494 |
| JHUNIV 013 | LEYFQH | 4495 |
| JHUNIV 014 | NEYFQH | 4496 |
| JHUNIV 015 | IEYFQH | 4497 |
| JHUNIV 016 | DEYFQH | 4498 |
| JHUNIV 017 | GEYFQH | 4499 |
| JHUNIV 018 | VEYFQH | 4500 |
| JHUNIV 019 | YEYFQH | 4501 |
| JHUNIV 020 | NYFQH | 4502 |
| JHUNIV 021 | QYFQH | 4503 |
| JHUNIV 022 | LYFQH | 4504 |
| JHUNIV 023 | SYFQH | 4505 |
| JHUNIV 024 | RYFQH | 4506 |
| JHUNIV 025 | PYFQH | 4507 |
| JHUNIV 026 | IYFQH | 4508 |
| JHUNIV 027 | TYFQH | 4509 |
| JHUNIV 028 | GYFQH | 4510 |
| JHUNIV 029 | VYFQH | 4511 |
| JHUNIV 030 | AYFQH | 4512 |
| JHUNIV 031 | NFQH | 4513 |

TABLE 13-continued

Theoretical segment pool of 285 H3-JH segments.

| H3-JH Segment Name | Amino Acid Sequence | SEQ ID NO |
|---|---|---|
| JHUNIV 032 | DFQH | 4514 |
| JHUNIV 033 | HFQH | 4515 |
| JHUNIV 034 | FFQH | 4516 |
| JHUNIV 035 | SFQH | 4517 |
| JHUNIV 036 | RFQH | 4518 |
| JHUNIV 037 | LFQH | 4519 |
| JHUNIV 038 | PFQH | 4520 |
| JHUNIV 039 | IFQH | 4521 |
| JHUNIV 040 | TFQR | 4522 |
| JHUNIV 041 | GFQH | 4523 |
| JHUNIV 042 | VFQH | 4524 |
| JHUNIV 043 | AFQH | 4525 |
| JHUNIV 044 | AEYFQH | 4526 |
| JHUNIV 045 | YWYFDL | 4527 |
| JHUNIV 046 | WYFDL | 4528 |
| JHUNIV 047 | YFDL | 4529 |
| JHUNIV 048 | FDL | n/a |
| JHUNIV 049 | DL | n/a |
| JHUNIV 050 | L | n/a |
| JHUNIV 051 | DWYFDL | 4530 |
| JHUNIV 052 | HWYFDL | 4531 |
| JHUNIV 053 | NWYFDL | 4532 |
| JHUNIV 054 | GYFDL | 4533 |
| JHUNIV 055 | RYFDL | 4534 |
| JHUNIV 056 | HFDL | 4535 |
| JHUNIV 057 | NFDL | 4536 |
| JHUNIV 058 | DFDL | 4537 |
| JHUNIV 059 | DAFDI | 4538 |
| JHUNIV 060 | AFDI | 4539 |
| JHUNIV 061 | FDI | n/a |
| JHUNIV 062 | DI | n/a |
| JHUNIV 063 | I | n/a |
| JHUNIV 064 | YAFDI | 4540 |
| JHUNIV 065 | HAFDI | 4541 |
| JHUNIV 066 | FAFDI | 4542 |
| JHUNIV 067 | SAFDI | 4543 |
| JHUNIV 068 | RAFDI | 4544 |

TABLE 13-continued

Theoretical segment pool of 285 H3-JH segments.

| H3-JH Segment Name | Amino Acid Sequence | SEQ ID NO |
|---|---|---|
| JHUNIV 069 | LAFDI | 4545 |
| JHUNIV 070 | PAFDI | 4546 |
| JHUNIV 071 | IAFDI | 4547 |
| JHUNIV 072 | TAFDI | 4548 |
| JHUNIV 073 | GAFDI | 4549 |
| JHUNIV 074 | VAFDI | 4550 |
| JHUNIV 075 | AAFDI | 4551 |
| JHUNIV 076 | TFDI | 4552 |
| JHUNIV 077 | SFDI | 4553 |
| JHUNIV 078 | PFDI | 4554 |
| JHUNIV 079 | FFDI | 4555 |
| JHUNIV 080 | HFDI | 4556 |
| JHUNIV 081 | RFDI | 4557 |
| JHUNIV 082 | LFDI | 4558 |
| JHUNIV 083 | NFDI | 4559 |
| JHUNIV 084 | IFDI | 4560 |
| JHUNIV 085 | DFDI | 4561 |
| JHUNIV 086 | GFDI | 4562 |
| JHUNIV 087 | VFDI | 4563 |
| JHUNIV 088 | YFDI | 4564 |
| JHUNIV 089 | IDI | n/a |
| JHUNIV 090 | VDI | n/a |
| JHUNIV 091 | LDI | n/a |
| JHUNIV 092 | SDI | n/a |
| JHUNIV 093 | HDI | n/a |
| JHUNIV 094 | RDI | n/a |
| JHUNIV 095 | PDI | n/a |
| JHUNIV 096 | NDI | n/a |
| JHUNIV 097 | TDI | n/a |
| JHUNIV 098 | DDI | n/a |
| JHUNIV 099 | GDI | n/a |
| JHUNIV 100 | ADI | n/a |
| JHUNIV 101 | YDI | n/a |
| JHUNIV 102 | NAFDI | 4565 |
| JHUNIV 103 | DYFDY | 4566 |
| JHUNIV 104 | YFDY | 4567 |
| JHUNIV 105 | FDY | n/a |

TABLE 13-continued

Theoretical segment pool of 285 H3-JH segments.

| H3-JH Segment Name | Amino Acid Sequence | SEQ ID NO |
|---|---|---|
| JHUNIV 106 | DY | n/a |
| JHUNIV 107 | Y | n/a |
| JHUNIV 108 | YYFDY | 4568 |
| JHUNIV 109 | HYFDY | 4569 |
| JHUNIV 110 | FYFDY | 4570 |
| JHUNIV 111 | SYFDY | 4571 |
| JHUNIV 112 | RYFDY | 4572 |
| JHUNIV 113 | LYFDY | 4573 |
| JHUNIV 114 | PYFDY | 4574 |
| JHUNIV 115 | IYFDY | 4575 |
| JHUNIV 116 | TYFDY | 4576 |
| JHUNIV 117 | GYFDY | 4577 |
| JHUNIV 118 | VYFDY | 4578 |
| JHUNIV 119 | AYFDY | 4579 |
| JHUNIV 120 | NFDY | 4580 |
| JHUNIV 121 | DFDY | 4581 |
| JHUNIV 122 | HFDY | 4582 |
| JHUNIV 123 | FFDY | 4583 |
| JHUNIV 124 | SFDY | 4584 |
| JHUNIV 125 | RFDY | 4585 |
| JHUNIV 126 | LFDY | 4586 |
| JHUNIV 127 | PFDY | 4587 |
| JHUNIV 128 | IFDY | 4588 |
| JHUNIV 129 | TFDY | 4589 |
| JHUNIV 130 | GFDY | 4590 |
| JHUNIV 131 | VFDY | 4591 |
| JHUNIV 132 | AFDY | 4592 |
| JHUNIV 133 | IDY | n/a |
| JHUNIV 134 | VDY | n/a |
| JHUNIV 135 | LDY | n/a |
| JHUNIV 136 | SDY | n/a |
| JHUNIV 137 | HDY | n/a |
| JHUNIV 138 | RDY | n/a |
| JHUNIV 139 | PDY | n/a |
| JHUNIV 140 | NDY | n/a |
| JHUNIV 141 | TDY | n/a |
| JHUNIV 142 | DDY | n/a |

TABLE 13-continued

Theoretical segment pool of 285 H3-JH segments.

| H3-JH Segment Name | Amino Acid Sequence | SEQ ID NO |
|---|---|---|
| JHUNIV 143 | GDY | n/a |
| JHUNIV 144 | ADY | n/a |
| JHUNIV 145 | YDY | n/a |
| JHUNIV 146 | NYFDY | 4593 |
| JHUNIV 147 | DNWFDP | 4594 |
| JHUNIV 148 | NWFDP | 4595 |
| JHUNIV 149 | WFDP | 4596 |
| JHUNIV 150 | FDP | n/a |
| JHUNIV 151 | DP | n/a |
| JHUNIV 152 | P | n/a |
| JHUNIV 153 | YNWFDP | 4597 |
| JHUNIV 154 | HNWFDP | 4598 |
| JHUNIV 155 | FNWFDP | 4599 |
| JHUNIV 156 | SNWFDP | 4600 |
| JHUNIV 157 | RNWFDP | 4601 |
| JHUNIV 158 | LNWFDP | 4602 |
| JHUNIV 159 | PNWFDP | 4603 |
| JHUNIV 160 | INWFDP | 4604 |
| JHUNIV 161 | TNWFDP | 4605 |
| JHUNIV 162 | GNWFDP | 4606 |
| JHUNIV 163 | VNWFDP | 4607 |
| JHUNIV 164 | ANWFDP | 4608 |
| JHUNIV 165 | DWFDP | 4609 |
| JHUNIV 166 | YWFDP | 4610 |
| JHUNIV 167 | HWFDP | 4611 |
| JHUNIV 168 | FWFDP | 4612 |
| JHUNIV 169 | SWFDP | 4613 |
| JHUNIV 170 | RWFDP | 4614 |
| JHUNIV 171 | LWFDP | 4615 |
| JHUNIV 172 | PWFDP | 4616 |
| JHUNIV 173 | IWFDP | 4617 |
| JHUNIV 174 | TWFDP | 4618 |
| JHUNIV 175 | GWFDP | 4619 |
| JHUNIV 176 | VWFDP | 4620 |
| JHUNIV 177 | AWFDP | 4621 |
| JHUNIV 178 | RFDP | 4622 |
| JHUNIV 179 | GFDP | 4623 |

TABLE 13-continued

Theoretical segment pool of 285 H3-JH segments.

| H3-JH Segment Name | Amino Acid Sequence | SEQ ID NO |
|---|---|---|
| JHUNIV 180 | LFDP | 4624 |
| JHUNIV 181 | SFDP | 4625 |
| JHUNIV 182 | QFDP | 4626 |
| JHUNIV 183 | PFDP | 4627 |
| JHUNIV 184 | KFDP | 4628 |
| JHUNIV 185 | MFDP | 4629 |
| JHUNIV 186 | TFDP | 4630 |
| JHUNIV 187 | EFDP | 4631 |
| JHUNIV 188 | VFDP | 4632 |
| JHUNIV 189 | AFDP | 4633 |
| JHUNIV 190 | NNWFDP | 4634 |
| JHUNIV 191 | DYYYYYGMDV | 4635 |
| JHUNIV 192 | YYYYYGMDV | 4636 |
| JHUNIV 193 | YYYYGMDV | 4637 |
| JHUNIV 194 | YYYGMDV | 4638 |
| JHUNIV 195 | YYGMDV | 4639 |
| JHUNIV 196 | YGMDV | 4640 |
| JHUNIV 197 | GMDV | 4641 |
| JHUNIV 198 | MDV | n/a |
| JHUNIV 199 | DV | n/a |
| JHUNIV 200 | V | n/a |
| JHUNIV 201 | YYYYYYGMDV | 4642 |
| JHUNIV 202 | HYYYYYGMDV | 4643 |
| JHUNIV 203 | FYYYYYGMDV | 4644 |
| JHUNIV 204 | SYYYYYGMDV | 4645 |
| JHUNIV 205 | RYYYYYGMDV | 4646 |
| JHUNIV 206 | LYYYYYGMDV | 4647 |
| JHUNIV 207 | PYYYYYGMDV | 4648 |
| JHUNIV 208 | IYYYYYGMDV | 4649 |
| JHUNIV 209 | TYYYYYGMDV | 4650 |
| JHUNIV 210 | GYYYYYGMDV | 4651 |
| JHUNIV 211 | VYYYYYGMDV | 4652 |
| JHUNIV 212 | AYYYYYGMDV | 4653 |
| JHUNIV 213 | NYYYYGMDV | 4654 |
| JHUNIV 214 | DYYYYGMDV | 4655 |
| JHUNIV 215 | HYYYYGMDV | 4656 |
| JHUNIV 216 | FYYYYGMDV | 4657 |

TABLE 13-continued

Theoretical segment pool of 285 H3-JH segments.

| H3-JH Segment Name | Amino Acid Sequence | SEQ ID NO |
|---|---|---|
| JHUNIV 217 | SYYYYGMDV | 4658 |
| JHUNIV 218 | RYYYYGMDV | 4659 |
| JHUNIV 219 | LYYYYGMDV | 4660 |
| JHUNIV 220 | PYYYYGMDV | 4661 |
| JHUNIV 221 | IYYYYGMDV | 4662 |
| JHUNIV 222 | TYYYYGMDV | 4663 |
| JHUNIV 223 | GYYYYGMDV | 4664 |
| JHUNIV 224 | VYYYYGMDV | 4665 |
| JHUNIV 225 | AYYYYGMDV | 4666 |
| JHUNIV 226 | NYYYGMDV | 4667 |
| JHUNIV 227 | DYYYGMDV | 4668 |
| JHUNIV 228 | HYYYGMDV | 4669 |
| JHUNIV 229 | FYYYGMDV | 4670 |
| JHUNIV 230 | SYYYGMDV | 4671 |
| JHUNIV 231 | RYYYGMDV | 4672 |
| JHUNIV 232 | LYYYGMDV | 4673 |
| JHUNIV 233 | PYYYGMDV | 4674 |
| JHUNIV 234 | IYYYGMDV | 4675 |
| JHUNIV 235 | TYYYGMDV | 4676 |
| JHUNIV 236 | GYYYGMDV | 4677 |
| JHUNIV 237 | VYYYGMDV | 4678 |
| JHUNIV 238 | AYYYGMDV | 4679 |
| JHUNIV 239 | NYYYYYGMDV | 4680 |
| JHUNIV 240 | DYYYYYYMDV | 4681 |
| JHUNIV 241 | YYYYYYMDV | 4682 |
| JHUNIV 242 | YYYYYMDV | 4683 |
| JHUNIV 243 | YYYYMDV | 4684 |
| JHUNIV 244 | YYYMDV | 4685 |
| JHUNIV 245 | YYMDV | 4686 |
| JHUNIV 246 | YMDV | 4687 |
| JHUNIV 247 | YYYYYYYMDV | 4688 |
| JHUNIV 248 | HYYYYYYMDV | 4689 |
| JHUNIV 249 | FYYYYYYMDV | 4690 |
| JHUNIV 250 | SYYYYYYMDV | 4691 |
| JHUNIV 251 | RYYYYYYMDV | 4692 |
| JHUNIV 252 | LYYYYYYMDV | 4693 |
| JHUNIV 253 | PYYYYYYMDV | 4694 |

TABLE 13-continued

Theoretical segment pool of 285 H3-JH segments.

| H3-JH Segment Name | Amino Acid Sequence | SEQ ID NO |
|---|---|---|
| JHUNIV 254 | IYYYYYYMDV | 4695 |
| JHUNIV 255 | TYYYYYYMDV | 4696 |
| JHUNIV 256 | GYYYYYYMDV | 4697 |
| JHUNIV 257 | VYYYYYYMDV | 4698 |
| JHUNIV 258 | AYYYYYYMDV | 4699 |
| JHUNIV 259 | NYYYYYMDV | 4700 |
| JHUNIV 260 | DYYYYYMDV | 4701 |
| JHUNIV 261 | HYYYYYMDV | 4702 |
| JHUNIV 262 | FYYYYYMDV | 4703 |
| JHUNIV 263 | SYYYYYMDV | 4704 |
| JHUNIV 264 | RYYYYYMDV | 4705 |
| JHUNIV 265 | LYYYYYMDV | 4706 |
| JHUNIV 266 | PYYYYYMDV | 4707 |
| JHUNIV 267 | IYYYYYMDV | 4708 |
| JHUNIV 268 | TYYYYYMDV | 4709 |
| JHUNIV 269 | GYYYYYMDV | 4710 |
| JHUNIV 270 | VYYYYYMDV | 4711 |
| JHUNIV 271 | AYYYYYMDV | 4712 |
| JHUNIV 272 | NYYYYMDV | 4713 |
| JHUNIV 273 | DYYYYMDV | 4714 |
| JHUNIV 274 | HYYYYMDV | 4715 |
| JHUNIV 275 | FYYYYMDV | 4716 |
| JHUNIV 276 | SYYYYMDV | 4717 |
| JHUNIV 277 | RYYYYMDV | 4718 |
| JHUNIV 278 | LYYYYMDV | 4719 |
| JHUNIV 279 | PYYYYMDV | 4720 |
| JHUNIV 280 | IYYYYMDV | 4721 |
| JHUNIV 281 | TYYYYMDV | 4722 |
| JHUNIV 282 | GYYYYMDV | 4723 |
| JHUNIV 283 | VYYYYMDV | 4724 |
| JHUNIV 284 | AYYYYMDV | 4725 |
| JHUNIV 285 | NYYYYYYMDV | 4726 |

TABLE 14

Twelve germline IGHJ genes and alleles.

| IGHJ Gene | DNA Sequence | SEQ ID NO |
|---|---|---|
| IGHJ1-01 | GCTGAATACTTCCAGCACTGGGGCCAGGGCACCCTGGTCACCGTCTCCTCAG | 4727 |
| IGHJ2-01 | CTACTGGTACTTCGATCTCTGGGGCCGTGGCACCCTGGTCACTGTCTCCTCAG | 4728 |
| IGHJ3-01 | ATGCTTTTGATGTCTGGGGCCAAGGGACAATGGTCACCGTCTCTTCAG | 4729 |
| IGHJ3-02 | ATGCTTTTGATATCTGGGGCCAAGGGACAATGGTCACCGTCTCTTCAG | 4730 |
| IGHJ4-01 | ACTACTTTGACTACTGGGGCCAAGGAACCCTGGTCACCGTCTCCTCAG | 4731 |
| IGHJ4-02 | ACTACTTTGACTACTGGGGCCAGGGAACCCTGGTCACCGTCTCCTCAG | 4732 |
| IGHJ4-03 | GCTACTTTGACTACTGGGGCCAAGGGACCCTGGTCACCGTCTCCTCAG | 4733 |
| IGHJ5-01 | ACAACTGGTTCGACTCCTGGGGCCAAGGAACCCTGGTCACCGTCTCCTCAG | 4734 |
| IGHJ5-02 | ACAACTGGTTCGACCCCTGGGGCCAGGGAACCCTGGTCACCGTCTCCTCAG | 4735 |
| IGHJ6-01 | ATTACTACTACTACTACGGTATGGACGTCTGGGGGCAAGGGACCACGGTCACCGTCT CCTCAG | 4736 |
| IGHJ6-02 | ATTACTACTACTACTACGGTATGGACGTCTGGGGCCAAGGGACCACGGTCACCGTCT CCTCAG | 4737 |
| IGHJ6-03 | ATTACTACTACTACTACTACATGGACGTCTGGGGCAAAGGGACCACGGTCACCGTCT CCTCAG | 4738 |

TABLE 15

Theoretical segment pool of 248 parent H3-JH segments.

| H3-JH Parent Segment Name | Amino Acid Sequence | SEQ ID NO | H3-JH Parent Segment Name | Amino Acid Sequence | SEQ ID NO |
|---|---|---|---|---|---|
| JHparent001 | ADI | n/a | JHparent125 | TAFDI | 4548 |
| JHparent002 | ADY | n/a | JHparent126 | TWFDP | 4618 |
| JHparent003 | DDI | n/a | JHparent127 | TYFDY | 4576 |
| JHparent004 | DDY | n/a | JHparent128 | TYFQH | 4509 |
| JHparent005 | GDI | n/a | JHparent129 | VAFDI | 4550 |
| JHparent006 | GDY | n/a | JHparent130 | VWFDP | 4620 |
| JHparent007 | HDI | n/a | JHparent131 | VYFDY | 4578 |
| JHparent008 | HDY | n/a | JHparent132 | VYFQH | 4511 |
| JHparent009 | IDI | n/a | JHparent133 | WYFDL | 4528 |
| JHparent010 | IDY | n/a | JHparent134 | YAFDI | 4540 |
| JHparent011 | LDI | n/a | JHparent135 | YWFDP | 4610 |
| JHparent012 | LDY | n/a | JHparent136 | YYFDY | 4568 |
| JHparent013 | NDI | n/a | JHparent137 | AEYFQH | 4526 |
| JHparent014 | NDY | n/a | JHparent138 | ANWFDP | 4608 |
| JHparent015 | PDI | n/a | JHparent139 | DEYFQH | 4498 |
| JHparent016 | PDY | n/a | JHparent140 | DNWFDP | 4594 |
| JHparent017 | RDI | n/a | JHparent141 | DWYFDL | 4530 |
| JHparent018 | RDY | n/a | JHparent142 | FEYFQH | 4492 |
| JHparent019 | SDI | n/a | JHparent143 | FNWFDP | 4599 |
| JHparent020 | SDY | n/a | JHparent144 | GEYFQH | 4499 |
| JHparent021 | TDI | n/a | JHparent145 | GNWFDP | 4606 |
| JHparent022 | TDY | n/a | JHparent146 | HEYFQH | 4493 |
| JHparent023 | VDI | n/a | JHparent147 | HNWFDP | 4598 |
| JHparent024 | VDY | n/a | JHparent148 | HWYFDL | 4531 |
| JHparent025 | YDI | n/a | JHparent149 | IEYFQH | 4497 |
| JHparent026 | YDY | n/a | JHparent150 | INWFDP | 4604 |
| JHparent027 | AFDP | 4633 | JHparent151 | LEYFQH | 4495 |
| JHparent028 | AFDY | 4592 | JHparent152 | LNWFDP | 4602 |
| JHparent029 | AFQH | 4525 | JHparent153 | NEYFQH | 4496 |
| JHparent030 | DFDI | 4561 | JHparent154 | NNWFDP | 4634 |
| JHparent031 | DFDL | 4537 | JHparent155 | NWYFDL | 4532 |
| JHparent032 | DFDY | 4581 | JHparent156 | PEYFQH | 4491 |
| JHparent033 | DFQH | 4514 | JHparent157 | PNWFDP | 4603 |
| JHparent034 | EFDP | 4631 | JHparent158 | REYFQH | 4494 |
| JHparent035 | FFDI | 4555 | JHparent159 | RNWFDP | 4601 |
| JHparent036 | FFDY | 4583 | JHparent160 | SEYFQH | 4490 |
| JHparent037 | FFQH | 4516 | JHparent161 | SNWFDP | 4600 |

TABLE 15-continued

| Theoretical segment pool of 248 parent H3-JH segments. | | | | | |
|---|---|---|---|---|---|
| H3-JH Parent Segment Name | Amino Acid Sequence | SEQ ID NO | H3-JH Parent Segment Name | Amino Acid Sequence | SEQ ID NO |
| JHparent038 | GFDI | 4562 | JHparent162 | TEYFQH | 4487 |
| JHparent039 | GFDP | 4623 | JHparent163 | TNWFDP | 4605 |
| JHparent040 | GFDY | 4590 | JHparent164 | VEYFQH | 4500 |
| JHparent041 | GFQH | 4523 | JHparent165 | VNWFDP | 4607 |
| JHparent042 | HFDI | 4556 | JHparent166 | YEYFQH | 4501 |
| JHparent043 | HFDL | 4535 | JHparent167 | YNWFDP | 4597 |
| JHparent044 | HFDY | 4582 | JHparent168 | YWYFDL | 4527 |
| JHparent045 | HFQH | 4515 | JHparent169 | AYYYGMDV | 4679 |
| JHparent046 | IFDI | 4560 | JHparent170 | AYYYYMDV | 4725 |
| JHparent047 | IFDY | 4588 | JHparent171 | DYYYGMDV | 4668 |
| JHparent048 | IFQH | 4521 | JHparent172 | DYYYYMDV | 4714 |
| JHparent049 | KFDP | 4628 | JHparent173 | FYYYGMDV | 4670 |
| JHparent050 | LFDI | 4558 | JHparent174 | FYYYYMDV | 4716 |
| JHparent051 | LFDP | 4624 | JHparent175 | GYYYGMDV | 4677 |
| JHparent052 | LFDY | 4586 | JHparent176 | GYYYYMDV | 4723 |
| JHparent053 | LFQH | 4519 | JHparent177 | HYYYGMDV | 4669 |
| JHparent054 | MFDP | 4629 | JHparent178 | HYYYYMDV | 4715 |
| JHparent055 | NFDI | 4559 | JHparent179 | IYYYGMDV | 4675 |
| JHparent056 | NFDL | 4536 | JHparent180 | IYYYYMDV | 4721 |
| JHparent057 | NFDY | 4580 | JHparent181 | LYYYGMDV | 4673 |
| JHparent058 | NFQH | 4513 | JHparent182 | LYYYYMDV | 4719 |
| JHparent059 | PFDI | 4554 | JHparent183 | NYYYGMDV | 4667 |
| JHparent060 | PFDP | 4627 | JHparent184 | NYYYYMDV | 4713 |
| JHparent061 | PFDY | 4587 | JHparent185 | PYYYGMDV | 4674 |
| JHparent062 | PFQH | 4520 | JHparent186 | PYYYYMDV | 4720 |
| JHparent063 | QFDP | 4626 | JHparent187 | RYYYGMDV | 4672 |
| JHparent064 | RFDI | 4557 | JHparent188 | RYYYYMDV | 4718 |
| JHparent065 | RFDP | 4622 | JHparent189 | SYYYGMDV | 4671 |
| JHparent066 | RFDY | 4585 | JHparent190 | SYYYYMDV | 4717 |
| JHparent067 | RFQH | 4518 | JHparent191 | TYYYGMDV | 4676 |
| JHparent068 | SFDI | 4553 | JHparent192 | TYYYYMDV | 4722 |
| JHparent069 | SFDP | 4625 | JHparent193 | VYYYGMDV | 4678 |
| JHparent070 | SFDY | 4584 | JHparent194 | VYYYYMDV | 4724 |
| JHparent071 | SFQH | 4517 | JHparent195 | AYYYYGMDV | 4666 |
| JHparent072 | TFDI | 4552 | JHparent196 | AYYYYYMDV | 4712 |
| JHparent073 | TFDP | 4630 | JHparent197 | DYYYYGMDV | 4655 |

TABLE 15-continued

Theoretical segment pool of 248 parent H3-JH segments.

| H3-JH Parent Segment Name | Amino Acid Sequence | SEQ ID NO | H3-JH Parent Segment Name | Amino Acid Sequence | SEQ ID NO |
|---|---|---|---|---|---|
| JHparent074 | TFDY | 4589 | JHparent198 | DYYYYYMDV | 4701 |
| JHparent075 | TFQH | 4522 | JHparent199 | FYYYYGMDV | 4657 |
| JHparent076 | VFDI | 4563 | JHparent200 | FYYYYYMDV | 4703 |
| JHparent077 | VFDP | 4632 | JHparent201 | GYYYYGMDV | 4664 |
| JHparent078 | VFDY | 4591 | JHparent202 | GYYYYYMDV | 4710 |
| JHparent079 | VFQH | 4524 | JHparent203 | HYYYYGMDV | 4656 |
| JHparent080 | YFDI | 4564 | JHparent204 | HYYYYYMDV | 4702 |
| JHparent081 | YFDL | 4529 | JHparent205 | IYYYYGMDV | 4662 |
| JHparent082 | AAFDI | 4551 | JHparent206 | IYYYYYMDV | 4708 |
| JHparent083 | AWFDP | 4621 | JHparent207 | LYYYYGMDV | 4660 |
| JHparent084 | AYFDY | 4579 | JHparent208 | LYYYYYMDV | 4706 |
| JHparent085 | AYFQH | 4512 | JHparent209 | NYYYYGMDV | 4654 |
| JHparent086 | DAFDI | 4538 | JHparent210 | NYYYYYMDV | 4700 |
| JHparent087 | DWFDP | 4609 | JHparent211 | PYYYYGMDV | 4661 |
| JHparent088 | DYFDY | 4566 | JHparent212 | PYYYYYMDV | 4707 |
| JHparent089 | FAFDI | 4542 | JHparent213 | RYYYYGMDV | 4659 |
| JHparent090 | FWFDP | 4612 | JHparent214 | RYYYYYMDV | 4705 |
| JHparent091 | FYFDY | 4570 | JHparent215 | SYYYYGMDV | 4658 |
| JHparent092 | GAFDI | 4549 | JHparent216 | SYYYYYMDV | 4704 |
| JHparent093 | GWFDP | 4619 | JHparent217 | TYYYYGMDV | 4663 |
| JHparent094 | GYFDL | 4533 | JHparent218 | TYYYYYMDV | 4709 |
| JHparent095 | GYFDY | 4577 | JHparent219 | VYYYYGMDV | 4665 |
| JHparent096 | GYFQH | 4510 | JHparent220 | VYYYYYMDV | 4711 |
| JHparent097 | HAFDI | 4541 | JHparent221 | AYYYYYGMDV | 4653 |
| JHparent098 | HWFDP | 4611 | JHparent222 | AYYYYYYMDV | 4699 |
| JHparent099 | HYFDY | 4569 | JHparent223 | DYYYYYGMDV | 4635 |
| JHparent100 | IAFDI | 4547 | JHparent224 | DYYYYYYMDV | 4681 |
| JHparent101 | IWFDP | 4617 | JHparent225 | FYYYYYGMDV | 4644 |
| JHparent102 | IYFDY | 4575 | JHparent226 | FYYYYYYMDV | 4690 |
| JHparent103 | IYFQH | 4508 | JHparent227 | GYYYYYGMDV | 4651 |
| JHparent104 | KYFQH | 4502 | JHparent228 | GYYYYYYMDV | 4697 |
| JHparent105 | LAFDI | 4545 | JHparent229 | HYYYYYGMDV | 4643 |
| JHparent106 | LWFDP | 4615 | JHparent230 | HYYYYYYMDV | 4689 |
| JHparent107 | LYFDY | 4573 | JHparent231 | IYYYYYGMDV | 4649 |
| JHparent108 | LYFQH | 4504 | JHparent232 | IYYYYYYMDV | 4695 |
| JHparent109 | NAFDI | 4565 | JHparent233 | LYYYYYGMDV | 4647 |
| JHparent110 | NYFDY | 4593 | JHparent234 | LYYYYYYMDV | 4693 |

TABLE 15-continued

Theoretical segment pool of 248 parent H3-JH segments.

| H3-JH Parent Segment Name | Amino Acid Sequence | SEQ ID NO | H3-JH Parent Segment Name | Amino Acid Sequence | SEQ ID NO |
|---|---|---|---|---|---|
| JHparent111 | PAFDI | 4546 | JHparent235 | NYYYYYGMDV | 4680 |
| JHparent112 | PWFDP | 4616 | JHparent236 | NYYYYYYMDV | 4726 |
| JHparent113 | PYFDY | 4574 | JHparent237 | PYYYYYGMDV | 4648 |
| JHparent114 | PYFQH | 4507 | JHparent238 | PYYYYYYMDV | 4694 |
| JHparent115 | QYFQH | 4503 | JHparent239 | RYYYYYGMDV | 4646 |
| JHparent116 | RAFDI | 4544 | JHparent240 | RYYYYYYMDV | 4692 |
| JHparent117 | RWFDP | 4614 | JHparent241 | SYYYYYGMDV | 4645 |
| JHparent118 | RYFDL | 4534 | JHparent242 | SYYYYYYMDV | 4691 |
| JHparent119 | RYFDY | 4572 | JHparent243 | TYYYYYGMDV | 4650 |
| JHparent120 | RYFQH | 4506 | JHparent244 | TYYYYYYMDV | 4696 |
| JHparent121 | SAFDI | 4543 | JHparent245 | VYYYYYGMDV | 4652 |
| JHparent122 | SWFDP | 4613 | JHparent246 | VYYYYYYMDV | 4698 |
| JHparent123 | SYFDY | 4571 | JHparent247 | YYYYYYGMDV | 4642 |
| JHparent124 | SYFQH | 4505 | JHparent248 | YYYYYYYMDV | 4688 |

TABLE 16

Polynucleotide sequences of 27 human IGHD genes and alleles.

| IGHD Gene | Polynucleotide Sequence | SEQ ID NO |
|---|---|---|
| IGHD1-(1)-01 | GGTACAACTGGAACGAC | 4739 |
| IGHD1-20 | GGTATAACTGGAACGAC | 4740 |
| IGHD1-26 | GGTATAGTGGGAGCTACTAC | 4741 |
| IGHD1-7 | GGTATAACTGGAACTAC | 4742 |
| IGHD2-15-01 | AGGATATTGTAGTGGTGGTAGCTGCTACTCC | 4743 |
| IGHD2-2-x | AGGATATTGTAGTAGTACCAGCTGCTATGCC | 4744 |
| IGHD2-2-y | AGGATATTGTAGTAGTACCAGCTGCTATACC | 4745 |
| IGHD2-2-z | TGGATATTGTAGTAGTACCAGCTGCTATGCC | 4746 |
| IGHD2-21-01 | AGCATATTGTGGTGGTGATTGCTATTCC | 4747 |
| IGHD2-21-02 | AGCATATTGTGGTGGTGACTGCTATTCC | 4748 |
| IGHD2-8-01 | AGGATATTGTACTAATGGTGTATGCTATACC | 4749 |
| IGHD3-10-01 | GTATTACTATGGTTCGGGGAGTTATTATAAC | 4750 |
| IGHD3-10-03 | GTATTACTATGGTTCAGGGAGTTATTATAAC | 4751 |
| IGHD3-16-02 | GTATTATGATTACGTTTGGGGGAGTTATGCTTATACC | 4752 |
| IGHD3-22-01 | GTATTACTATGATAGTAGTGGTTATTACTAC | 4753 |
| IGHD3-3-01 | GTATTACGATTTTTGGAGTGGTTATTATACC | 4754 |
| IGHD3-9-01 | GTATTACGATATTTTGACTGGTTATTATAAC | 4755 |
| IGHD4-17 | TGACTACGGTGACTAC | 4756 |

TABLE 16-continued

| Polynucleotide sequences of 27 human IGHD genes and alleles. | | |
|---|---|---|
| IGHD Gene | Polynucleotide Sequence | SEQ ID NO |
| IGHD4-23-01 | TGACTACGGTGGTAACTCC | 4757 |
| IGHD4-4/11-01 | TGACTACAGTAACTAC | 4758 |
| IGHD5-12-01 | GTGGATATAGTGGCTACGATTAC | 4759 |
| IGHD5-24-01 | GTAGAGATGGCTACAATTAC | 4760 |
| IGHD5-5/18-01 | GTGGATACAGCTATGGTTAC | 4761 |
| IGHD6-13-01 | GGGTATAGCAGCAGCTGGTAC | 4762 |
| IGHD6-19-01 | GGGTATAGCAGTGGCTGGTAC | 4763 |
| IGHD6-6-01 | GAGTATAGCAGCTCGTCC | 4764 |
| IGHD7-27-01 | CTAACTGGGGA | 4765 |

TABLE 17

Theoretical segment pool of 73 DH parent Segments. "Z" represents a stop codon.

| DH Parent Segment Name | Amino Acid Sequence | SEQ ID NO | DH Parent Segment Name | Amino Acid Sequence | SEQ ID NO |
|---|---|---|---|---|---|
| DHparent001 | LTG | n/a | DHparent038 | WIZWLRL | 4776 |
| DHparent002 | NWG | n/a | DHparent039 | VDIVATIT | 4369 |
| DHparent003 | ZLG | n/a | DHparent040 | AYCGGDCYS | 3862 |
| DHparent004 | DYGDY | 4348 | DHparent041 | HIVVVIAIP | 3871 |
| DHparent005 | DYSNY | 4366 | DHparent042 | HIVVVTAIP | 3891 |
| DHparent006 | TTVTT | 4351 | DHparent043 | SILWWZLLF | 4777 |
| DHparent007 | VQLER | 3737 | DHparent044 | DIVLMVYAIP | 3920 |
| DHparent008 | VZLEL | 4766 | DHparent045 | DIVVVPAAIP | 3846 |
| DHparent009 | VZLER | 4767 | DHparent046 | DIVVVPAAMP | 3816 |
| DHparent010 | VZQLV | 4768 | DHparent047 | DIVVVVAATP | 3777 |
| DHparent011 | YNWND | 3740 | DHparent048 | GYCSGGSCYS | 3767 |
| DHparent012 | YNWNY | 3765 | DHparent049 | GYCSSTSCYA | 3806 |
| DHparent013 | ZLQZL | 4769 | DHparent050 | GYCSSTSCYT | 3843 |
| DHparent014 | ZLRZL | 4770 | DHparent051 | GYCTNGVCYT | 3910 |
| DHparent015 | DYGGNS | 4354 | DHparent052 | ITIFGVVIIP | 4269 |
| DHparent016 | EYSSSS | 4476 | DHparent053 | ITIFZLVIIT | 4778 & 8746 |
| DHparent017 | GITGTT | 3743 | DHparent054 | ITMIVVVITT | 4189 |
| DHparent018 | GTTGTT | 3731 | DHparent055 | ITMVQGVIIT | 4040 |
| DHparent019 | GYSYGY | 4429 | DHparent056 | ITMVRGVIIT | 3994 |
| DHparent020 | RDGYNY | 4407 | DHparent057 | RILYZWCMLY | 4779 & 8747 |
| DHparent021 | SIAARP | 4481 | DHparent058 | RILZWWZLLL | 4780 |
| DHparent022 | TTVVTP | 4360 | DHparent059 | RILZZYQLLC | 4781 |

TABLE 17-continued

| Theoretical segment pool of 73 DH parent Segments. "Z" represents a stop codon. | | | | | |
|---|---|---|---|---|---|
| DH Parent Segment Name | Amino Acid Sequence | SEQ ID NO | DH Parent Segment Name | Amino Acid Sequence | SEQ ID NO |
| DHparent023 | VZQQLV | 4771 | DHparent060 | RILZZYQLLY | 4782 |
| DHparent024 | VZQWLV | 4772 | DHparent061 | VLLWFGELLZ | 4783 |
| DHparent025 | VZWELL | 4773 | DHparent062 | VLLWFRELLZ | 4784 |
| DHparent026 | WIQLWL | 4423 | DHparent063 | VLLZZZWLLL | 4785 |
| DHparent027 | YSGSYY | 3759 | DHparent064 | VLRFLEWLLY | 4214 |
| DHparent028 | ZLRWZL | 4774 | DHparent065 | VLRYFDWLLZ | 4786 |
| DHparent029 | ZRWLQL | 4775 | DHparent066 | WILZZYQLLC | 4787 |
| DHparent030 | GIAAAGT | 4445 | DHparent067 | YYDFWSGYYT | 4242 |
| DHparent031 | GIAVAGT | 4465 | DHparent068 | YYDILTGYYN | 4318 |
| DHparent032 | GIVGATT | 3748 | DHparent069 | YYYDSSGYYY | 4161 |
| DHparent033 | GYSGYDY | 4385 | DHparent070 | YYYGSGSYYN | 3969 |
| DHparent034 | GYSSGWY | 4456 | DHparent071 | IMITFGGVMLIP | 4115 |
| DHparent035 | GYSSSWY | 4435 | DHparent072 | VLZLRLGELCLY | 4788 |
| DHparent036 | VDTAMVT | 4413 | DHparent073 | YYDYVWGSYAYT | 4070 |
| DHparent037 | VEMATIT | 4395 | | | |

TABLE 18

| Application of Equation 1 to Test Case 1. | | |
|---|---|---|
| Type | Segment | Weight |
| TN1 | R | 1.0 |
| DH | TA | 1.0 |
| N2 | H | 1.0 |
| H3-JH | HFDY (SEC ID NO: 4582) | 1.0 |

TABLE 19

| Application of Equation 1 to Test Cases 2.1 and 2.1. | | |
|---|---|---|
| Type | Segment | Weight |
| TN1 | V and VG | 0.5 each |
| DH | GIVGA (SEQ ID NO: 3751) and IVGA (SEQ ID NO: 3755) | 0.5 each |
| N2 | AS | 1.0 |
| H3-JH | Y | 1.0 |

TABLE 20

| APPLICATION of Equation 1 to Test Case 3.1. | | |
|---|---|---|
| Type | Segment | Weight |
| TN1 | DR | 1.0 |
| DH | YSGYD (SEQ ID NO: 4389) | 0.8 |
| N2 | LG | 1.0 |
| H3-JH | Y | 1.0 |

TABLE 21

| Application of Equation 1 to Test Cases 4.1 and 4.2. | | |
|---|---|---|
| Type | Segment | Weight |
| TN1 | "-" and G | 0.5 each |
| DH | GIAAA (SEQ ID NO: 4448) and IAAA (SEQ ID NO: 4452) | 0.5 each |
| N2 | D | 1.0 |
| H3-JH | SNWFDP (SEQ ID NO: 4600 | 0.83 |

TABLE 22

Application of Equation 1 to all Test Cases.

| Type | Segments | Weight |
|---|---|---|
| TN1 | DR, R, VG, V, G and "_" | 0.25, 0.25, 0.125, 0.125, 0.125 and 0.125 respectively |
| DH | TA, YSGYD, (SEQ ID NO: 4389), IAAA, (SEQ ID NO: 4452), GIAAA, (SEQ ID NO: 4448), IVGA (SEQ ID NO: 3755), and GIVGA (SEQ ID NO: 3751) | 0.25, 0.20, 0.125, 0.125, 0.125 and 0.125 respectively |
| N2 | AS, H, D and LG | 0.25 each |
| H3-JH | Y, HFDY (SEQ ID NO: 4582) and SNWFDP (SEQ ID NO: 4600). | 0.50, 0.25 and 0.209 |

TABLE 23

Segments used in Exemplary Library Design 1 (ELD-1). The sequences collectively form a theoretical segment pool that comprises individual theoretical segment pools of TN1, DH, N2, and H3-JH segments.

| Segment No. | TN1 | SEQ ID NO | DH | SEQ ID NO | N2 | H3-JH | SEQ ID NO |
|---|---|---|---|---|---|---|---|
| 1 | — | n/a | YYYDSSGYY | 4162 | — | DAFDI | 4538 |
| 2 | G | n/a | YGDY | 4350 | Y | YYFDY | 4568 |
| 3 | D | n/a | DYGDY | 4348 | G | Y | n/a |
| 4 | A | n/a | YYYDSSGY | 4164 | D | FDY | n/a |
| 5 | V | n/a | YCSSTSCY | 3810 | S | DY | n/a |
| 6 | DR | n/a | YYDSSGY | 4168 | P | YGMDV | 4640 |
| 7 | S | n/a | YCSGGSCY | 3771 | F | | n/a |
| 8 | L | n/a | YCSSTSC | 3812 | L | LDY | n/a |
| 9 | DL | n/a | GG | n/a | A | GAFDI | 4549 |
| 10 | R | n/a | RG | n/a | E | YFDY | 4567 |
| 11 | GR | n/a | SGSY | 3763 | V | YYGMDV | 4639 |
| 12 | T | n/a | YYDSSGYY | 4165 | H | AFDI | 4539 |
| 13 | GG | n/a | SS | n/a | T | PFDY | 4587 |
| 14 | E | n/a | YDFWSGY | 4249 | R | GMDV | 4641 |
| 15 | DS | n/a | GYCSSTSC | 3809 | W | GWFDP | 4619 |
| 16 | VG | n/a | DY | n/a | SG | YYYYGMDV | 4637 |
| 17 | DG | n/a | YYYDSSG | 4167 | I | IDY | n/a |
| 18 | AP | n/a | CSSTSCY | 3813 | RG | GYFDY | 4577 |
| 19 | GL | n/a | YYDFWSGY | 4245 | K | GFDY | 4590 |
| 20 | GS | n/a | SSGWY | 4461 | LG | MDV | n/a |
| 21 | DRG | n/a | AG | n/a | Q | VDY | n/a |
| 22 | DLG | n/a | DSSGY | 4179 | GP | YYYGMDV | 4638 |
| 23 | VP | n/a | SSSW | 4443 | PG | NWFDP | 4595 |
| 24 | DP | n/a | VGAT | 3756 | LP | PDY | n/a |
| 25 | P | n/a | SY | n/a | AG | WFDP | 4596 |

TABLE 23-continued

Segments used in Exemplary Library Design 1 (ELD-1). The sequences collectively form a theoretical segment pool that comprises individual theoretical segment pools of TN1, DH, N2, and H3-JH segments.

| Segment No. | TN1 | SEQ ID NO | DH | SEQ ID NO | N2 | H3-JH | SEQ ID NO |
|---|---|---|---|---|---|---|---|
| 26 | EG | n/a | DTAM | 4420 | GS | NFDY | 4580 |
| 27 | GA | n/a | IAAAG | 4449 | TS | YWYFDL | 4527 |
| 28 | AG | n/a | YSSSW | 4439 | SS | NAFDI | 4565 |
| 29 | GV | n/a | GS | n/a | GG | HFDY | 4582 |
| 30 | GP | n/a | YYDSSG | 4172 | YS | SFDY | 4584 |
| 31 | ER | n/a | VG | n/a | M | YYYYYGMDV | 4636 |
| 32 | DV | n/a | YSSSWY | 4437 | SL | DYYYGMDV | 4668 |
| 33 | VGG | n/a | YCSGGSC | 3773 | SP | DFDY | 4581 |
| 34 | SG | n/a | YDSSGYY | 4169 | SD | YNWFDP | 4597 |
| 35 | GRG | n/a | GI | n/a | AP | DYYYYGMDV | 4655 |
| 36 | DA | n/a | GYCSGGSCY | 3768 | GR | YYYMDV | 4685 |
| 37 | DRP | n/a | YSSS | 4442 | TG | LFDY | 4586 |
| 38 | DSG | n/a | SSGW | 4463 | SR | DYFDY | 4566 |
| 39 | GPR | n/a | TA | n/a | LD | NYYYYGMDV | 4654 |
| 40 | DT | n/a | DSSGYY | 4174 | LS | GDY | n/a |
| 41 | GGG | n/a | GYCSSTSCY | 3807 | GA | YDY | n/a |
| 42 | DRGG | 3720 | TTVT | 4352 | VG | SYFDY | 4571 |
| 43 | PL | n/a | YSSGWY | 4458 | PP | YYMDV | 4686 |
| 44 | DPS | n/a | GW | n/a | RR | TFDY | 4589 |
| 45 | LP | n/a | LG | n/a | GSG | YYYYYYGMDV | 4642 |
| 46 | RG | n/a | DYGD | 4349 | GT | FFDY | 4583 |
| 47 | GT | n/a | TVTT | 4353 | TP | SYYYYGMDV | 4658 |
| 48 | LG | n/a | AAA | n/a | RP | VFDY | 4591 |
| 49 | DLP | n/a | YSSGW | 4460 | RD | YAFDI | 4540 |
| 50 | DGR | n/a | LV | n/a | QL | SDY | n/a |
| 51 | ERG | n/a | YYDFWSGYY | 4243 | TT | WYFDL | 4528 |
| 52 | DGS | n/a | YYDSSGYYY | 4163 | PL | DWFDP | 4609 |
| 53 | ES | n/a | YYDFWSG | 4248 | RS | AFDY | 4592 |
| 54 | PS | n/a | YGD | n/a | WS | PYYYYGMDV | 4661 |
| 55 | GGS | n/a | YG | n/a | RV | HYFDY | 4569 |
| 56 | DPR | n/a | GT | n/a | RF | DV | n/a |
| 57 | EA | n/a | YSGSY | 3760 | SF | RFDY | 4585 |
| 58 | GGR | n/a | YYYGSGSY | 3972 | PT | NYFDY | 4593 |
| 59 | DGG | n/a | LR | n/a | PS | IFDY | 4588 |
| 60 | SP | n/a | SSS | n/a | AT | ADY | n/a |
| 61 | DPG | n/a | GD | n/a | RL | HYYYGMDV | 4669 |

TABLE 23-continued

Segments used in Exemplary Library Design 1 (ELD-1). The sequences collectively form a theoretical segment pool that comprises individual theoretical segment pools of TN1, DH, N2, and H3-JH segments.

| Segment No. | TN1 | SEQ ID NO | DH | SEQ ID NO | N2 | H3-JH | SEQ ID NO |
|---|---|---|---|---|---|---|---|
| 62 | DSGG | 3723 | CSGGSCY | 3774 | SV | GYYYYYGMDV | 4651 |
| 63 | DPL | n/a | GY | n/a | RA | DWYFDL | 4530 |
| 64 | TP | n/a | YCGGDCY | 3866 | GRG | GYYYGMDV | 4677 |
| 65 | AGG | n/a | QWLV | 4475 | VP | YYYYMDV | 4684 |
| 66 | PR | n/a | IAAA | 4452 | SQ | V | n/a |
| 67 | DGT | n/a | QG | n/a | AS | FDP | n/a |
| 68 | GLG | n/a | YCSSTSCYT | 3844 | PR | DDY | n/a |
| 69 | DSP | n/a | SG | n/a | VD | GYYYYGMDV | 4664 |
| 70 | GGV | n/a | TTVTT | 4351 | GV | YMDV | 4687 |
| 71 | GPS | n/a | QQL | n/a | LT | NWYFDL | 4532 |
| 72 | GVG | n/a | IAVA | 4472 | TR | PYFDY | 4574 |
| 73 | GGA | n/a | GDY | n/a | VS | FDI | n/a |
| 74 | RP | n/a | YYYDSSGYYY | 4161 | SGL | NDY | n/a |
| 75 | DPP | n/a | DGYN | 4411 | RGG | HYYYYYGMDV | 4643 |
| 76 | DPT | n/a | CSSTSC | 3814 | LR | VYYYGMDV | 4678 |
| 77 | EV | n/a | IVVVPAAI | 3849 | SGG | VYFDY | 4578 |
| 78 | GAP | n/a | AVAG | 4473 | SA | SNWFDP | 4600 |
| 79 | DGRG | 3702 | AA | n/a | AY | NYYYGMDV | 4667 |
| 80 | GPP | n/a | DSSG | 4185 | LE | LYYYYGMDV | 4660 |
| 81 | DLGG | 3714 | VR | n/a | TGG | DYYYYYGMDV | 4635 |
| 82 | ET | n/a | YDFWSG | 4253 | GL | AAFDI | 4551 |
| 83 | DGGP | 3681 | GYSSSWY | 4435 | GAG | SWFDP | 4613 |
| 84 | DGGR | 3684 | SGW | n/a | TA | SYYYYYGMDV | 4645 |
| 85 | DGSG | 3705 | WG | n/a | IS | SYYYGMDV | 4671 |
| 86 | GTG | n/a | SGSYY | 3761 | ST | P | n/a |
| 87 | DPGG | 3717 | RY | n/a | SSE | YYYYYMDV | 4683 |
| 88 | DGGS | 3687 | DS | n/a | GLG | RAFDI | 4544 |
| 89 | GGT | n/a | TT | n/a | PRP | RYFDY | 4572 |
| 90 | GGRG | 3703 | YCSGGSCYS | 3769 | RPL | FYYYYGMDV | 4657 |
| 91 | EGR | n/a | PA | n/a | EA | GNWFDP | 4606 |
| 92 | DGA | n/a | IVVVPAA | 3823 | LGG | RWFDP | 4614 |
| 93 | DGL | n/a | IAAAGT | 4447 | FS | GFDP | 4623 |
| 94 | EL | n/a | AAAG | 4453 | DL | DYYYYMDV | 4714 |
| 95 | EGG | n/a | GYCSGGSC | 3770 | GGG | PYYYGMDV | 4674 |
| 96 | LGG | n/a | SGWY | 4464 | AR | DP | n/a |
| 97 | DPA | n/a | DYGGN | 4355 | RE | HAFDI | 4541 |

TABLE 23-continued

Segments used in Exemplary Library Design 1 (ELD-1). The sequences collectively form a theoretical segment pool that comprises individual theoretical segment pools of TN1, DH, N2, and H3-JH segments.

| Segment No. | TN1 | SEQ ID NO | DH | SEQ ID NO | N2 | H3-JH | SEQ ID NO |
|---|---|---|---|---|---|---|---|
| 98 | EGV | n/a | YYYDS | 4176 | PA | DNWFDP | 4594 |
| 99 | GSG | n/a | YSSG | 4462 | PTQ | LNWFDP | 4602 |
| 100 | GGP | n/a | YDSSGY | 4173 | AGG | AYYYYGMDV | 4666 |
| 101 | | | VAG | n/a | GGV | | |
| 102 | | | SSW | n/a | SI | | |
| 103 | | | GSGSY | 3987 | SAA | | |
| 104 | | | SSSS | 4480 | GGS | | |
| 105 | | | NW | n/a | GGA | | |
| 106 | | | DFWSGY | 4254 | GPG | | |
| 107 | | | QQLV | 4455 | PGG | | |
| 108 | | | YGGN | 4358 | AAE | | |
| 109 | | | YDSSG | 4178 | GGR | | |
| 110 | | | GYSYG | 4430 | TW | | |
| 111 | | | TV | n/a | GGP | | |
| 112 | | | NG | n/a | GGL | | |
| 113 | | | IVGAT | 3752 | VGG | | |
| 114 | | | IVGA | 3755 | GTG | | |
| 115 | | | YGSGSY | 3981 | NR | | |
| 116 | | | SSWY | 4444 | NTP | | |
| 117 | | | ST | n/a | PV | | |
| 118 | | | DFWSGYY | 4250 | EK | | |
| 119 | | | GSY | n/a | GVG | | |
| 120 | | | YYDSS | 4177 | KV | | |
| 121 | | | VGA | n/a | EKR | | |
| 122 | | | AT | n/a | QT | | |
| 123 | | | RP | n/a | SE | | |
| 124 | | | YYYGSGS | 3975 | SAL | | |
| 125 | | | GIAAAG | 4446 | FH | | |
| 126 | | | SGY | n/a | RH | | |
| 127 | | | TG | n/a | PTA | | |
| 128 | | | LT | n/a | HL | | |
| 129 | | | RD | n/a | WGT | | |
| 130 | | | WEL | n/a | REL | | |
| 131 | | | YSYG | 4433 | NT | | |
| 132 | | | TVT | n/a | HW | | |
| 133 | | | GYCSGGSCYS | 3767 | PKS | | |

TABLE 23-continued

Segments used in Exemplary Library Design 1 (ELD-1). The sequences collectively form a theoretical segment pool that comprises individual theoretical segment pools of TN1, DH, N2, and H3-JH segments.

| Segment No. | TN1 | SEQ ID NO | DH | SEQ ID NO | N2 | H3-JH | SEQ ID NO |
|---|---|---|---|---|---|---|---|
| 134 | | | AR | n/a | DT | | |
| 135 | | | YYGSGSY | 3976 | DTL | | |
| 136 | | | RW | n/a | SK | | |
| 137 | | | DIVVVPA | 3822 | TGL | | |
| 138 | | | YSGS | 3762 | AYH | | |
| 139 | | | GYSSSW | 4436 | TSR | | |
| 140 | | | YSSSS | 4478 | GGT | | |
| 141 | | | YYYDSS | 4171 | QE | | |
| 142 | | | QL | n/a | | | |
| 143 | | | GYSGYD | 4386 | | | |
| 144 | | | GE | n/a | | | |
| 145 | | | MA | n/a | | | |
| 146 | | | DSS | n/a | | | |
| 147 | | | RF | n/a | | | |
| 148 | | | DTAMV | 4417 | | | |
| 149 | | | YYGSGSYY | 3973 | | | |
| 150 | | | VDTAMV | 4414 | | | |
| 151 | | | FGVV | 4293 | | | |
| 152 | | | EYSSS | 4477 | | | |
| 153 | | | TTV | n/a | | | |
| 154 | | | SWY | n/a | | | |
| 155 | | | IAARP | 4483 | | | |
| 156 | | | VE | n/a | | | |
| 157 | | | SIAA | 4484 | | | |
| 158 | | | YSGYD | 4389 | | | |
| 159 | | | DIVVVPAA | 3819 | | | |
| 160 | | | CSGGSC | 3775 | | | |
| 161 | | | DW | n/a | | | |
| 162 | | | TS | n/a | | | |
| 163 | | | RL | n/a | | | |
| 164 | | | YSS | n/a | | | |
| 165 | | | GN | n/a | | | |
| 166 | | | SN | n/a | | | |
| 167 | | | GYSY | 4432 | | | |
| 168 | | | YYDS | 4183 | | | |
| 169 | | | VDTAM | 4416 | | | |

TABLE 23-continued

Segments used in Exemplary Library Design 1 (ELD-1). The sequences collectively form a theoretical segment pool that comprises individual theoretical segment pools of TN1, DH, N2, and H3-JH segments.

| Segment No. | TN1 | SEQ ID NO | DH | SEQ ID NO | N2 | H3-JH | SEQ ID NO |
|---|---|---|---|---|---|---|---|
| 170 | | | LE | n/a | | | |
| 171 | | | AVAGT | 4470 | | | |
| 172 | | | YSY | n/a | | | |
| 173 | | | SW | n/a | | | |
| 174 | | | SSG | n/a | | | |
| 175 | | | FGV | n/a | | | |
| 176 | | | VP | n/a | | | |
| 177 | | | VA | n/a | | | |
| 178 | | | SYY | n/a | | | |
| 179 | | | QWL | n/a | | | |
| 180 | | | GSG | n/a | | | |
| 181 | | | TIFGVV | 4280 | | | |
| 182 | | | AVA | n/a | | | |
| 183 | | | FWSGY | 4260 | | | |
| 184 | | | YSGSYY | 3759 | | | |
| 185 | | | IAVAG | 4469 | | | |
| 186 | | | YS | n/a | | | |
| 187 | | | YQL | n/a | | | |
| 188 | | | SIAAR | 4482 | | | |
| 189 | | | YCGGDC | 3868 | | | |
| 190 | | | NWNY | 3766 | | | |
| 191 | | | SSSWY | 4440 | | | |
| 192 | | | GIAVA | 4468 | | | |
| 193 | | | YSYGY | 4431 | | | |
| 194 | | | GIAAA | 4448 | | | |
| 195 | | | YYG | n/a | | | |
| 196 | | | AAG | n/a | | | |
| 197 | | | AV | n/a | | | |
| 198 | | | AYCGGDCY | 3863 | | | |
| 199 | | | YYGSGS | 3980 | | | |
| 200 | | | EY | n/a | | | |

TABLE 24

Segments used in Exemplary Library Design 2 (ELD-2). The sequences collectively form a theoretical segment pool that comprises individual theoretical segment pools of TN1, DH, N2, and H3-JH segments.

| Segment No. | TN1 | SEQ ID NO | DH | SEQ ID NO | N2 | SEQ ID NO | H3-JH | SEQ ID NO |
|---|---|---|---|---|---|---|---|---|
| 1 | — | n/a | YYYDSSGYY | 4162 | — | n/a | DAFDI | 4538 |
| 2 | G | n/a | YGDY | 4350 | G | n/a | YYFDY | 4568 |
| 3 | D | n/a | DYGDY | 4348 | D | n/a | Y | n/a |
| 4 | A | n/a | YYYDSSGY | 4164 | A | n/a | FDY | n/a |
| 5 | V | n/a | YCSSTSCY | 3810 | v | n/a | DY | n/a |
| 6 | S | n/a | YYDSSGY | 4168 | s | n/a | YGMDV | 4640 |
| 7 | DR | n/a | YCSGGSCY | 3771 | DR | n/a | — | n/a |
| 8 | L | n/a | YCSSTSC | 3812 | L | n/a | LDY | n/a |
| 9 | R | n/a | GG | n/a | R | n/a | GAFDI | 4549 |
| 10 | DL | n/a | RG | n/a | DL | n/a | YFDY | 4567 |
| 11 | T | n/a | SGSY | 3763 | T | n/a | YYGMDV | 4639 |
| 12 | E | n/a | YYDSSGYY | 4165 | E | n/a | AFDI | 4539 |
| 13 | GR | n/a | SS | n/a | GR | n/a | PFDY | 4587 |
| 14 | GG | n/a | YDFWSGY | 4249 | GG | n/a | GMDV | 4641 |
| 15 | DG | n/a | GYCSSTSC | 3809 | DG | n/a | GWFDP | 4619 |
| 16 | DS | n/a | DY | n/a | DS | n/a | YYYYGMDV | 4637 |
| 17 | VG | n/a | YYYDSSG | 4167 | VG | n/a | IDY | n/a |
| 18 | EG | n/a | CSSTSCY | 3813 | EG | n/a | GYFDY | 4577 |
| 19 | P | n/a | YYDFWSGY | 4245 | P | n/a | GFDY | 4590 |
| 20 | GL | n/a | SSGWY | 4461 | GL | n/a | MDV | n/a |
| 21 | GS | n/a | AG | n/a | GS | n/a | VDY | n/a |
| 22 | DP | n/a | DSSGY | 4179 | DP | n/a | YYYGMDV | 4638 |
| 23 | GP | n/a | SSSW | 4443 | GP | n/a | NWFDP | 4595 |
| 24 | GA | n/a | VGAT | 3756 | GA | n/a | PDY | n/a |
| 25 | GV | n/a | SY | n/a | GV | n/a | WFDP | 4596 |
| 26 | H | n/a | DTAM | 4420 | H | n/a | NFDY | 4580 |
| 27 | DRG | n/a | IAAAG | 4449 | DRG | n/a | YWYFDL | 4527 |
| 28 | DQ | n/a | YSSSW | 4439 | DQ | n/a | NAFDI | 4565 |
| 29 | AG | n/a | GS | n/a | AG | n/a | HFDY | 4582 |
| 30 | DLG | n/a | YYDSSG | 4172 | DLG | n/a | SFDY | 4584 |
| 31 | DV | n/a | VG | n/a | DV | n/a | YYYYYGMDV | 4636 |
| 32 | Q | n/a | YSSSWY | 4437 | Q | n/a | DYYYGMDV | 4668 |
| 33 | N | n/a | YCSGGSC | 3773 | N | n/a | DFDY | 4581 |
| 34 | AP | n/a | YDSSGYY | 4169 | AP | n/a | YNWFDP | 4597 |
| 35 | GGG | n/a | GI | n/a | GGG | n/a | DYYYYGMDV | 4655 |
| 36 | DH | n/a | GYCSGGSCY | 3768 | DH | n/a | YYYMDV | 4685 |
| 37 | VP | n/a | YSSS | 4442 | VP | n/a | LFDY | 4586 |

TABLE 24-continued

Segments used in Exemplary Library Design 2 (ELD-2). The sequences collectively form a theoretical segment pool that comprises individual theoretical segment pools of TN1, DH, N2, and H3-JH segments.

| Segment No. | TN1 | SEQ ID NO | DH | SEQ ID NO | N2 | SEQ ID NO | H3-JH | SEQ ID NO |
|---|---|---|---|---|---|---|---|---|
| 38 | SG | n/a | SSGW | 4463 | SG | n/a | DYFDY | 4566 |
| 39 | GRG | n/a | TA | n/a | GRG | n/a | NYYYYGMDV | 4654 |
| 40 | AR | n/a | DSSGYY | 4174 | AR | n/a | GDY | n/a |
| 41 | RG | n/a | GYCSSTSCY | 3807 | RG | n/a | YDY | n/a |
| 42 | ER | n/a | TTVT | 4352 | ER | n/a | SYFDY | 4571 |
| 43 | DA | n/a | YSSGWY | 4458 | DA | n/a | YYMDV | 4686 |
| 44 | AS | n/a | GW | n/a | AS | n/a | TFDY | 4589 |
| 45 | PL | n/a | LG | n/a | PL | n/a | YYYYYYGMDV | 4642 |
| 46 | DQG | n/a | DYGD | 4349 | DQG | n/a | FFDY | 4583 |
| 47 | VL | n/a | TVTT | 4353 | VL | n/a | SYYYYGMDV | 4658 |
| 48 | GT | n/a | AAA | n/a | GT | n/a | VFDY | 4591 |
| 49 | DGG | n/a | YSSGW | 4460 | DGG | n/a | YAFDI | 4540 |
| 50 | DSG | n/a | LV | n/a | DSG | n/a | SDY | n/a |
| 51 | VGG | n/a | YYDFWSGYY | 4243 | VGG | n/a | WYFDL | 4528 |
| 52 | F | n/a | YYDSSGYYY | 4163 | F | n/a | DWFDP | 4609 |
| 53 | AL | n/a | YYDFWSG | 4248 | AL | n/a | AFDY | 4592 |
| 54 | PS | n/a | YGD | n/a | PS | n/a | PYYYYGMDV | 4661 |
| 55 | ES | n/a | YG | n/a | ES | n/a | HYFDY | 4569 |
| 56 | ERG | n/a | GT | n/a | ERG | n/a | DV | n/a |
| 57 | GGV | n/a | YSGSY | 3760 | GGV | n/a | RFDY | 4585 |
| 58 | DRP | n/a | YYYGSGSY | 3972 | DRP | n/a | NYFDY | 4593 |
| 59 | EA | n/a | LR | n/a | EA | n/a | IFDY | 4588 |
| 60 | TP | n/a | SSS | n/a | TP | n/a | ADY | n/a |
| 61 | GPR | n/a | GD | n/a | GPR | n/a | HYYYGMDV | 4669 |
| 62 | LH | n/a | CSGGSCY | 3774 | LH | n/a | GYYYYYGMDV | 4651 |
| 63 | SR | n/a | GY | n/a | SR | n/a | DWYFDL | 4530 |
| 64 | LP | n/a | YCGGDCY | 3866 | LP | n/a | GYYYGMDV | 4677 |
| 65 | LG | n/a | QWLV | 4475 | LG | n/a | YYYYMDV | 4684 |
| 66 | DT | n/a | IAAA | 4452 | DT | n/a | V | n/a |
| 67 | VA | n/a | QG | n/a | VA | n/a | FDP | n/a |
| 68 | SL | n/a | YCSSTSCYT | 3844 | Sm | n/a | DDY | n/a |
| 69 | EGG | n/a | SG | n/a | EGG | n/a | GYYYYGMDV | 4664 |
| 70 | DRS | n/a | TTVTT | 4351 | DRS | n/a | YMDV | 4687 |
| 71 | K | n/a | QQL | n/a | K | n/a | NWYFDL | 4532 |
| 72 | DPG | n/a | IAVA | 4472 | DPG | n/a | PYFDY | 4574 |
| 73 | I | n/a | GDY | n/a | I | n/a | FDI | n/a |

TABLE 24-continued

Segments used in Exemplary Library Design 2 (ELD-2). The sequences collectively form a theoretical segment pool that comprises individual theoretical segment pools of TN1, DH, N2, and H3-JH segments.

| Segment No. | TN1 | SEQ ID NO | DH | SEQ ID NO | N2 | SEQ ID NO | H3-JH | SEQ ID NO |
|---|---|---|---|---|---|---|---|---|
| 74 | GD | n/a | YYYDSSGYYY | 4161 | GD | n/a | NDY | n/a |
| 75 | DGT | n/a | DGYN | 4411 | DGT | n/a | HYYYYYGMDV | 4643 |
| 76 | GPP | n/a | CSSTSC | 3814 | GPP | n/a | VYYYGMDV | 4678 |
| 77 | DPP | n/a | IVVVPAAI | 3849 | DPP | n/a | VYFDY | 4578 |
| 78 | RR | n/a | AVAG | 4473 | RR | n/a | SNWFDP | 4600 |
| 79 | EGV | n/a | AA | n/a | EGV | n/a | NYYYGMDV | 4667 |
| 80 | GF | n/a | DSSG | 4185 | GF | n/a | LYYYYGMDV | 4660 |
| 81 | GVG | n/a | VR | n/a | GVG | n/a | DYYYYYGMDV | 4635 |
| 82 | DPS | n/a | YDFWSG | 4253 | DPS | n/a | AAFDI | 4551 |
| 83 | VD | n/a | GYSSSWY | 4435 | VD | n/a | SWFDP | 4613 |
| 84 | GGT | n/a | SGW | n/a | GGT | n/a | SYYYYYGMDV | 4645 |
| 85 | DK | n/a | WG | n/a | DK | n/a | SYYYGMDV | 4671 |
| 86 | GTG | n/a | SGSYY | 3761 | GTG | n/a | P | n/a |
| 87 | DF | n/a | RY | n/a | DF | n/a | YYYYYMDV | 4683 |
| 88 | GQ | n/a | DS | n/a | GQ | n/a | RAFDI | 4544 |
| 89 | SP | n/a | TT | n/a | SP | n/a | RYFDY | 4572 |
| 90 | QG | n/a | YCSGGSCYS | 3769 | QG | n/a | FYYYYGMDV | 4657 |
| 91 | DLT | n/a | PA | n/a | DLT | n/a | GNWFDP | 4606 |
| 92 | AK | n/a | IVVVPAA | 3823 | AK | n/a | RWFDP | 4614 |
| 93 | GPS | n/a | IAAAGT | 4447 | GPS | n/a | GFDP | 4623 |
| 94 | QR | n/a | AAAG | 4453 | QR | n/a | DYYYYMDV | 4714 |
| 95 | VR | n/a | GYCSGGSC | 3770 | VR | n/a | PYYYGMDV | 4674 |
| 96 | DSP | n/a | SGWY | 4464 | DSP | n/a | DP | n/a |
| 97 | DPL | n/a | DYGGN | 4355 | DPL | n/a | HAFDI | 4541 |
| 98 | EGR | n/a | YYYDS | 4176 | EGR | n/a | DNWFDP | 4594 |
| 99 | GRRG | 4789 | YSSG | 4462 | GRRG | 4789 | LNWFDP | 4602 |
| 100 | EV | n/a | YDSSGY | 4173 | EV | n/a | AYYYYGMDV | 4666 |
| 101 | | | VAG | n/a | RP | n/a | | |
| 102 | | | SSW | n/a | GH | n/a | | |
| 103 | | | GSGSY | 3987 | DGR | n/a | | |
| 104 | | | SSSS | 4480 | AA | n/a | | |
| 105 | | | NW | n/a | DD | n/a | | |
| 106 | | | DFWSGY | 4254 | W | n/a | | |
| 107 | | | QQLV | 4455 | GGS | n/a | | |
| 108 | | | YGGN | 4358 | DIS | n/a | | |
| 109 | | | YDSSG | 4178 | GGA | n/a | | |
| 110 | | | GYSYG | 4430 | GK | n/a | | |

TABLE 24-continued

Segments used in Exemplary Library Design 2 (ELD-2). The sequences collectively form a theoretical segment pool that comprises individual theoretical segment pools of TN1, DH, N2, and H3-JH segments.

| Segment No. | TN1 | SEQ ID NO | DH | SEQ ID NO | N2 | SEQ ID NO | H3-JH | SEQ ID NO |
|---|---|---|---|---|---|---|---|---|
| 111 | | | TV | n/a | DGP | n/a | | |
| 112 | | | NG | n/a | DLK | n/a | | |
| 113 | | | IVGAT | 3752 | ET | n/a | | |
| 114 | | | IVGA | 3755 | TT | n/a | | |
| 115 | | | YGSGSY | 3981 | VH | n/a | | |
| 116 | | | SSWY | 4444 | AE | n/a | | |
| 117 | | | ST | n/a | VS | n/a | | |
| 118 | | | DFWSGYY | 4250 | LGG | n/a | | |
| 119 | | | GSY | n/a | C | n/a | | |
| 120 | | | YYDSS | 4177 | DKG | n/a | | |
| 121 | | | VGA | n/a | HA | n/a | | |
| 122 | | | AT | n/a | VI | n/a | | |
| 123 | | | RP | n/a | HP | n/a | | |
| 124 | | | YYYGSGS | 3975 | GGE | n/a | | |
| 125 | | | GIAAAG | 4446 | EP | n/a | | |
| 126 | | | SGY | n/a | EF | n/a | | |
| 127 | | | TG | n/a | DRN | n/a | | |
| 128 | | | LT | n/a | DWG | n/a | | |
| 129 | | | RD | n/a | GE | n/a | | |
| 130 | | | WEL | n/a | DRA | n/a | | |
| 131 | | | YSYG | 4433 | VN | n/a | | |
| 132 | | | TVT | n/a | DRE | n/a | | |
| 133 | | | GYCSGGSCYS | 3767 | DLA | n/a | | |
| 134 | | | AR | n/a | EN | n/a | | |
| 135 | | | YYGSGSY | 3976 | VT | n/a | | |
| 136 | | | RW | n/a | HG | n/a | | |
| 137 | | | DIVVVPA | 3822 | RA | n/a | | |
| 138 | | | YSGS | 3762 | M | n/a | | |
| 139 | | | GYSSSW | 4436 | DVP | n/a | | |
| 140 | | | YSSSS | 4478 | GAP | n/a | | |
| 141 | | | YYYDSS | 4171 | GLG | n/a | | |
| 142 | | | QL | n/a | GPG | n/a | | |
| 143 | | | GYSGYD | 4386 | PG | n/a | | |
| 144 | | | GE | n/a | DSS | n/a | | |
| 145 | | | MA | n/a | SS | n/a | | |
| 146 | | | DSS | n/a | AGG | n/a | | |

TABLE 24-continued

Segments used in Exemplary Library Design 2 (ELD-2). The sequences collectively form a theoretical segment pool that comprises individual theoretical segment pools of TN1, DH, N2, and H3-JH segments.

| Segment No. | TN1 | SEQ ID NO | DH | SEQ ID NO | N2 | SEQ ID NO | H3-JH | SEQ ID NO |
|---|---|---|---|---|---|---|---|---|
| 147 | | | RF | n/a | GGR | n/a | | |
| 148 | | | DTAMV | 4417 | GPN | n/a | | |
| 149 | | | YYGSGSYY | 3973 | DRL | n/a | | |
| 150 | | | VDTAMV | 4414 | GRR | n/a | | |
| 151 | | | FGVV | 4293 | DSGG | 3723 | | |
| 152 | | | EYSSS | 4477 | TR | n/a | | |
| 153 | | | TTV | n/a | DLS | n/a | | |
| 154 | | | SWY | n/a | RGG | n/a | | |
| 155 | | | IAARP | 4483 | Y | n/a | | |
| 156 | | | VE | n/a | EVR | n/a | | |
| 157 | | | SIAA | 4484 | LI | n/a | | |
| 158 | | | YSGYD | 4389 | TF | n/a | | |
| 159 | | | DIVVVPAA | 3819 | LK | n/a | | |
| 160 | | | CSGGSC | 3775 | DLE | n/a | | |
| 161 | | | DW | n/a | GY | n/a | | |
| 162 | | | TS | n/a | DGS | n/a | | |
| 163 | | | RL | n/a | GVR | n/a | | |
| 164 | | | YSS | n/a | GQR | n/a | | |
| 165 | | | GN | n/a | EGL | n/a | | |
| 166 | | | SN | n/a | VLG | n/a | | |
| 167 | | | GYSY | 4432 | QP | n/a | | |
| 168 | | | YYDS | 4183 | VM | n/a | | |
| 169 | | | VDTAM | 4416 | VE | n/a | | |
| 170 | | | LE | n/a | DQGG | 4790 | | |
| 171 | | | AVAGT | 4470 | PN | n/a | | |
| 172 | | | YSY | n/a | DGL | n/a | | |
| 173 | | | SW | n/a | PV | n/a | | |
| 174 | | | SSG | n/a | HR | n/a | | |
| 175 | | | FGV | n/a | AD | n/a | | |
| 176 | | | VP | n/a | DLF | n/a | | |
| 177 | | | VA | n/a | LD | n/a | | |
| 178 | | | SYY | n/a | GGD | n/a | | |
| 179 | | | QWL | n/a | DRR | n/a | | |
| 180 | | | GSG | n/a | DHH | n/a | | |
| 181 | | | TIFGVV | 4280 | DW | n/a | | |
| 182 | | | AVA | n/a | DAS | n/a | | |
| 183 | | | FWSGY | 4260 | GW | n/a | | |

TABLE 24-continued

Segments used in Exemplary Library Design 2 (ELD-2). The sequences collectively form a theoretical segment pool that comprises individual theoretical segment pools of TN1, DH, N2, and H3-JH segments.

| Segment No. | TN1 | SEQ ID NO | DH | SEQ ID NO | N2 | SEQ ID NO | H3-JH | SEQ ID NO |
|---|---|---|---|---|---|---|---|---|
| 184 | | | YSGSYY | 3759 | SC | n/a | | |
| 185 | | | IAVAG | 4469 | GLR | n/a | | |
| 186 | | | YS | n/a | DGA | n/a | | |
| 187 | | | YQL | n/a | LA | n/a | | |
| 188 | | | SIAAR | 4482 | EEG | n/a | | |
| 189 | | | YCGGDC | 3868 | AV | n/a | | |
| 190 | | | NWNY | 3766 | VQ | n/a | | |
| 191 | | | SSSWY | 4440 | AH | n/a | | |
| 192 | | | GIAVA | 4468 | RS | n/a | | |
| 193 | | | YSYGY | 4431 | WA | n/a | | |
| 194 | | | GIAAA | 4448 | LR | n/a | | |
| 195 | | | YYG | n/a | GSG | n/a | | |
| 196 | | | AAG | n/a | GGSG | 3706 | | |
| 197 | | | AV | n/a | DLR | n/a | | |
| 198 | | | AYCGGDCY | 3863 | VWG | n/a | | |
| 199 | | | YYGSGS | 3980 | HL | n/a | | |
| 200 | | | EY | n/a | EH | n/a | | |

TABLE 25

Segments used in Exemplary Library Design 3 (ELD-3). The sequences collectively form a theoretical segment pool that comprises individual theoretical segment pools of TN1, DH, N2, and H3-JH segments.

| Segment No. | TN1 (plus AR Or AK)[1] | SEQ ID NO | TN1 Nucleotides (plus AR or AK)[1] | SEQ ID NO | DH | SEQ ID NO | DH Nucleotides | SEQ ID NO |
|---|---|---|---|---|---|---|---|---|
| 1 | AR | n/a | GCCAGA | n/a | GT | n/a | GGTACT | n/a |
| 2 | ARE | n/a | GCCAGAGAG | n/a | TT | n/a | ACTACT | n/a |
| 3 | ARD | n/a | GCCAGAGAC | n/a | TG | n/a | ACAGGC | n/a |
| 4 | ARG | n/a | GCCAGAGGA | n/a | ER | n/a | GAGCGT | n/a |
| 5 | AREG | 4791 | GCCAGAGAGGGA | 4963 | QLE | n/a | CAATTAGAG | n/a |
| 6 | ARDG | 4792 | GCCAGAGACGGA | 4964 | LER | n/a | TTAGAGCGT | n/a |
| 7 | ARGG | 4793 | GCCAGAGGTGGA | 4965 | VGAT | 3756 | GTTGGCGCAACT | 5135 |
| 8 | ARA | n/a | GCCAGGAGA | n/a | YSG | n/a | TATAGTGGT | n/a |
| 9 | ARER | 4794 | GCCAGAGAGAGA | 4966 | YSGSY | 3760 | TACTCTGGCTCTTAT | 5136 |
| 10 | ARDR | 4795 | GCCAGAGACAGA | 4967 | VG | n/a | GTAGGC | n/a |
| 11 | ARGR | 4796 | GCCAGAGGCAGA | 4968 | AT | n/a | GCCACT | n/a |
| 12 | ARS | n/a | GCCAGATCT | n/a | WEL | n/a | TGGGAGCTT | n/a |

TABLE 25-continued

Segments used in Exemplary Library Design 3 (ELD-3). The sequences collectively form a theoretical segment pool that comprises individual theoretical segment pools of TN1, DH, N2, and H3-JH segments.

| | | | | | | | | |
|---|---|---|---|---|---|---|---|---|
| 13 | ARES | 4797 | GCCAGAGAATCT | 4969 | YS | n/a | TACAGC | n/a |
| 14 | ARDS | 4798 | GCCAGAGACTCT | 4970 | SG | n/a | AGTGGT | n/a |
| 15 | ARGS | 4799 | GCCAGAGGTTCT | 4971 | GS | n/a | GGTTCT | n/a |
| 16 | ARP | n/a | GCCAGACCT | n/a | SY | n/a | AGCTAC | n/a |
| 17 | ARDP | 4800 | GCCAGAGACCCT | 4972 | CSSTSC | 3814 | TGTAGTAGTACAAGTTGC | 5137 |
| 18 | ARGP | 4801 | GCCAGAGGGCCT | 4973 | CSSTSCY | 3813 | TGCTCATCTACATCATGCTAT | 5138 |
| 19 | ARL | n/a | GCCAGATTG | n/a | YCSSTSC | 3812 | TATTGTTCAAGTACATCTTGT | 5139 |
| 20 | ARDL | 4802 | GCCAGAGACTTG | 4974 | GYCSSTSC | 3809 | GGGTATTGCTCCAGTACCTCATGT | 5140 |
| 21 | ARGL | 4803 | GCCAGAGGGTTG | 4975 | YCSSTSCY | 3810 | TACTGCAGCAGCACAAGTTGTTAC | 5141 |
| 22 | ARA | n/a | GCCAGAGCT | n/a | GYCSSTSCY | 3807 | GGGTATTGCAGTTCAACTAGTTGTTAT | 5142 |
| 23 | AREA | 4804 | GCCAGAGAGGCT | 4976 | YCSSTSCYT | 3844 | TACTGTTCATCAACCTCCTGTTATACT | 5143 |
| 24 | ARDA | 4805 | GCCAGAGATGCT | 4977 | PAA | n/a | CCTGCCGCT | n/a |
| 25 | ARGA | 4806 | GCCAGAGGTGCT | 4978 | CSGGSCY | 3774 | TGCTCTGGGGGTAGCTGCTAT | 5144 |
| 26 | ART | n/a | GCCAGAACT | n/a | YCSGGSC | 3773 | TACTGTAGCGGTGGTAGTTGC | 5145 |
| 27 | ARET | 4807 | GCCAGAGAGACT | 4979 | GYCSGGSC | 3770 | GGATACTGTAGTGGCGGATCCTGC | 5146 |
| 28 | ARDT | 4808 | GCCAGAGATACT | 4980 | YCSGGSCY | 3771 | TACTGCTCCGGAGGAAGTTGTTAT | 5147 |
| 29 | ARGT | 4809 | GCCAGAGGCACT | 4981 | GYCSGGSCY | 3768 | GGTTATTGCAGTGGGGGTTCATGTTAC | 5148 |
| 30 | ARV | n/a | GCCAGAGTG | n/a | YCSGGSCYS | 3769 | TACTGTTCCGGAGGTAGCTGTTACTCT | 5149 |
| 31 | AREV | 4810 | GCCAGAGAGGTG | 4982 | RI | n/a | AGAATC | n/a |
| 32 | ARDV | 4811 | GCCAGAGATGTG | 4983 | GY | n/a | GGATAT | n/a |
| 33 | ARGV | 4812 | GCCAGAGGGGTG | 4984 | GG | n/a | GGCGGT | n/a |
| 34 | AREG G | 4813 | GCCAGAGAGGGAG GA | 4985 | ATP | n/a | GCTACCCCT | n/a |
| 35 | ARDG G | 4814 | GCCAGAGATGGTG GA | 4986 | DI | n/a | GACATC | n/a |
| 36 | ARGG G | 4815 | GCCAGAGGTGGAG GA | 4987 | TP | n/a | ACTCCT | n/a |
| 37 | ARDG R | 4816 | GCCAGAGACGGCA GA | 4988 | GD | n/a | GGAGAT | n/a |
| 38 | ARGG S | 4817 | GCCAGAGGCGGTT CT | 4989 | AYCGGDCY | 3863 | GCCTATTGCGGTGGTGACTGCTAT | 5150 |
| 39 | ARGG P | 4818 | GCCAGAGGTGGGC CT | 4990 | AYCGGDC | 3865 | GCATATTGCGGAGGGGATTGC | 5151 |
| 40 | ARGG A | 4819 | GCCAGAGGAGGTG CT | 4991 | YCGGDCY | 3866 | TATTGTGGTGGGGACTGCTAT | 5152 |
| 41 | ARDG T | 4820 | GCCAGAGACGGTA CT | 4992 | YCGGDC | 3868 | TACTGCGGAGGCGATTGC | 5153 |
| 42 | ARGG T | 4821 | GCCAGAGGTGGAA CT | 4993 | HI | n/a | CACATC | n/a |
| 43 | AREG V | 4822 | GCCAGAGAGGGAG TG | 4994 | TA | n/a | ACAGCT | n/a |
| 44 | ARGG V | 4823 | GCCAGAGGTGGCG TG | 4995 | GYCSSTSCYA | 3806 | GGGTACTGCTCTAGCACTTCATGCTACGCC | 5154 |

TABLE 25-continued

Segments used in Exemplary Library Design 3 (ELD-3). The sequences collectively form a theoretical segment pool that comprises individual theoretical segment pools of TN1, DH, N2, and H3-JH segments.

| | | | | | | | | |
|---|---|---|---|---|---|---|---|---|
| 45 | ARRG | 4824 | GCCAGAAGAGGA | 4996 | SS | n/a | AGTTCT | n/a |
| 46 | ARERG | 4825 | GCCAGAGAGCGTGGA | 4997 | ST | n/a | AGTACT | n/a |
| 47 | ARDRG | 4826 | GCCAGAGATCGTGGA | 4998 | TS | n/a | ACCAGC | n/a |
| 48 | ARGRG | 4827 | GCCAGAGGCAGGGGA | 4999 | PAAMP | 3835 | CCAGCAGCTATGCCT | 5155 |
| 49 | ARSG | 4828 | GCCAGATCAGGA | 5000 | PA | n/a | CCCGCC | n/a |
| 50 | ARDSG | 4829 | GCCAGAGACTCAGGA | 5001 | MP | n/a | ATGCCT | n/a |
| 51 | ARDPG | 4830 | GCCAGAGATCCAGGA | 5002 | VYAIP | 3940 | GTCTATGCAATTCCT | 5156 |
| 52 | ARLG | 4831 | GCCAGATTGGGA | 5003 | WFGE | 3966 | TGGTTTGGGGAG | 5157 |
| 53 | ARDLG | 4832 | GCCAGAGACTTGGGA | 5004 | FGE | n/a | TTTGGAGAG | n/a |
| 54 | ARAG | 4833 | GCCAGAGCTGGA | 5005 | GEL | n/a | GGCGAGCTT | n/a |
| 55 | ARVG | 4834 | GCCAGAGTGGGA | 5006 | WFG | n/a | TGGTTCGGT | n/a |
| 56 | ARGVG | 4835 | GCCAGAGGCGTATGA | 5007 | GSG | n/a | GGTTCAGGC | n/a |
| 57 | ARPR | 4836 | GCCAGACCCAGA | 5008 | SGSY | 3763 | AGTGGATCTTAT | 5158 |
| 58 | ARGPR | 4837 | GCCAGAGGACCAAGA | 5009 | YYGS | 3990 | TATTATGGCAGT | 5159 |
| 59 | ARPS | 4838 | GCCAGACCATCT | 5010 | YYYG | 3969 | TACTACTATGGC | 5160 |
| 60 | ARDPS | 4839 | GCCAGAGATCCCTCT | 5011 | GSGSY | 3987 | GGCAGCGGTTCCTAC | 5161 |
| 61 | ARGPS | 4840 | GCAAGAGGACCTTCT | 5012 | SGSYY | 3761 | AGTGGATCCTATTAC | 5162 |
| 62 | ARDPP | 4841 | GC CAGAGACCCACCT | 5013 | YYYGSG | 3979 | TATTACTACGGGTCTGGC | 5163 |
| 63 | ARGPP | 4842 | GCCAGAGGACCGCCT | 5014 | SGS | n/a | AGCGGCAGT | n/a |
| 64 | ARPL | 4843 | GCCAGACCGTTG | 5015 | YYYGSGS | 3975 | TATTACTACGGATCTGGCTCT | 5164 |
| 65 | ARDPL | 4844 | GCCAGAGATCCTTTG | 5016 | YYYGSGSY | 3972 | TATTACTATGGCTCTGGTAGCTAC | 5165 |
| 66 | ARRP | 4845 | GCCAGAAGGCCT | 5027 | YGS | n/a | TATGGCTCC | n/a |
| 67 | ARDRP | 4846 | GCCAGAGCCGTCCT | 5018 | YYG | n/a | TACTATGGT | n/a |
| 68 | ARSP | 4847 | GCCAGATCACCT | 5019 | YYY | n/a | TATTATTAT | n/a |
| 69 | ARLP | 4848 | GCCAGACTTCCT | 5020 | MVRG | 4017 | ATGGTAAGAGGT | 5166 |
| 70 | ARAP | 4849 | GCCAGAGCCCCT | 5021 | TMVRG | 4010 | ACCATGGTGAGGGGT | 5167 |
| 71 | ARTP | 4850 | GCCAGAACTCCT | 5022 | RGV | n/a | AGAGGAGTT | n/a |
| 72 | ARVP | 4851 | GCCAGAGTCCCT | 5023 | VRG | n/a | GTCAGAGGC | n/a |
| 73 | ARVGG | 4852 | GCCAGAGTTGGAGGA | 5024 | FG | n/a | TTCGGC | n/a |
| 74 | ARQ | n/a | GCAAGACAG | n/a | GE | n/a | GGCGAG | n/a |
| 75 | ARH | n/a | GCCAGACAC | n/a | YG | n/a | TACGGC | n/a |

TABLE 25-continued

Segments used in Exemplary Library Design 3 (ELD-3). The sequences collectively form a theoretical segment pool that comprises individual theoretical segment pools of TN1, DH, N2, and H3-JH segments.

| 76 | ARDQ | 4853 | GCCAGGGACCAG | 5025 | VR | n/a | GTGCGT | n/a |
|---|---|---|---|---|---|---|---|---|
| 77 | ARDH | 4854 | GCAAGAGACCAC | 5026 | RG | n/a | AGAGGT | n/a |
| 78 | ARAR | 4855 | GCAAGGGCTAGA | 5027 | FRE | n/a | TTCAGGGAG | n/a |
| 79 | ARAS | 4856 | GCTAGGGCATCT | 5028 | RE | n/a | AGAGAG | n/a |
| 80 | ARDQG | 4857 | GCTAGGGATCAGGGA | 5029 | QG | n/a | CAAGGT | n/a |
| 81 | ARSR | 4858 | GCTAGATCAAGA | 5030 | LR | n/a | TTACGT | n/a |
| 82 | ARDRS | 4859 | GCCAGGGACAGGTCT | 5031 | YYDYVWGSYAYT | 4070 | TACTATGATTACGTCTGGGGGTCTTATGCTTACACT | 5168 |
| 83 | ARSL | 4860 | GCTAGATCTTTG | 5032 | YYDYVWGSYAY | 4071 | TACTACGACTATGTATGGGGCTCATATGCTTAC | 5169 |
| 84 | ARLH | 4861 | GCTAGGTTGCAC | 5033 | YYDYVWGSYA | 4073 | TACTACGATTACGTATGGGGAAGCTACGCT | 5170 |
| 85 | ARDLT | 4862 | GCCAGGGATTTGACT | 5034 | YDYYWGSYAY | 4074 | TATGATTATGTGTGGGGGTCATACGCATAC | 5171 |
| 86 | ARK | n/a | GCCAGAAAG | n/a | DY | n/a | GATTAC | n/a |
| 87 | ARAE | 4863 | GCAAGAGCCGAG | 5035 | WG | n/a | TGGGGC | n/a |
| 88 | ARDLS | 4864 | GCAAGGGATTTGTCT | 5036 | DYVWGSYAYT | 4075 | GATTATGTGTGGGGGTCTTACGCCTACACC | 5172 |
| 89 | ARGD | 4865 | GCTAGAGGGGAC | 5037 | YDYVWGSYA | 4077 | TACGACTATGTGTGGGGTTCCTATGCT | 5173 |
| 90 | ARRR | 4866 | GCTAGGAGGAGA | 5038 | YYDS | 4183 | TACTACGATTCC | 5174 |
| 91 | ARDK | 4867 | GCTAGAGATAAG | 5039 | YYYD | 4182 | TATTATTATGAC | 5175 |
| 92 | ARVS | 4868 | GCTAGAGTATCT | 5040 | DSSGY | 4179 | GACAGTTCCGGGTAC | 5176 |
| 93 | ARDRL | 4864869 | GCCAGAGACAGGTTG | 5041 | YDSSG | 4178 | TATGATAGCTCAGGT | 5177 |
| 94 | ARGQ | 4870 | GCTAGGGGCCAG | 5042 | YYDSS | 4177 | TACTATGACTCATCC | 5178 |
| 95 | ARVR | 4871 | GCCAGGGTCAGA | 5043 | YYYDS | 4176 | TATTATTACGATAGT | 5179 |
| 96 | ARAK | 4872 | GCTAGGGCTAAG | 5044 | GYY | n/a | GGATATTAC | n/a |
| 97 | ARGK | 4873 | GCCAGGGGTAAG | 5045 | DSSGYY | 4174 | GATTCTTCCGGGTACTAC | 0 |
| 98 | ARDIS | 4874 | GCAAGGGATATTTCT | 5046 | YDSSGY | 4173 | TATGATTCCAGCGGATAC | 5181 |
| 99 | ARDFT | 4875 | GCTAGGGATTTCACT | 5047 | YYDSSG | 4172 | TACTACGATAGCTCCGGT | 5182 |
| 100 | ARQG | 4876 | GCCAGGCAGGGA | 5048 | YYYDSS | 4171 | TATTATTACGACTCTTCC | 5183 |
| 101 | AK | n/a | GCCAAG | n/a | YDSSGYY | 4169 | TACGACTCTTCTGGTTATTAC | 5184 |
| 102 | AKE | n/a | GCCAAGGAG | n/a | YYDSSGY | 4168 | TATTATGACAGCAGCGGGTAT | 5185 |
| 103 | AKD | n/a | GCCAAGGAC | n/a | YYYDSSG | 4167 | TACTACTACGATTCCAGCGGT | 5186 |
| 104 | AKG | n/a | GCCAAGGGA | n/a | YDSYSGYYY | 4166 | TACGACAGTTCCGGATATTATTAC | 5187 |
| 105 | AKEG | 4877 | GCCAAGGAAGGA | 5049 | SGY | n/a | AGCGGATAT | n/a |
| 106 | AKDG | 4878 | GCCAAGGACGGA | 5050 | YYDSSGYY | 4165 | TACTATGATAGTAGTGGGTACTAT | 5188 |
| 107 | AKGG | 4879 | GCCAAGGGCGGA | 5051 | YYYDSSGY | 4164 | TACTACTATGACAGCTCAGGGTAT | 5189 |
| 108 | AKR | n/a | GCCAAGAGA | n/a | YYDSSGYYY | 4163 | TATTACGACAGCAGTGGCTACTACTAT | 5190 |
| 109 | AKER | 4880 | GCCAAGGAAAGA | 5052 | YYYDSSGYY | 4162 | TACTACTACGATAGCTCTGGATACTAT | 5191 |

TABLE 25-continued

Segments used in Exemplary Library Design 3 (ELD-3). The sequences collectively form a theoretical segment pool that comprises individual theoretical segment pools of TN1, DH, N2, and H3-JH segments.

| | | | | | | | | |
|---|---|---|---|---|---|---|---|---|
| 110 | AKDR | 4881 | GCCAAGGACAGA | 5053 | YYYDSSGYYY | 5161 | TATTATTACGATTCCAGTGGTTATTATTAT | 5192 |
| 111 | AKGR | 4882 | GCCAAGGGCAGA | 5054 | YDS | n/a | TACGACTCC | n/a |
| 112 | AKS | n/a | GCCAAGTCT | n/a | YYD | n/a | TACTATGAC | n/a |
| 113 | AKES | 4883 | GCCAAGGAATCT | 5055 | DSSG | 4185 | GACTCATCCGGT | 5193 |
| 114 | AKDS | 4884 | GCCAAGGATTCT | 5056 | GYYY | 4188 | GGTTACTATTAC | 5194 |
| 115 | AKGS | 4885 | GCCAAGGGATCT | 5057 | SGYY | 4187 | AGCGGCTACTAT | 5195 |
| 116 | AKP | n/a | GCCAAGCCT | n/a | DS | n/a | GACTCT | n/a |
| 117 | AKDP | 4886 | GCCAAGGATCCT | 5058 | RFLEW | 4231 | AGATTTTTGGAGTGG | 5196 |
| 118 | AKGP | 4887 | GCCAAGGGTCCT | 5059 | EWL | n/a | GAATGGCTT | n/a |
| 119 | AKL | n/a | GCCAAGTTG | n/a | RF | n/a | AGATTC | n/a |
| 120 | AXDL | 4888 | GCCAAGGACTTG | 5060 | YYDFWSGYYT | 4242 | TACTATGATTTTGGAGTGGATATTATACC | 5197 |
| 121 | AKGL | 4889 | GCCAAGGGGTTG | 5061 | YDFWSG | 4253 | TATGATTTTTGGTCTGGT | 5198 |
| 122 | AKA | n/a | GCCAAGGCT | n/a | DFWSGY | 4254 | GATTTTTGGAGCGGCTAT | 5199 |
| 123 | AKEA | 4890 | GCCAAGGAAGCT | 5062 | FWSGY | 4260 | TTTTGGAGCGGGTAT | 5200 |
| 124 | AKDA | 4891 | GCCAAGGACGCT | 5063 | YYDFWSGYY | 4243 | TACTACGACTTCTGGAGCGGGTATTAC | 5201 |
| 125 | AKGA | 4892 | GCCAAGGGCGCT | 5064 | YYDFWSGY | 4245 | TACTACGATTTTTGGTCTGGATAT | 5202 |
| 126 | AKT | n/a | GCCAAGACT | n/a | YDFWSGYY | 4246 | TATGACTTTTGGAGTGGTTACTAC | 5203 |
| 127 | AKET | 4893 | GCCAAGGAAACT | 5065 | YYDFWSG | 4248 | TACTACGATTTCTGGTCAGGC | 5204 |
| 128 | AKDT | 4894 | GCCAAGGATACT | 5066 | YDFWSGY | 4249 | TATGACTTCTGGAGTGGTTAC | 5205 |
| 129 | AKGT | 4895 | GCCAAGGGAACT | 5067 | DFWSGYY | 4250 | GACTTCTGGTCAGGATACTAC | 5206 |
| 130 | AKV | n/a | GCCAAGGTG | n/a | VLRYF | 4307 | GTGTTGAGGTACTTC | 5207 |
| 131 | AKEV | 4896 | GCCAAGGAAGTG | 5068 | LRYFD | 4308 | TTAAGATACTTTGAT | 5208 |
| 132 | AKDV | 4897 | GCCAAGGACGTG | 5069 | RYFDW | 4309 | AGATACTTTGATTGG | 5209 |
| 133 | AKGV | 4898 | GCCAAGGGCGTG | 5070 | VLRY | 4312 | GTGTTGAGGTAT | 5210 |
| 134 | AKEG G | 4899 | GCCAAGGAGGGAG GA | 5071 | LRYF | 4313 | TTGAGATATTTC | 5211 |
| 135 | AKDG G | 4900 | GCCAAGGACGGTG GA | 5072 | RYFD | 4314 | AGATACTTTGAT | 5212 |
| 136 | AKGG G | 4901 | GCCAAGGGAGGAG GA | 5073 | VLRYFDWL | 4298 | GTCTTAAGGTACTTCGATTGGCTT | 5213 |
| 137 | AKDG R | 4902 | GCCAAGGACGGTA GA | 5074 | LRY | n/a | TTAAGATAC | n/a |
| 138 | AKGG S | 4903 | GCCAAGGGAGGTT CT | 5075 | RYF | n/a | AGATACTTC | n/a |
| 139 | AKGG P | 4904 | GCCAAGGGAGGTC CT | 5076 | RY | n/a | AGATAT | n/a |
| 140 | AKGG A | 4905 | GCCAAGGGAGGCG CT | 5077 | FD | n/a | TTCGAT | n/a |
| 141 | AKDG T | 4906 | GCCAAGGATGGCA CT | 5078 | DW | n/a | GATTGG | n/a |
| 142 | AKGG T | 4907 | GCCAAGGGAGGCA CT | 5079 | VLRYFDW | 4300 | GTCTTAAGATACTTTGATTGG | 5214 |

TABLE 25-continued

Segments used in Exemplary Library Design 3 (ELD-3). The sequences collectively form a theoretical segment pool that comprises individual theoretical segment pools of TN1, DH, N2, and H3-JH segments.

| | | | | | | | | |
|---|---|---|---|---|---|---|---|---|
| 143 | AKEGV | 4908 | GCCAAGGAAGGAGTG | 5080 | VLRYFD | 4303 | GTGTTGAGGTACTTTGAC | 5215 |
| 144 | AKGGV | 4909 | GCCAAGGGCGGTGTG | 5081 | LRYFDW | 4304 | TTAAGATACTTCGATTGG | 5216 |
| 145 | AKRG | 4910 | GCCAAGAGAGGA | 5082 | RYFDWL | 4305 | AGATATTTCGACTGGCTT | 5217 |
| 146 | AKERG | 4911 | GCCAAGGAGAGAGGA | 5083 | YDILTGYY | 4322 | TATGACATATTGACTGGCTACTAC | 5218 |
| 147 | AKDRG | 4912 | GCCAAGGATAGGGGA | 5084 | YDILTGY | 4325 | TATGATATATTAACTGGGTAC | 5219 |
| 148 | AKGRG | 4913 | GCCAAGGGTAGGGGA | 5085 | DILTGYY | 4326 | GATATCTTAACCGGGTATTAT | 5220 |
| 149 | AKSG | 4914 | GCCAAGTCTGGA | 5086 | DYG | n/a | GATTATGGT | n/a |
| 150 | AKDSG | 4915 | GCCAAGGATAGTGGA | 5087 | GDY | n/a | GGGGACTAC | n/a |
| 151 | AKDPG | 4916 | GCCAAGGACCCCGGA | 5088 | YGD | n/a | TACGGTGAC | n/a |
| 152 | AKLG | 4917 | GCCAAGTTAGGA | 5089 | DYGD | 4349 | GATTACGGCGAT | 5221 |
| 153 | AKDLG | 4918 | GCCAAGGATCTTGGA | 5090 | YGDY | 4350 | TACGGCGATTAT | 5222 |
| 154 | AKAG | 4919 | GCCAAGGCTGGA | 5091 | DYGDY | 4348 | GACTACGGAGATTAT | 5223 |
| 155 | AKVG | 4920 | GCCAAGGTAGGA | 5092 | TTVTT | 4351 | ACCACAGTAACCACC | 5224 |
| 156 | AKGVG | 4921 | GCCAAGGGTGTCGGA | 5093 | TTVT | 4352 | ACAACTGTGACT | 5225 |
| 157 | AKPR | 4922 | GCCAAGCCTAGA | 5094 | TVTT | 4353 | ACAGTAACTACT | 5226 |
| 158 | AKGPR | 4923 | GCCAAGGGCCCCAGA | 5095 | RW | n/a | AGATGG | n/a |
| 159 | AKPS | 4924 | GCCAAGCCTTCT | 5096 | VTP | n/a | GTAACTCCT | n/a |
| 160 | AKDPS | 4925 | GCCAAGGATCCCTCT | 5097 | VD | n/a | GTTGAC | n/a |
| 161 | AKGPS | 4926 | GCCAAAGGGCCATCT | 5098 | GYSGYD | 4386 | GGCTACTCAGGATACGAC | 5227 |
| 162 | AKDPP | 4927 | GCCAAGGATCCACCT | 5099 | YSGYD | 4389 | TATAGCGGATATGAC | 5228 |
| 163 | AKGPP | 4928 | GCCAAGGGCCCTCCT | 5100 | RD | n/a | AGAGAT | n/a |
| 164 | AKPL | 4929 | GCCAAGCCGTTG | 5101 | RDGY | 4410 | AGAGATGGTTAC | 5229 |
| 165 | AKDPL | 4930 | GCCAAGGACCCTTTG | 5102 | RDG | n/a | AGAGATGGT | n/a |
| 166 | AKRP | 4931 | GCCAAGAGGCCT | 5103 | DTAM | 4420 | GATACTGCTATG | 5230 |
| 167 | AKDRP | 4932 | GCCAAGGACCGTCCT | 5104 | YGY | n/a | TACGGCTAC | n/a |
| 168 | AKSP | 4933 | GCCAAGAGTCCT | 5105 | YSY | n/a | TATTCTTAC | n/a |
| 169 | AKLP | 4934 | GCCAAGCTACCT | 5106 | YSYG | 4433 | TATTCATATGGT | 5231 |
| 170 | AKAP | 4935 | GCCAAGGCTCCT | 5107 | GYSYG | 4430 | GGATATAGTTATGGC | 5232 |
| 171 | AKTP | 4936 | GCCAAGACGCCT | 5108 | SSS | n/a | AGTTCAAGC | n/a |
| 172 | AKVP | 4937 | GCCAAGGTACCT | 5109 | YSSSWY | 4437 | TACAGTAGCTCTTGGTAC | 5233 |

TABLE 25-continued

Segments used in Exemplary Library Design 3 (ELD-3). The sequences collectively form a theoretical segment pool that comprises individual theoretical segment pools of TN1, DH, N2, and H3-JH segments.

| | | | | | | | | |
|---|---|---|---|---|---|---|---|---|
| 173 | AKVGG | 4938 | GCCAAGGTGGGTGGA | 5110 | GYSSSWY | 4435 | GGCTACAGTTCAAGCTGGTAT | 5234 |
| 174 | AKQ | n/a | GCAAAACAG | n/a | SSW | n/a | AGTTCCTGG | n/a |
| 175 | AKH | n/a | GCCAAACAC | n/a | SWY | n/a | AGCTGGTAC | n/a |
| 176 | AKDQ | 4939 | GCCAAGGATCAG | 5111 | SSSW | 4443 | AGTAGCTCTTGG | 5235 |
| 177 | AKDH | 4940 | GCTAAAGACCAC | 5112 | YSSS | 4442 | TACAGCAGCTCC | 5236 |
| 178 | AKAR | 4941 | GCCAAGGCAAGA | 5113 | YSSSW | 4449 | TACTCTTCCTCATGG | 5237 |
| 179 | AKAS | 4942 | GCCAAGGCATCT | 5114 | SW | n/a | AGCTGG | n/a |
| 180 | AKDQG | 4943 | GCAAAGGATCAGGGA | 5115 | AG | n/a | GCTGGT | n/a |
| 181 | AKSR | 4944 | GCCAAGAGTAGA | 5116 | QQLV | 4455 | CAGCAATTGGTT | 5238 |
| 182 | AKDRS | 4945 | GCAAAAGACAGGTCT | 5117 | QQL | n/a | CAGCAACTT | n/a |
| 183 | AKSL | 4946 | GCAAAGAGCTTG | 5118 | GWY | n/a | GGTTGGTAC | n/a |
| 184 | AKLH | 4947 | GCTAAATTGCAC | 5119 | SSGWY | 4461 | AGCTCTGGATGGTAC | 5239 |
| 185 | AKDLT | 4948 | GCCAAGGACTTGACT | 5120 | YSSGW | 4460 | TATAGTAGCGGATGG | 5240 |
| 186 | AKK | n/a | GCTAAAAAG | n/a | YSSGWY | 4458 | TATAGCAGCGGTTGGTAC | 5241 |
| 187 | AKAE | 4949 | GCTAAAGCAGAG | 5121 | GYSSGWY | 4456 | GGTTATTCATCAGGTTGGTAT | 5242 |
| 188 | AKDLS | 4950 | GCAAAAGACTTGTCT | 5122 | SGW | n/a | AGTGGTTGG | n/a |
| 189 | AKGD | 4951 | GCAAAAGGGGAC | 5123 | YSS | n/a | TACAGTTCC | n/a |
| 190 | AKAR | 4952 | GCAAAAAGGAGA | 5124 | SGWY | 4464 | AGTGGTTGGTAT | 5243 |
| 191 | AKDK | 4953 | GCAAAAGACAAG | 5125 | SSGW | 4463 | AGTTCCGGTTGG | 5244 |
| 192 | AKVS | 4954 | GCCAAAGTATCT | 5126 | YSSG | 4462 | TACTCAAGTGGT | 5245 |
| 193 | AKDRL | 4955 | GCAAAAGACAGGTTG | 5127 | GW | n/a | GGTTGG | n/a |
| 194 | AKGQ | 4956 | GCCAAAGGACAG | 5128 | QWLV | 4475 | CAGTGGTTAGTT | 5246 |
| 195 | AKVR | 4957 | GCAAAAGTCAGA | 5129 | EYSS | 4479 | GAGTACTCATCC | 5247 |
| 196 | AKAK | 4958 | GCAAAGGCAAAG | 5130 | SIAARP | 4481 | AGCATAGCAGCAAGGCCT | 5248 |
| 197 | AKGK | 4959 | GCAAAGGGCAAG | 5131 | RP | n/a | CGTCCT | n/a |
| 198 | AKDIS | 4960 | GCAAAGGACATTTCT | 5132 | IAARP | 4483 | ATAGCAGCAAGGCCT | 5249 |
| 199 | AKDFT | 4961 | GCTAAAGATTTCACT | 5133 | AARP | 4486 | GCCGCAAGACCT | 5250 |
| 200 | AKQG | 4962 | GCCAAGCAAGGA | 5134 | ARP | n/a | GCTAGACCT | n/a |

| Segment No. | N2 | N2 Nucleotides | H3-JH | SEQ ID NO | H3-JH Nucleotides | SEQ ID NO |
|---|---|---|---|---|---|---|
| 1 | — | — | — | n/a | — | n/a |
| 2 | A | GCT | Y | n/a | TAT | n/a |
| 3 | D | GAT | DI | n/a | GATATT | n/a |
| 4 | E | GAG | DL | n/a | GACTTG | n/a |

TABLE 25-continued

Segments used in Exemplary Library Design 3 (ELD-3). The sequences collectively form a theoretical segment pool that comprises individual theoretical segment pools of TN1, DH, N2, and H3-JH segments.

| | | | | | | |
|---|---|---|---|---|---|---|
| 5 | F | TTC | DP | n/a | GATCCT | n/a |
| 6 | G | GGC | DV | n/a | GATGTA | n/a |
| 7 | H | CAT | DY | n/a | GACTAT | n/a |
| 8 | I | ATC | QH | n/a | CAGCAC | n/a |
| 9 | K | AAA | ADY | n/a | GCTGATTAT | n/a |
| 10 | L | CTG | DDY | n/a | GATGACTAT | n/a |
| 11 | M | ATG | FDI | n/a | TTTGACATT | n/a |
| 12 | P | CCT | FDL | n/a | TTCGACTTA | n/a |
| 13 | Q | CAG | FDP | n/a | TTTGACCCT | n/a |
| 14 | R | AGG | FDY | n/a | TTCGACTAT | n/a |
| 15 | S | TCA | FQH | n/a | TTCCAGCAC | n/a |
| 16 | T | ACC | GDY | n/a | GGTGACTAC | n/a |
| 17 | V | GTT | IDY | n/a | ATCGACTAT | n/a |
| 18 | W | TGG | LDY | n/a | TTGGACTAT | n/a |
| 19 | Y | TAC | MDV | n/a | ATGGATGTG | n/a |
| 20 | AD | GCTGAT | PDY | n/a | CCAGATTAT | n/a |
| 21 | AG | GCAGGC | SDY | n/a | TCTGATTAC | n/a |
| 22 | AP | GCCCCA | VDY | n/a | GTTGACTAC | n/a |
| 23 | AQ | GCTCAG | YDY | n/a | TATGATTAC | n/a |
| 24 | AR | GCTAGG | AFDI | 4539 | GCCTTCGATATC | 5251 |
| 25 | AS | GCTAGT | AFDY | 4592 | GCCTTCGATTAC | 5252 |
| 26 | AT | GCTACC | DFDY | 4581 | GATTTCGACTAT | 5253 |
| 27 | AY | GCCTAC | FFDY | 4583 | TTCTTCGATTAC | 5254 |
| 28 | DA | GACGCC | GFDP | 4623 | GGGTTGACCCA | 5255 |
| 29 | DD | GACGAT | GFDY | 4590 | GGGTTCGACTAC | 5256 |
| 30 | DE | GACGAG | GMDV | 4641 | GGCATGGATGTA | 5257 |
| 31 | DG | GATGGT | HFDY | 4582 | CACTTTGACTAT | 5258 |
| 32 | DL | GACTTG | IFDY | 4588 | ATATTCGATTAC | 5259 |
| 33 | DP | GACCCT | LFDY | 4586 | TTATTTGATTAT | 5260 |
| 34 | DS | GACTCC | NFDY | 4580 | AACTTTGATTAC | 5261 |
| 35 | DY | GATTAT | PFDY | 4587 | CCCTTCGACTAT | 5262 |
| 36 | EA | GAGGCC | RFDY | 4585 | AGGTTTGACTAT | 5263 |
| 37 | ED | GAGGAC | SFDY | 4584 | AGTTTCGATTAC | 5264 |
| 38 | EG | GAAGGA | TFDY | 4589 | ACATTTGACTAC | 5265 |
| 39 | EK | GAGAAA | VFDY | 4591 | GTTTTCGATTAT | 5266 |
| 40 | ER | GAAAGA | WFDP | 4596 | TGGTTCGATCCA | 5267 |
| 41 | ES | GAATCT | YFDL | 4529 | TATTTCGACTTA | 5268 |
| 42 | ET | GAAACA | YFDY | 4567 | TACTTCGATTAC | 5269 |

TABLE 25-continued

Segments used in Exemplary Library Design 3 (ELD-3). The sequences collectively form a theoretical segment pool that comprises individual theoretical segment pools of TN1, DH, N2, and H3-JH segments.

| | | | | | |
|---|---|---|---|---|---|
| 43 | FA | TTCGCT | YFQH | 4489 TATTTCCAGCAC | 5270 |
| 44 | FH | TTCCAT | YMDV | 4687 TATATGGATGTC | 5271 |
| 45 | FL | TTCTTG | DAFDI | 4538 GATGCCTTCGACATA | 5272 |
| 46 | FR | TTTAGG | DWFDP | 4609 GACTGGTTTGACCCC | 5273 |
| 47 | FS | TTTAGT | DYFDY | 4566 GACTACTTTGATTAC | 5274 |
| 48 | GA | GGAGCC | EYFQH | 4488 GAATACTTCCAACAC | 5275 |
| 49 | GD | GGTGAT | GAFDI | 4549 GGCGCATTCGATATT | 5276 |
| 50 | GE | GGTGAG | GWFDP | 4619 GGGTGGTTTGATCCA | 5277 |
| 51 | GG | GGAGGC | GYFDY | 4577 GGCTATTTTGACTAC | 5278 |
| 52 | GL | GGATTG | HAFDI | 4541 CATGCTTTTGATATA | 5279 |
| 53 | GP | GGACCA | HYFDY | 4569 CATTACTTCGATTAC | 5280 |
| 54 | GR | GGTAGG | NAFDI | 4565 AACGCATTCGATATT | 5281 |
| 55 | GS | GGCAGT | NWFDP | 4595 AACTGGTTCGATCCA | 5282 |
| 56 | GT | GGAACA | NYFDY | 4593 AATTATTTCGACTAT | 5283 |
| 57 | GV | GGAGTT | PYFDY | 4574 CCCTACTTTGACTAT | 5284 |
| 58 | GW | GGATGG | RAFDI | 4544 AGAGCCTTTGATATC | 5285 |
| 59 | GY | GGATAT | RYFDY | 4572 AGGTACTTCGATTAC | 5286 |
| 60 | HE | CATGAG | SWFDP | 4613 TCATGGTTCGACCCC | 5287 |
| 61 | HL | CATTTG | SYFDY | 4571 AGTTACTTTGACTAT | 5288 |
| 62 | HP | CATCCT | TYFDY | 4576 ACTTATTTCGACTAC | 5289 |
| 63 | HS | CACTCC | VAFDI | 4550 GTGGCCTTCGACATT | 5290 |
| 64 | IF | ATCTTC | VYFDY | 4578 GTCTATTTTGATTAT | 5291 |
| 65 | IG | ATCGGC | WYFDL | 4528 TGGTATTTCGATTTG | 5292 |
| 66 | IR | ATAAGG | YAFDI | 4540 TACGCATTTGACATC | 5293 |
| 67 | IS | ATCAGT | YGMDV | 4640 TACGGCATGGACGTG | 5294 |
| 68 | KG | AAAGGA | YYFDY | 4568 TATTATTTTGATTAC | 5295 |
| 69 | KR | AAGAGA | YYMDV | 4686 TATTATATGGACGTC | 5296 |
| 70 | KV | AAAGTG | AEYFQH | 4526 GCAGAGTACTTCCAGCAC | 5297 |
| 71 | LD | TTGGAT | DNWFDP | 4594 GACAATTGGTTTGATCCC | 5298 |
| 72 | LE | TTAGAG | DWYFDL | 4530 GATTGGTACTTCGACTTG | 5299 |
| 73 | LG | TTAGGT | GNWFDP | 4606 GGGAATTGGTTTGATCCT | 5300 |
| 74 | LH | TTACAT | NWYFDL | 4532 AACTGGTATTTCGACTTA | 5301 |
| 75 | LL | TTATTG | PNWFDP | 4603 CCCAATTGGTTTGATCCA | 5302 |
| 76 | LP | TTACCA | SNWFDP | 4600 AGTAATTGGTTTGACCCC | 5303 |
| 77 | LR | TTGAGG | YNWFDP | 4597 TATAATTGGTTTGATCCT | 5304 |
| 78 | LS | TTAAGC | YWYFDL | 4527 TATTGGTATTTTGATTTG | 5305 |
| 79 | LT | TTGACA | YYGMDV | 4639 TACTATGGGATGGACGTG | 5306 |
| 80 | LV | TTGGTA | YYYMDV | 4685 TACTATTACATGGACGTT | 5307 |

TABLE 25-continued

Segments used in Exemplary Library Design 3 (ELD-3). The sequences collectively form a theoretical segment pool that comprises individual theoretical segment pools of TN1, DH, N2, and H3-JH segments.

| | | | | | | |
|---|---|---|---|---|---|---|
| 81 | LW | TTGTGG | YYYGMDV | 4638 | TATTATTACGGTATGGACGTC | 5308 |
| 82 | LY | TTGTAC | YYYYMDV | 4684 | TACTATTATTACATGGATGTC | 5309 |
| 83 | MG | ATGGGC | DYYYGMDV | 4668 | GACTATTATTACGGTATGGATGTT | 5310 |
| 84 | MT | ATGACC | GYYYGMDV | 4677 | GGCTACTATTATGGTATGGACGTC | 5311 |
| 85 | PA | CCTGCT | HYYYGMDV | 4669 | CATTACTACTATGGGATGGATGTA | 5312 |
| 86 | PD | CCTGAT | NYYYYMDV | 4713 | AACTATTATTATTATATGGATGTC | 5313 |
| 87 | PE | CCTGAG | PYYYYMDV | 4720 | CCCTACTACTACTATATGGATGTG | 5314 |
| 88 | PF | CCTTTC | RYYYYMDV | 4718 | AGGTATTACTACTACATGGACGTC | 5315 |
| 89 | PG | CCTGGT | YYYYGMDV | 4637 | TACTATTATTATGGGATGGATGTG | 5316 |
| 90 | PH | CCACAT | DYYYYGMDV | 4665 | GATTACTATTATTACGGAATGGATGTT | 5317 |
| 91 | PL | CCATTA | GYYYYGMDV | 4654 | GGGTATTACTACTACGGCATGGACGTA | 5318 |
| 92 | PP | CCTCCA | NYYYYGMDV | 4654 | AATTACTATTACTATGGCATGGATGTG | 5319 |
| 93 | PQ | CCTCAG | PYYYYGMDV | 4661 | CCATATTACTATTACGGCATGGATGTC | 5320 |
| 94 | PR | CCAAGG | SYYYYGMDV | 4658 | AGCTACTACTACTACGGAATGGACGTC | 5321 |
| 95 | PS | CCTTCT | YYYYYGMDV | 4636 | TACTACTACTATTACGGTATGGACGTA | 5322 |
| 96 | PT | CCTACA | DYYYYYYMDV | 4681 | GATTATTATTACTACTACTACATGGATGTA | 5323 |
| 97 | PV | CCTGTT | GYYYYYGMDV | 4651 | GGTTATTATTACTACTATGGGATGGATGTA | 5324 |
| 98 | QG | CAGGGC | HYYYYYGMDV | 4643 | CACTACTATTATTATTACGGGATGGATGTA | 5325 |
| 99 | QL | CAATTA | RYYYYYYMDV | 4692 | AGATACTACTACTATTATTACATGGATGTA | 5326 |
| 100 | QP | CAGCCA | YYYYYYGMDV | 4642 | TATTACTACTATTACTATGGTATGGACGTT | 5327 |
| 101 | QS | CAGTCA | | | | |
| 102 | QT | CAGACT | | | | |
| 103 | RA | AGGGCT | | | | |
| 104 | RD | AGGGAC | | | | |
| 105 | RE | AGGGAG | | | | |
| 106 | RF | AGATTC | | | | |
| 107 | RG | AGGGGA | | | | |
| 108 | RH | AGGCAT | | | | |
| 109 | RL | AGATTA | | | | |
| 110 | am | AGGATG | | | | |
| 111 | RP | AGGCCA | | | | |
| 112 | RR | CGTAGA | | | | |
| 113 | RS | AGAAGT | | | | |
| 114 | RV | AGAGTG | | | | |
| 115 | RY | AGATAT | | | | |
| 116 | SA | TCAGCC | | | | |

TABLE 25-continued

Segments used in Exemplary Library Design 3 (ELD-3). The sequences collectively form a theoretical segment pool that comprises individual theoretical segment pools of TN1, DH, N2, and H3-JH segments.

| | | |
|---|---|---|
| 117 | SD | TCAGAC |
| 118 | SE | TCCGAG |
| 119 | SF | TCATTC |
| 120 | SG | AGCGGA |
| 121 | SH | AGTCAC |
| 122 | SI | TCTATC |
| 123 | SK | AGTAAA |
| 124 | SL | TCCTTG |
| 125 | SP | AGCCCA |
| 126 | SQ | AGCCAA |
| 127 | SR | TCAAGA |
| 128 | SS | TCCTCA |
| 129 | ST | AGTACA |
| 130 | SV | TCAGTA |
| 131 | SW | TCATGG |
| 132 | SY | TCTTAC |
| 133 | TA | ACCGCC |
| 134 | TG | ACTGGC |
| 135 | TP | ACACCA |
| 136 | TR | ACAAGA |
| 137 | TS | ACATCT |
| 138 | TT | ACTACT |
| 139 | TV | ACAGTT |
| 140 | TW | ACTTGG |
| 141 | TY | ACTTAT |
| 142 | VA | GTAGCC |
| 143 | VD | GTCGAC |
| 144 | VG | GTTGGA |
| 145 | VL | GTCTTG |
| 146 | VP | GTTCCT |
| 147 | VR | GTGAGA |
| 148 | VS | GTTTCA |
| 149 | VT | GTTACC |
| 150 | VV | GTAGTA |
| 151 | WG | TGGGGT |
| 152 | WS | TGGTCA |
| 153 | YA | TACGCT |
| 154 | YD | TATGAC |

TABLE 25-continued

Segments used in Exemplary Library Design 3 (ELD-3). The sequences collectively form a theoretical segment pool that comprises individual theoretical segment pools of TN1, DH, N2, and H3-JH segments.

| | | |
|---|---|---|
| 155 | YE | TATGAG |
| 156 | YS | TATTCT |
| 157 | AA A | GCTGCCGCT |
| 158 | AG M | GCAGGCATG |
| 159 | DG G | GATGGGGGT |
| 160 | DG V | GATGGTGTA |
| 161 | FG G | TTCGGGGGC |
| 162 | GA G | GGAGCTGGA |
| 163 | GG A | GGAGGGGCC |
| 164 | GG G | GGAGGCGGT |
| 165 | GG L | GGAGGCTTA |
| 166 | GG R | GGTGGTAGA |
| 167 | GG S | GGCGGGAGC |
| 168 | GG V | GGTGGGGTA |
| 169 | GL G | GGATTAGGC |
| 170 | GP G | GGCCCCGGC |
| 171 | GP P | GGACCACCT |
| 172 | GR G | GGAAGGGGC |
| 173 | GS G | GGATCTGGC |
| 174 | GT G | GGAACTGGC |
| 175 | GV G | GGAGTAGGT |
| 176 | LG G | TTGGGAGGC |
| 177 | LG H | TTGGGCCAC |
| 178 | PG G | CCTGGCGGC |
| 179 | PK Q | CCAAAGCAG |
| 180 | PK R | CCTAAAAGG |

TABLE 25-continued

Segments used in Exemplary Library Design 3 (ELD-3). The sequences collectively form a theoretical segment pool that comprises individual theoretical segment pools of TN1, DH, N2, and H3-JH segments.

| | | |
|---|---|---|
| 181 | PTQ | CCAACTCAG |
| 182 | RFE | AGGTTTGAG |
| 183 | RGG | AGGGGAGGT |
| 184 | RGL | AGGGGATTG |
| 185 | RG | AGGGGTAGT |
| 186 | RPL | AGGCCATTA |
| 187 | RPY | AGGCCATAT |
| 188 | SAA | TCTGCCGCC |
| 189 | SGE | AGCGGGGAG |
| 190 | SGG | TCTGGCGGC |
| 191 | SGKL | TCAGGGTTA |
| 192 | SGW | AGCGGTTGG |
| 193 | SGY | AGCGGCTAC |
| 194 | SRG | TCAAGAGGT |
| 195 | SSE | TCATCAGAG |
| 196 | SSW | AGCTCATGG |
| 197 | TGG | ACCGGTGGC |
| 198 | VGR | GTTGGCAGA |
| 199 | VQG | GTGCAAGGA |
| 200 | VTA | GTCACAGCT |

[1]"AR" and "AK" refer to the last two C-terminal amino acids of the heavy chain chassis used in the current example. They are not part of the TN1 segment.

TABLE 26

Theoretical segment pool of 300 TN1 segments (plus AR/AK; which is not part of TN1) used in the library of Example 12.

| Peptide (plus AR or AK)[1] | SEQ ID NO | Nucleotide (plus AR or AK)[1] | SEQ ID NO | In ELD-3? |
|---|---|---|---|---|
| AR | n/a | GCCAGA | n/a | YES |
| AK | n/a | GCCAAG | n/a | YES |

TABLE 26-continued

| Theoretical segment pool of 300 TN1 segments (plus AR/AK; which is not part of TN1) used in the library of Example 12. | | | | |
|---|---|---|---|---|
| Peptide (plus AR or AK)[1] | SEQ ID NO | Nucleotide (plus AR or AK)[1] | SEQ ID NO | In ELD-3? |
| ARE | n/a | GCCAGAGAG | n/a | YES |
| AKE | n/a | GCCAAGGAG | n/a | YES |
| ARD | n/a | GCCAGAGAC | n/a | YES |
| AKD | n/a | GCCAAGGAC | n/a | YES |
| ARG | n/a | GCCAGAGGA | n/a | YES |
| AKG | n/a | GCCAAGGGA | n/a | YES |
| AREG | 4791 | GCCAGAGAGGGA | 4963 | YES |
| AKEG | 4877 | GCCAAGGAAGGA | 5049 | YES |
| ARDG | 4792 | GCCAGAGACGGA | 4964 | YES |
| AKDG | 4878 | GCCAAGGACGGA | 5050 | YES |
| ARGG | 4793 | GCCAGAGGTGGA | 4965 | YES |
| AKGG | 4879 | GCCAAGGGCGGA | 5051 | YES |
| ARR | n/a | GCCAGGAGA | n/a | YES |
| AKR | n/a | GCCAAGAGA | n/a | YES |
| ARER | 4794 | GCCAGAGAGAGA | 4966 | YES |
| AKER | 4880 | GCCAAGGAAAGA | 5052 | YES |
| ARDR | 4795 | GCCAGAGACAGA | 4967 | YES |
| AKDR | 4881 | GCCAAGGACAGA | 5053 | YES |
| ARGR | 4796 | GCCAGAGGCAGA | 4968 | YES |
| AKGR | 4882 | GCCAAGGGCAGA | 5054 | YES |
| ARS | n/a | GCCAGATCT | n/a | YES |
| AKS | n/a | GCCAAGTCT | n/a | YES |
| ARES | 4797 | GCCAGAGAATCT | 4969 | YES |
| AKES | 4883 | GCCAAGGAATCT | 5055 | YES |
| ARDS | 4798 | GCCAGAGACTCT | 4970 | YES |
| AKDS | 4884 | GCCAAGGATTCT | 5056 | YES |
| ARGS | 4799 | GCCAGAGGTTCT | 4971 | YES |
| AKGS | 4885 | GCCAAGGGATCT | 5057 | YES |
| ARP | n/a | GCCAGACCT | n/a | YES |
| AKP | n/a | GCCAAGCCT | n/a | YES |
| AREP | 5328 | GCCAGAGAGCCT | 5428 | NO |
| AKEP | 5329 | GCCAAGGAGCCT | 5429 | NO |
| ARDP | 4800 | GCCAGAGACCCT | 4972 | YES |
| AKDP | 4886 | GCCAAGGATCCT | 5058 | YES |
| ARGP | 4801 | GCCAGAGGGCCT | 4973 | YES |
| AKGP | 4887 | GCCAAGGGTCCT | 5059 | YES |
| ARL | n/a | GCCAGATTG | n/a | YES |

TABLE 26-continued

Theoretical segment pool of 300 TN1 segments (plus AR/AK; which is not part of TN1) used in the library of Example 12.

| Peptide (plus AR or AK)[1] | SEQ ID NO | Nucleotide (plus AR or AK)[1] | SEQ ID NO | In ELD-3? |
|---|---|---|---|---|
| AKL | n/a | GCCAAGTTG | n/a | YES |
| AREL | 5330 | GCCAGAGAGTTG | 5430 | NO |
| AKEL | 5331 | GCCAAGGAATTG | 5431 | NO |
| ARDL | 4802 | GCCAGAGACTTG | 4974 | YES |
| AKDL | 4888 | GCCAAGGACTTG | 5060 | YES |
| ARGL | 4803 | GCCAGAGGGTTG | 4975 | YES |
| AKGL | 4889 | GCCAAGGGGTTG | 5061 | YES |
| ARA | n/a | GCCAGAGCT | n/a | YES |
| AKA | n/a | GCCAAGGCT | n/a | YES |
| AREA | 4804 | GCCAGAGAGGCT | 4976 | YES |
| AKEA | 4890 | GCCAAGGAAGCT | 5062 | YES |
| ARDA | 4805 | GCCAGAGATGCT | 4977 | YES |
| AKDA | 4891 | GCCAAGGACGCT | 5063 | YES |
| ARGA | 4806 | GCCAGAGGTGCT | 4978 | YES |
| AKGA | 4892 | GCCAAGGGCGCT | 5064 | YES |
| ART | n/a | GCCAGAACT | n/a | YES |
| AKT | n/a | GCCAAGACT | n/a | YES |
| ARET | 4807 | GCCAGAGAGACT | 4979 | YES |
| AKET | 4893 | GCCAAGGAAACT | 5065 | YES |
| ARDT | 4808 | GCCAGAGATACT | 4980 | YES |
| AKDT | 4894 | GCCAAGGATACT | 5066 | YES |
| ARGT | 4809 | GCCAGAGGCACT | 4981 | YES |
| AKGT | 4895 | GCCAAGGGAACT | 5067 | YES |
| ARV | n/a | GCCAGAGTG | n/a | YES |
| AKV | n/a | GCCAAGGTG | n/a | YES |
| AREV | 4810 | GCCAGAGAGGTG | 4982 | YES |
| AKEV | 4896 | GCCAAGGAAGTG | 5068 | YES |
| ARDV | 4811 | GCCAGAGATGTG | 4983 | YES |
| AKDV | 4897 | GCCAAGGACGTG | 5069 | YES |
| ARGV | 4812 | GCCAGAGGGGTG | 4984 | YES |
| AKGV | 4898 | GCCAAGGGCGTG | 5070 | YES |
| AREGG | 4813 | GCCAGAGAGGGAGGA | 4985 | YES |
| AKEGG | 4899 | GCCAAGGAGGGAGGA | 5071 | YES |
| ARDGG | 4814 | GCCAGAGATGGTGGA | 4986 | YES |
| AKDGG | 4900 | GCCAAGGACGGTGGA | 5072 | YES |
| ARGGG | 4815 | GCCAGAGGTGGAGGA | 4987 | YES |
| AKGGG | 4901 | GCCAAGGGAGGAGGA | 5073 | YES |

TABLE 26-continued

Theoretical segment pool of 300 TN1 segments (plus AR/AK; which is not part of TN1) used in the library of Example 12.

| Peptide (plus AR or AK)[1] | SEQ ID NO | Nucleotide (plus AR or AK)[1] | SEQ ID NO | In ELD-3? |
|---|---|---|---|---|
| AREGR | 5332 | GCCAGAGAAGGGAGA | 5432 | NO |
| AKEGR | 5333 | GCCAAGGAAGGCAGA | 5433 | NO |
| ARDGR | 4816 | GCCAGAGACGGCAGA | 4988 | YES |
| AKDGR | 4902 | GCCAAGGACGGTAGA | 5074 | YES |
| ARGGR | 5334 | GCCAGAGGAGGTAGA | 5434 | NO |
| AKGGR | 5335 | GCCAAGGGAGGTAGA | 5435 | NO |
| AREGS | 5336 | GCCAGAGAAGGATCT | 5436 | NO |
| AKEGS | 5337 | GCCAAGGAAGGATCT | 5437 | NO |
| ARDGS | 5338 | GCCAGAGACGGATCT | 5438 | NO |
| AKDGS | 5339 | GCCAAGGATGGTTCT | 5439 | NO |
| ARGGS | 4817 | GCCAGAGGCGGTTCT | 4989 | YES |
| AKGGS | 4903 | GCCAAGGGAGGTTCT | 5075 | YES |
| AREGP | 5340 | GCCAGAGAAGGTCCT | 5440 | NO |
| AKEGP | 5341 | GCCAAGGAGGGGCCT | 5441 | NO |
| ARDGP | 5342 | GCCAGAGACGGTCCT | 5442 | NO |
| AKDGP | 5343 | GCCAAGGACGGTCCT | 5443 | NO |
| ARGGP | 4818 | GCCAGAGGTGGGCCT | 4990 | YES |
| AKGGP | 4904 | GCCAAGGGAGGTCCT | 5076 | YES |
| AREGL | 5344 | GCCAGAGAGGGCTTG | 5444 | NO |
| AKEGL | 5345 | GCCAAGGAAGGGTTG | 5445 | NO |
| ARDGL | 5346 | GCCAGAGATGGGTTG | 5446 | NO |
| AKDGL | 5347 | GCCAAGGACGGTTTG | 5447 | NO |
| ARGGL | 5348 | GCCAGAGGTGGATTG | 5448 | NO |
| AKGGL | 5349 | GCCAAGGGAGGGTTG | 5449 | NO |
| AREGA | 5350 | GCCAGAGAAGGAGCT | 5450 | NO |
| AKEGA | 5351 | GCCAAGGAGGGAGCT | 5451 | NO |
| ARDGA | 5352 | GCCAGAGATGGCGCT | 5452 | NO |
| AKDGA | 5353 | GCCAAGGATGGAGCT | 5453 | NO |
| ARGGA | 4819 | GCCAGAGGAGGTGCT | 4991 | YES |
| AKGGA | 4905 | GCCAAGGGAGGCGCT | 5077 | YES |
| ARDGT | 4820 | GCCAGAGACGGTACT | 4992 | YES |
| AKDGT | 4906 | GCCAAGGATGGCACT | 5078 | YES |
| ARGGT | 4821 | GCCAGAGGTGGAACT | 4993 | YES |
| AKGGT | 4907 | GCCAAGGGAGGCACT | 5079 | YES |
| AREGV | 4822 | GCCAGAGAGGGAGTG | 4994 | YES |
| AKEGV | 4908 | GCCAAGGAAGGAGTG | 5080 | YES |
| ARDGV | 5354 | GCCAGAGATGGTGTG | 5454 | NO |

TABLE 26-continued

Theoretical segment pool of 300 TN1 segments (plus AR/AK; which is not part of TN1) used in the library of Example 12.

| Peptide (plus AR or AK)[1] | SEQ ID NO | Nucleotide (plus AR or AK)[1] | SEQ ID NO | In ELD-3? |
|---|---|---|---|---|
| AKDGV | 5355 | GCCAAGGATGGTGTG | 5455 | NO |
| ARGGV | 4823 | GCCAGAGGTGGCGTG | 4995 | YES |
| AKGGV | 4909 | GCCAAGGGCGGTGTG | 5081 | YES |
| ARRG | 4824 | GCCAGAAGAGGA | 4996 | YES |
| AKRG | 4910 | GCCAAGAGAGGA | 5082 | YES |
| ARERG | 4825 | GCCAGAGAGCGTGGA | 4997 | YES |
| AKERG | 4911 | GCCAAGGAGAGAGGA | 5083 | YES |
| ARDRG | 4826 | GCCAGAGATCGTGGA | 4998 | YES |
| AKDRG | 4912 | GCCAAGGATAGGGGA | 5084 | YES |
| ARGRG | 4827 | GCCAGAGGCAGGGGA | 4999 | YES |
| AKGRG | 4913 | GCCAAGGGTAGGGGA | 5085 | YES |
| ARSG | 4828 | GCCAGATCAGGA | 5000 | YES |
| AKSG | 4914 | GCCAAGTCTGGA | 5086 | YES |
| ARESG | 5356 | GCCAGAGAGTCTGGA | 5456 | NO |
| AKESG | 5357 | GCCAAGGAAAGTGGA | 5457 | NO |
| ARDSG | 4829 | GCCAGAGACTCAGGA | 5001 | YES |
| AKDSG | 4915 | GCCAAGGATAGTGGA | 5087 | YES |
| ARGSG | 5358 | GCCAGAGGCTCTGGA | 5458 | NO |
| AKGSG | 5359 | GCCAAGGGGTCTGGA | 5459 | NO |
| ARPG | 5360 | GCCAGACCAGGA | 5460 | NO |
| AKPG | 5361 | GCCAAGCCCGGA | 5461 | NO |
| ARDPG | 4830 | GCCAGAGATCCAGGA | 5002 | YES |
| AKDPG | 4916 | GCCAAGGACCCCGGA | 5088 | YES |
| ARGPG | 5362 | GCCAGAGGACCTGGA | 5462 | NO |
| AKGPG | 5363 | GCCAAGGGGCCTGGA | 5463 | NO |
| ARLG | 4831 | GCCAGATTGGGA | 5003 | YES |
| AKLG | 4917 | GCCAAGTTAGGA | 5089 | YES |
| ARDLG | 4832 | GCCAGAGACTTGGGA | 5004 | YES |
| AKDLG | 4918 | GCCAAGGATCTTGGA | 5090 | YES |
| ARGLG | 5364 | GCCAGAGGACTAGGA | 5464 | NO |
| AKGLG | 5365 | GCCAAGGGTTTGGGA | 5465 | NO |
| ARAG | 4833 | GCCAGAGCTGGA | 5005 | YES |
| AKAG | 4919 | GCCAAGGCTGGA | 5091 | YES |
| AREAG | 5366 | GCCAGAGAAGCCGGA | 5466 | NO |
| AKEAG | 5367 | GCCAAGGAGGCTGGA | 5467 | NO |
| ARDAG | 5368 | GCCAGAGACGCAGGA | 5468 | NO |
| AKDAG | 5369 | GCCAAGGATGCCGGA | 5469 | NO |

TABLE 26-continued

Theoretical segment pool of 300 TN1 segments (plus AR/AK; which is not part of TN1) used in the library of Example 12.

| Peptide (plus AR or AK)[1] | SEQ ID NO | Nucleotide (plus AR or AK)[1] | SEQ ID NO | In ELD-3? |
|---|---|---|---|---|
| ARGAG | 5370 | GCCAGAGGTGCCGGA | 5470 | NO |
| AKGAG | 5371 | GCCAAGGGAGCAGGA | 5471 | NO |
| ARTG | 5372 | GCCAGAACTGGA | 5472 | NO |
| AKTG | 5373 | GCCAAGACCGGA | 5473 | NO |
| ARDTG | 5374 | GCCAGAGACACGGGA | 5474 | NO |
| AKDTG | 5375 | GCCAAGGATACGGGA | 5475 | NO |
| ARVG | 4834 | GCCAGAGTGGGA | 5006 | YES |
| AKVG | 4920 | GCCAAGGTAGGA | 5092 | YES |
| AREVG | 5376 | GCCAGAGAAGTCGGA | 5476 | NO |
| AKEVG | 5377 | GCCAAGGAGGTAGGA | 5477 | NO |
| ARDVG | 5378 | GCCAGAGATGTAGGA | 5478 | NO |
| AKDVG | 5379 | GCCAAGGACGTAGGA | 5479 | NO |
| ARGVG | 4835 | GCCAGAGGCGTAGGA | 5007 | YES |
| AKGVG | 4921 | GCCAAGGGTGTCGGA | 5093 | YES |
| ARPR | 4836 | GCCAGACCCAGA | 5008 | YES |
| AKPR | 4922 | GCCAAGCCTAGA | 5094 | YES |
| ARDPR | 5380 | GCCAGAGATCCAAGA | 5480 | NO |
| AKDPR | 5381 | GCCAAGGATCCTAGA | 5481 | NO |
| ARGPR | 4837 | GCCAGAGGACCAAGA | 5009 | YES |
| AKGPR | 4923 | GCCAAGGGCCCCAGA | 5095 | YES |
| ARPS | 4838 | GCCAGACCATCT | 5010 | YES |
| AKPS | 4924 | GCCAAGCCTTCT | 5096 | YES |
| ARDPS | 4839 | GCCAGAGATCCCTCT | 5011 | YES |
| AKDPS | 4925 | GCCAAGGATCCCTCT | 5097 | YES |
| ARGPS | 4840 | GCAAGAGGACCTTCT | 5012 | YES |
| AKGPS | 4926 | GCCAAAGGGCCATCT | 5098 | YES |
| ARPP | 5382 | GCCAGACCACCT | 5482 | NO |
| AKPP | 5383 | GCCAAGCCACCT | 5483 | NO |
| ARDPP | 4841 | GCCAGAGACCCACCT | 5013 | YES |
| AKDPP | 4927 | GCCAAGGATCCACCT | 5099 | YES |
| ARGPP | 4842 | GCCAGAGGACCGCCT | 5014 | YES |
| AKGPP | 4928 | GCCAAGGGCCCTCCT | 5100 | YES |
| ARPL | 4843 | GCCAGACCGTTG | 5015 | YES |
| AKPL | 4929 | GCCAAGCCGTTG | 5101 | YES |
| ARDPL | 4844 | GCCAGAGATCCTTTG | 5016 | YES |
| AKDPL | 4930 | GCCAAGGACCCTTTG | 5102 | YES |
| ARGPL | 5384 | GCCAGAGGTCCCTTG | 5484 | NO |

TABLE 26-continued

Theoretical segment pool of 300 TN1 segments (plus AR/AK; which is not part of TN1) used in the library of Example 12.

| Peptide (plus AR or AK)[1] | SEQ ID NO | Nucleotide (plus AR or AK)[1] | SEQ ID NO | In ELD-3? |
|---|---|---|---|---|
| AKGPL | 5385 | GCCAAGGGGCCGTTG | 5485 | NO |
| ARPA | 5386 | GCCAGACCAGCT | 5486 | NO |
| AKPA | 5387 | GCCAAGCCGGCT | 5487 | NO |
| ARDPA | 5388 | GCCAGAGATCCCGCT | 5488 | NO |
| AKDPA | 5389 | GCCAAGGACCCCGCT | 5489 | NO |
| ARPT | 5390 | GCCAGACCTACT | 5490 | NO |
| AKPT | 5391 | GCCAAGCCTACT | 5491 | NO |
| ARDPT | 5392 | GCCAGAGATCCGACT | 5492 | NO |
| AKDPT | 5393 | GCCAAGGACCCTACT | 5493 | NO |
| ARGPT | 5394 | GCCAGAGGACCCACT | 5494 | NO |
| AKGPT | 5395 | GCCAAGGGGCCCACT | 5495 | NO |
| ARPV | 5396 | GCCAGACCGGTG | 5496 | NO |
| AKPV | 5397 | GCCAAGCCAGTG | 5497 | NO |
| ARDPV | 5398 | GCCAGAGATCCGGTG | 5498 | NO |
| AKDPV | 5399 | GCCAAGGACCCTGTG | 5499 | NO |
| ARRP | 4845 | GCCAGAAGGCCT | 5017 | YES |
| AKRP | 4931 | GCCAAGAGGCCT | 5103 | YES |
| ARDRP | 4846 | GCCAGAGACCGTCCT | 5018 | YES |
| AKDRP | 4932 | GCCAAGGACCGTCCT | 5104 | YES |
| ARGRP | 5400 | GCCAGAGGAAGGCCT | 5500 | NO |
| AKGRP | 5401 | GCCAAGGGCCGTCCT | 5501 | NO |
| ARSP | 4847 | GCCAGATCACCT | 5019 | YES |
| AKSP | 4933 | GCCAAGAGTCCT | 5105 | YES |
| ARDSP | 5402 | GCCAGAGACTCTCCT | 5502 | NO |
| AKDSP | 5403 | GCCAAGGACTCCCCT | 5503 | NO |
| ARGSP | 5404 | GCCAGAGGTTCCCCT | 5504 | NO |
| AKGSP | 5405 | GCCAAGGGTTCACCT | 5505 | NO |
| ARLP | 4848 | GCCAGACTTCCT | 5020 | YES |
| AKLP | 4934 | GCCAAGCTACCT | 5106 | YES |
| ARDLP | 5406 | GCCAGAGATCTTCCT | 5506 | NO |
| AKDLP | 5407 | GCCAAGGATCTACCT | 5507 | NO |
| ARAP | 4849 | GCCAGAGCCCCT | 5021 | YES |
| AKAP | 4935 | GCCAAGGCTCCT | 5107 | YES |
| ARDAP | 5408 | GCCAGAGATGCTCCT | 5508 | NO |
| AKDAP | 5409 | GCCAAGGATGCTCCT | 5509 | NO |
| ARGAP | 5410 | GCCAGAGGGGCCCCT | 5510 | NO |
| AKGAP | 5411 | GCCAAGGGTGCCCCT | 5511 | NO |

TABLE 26-continued

Theoretical segment pool of 300 TN1 segments (plus AR/AK; which is not part of TN1) used in the library of Example 12.

| Peptide (plus AR or AK)[1] | SEQ ID NO | Nucleotide (plus AR or AK)[1] | SEQ ID NO | In ELD-3? |
|---|---|---|---|---|
| ARTP | 4850 | GCCAGAACTCCT | 5022 | YES |
| AKTP | 4936 | GCCAAGACGCCT | 5108 | YES |
| ARDTP | 5412 | GCCAGAGATACCCCT | 5512 | NO |
| AKDTP | 5413 | GCCAAGGACACGCCT | 5513 | NO |
| ARVP | 4851 | GCCAGAGTCCCT | 5023 | YES |
| AKVP | 4937 | GCCAAGGTACCT | 5109 | YES |
| ARAGG | 5414 | GCCAGAGCTGGCGGA | 5514 | NO |
| AKAGG | 5415 | GCCAAGGCCGGTGGA | 5515 | NO |
| ARDGGG | 5416 | GCCAGAGATGGTGGCGGA | 5516 | NO |
| AKDGGG | 5417 | GCCAAGGACGGCGGTGGA | 5517 | NO |
| ARLGG | 5418 | GCCAGATTGGGCGGA | 5518 | NO |
| AKLGG | 5419 | GCCAAGCTAGGCGGA | 5519 | NO |
| ARDLGG | 5420 | GCCAGAGATTTGGGTGGA | 5520 | NO |
| AKDLGG | 5421 | GCCAAGGATTTGGGTGGA | 5521 | NO |
| ARRGG | 5422 | GCCAGAAGAGGTGGA | 5522 | NO |
| AKRGG | 5423 | GCCAAGAGAGGAGGA | 5523 | NO |
| ARDRGG | 5424 | GCCAGAGACCGTGGCGGA | 5524 | NO |
| AKDRGG | 5425 | GCCAAGGACAGAGGTGGA | 5525 | NO |
| ARSGG | 5426 | GCCAGATCAGGCGGA | 5526 | NO |
| AKSGG | 5427 | GCCAAGTCCGGTGGA | 5527 | NO |
| ARVGG | 4852 | GCCAGAGTTGGAGGA | 5024 | YES |
| AKVGG | 4938 | GCCAAGGTGGGTGGA | 5110 | YES |
| ARQ | n/a | GCAAGACAG | n/a | YES |
| AKQ | n/a | GCAAAACAG | n/a | YES |
| ARH | n/a | GCCAGACAC | n/a | YES |
| AKH | n/a | GCCAAACAC | n/a | YES |
| ARDQ | 4853 | GCCAGGGACCAG | 5025 | YES |
| AKDQ | 4939 | GCCAAGGATCAG | 5111 | YES |
| ARDH | 4854 | GCAAGAGACCAC | 5026 | YES |
| AKDH | 4940 | GCTAAAGACCAC | 5112 | YES |
| ARAR | 4855 | GCAAGGGCTAGA | 5027 | YES |
| AKAR | 4941 | GCCAAGGCAAGA | 5113 | YES |
| ARAS | 4856 | GCTAGGGCATCT | 5028 | YES |
| AKAS | 4942 | GCCAAGGCATCT | 5114 | YES |
| ARDQG | 4857 | GCTAGGGATCAGGGA | 5029 | YES |
| AKDQG | 4943 | GCAAAGGATCAGGGA | 5115 | YES |
| ARSR | 4858 | GCTAGATCAAGA | 5030 | YES |

TABLE 26-continued

Theoretical segment pool of 300 TN1 segments (plus AR/AK; which is not part of TN1) used in the library of Example 12.

| Peptide (plus AR or AK)[1] | SEQ ID NO | Nucleotide (plus AR or AK)[1] | SEQ ID NO | In ELD-3? |
|---|---|---|---|---|
| AKSR | 4944 | GCCAAGAGTAGA | 5116 | YES |
| ARDRS | 4859 | GCCAGGGACAGGTCT | 5031 | YES |
| AKDRS | 4945 | GCAAAAGACAGGTCT | 5117 | YES |
| ARSL | 4860 | GCTAGATCTTTG | 5032 | YES |
| AKSL | 4946 | GCAAAGAGCTTG | 5118 | YES |
| ARLH | 4861 | GCTAGGTTGCAC | 5033 | YES |
| AKLH | 4947 | GCTAAATTGCAC | 5119 | YES |
| ARDLT | 4862 | GCCAGGGATTTGACT | 5034 | YES |
| AKDLT | 4948 | GCCAAGGACTTGACT | 5120 | YES |
| ARK | n/a | GCCAGAAAG | n/a | YES |
| AKK | n/a | GCTAAAAAG | n/a | YES |
| ARAE | 4863 | GCAAGAGCCGAG | 5035 | YES |
| AKAE | 4949 | GCTAAAGCAGAG | 5121 | YES |
| ARDLS | 4864 | GCAAGGGATTTGTCT | 5036 | YES |
| AKDLS | 4950 | GCAAAAGACTTGTCT | 5122 | YES |
| ARGD | 4865 | GCTAGAGGGGAC | 5037 | YES |
| AKGD | 4951 | GCAAAAGGGGAC | 5123 | YES |
| ARRR | 4866 | GCTAGGAGGAGA | 5038 | YES |
| AKRR | 4952 | GCAAAAAGGAGA | 5124 | YES |
| ARDK | 4867 | GCTAGAGATAAG | 5039 | YES |
| AKDK | 4953 | GCAAAAGACAAG | 5125 | YES |
| ARVS | 4868 | GCTAGAGTATCT | 5040 | YES |
| AKVS | 4954 | GCCAAAGTATCT | 5126 | YES |
| ARDRL | 4869 | GCCAGAGACAGGTTG | 5041 | YES |
| AKDRL | 4955 | GCAAAAGACAGGTTG | 5127 | YES |
| ARGQ | 4870 | GCTAGGGGCCAG | 5042 | YES |
| AKGQ | 4956 | GCCAAAGGACAG | 5128 | YES |
| ARVR | 4871 | GCCAGGGTCAGA | 5043 | YES |
| AKVR | 4957 | GCAAAAGTCAGA | 5129 | YES |
| ARAK | 4872 | GCTAGGGCTAAG | 5044 | YES |
| AKAK | 4958 | GCAAAGGCAAAG | 5130 | YES |
| ARGK | 4873 | GCCAGGGGTAAG | 5045 | YES |
| AKGK | 4959 | GCAAAGGGCAAG | 5131 | YES |
| ARDIS | 4874 | GCAAGGGATATTTCT | 5046 | YES |
| AKDIS | 4960 | GCAAAGGACATTTCT | 5132 | YES |
| ARDFT | 4875 | GCTAGGGATTTCACT | 5047 | YES |
| AKDFT | 4961 | GCTAAAGATTTCACT | 5133 | YES |

TABLE 26-continued

Theoretical segment pool of 300 TN1 segments (plus AR/AK; which is not part of TN1) used in the library of Example 12.

| Peptide (plus AR or AK)[1] | SEQ ID NO | Nucleotide (plus AR or AK)[1] | SEQ ID NO | In ELD-3? |
|---|---|---|---|---|
| ARQG | 4876 | GCCAGGCAGGGA | 5048 | YES |
| AKQG | 4962 | GCCAAGCAAGGA | 5134 | YES |

[1]"AR" and "AK" refer to the last two C-terminal amino acids of the heavy chain chassis used in the current example. They are not part of the TN1 segment.

TABLE 27

Theoretical segment pool of degenerate oligonucleotide sequences encoding DH segments of Example 13.

| Name | Degenerate Oligo | Peptide Length | SEQ ID NO |
|---|---|---|---|
| DH 001 | KHTGAK | 2 | n/a |
| DH 002 | KHTKGG | 2 | n/a |
| DH 003 | KHTCMT | 2 | n/a |
| DH 004 | KHTMCT | 2 | n/a |
| DH 005 | GVCWSG | 2 | n/a |
| DH 006 | SVCYAT | 2 | n/a |
| DH 007 | BYCSAG | 2 | n/a |
| DH 008 | SBAMAG | 2 | n/a |
| DH 009 | VSCMAA | 2 | n/a |
| DH 010 | GRABYT | 2 | n/a |
| DH 011 | GRAKBG | 2 | n/a |
| DH 012 | RDAGAK | 2 | n/a |
| DH 013 | RDAGRT | 2 | n/a |
| DH 014 | YHTSAC | 2 | n/a |
| DH 015 | YHTKAC | 2 | n/a |
| DH 016 | YHTMCG | 2 | n/a |
| DH 017 | MHAGAW | 2 | n/a |
| DH 018 | MHAGRT | 2 | n/a |
| DH 019 | MHAMCT | 2 | n/a |
| DH 020 | MBCYAT | 2 | n/a |
| DH 021 | CVACNG | 2 | n/a |
| DH 022 | MSCAHG | 2 | n/a |
| DH 023 | CRGKBG | 2 | n/a |
| DH 024 | WSGHCT | 2 | n/a |
| DH 025 | WGGKHT | 2 | n/a |
| DH 026 | BGGSAK | 2 | n/a |
| DH 027 | BWCAMA | 2 | n/a |
| DH 028 | BHCTGG | 2 | n/a |

TABLE 27-continued

Theoretical segment pool of degenerate oligonucleotide sequences encoding DH segments of Example 13.

| Name | Degenerate Oligo | Peptide Length | SEQ ID NO |
|---|---|---|---|
| DH 029 | TGGVBT | 2 | n/a |
| DH 030 | BHCAGT | 2 | n/a |
| DH 031 | SRTATT | 2 | n/a |
| DH 032 | ACABHT | 2 | n/a |
| DH 033 | SVCGCT | 2 | n/a |
| DH 034 | ATGSVT | 2 | n/a |
| DH 035 | SWGAGG | 2 | n/a |
| DH 036 | GTAGCAVBT | 3 | n/a |
| DH 037 | DBGSWACTT | 3 | n/a |
| DH 038 | VNCBCAGGT | 3 | n/a |
| DH 039 | VNCDCATAT | 3 | n/a |
| DH 040 | VHAKKGTTG | 3 | n/a |
| DH 041 | CCAGCABHT | 3 | n/a |
| DH 042 | VHASRACTT | 3 | n/a |
| DH 043 | BHCAGCRST | 3 | n/a |
| DH 044 | BHCGGAKMT | 3 | n/a |
| DH 045 | BHCGGAGDT | 3 | n/a |
| DH 046 | BHCAGCKMT | 3 | n/a |
| DH 047 | NHCCRACTT | 3 | n/a |
| DH 048 | NHCAGCKGG | 3 | n/a |
| DH 049 | BHCGGAKSG | 3 | n/a |
| DH 050 | VBCGGAGNT | 3 | n/a |
| DH 051 | NHCAGCGVT | 3 | n/a |
| DH 052 | NHCTACGVT | 3 | n/a |
| DH 053 | NHCAGCGVG | 3 | n/a |
| DH 054 | VHATGGSYG | 3 | n/a |
| DH 055 | VNCGHCTAT | 3 | n/a |
| DH 056 | GGTRNACTT | 3 | n/a |

TABLE 27-continued

Theoretical segment pool of degenerate oligonucleotide sequences encoding DH segments of Example 13.

| Name | Degenerate Oligo | Peptide Length | SEQ ID NO |
|---|---|---|---|
| DH 057 | NHCABAGGT | 3 | n/a |
| DH 058 | VHAGCAGNT | 3 | n/a |
| DH 059 | DBGKYCGGT | 3 | n/a |
| DH 060 | BHCGGARKT | 3 | n/a |
| DH 061 | NHCGTAGVT | 3 | n/a |
| DH 062 | VNTTHCTAT | 3 | n/a |
| DH 063 | GTAGTABHT | 3 | n/a |
| DH 064 | VBCGNCCTT | 3 | n/a |
| DH 065 | BHCGGAGNG | 3 | n/a |
| DH 066 | VNCGHCGGT | 3 | n/a |
| DH 067 | AGGBHCGGT | 3 | n/a |
| DH 068 | VNCTBGTAT | 3 | n/a |
| DH 069 | VNCTBGCTT | 3 | n/a |
| DH 070 | NHCKACTAT | 3 | n/a |
| DH 071 | CTARNACTT | 3 | n/a |
| DH 072 | NHCBCAGGT | 3 | n/a |
| DH 073 | NHCTACBAT | 3 | n/a |
| DH 074 | BHCACAGCCAKS | 4 | 5528 |
| DH 075 | VHGGBAGCAACT | 4 | 5529 |
| DH 076 | DBGTTCGGAGNG | 4 | 5530 |
| DH 077 | BHCGGAKMCTAT | 4 | 5531 |
| DH 078 | TACAGCAGCVBT | 4 | 5532 |
| DH 079 | VHGGTARSAGGT | 4 | 5533 |
| DH 080 | VBCGACGGATHT | 4 | 5534 |
| DH 081 | NHCTACGGAGVT | 4 | 5535 |
| DH 082 | VHGRYGGCAACT | 4 | 5536 |
| DH 083 | VHATACAGCRST | 4 | 5537 |
| DH 084 | CAGTGGCTABHT | 4 | 5538 |
| DH 085 | VHAGTAGCAGNT | 4 | 5539 |
| DH 086 | VBCACAGTARMG | 4 | 5540 |
| DH 087 | AGCAGCAGCDBG | 4 | 5541 |
| DH 088 | NHCTMCTACGGT | 4 | 5542 |
| DH 089 | BHCAGCTGGTHT | 4 | 5543 |
| DH 090 | VHACAACTAGNT | 4 | 5544 |
| DH 091 | BHCGGAAGCKMT | 4 | 5545 |
| DH 092 | BHCGGATSGTAT | 4 | 5546 |
| DH 093 | NHCAGCGGABGG | 4 | 5547 |
| DH 094 | BHCGGATACKMT | 4 | 5548 |
| DH 095 | VHAGTAACARMG | 4 | 5549 |
| DH 096 | GCAGCAGCAVBT | 4 | 5550 |
| DH 097 | VBCAYATTCGGT | 4 | 5551 |
| DH 098 | GTAGCAGCAVHA | 4 | 5552 |
| DH 099 | NHCTACTACGVT | 4 | 5553 |
| DH 100 | VBCKMCGGATAT | 4 | 5554 |
| DH 101 | VHACAACTAKKG | 4 | 5555 |
| DH 102 | VHGGGARKCGCT | 4 | 5556 |
| DH 103 | VBTBTCGGAGAG | 4 | 5557 |
| DH 104 | BHCTACAGCKMT | 4 | 5558 |
| DH 105 | VHAGTASSAGCT | 4 | 5559 |
| DH 106 | VBTCDAGGAGTT | 4 | 5560 |
| DH 107 | GACAGCAGCDBG | 4 | 5561 |
| DH 108 | VBCGVCTACAGT | 4 | 5562 |
| DH 109 | NHCTACGGAKCT | 4 | 5563 |
| DH 110 | NHCTACTACTHT | 4 | 5564 |
| DH 111 | BHCVGCTACAGT | 4 | 5565 |
| DH 112 | VBCTGGTTCGGT | 4 | 5566 |
| DH 113 | VNCTACTACTHT | 4 | 5567 |
| DH 114 | VHABTCGGAGGT | 4 | 5568 |
| DH 115 | NHCATGGTAAGAGVT | 5 | 5569 |
| DH 116 | NHCTACGGAGACTHT | 5 | 5570 |
| DH 117 | VBCTACAGCTACGNT | 5 | 5571 |
| DH 118 | VNCAGCGGAAGCTHT | 5 | 5572 |
| DH 119 | VBCTTTCTAGAATBG | 5 | 5573 |
| DH 120 | BHCGGAAGCTACKMT | 5 | 5574 |
| DH 121 | NHCAGCGGAAGCTHT | 5 | 5575 |
| DH 122 | BHCAGCAGCAGCTBG | 5 | 5576 |
| DH 123 | BHCAGCAGCGGATBG | 5 | 5577 |
| DH 124 | VBCACAGTAACAANA | 5 | 5578 |
| DH 125 | BHCAGCAGCAGCTHT | 5 | 5579 |
| DH 126 | NHCAGCGGATGGTHT | 5 | 5580 |
| DH 127 | NHCAGCGGATACGVT | 5 | 5581 |
| DH 128 | NHCTACTACGACABT | 5 | 5582 |

TABLE 27-continued

Theoretical segment pool of degenerate oligonucleotide sequences encoding DH segments of Example 13.

| Name | Degenerate Oligo | Peptide Length | SEQ ID NO |
|---|---|---|---|
| DH 129 | BHCAGCAGCGGATHT | 5 | 5583 |
| DH 130 | VHAGCAGCAAGACNT | 5 | 5584 |
| DH 131 | VHGTACTACTACGVT | 5 | 5585 |
| DH 132 | VBCACAATGGTACRG | 5 | 5586 |
| DH 133 | NHCATGGTACRAGGT | 5 | 5587 |
| DH 134 | NHCTSGGGAAGCTAT | 5 | 5588 |
| DH 135 | BHCAGCAGCAGCTGGTHT | 6 | 5589 |
| DH 136 | NHCTACTACGACAGCABT | 6 | 5590 |
| DH 137 | VBCTACAGCGGATACGNT | 6 | 5591 |
| DH 138 | BHCAGCAGCGGATGGTHT | 6 | 5592 |
| DH 139 | NHCTACTACGGAAGCGVT | 6 | 5593 |
| DH 140 | BHCAGCAGCGGATACTHT | 6 | 5594 |
| DH 141 | NHCTACGACAGCAGCGVT | 6 | 5595 |
| DH 142 | NHCGACTTCTGGAGCGVT | 6 | 5596 |
| DH 143 | BHCGACAGCAGCGGATHT | 6 | 5597 |
| DH 144 | SNATACTTCGACTGGYYT | 6 | 5598 |
| DH 145 | TGTRGCRGCACAAGCTGT | 6 | 5599 |
| DH 146 | NHCTACTACGGAAGCGVG | 6 | 5600 |
| DH 147 | TGTRGCRGCGGAAGCTGT | 6 | 5601 |
| DH 148 | NHCTTTTGGAGCGGATHT | 6 | 5602 |
| DH 149 | NHCTACTACGACAGCAGCGVT | 7 | 5603 |
| DH 150 | NHCGACATACTAACAGGATHT | 7 | 5604 |
| DH 151 | NHCTACGACTTCTGGAGCGVT | 7 | 5605 |
| DH 152 | BHCTGTAGCAGCACAAGCTGT | 7 | 5606 |
| DH 153 | DBGTACAGCAGCAGCTGGTHT | 7 | 5607 |
| DH 154 | NHCTACGACAGCAGCGGATHT | 7 | 5608 |
| DH 155 | NHCTACTACGGAAGCGGAABT | 7 | 5609 |
| DH 156 | DBGTACAGCAGCGGATGGTHT | 7 | 5610 |
| DH 157 | BHCTGTAGCGGAGGAAGCTGT | 7 | 5611 |
| DH 158 | TGTAGCGGAGGAAGCTGTYHT | 7 | 5612 |
| DH 159 | TGTAGCAGCACAAGCTGTYHT | 7 | 5613 |
| DH 160 | NHCTGTGGAGGAGACTGTTHT | 7 | 5614 |
| DH 161 | NHCGACTTCTGGAGCGGATHT | 7 | 5615 |
| DH 162 | BHCGACAGCAGCGGATACTHT | 7 | 5616 |
| DH 163 | VHATACTGTGGAGGAGACTGT | 7 | 5617 |
| DH 164 | NHCTACTACGACAGCAGCGGATHT | 8 | 5618 |
| DH 165 | NHCTACTACGGAAGCGGAAGCTHT | 8 | 5619 |
| DH 166 | VBCTACTGTAGCAGCACAAGCTGT | 8 | 5620 |
| DH 167 | VBCTACTGTAGCGGAGGAAGCTGT | 8 | 5621 |
| DH 168 | NHCTACGACTTCTGGAGCGGATHT | 8 | 5622 |
| DH 169 | NHCGACATACTAACAGGATACTHT | 8 | 5623 |
| DH 170 | BHCTGTAGCGGAGGAAGCTGTTHT | 8 | 5624 |
| DH 171 | BHCTGTAGCAGCACAAGCTGTTHT | 8 | 5625 |
| DH 172 | VHATACTGTGGAGGAGACTGTTHT | 8 | 5626 |
| DH 173 | NHCTACGACAGCAGCGGATACTHT | 8 | 5627 |
| DH 174 | VNCTACTACGGAAGCGGAAGCTMT | 8 | 5628 |
| DH 175 | NHCGACTTCTGGAGCGGATACTHT | 8 | 5629 |
| DH 176 | VHACTAAGATACTTCGACTGGYWT | 8 | 5630 |
| DH 177 | NHCTACTACGACAGCAGCGGATACTHT | 9 | 5631 |
| DH 178 | VBCTACTGTAGCGGAGGAAGCTGTTHT | 9 | 5632 |
| DH 179 | VBCTACTGTAGCAGCACAAGCTGTTHT | 9 | 5633 |
| DH 180 | NHCTACGACTTCTGGAGCGGATACTHT | 9 | 5634 |
| DH 181 | BHCTGTAGCGGAGGAAGCTGTTACTHT | 9 | 5635 |
| DH 182 | NHCTACTACGACAGCAGCGGATACTACTHT | 10 | 5636 |
| DH 183 | NHCTACGACTACGTATGGGGAAGCTACGCATHT | 11 | 5637 |
| DH 184 | NHCTACGACTACGTATGGGGAAGCTACGCATACAHA | 12 | 5638 |

TABLE 28

Theoretical segment pool of unique DH polypeptide segments encoded by the degenerate oligonucleotides of Table 27.

| Name | Sequence | Length | SEQ ID NO |
|---|---|---|---|
| PDH 0001 | YE | 2 | n/a |
| PDH 0002 | DD | 2 | n/a |
| PDH 0003 | VD | 2 | n/a |
| PDH 0004 | FD | 2 | n/a |
| PDH 0005 | AE | 2 | n/a |
| PDH 0006 | SD | 2 | n/a |
| PDH 0007 | YD | 2 | n/a |
| PDH 0008 | VE | 2 | n/a |
| PDH 0009 | DE | 2 | n/a |

TABLE 28-continued

Theoretical segment pool of unique DH polypeptide segments encoded by the degenerate oligonucleotides of Table 27.

| Name | Sequence | Length | SEQ ID NO |
|---|---|---|---|
| PDH 0010 | AD | 2 | n/a |
| PDH 0011 | FE | 2 | n/a |
| PDH 0012 | SE | 2 | n/a |
| PDH 0013 | VG | 2 | n/a |
| PDH 0014 | FW | 2 | n/a |
| PDH 0015 | YG | 2 | n/a |
| PDH 0016 | DW | 2 | n/a |
| PDH 0017 | FG | 2 | n/a |
| PDH 0018 | AW | 2 | n/a |
| PDH 0019 | DG | 2 | n/a |
| PDH 0020 | YW | 2 | n/a |
| PDH 0021 | SG | 2 | n/a |
| PDH 0022 | AG | 2 | n/a |
| PDH 0023 | VW | 2 | n/a |
| PDH 0024 | SW | 2 | n/a |
| PDH 0025 | VP | 2 | n/a |
| PDH 0026 | DH | 2 | n/a |
| PDH 0027 | DP | 2 | n/a |
| PDH 0028 | YP | 2 | n/a |
| PDH 0029 | SH | 2 | n/a |
| PDH 0030 | VH | 2 | n/a |
| PDH 0031 | FH | 2 | n/a |
| PDH 0032 | YH | 2 | n/a |
| PDH 0033 | FP | 2 | n/a |
| PDH 0034 | AP | 2 | n/a |
| PDH 0035 | SP | 2 | n/a |
| PDH 0036 | AH | 2 | n/a |
| PDH 0037 | YT | 2 | n/a |
| PDH 0038 | DT | 2 | n/a |
| PDH 0039 | AT | 2 | n/a |
| PDH 0040 | ST | 2 | n/a |
| PDH 0041 | FT | 2 | n/a |
| PDH 0042 | VT | 2 | n/a |
| PDH 0043 | AS | 2 | n/a |
| PDH 0044 | AR | 2 | n/a |
| PDH 0045 | DS | 2 | n/a |
| PDH 0046 | GT | 2 | n/a |

TABLE 28-continued

Theoretical segment pool of unique DH polypeptide segments encoded by the degenerate oligonucleotides of Table 27.

| Name | Sequence | Length | SEQ ID NO |
|---|---|---|---|
| PDH 0047 | GS | 2 | n/a |
| PDH 0048 | GW | 2 | n/a |
| PDH 0049 | GR | 2 | n/a |
| PDH 0050 | DR | 2 | n/a |
| PDH 0051 | PH | 2 | n/a |
| PDH 0052 | RH | 2 | n/a |
| PDH 0053 | PY | 2 | n/a |
| PDH 0054 | GH | 2 | n/a |
| PDH 0055 | GY | 2 | n/a |
| PDH 0056 | RY | 2 | n/a |
| PDH 0057 | HH | 2 | n/a |
| PDH 0058 | HY | 2 | n/a |
| PDH 0059 | DY | 2 | n/a |
| PDH 0060 | AY | 2 | n/a |
| PDH 0061 | AQ | 2 | n/a |
| PDH 0062 | FQ | 2 | n/a |
| PDH 0063 | LE | 2 | n/a |
| PDH 0064 | PE | 2 | n/a |
| PDH 0065 | LQ | 2 | n/a |
| PDH 0066 | PQ | 2 | n/a |
| PDH 0067 | VQ | 2 | n/a |
| PDH 0068 | SQ | 2 | n/a |
| PDH 0069 | RK | 2 | n/a |
| PDH 0070 | GK | 2 | n/a |
| PDH 0071 | AK | 2 | n/a |
| PDH 0072 | RQ | 2 | n/a |
| PDH 0073 | GQ | 2 | n/a |
| PDH 0074 | LK | 2 | n/a |
| PDH 0075 | VK | 2 | n/a |
| PDH 0076 | PK | 2 | n/a |
| PDH 0077 | SK | 2 | n/a |
| PDH 0078 | TK | 2 | n/a |
| PDH 0079 | TQ | 2 | n/a |
| PDH 0080 | GL | 2 | n/a |
| PDH 0081 | GP | 2 | n/a |
| PDH 0082 | GV | 2 | n/a |
| PDH 0083 | EF | 2 | n/a |

TABLE 28-continued

Theoretical segment pool of unique DH polypeptide segments encoded by the degenerate oligonucleotides of Table 27.

| Name | Sequence | Length | SEQ ID NO |
|---|---|---|---|
| PDH 0084 | GF | 2 | n/a |
| PDH 0085 | EL | 2 | n/a |
| PDH 0086 | EA | 2 | n/a |
| PDH 0087 | ES | 2 | n/a |
| PDH 0088 | EP | 2 | n/a |
| PDH 0089 | GA | 2 | n/a |
| PDH 0090 | EV | 2 | n/a |
| PDH 0091 | GG | 2 | n/a |
| PDH 0092 | EG | 2 | n/a |
| PDH 0093 | EW | 2 | n/a |
| PDH 0094 | IE | 2 | n/a |
| PDH 0095 | RE | 2 | n/a |
| PDH 0096 | KE | 2 | n/a |
| PDH 0097 | GD | 2 | n/a |
| PDH 0098 | ID | 2 | n/a |
| PDH 0099 | RD | 2 | n/a |
| PDH 0100 | EE | 2 | n/a |
| PDH 0101 | GE | 2 | n/a |
| PDH 0102 | KD | 2 | n/a |
| PDH 0103 | ED | 2 | n/a |
| PDH 0104 | IG | 2 | n/a |
| PDH 0105 | RG | 2 | n/a |
| PDH 0106 | KG | 2 | n/a |
| PDH 0107 | LD | 2 | n/a |
| PDH 0108 | LH | 2 | n/a |
| PDH 0109 | PD | 2 | n/a |
| PDH 0110 | HD | 2 | n/a |
| PDH 0111 | SY | 2 | n/a |
| PDH 0112 | FY | 2 | n/a |
| PDH 0113 | YY | 2 | n/a |
| PDH 0114 | LY | 2 | n/a |
| PDH 0115 | LT | 2 | n/a |
| PDH 0116 | HP | 2 | n/a |
| PDH 0117 | HT | 2 | n/a |
| PDH 0118 | LP | 2 | n/a |
| PDH 0119 | PT | 2 | n/a |
| PDH 0120 | PP | 2 | n/a |

TABLE 28-continued

Theoretical segment pool of unique DH polypeptide segments encoded by the degenerate oligonucleotides of Table 27.

| Name | Sequence | Length | SEQ ID NO |
|---|---|---|---|
| PDH 0121 | TE | 2 | n/a |
| PDH 0122 | QE | 2 | n/a |
| PDH 0123 | TD | 2 | n/a |
| PDH 0124 | QD | 2 | n/a |
| PDH 0125 | PG | 2 | n/a |
| PDH 0126 | LG | 2 | n/a |
| PDH 0127 | TG | 2 | n/a |
| PDH 0128 | QG | 2 | n/a |
| PDH 0129 | QP | 2 | n/a |
| PDH 0130 | QT | 2 | n/a |
| PDH 0131 | KT | 2 | n/a |
| PDH 0132 | KP | 2 | n/a |
| PDH 0133 | IP | 2 | n/a |
| PDH 0134 | TP | 2 | n/a |
| PDH 0135 | TT | 2 | n/a |
| PDH 0136 | IT | 2 | n/a |
| PDH 0137 | IH | 2 | n/a |
| PDH 0138 | IY | 2 | n/a |
| PDH 0139 | TH | 2 | n/a |
| PDH 0140 | TY | 2 | n/a |
| PDH 0141 | RR | 2 | n/a |
| PDH 0142 | QL | 2 | n/a |
| PDH 0143 | QQ | 2 | n/a |
| PDH 0144 | PL | 2 | n/a |
| PDH 0145 | RP | 2 | n/a |
| PDH 0146 | PR | 2 | n/a |
| PDH 0147 | RL | 2 | n/a |
| PDH 0148 | QR | 2 | n/a |
| PDH 0149 | PM | 2 | n/a |
| PDH 0150 | TM | 2 | n/a |
| PDH 0151 | RT | 2 | n/a |
| PDH 0152 | RM | 2 | n/a |
| PDH 0153 | SM | 2 | n/a |
| PDH 0154 | QA | 2 | n/a |
| PDH 0155 | RA | 2 | n/a |
| PDH 0156 | QS | 2 | n/a |
| PDH 0157 | QV | 2 | n/a |

TABLE 28-continued

Theoretical segment pool of unique DH polypeptide segments encoded by the degenerate oligonucleotides of Table 27.

| Name | Sequence | Length | SEQ ID NO |
|---|---|---|---|
| PDH 0158 | RS | 2 | n/a |
| PDH 0159 | QW | 2 | n/a |
| PDH 0160 | RW | 2 | n/a |
| PDH 0161 | RV | 2 | n/a |
| PDH 0162 | WS | 2 | n/a |
| PDH 0163 | WT | 2 | n/a |
| PDH 0164 | TS | 2 | n/a |
| PDH 0165 | WP | 2 | n/a |
| PDH 0166 | SS | 2 | n/a |
| PDH 0167 | WV | 2 | n/a |
| PDH 0168 | WF | 2 | n/a |
| PDH 0169 | RF | 2 | n/a |
| PDH 0170 | WA | 2 | n/a |
| PDH 0171 | WD | 2 | n/a |
| PDH 0172 | WY | 2 | n/a |
| PDH 0173 | WQ | 2 | n/a |
| PDH 0174 | WE | 2 | n/a |
| PDH 0175 | WH | 2 | n/a |
| PDH 0176 | YK | 2 | n/a |
| PDH 0177 | FK | 2 | n/a |
| PDH 0178 | DK | 2 | n/a |
| PDH 0179 | HK | 2 | n/a |
| PDH 0180 | LW | 2 | n/a |
| PDH 0181 | PW | 2 | n/a |
| PDH 0182 | HW | 2 | n/a |
| PDH 0183 | WI | 2 | n/a |
| PDH 0184 | WG | 2 | n/a |
| PDH 0185 | WL | 2 | n/a |
| PDH 0186 | WR | 2 | n/a |
| PDH 0187 | YS | 2 | n/a |
| PDH 0188 | LS | 2 | n/a |
| PDH 0189 | HS | 2 | n/a |
| PDH 0190 | FS | 2 | n/a |
| PDH 0191 | PS | 2 | n/a |
| PDH 0192 | VS | 2 | n/a |
| PDH 0193 | GI | 2 | n/a |
| PDH 0194 | HI | 2 | n/a |

TABLE 28-continued

Theoretical segment pool of unique DH polypeptide segments encoded by the degenerate oligonucleotides of Table 27.

| Name | Sequence | Length | SEQ ID NO |
|---|---|---|---|
| PDH 0195 | RI | 2 | n/a |
| PDH 0196 | DI | 2 | n/a |
| PDH 0197 | TF | 2 | n/a |
| PDH 0198 | TL | 2 | n/a |
| PDH 0199 | TV | 2 | n/a |
| PDH 0200 | TA | 2 | n/a |
| PDH 0201 | PA | 2 | n/a |
| PDH 0202 | HA | 2 | n/a |
| PDH 0203 | DA | 2 | n/a |
| PDH 0204 | AA | 2 | n/a |
| PDH 0205 | MR | 2 | n/a |
| PDH 0206 | MA | 2 | n/a |
| PDH 0207 | MD | 2 | n/a |
| PDH 0208 | MP | 2 | n/a |
| PDH 0209 | MH | 2 | n/a |
| PDH 0210 | MG | 2 | n/a |
| PDH 0211 | VR | 2 | n/a |
| PDH 0212 | ER | 2 | n/a |
| PDH 0213 | LR | 2 | n/a |
| PDH 0214 | VAL | 3 | n/a |
| PDH 0215 | VAR | 3 | n/a |
| PDH 0216 | VAI | 3 | n/a |
| PDH 0217 | VAA | 3 | n/a |
| PDH 0218 | VAT | 3 | n/a |
| PDH 0219 | VAP | 3 | n/a |
| PDH 0220 | VAV | 3 | n/a |
| PDH 0221 | VAG | 3 | n/a |
| PDH 0222 | VAS | 3 | n/a |
| PDH 0223 | VVL | 3 | n/a |
| PDH 0224 | VEL | 3 | n/a |
| PDH 0225 | REL | 3 | n/a |
| PDH 0226 | TLL | 3 | n/a |
| PDH 0227 | WEL | 3 | n/a |
| PDH 0228 | RLL | 3 | n/a |
| PDH 0229 | TQL | 3 | n/a |
| PDH 0230 | RVL | 3 | n/a |
| PDH 0231 | GLL | 3 | n/a |

TABLE 28-continued

Theoretical segment pool of unique DH polypeptide segments encoded by the degenerate oligonucleotides of Table 27.

| Name | Sequence | Length | SEQ ID NO |
|---|---|---|---|
| PDH 0232 | TEL | 3 | n/a |
| PDH 0233 | GVL | 3 | n/a |
| PDH 0234 | LQL | 3 | n/a |
| PDH 0235 | MEL | 3 | n/a |
| PDH 0236 | SLL | 3 | n/a |
| PDH 0237 | LVL | 3 | n/a |
| PDH 0238 | MQL | 3 | n/a |
| PDH 0239 | AVL | 3 | n/a |
| PDH 0240 | AQL | 3 | n/a |
| PDH 0241 | SQL | 3 | n/a |
| PDH 0242 | GQL | 3 | n/a |
| PDH 0243 | LEL | 3 | n/a |
| PDH 0244 | TVL | 3 | n/a |
| PDH 0245 | RQL | 3 | n/a |
| PDH 0246 | LLL | 3 | n/a |
| PDH 0247 | VQL | 3 | n/a |
| PDH 0248 | ALL | 3 | n/a |
| PDH 0249 | AEL | 3 | n/a |
| PDH 0250 | WLL | 3 | n/a |
| PDH 0251 | WVL | 3 | n/a |
| PDH 0252 | SEL | 3 | n/a |
| PDH 0253 | VLL | 3 | n/a |
| PDH 0254 | MVL | 3 | n/a |
| PDH 0255 | GEL | 3 | n/a |
| PDH 0256 | MLL | 3 | n/a |
| PDH 0257 | SVL | 3 | n/a |
| PDH 0258 | WQL | 3 | n/a |
| PDH 0259 | ISG | 3 | n/a |
| PDH 0260 | DSG | 3 | n/a |
| PDH 0261 | VPG | 3 | n/a |
| PDH 0262 | VSG | 3 | n/a |
| PDH 0263 | GAG | 3 | n/a |
| PDH 0264 | IPG | 3 | n/a |
| PDH 0265 | APG | 3 | n/a |
| PDH 0266 | TSG | 3 | n/a |
| PDH 0267 | DPG | 3 | n/a |
| PDH 0268 | LSG | 3 | n/a |

TABLE 28-continued

Theoretical segment pool of unique DH polypeptide segments encoded by the degenerate oligonucleotides of Table 27.

| Name | Sequence | Length | SEQ ID NO |
|---|---|---|---|
| PDH 0269 | LAG | 3 | n/a |
| PDH 0270 | NPG | 3 | n/a |
| PDH 0271 | PAG | 3 | n/a |
| PDH 0272 | SAG | 3 | n/a |
| PDH 0273 | ASG | 3 | n/a |
| PDH 0274 | RPG | 3 | n/a |
| PDH 0275 | HPG | 3 | n/a |
| PDH 0276 | GSG | 3 | n/a |
| PDH 0277 | GPG | 3 | n/a |
| PDH 0278 | IAG | 3 | n/a |
| PDH 0279 | LPG | 3 | n/a |
| PDH 0280 | AAG | 3 | n/a |
| PDH 0281 | TPG | 3 | n/a |
| PDH 0282 | PSG | 3 | n/a |
| PDH 0283 | PPG | 3 | n/a |
| PDH 0284 | SPG | 3 | n/a |
| PDH 0285 | RAG | 3 | n/a |
| PDH 0286 | HAG | 3 | n/a |
| PDH 0287 | SSG | 3 | n/a |
| PDH 0288 | HSG | 3 | n/a |
| PDH 0289 | RSG | 3 | n/a |
| PDH 0290 | TAG | 3 | n/a |
| PDH 0291 | DAG | 3 | n/a |
| PDH 0292 | NAG | 3 | n/a |
| PDH 0293 | NSG | 3 | n/a |
| PDH 0294 | GTY | 3 | n/a |
| PDH 0295 | ITY | 3 | n/a |
| PDH 0296 | LTY | 3 | n/a |
| PDH 0297 | ISY | 3 | n/a |
| PDH 0298 | GAY | 3 | n/a |
| PDH 0299 | LAY | 3 | n/a |
| PDH 0300 | HSY | 3 | n/a |
| PDH 0301 | AAY | 3 | n/a |
| PDH 0302 | ASY | 3 | n/a |
| PDH 0303 | TAY | 3 | n/a |
| PDH 0304 | NAY | 3 | n/a |
| PDH 0305 | HTY | 3 | n/a |

TABLE 28-continued

Theoretical segment pool of unique DH polypeptide segments encoded by the degenerate oligonucleotides of Table 27.

| Name | Sequence | Length | SEQ ID NO |
|---|---|---|---|
| PDH 0306 | RTY | 3 | n/a |
| PDH 0307 | PTY | 3 | n/a |
| PDH 0308 | RAY | 3 | n/a |
| PDH 0309 | ATY | 3 | n/a |
| PDH 0310 | STY | 3 | n/a |
| PDH 0311 | DSY | 3 | n/a |
| PDH 0312 | GSY | 3 | n/a |
| PDH 0313 | IAY | 3 | n/a |
| PDH 0314 | PAY | 3 | n/a |
| PDH 0315 | VTY | 3 | n/a |
| PDH 0316 | PSY | 3 | n/a |
| PDH 0317 | TTY | 3 | n/a |
| PDH 0318 | VAY | 3 | n/a |
| PDH 0319 | NTY | 3 | n/a |
| PDH 0320 | DAY | 3 | n/a |
| PDH 0321 | TSY | 3 | n/a |
| PDH 0322 | DTY | 3 | n/a |
| PDH 0323 | RSY | 3 | n/a |
| PDH 0324 | SSY | 3 | n/a |
| PDH 0325 | NSY | 3 | n/a |
| PDH 0326 | SAY | 3 | n/a |
| PDH 0327 | HAY | 3 | n/a |
| PDH 0328 | LSY | 3 | n/a |
| PDH 0329 | VSY | 3 | n/a |
| PDH 0330 | IVL | 3 | n/a |
| PDH 0331 | KWL | 3 | n/a |
| PDH 0332 | KVL | 3 | n/a |
| PDH 0333 | PLL | 3 | n/a |
| PDH 0334 | LGL | 3 | n/a |
| PDH 0335 | QWL | 3 | n/a |
| PDH 0336 | EGL | 3 | n/a |
| PDH 0337 | EWL | 3 | n/a |
| PDH 0338 | EVL | 3 | n/a |
| PDH 0339 | QLL | 3 | n/a |
| PDH 0340 | AGL | 3 | n/a |
| PDH 0341 | VWL | 3 | n/a |
| PDH 0342 | ELL | 3 | n/a |

TABLE 28-continued

Theoretical segment pool of unique DH polypeptide segments encoded by the degenerate oligonucleotides of Table 27.

| Name | Sequence | Length | SEQ ID NO |
|---|---|---|---|
| PDH 0343 | KGL | 3 | n/a |
| PDH 0344 | ILL | 3 | n/a |
| PDH 0345 | IGL | 3 | n/a |
| PDH 0346 | AWL | 3 | n/a |
| PDH 0347 | LWL | 3 | n/a |
| PDH 0348 | QGL | 3 | n/a |
| PDH 0349 | PVL | 3 | n/a |
| PDH 0350 | VGL | 3 | n/a |
| PDH 0351 | IWL | 3 | n/a |
| PDH 0352 | KLL | 3 | n/a |
| PDH 0353 | PGL | 3 | n/a |
| PDH 0354 | PWL | 3 | n/a |
| PDH 0355 | QVL | 3 | n/a |
| PDH 0356 | TGL | 3 | n/a |
| PDH 0357 | TWL | 3 | n/a |
| PDH 0358 | PAD | 3 | n/a |
| PDH 0359 | PAL | 3 | n/a |
| PDH 0360 | PAA | 3 | n/a |
| PDH 0361 | PAH | 3 | n/a |
| PDH 0362 | PAP | 3 | n/a |
| PDH 0363 | PAS | 3 | n/a |
| PDH 0364 | PAF | 3 | n/a |
| PDH 0365 | PAV | 3 | n/a |
| PDH 0366 | IQL | 3 | n/a |
| PDH 0367 | KRL | 3 | n/a |
| PDH 0368 | PRL | 3 | n/a |
| PDH 0369 | KQL | 3 | n/a |
| PDH 0370 | QRL | 3 | n/a |
| PDH 0371 | KEL | 3 | n/a |
| PDH 0372 | EEL | 3 | n/a |
| PDH 0373 | PEL | 3 | n/a |
| PDH 0374 | VRL | 3 | n/a |
| PDH 0375 | QEL | 3 | n/a |
| PDH 0376 | LRL | 3 | n/a |
| PDH 0377 | IEL | 3 | n/a |
| PDH 0378 | QQL | 3 | n/a |
| PDH 0379 | IRL | 3 | n/a |

TABLE 28-continued

Theoretical segment pool of unique DH polypeptide segments encoded by the degenerate oligonucleotides of Table 27.

| Name | Sequence | Length | SEQ ID NO |
|---|---|---|---|
| PDH 0380 | EQL | 3 | n/a |
| PDH 0381 | ERL | 3 | n/a |
| PDH 0382 | TRL | 3 | n/a |
| PDH 0383 | ARL | 3 | n/a |
| PDH 0384 | PQL | 3 | n/a |
| PDH 0385 | HSS | 3 | n/a |
| PDH 0386 | VST | 3 | n/a |
| PDH 0387 | HSA | 3 | n/a |
| PDH 0388 | YSG | 3 | n/a |
| PDH 0389 | ASS | 3 | n/a |
| PDH 0390 | HST | 3 | n/a |
| PDH 0391 | VSS | 3 | n/a |
| PDH 0392 | YSA | 3 | n/a |
| PDH 0393 | DST | 3 | n/a |
| PDH 0394 | PST | 3 | n/a |
| PDH 0395 | AST | 3 | n/a |
| PDH 0396 | FSS | 3 | n/a |
| PDH 0397 | LST | 3 | n/a |
| PDH 0398 | SST | 3 | n/a |
| PDH 0399 | FST | 3 | n/a |
| PDH 0400 | FSG | 3 | n/a |
| PDH 0401 | SSS | 3 | n/a |
| PDH 0402 | LSA | 3 | n/a |
| PDH 0403 | LSS | 3 | n/a |
| PDH 0404 | PSA | 3 | n/a |
| PDH 0405 | DSA | 3 | n/a |
| PDH 0406 | ASA | 3 | n/a |
| PDH 0407 | SSA | 3 | n/a |
| PDH 0408 | DSS | 3 | n/a |
| PDH 0409 | PSS | 3 | n/a |
| PDH 0410 | YSS | 3 | n/a |
| PDH 0411 | FSA | 3 | n/a |
| PDH 0412 | YST | 3 | n/a |
| PDH 0413 | VSA | 3 | n/a |
| PDH 0414 | SGA | 3 | n/a |
| PDH 0415 | AGD | 3 | n/a |
| PDH 0416 | LGA | 3 | n/a |

TABLE 28-continued

Theoretical segment pool of unique DH polypeptide segments encoded by the degenerate oligonucleotides of Table 27.

| Name | Sequence | Length | SEQ ID NO |
|---|---|---|---|
| PDH 0417 | SGY | 3 | n/a |
| PDH 0418 | SGD | 3 | n/a |
| PDH 0419 | FGY | 3 | n/a |
| PDH 0420 | DGY | 3 | n/a |
| PDH 0421 | LGS | 3 | n/a |
| PDH 0422 | FGS | 3 | n/a |
| PDH 0423 | DGS | 3 | n/a |
| PDH 0424 | YGS | 3 | n/a |
| PDH 0425 | YGA | 3 | n/a |
| PDH 0426 | VGD | 3 | n/a |
| PDH 0427 | PGS | 3 | n/a |
| PDH 0428 | VGY | 3 | n/a |
| PDH 0429 | VGS | 3 | n/a |
| PDH 0430 | VGA | 3 | n/a |
| PDH 0431 | LGD | 3 | n/a |
| PDH 0432 | AGY | 3 | n/a |
| PDH 0433 | LGY | 3 | n/a |
| PDH 0434 | HGD | 3 | n/a |
| PDH 0435 | HGA | 3 | n/a |
| PDH 0436 | PGA | 3 | n/a |
| PDH 0437 | YGD | 3 | n/a |
| PDH 0438 | PGD | 3 | n/a |
| PDH 0439 | YGY | 3 | n/a |
| PDH 0440 | PGY | 3 | n/a |
| PDH 0441 | SGS | 3 | n/a |
| PDH 0442 | HGY | 3 | n/a |
| PDH 0443 | FGD | 3 | n/a |
| PDH 0444 | FGA | 3 | n/a |
| PDH 0445 | AGS | 3 | n/a |
| PDH 0446 | DGD | 3 | n/a |
| PDH 0447 | DGA | 3 | n/a |
| PDH 0448 | HGS | 3 | n/a |
| PDH 0449 | AGA | 3 | n/a |
| PDH 0450 | SGV | 3 | n/a |
| PDH 0451 | LGV | 3 | n/a |
| PDH 0452 | AGG | 3 | n/a |
| PDH 0453 | SGG | 3 | n/a |

TABLE 28-continued

Theoretical segment pool of unique DH polypeptide segments encoded by the degenerate oligonucleotides of Table 27.

| Name | Sequence | Length | SEQ ID NO |
|---|---|---|---|
| PDH 0454 | DGV | 3 | n/a |
| PDH 0455 | PGV | 3 | n/a |
| PDH 0456 | HGV | 3 | n/a |
| PDH 0457 | YGV | 3 | n/a |
| PDH 0458 | LGG | 3 | n/a |
| PDH 0459 | VGG | 3 | n/a |
| PDH 0460 | VGV | 3 | n/a |
| PDH 0461 | FGV | 3 | n/a |
| PDH 0462 | PGG | 3 | n/a |
| PDH 0463 | YGG | 3 | n/a |
| PDH 0464 | HGG | 3 | n/a |
| PDH 0465 | DGG | 3 | n/a |
| PDH 0466 | AGV | 3 | n/a |
| PDH 0467 | FGG | 3 | n/a |
| PDH 0468 | HSD | 3 | n/a |
| PDH 0469 | YSD | 3 | n/a |
| PDH 0470 | ASD | 3 | n/a |
| PDH 0471 | FSY | 3 | n/a |
| PDH 0472 | FSD | 3 | n/a |
| PDH 0473 | SSD | 3 | n/a |
| PDH 0474 | VSD | 3 | n/a |
| PDH 0475 | PSD | 3 | n/a |
| PDH 0476 | LSD | 3 | n/a |
| PDH 0477 | YSY | 3 | n/a |
| PDH 0478 | DSD | 3 | n/a |
| PDH 0479 | SRL | 3 | n/a |
| PDH 0480 | DQL | 3 | n/a |
| PDH 0481 | FRL | 3 | n/a |
| PDH 0482 | YRL | 3 | n/a |
| PDH 0483 | HQL | 3 | n/a |
| PDH 0484 | NQL | 3 | n/a |
| PDH 0485 | NRL | 3 | n/a |
| PDH 0486 | FQL | 3 | n/a |
| PDH 0487 | DRL | 3 | n/a |
| PDH 0488 | HRL | 3 | n/a |
| PDH 0489 | YQL | 3 | n/a |
| PDH 0490 | VSW | 3 | n/a |

TABLE 28-continued

Theoretical segment pool of unique DH polypeptide segments encoded by the degenerate oligonucleotides of Table 27.

| Name | Sequence | Length | SEQ ID NO |
|---|---|---|---|
| PDH 0491 | PSW | 3 | n/a |
| PDH 0492 | HSW | 3 | n/a |
| PDH 0493 | NSW | 3 | n/a |
| PDH 0494 | FSW | 3 | n/a |
| PDH 0495 | ASW | 3 | n/a |
| PDH 0496 | TSW | 3 | n/a |
| PDH 0497 | LSW | 3 | n/a |
| PDH 0498 | DSW | 3 | n/a |
| PDH 0499 | ISW | 3 | n/a |
| PDH 0500 | SSW | 3 | n/a |
| PDH 0501 | YSW | 3 | n/a |
| PDH 0502 | SGW | 3 | n/a |
| PDH 0503 | FGW | 3 | n/a |
| PDH 0504 | LGW | 3 | n/a |
| PDH 0505 | AGW | 3 | n/a |
| PDH 0506 | VGW | 3 | n/a |
| PDH 0507 | YGW | 3 | n/a |
| PDH 0508 | PGW | 3 | n/a |
| PDH 0509 | DGW | 3 | n/a |
| PDH 0510 | HGW | 3 | n/a |
| PDH 0511 | IGD | 3 | n/a |
| PDH 0512 | GGA | 3 | n/a |
| PDH 0513 | IGG | 3 | n/a |
| PDH 0514 | GGD | 3 | n/a |
| PDH 0515 | GGV | 3 | n/a |
| PDH 0516 | RGD | 3 | n/a |
| PDH 0517 | TGV | 3 | n/a |
| PDH 0518 | RGV | 3 | n/a |
| PDH 0519 | GGG | 3 | n/a |
| PDH 0520 | IGA | 3 | n/a |
| PDH 0521 | IGV | 3 | n/a |
| PDH 0522 | RGG | 3 | n/a |
| PDH 0523 | RGA | 3 | n/a |
| PDH 0524 | TGD | 3 | n/a |
| PDH 0525 | TGA | 3 | n/a |
| PDH 0526 | TGG | 3 | n/a |
| PDH 0527 | NSA | 3 | n/a |

TABLE 28-continued

Theoretical segment pool of unique DH polypeptide segments encoded by the degenerate oligonucleotides of Table 27.

| Name | Sequence | Length | SEQ ID NO |
|---|---|---|---|
| PDH 0528 | NSD | 3 | n/a |
| PDH 0529 | TSD | 3 | n/a |
| PDH 0530 | TSA | 3 | n/a |
| PDH 0531 | ISA | 3 | n/a |
| PDH 0532 | ISD | 3 | n/a |
| PDH 0533 | HYD | 3 | n/a |
| PDH 0534 | HYG | 3 | n/a |
| PDH 0535 | FYD | 3 | n/a |
| PDH 0536 | FYG | 3 | n/a |
| PDH 0537 | LYA | 3 | n/a |
| PDH 0538 | LYD | 3 | n/a |
| PDH 0539 | VYA | 3 | n/a |
| PDH 0540 | VYD | 3 | n/a |
| PDH 0541 | TYA | 3 | n/a |
| PDH 0542 | LYG | 3 | n/a |
| PDH 0543 | DYD | 3 | n/a |
| PDH 0544 | HYA | 3 | n/a |
| PDH 0545 | TYD | 3 | n/a |
| PDH 0546 | TYG | 3 | n/a |
| PDH 0547 | YYA | 3 | n/a |
| PDH 0548 | DYG | 3 | n/a |
| PDH 0549 | YYD | 3 | n/a |
| PDH 0550 | NYG | 3 | n/a |
| PDH 0551 | NYD | 3 | n/a |
| PDH 0552 | PYG | 3 | n/a |
| PDH 0553 | YYG | 3 | n/a |
| PDH 0554 | PYD | 3 | n/a |
| PDH 0555 | NYA | 3 | n/a |
| PDH 0556 | FYA | 3 | n/a |
| PDH 0557 | PYA | 3 | n/a |
| PDH 0558 | VYG | 3 | n/a |
| PDH 0559 | AYD | 3 | n/a |
| PDH 0560 | IYG | 3 | n/a |
| PDH 0561 | AYA | 3 | n/a |
| PDH 0562 | SYG | 3 | n/a |
| PDH 0563 | IYD | 3 | n/a |
| PDH 0564 | IYA | 3 | n/a |

TABLE 28-continued

Theoretical segment pool of unique DH polypeptide segments encoded by the degenerate oligonucleotides of Table 27.

| Name | Sequence | Length | SEQ ID NO |
|---|---|---|---|
| PDH 0565 | AYG | 3 | n/a |
| PDH 0566 | DYA | 3 | n/a |
| PDH 0567 | SYD | 3 | n/a |
| PDH 0568 | SYA | 3 | n/a |
| PDH 0569 | TSE | 3 | n/a |
| PDH 0570 | HSE | 3 | n/a |
| PDH 0571 | YSE | 3 | n/a |
| PDH 0572 | ASE | 3 | n/a |
| PDH 0573 | NSE | 3 | n/a |
| PDH 0574 | FSE | 3 | n/a |
| PDH 0575 | DSE | 3 | n/a |
| PDH 0576 | ISE | 3 | n/a |
| PDH 0577 | SSE | 3 | n/a |
| PDH 0578 | VSE | 3 | n/a |
| PDH 0579 | PSE | 3 | n/a |
| PDH 0580 | LSE | 3 | n/a |
| PDH 0581 | EWP | 3 | n/a |
| PDH 0582 | PWP | 3 | n/a |
| PDH 0583 | KWA | 3 | n/a |
| PDH 0584 | IWP | 3 | n/a |
| PDH 0585 | LWA | 3 | n/a |
| PDH 0586 | LWV | 3 | n/a |
| PDH 0587 | AWV | 3 | n/a |
| PDH 0588 | AWA | 3 | n/a |
| PDH 0589 | PWA | 3 | n/a |
| PDH 0590 | QWP | 3 | n/a |
| PDH 0591 | PWV | 3 | n/a |
| PDH 0592 | TWV | 3 | n/a |
| PDH 0593 | TWP | 3 | n/a |
| PDH 0594 | QWA | 3 | n/a |
| PDH 0595 | KWP | 3 | n/a |
| PDH 0596 | QWV | 3 | n/a |
| PDH 0597 | EWV | 3 | n/a |
| PDH 0598 | VWA | 3 | n/a |
| PDH 0599 | AWP | 3 | n/a |
| PDH 0600 | VWV | 3 | n/a |
| PDH 0601 | TWA | 3 | n/a |

TABLE 28-continued

Theoretical segment pool of unique DH polypeptide segments encoded by the degenerate oligonucleotides of Table 27.

| Name | Sequence | Length | SEQ ID NO |
|---|---|---|---|
| PDH 0602 | EWA | 3 | n/a |
| PDH 0603 | IWV | 3 | n/a |
| PDH 0604 | VWP | 3 | n/a |
| PDH 0605 | IWA | 3 | n/a |
| PDH 0606 | LWP | 3 | n/a |
| PDH 0607 | KWV | 3 | n/a |
| PDH 0608 | HDY | 3 | n/a |
| PDH 0609 | IVY | 3 | n/a |
| PDH 0610 | PVY | 3 | n/a |
| PDH 0611 | AVY | 3 | n/a |
| PDH 0612 | GVY | 3 | n/a |
| PDH 0613 | LVY | 3 | n/a |
| PDH 0614 | GDY | 3 | n/a |
| PDH 0615 | ADY | 3 | n/a |
| PDH 0616 | VVY | 3 | n/a |
| PDH 0617 | NVY | 3 | n/a |
| PDH 0618 | SDY | 3 | n/a |
| PDH 0619 | RVY | 3 | n/a |
| PDH 0620 | LDY | 3 | n/a |
| PDH 0621 | HVY | 3 | n/a |
| PDH 0622 | PDY | 3 | n/a |
| PDH 0623 | RDY | 3 | n/a |
| PDH 0624 | SVY | 3 | n/a |
| PDH 0625 | IDY | 3 | n/a |
| PDH 0626 | DDY | 3 | n/a |
| PDH 0627 | NDY | 3 | n/a |
| PDH 0628 | VDY | 3 | n/a |
| PDH 0629 | DVY | 3 | n/a |
| PDH 0630 | TVY | 3 | n/a |
| PDH 0631 | TDY | 3 | n/a |
| PDH 0632 | GKL | 3 | n/a |
| PDH 0633 | GIL | 3 | n/a |
| PDH 0634 | GRL | 3 | n/a |
| PDH 0635 | GGL | 3 | n/a |
| PDH 0636 | GAL | 3 | n/a |
| PDH 0637 | GTL | 3 | n/a |
| PDH 0638 | LRG | 3 | n/a |

TABLE 28-continued

Theoretical segment pool of unique DH polypeptide segments encoded by the degenerate oligonucleotides of Table 27.

| Name | Sequence | Length | SEQ ID NO |
|---|---|---|---|
| PDH 0639 | DTG | 3 | n/a |
| PDH 0640 | ARG | 3 | n/a |
| PDH 0641 | YIG | 3 | n/a |
| PDH 0642 | ITG | 3 | n/a |
| PDH 0643 | PIG | 3 | n/a |
| PDH 0644 | DIG | 3 | n/a |
| PDH 0645 | ATG | 3 | n/a |
| PDH 0646 | STG | 3 | n/a |
| PDH 0647 | HTG | 3 | n/a |
| PDH 0648 | VRG | 3 | n/a |
| PDH 0649 | YRG | 3 | n/a |
| PDH 0650 | NIG | 3 | n/a |
| PDH 0651 | VIG | 3 | n/a |
| PDH 0652 | IRG | 3 | n/a |
| PDH 0653 | LTG | 3 | n/a |
| PDH 0654 | SRG | 3 | n/a |
| PDH 0655 | VTG | 3 | n/a |
| PDH 0656 | AIG | 3 | n/a |
| PDH 0657 | IIG | 3 | n/a |
| PDH 0658 | FTG | 3 | n/a |
| PDH 0659 | HIG | 3 | n/a |
| PDH 0660 | HRG | 3 | n/a |
| PDH 0661 | PTG | 3 | n/a |
| PDH 0662 | YTG | 3 | n/a |
| PDH 0663 | PRG | 3 | n/a |
| PDH 0664 | TIG | 3 | n/a |
| PDH 0665 | DRG | 3 | n/a |
| PDH 0666 | TRG | 3 | n/a |
| PDH 0667 | FIG | 3 | n/a |
| PDH 0668 | NTG | 3 | n/a |
| PDH 0669 | FRG | 3 | n/a |
| PDH 0670 | LIG | 3 | n/a |
| PDH 0671 | NRG | 3 | n/a |
| PDH 0672 | TTG | 3 | n/a |
| PDH 0673 | SIG | 3 | n/a |
| PDH 0674 | EAG | 3 | n/a |
| PDH 0675 | KAV | 3 | n/a |

TABLE 28-continued

Theoretical segment pool of unique DH polypeptide segments encoded by the degenerate oligonucleotides of Table 27.

| Name | Sequence | Length | SEQ ID NO |
|---|---|---|---|
| PDH 0676 | IAD | 3 | n/a |
| PDH 0677 | IAV | 3 | n/a |
| PDH 0678 | KAD | 3 | n/a |
| PDH 0679 | QAA | 3 | n/a |
| PDH 0680 | LAA | 3 | n/a |
| PDH 0681 | QAD | 3 | n/a |
| PDH 0682 | AAD | 3 | n/a |
| PDH 0683 | AAA | 3 | n/a |
| PDH 0684 | LAD | 3 | n/a |
| PDH 0685 | VAD | 3 | n/a |
| PDH 0686 | TAA | 3 | n/a |
| PDH 0687 | TAD | 3 | n/a |
| PDH 0688 | TAV | 3 | n/a |
| PDH 0689 | EAA | 3 | n/a |
| PDH 0690 | AAV | 3 | n/a |
| PDH 0691 | QAV | 3 | n/a |
| PDH 0692 | EAV | 3 | n/a |
| PDH 0693 | LAV | 3 | n/a |
| PDH 0694 | QAG | 3 | n/a |
| PDH 0695 | KAA | 3 | n/a |
| PDH 0696 | IAA | 3 | n/a |
| PDH 0697 | KAG | 3 | n/a |
| PDH 0698 | EAD | 3 | n/a |
| PDH 0699 | WVG | 3 | n/a |
| PDH 0700 | VFG | 3 | n/a |
| PDH 0701 | SFG | 3 | n/a |
| PDH 0702 | RFG | 3 | n/a |
| PDH 0703 | WAG | 3 | n/a |
| PDH 0704 | WFG | 3 | n/a |
| PDH 0705 | SVG | 3 | n/a |
| PDH 0706 | TVG | 3 | n/a |
| PDH 0707 | GFG | 3 | n/a |
| PDH 0708 | MVG | 3 | n/a |
| PDH 0709 | MFG | 3 | n/a |
| PDH 0710 | LVG | 3 | n/a |
| PDH 0711 | WSG | 3 | n/a |
| PDH 0712 | AFG | 3 | n/a |

TABLE 28-continued

Theoretical segment pool of unique DH polypeptide segments encoded by the degenerate oligonucleotides of Table 27.

| Name | Sequence | Length | SEQ ID NO |
|---|---|---|---|
| PDH 0713 | MAG | 3 | n/a |
| PDH 0714 | LFG | 3 | n/a |
| PDH 0715 | MSG | 3 | n/a |
| PDH 0716 | VVG | 3 | n/a |
| PDH 0717 | RVG | 3 | n/a |
| PDH 0718 | AVG | 3 | n/a |
| PDH 0719 | GVG | 3 | n/a |
| PDH 0720 | TFG | 3 | n/a |
| PDH 0721 | DGI | 3 | n/a |
| PDH 0722 | LGI | 3 | n/a |
| PDH 0723 | SGI | 3 | n/a |
| PDH 0724 | HGI | 3 | n/a |
| PDH 0725 | PGI | 3 | n/a |
| PDH 0726 | VGI | 3 | n/a |
| PDH 0727 | YGI | 3 | n/a |
| PDH 0728 | FGI | 3 | n/a |
| PDH 0729 | AGI | 3 | n/a |
| PDH 0730 | DVD | 3 | n/a |
| PDH 0731 | FVA | 3 | n/a |
| PDH 0732 | DVA | 3 | n/a |
| PDH 0733 | YVD | 3 | n/a |
| PDH 0734 | YVA | 3 | n/a |
| PDH 0735 | DVG | 3 | n/a |
| PDH 0736 | HVG | 3 | n/a |
| PDH 0737 | VVD | 3 | n/a |
| PDH 0738 | HVD | 3 | n/a |
| PDH 0739 | VVA | 3 | n/a |
| PDH 0740 | IVA | 3 | n/a |
| PDH 0741 | AVD | 3 | n/a |
| PDH 0742 | YVG | 3 | n/a |
| PDH 0743 | TVD | 3 | n/a |
| PDH 0744 | FVG | 3 | n/a |
| PDH 0745 | FVD | 3 | n/a |
| PDH 0746 | TVA | 3 | n/a |
| PDH 0747 | PVG | 3 | n/a |
| PDH 0748 | PVA | 3 | n/a |
| PDH 0749 | AVA | 3 | n/a |

TABLE 28-continued

Theoretical segment pool of unique DH polypeptide segments encoded by the degenerate oligonucleotides of Table 27.

| Name | Sequence | Length | SEQ ID NO |
|---|---|---|---|
| PDH 0750 | PVD | 3 | n/a |
| PDH 0751 | NVG | 3 | n/a |
| PDH 0752 | IVD | 3 | n/a |
| PDH 0753 | HVA | 3 | n/a |
| PDH 0754 | SVA | 3 | n/a |
| PDH 0755 | SVD | 3 | n/a |
| PDH 0756 | IVG | 3 | n/a |
| PDH 0757 | NVA | 3 | n/a |
| PDH 0758 | LVD | 3 | n/a |
| PDH 0759 | LVA | 3 | n/a |
| PDH 0760 | NVD | 3 | n/a |
| PDH 0761 | AYY | 3 | n/a |
| PDH 0762 | LFY | 3 | n/a |
| PDH 0763 | RFY | 3 | n/a |
| PDH 0764 | IFY | 3 | n/a |
| PDH 0765 | TYY | 3 | n/a |
| PDH 0766 | RYY | 3 | n/a |
| PDH 0767 | PYY | 3 | n/a |
| PDH 0768 | VYY | 3 | n/a |
| PDH 0769 | SFY | 3 | n/a |
| PDH 0770 | GYY | 3 | n/a |
| PDH 0771 | GFY | 3 | n/a |
| PDH 0772 | DFY | 3 | n/a |
| PDH 0773 | VFY | 3 | n/a |
| PDH 0774 | HYY | 3 | n/a |
| PDH 0775 | SYY | 3 | n/a |
| PDH 0776 | PFY | 3 | n/a |
| PDH 0777 | LYY | 3 | n/a |
| PDH 0778 | IYY | 3 | n/a |
| PDH 0779 | TFY | 3 | n/a |
| PDH 0780 | NFY | 3 | n/a |
| PDH 0781 | HFY | 3 | n/a |
| PDH 0782 | AFY | 3 | n/a |
| PDH 0783 | DYY | 3 | n/a |
| PDH 0784 | NYY | 3 | n/a |
| PDH 0785 | VVV | 3 | n/a |
| PDH 0786 | VVF | 3 | n/a |

TABLE 28-continued

Theoretical segment pool of unique DH polypeptide segments encoded by the degenerate oligonucleotides of Table 27.

| Name | Sequence | Length | SEQ ID NO |
|---|---|---|---|
| PDH 0787 | VVP | 3 | n/a |
| PDH 0788 | VVH | 3 | n/a |
| PDH 0789 | VVS | 3 | n/a |
| PDH 0790 | GDL | 3 | n/a |
| PDH 0791 | SAL | 3 | n/a |
| PDH 0792 | RAL | 3 | n/a |
| PDH 0793 | RGL | 3 | n/a |
| PDH 0794 | IAL | 3 | n/a |
| PDH 0795 | LDL | 3 | n/a |
| PDH 0796 | TDL | 3 | n/a |
| PDH 0797 | ADL | 3 | n/a |
| PDH 0798 | VDL | 3 | n/a |
| PDH 0799 | IDL | 3 | n/a |
| PDH 0800 | SDL | 3 | n/a |
| PDH 0801 | TAL | 3 | n/a |
| PDH 0802 | RDL | 3 | n/a |
| PDH 0803 | AAL | 3 | n/a |
| PDH 0804 | SGL | 3 | n/a |
| PDH 0805 | PDL | 3 | n/a |
| PDH 0806 | LAL | 3 | n/a |
| PDH 0807 | AGE | 3 | n/a |
| PDH 0808 | SGE | 3 | n/a |
| PDH 0809 | HGE | 3 | n/a |
| PDH 0810 | LGE | 3 | n/a |
| PDH 0811 | VGE | 3 | n/a |
| PDH 0812 | PGE | 3 | n/a |
| PDH 0813 | YGE | 3 | n/a |
| PDH 0814 | DGE | 3 | n/a |
| PDH 0815 | FGE | 3 | n/a |
| PDH 0816 | SDG | 3 | n/a |
| PDH 0817 | NDG | 3 | n/a |
| PDH 0818 | GDG | 3 | n/a |
| PDH 0819 | HDG | 3 | n/a |
| PDH 0820 | ADG | 3 | n/a |
| PDH 0821 | TDG | 3 | n/a |
| PDH 0822 | IDG | 3 | n/a |
| PDH 0823 | DDG | 3 | n/a |

TABLE 28-continued

Theoretical segment pool of unique DH polypeptide segments encoded by the degenerate oligonucleotides of Table 27.

| Name | Sequence | Length | SEQ ID NO |
|---|---|---|---|
| PDH 0824 | VDG | 3 | n/a |
| PDH 0825 | RDG | 3 | n/a |
| PDH 0826 | LDG | 3 | n/a |
| PDH 0827 | PDG | 3 | n/a |
| PDH 0828 | RHG | 3 | n/a |
| PDH 0829 | RLG | 3 | n/a |
| PDH 0830 | RYG | 3 | n/a |
| PDH 0831 | DLY | 3 | n/a |
| PDH 0832 | IWY | 3 | n/a |
| PDH 0833 | LWY | 3 | n/a |
| PDH 0834 | ALY | 3 | n/a |
| PDH 0835 | RWY | 3 | n/a |
| PDH 0836 | SLY | 3 | n/a |
| PDH 0837 | HLY | 3 | n/a |
| PDH 0838 | ILY | 3 | n/a |
| PDH 0839 | SWY | 3 | n/a |
| PDH 0840 | GLY | 3 | n/a |
| PDH 0841 | RLY | 3 | n/a |
| PDH 0842 | DWY | 3 | n/a |
| PDH 0843 | NLY | 3 | n/a |
| PDH 0844 | VWY | 3 | n/a |
| PDH 0845 | GWY | 3 | n/a |
| PDH 0846 | AWY | 3 | n/a |
| PDH 0847 | HWY | 3 | n/a |
| PDH 0848 | PLY | 3 | n/a |
| PDH 0849 | LLY | 3 | n/a |
| PDH 0850 | TWY | 3 | n/a |
| PDH 0851 | TLY | 3 | n/a |
| PDH 0852 | NWY | 3 | n/a |
| PDH 0853 | VLY | 3 | n/a |
| PDH 0854 | PWY | 3 | n/a |
| PDH 0855 | GSL | 3 | n/a |
| PDH 0856 | ISL | 3 | n/a |
| PDH 0857 | DWL | 3 | n/a |
| PDH 0858 | SSL | 3 | n/a |
| PDH 0859 | TSL | 3 | n/a |
| PDH 0860 | VSL | 3 | n/a |

TABLE 28-continued

Theoretical segment pool of unique DH polypeptide segments encoded by the degenerate oligonucleotides of Table 27.

| Name | Sequence | Length | SEQ ID NO |
|---|---|---|---|
| PDH 0861 | DSL | 3 | n/a |
| PDH 0862 | HWL | 3 | n/a |
| PDH 0863 | ASL | 3 | n/a |
| PDH 0864 | SWL | 3 | n/a |
| PDH 0865 | NWL | 3 | n/a |
| PDH 0866 | NLL | 3 | n/a |
| PDH 0867 | DLL | 3 | n/a |
| PDH 0868 | RSL | 3 | n/a |
| PDH 0869 | PSL | 3 | n/a |
| PDH 0870 | HLL | 3 | n/a |
| PDH 0871 | GWL | 3 | n/a |
| PDH 0872 | HSL | 3 | n/a |
| PDH 0873 | NSL | 3 | n/a |
| PDH 0874 | LSL | 3 | n/a |
| PDH 0875 | RWL | 3 | n/a |
| PDH 0876 | FDY | 3 | n/a |
| PDH 0877 | YYY | 3 | n/a |
| PDH 0878 | FYY | 3 | n/a |
| PDH 0879 | YDY | 3 | n/a |
| PDH 0880 | LIL | 3 | n/a |
| PDH 0881 | LKL | 3 | n/a |
| PDH 0882 | LTL | 3 | n/a |
| PDH 0883 | YAG | 3 | n/a |
| PDH 0884 | FPG | 3 | n/a |
| PDH 0885 | YPG | 3 | n/a |
| PDH 0886 | FAG | 3 | n/a |
| PDH 0887 | FYH | 3 | n/a |
| PDH 0888 | LYH | 3 | n/a |
| PDH 0889 | IYH | 3 | n/a |
| PDH 0890 | SYH | 3 | n/a |
| PDH 0891 | TYH | 3 | n/a |
| PDH 0892 | YYH | 3 | n/a |
| PDH 0893 | NYH | 3 | n/a |
| PDH 0894 | PYH | 3 | n/a |
| PDH 0895 | AYH | 3 | n/a |
| PDH 0896 | VYH | 3 | n/a |
| PDH 0897 | HYH | 3 | n/a |

TABLE 28-continued

Theoretical segment pool of unique DH polypeptide segments encoded by the degenerate oligonucleotides of Table 27.

| Name | Sequence | Length | SEQ ID NO |
|---|---|---|---|
| PDH 0898 | DYH | 3 | n/a |
| PDH 0899 | YTAM | 4 | 5639 |
| PDH 0900 | HTAI | 4 | 5640 |
| PDH 0901 | YTAS | 4 | 5641 |
| PDH 0902 | YTAI | 4 | 5642 |
| PDH 0903 | YTAR | 4 | 5643 |
| PDH 0904 | PTAS | 4 | 5644 |
| PDH 0905 | LTAM | 4 | 5645 |
| PDH 0906 | DTAI | 4 | 5646 |
| PDH 0907 | FTAS | 4 | 5647 |
| PDH 0908 | FTAM | 4 | 5648 |
| PDH 0909 | LTAS | 4 | 5649 |
| PDH 0910 | ATAI | 4 | 5650 |
| PDH 0911 | STAI | 4 | 5651 |
| PDH 0912 | FTAR | 4 | 5652 |
| PDH 0913 | DTAM | 4 | 4420 |
| PDH 0914 | STAR | 4 | 5653 |
| PDH 0915 | LTAR | 4 | 5654 |
| PDH 0916 | FTAI | 4 | 5655 |
| PDH 0917 | LTAI | 4 | 5656 |
| PDH 0918 | STAM | 4 | 5657 |
| PDH 0919 | ATAM | 4 | 5658 |
| PDH 0920 | STAS | 4 | 5659 |
| PDH 0921 | ATAR | 4 | 5660 |
| PDH 0922 | HTAS | 4 | 5661 |
| PDH 0923 | HTAM | 4 | 5662 |
| PDH 0924 | VTAI | 4 | 3907 |
| PDH 0925 | DTAR | 4 | 5663 |
| PDH 0926 | HTAR | 4 | 5664 |
| PDH 0927 | ATAS | 4 | 5665 |
| PDH 0928 | VTAM | 4 | 5666 |
| PDH 0929 | PTAR | 4 | 5667 |
| PDH 0930 | DTAS | 4 | 5668 |
| PDH 0931 | VTAS | 4 | 5669 |
| PDH 0932 | PTAM | 4 | 5670 |
| PDH 0933 | VTAR | 4 | 5671 |
| PDH 0934 | PTAI | 4 | 5672 |

TABLE 28-continued

Theoretical segment pool of unique DH polypeptide segments encoded by the degenerate oligonucleotides of Table 27.

| Name | Sequence | Length | SEQ ID NO |
|---|---|---|---|
| PDH 0935 | LVAT | 4 | 5673 |
| PDH 0936 | LAAT | 4 | 5674 |
| PDH 0937 | MVAT | 4 | 5675 |
| PDH 0938 | TGAT | 4 | 5676 |
| PDH 0939 | AVAT | 4 | 5677 |
| PDH 0940 | VAAT | 4 | 3803 |
| PDH 0941 | PAAT | 4 | 5678 |
| PDH 0942 | KGAT | 4 | 5679 |
| PDH 0943 | EGAT | 4 | 5680 |
| PDH 0944 | PVAT | 4 | 5681 |
| PDH 0945 | AGAT | 4 | 5682 |
| PDH 0946 | QAAT | 4 | 5683 |
| PDH 0947 | AAAT | 4 | 5684 |
| PDH 0948 | VVAT | 4 | 5685 |
| PDH 0949 | VGAT | 4 | 3756 |
| PDH 0950 | TVAT | 4 | 5686 |
| PDH 0951 | EVAT | 4 | 5687 |
| PDH 0952 | LGAT | 4 | 5688 |
| PDH 0953 | KAAT | 4 | 5689 |
| PDH 0954 | MGAT | 4 | 5690 |
| PDH 0955 | PGAT | 4 | 5691 |
| PDH 0956 | QVAT | 4 | 5692 |
| PDH 0957 | KVAT | 4 | 5693 |
| PDH 0958 | EAAT | 4 | 5694 |
| PDH 0959 | TAAT | 4 | 5695 |
| PDH 0960 | MAAT | 4 | 5696 |
| PDH 0961 | QGAT | 4 | 5697 |
| PDH 0962 | RFGA | 4 | 5698 |
| PDH 0963 | MFGE | 4 | 5699 |
| PDH 0964 | MFGA | 4 | 5700 |
| PDH 0965 | VFGG | 4 | 5701 |
| PDH 0966 | RFGE | 4 | 5702 |
| PDH 0967 | MFGV | 4 | 5703 |
| PDH 0968 | VFGA | 4 | 5704 |
| PDH 0969 | VFGE | 4 | 5705 |
| PDH 0970 | VFGV | 4 | 5706 |
| PDH 0971 | MFGG | 4 | 5707 |

TABLE 28-continued

Theoretical segment pool of unique DH polypeptide segments encoded by the degenerate oligonucleotides of Table 27.

| Name | Sequence | Length | SEQ ID NO |
|---|---|---|---|
| PDH 0972 | LFGV | 4 | 5708 |
| PDH 0973 | SFGE | 4 | 5709 |
| PDH 0974 | SFGA | 4 | 5710 |
| PDH 0975 | RFGG | 4 | 5711 |
| PDH 0976 | SFGV | 4 | 5712 |
| PDH 0977 | LFGA | 4 | 5713 |
| PDH 0978 | SFGG | 4 | 5714 |
| PDH 0979 | LFGG | 4 | 5715 |
| PDH 0980 | LFGE | 4 | 5716 |
| PDH 0981 | WFGE | 4 | 3966 |
| PDH 0982 | WFGG | 4 | 5717 |
| PDH 0983 | WFGV | 4 | 5718 |
| PDH 0984 | WFGA | 4 | 5719 |
| PDH 0985 | TFGG | 4 | 4154 |
| PDH 0986 | TFGE | 4 | 5720 |
| PDH 0987 | AFGV | 4 | 5721 |
| PDH 0988 | AFGA | 4 | 5722 |
| PDH 0989 | GFGV | 4 | 5723 |
| PDH 0990 | GFGA | 4 | 5724 |
| PDH 0991 | GFGG | 4 | 5725 |
| PDH 0992 | TFGV | 4 | 5726 |
| PDH 0993 | AFGE | 4 | 5727 |
| PDH 0994 | TFGA | 4 | 5728 |
| PDH 0995 | RFGV | 4 | 5729 |
| PDH 0996 | AFGG | 4 | 5730 |
| PDH 0997 | GFGE | 4 | 5731 |
| PDH 0998 | AGDY | 4 | 5732 |
| PDH 0999 | PGYY | 4 | 5733 |
| PDH 1000 | VGAY | 4 | 5734 |
| PDH 1001 | HGSY | 4 | 5735 |
| PDH 1002 | SGSY | 4 | 3763 |
| PDH 1003 | PGDY | 4 | 5736 |
| PDH 1004 | LGDY | 4 | 5737 |
| PDH 1005 | DGAY | 4 | 5738 |
| PDH 1006 | FGDY | 4 | 5739 |
| PDH 1007 | LGAY | 4 | 5740 |
| PDH 1008 | DGYY | 4 | 5741 |
| PDH 1009 | VGSY | 4 | 5742 |
| PDH 1010 | YGAY | 4 | 5743 |
| PDH 1011 | FGYY | 4 | 5744 |
| PDH 1012 | DGDY | 4 | 5745 |
| PDH 1013 | AGYY | 4 | 5746 |
| PDH 1014 | YGSY | 4 | 5747 |
| PDH 1015 | VGYY | 4 | 5748 |
| PDH 1016 | AGAY | 4 | 5749 |
| PDH 1017 | DGSY | 4 | 5750 |
| PDH 1018 | HGDY | 4 | 5751 |
| PDH 1019 | FGAY | 4 | 5752 |
| PDH 1020 | HGYY | 4 | 5753 |
| PDH 1021 | YGYY | 4 | 5754 |
| PDH 1022 | SGYY | 4 | 4187 |
| PDH 1023 | SGAY | 4 | 5755 |
| PDH 1024 | AGSY | 4 | 5756 |
| PDH 1025 | HGAY | 4 | 5757 |
| PDH 1026 | PGAY | 4 | 5758 |
| PDH 1027 | PGSY | 4 | 5759 |
| PDH 1028 | LGSY | 4 | 5760 |
| PDH 1029 | VGDY | 4 | 5761 |
| PDH 1030 | SGDY | 4 | 5762 |
| PDH 1031 | LGYY | 4 | 5763 |
| PDH 1032 | FGSY | 4 | 5764 |
| PDH 1033 | YGDY | 4 | 4350 |
| PDH 1034 | YSSV | 4 | 5765 |
| PDH 1035 | YSSI | 4 | 5766 |
| PDH 1036 | YSSS | 4 | 4442 |
| PDH 1037 | YSSR | 4 | 5767 |
| PDH 1038 | YSSP | 4 | 5768 |
| PDH 1039 | YSSA | 4 | 5769 |
| PDH 1040 | YSSL | 4 | 5770 |
| PDH 1041 | YSSG | 4 | 4462 |
| PDH 1042 | YSST | 4 | 5771 |
| PDH 1043 | EVRG | 4 | 5772 |
| PDH 1044 | PVRG | 4 | 5773 |
| PDH 1045 | PVTG | 4 | 5774 |

TABLE 28-continued

Theoretical segment pool of unique DH polypeptide segments encoded by the degenerate oligonucleotides of Table 27.

| Name | Sequence | Length | SEQ ID NO |
|---|---|---|---|
| PDH 1046 | EVAG | 4 | 5775 |
| PDH 1047 | MVTG | 4 | 5776 |
| PDH 1048 | MVGG | 4 | 5777 |
| PDH 1049 | EVGG | 4 | 3728 |
| PDH 1050 | QVRG | 4 | 5778 |
| PDH 1051 | MVRG | 4 | 4017 |
| PDH 1052 | QVGG | 4 | 5779 |
| PDH 1053 | VVAG | 4 | 5780 |
| PDH 1054 | EVTG | 4 | 5781 |
| PDH 1055 | VVRG | 4 | 5782 |
| PDH 1056 | PVAG | 4 | 5783 |
| PDH 1057 | LVAG | 4 | 5784 |
| PDH 1058 | LVRG | 4 | 5785 |
| PDH 1059 | QVTG | 4 | 5786 |
| PDH 1060 | PVGG | 4 | 5787 |
| PDH 1061 | AVGG | 4 | 5788 |
| PDH 1062 | TVGG | 4 | 5789 |
| PDH 1063 | KVGG | 4 | 5790 |
| PDH 1064 | TVAG | 4 | 5791 |
| PDH 1065 | AVTG | 4 | 5792 |
| PDH 1066 | KVRG | 4 | 5793 |
| PDH 1067 | LVTG | 4 | 5794 |
| PDH 1068 | AVRG | 4 | 5795 |
| PDH 1069 | LVGG | 4 | 5796 |
| PDH 1070 | AVAG | 4 | 4473 |
| PDH 1071 | QVAG | 4 | 5797 |
| PDH 1072 | KVTG | 4 | 5798 |
| PDH 1073 | TVTG | 4 | 5799 |
| PDH 1074 | VVGG | 4 | 5800 |
| PDH 1075 | KVAG | 4 | 5801 |
| PDH 1076 | MVAG | 4 | 5802 |
| PDH 1077 | VVTG | 4 | 5803 |
| PDH 1078 | TVRG | 4 | 5804 |
| PDH 1079 | SDGY | 4 | 5805 |
| PDH 1080 | IDGF | 4 | 5806 |
| PDH 1081 | ADGY | 4 | 5807 |
| PDH 1082 | ADGS | 4 | 5808 |
| PDH 1083 | RDGF | 4 | 5809 |
| PDH 1084 | IDGS | 4 | 5810 |
| PDH 1085 | GDGS | 4 | 5811 |
| PDH 1086 | LDGY | 4 | 5812 |
| PDH 1087 | GDGY | 4 | 5813 |
| PDH 1088 | IDGY | 4 | 5814 |
| PDH 1089 | SDGS | 4 | 5815 |
| PDH 1090 | SDGF | 4 | 5816 |
| PDH 1091 | VDGF | 4 | 5817 |
| PDH 1092 | GDGF | 4 | 5818 |
| PDH 1093 | TDGY | 4 | 5819 |
| PDH 1094 | RDGY | 4 | 4410 |
| PDH 1095 | VDGY | 4 | 5820 |
| PDH 1096 | TDGS | 4 | 5821 |
| PDH 1097 | RDGS | 4 | 5822 |
| PDH 1098 | LDGF | 4 | 5823 |
| PDH 1099 | VDGS | 4 | 5824 |
| PDH 1100 | ADGF | 4 | 5825 |
| PDH 1101 | LDGS | 4 | 5826 |
| PDH 1102 | PDGS | 4 | 5827 |
| PDH 1103 | PDGF | 4 | 5828 |
| PDH 1104 | PDGY | 4 | 5829 |
| PDH 1105 | TDGF | 4 | 5830 |
| PDH 1106 | NYGG | 4 | 5831 |
| PDH 1107 | TYGD | 4 | 5832 |
| PDH 1108 | LYGD | 4 | 5833 |
| PDH 1109 | FYGG | 4 | 5834 |
| PDH 1110 | SYGG | 4 | 5835 |
| PDH 1111 | TYGG | 4 | 5836 |
| PDH 1112 | LYGA | 4 | 5837 |
| PDH 1113 | SYGA | 4 | 5838 |
| PDH 1114 | LYGG | 4 | 5839 |
| PDH 1115 | VYGD | 4 | 5840 |
| PDH 1116 | SYGD | 4 | 5841 |
| PDH 1117 | AYGG | 4 | 5842 |
| PDH 1118 | VYGG | 4 | 5843 |
| PDH 1119 | HYGG | 4 | 5844 |

TABLE 28-continued

Theoretical segment pool of unique DH polypeptide segments encoded by the degenerate oligonucleotides of Table 27.

| Name | Sequence | Length | SEQ ID NO |
|---|---|---|---|
| PDH 1120 | FYGA | 4 | 5845 |
| PDH 1121 | NYGD | 4 | 5846 |
| PDH 1122 | TYGA | 4 | 5847 |
| PDH 1123 | FYGD | 4 | 5848 |
| PDH 1124 | IYGD | 4 | 5849 |
| PDH 1125 | DYGD | 4 | 4349 |
| PDH 1126 | PYGD | 4 | 5850 |
| PDH 1127 | DYGA | 4 | 5851 |
| PDH 1128 | HYGA | 4 | 5852 |
| PDH 1129 | PYGA | 4 | 5853 |
| PDH 1130 | PYGG | 4 | 5854 |
| PDH 1131 | HYGD | 4 | 5855 |
| PDH 1132 | AYGA | 4 | 5856 |
| PDH 1133 | VYGA | 4 | 5857 |
| PDH 1134 | YYGD | 4 | 5858 |
| PDH 1135 | AYGD | 4 | 5859 |
| PDH 1136 | NYGA | 4 | 5860 |
| PDH 1137 | YYGA | 4 | 5861 |
| PDH 1138 | YYGG | 4 | 5862 |
| PDH 1139 | IYGG | 4 | 5863 |
| PDH 1140 | IYGA | 4 | 5864 |
| PDH 1141 | DYGG | 4 | 4357 |
| PDH 1142 | LMAT | 4 | 5865 |
| PDH 1143 | VTAT | 4 | 5866 |
| PDH 1144 | KMAT | 4 | 5867 |
| PDH 1145 | QMAT | 4 | 5868 |
| PDH 1146 | ETAT | 4 | 5869 |
| PDH 1147 | TTAT | 4 | 5870 |
| PDH 1148 | TMAT | 4 | 5871 |
| PDH 1149 | PTAT | 4 | 5872 |
| PDH 1150 | VMAT | 4 | 5873 |
| PDH 1151 | LTAT | 4 | 5874 |
| PDH 1152 | KTAT | 4 | 5875 |
| PDH 1153 | MMAT | 4 | 5876 |
| PDH 1154 | ATAT | 4 | 5877 |
| PDH 1155 | QTAT | 4 | 5878 |
| PDH 1156 | PMAT | 4 | 5879 |

TABLE 28-continued

Theoretical segment pool of unique DH polypeptide segments encoded by the degenerate oligonucleotides of Table 27.

| Name | Sequence | Length | SEQ ID NO |
|---|---|---|---|
| PDH 1157 | MTAT | 4 | 5880 |
| PDH 1158 | EMAT | 4 | 4402 |
| PDH 1159 | AMAT | 4 | 5881 |
| PDH 1160 | TYSA | 4 | 5882 |
| PDH 1161 | LYSS | 4 | 5883 |
| PDH 1162 | LYST | 4 | 5884 |
| PDH 1163 | QYSS | 4 | 5885 |
| PDH 1164 | VYST | 4 | 5886 |
| PDH 1165 | VYSS | 4 | 5887 |
| PDH 1166 | AYSA | 4 | 5888 |
| PDH 1167 | PYSG | 4 | 5889 |
| PDH 1168 | PYST | 4 | 5890 |
| PDH 1169 | VYSA | 4 | 5891 |
| PDH 1170 | PYSS | 4 | 5892 |
| PDH 1171 | VYSG | 4 | 5893 |
| PDH 1172 | PYSA | 4 | 5894 |
| PDH 1173 | KYST | 4 | 5895 |
| PDH 1174 | QYST | 4 | 5896 |
| PDH 1175 | TYSG | 4 | 5897 |
| PDH 1176 | TYST | 4 | 5898 |
| PDH 1177 | QYSA | 4 | 5899 |
| PDH 1178 | AYSS | 4 | 5900 |
| PDH 1179 | TYSS | 4 | 5901 |
| PDH 1180 | IYSA | 4 | 5902 |
| PDH 1181 | AYST | 4 | 5903 |
| PDH 1182 | IYSG | 4 | 5904 |
| PDH 1183 | EYSS | 4 | 4479 |
| PDH 1184 | KYSG | 4 | 5905 |
| PDH 1185 | EYSA | 4 | 5906 |
| PDH 1186 | LYSG | 4 | 5907 |
| PDH 1187 | AYSG | 4 | 5908 |
| PDH 1188 | EYSG | 4 | 5909 |
| PDH 1189 | LYSA | 4 | 5910 |
| PDH 1190 | QYSG | 4 | 5911 |
| PDH 1191 | IYST | 4 | 5912 |
| PDH 1192 | EYST | 4 | 5913 |
| PDH 1193 | KYSS | 4 | 5914 |

TABLE 28-continued

Theoretical segment pool of unique DH polypeptide segments encoded by the degenerate oligonucleotides of Table 27.

| Name | Sequence | Length | SEQ ID NO |
|---|---|---|---|
| PDH 1194 | IYSS | 4 | 5915 |
| PDH 1195 | KYSA | 4 | 5916 |
| PDH 1196 | QWLS | 4 | 5917 |
| PDH 1197 | QWLL | 4 | 5918 |
| PDH 1198 | QWLP | 4 | 5919 |
| PDH 1199 | QWLD | 4 | 5920 |
| PDH 1200 | QWLY | 4 | 5921 |
| PDH 1201 | QWLA | 4 | 5922 |
| PDH 1202 | QWLV | 4 | 4475 |
| PDH 1203 | QWLH | 4 | 5923 |
| PDH 1204 | QWLF | 4 | 5924 |
| PDH 1205 | PVAD | 4 | 5925 |
| PDH 1206 | PVAA | 4 | 5926 |
| PDH 1207 | IVAA | 4 | 5927 |
| PDH 1208 | EVAA | 4 | 5928 |
| PDH 1209 | EVAV | 4 | 5929 |
| PDH 1210 | VVAA | 4 | 3802 |
| PDH 1211 | IVAD | 4 | 5930 |
| PDH 1212 | EVAD | 4 | 5931 |
| PDH 1213 | IVAG | 4 | 5932 |
| PDH 1214 | QVAD | 4 | 5933 |
| PDH 1215 | AVAA | 4 | 5934 |
| PDH 1216 | AVAV | 4 | 5935 |
| PDH 1217 | AVAD | 4 | 5936 |
| PDH 1218 | KVAA | 4 | 5937 |
| PDH 1219 | QVAA | 4 | 5938 |
| PDH 1220 | TVAV | 4 | 5939 |
| PDH 1221 | LVAD | 4 | 5940 |
| PDH 1222 | LVAA | 4 | 5941 |
| PDH 1223 | IVAV | 4 | 5942 |
| PDH 1224 | VVAD | 4 | 5943 |
| PDH 1225 | VVAV | 4 | 5944 |
| PDH 1226 | QVAV | 4 | 5945 |
| PDH 1227 | PVAV | 4 | 5946 |
| PDH 1228 | KVAV | 4 | 5947 |
| PDH 1229 | LVAV | 4 | 5948 |
| PDH 1230 | TVAD | 4 | 5949 |

TABLE 28-continued

Theoretical segment pool of unique DH polypeptide segments encoded by the degenerate oligonucleotides of Table 27.

| Name | Sequence | Length | SEQ ID NO |
|---|---|---|---|
| PDH 1231 | KVAD | 4 | 5950 |
| PDH 1232 | TVAA | 4 | 5951 |
| PDH 1233 | STVA | 4 | 5952 |
| PDH 1234 | STVK | 4 | 5953 |
| PDH 1235 | RTVA | 4 | 5954 |
| PDH 1236 | ITVT | 4 | 5955 |
| PDH 1237 | PTVA | 4 | 5956 |
| PDH 1238 | ATVT | 4 | 5957 |
| PDH 1239 | ATVK | 4 | 5958 |
| PDH 1240 | VTVK | 4 | 5959 |
| PDH 1241 | TTVK | 4 | 5960 |
| PDH 1242 | PTVE | 4 | 5961 |
| PDH 1243 | VTVT | 4 | 5962 |
| PDH 1244 | STVT | 4 | 5963 |
| PDH 1245 | VTVE | 4 | 5964 |
| PDH 1246 | TTVT | 4 | 4352 |
| PDH 1247 | LTVA | 4 | 5965 |
| PDH 1248 | RTVT | 4 | 5966 |
| PDH 1249 | LTVE | 4 | 5967 |
| PDH 1250 | TTVE | 4 | 5968 |
| PDH 1251 | RTVK | 4 | 5969 |
| PDH 1252 | VTVA | 4 | 5970 |
| PDH 1253 | STVE | 4 | 5971 |
| PDH 1254 | ATVA | 4 | 5972 |
| PDH 1255 | GTVE | 4 | 5973 |
| PDH 1256 | GTVA | 4 | 5974 |
| PDH 1257 | ITVE | 4 | 5975 |
| PDH 1258 | PTVT | 4 | 5976 |
| PDH 1259 | ITVA | 4 | 5977 |
| PDH 1260 | ATVE | 4 | 5978 |
| PDH 1261 | GTVK | 4 | 5979 |
| PDH 1262 | LTVK | 4 | 5980 |
| PDH 1263 | ITVK | 4 | 5981 |
| PDH 1264 | RTVE | 4 | 5982 |
| PDH 1265 | LTVT | 4 | 5983 |
| PDH 1266 | TTVA | 4 | 5984 |
| PDH 1267 | PTVK | 4 | 5985 |

TABLE 28-continued

Theoretical segment pool of unique DH polypeptide segments encoded by the degenerate oligonucleotides of Table 27.

| Name | Sequence | Length | SEQ ID NO |
|---|---|---|---|
| PDH 1268 | GTVT | 4 | 5986 |
| PDH 1269 | SSSA | 4 | 5987 |
| PDH 1270 | SSSS | 4 | 4480 |
| PDH 1271 | SSSL | 4 | 5988 |
| PDH 1272 | SSSW | 4 | 4443 |
| PDH 1273 | SSSR | 4 | 5989 |
| PDH 1274 | SSSV | 4 | 5990 |
| PDH 1275 | SSST | 4 | 5991 |
| PDH 1276 | SSSM | 4 | 5992 |
| PDH 1277 | SSSG | 4 | 5993 |
| PDH 1278 | LSYG | 4 | 5994 |
| PDH 1279 | PYYG | 4 | 5995 |
| PDH 1280 | ASYG | 4 | 5996 |
| PDH 1281 | FYYG | 4 | 5997 |
| PDH 1282 | DSYG | 4 | 5998 |
| PDH 1283 | VYYG | 4 | 5999 |
| PDH 1284 | IYYG | 4 | 6000 |
| PDH 1285 | DYYG | 4 | 6001 |
| PDH 1286 | HYYG | 4 | 6002 |
| PDH 1287 | SYYG | 4 | 6003 |
| PDH 1288 | YYYG | 4 | 3989 |
| PDH 1289 | VSYG | 4 | 6004 |
| PDH 1290 | NSYG | 4 | 6005 |
| PDH 1291 | SSYG | 4 | 6006 |
| PDH 1292 | FSYG | 4 | 6007 |
| PDH 1293 | ISYG | 4 | 6008 |
| PDH 1294 | TSYG | 4 | 6009 |
| PDH 1295 | LYYG | 4 | 6010 |
| PDH 1296 | PSYG | 4 | 6011 |
| PDH 1297 | AYYG | 4 | 6012 |
| PDH 1298 | YSYG | 4 | 4433 |
| PDH 1299 | HSYG | 4 | 6013 |
| PDH 1300 | NYYG | 4 | 6014 |
| PDH 1301 | TYYG | 4 | 6015 |
| PDH 1302 | FSWY | 4 | 6016 |
| PDH 1303 | SSWF | 4 | 6017 |
| PDH 1304 | DSWS | 4 | 6018 |

TABLE 28-continued

Theoretical segment pool of unique DH polypeptide segments encoded by the degenerate oligonucleotides of Table 27.

| Name | Sequence | Length | SEQ ID NO |
|---|---|---|---|
| PDH 1305 | LSWS | 4 | 6019 |
| PDH 1306 | DSWY | 4 | 6020 |
| PDH 1307 | LSWF | 4 | 6021 |
| PDH 1308 | LSWY | 4 | 6022 |
| PDH 1309 | VSWS | 4 | 6023 |
| PDH 1310 | HSWY | 4 | 6024 |
| PDH 1311 | SSWS | 4 | 6025 |
| PDH 1312 | PSWS | 4 | 6026 |
| PDH 1313 | SSWY | 4 | 4444 |
| PDH 1314 | FSWF | 4 | 6027 |
| PDH 1315 | FSWS | 4 | 6028 |
| PDH 1316 | PSWF | 4 | 6029 |
| PDH 1317 | VSWF | 4 | 6030 |
| PDH 1318 | HSWF | 4 | 6031 |
| PDH 1319 | VSWY | 4 | 6032 |
| PDH 1320 | HSWS | 4 | 6033 |
| PDH 1321 | DSWF | 4 | 6034 |
| PDH 1322 | PSWY | 4 | 6035 |
| PDH 1323 | ASWY | 4 | 6036 |
| PDH 1324 | YSWS | 4 | 6037 |
| PDH 1325 | ASWF | 4 | 6038 |
| PDH 1326 | ASWS | 4 | 6039 |
| PDH 1327 | YSWF | 4 | 6040 |
| PDH 1328 | YSWY | 4 | 6041 |
| PDH 1329 | IQLV | 4 | 6042 |
| PDH 1330 | AQLG | 4 | 6043 |
| PDH 1331 | IQLA | 4 | 6044 |
| PDH 1332 | EQLV | 4 | 6045 |
| PDH 1333 | AQLA | 4 | 6046 |
| PDH 1334 | IQLG | 4 | 6047 |
| PDH 1335 | KQLD | 4 | 6048 |
| PDH 1336 | TQLV | 4 | 6049 |
| PDH 1337 | QQLA | 4 | 6050 |
| PDH 1338 | AQLD | 4 | 6051 |
| PDH 1339 | IQLD | 4 | 6052 |
| PDH 1340 | AQLV | 4 | 6053 |
| PDH 1341 | KQLA | 4 | 6054 |

TABLE 28-continued

Theoretical segment pool of unique DH polypeptide segments encoded by the degenerate oligonucleotides of Table 27.

| Name | Sequence | Length | SEQ ID NO |
|---|---|---|---|
| PDH 1342 | KQLG | 4 | 6055 |
| PDH 1343 | LQLD | 4 | 6056 |
| PDH 1344 | LQLG | 4 | 6057 |
| PDH 1345 | TQLA | 4 | 6058 |
| PDH 1346 | VQLD | 4 | 6059 |
| PDH 1347 | TQLD | 4 | 6060 |
| PDH 1348 | VQLA | 4 | 6061 |
| PDH 1349 | EQLD | 4 | 6062 |
| PDH 1350 | VQLG | 4 | 6063 |
| PDH 1351 | TQLG | 4 | 6064 |
| PDH 1352 | PQLD | 4 | 6065 |
| PDH 1353 | QQLV | 4 | 4455 |
| PDH 1354 | QQLD | 4 | 6066 |
| PDH 1355 | PQLA | 4 | 6067 |
| PDH 1356 | PQLG | 4 | 6068 |
| PDH 1357 | VQLV | 4 | 6069 |
| PDH 1358 | QQLG | 4 | 6070 |
| PDH 1359 | KQLV | 4 | 6071 |
| PDH 1360 | LQLV | 4 | 6072 |
| PDH 1361 | LQLA | 4 | 6073 |
| PDH 1362 | EQLA | 4 | 6074 |
| PDH 1363 | PQLV | 4 | 6075 |
| PDH 1364 | EQLG | 4 | 6076 |
| PDH 1365 | DGSA | 4 | 6077 |
| PDH 1366 | DGSS | 4 | 6078 |
| PDH 1367 | SGSA | 4 | 6079 |
| PDH 1368 | DGSD | 4 | 6080 |
| PDH 1369 | SGSD | 4 | 6081 |
| PDH 1370 | PGSD | 4 | 6082 |
| PDH 1371 | FGSS | 4 | 6083 |
| PDH 1372 | HGSA | 4 | 6084 |
| PDH 1373 | YGSS | 4 | 6085 |
| PDH 1374 | FGSA | 4 | 6086 |
| PDH 1375 | FGSD | 4 | 6087 |
| PDH 1376 | LGSA | 4 | 6088 |
| PDH 1377 | LGSS | 4 | 6089 |
| PDH 1378 | AGSD | 4 | 6090 |
| PDH 1379 | VGSS | 4 | 6091 |
| PDH 1380 | AGSS | 4 | 6092 |
| PDH 1381 | HGSD | 4 | 6093 |
| PDH 1382 | VGSA | 4 | 6094 |
| PDH 1383 | YGSA | 4 | 6095 |
| PDH 1384 | YGSD | 4 | 6096 |
| PDH 1385 | AGSA | 4 | 6097 |
| PDH 1386 | HGSS | 4 | 6098 |
| PDH 1387 | VGSD | 4 | 6099 |
| PDH 1388 | PGSA | 4 | 6100 |
| PDH 1389 | PGSS | 4 | 6101 |
| PDH 1390 | SGSS | 4 | 6102 |
| PDH 1391 | LGSD | 4 | 6103 |
| PDH 1392 | SGWY | 4 | 4464 |
| PDH 1393 | PGWY | 4 | 6104 |
| PDH 1394 | FGWY | 4 | 6105 |
| PDH 1395 | YGWY | 4 | 6106 |
| PDH 1396 | AGWY | 4 | 6107 |
| PDH 1397 | VGWY | 4 | 6108 |
| PDH 1398 | LGWY | 4 | 6109 |
| PDH 1399 | DGWY | 4 | 6110 |
| PDH 1400 | HGWY | 4 | 6111 |
| PDH 1401 | PSGW | 4 | 6112 |
| PDH 1402 | YSGW | 4 | 6113 |
| PDH 1403 | FSGR | 4 | 6114 |
| PDH 1404 | VSGG | 4 | 6115 |
| PDH 1405 | NSGR | 4 | 6116 |
| PDH 1406 | DSGR | 4 | 6117 |
| PDH 1407 | ASGR | 4 | 6118 |
| PDH 1408 | FSGW | 4 | 6119 |
| PDH 1409 | DSGW | 4 | 6120 |
| PDH 1410 | VSGR | 4 | 6121 |
| PDH 1411 | ISGW | 4 | 6122 |
| PDH 1412 | LSGW | 4 | 6123 |
| PDH 1413 | DSGG | 4 | 3723 |
| PDH 1414 | HSGR | 4 | 6124 |
| PDH 1415 | NSGW | 4 | 6125 |

TABLE 28-continued

Theoretical segment pool of unique DH polypeptide segments encoded by the degenerate oligonucleotides of Table 27.

| Name | Sequence | Length | SEQ ID NO |
|---|---|---|---|
| PDH 1416 | HSGG | 4 | 6126 |
| PDH 1417 | HSGW | 4 | 6127 |
| PDH 1418 | ISGG | 4 | 6128 |
| PDH 1419 | YSGR | 4 | 6129 |
| PDH 1420 | ISGR | 4 | 6130 |
| PDH 1421 | YSGG | 4 | 6131 |
| PDH 1422 | NSGG | 4 | 6132 |
| PDH 1423 | SSGW | 4 | 4463 |
| PDH 1424 | VSGW | 4 | 6133 |
| PDH 1425 | SSGR | 4 | 6134 |
| PDH 1426 | LSGR | 4 | 6135 |
| PDH 1427 | PSGR | 4 | 6136 |
| PDH 1428 | FSGG | 4 | 6137 |
| PDH 1429 | TSGR | 4 | 6138 |
| PDH 1430 | TSGW | 4 | 6139 |
| PDH 1431 | ASGG | 4 | 6140 |
| PDH 1432 | LSGG | 4 | 6141 |
| PDH 1433 | ASGW | 4 | 6142 |
| PDH 1434 | PSGG | 4 | 6143 |
| PDH 1435 | TSGG | 4 | 6144 |
| PDH 1436 | SSGG | 4 | 6145 |
| PDH 1437 | VGYD | 4 | 6146 |
| PDH 1438 | AGYD | 4 | 6147 |
| PDH 1439 | DGYD | 4 | 6148 |
| PDH 1440 | AGYA | 4 | 6149 |
| PDH 1441 | DGYA | 4 | 6150 |
| PDH 1442 | FGYA | 4 | 6151 |
| PDH 1443 | FGYD | 4 | 6152 |
| PDH 1444 | PGYA | 4 | 6153 |
| PDH 1445 | DGYS | 4 | 6154 |
| PDH 1446 | YGYA | 4 | 6155 |
| PDH 1447 | FGYS | 4 | 6156 |
| PDH 1448 | VGYA | 4 | 6157 |
| PDH 1449 | PGYD | 4 | 6158 |
| PDH 1450 | PGYS | 4 | 6159 |
| PDH 1451 | VGYS | 4 | 6160 |
| PDH 1452 | YGYD | 4 | 6161 |

TABLE 28-continued

Theoretical segment pool of unique DH polypeptide segments encoded by the degenerate oligonucleotides of Table 27.

| Name | Sequence | Length | SEQ ID NO |
|---|---|---|---|
| PDH 1453 | HGYA | 4 | 6162 |
| PDH 1454 | YGYS | 4 | 6163 |
| PDH 1455 | HGYD | 4 | 6164 |
| PDH 1456 | SGYS | 4 | 6165 |
| PDH 1457 | LGYA | 4 | 6166 |
| PDH 1458 | HGYS | 4 | 6167 |
| PDH 1459 | LGYD | 4 | 6168 |
| PDH 1460 | AGYS | 4 | 6169 |
| PDH 1461 | LGYS | 4 | 6170 |
| PDH 1462 | SGYD | 4 | 4393 |
| PDH 1463 | SGYA | 4 | 6171 |
| PDH 1464 | QVTA | 4 | 6172 |
| PDH 1465 | PVTA | 4 | 6173 |
| PDH 1466 | LVTT | 4 | 6174 |
| PDH 1467 | PVTT | 4 | 6175 |
| PDH 1468 | PVTE | 4 | 6176 |
| PDH 1469 | QVTT | 4 | 6177 |
| PDH 1470 | AVTA | 4 | 6178 |
| PDH 1471 | QVTK | 4 | 6179 |
| PDH 1472 | IVTA | 4 | 6180 |
| PDH 1473 | PVTK | 4 | 6181 |
| PDH 1474 | LVTK | 4 | 6182 |
| PDH 1475 | AVTE | 4 | 6183 |
| PDH 1476 | LVTA | 4 | 6184 |
| PDH 1477 | EVTA | 4 | 6185 |
| PDH 1478 | LVTE | 4 | 6186 |
| PDH 1479 | EVTE | 4 | 6187 |
| PDH 1480 | IVTE | 4 | 6188 |
| PDH 1481 | VVTA | 4 | 3906 |
| PDH 1482 | TVTK | 4 | 6189 |
| PDH 1483 | TVTT | 4 | 4353 |
| PDH 1484 | IVTT | 4 | 6190 |
| PDH 1485 | VVTE | 4 | 6191 |
| PDH 1486 | IVTK | 4 | 6192 |
| PDH 1487 | TVTE | 4 | 6193 |
| PDH 1488 | AVTT | 4 | 6194 |
| PDH 1489 | KVTA | 4 | 6195 |

TABLE 28-continued

Theoretical segment pool of unique DH polypeptide segments encoded by the degenerate oligonucleotides of Table 27.

| Name | Sequence | Length | SEQ ID NO |
|---|---|---|---|
| PDH 1490 | KVTE | 4 | 6196 |
| PDH 1491 | AVTK | 4 | 6197 |
| PDH 1492 | EVTK | 4 | 6198 |
| PDH 1493 | KVTK | 4 | 6199 |
| PDH 1494 | VVTK | 4 | 6200 |
| PDH 1495 | TVTA | 4 | 6201 |
| PDH 1496 | QVTE | 4 | 6202 |
| PDH 1497 | VVTT | 4 | 6203 |
| PDH 1498 | EVTT | 4 | 6204 |
| PDH 1499 | KVTT | 4 | 6205 |
| PDH 1500 | AAAG | 4 | 4453 |
| PDH 1501 | AAAS | 4 | 6206 |
| PDH 1502 | AAAL | 4 | 6207 |
| PDH 1503 | AAAR | 4 | 6208 |
| PDH 1504 | AAAI | 4 | 6209 |
| PDH 1505 | AAAV | 4 | 6210 |
| PDH 1506 | AAAP | 4 | 6211 |
| PDH 1507 | AAAA | 4 | 6212 |
| PDH 1508 | AIFG | 4 | 6213 |
| PDH 1509 | ATFG | 4 | 6214 |
| PDH 1510 | PTFG | 4 | 6215 |
| PDH 1511 | TTFG | 4 | 6216 |
| PDH 1512 | ITFG | 4 | 4153 |
| PDH 1513 | RTFG | 4 | 6217 |
| PDH 1514 | STFG | 4 | 6218 |
| PDH 1515 | SIFG | 4 | 6219 |
| PDH 1516 | LIFG | 4 | 6220 |
| PDH 1517 | RIFG | 4 | 6221 |
| PDH 1518 | TIFG | 4 | 4291 |
| PDH 1519 | GIFG | 4 | 6222 |
| PDH 1520 | IIFG | 4 | 6223 |
| PDH 1521 | LTFG | 4 | 6224 |
| PDH 1522 | VIFG | 4 | 6225 |
| PDH 1523 | PIFG | 4 | 6226 |
| PDH 1524 | GTFG | 4 | 6227 |
| PDH 1525 | VTFG | 4 | 6228 |
| PDH 1526 | VAAK | 4 | 6229 |

TABLE 28-continued

Theoretical segment pool of unique DH polypeptide segments encoded by the degenerate oligonucleotides of Table 27.

| Name | Sequence | Length | SEQ ID NO |
|---|---|---|---|
| PDH 1527 | VAAL | 4 | 6230 |
| PDH 1528 | VAAP | 4 | 6231 |
| PDH 1529 | VAAQ | 4 | 6232 |
| PDH 1530 | VAAA | 4 | 6233 |
| PDH 1531 | VAAE | 4 | 6234 |
| PDH 1532 | VAAV | 4 | 6235 |
| PDH 1533 | VAAI | 4 | 6236 |
| PDH 1534 | YYYD | 4 | 4182 |
| PDH 1535 | VYYA | 4 | 6237 |
| PDH 1536 | AYYD | 4 | 6238 |
| PDH 1537 | YYYA | 4 | 6239 |
| PDH 1538 | PYYD | 4 | 6240 |
| PDH 1539 | IYYD | 4 | 6241 |
| PDH 1540 | VYYD | 4 | 6242 |
| PDH 1541 | IYYA | 4 | 6243 |
| PDH 1542 | TYYA | 4 | 6244 |
| PDH 1543 | LYYD | 4 | 6245 |
| PDH 1544 | DYYD | 4 | 6246 |
| PDH 1545 | SYYD | 4 | 6247 |
| PDH 1546 | LYYA | 4 | 6248 |
| PDH 1547 | HYYA | 4 | 6249 |
| PDH 1548 | DYYA | 4 | 6250 |
| PDH 1549 | SYYA | 4 | 6251 |
| PDH 1550 | FYYD | 4 | 6252 |
| PDH 1551 | FYYA | 4 | 6253 |
| PDH 1552 | PYYA | 4 | 6254 |
| PDH 1553 | AYYA | 4 | 6255 |
| PDH 1554 | HYYD | 4 | 6256 |
| PDH 1555 | NYYA | 4 | 6257 |
| PDH 1556 | TYYD | 4 | 6258 |
| PDH 1557 | NYYD | 4 | 6259 |
| PDH 1558 | GYGY | 4 | 6260 |
| PDH 1559 | LYGY | 4 | 6261 |
| PDH 1560 | SSGY | 4 | 4186 |
| PDH 1561 | RYGY | 4 | 6262 |
| PDH 1562 | TYGY | 4 | 6263 |
| PDH 1563 | TSGY | 4 | 6264 |

TABLE 28-continued

Theoretical segment pool of unique DH polypeptide segments encoded by the degenerate oligonucleotides of Table 27.

| Name | Sequence | Length | SEQ ID NO |
|---|---|---|---|
| PDH 1564 | VYGY | 4 | 6265 |
| PDH 1565 | ISGY | 4 | 6266 |
| PDH 1566 | ASGY | 4 | 6267 |
| PDH 1567 | PSGY | 4 | 6268 |
| PDH 1568 | RSGY | 4 | 6269 |
| PDH 1569 | GAGY | 4 | 6270 |
| PDH 1570 | AAGY | 4 | 6271 |
| PDH 1571 | LSGY | 4 | 6272 |
| PDH 1572 | SYGY | 4 | 4434 |
| PDH 1573 | VSGY | 4 | 6273 |
| PDH 1574 | VAGY | 4 | 6274 |
| PDH 1575 | TAGY | 4 | 6275 |
| PDH 1576 | PAGY | 4 | 6276 |
| PDH 1577 | SAGY | 4 | 6277 |
| PDH 1578 | RAGY | 4 | 6278 |
| PDH 1579 | IAGY | 4 | 6279 |
| PDH 1580 | AYGY | 4 | 6280 |
| PDH 1581 | PYGY | 4 | 6281 |
| PDH 1582 | LAGY | 4 | 6282 |
| PDH 1583 | IYGY | 4 | 6283 |
| PDH 1584 | GSGY | 4 | 6284 |
| PDH 1585 | LQLL | 4 | 6285 |
| PDH 1586 | AQLW | 4 | 6286 |
| PDH 1587 | TQLW | 4 | 6287 |
| PDH 1588 | QQLL | 4 | 6288 |
| PDH 1589 | IQLW | 4 | 4427 |
| PDH 1590 | EQLL | 4 | 6289 |
| PDH 1591 | QQLW | 4 | 6290 |
| PDH 1592 | IQLL | 4 | 6291 |
| PDH 1593 | EQLW | 4 | 6292 |
| PDH 1594 | VQLW | 4 | 6293 |
| PDH 1595 | KQLW | 4 | 6294 |
| PDH 1596 | KQLL | 4 | 6295 |
| PDH 1597 | PQLW | 4 | 6296 |
| PDH 1598 | VQLL | 4 | 6297 |
| PDH 1599 | TQLL | 4 | 6298 |
| PDH 1600 | PQLL | 4 | 6299 |

TABLE 28-continued

Theoretical segment pool of unique DH polypeptide segments encoded by the degenerate oligonucleotides of Table 27.

| Name | Sequence | Length | SEQ ID NO |
|---|---|---|---|
| PDH 1601 | LQLW | 4 | 6300 |
| PDH 1602 | AQLL | 4 | 6301 |
| PDH 1603 | LGVA | 4 | 6302 |
| PDH 1604 | LGGA | 4 | 6303 |
| PDH 1605 | KGIA | 4 | 6304 |
| PDH 1606 | KGSA | 4 | 6305 |
| PDH 1607 | VGIA | 4 | 6306 |
| PDH 1608 | KGGA | 4 | 6307 |
| PDH 1609 | MGGA | 4 | 6308 |
| PDH 1610 | TGGA | 4 | 6309 |
| PDH 1611 | QGSA | 4 | 6310 |
| PDH 1612 | QGIA | 4 | 6311 |
| PDH 1613 | EGSA | 4 | 6312 |
| PDH 1614 | PGVA | 4 | 6313 |
| PDH 1615 | QGVA | 4 | 6314 |
| PDH 1616 | EGIA | 4 | 6315 |
| PDH 1617 | AGVA | 4 | 6316 |
| PDH 1618 | MGVA | 4 | 6317 |
| PDH 1619 | EGGA | 4 | 3671 |
| PDH 1620 | PGIA | 4 | 6318 |
| PDH 1621 | AGGA | 4 | 6319 |
| PDH 1622 | VGGA | 4 | 6320 |
| PDH 1623 | EGVA | 4 | 6321 |
| PDH 1624 | PGGA | 4 | 6322 |
| PDH 1625 | QGGA | 4 | 6323 |
| PDH 1626 | AGIA | 4 | 6324 |
| PDH 1627 | LGIA | 4 | 6325 |
| PDH 1628 | MGIA | 4 | 6326 |
| PDH 1629 | TGSA | 4 | 6327 |
| PDH 1630 | TGIA | 4 | 6328 |
| PDH 1631 | MGSA | 4 | 6329 |
| PDH 1632 | KGVA | 4 | 6330 |
| PDH 1633 | TGVA | 4 | 6331 |
| PDH 1634 | VGVA | 4 | 6332 |
| PDH 1635 | PFGE | 4 | 6333 |
| PDH 1636 | VVGE | 4 | 6334 |
| PDH 1637 | ALGE | 4 | 6335 |

TABLE 28-continued

Theoretical segment pool of unique DH polypeptide segments encoded by the degenerate oligonucleotides of Table 27.

| Name | Sequence | Length | SEQ ID NO |
|---|---|---|---|
| PDH 1638 | IFGE | 4 | 6336 |
| PDH 1639 | PLGE | 4 | 6337 |
| PDH 1640 | ILGE | 4 | 6338 |
| PDH 1641 | PVGE | 4 | 6339 |
| PDH 1642 | RVGE | 4 | 6340 |
| PDH 1643 | LLGE | 4 | 6341 |
| PDH 1644 | SVGE | 4 | 6342 |
| PDH 1645 | GLGE | 4 | 6343 |
| PDH 1646 | IVGE | 4 | 6344 |
| PDH 1647 | RLGE | 4 | 4068 |
| PDH 1648 | LVGE | 4 | 6345 |
| PDH 1649 | SLGE | 4 | 6346 |
| PDH 1650 | TLGE | 4 | 6347 |
| PDH 1651 | VLGE | 4 | 6348 |
| PDH 1652 | TVGE | 4 | 6349 |
| PDH 1653 | GVGE | 4 | 6350 |
| PDH 1654 | AVGE | 4 | 6351 |
| PDH 1655 | PYSY | 4 | 6352 |
| PDH 1656 | PYSD | 4 | 6353 |
| PDH 1657 | DYSD | 4 | 6354 |
| PDH 1658 | DYSA | 4 | 6355 |
| PDH 1659 | SYSD | 4 | 6356 |
| PDH 1660 | FYSY | 4 | 6357 |
| PDH 1661 | VYSY | 4 | 6358 |
| PDH 1662 | FYSS | 4 | 6359 |
| PDH 1663 | SYSS | 4 | 6360 |
| PDH 1664 | YYSS | 4 | 6361 |
| PDH 1665 | YYSY | 4 | 6362 |
| PDH 1666 | AYSY | 4 | 6363 |
| PDH 1667 | AYSD | 4 | 6364 |
| PDH 1668 | HYSY | 4 | 6365 |
| PDH 1669 | VYSD | 4 | 6366 |
| PDH 1670 | FYSA | 4 | 6367 |
| PDH 1671 | SYSY | 4 | 6368 |
| PDH 1672 | SYSA | 4 | 6369 |
| PDH 1673 | FYSD | 4 | 6370 |
| PDH 1674 | YYSD | 4 | 6371 |

TABLE 28-continued

Theoretical segment pool of unique DH polypeptide segments encoded by the degenerate oligonucleotides of Table 27.

| Name | Sequence | Length | SEQ ID NO |
|---|---|---|---|
| PDH 1675 | LYSY | 4 | 6372 |
| PDH 1676 | YYSA | 4 | 6373 |
| PDH 1677 | HYSS | 4 | 6374 |
| PDH 1678 | DYSS | 4 | 6375 |
| PDH 1679 | HYSA | 4 | 6376 |
| PDH 1680 | DYSY | 4 | 6377 |
| PDH 1681 | HYSD | 4 | 6378 |
| PDH 1682 | LYSD | 4 | 6379 |
| PDH 1683 | AVPA | 4 | 6380 |
| PDH 1684 | AVRA | 4 | 6381 |
| PDH 1685 | PVRA | 4 | 6382 |
| PDH 1686 | PVPA | 4 | 6383 |
| PDH 1687 | IVGA | 4 | 3755 |
| PDH 1688 | EVPA | 4 | 6384 |
| PDH 1689 | LVGA | 4 | 6385 |
| PDH 1690 | IVRA | 4 | 6386 |
| PDH 1691 | QVGA | 4 | 6387 |
| PDH 1692 | IVPA | 4 | 6388 |
| PDH 1693 | EVGA | 4 | 6389 |
| PDH 1694 | LVPA | 4 | 6390 |
| PDH 1695 | QVPA | 4 | 6391 |
| PDH 1696 | AVGA | 4 | 6392 |
| PDH 1697 | QVRA | 4 | 6393 |
| PDH 1698 | TVRA | 4 | 6394 |
| PDH 1699 | KVGA | 4 | 6395 |
| PDH 1700 | VVPA | 4 | 3837 |
| PDH 1701 | VVGA | 4 | 6396 |
| PDH 1702 | EVRA | 4 | 6397 |
| PDH 1703 | LVRA | 4 | 6398 |
| PDH 1704 | VVRA | 4 | 6399 |
| PDH 1705 | PVGA | 4 | 6400 |
| PDH 1706 | TVGA | 4 | 6401 |
| PDH 1707 | KVRA | 4 | 6402 |
| PDH 1708 | KVPA | 4 | 6403 |
| PDH 1709 | TVPA | 4 | 6404 |
| PDH 1710 | GRGV | 4 | 6405 |
| PDH 1711 | SRGV | 4 | 6406 |

TABLE 28-continued

Theoretical segment pool of unique DH polypeptide segments encoded by the degenerate oligonucleotides of Table 27.

| Name | Sequence | Length | SEQ ID NO |
|---|---|---|---|
| PDH 1712 | ILGV | 4 | 6407 |
| PDH 1713 | AQGV | 4 | 6408 |
| PDH 1714 | TQGV | 4 | 6409 |
| PDH 1715 | VQGV | 4 | 4062 |
| PDH 1716 | PQGV | 4 | 6410 |
| PDH 1717 | SQGV | 4 | 6411 |
| PDH 1718 | RRGV | 4 | 6412 |
| PDH 1719 | PLGV | 4 | 6413 |
| PDH 1720 | PRGV | 4 | 6414 |
| PDH 1721 | IRGV | 4 | 6415 |
| PDH 1722 | ALGV | 4 | 6416 |
| PDH 1723 | VRGV | 4 | 4018 |
| PDH 1724 | TRGV | 4 | 6417 |
| PDH 1725 | TLGV | 4 | 6418 |
| PDH 1726 | GQGV | 4 | 6419 |
| PDH 1727 | RQGV | 4 | 6420 |
| PDH 1728 | ARGV | 4 | 4812 |
| PDH 1729 | RLGV | 4 | 6421 |
| PDH 1730 | LRGV | 4 | 6422 |
| PDH 1731 | SLGV | 4 | 6423 |
| PDH 1732 | VLGV | 4 | 6424 |
| PDH 1733 | IQGV | 4 | 6425 |
| PDH 1734 | LLGV | 4 | 6426 |
| PDH 1735 | LQGV | 4 | 6427 |
| PDH 1736 | GLGV | 4 | 6428 |
| PDH 1737 | DSSW | 4 | 6429 |
| PDH 1738 | DSSR | 4 | 6430 |
| PDH 1739 | DSSV | 4 | 6431 |
| PDH 1740 | DSST | 4 | 6432 |
| PDH 1741 | DSSM | 4 | 6433 |
| PDH 1742 | DSSG | 4 | 4185 |
| PDH 1743 | DSSA | 4 | 6434 |
| PDH 1744 | DSSS | 4 | 6435 |
| PDH 1745 | DSSL | 4 | 6436 |
| PDH 1746 | TGYS | 4 | 6437 |
| PDH 1747 | SDYS | 4 | 6438 |
| PDH 1748 | IAYS | 4 | 6439 |

TABLE 28-continued

Theoretical segment pool of unique DH polypeptide segments encoded by the degenerate oligonucleotides of Table 27.

| Name | Sequence | Length | SEQ ID NO |
|---|---|---|---|
| PDH 1749 | VDYS | 4 | 6440 |
| PDH 1750 | LDYS | 4 | 6441 |
| PDH 1751 | PDYS | 4 | 6442 |
| PDH 1752 | SAYS | 4 | 6443 |
| PDH 1753 | TDYS | 4 | 6444 |
| PDH 1754 | LAYS | 4 | 6445 |
| PDH 1755 | GAYS | 4 | 6446 |
| PDH 1756 | GDYS | 4 | 6447 |
| PDH 1757 | VAYS | 4 | 6448 |
| PDH 1758 | RDYS | 4 | 6449 |
| PDH 1759 | IDYS | 4 | 6450 |
| PDH 1760 | RAYS | 4 | 6451 |
| PDH 1761 | PAYS | 4 | 6452 |
| PDH 1762 | ADYS | 4 | 6453 |
| PDH 1763 | TAYS | 4 | 6454 |
| PDH 1764 | IGYS | 4 | 6455 |
| PDH 1765 | GGYS | 4 | 6456 |
| PDH 1766 | RGYS | 4 | 6457 |
| PDH 1767 | AAYS | 4 | 6458 |
| PDH 1768 | LYGS | 4 | 6459 |
| PDH 1769 | TYGS | 4 | 6460 |
| PDH 1770 | DYGS | 4 | 6461 |
| PDH 1771 | SYGS | 4 | 6462 |
| PDH 1772 | FYGS | 4 | 6463 |
| PDH 1773 | YYGS | 4 | 3990 |
| PDH 1774 | NYGS | 4 | 6464 |
| PDH 1775 | HYGS | 4 | 6465 |
| PDH 1776 | VYGS | 4 | 6466 |
| PDH 1777 | AYGS | 4 | 6467 |
| PDH 1778 | PYGS | 4 | 6468 |
| PDH 1779 | IYGS | 4 | 6469 |
| PDH 1780 | YYYS | 4 | 6470 |
| PDH 1781 | SYYS | 4 | 6471 |
| PDH 1782 | YYYY | 4 | 6472 |
| PDH 1783 | PYYF | 4 | 6473 |
| PDH 1784 | FYYS | 4 | 6474 |
| PDH 1785 | NYYS | 4 | 6475 |

TABLE 28-continued

Theoretical segment pool of unique DH polypeptide segments encoded by the degenerate oligonucleotides of Table 27.

| Name | Sequence | Length | SEQ ID NO |
|---|---|---|---|
| PDH 1786 | NYYF | 4 | 6476 |
| PDH 1787 | FYYF | 4 | 6477 |
| PDH 1788 | FYYY | 4 | 6478 |
| PDH 1789 | AYYY | 4 | 6479 |
| PDH 1790 | SYYY | 4 | 6480 |
| PDH 1791 | DYYY | 4 | 6481 |
| PDH 1792 | AYYS | 4 | 6482 |
| PDH 1793 | IYYY | 4 | 6483 |
| PDH 1794 | LYYY | 4 | 6484 |
| PDH 1795 | DYYS | 4 | 6485 |
| PDH 1796 | AYYF | 4 | 6486 |
| PDH 1797 | PYYS | 4 | 6487 |
| PDH 1798 | IYYS | 4 | 6488 |
| PDH 1799 | YYYF | 4 | 6489 |
| PDH 1800 | HYYS | 4 | 6490 |
| PDH 1801 | PYYY | 4 | 6491 |
| PDH 1802 | HYYF | 4 | 6492 |
| PDH 1803 | HYYY | 4 | 6493 |
| PDH 1804 | LYYS | 4 | 6494 |
| PDH 1805 | VYYF | 4 | 6495 |
| PDH 1806 | SYYF | 4 | 6496 |
| PDH 1807 | IYYF | 4 | 6497 |
| PDH 1808 | LYYF | 4 | 6498 |
| PDH 1809 | DYYF | 4 | 6499 |
| PDH 1810 | TYYS | 4 | 6500 |
| PDH 1811 | NYYY | 4 | 6501 |
| PDH 1812 | TYYF | 4 | 6502 |
| PDH 1813 | TYYY | 4 | 6503 |
| PDH 1814 | VYYS | 4 | 6504 |
| PDH 1815 | VYYY | 4 | 6505 |
| PDH 1816 | FSYS | 4 | 6506 |
| PDH 1817 | VRYS | 4 | 6507 |
| PDH 1818 | YSYS | 4 | 6508 |
| PDH 1819 | LRYS | 4 | 6509 |
| PDH 1820 | ARYS | 4 | 6510 |
| PDH 1821 | FRYS | 4 | 6511 |
| PDH 1822 | SRYS | 4 | 6512 |

TABLE 28-continued

Theoretical segment pool of unique DH polypeptide segments encoded by the degenerate oligonucleotides of Table 27.

| Name | Sequence | Length | SEQ ID NO |
|---|---|---|---|
| PDH 1823 | DSYS | 4 | 6513 |
| PDH 1824 | LSYS | 4 | 6514 |
| PDH 1825 | HRYS | 4 | 6515 |
| PDH 1826 | PSYS | 4 | 6516 |
| PDH 1827 | HSYS | 4 | 6517 |
| PDH 1828 | ASYS | 4 | 6518 |
| PDH 1829 | YRYS | 4 | 6519 |
| PDH 1830 | SSYS | 4 | 6520 |
| PDH 1831 | PRYS | 4 | 6521 |
| PDH 1832 | VSYS | 4 | 6522 |
| PDH 1833 | DRYS | 4 | 6523 |
| PDH 1834 | TWFG | 4 | 6524 |
| PDH 1835 | GWFG | 4 | 6525 |
| PDH 1836 | RWFG | 4 | 6526 |
| PDH 1837 | PWFG | 4 | 6527 |
| PDH 1838 | LWFG | 4 | 3965 |
| PDH 1839 | VWFG | 4 | 6528 |
| PDH 1840 | SWFG | 4 | 6529 |
| PDH 1841 | AWFG | 4 | 6530 |
| PDH 1842 | IWFG | 4 | 6531 |
| PDH 1843 | RYYY | 4 | 6532 |
| PDH 1844 | RYYS | 4 | 6533 |
| PDH 1845 | RYYF | 4 | 6534 |
| PDH 1846 | GYYF | 4 | 6535 |
| PDH 1847 | GYYS | 4 | 6536 |
| PDH 1848 | GYYY | 4 | 4188 |
| PDH 1849 | KFGG | 4 | 6537 |
| PDH 1850 | ALGG | 4 | 6538 |
| PDH 1851 | ILGG | 4 | 6539 |
| PDH 1852 | EFGG | 4 | 6540 |
| PDH 1853 | QFGG | 4 | 6541 |
| PDH 1854 | PLGG | 4 | 6542 |
| PDH 1855 | VLGG | 4 | 6543 |
| PDH 1856 | IVGG | 4 | 6544 |
| PDH 1857 | LLGG | 4 | 6545 |
| PDH 1858 | QLGG | 4 | 6546 |
| PDH 1859 | KLGG | 4 | 6547 |

TABLE 28-continued

Theoretical segment pool of unique DH polypeptide segments encoded by the degenerate oligonucleotides of Table 27.

| Name | Sequence | Length | SEQ ID NO |
|---|---|---|---|
| PDH 1860 | IFGG | 4 | 6548 |
| PDH 1861 | ELGG | 4 | 3713 |
| PDH 1862 | PFGG | 4 | 6549 |
| PDH 1863 | TLGG | 4 | 6550 |
| PDH 1864 | YMVRD | 5 | 6551 |
| PDH 1865 | SMVRG | 5 | 6552 |
| PDH 1866 | FMVRD | 5 | 6553 |
| PDH 1867 | FMVRA | 5 | 6554 |
| PDH 1868 | DMVRA | 5 | 6555 |
| PDH 1869 | HMVRG | 5 | 6556 |
| PDH 1870 | LMVRG | 5 | 6557 |
| PDH 1871 | DMVRD | 5 | 6558 |
| PDH 1872 | LMVRA | 5 | 6559 |
| PDH 1873 | DMVRG | 5 | 6560 |
| PDH 1874 | AMVRA | 5 | 6561 |
| PDH 1875 | AMVRD | 5 | 6562 |
| PDH 1876 | NMVRA | 5 | 6563 |
| PDH 1877 | NMVRG | 5 | 6564 |
| PDH 1878 | FMVRG | 5 | 6565 |
| PDH 1879 | SMVRD | 5 | 6566 |
| PDH 1880 | YMVRA | 5 | 6567 |
| PDH 1881 | SMVRA | 5 | 6568 |
| PDH 1882 | PMVRD | 5 | 6569 |
| PDH 1883 | YMVRG | 5 | 6570 |
| PDH 1884 | TMVRG | 5 | 4010 |
| PDH 1885 | PMVRA | 5 | 6571 |
| PDH 1886 | PMVRG | 5 | 6572 |
| PDH 1887 | VMVRA | 5 | 6573 |
| PDH 1888 | NMVRD | 5 | 6574 |
| PDH 1889 | VMVRG | 5 | 6575 |
| PDH 1890 | TMVRD | 5 | 6576 |
| PDH 1891 | VMVRD | 5 | 6577 |
| PDH 1892 | TMVRA | 5 | 6578 |
| PDH 1893 | AMVRG | 5 | 6579 |
| PDH 1894 | LMVRD | 5 | 6580 |
| PDH 1895 | HMVRD | 5 | 6581 |
| PDH 1896 | HMVRA | 5 | 6582 |

TABLE 28-continued

Theoretical segment pool of unique DH polypeptide segments encoded by the degenerate oligonucleotides of Table 27.

| Name | Sequence | Length | SEQ ID NO |
|---|---|---|---|
| PDH 1897 | IMVRD | 5 | 6583 |
| PDH 1898 | IMVRA | 5 | 6584 |
| PDH 1899 | IMVRG | 5 | 6585 |
| PDH 1900 | AYGDF | 5 | 6586 |
| PDH 1901 | VYGDS | 5 | 6587 |
| PDH 1902 | DYGDY | 5 | 4348 |
| PDH 1903 | NYGDF | 5 | 6588 |
| PDH 1904 | DYGDS | 5 | 6589 |
| PDH 1905 | HYGDS | 5 | 6590 |
| PDH 1906 | HYGDY | 5 | 6591 |
| PDH 1907 | IYGDS | 5 | 6592 |
| PDH 1908 | LYGDS | 5 | 6593 |
| PDH 1909 | LYGDF | 5 | 6594 |
| PDH 1910 | AYGDY | 5 | 6595 |
| PDH 1911 | AYGDS | 5 | 6596 |
| PDH 1912 | SYGDS | 5 | 6597 |
| PDH 1913 | SYGDY | 5 | 6598 |
| PDH 1914 | NYGDS | 5 | 6599 |
| PDH 1915 | HYGDF | 5 | 6600 |
| PDH 1916 | FYGDS | 5 | 6601 |
| PDH 1917 | IYGDF | 5 | 6602 |
| PDH 1918 | FYGDY | 5 | 6603 |
| PDH 1919 | VYGDY | 5 | 6604 |
| PDH 1920 | NYGDY | 5 | 6605 |
| PDH 1921 | YYGDS | 5 | 6606 |
| PDH 1922 | YYGDF | 5 | 6607 |
| PDH 1923 | PYGDY | 5 | 6608 |
| PDH 1924 | SYGDF | 5 | 6609 |
| PDH 1925 | TYGDS | 5 | 6610 |
| PDH 1926 | TYGDY | 5 | 6611 |
| PDH 1927 | LYGDY | 5 | 6612 |
| PDH 1928 | DYGDF | 5 | 6613 |
| PDH 1929 | IYGDY | 5 | 6614 |
| PDH 1930 | VYGDF | 5 | 6615 |
| PDH 1931 | FYGDF | 5 | 6616 |
| PDH 1932 | TYGDF | 5 | 6617 |
| PDH 1933 | PYGDF | 5 | 6618 |

TABLE 28-continued

Theoretical segment pool of unique DH polypeptide segments encoded by the degenerate oligonucleotides of Table 27.

| Name | Sequence | Length | SEQ ID NO |
|---|---|---|---|
| PDH 1934 | PYGDS | 5 | 6619 |
| PDH 1935 | YYGDY | 5 | 6620 |
| PDH 1936 | TYSYD | 5 | 6621 |
| PDH 1937 | PYSYG | 5 | 6622 |
| PDH 1938 | RYSYD | 5 | 6623 |
| PDH 1939 | AYSYV | 5 | 6624 |
| PDH 1940 | PYSYA | 5 | 6625 |
| PDH 1941 | TYSYV | 5 | 6626 |
| PDH 1942 | PYSYD | 5 | 6627 |
| PDH 1943 | TYSYG | 5 | 6628 |
| PDH 1944 | AYSYD | 5 | 6629 |
| PDH 1945 | RYSYA | 5 | 6630 |
| PDH 1946 | PYSYV | 5 | 6631 |
| PDH 1947 | GYSYG | 5 | 4430 |
| PDH 1948 | GYSYA | 5 | 6632 |
| PDH 1949 | GYSYD | 5 | 6633 |
| PDH 1950 | GYSYV | 5 | 6634 |
| PDH 1951 | LYSYG | 5 | 6635 |
| PDH 1952 | SYSYV | 5 | 6636 |
| PDH 1953 | LYSYA | 5 | 6637 |
| PDH 1954 | LYSYD | 5 | 6638 |
| PDH 1955 | RYSYV | 5 | 6639 |
| PDH 1956 | IYSYD | 5 | 6640 |
| PDH 1957 | VYSYV | 5 | 6641 |
| PDH 1958 | IYSYG | 5 | 6642 |
| PDH 1959 | IYSYA | 5 | 6643 |
| PDH 1960 | IYSYV | 5 | 6644 |
| PDH 1961 | RYSYG | 5 | 6645 |
| PDH 1962 | VYSYA | 5 | 6646 |
| PDH 1963 | AYSYA | 5 | 6647 |
| PDH 1964 | SYSYA | 5 | 6648 |
| PDH 1965 | VYSYG | 5 | 6649 |
| PDH 1966 | AYSYG | 5 | 6650 |
| PDH 1967 | VYSYD | 5 | 6651 |
| PDH 1968 | TYSYA | 5 | 6652 |
| PDH 1969 | SYSYD | 5 | 6653 |
| PDH 1970 | SYSYG | 5 | 6654 |

TABLE 28-continued

Theoretical segment pool of unique DH polypeptide segments encoded by the degenerate oligonucleotides of Table 27.

| Name | Sequence | Length | SEQ ID NO |
|---|---|---|---|
| PDH 1971 | LYSYV | 5 | 6655 |
| PDH 1972 | GSGSS | 5 | 6656 |
| PDH 1973 | GSGSF | 5 | 6657 |
| PDH 1974 | ASGSS | 5 | 6658 |
| PDH 1975 | RSGSY | 5 | 6659 |
| PDH 1976 | NSGSY | 5 | 6660 |
| PDH 1977 | NSGSS | 5 | 6661 |
| PDH 1978 | TSGSS | 5 | 6662 |
| PDH 1979 | RSGSS | 5 | 6663 |
| PDH 1980 | SSGSY | 5 | 6664 |
| PDH 1981 | VSGSF | 5 | 6665 |
| PDH 1982 | HSGSY | 5 | 6666 |
| PDH 1983 | TSGSY | 5 | 6667 |
| PDH 1984 | SSGSF | 5 | 6668 |
| PDH 1985 | LSGSF | 5 | 6669 |
| PDH 1986 | NSGSF | 5 | 6670 |
| PDH 1987 | PSGSY | 5 | 6671 |
| PDH 1988 | TSGSF | 5 | 6672 |
| PDH 1989 | PSGSS | 5 | 6673 |
| PDH 1990 | PSGSF | 5 | 6674 |
| PDH 1991 | GSGSY | 5 | 3987 |
| PDH 1992 | ISGSS | 5 | 6675 |
| PDH 1993 | ISGSY | 5 | 6676 |
| PDH 1994 | ASGSY | 5 | 6677 |
| PDH 1995 | RSGSF | 5 | 6678 |
| PDH 1996 | DSGSS | 5 | 6679 |
| PDH 1997 | DSGSY | 5 | 6680 |
| PDH 1998 | LSGSS | 5 | 6681 |
| PDH 1999 | SSGSS | 5 | 6682 |
| PDH 2000 | HSGSF | 5 | 6683 |
| PDH 2001 | HSGSS | 5 | 6684 |
| PDH 2002 | LSGSY | 5 | 6685 |
| PDH 2003 | ASGSF | 5 | 6686 |
| PDH 2004 | VSGSY | 5 | 6687 |
| PDH 2005 | ISGSF | 5 | 6688 |
| PDH 2006 | VSGSS | 5 | 6689 |
| PDH 2007 | DSGSF | 5 | 6690 |

TABLE 28-continued

Theoretical segment pool of unique DH polypeptide segments encoded by the degenerate oligonucleotides of Table 27.

| Name | Sequence | Length | SEQ ID NO |
|---|---|---|---|
| PDH 2008 | IFLES | 5 | 6691 |
| PDH 2009 | IFLEL | 5 | 6692 |
| PDH 2010 | RFLES | 5 | 6693 |
| PDH 2011 | LFLEL | 5 | 6694 |
| PDH 2012 | TFLES | 5 | 6695 |
| PDH 2013 | GFLEW | 5 | 6696 |
| PDH 2014 | GFLES | 5 | 6697 |
| PDH 2015 | TFLEW | 5 | 6698 |
| PDH 2016 | TFLEL | 5 | 6699 |
| PDH 2017 | VFLEW | 5 | 6700 |
| PDH 2018 | SFLEL | 5 | 6701 |
| PDH 2019 | VFLES | 5 | 6702 |
| PDH 2020 | GFLEL | 5 | 6703 |
| PDH 2021 | VFLEL | 5 | 6704 |
| PDH 2022 | AFLEL | 5 | 6705 |
| PDH 2023 | PFLES | 5 | 6706 |
| PDH 2024 | SFLEW | 5 | 6707 |
| PDH 2025 | AFLES | 5 | 6708 |
| PDH 2026 | AFLEW | 5 | 6709 |
| PDH 2027 | LFLEW | 5 | 6710 |
| PDH 2028 | PFLEL | 5 | 6711 |
| PDH 2029 | RFLEW | 5 | 4231 |
| PDH 2030 | RFLEL | 5 | 6712 |
| PDH 2031 | LFLES | 5 | 6713 |
| PDH 2032 | PFLEW | 5 | 6714 |
| PDH 2033 | SFLES | 5 | 6715 |
| PDH 2034 | IFLEW | 5 | 6716 |
| PDH 2035 | PGSYS | 5 | 6717 |
| PDH 2036 | AGSYA | 5 | 6718 |
| PDH 2037 | HGSYS | 5 | 6719 |
| PDH 2038 | HGSYY | 5 | 6720 |
| PDH 2039 | PGSYY | 5 | 6721 |
| PDH 2040 | SGSYS | 5 | 6722 |
| PDH 2041 | SGSYD | 5 | 6723 |
| PDH 2042 | SGSYA | 5 | 6724 |
| PDH 2043 | LGSYS | 5 | 6725 |
| PDH 2044 | VGSYS | 5 | 6726 |

TABLE 28-continued

Theoretical segment pool of unique DH polypeptide segments encoded by the degenerate oligonucleotides of Table 27.

| Name | Sequence | Length | SEQ ID NO |
|---|---|---|---|
| PDH 2045 | DGSYY | 5 | 6727 |
| PDH 2046 | FGSYS | 5 | 6728 |
| PDH 2047 | FGSYY | 5 | 6729 |
| PDH 2048 | HGSYD | 5 | 6730 |
| PDH 2049 | LGSYA | 5 | 6731 |
| PDH 2050 | HGSYA | 5 | 6732 |
| PDH 2051 | LGSYD | 5 | 6733 |
| PDH 2052 | DGSYS | 5 | 6734 |
| PDH 2053 | VGSYD | 5 | 6735 |
| PDH 2054 | VGSYY | 5 | 6736 |
| PDH 2055 | AGSYY | 5 | 6737 |
| PDH 2056 | YGSYS | 5 | 6738 |
| PDH 2057 | AGSYS | 5 | 6739 |
| PDH 2058 | AGSYD | 5 | 6740 |
| PDH 2059 | VGSYA | 5 | 6741 |
| PDH 2060 | DGSYD | 5 | 6742 |
| PDH 2061 | FGSYD | 5 | 6743 |
| PDH 2062 | DGSYA | 5 | 6744 |
| PDH 2063 | YGSYA | 5 | 6745 |
| PDH 2064 | FGSYA | 5 | 6746 |
| PDH 2065 | YGSYD | 5 | 6747 |
| PDH 2066 | LGSYY | 5 | 6748 |
| PDH 2067 | SGSYY | 5 | 3761 |
| PDH 2068 | PGSYA | 5 | 6749 |
| PDH 2069 | PGSYD | 5 | 6750 |
| PDH 2070 | YGSYY | 5 | 6751 |
| PDH 2071 | FSGSF | 5 | 6752 |
| PDH 2072 | FSGSY | 5 | 6753 |
| PDH 2073 | YSGSF | 5 | 6754 |
| PDH 2074 | YSGSS | 5 | 6755 |
| PDH 2075 | FSGSS | 5 | 6756 |
| PDH 2076 | YSGSY | 5 | 3760 |
| PDH 2077 | ASSSW | 5 | 6757 |
| PDH 2078 | VSSSS | 5 | 6758 |
| PDH 2079 | YSSSS | 5 | 4478 |
| PDH 2080 | YSSSL | 5 | 6759 |
| PDH 2081 | VSSSW | 5 | 6760 |

TABLE 28-continued

Theoretical segment pool of unique DH polypeptide segments encoded by the degenerate oligonucleotides of Table 27.

| Name | Sequence | Length | SEQ ID NO |
|---|---|---|---|
| PDH 2082 | ASSSL | 5 | 6761 |
| PDH 2083 | HSSSL | 5 | 6762 |
| PDH 2084 | PSSSL | 5 | 6763 |
| PDH 2085 | ASSSS | 5 | 6764 |
| PDH 2086 | HSSSW | 5 | 6765 |
| PDH 2087 | VSSSL | 5 | 6766 |
| PDH 2088 | FSSSL | 5 | 6767 |
| PDH 2089 | HSSSS | 5 | 6768 |
| PDH 2090 | FSSSW | 5 | 6769 |
| PDH 2091 | SSSSS | 5 | 6770 |
| PDH 2092 | DSSSS | 5 | 6771 |
| PDH 2093 | SSSSL | 5 | 6772 |
| PDH 2094 | FSSSS | 5 | 6773 |
| PDH 2095 | LSSSW | 5 | 6774 |
| PDH 2096 | DSSSL | 5 | 6775 |
| PDH 2097 | LSSSS | 5 | 6776 |
| PDH 2098 | LSSSL | 5 | 6777 |
| PDH 2099 | SSSSW | 5 | 6778 |
| PDH 2100 | DSSSW | 5 | 6779 |
| PDH 2101 | PSSSW | 5 | 6780 |
| PDH 2102 | PSSSS | 5 | 6781 |
| PDH 2103 | YSSSW | 5 | 4439 |
| PDH 2104 | HSSGW | 5 | 6782 |
| PDH 2105 | FSSGL | 5 | 6783 |
| PDH 2106 | SSSGW | 5 | 6784 |
| PDH 2107 | SSSGS | 5 | 6785 |
| PDH 2108 | DSSGL | 5 | 6786 |
| PDH 2109 | HSSGS | 5 | 6787 |
| PDH 2110 | FSSGW | 5 | 6788 |
| PDH 2111 | ASSGW | 5 | 6789 |
| PDH 2112 | DSSGW | 5 | 6790 |
| PDH 2113 | DSSGS | 5 | 6791 |
| PDH 2114 | ASSGL | 5 | 6792 |
| PDH 2115 | LSSGL | 5 | 6793 |
| PDH 2116 | FSSGS | 5 | 6794 |
| PDH 2117 | ASSGS | 5 | 6795 |
| PDH 2118 | PSSGS | 5 | 6796 |

TABLE 28-continued

Theoretical segment pool of unique DH polypeptide segments encoded by the degenerate oligonucleotides of Table 27.

| Name | Sequence | Length | SEQ ID NO |
|---|---|---|---|
| PDH 2119 | LSSGW | 5 | 6797 |
| PDH 2120 | LSSGS | 5 | 6798 |
| PDH 2121 | YSSGL | 5 | 6799 |
| PDH 2122 | VSSGS | 5 | 6800 |
| PDH 2123 | PSSGW | 5 | 6801 |
| PDH 2124 | PSSGL | 5 | 6802 |
| PDH 2125 | VSSGL | 5 | 6803 |
| PDH 2126 | VSSGW | 5 | 6804 |
| PDH 2127 | YSSGW | 5 | 4460 |
| PDH 2128 | SSSGL | 5 | 6805 |
| PDH 2129 | HSSGL | 5 | 6806 |
| PDH 2130 | YSSGS | 5 | 6807 |
| PDH 2131 | VTVTT | 5 | 6808 |
| PDH 2132 | RTVTT | 5 | 6809 |
| PDH 2133 | LTVTK | 5 | 6810 |
| PDH 2134 | ATVTK | 5 | 6811 |
| PDH 2135 | GTVTT | 5 | 6812 |
| PDH 2136 | VTVTK | 5 | 6813 |
| PDH 2137 | LTVTR | 5 | 6814 |
| PDH 2138 | ATVTT | 5 | 6815 |
| PDH 2139 | RTVTR | 5 | 6816 |
| PDH 2140 | VTVTR | 5 | 6817 |
| PDH 2141 | TTVTK | 5 | 6818 |
| PDH 2142 | GTVTR | 5 | 6819 |
| PDH 2143 | TTVTI | 5 | 6820 |
| PDH 2144 | RTVTK | 5 | 6821 |
| PDH 2145 | LTVTT | 5 | 6822 |
| PDH 2146 | VTVTI | 5 | 6823 |
| PDH 2147 | GTVTK | 5 | 6824 |
| PDH 2148 | TTVTR | 5 | 6825 |
| PDH 2149 | GTVTI | 5 | 6826 |
| PDH 2150 | PTVTI | 5 | 6827 |
| PDH 2151 | TTVTT | 5 | 4351 |
| PDH 2152 | STVTT | 5 | 6828 |
| PDH 2153 | STVTI | 5 | 6829 |
| PDH 2154 | ITVTI | 5 | 6830 |
| PDH 2155 | STVTK | 5 | 6831 |

TABLE 28-continued

Theoretical segment pool of unique DH polypeptide segments encoded by the degenerate oligonucleotides of Table 27.

| Name | Sequence | Length | SEQ ID NO |
|---|---|---|---|
| PDH 2156 | STVTR | 5 | 6832 |
| PDH 2157 | ATVTI | 5 | 6833 |
| PDH 2158 | ITVTT | 5 | 6834 |
| PDH 2159 | ITVTR | 5 | 6835 |
| PDH 2160 | LTVTI | 5 | 6836 |
| PDH 2161 | PTVTR | 5 | 6837 |
| PDH 2162 | ATVTR | 5 | 6838 |
| PDH 2163 | PTVTK | 5 | 6839 |
| PDH 2164 | RTVTI | 5 | 6840 |
| PDH 2165 | ITVTK | 5 | 6841 |
| PDH 2166 | PTVTT | 5 | 6842 |
| PDH 2167 | ASSSF | 5 | 6843 |
| PDH 2168 | ASSSY | 5 | 6844 |
| PDH 2169 | PSSSF | 5 | 6845 |
| PDH 2170 | HSSSF | 5 | 6846 |
| PDH 2171 | VSSSY | 5 | 6847 |
| PDH 2172 | YSSSF | 5 | 6848 |
| PDH 2173 | FSSSF | 5 | 6849 |
| PDH 2174 | HSSSY | 5 | 6850 |
| PDH 2175 | VSSSF | 5 | 6851 |
| PDH 2176 | SSSSY | 5 | 6852 |
| PDH 2177 | SSSSF | 5 | 6853 |
| PDH 2178 | LSSSY | 5 | 6854 |
| PDH 2179 | DSSSY | 5 | 6855 |
| PDH 2180 | FSSSY | 5 | 6856 |
| PDH 2181 | PSSSY | 5 | 6857 |
| PDH 2182 | YSSSY | 5 | 6858 |
| PDH 2183 | DSSSF | 5 | 6859 |
| PDH 2184 | LSSSF | 5 | 6860 |
| PDH 2185 | FSGWF | 5 | 6861 |
| PDH 2186 | FSGWS | 5 | 6862 |
| PDH 2187 | ISGWY | 5 | 6863 |
| PDH 2188 | FSGWY | 5 | 6864 |
| PDH 2189 | ISGWS | 5 | 6865 |
| PDH 2190 | PSGWS | 5 | 6866 |
| PDH 2191 | DSGWF | 5 | 6867 |
| PDH 2192 | PSGWY | 5 | 6868 |

TABLE 28-continued

Theoretical segment pool of unique DH polypeptide segments encoded by the degenerate oligonucleotides of Table 27.

| Name | Sequence | Length | SEQ ID NO |
|---|---|---|---|
| PDH 2193 | PSGWF | 5 | 6869 |
| PDH 2194 | TSGWY | 5 | 6870 |
| PDH 2195 | ASGWF | 5 | 6871 |
| PDH 2196 | LSGWF | 5 | 6872 |
| PDH 2197 | ISGWF | 5 | 6873 |
| PDH 2198 | SSGWY | 5 | 4461 |
| PDH 2199 | SSGWS | 5 | 6874 |
| PDH 2200 | SSGWF | 5 | 6875 |
| PDH 2201 | NSGWS | 5 | 6876 |
| PDH 2202 | NSGWY | 5 | 6877 |
| PDH 2203 | NSGWF | 5 | 6878 |
| PDH 2204 | VSGWS | 5 | 6879 |
| PDH 2205 | VSGWY | 5 | 6880 |
| PDH 2206 | YSGWF | 5 | 6881 |
| PDH 2207 | LSGWS | 5 | 6882 |
| PDH 2208 | ASGWY | 5 | 6883 |
| PDH 2209 | LSGWY | 5 | 6884 |
| PDH 2210 | TSGWF | 5 | 6885 |
| PDH 2211 | TSGWS | 5 | 6886 |
| PDH 2212 | DSGWY | 5 | 6887 |
| PDH 2213 | DSGWS | 5 | 6888 |
| PDH 2214 | ASGWS | 5 | 6889 |
| PDH 2215 | HSGWF | 5 | 6890 |
| PDH 2216 | HSGWS | 5 | 6891 |
| PDH 2217 | YSGWS | 5 | 6892 |
| PDH 2218 | HSGWY | 5 | 6893 |
| PDH 2219 | YSGWY | 5 | 6894 |
| PDH 2220 | VSGWF | 5 | 6895 |
| PDH 2221 | ISGYD | 5 | 6896 |
| PDH 2222 | HSGYA | 5 | 6897 |
| PDH 2223 | ISGYA | 5 | 6898 |
| PDH 2224 | HSGYG | 5 | 6899 |
| PDH 2225 | TSGYD | 5 | 6900 |
| PDH 2226 | TSGYA | 5 | 6901 |
| PDH 2227 | DSGYA | 5 | 6902 |
| PDH 2228 | LSGYA | 5 | 6903 |
| PDH 2229 | FSGYA | 5 | 6904 |

TABLE 28-continued

Theoretical segment pool of unique DH polypeptide segments encoded by the degenerate oligonucleotides of Table 27.

| Name | Sequence | Length | SEQ ID NO |
|---|---|---|---|
| PDH 2230 | LSGYD | 5 | 6905 |
| PDH 2231 | FSGYG | 5 | 6906 |
| PDH 2232 | SSGYD | 5 | 6907 |
| PDH 2233 | SSGYA | 5 | 6908 |
| PDH 2234 | ISGYG | 5 | 6909 |
| PDH 2235 | HSGYD | 5 | 6910 |
| PDH 2236 | ASGYD | 5 | 6911 |
| PDH 2237 | YSGYA | 5 | 6912 |
| PDH 2238 | YSGYD | 5 | 4389 |
| PDH 2239 | VSGYA | 5 | 6913 |
| PDH 2240 | VSGYG | 5 | 6914 |
| PDH 2241 | SSGYG | 5 | 6915 |
| PDH 2242 | DSGYD | 5 | 6916 |
| PDH 2243 | DSGYG | 5 | 6917 |
| PDH 2244 | FSGYD | 5 | 6918 |
| PDH 2245 | LSGYG | 5 | 6919 |
| PDH 2246 | TSGYG | 5 | 6920 |
| PDH 2247 | NSGYA | 5 | 6921 |
| PDH 2248 | NSGYG | 5 | 6922 |
| PDH 2249 | NSGYD | 5 | 6923 |
| PDH 2250 | PSGYA | 5 | 6924 |
| PDH 2251 | PSGYG | 5 | 6925 |
| PDH 2252 | PSGYD | 5 | 6926 |
| PDH 2253 | ASGYG | 5 | 6927 |
| PDH 2254 | VSGYD | 5 | 6928 |
| PDH 2255 | ASGYA | 5 | 6929 |
| PDH 2256 | YSGYG | 5 | 6930 |
| PDH 2257 | FYYDS | 5 | 6931 |
| PDH 2258 | YYYDT | 5 | 6932 |
| PDH 2259 | DYYDS | 5 | 6933 |
| PDH 2260 | AYYDS | 5 | 6934 |
| PDH 2261 | AYYDT | 5 | 6935 |
| PDH 2262 | DYYDI | 5 | 6936 |
| PDH 2263 | VYYDI | 5 | 6937 |
| PDH 2264 | FYYDT | 5 | 6938 |
| PDH 2265 | LYYDI | 5 | 6939 |
| PDH 2266 | PYYDI | 5 | 6940 |

TABLE 28-continued

Theoretical segment pool of unique DH polypeptide segments encoded by the degenerate oligonucleotides of Table 27.

| Name | Sequence | Length | SEQ ID NO |
|---|---|---|---|
| PDH 2267 | HYYDI | 5 | 6941 |
| PDH 2268 | IYYDI | 5 | 6942 |
| PDH 2269 | LYYDS | 5 | 6943 |
| PDH 2270 | SYYDI | 5 | 6944 |
| PDH 2271 | NYYDT | 5 | 6945 |
| PDH 2272 | NYYDS | 5 | 6946 |
| PDH 2273 | SYYDT | 5 | 6947 |
| PDH 2274 | AYYDI | 5 | 6948 |
| PDH 2275 | SYYDS | 5 | 6949 |
| PDH 2276 | DYYDT | 5 | 6950 |
| PDH 2277 | VYYDT | 5 | 6951 |
| PDH 2278 | YYYDI | 5 | 6952 |
| PDH 2279 | VYYDS | 5 | 6953 |
| PDH 2280 | FYYDI | 5 | 6954 |
| PDH 2281 | YYYDS | 5 | 4176 |
| PDH 2282 | TYYDT | 5 | 6955 |
| PDH 2283 | NYYDI | 5 | 6956 |
| PDH 2284 | HYYDS | 5 | 6957 |
| PDH 2285 | LYYDT | 5 | 6958 |
| PDH 2286 | IYYDT | 5 | 6959 |
| PDH 2287 | IYYDS | 5 | 6960 |
| PDH 2288 | PYYDT | 5 | 6961 |
| PDH 2289 | PYYDS | 5 | 6962 |
| PDH 2290 | TYYDI | 5 | 6963 |
| PDH 2291 | HYYDT | 5 | 6964 |
| PDH 2292 | TYYDS | 5 | 6965 |
| PDH 2293 | DSSGY | 5 | 4179 |
| PDH 2294 | SSSGY | 5 | 6966 |
| PDH 2295 | DSSGF | 5 | 6967 |
| PDH 2296 | HSSGY | 5 | 6968 |
| PDH 2297 | SSSGF | 5 | 6969 |
| PDH 2298 | ASSGF | 5 | 6970 |
| PDH 2299 | ASSGY | 5 | 6971 |
| PDH 2300 | LSSGF | 5 | 6972 |
| PDH 2301 | FSSGY | 5 | 6973 |
| PDH 2302 | FSSGF | 5 | 6974 |
| PDH 2303 | YSSGF | 5 | 6975 |

TABLE 28-continued

Theoretical segment pool of unique DH polypeptide segments encoded by the degenerate oligonucleotides of Table 27.

| Name | Sequence | Length | SEQ ID NO |
|---|---|---|---|
| PDH 2304 | PSSGY | 5 | 6976 |
| PDH 2305 | VSSGY | 5 | 6977 |
| PDH 2306 | LSSGY | 5 | 6978 |
| PDH 2307 | HSSGF | 5 | 6979 |
| PDH 2308 | PSSGF | 5 | 6980 |
| PDH 2309 | VSSGF | 5 | 6981 |
| PDH 2310 | YSSGY | 5 | 6982 |
| PDH 2311 | QAARH | 5 | 6983 |
| PDH 2312 | QAARP | 5 | 6984 |
| PDH 2313 | TAARR | 5 | 6985 |
| PDH 2314 | QAARL | 5 | 6986 |
| PDH 2315 | KAARR | 5 | 6987 |
| PDH 2316 | KAARP | 5 | 6988 |
| PDH 2317 | KAARH | 5 | 6989 |
| PDH 2318 | TAARH | 5 | 6990 |
| PDH 2319 | TAARP | 5 | 6991 |
| PDH 2320 | EAARL | 5 | 6992 |
| PDH 2321 | EAARP | 5 | 6993 |
| PDH 2322 | AAARL | 5 | 6994 |
| PDH 2323 | LAARL | 5 | 6995 |
| PDH 2324 | IAARL | 5 | 6996 |
| PDH 2325 | IAARH | 5 | 6997 |
| PDH 2326 | LAARR | 5 | 6998 |
| PDH 2327 | LAARH | 5 | 6999 |
| PDH 2328 | EAARH | 5 | 7000 |
| PDH 2329 | IAARR | 5 | 7001 |
| PDH 2330 | QAARR | 5 | 7002 |
| PDH 2331 | IAARP | 5 | 4483 |
| PDH 2332 | EAARR | 5 | 7003 |
| PDH 2333 | KAARL | 5 | 7004 |
| PDH 2334 | PAARR | 5 | 7005 |
| PDH 2335 | PAARP | 5 | 7006 |
| PDH 2336 | PAARH | 5 | 7007 |
| PDH 2337 | PAARL | 5 | 7008 |
| PDH 2338 | VAARR | 5 | 7009 |
| PDH 2339 | AAARH | 5 | 7010 |
| PDH 2340 | VAARP | 5 | 7011 |

TABLE 28-continued

Theoretical segment pool of unique DH polypeptide segments encoded by the degenerate oligonucleotides of Table 27.

| Name | Sequence | Length | SEQ ID NO |
|---|---|---|---|
| PDH 2341 | VAARH | 5 | 7012 |
| PDH 2342 | AAARP | 5 | 7013 |
| PDH 2343 | AAARR | 5 | 7014 |
| PDH 2344 | TAARL | 5 | 7015 |
| PDH 2345 | LAARP | 5 | 7016 |
| PDH 2346 | VAARL | 5 | 7017 |
| PDH 2347 | EYYYG | 5 | 7018 |
| PDH 2348 | VYYYD | 5 | 7019 |
| PDH 2349 | EYYYA | 5 | 7020 |
| PDH 2350 | VYYYG | 5 | 7021 |
| PDH 2351 | EYYYD | 5 | 7022 |
| PDH 2352 | PYYYD | 5 | 7023 |
| PDH 2353 | PYYYG | 5 | 7024 |
| PDH 2354 | AYYYG | 5 | 7025 |
| PDH 2355 | TYYYA | 5 | 7026 |
| PDH 2356 | TYYYG | 5 | 7027 |
| PDH 2357 | TYYYD | 5 | 7028 |
| PDH 2358 | QYYYA | 5 | 7029 |
| PDH 2359 | QYYYG | 5 | 7030 |
| PDH 2360 | QYYYD | 5 | 7031 |
| PDH 2361 | VYYYA | 5 | 7032 |
| PDH 2362 | LYYYG | 5 | 7033 |
| PDH 2363 | LYYYD | 5 | 7034 |
| PDH 2364 | LYYYA | 5 | 7035 |
| PDH 2365 | AYYYD | 5 | 7036 |
| PDH 2366 | AYYYA | 5 | 7037 |
| PDH 2367 | PYYYA | 5 | 7038 |
| PDH 2368 | MYYYD | 5 | 7039 |
| PDH 2369 | KYYYD | 5 | 7040 |
| PDH 2370 | KYYYG | 5 | 7041 |
| PDH 2371 | MYYYA | 5 | 7042 |
| PDH 2372 | KYYYA | 5 | 7043 |
| PDH 2373 | MYYYG | 5 | 7044 |
| PDH 2374 | LTMVR | 5 | 7045 |
| PDH 2375 | RTMVQ | 5 | 7046 |
| PDH 2376 | VTMVQ | 5 | 7047 |
| PDH 2377 | TTMVR | 5 | 7048 |

TABLE 28-continued

Theoretical segment pool of unique DH polypeptide segments encoded by the degenerate oligonucleotides of Table 27.

| Name | Sequence | Length | SEQ ID NO |
|---|---|---|---|
| PDH 2378 | LTMVQ | 5 | 7049 |
| PDH 2379 | STMVQ | 5 | 7050 |
| PDH 2380 | ATMVQ | 5 | 7051 |
| PDH 2381 | PTMVR | 5 | 7052 |
| PDH 2382 | RTMVR | 5 | 7053 |
| PDH 2383 | ITMVQ | 5 | 4055 |
| PDH 2384 | GTMVR | 5 | 7054 |
| PDH 2385 | VTMVR | 5 | 7055 |
| PDH 2386 | PTMVQ | 5 | 7056 |
| PDH 2387 | ITMVR | 5 | 4009 |
| PDH 2388 | ATMVR | 5 | 7057 |
| PDH 2389 | STMVR | 5 | 7058 |
| PDH 2390 | TTMVQ | 5 | 7059 |
| PDH 2391 | GTMVQ | 5 | 7060 |
| PDH 2392 | HMVQG | 5 | 7061 |
| PDH 2393 | DMVQG | 5 | 7062 |
| PDH 2394 | LMVQG | 5 | 7063 |
| PDH 2395 | SMVQG | 5 | 7064 |
| PDH 2396 | FMVQG | 5 | 7065 |
| PDH 2397 | NMVQG | 5 | 7066 |
| PDH 2398 | VMVQG | 5 | 7067 |
| PDH 2399 | TMVQG | 5 | 4056 |
| PDH 2400 | PMVQG | 5 | 7068 |
| PDH 2401 | YMVQG | 5 | 7069 |
| PDH 2402 | AMVQG | 5 | 7070 |
| PDH 2403 | IMVQG | 5 | 7071 |
| PDH 2404 | PWGSY | 5 | 7072 |
| PDH 2405 | TWGSY | 5 | 7073 |
| PDH 2406 | SWGSY | 5 | 7074 |
| PDH 2407 | HWGSY | 5 | 7075 |
| PDH 2408 | LWGSY | 5 | 7076 |
| PDH 2409 | DWGSY | 5 | 7077 |
| PDH 2410 | FWGSY | 5 | 7078 |
| PDH 2411 | AWGSY | 5 | 7079 |
| PDH 2412 | YWGSY | 5 | 7080 |
| PDH 2413 | IWGSY | 5 | 7081 |
| PDH 2414 | NWGSY | 5 | 7082 |

TABLE 28-continued

Theoretical segment pool of unique DH polypeptide segments encoded by the degenerate oligonucleotides of Table 27.

| Name | Sequence | Length | SEQ ID NO |
|---|---|---|---|
| PDH 2415 | VWGSY | 5 | 4102 |
| PDH 2416 | FSSSWF | 6 | 7083 |
| PDH 2417 | HSSSWS | 6 | 7084 |
| PDH 2418 | VSSSWF | 6 | 7085 |
| PDH 2419 | HSSSWY | 6 | 7086 |
| PDH 2420 | VSSSWS | 6 | 7087 |
| PDH 2421 | LSSSWY | 6 | 7088 |
| PDH 2422 | VSSSWY | 6 | 7089 |
| PDH 2423 | HSSSWF | 6 | 7090 |
| PDH 2424 | ASSSWY | 6 | 7091 |
| PDH 2425 | DSSSWS | 6 | 7092 |
| PDH 2426 | PSSSWY | 6 | 7093 |
| PDH 2427 | ASSSWS | 6 | 7094 |
| PDH 2428 | DSSSWF | 6 | 7095 |
| PDH 2429 | DSSSWY | 6 | 7096 |
| PDH 2430 | YSSSWS | 6 | 7097 |
| PDH 2431 | YSSSWF | 6 | 7098 |
| PDH 2432 | ASSSWF | 6 | 7099 |
| PDH 2433 | LSSSWS | 6 | 7100 |
| PDH 2434 | SSSSWS | 6 | 7101 |
| PDH 2435 | YSSSWY | 6 | 4437 |
| PDH 2436 | PSSSWS | 6 | 7102 |
| PDH 2437 | SSSSWY | 6 | 7103 |
| PDH 2438 | LSSSWF | 6 | 7104 |
| PDH 2439 | PSSSWF | 6 | 7105 |
| PDH 2440 | FSSSWS | 6 | 7106 |
| PDH 2441 | SSSSWF | 6 | 7107 |
| PDH 2442 | FSSSWY | 6 | 7108 |
| PDH 2443 | AYYDST | 6 | 7109 |
| PDH 2444 | AYYDSI | 6 | 7110 |
| PDH 2445 | YYYDST | 6 | 7111 |
| PDH 2446 | PYYDST | 6 | 7112 |
| PDH 2447 | VYYDSS | 6 | 7113 |
| PDH 2448 | NYYDSI | 6 | 7114 |
| PDH 2449 | PYYDSS | 6 | 7115 |
| PDH 2450 | YYYDSS | 6 | 4171 |
| PDH 2451 | YYYDSI | 6 | 7116 |

TABLE 28-continued

Theoretical segment pool of unique DH polypeptide segments encoded by the degenerate oligonucleotides of Table 27.

| Name | Sequence | Length | SEQ ID NO |
|---|---|---|---|
| PDH 2452 | VYYDST | 6 | 7117 |
| PDH 2453 | VYYDSI | 6 | 7118 |
| PDH 2454 | NYYDST | 6 | 7119 |
| PDH 2455 | LYYDST | 6 | 7120 |
| PDH 2456 | NYYDSS | 6 | 7121 |
| PDH 2457 | SYYDSI | 6 | 7122 |
| PDH 2458 | LYYDSS | 6 | 7123 |
| PDH 2459 | SYYDST | 6 | 7124 |
| PDH 2460 | LYYDSI | 6 | 7125 |
| PDH 2461 | SYYDSS | 6 | 7126 |
| PDH 2462 | DYYDSI | 6 | 7127 |
| PDH 2463 | DYYDST | 6 | 7128 |
| PDH 2464 | DYYDSS | 6 | 7129 |
| PDH 2465 | FYYDSS | 6 | 7130 |
| PDH 2466 | TYYDSI | 6 | 7131 |
| PDH 2467 | FYYDST | 6 | 7132 |
| PDH 2468 | IYYDST | 6 | 7133 |
| PDH 2469 | FYYDSI | 6 | 7134 |
| PDH 2470 | IYYDSS | 6 | 7135 |
| PDH 2471 | TYYDSS | 6 | 7136 |
| PDH 2472 | TYYDST | 6 | 7137 |
| PDH 2473 | HYYDSS | 6 | 7138 |
| PDH 2474 | HYYDST | 6 | 7139 |
| PDH 2475 | IYYDSI | 6 | 7140 |
| PDH 2476 | HYYDSI | 6 | 7141 |
| PDH 2477 | PYYDSI | 6 | 7142 |
| PDH 2478 | AYYDSS | 6 | 7143 |
| PDH 2479 | LYSGYA | 6 | 7144 |
| PDH 2480 | GYSGYV | 6 | 7145 |
| PDH 2481 | SYSGYD | 6 | 7146 |
| PDH 2482 | LYSGYD | 6 | 7147 |
| PDH 2483 | IYSGYV | 6 | 7148 |
| PDH 2484 | SYSGYG | 6 | 7149 |
| PDH 2485 | IYSGYG | 6 | 7150 |
| PDH 2486 | SYSGYA | 6 | 7151 |
| PDH 2487 | PYSGYG | 6 | 7152 |
| PDH 2488 | VYSGYD | 6 | 7153 |

TABLE 28-continued

Theoretical segment pool of unique DH polypeptide segments encoded by the degenerate oligonucleotides of Table 27.

| Name | Sequence | Length | SEQ ID NO |
|---|---|---|---|
| PDH 2489 | PYSGYA | 6 | 7154 |
| PDH 2490 | VYSGYV | 6 | 7155 |
| PDH 2491 | GYSGYG | 6 | 7156 |
| PDH 2492 | VYSGYA | 6 | 7157 |
| PDH 2493 | PYSGYV | 6 | 7158 |
| PDH 2494 | GYSGYA | 6 | 7159 |
| PDH 2495 | IYSGYD | 6 | 7160 |
| PDH 2496 | PYSGYD | 6 | 7161 |
| PDH 2497 | RYSGYV | 6 | 7162 |
| PDH 2498 | RYSGYA | 6 | 7163 |
| PDH 2499 | RYSGYG | 6 | 7164 |
| PDH 2500 | GYSGYD | 6 | 4386 |
| PDH 2501 | IYSGYA | 6 | 7165 |
| PDH 2502 | AYSGYA | 6 | 7166 |
| PDH 2503 | RYSGYD | 6 | 7167 |
| PDH 2504 | AYSGYG | 6 | 7168 |
| PDH 2505 | AYSGYD | 6 | 7169 |
| PDH 2506 | AYSGYV | 6 | 7170 |
| PDH 2507 | VYSGYG | 6 | 7171 |
| PDH 2508 | TYSGYV | 6 | 7172 |
| PDH 2509 | TYSGYD | 6 | 7173 |
| PDH 2510 | TYSGYA | 6 | 7174 |
| PDH 2511 | TYSGYG | 6 | 7175 |
| PDH 2512 | SYSGYV | 6 | 7176 |
| PDH 2513 | LYSGYV | 6 | 7177 |
| PDH 2514 | LYSGYG | 6 | 7178 |
| PDH 2515 | SSSGWF | 6 | 7179 |
| PDH 2516 | PSSGWY | 6 | 7180 |
| PDH 2517 | FSSGWF | 6 | 7181 |
| PDH 2518 | PSSGWS | 6 | 7182 |
| PDH 2519 | FSSGWS | 6 | 7183 |
| PDH 2520 | ASSGWY | 6 | 7184 |
| PDH 2521 | FSSGWY | 6 | 7185 |
| PDH 2522 | ASSGWS | 6 | 7186 |
| PDH 2523 | SSSGWS | 6 | 7187 |
| PDH 2524 | YSSGWY | 6 | 4458 |
| PDH 2525 | SSSGWY | 6 | 7188 |

TABLE 28-continued

Theoretical segment pool of unique DH polypeptide segments encoded by the degenerate oligonucleotides of Table 27.

| Name | Sequence | Length | SEQ ID NO |
|---|---|---|---|
| PDH 2526 | HSSGWS | 6 | 7189 |
| PDH 2527 | DSSGWS | 6 | 7190 |
| PDH 2528 | YSSGWS | 6 | 7191 |
| PDH 2529 | LSSGWF | 6 | 7192 |
| PDH 2530 | HSSGWY | 6 | 7193 |
| PDH 2531 | DSSGWF | 6 | 7194 |
| PDH 2532 | DSSGWY | 6 | 7195 |
| PDH 2533 | LSSGWY | 6 | 7196 |
| PDH 2534 | HSSGWF | 6 | 7197 |
| PDH 2535 | VSSGWS | 6 | 7198 |
| PDH 2536 | LSSGWS | 6 | 7199 |
| PDH 2537 | VSSGWY | 6 | 7200 |
| PDH 2538 | VSSGWF | 6 | 7201 |
| PDH 2539 | PSSGWF | 6 | 7202 |
| PDH 2540 | ASSGWF | 6 | 7203 |
| PDH 2541 | YSSGWF | 6 | 7204 |
| PDH 2542 | IYYGSA | 6 | 7205 |
| PDH 2543 | PYYGSG | 6 | 7206 |
| PDH 2544 | PYYGSA | 6 | 7207 |
| PDH 2545 | PYYGSD | 6 | 7208 |
| PDH 2546 | VYYGSD | 6 | 7209 |
| PDH 2547 | AYYGSA | 6 | 7210 |
| PDH 2548 | VYYGSA | 6 | 7211 |
| PDH 2549 | NYYGSA | 6 | 7212 |
| PDH 2550 | YYYGSA | 6 | 7213 |
| PDH 2551 | AYYGSD | 6 | 7214 |
| PDH 2552 | NYYGSD | 6 | 7215 |
| PDH 2553 | YYYGSD | 6 | 7216 |
| PDH 2554 | FYYGSD | 6 | 7217 |
| PDH 2555 | NYYGSG | 6 | 7218 |
| PDH 2556 | YYYGSG | 6 | 3979 |
| PDH 2557 | FYYGSA | 6 | 7219 |
| PDH 2558 | FYYGSG | 6 | 7220 |
| PDH 2559 | AYYGSG | 6 | 7221 |
| PDH 2560 | LYYGSG | 6 | 7222 |
| PDH 2561 | DYYGSD | 6 | 7223 |
| PDH 2562 | LYYGSA | 6 | 7224 |

TABLE 28-continued

Theoretical segment pool of unique DH polypeptide segments encoded by the degenerate oligonucleotides of Table 27.

| Name | Sequence | Length | SEQ ID NO |
|---|---|---|---|
| PDH 2563 | TYYGSD | 6 | 7225 |
| PDH 2564 | DYYGSG | 6 | 7226 |
| PDH 2565 | DYYGSA | 6 | 7227 |
| PDH 2566 | LYYGSD | 6 | 7228 |
| PDH 2567 | HYYGSD | 6 | 7229 |
| PDH 2568 | TYYGSA | 6 | 7230 |
| PDH 2569 | TYYGSG | 6 | 7231 |
| PDH 2570 | HYYGSA | 6 | 7232 |
| PDH 2571 | SYYGSG | 6 | 7233 |
| PDH 2572 | HYYGSG | 6 | 7234 |
| PDH 2573 | SYYGSD | 6 | 7235 |
| PDH 2574 | VYYGSG | 6 | 7236 |
| PDH 2575 | SYYGSA | 6 | 7237 |
| PDH 2576 | IYYGSG | 6 | 7238 |
| PDH 2577 | IYYGSD | 6 | 7239 |
| PDH 2578 | VSSGYS | 6 | 7240 |
| PDH 2579 | VSSGYY | 6 | 7241 |
| PDH 2580 | FSSGYY | 6 | 7242 |
| PDH 2581 | ASSGYF | 6 | 7243 |
| PDH 2582 | ASSGYS | 6 | 7244 |
| PDH 2583 | FSSGYS | 6 | 7245 |
| PDH 2584 | SSSGYY | 6 | 7246 |
| PDH 2585 | ASSGYY | 6 | 7247 |
| PDH 2586 | FSSGYF | 6 | 7248 |
| PDH 2587 | HSSGYY | 6 | 7249 |
| PDH 2588 | DSSGYY | 6 | 4174 |
| PDH 2589 | HSSGYS | 6 | 7250 |
| PDH 2590 | SSSGYS | 6 | 7251 |
| PDH 2591 | DSSGYS | 6 | 7252 |
| PDH 2592 | DSSGYF | 6 | 7253 |
| PDH 2593 | HSSGYF | 6 | 7254 |
| PDH 2594 | PSSGYF | 6 | 7255 |
| PDH 2595 | SSSGYF | 6 | 7256 |
| PDH 2596 | YSSGYY | 6 | 7257 |
| PDH 2597 | YSSGYF | 6 | 7258 |
| PDH 2598 | YSSGYS | 6 | 7259 |
| PDH 2599 | PSSGYS | 6 | 7260 |

TABLE 28-continued

Theoretical segment pool of unique DH polypeptide segments encoded by the degenerate oligonucleotides of Table 27.

| Name | Sequence | Length | SEQ ID NO |
|---|---|---|---|
| PDH 2600 | PSSGYY | 6 | 7261 |
| PDH 2601 | LSSGYY | 6 | 7262 |
| PDH 2602 | LSSGYF | 6 | 7263 |
| PDH 2603 | LSSGYS | 6 | 7264 |
| PDH 2604 | VSSGYF | 6 | 7265 |
| PDH 2605 | TYDSSD | 6 | 7266 |
| PDH 2606 | YYDSSA | 6 | 7267 |
| PDH 2607 | YYDSSG | 6 | 4172 |
| PDH 2608 | LYDSSD | 6 | 7268 |
| PDH 2609 | LYDSSA | 6 | 7269 |
| PDH 2610 | PYDSSA | 6 | 7270 |
| PDH 2611 | LYDSSG | 6 | 7271 |
| PDH 2612 | PYDSSD | 6 | 7272 |
| PDH 2613 | VYDSSD | 6 | 7273 |
| PDH 2614 | HYDSSG | 6 | 7274 |
| PDH 2615 | VYDSSG | 6 | 7275 |
| PDH 2616 | VYDSSA | 6 | 7276 |
| PDH 2617 | PYDSSG | 6 | 7277 |
| PDH 2618 | SYDSSA | 6 | 7278 |
| PDH 2619 | FYDSSG | 6 | 7279 |
| PDH 2620 | NYDSSA | 6 | 7280 |
| PDH 2621 | SYDSSG | 6 | 7281 |
| PDH 2622 | FYDSSA | 6 | 7282 |
| PDH 2623 | NYDSSD | 6 | 7283 |
| PDH 2624 | SYDSSD | 6 | 7284 |
| PDH 2625 | FYDSSD | 6 | 7285 |
| PDH 2626 | DYDSSG | 6 | 7286 |
| PDH 2627 | AYDSSG | 6 | 7287 |
| PDH 2628 | NYDSSG | 6 | 7288 |
| PDH 2629 | IYDSSA | 6 | 7289 |
| PDH 2630 | DYDSSD | 6 | 7290 |
| PDH 2631 | IYDSSG | 6 | 7291 |
| PDH 2632 | AYDSSD | 6 | 7292 |
| PDH 2633 | DYDSSA | 6 | 7293 |
| PDH 2634 | IYDSSD | 6 | 7294 |
| PDH 2635 | HYDSSA | 6 | 7295 |
| PDH 2636 | AYDSSA | 6 | 7296 |
| PDH 2637 | HYDSSD | 6 | 7297 |
| PDH 2638 | TYDSSG | 6 | 7298 |
| PDH 2639 | TYDSSA | 6 | 7299 |
| PDH 2640 | YYDSSD | 6 | 7300 |
| PDH 2641 | TDFWSA | 6 | 7301 |
| PDH 2642 | ADFWSG | 6 | 7302 |
| PDH 2643 | PDFWSG | 6 | 7303 |
| PDH 2644 | VDFWSD | 6 | 7304 |
| PDH 2645 | TDFWSD | 6 | 7305 |
| PDH 2646 | HDFWSA | 6 | 7306 |
| PDH 2647 | HDFWSD | 6 | 7307 |
| PDH 2648 | TDFWSG | 6 | 7308 |
| PDH 2649 | LDFWSA | 6 | 7309 |
| PDH 2650 | LDFWSG | 6 | 7310 |
| PDH 2651 | HDFWSG | 6 | 7311 |
| PDH 2652 | LDFWSD | 6 | 7312 |
| PDH 2653 | FDFWSG | 6 | 7313 |
| PDH 2654 | DDFWSD | 6 | 7314 |
| PDH 2655 | VDFWSA | 6 | 7315 |
| PDH 2656 | SDFWSD | 6 | 7316 |
| PDH 2657 | SDFWSG | 6 | 7317 |
| PDH 2658 | NDFWSD | 6 | 7318 |
| PDH 2659 | SDFWSA | 6 | 7319 |
| PDH 2660 | NDFWSA | 6 | 7320 |
| PDH 2661 | NDFWSG | 6 | 7321 |
| PDH 2662 | VDFWSG | 6 | 7322 |
| PDH 2663 | IDFWSD | 6 | 7323 |
| PDH 2664 | IDFWSG | 6 | 7324 |
| PDH 2665 | FDFWSA | 6 | 7325 |
| PDH 2666 | ADFWSD | 6 | 7326 |
| PDH 2667 | IDFWSA | 6 | 7327 |
| PDH 2668 | FDFWSD | 6 | 7328 |
| PDH 2669 | DDFWSG | 6 | 7329 |
| PDH 2670 | ADFWSA | 6 | 7330 |
| PDH 2671 | YDFWSA | 6 | 7331 |
| PDH 2672 | PDFWSD | 6 | 7332 |
| PDH 2673 | YDFWSG | 6 | 4253 |

TABLE 28-continued

Theoretical segment pool of unique DH polypeptide segments encoded by the degenerate oligonucleotides of Table 27.

| Name | Sequence | Length | SEQ ID NO |
|---|---|---|---|
| PDH 2674 | DDFWSA | 6 | 7333 |
| PDH 2675 | PDFWSA | 6 | 7334 |
| PDH 2676 | YDFWSD | 6 | 7335 |
| PDH 2677 | DDSSGY | 6 | 7336 |
| PDH 2678 | LDSSGY | 6 | 7337 |
| PDH 2679 | HDSSGS | 6 | 7338 |
| PDH 2680 | DDSSGF | 6 | 7339 |
| PDH 2681 | DDSSGS | 6 | 7340 |
| PDH 2682 | LDSSGS | 6 | 7341 |
| PDH 2683 | HDSSGY | 6 | 7342 |
| PDH 2684 | SDSSGS | 6 | 7343 |
| PDH 2685 | SDSSGF | 6 | 7344 |
| PDH 2686 | PDSSGS | 6 | 7345 |
| PDH 2687 | SDSSGY | 6 | 7346 |
| PDH 2688 | PDSSGY | 6 | 7347 |
| PDH 2689 | ADSSGY | 6 | 7348 |
| PDH 2690 | ADSSGS | 6 | 7349 |
| PDH 2691 | ADSSGF | 6 | 7350 |
| PDH 2692 | YDSSGF | 6 | 7351 |
| PDH 2693 | VDSSGF | 6 | 7352 |
| PDH 2694 | FDSSGF | 6 | 7353 |
| PDH 2695 | VDSSGY | 6 | 7354 |
| PDH 2696 | YDSSGY | 6 | 4173 |
| PDH 2697 | FDSSGS | 6 | 7355 |
| PDH 2698 | VDSSGS | 6 | 7356 |
| PDH 2699 | YDSSGS | 6 | 7357 |
| PDH 2700 | FDSSGY | 6 | 7358 |
| PDH 2701 | LDSSGF | 6 | 7359 |
| PDH 2702 | HDSSGF | 6 | 7360 |
| PDH 2703 | PDSSGF | 6 | 7361 |
| PDH 2704 | EYFDWS | 6 | 7362 |
| PDH 2705 | QYFDWL | 6 | 7363 |
| PDH 2706 | RYFDWF | 6 | 7364 |
| PDH 2707 | AYFDWF | 6 | 7365 |
| PDH 2708 | PYFDWF | 6 | 7366 |
| PDH 2709 | PYFDWP | 6 | 7367 |
| PDH 2710 | LYFDWP | 6 | 7368 |

TABLE 28-continued

Theoretical segment pool of unique DH polypeptide segments encoded by the degenerate oligonucleotides of Table 27.

| Name | Sequence | Length | SEQ ID NO |
|---|---|---|---|
| PDH 2711 | EYFDWP | 6 | 7369 |
| PDH 2712 | EYFDWL | 6 | 7370 |
| PDH 2713 | RYFDWL | 6 | 4305 |
| PDH 2714 | LYFDWL | 6 | 7371 |
| PDH 2715 | PYFDWL | 6 | 7372 |
| PDH 2716 | LYFDWS | 6 | 7373 |
| PDH 2717 | QYFDWS | 6 | 7374 |
| PDH 2718 | QYFDWF | 6 | 7375 |
| PDH 2719 | VYFDWF | 6 | 7376 |
| PDH 2720 | RYFDWP | 6 | 7377 |
| PDH 2721 | AYFDWP | 6 | 7378 |
| PDH 2722 | LYFDWF | 6 | 7379 |
| PDH 2723 | AYFDWL | 6 | 7380 |
| PDH 2724 | GYFDWF | 6 | 7381 |
| PDH 2725 | GYFDWS | 6 | 7382 |
| PDH 2726 | VYFDWL | 6 | 7383 |
| PDH 2727 | VYFDWS | 6 | 7384 |
| PDH 2728 | VYFDWP | 6 | 7385 |
| PDH 2729 | RYFDWS | 6 | 7386 |
| PDH 2730 | PYFDWS | 6 | 7387 |
| PDH 2731 | QYFDWP | 6 | 7388 |
| PDH 2732 | EYFDWF | 6 | 7389 |
| PDH 2733 | AYFDWS | 6 | 7390 |
| PDH 2734 | GYFDWL | 6 | 7391 |
| PDH 2735 | GYFDWP | 6 | 7392 |
| PDH 2736 | CGSTSC | 6 | 7393 |
| PDH 2737 | CSGTSC | 6 | 7394 |
| PDH 2738 | CSSTSC | 6 | 3814 |
| PDH 2739 | CGGTSC | 6 | 7395 |
| PDH 2740 | PYYGSE | 6 | 7396 |
| PDH 2741 | VYYGSE | 6 | 7397 |
| PDH 2742 | AYYGSE | 6 | 7398 |
| PDH 2743 | NYYGSE | 6 | 7399 |
| PDH 2744 | FYYGSE | 6 | 7400 |
| PDH 2745 | YYYGSE | 6 | 7401 |
| PDH 2746 | DYYGSE | 6 | 7402 |
| PDH 2747 | TYYGSE | 6 | 7403 |

TABLE 28-continued

Theoretical segment pool of unique DH polypeptide segments encoded by the degenerate oligonucleotides of Table 27.

| Name | Sequence | Length | SEQ ID NO |
|---|---|---|---|
| PDH 2748 | HYYGSE | 6 | 7404 |
| PDH 2749 | LYYGSE | 6 | 7405 |
| PDH 2750 | IYYGSE | 6 | 7406 |
| PDH 2751 | SYYGSE | 6 | 7407 |
| PDH 2752 | CSSGSC | 6 | 7408 |
| PDH 2753 | CGGGSC | 6 | 7409 |
| PDH 2754 | CGSGSC | 6 | 7410 |
| PDH 2755 | CSGGSC | 6 | 3775 |
| PDH 2756 | PFWSGS | 6 | 7411 |
| PDH 2757 | DFWSGF | 6 | 7412 |
| PDH 2758 | PFWSGY | 6 | 7413 |
| PDH 2759 | AFWSGY | 6 | 7414 |
| PDH 2760 | AFWSGS | 6 | 7415 |
| PDH 2761 | AFWSGF | 6 | 7416 |
| PDH 2762 | PFWSGF | 6 | 7417 |
| PDH 2763 | VFWSGY | 6 | 7418 |
| PDH 2764 | YFWSGF | 6 | 7419 |
| PDH 2765 | IFWSGS | 6 | 7420 |
| PDH 2766 | VFWSGF | 6 | 7421 |
| PDH 2767 | VFWSGS | 6 | 7422 |
| PDH 2768 | IFWSGF | 6 | 7423 |
| PDH 2769 | IFWSGY | 6 | 7424 |
| PDH 2770 | SFWSGF | 6 | 7425 |
| PDH 2771 | YFWSGY | 6 | 7426 |
| PDH 2772 | FFWSGS | 6 | 7427 |
| PDH 2773 | YFWSGS | 6 | 7428 |
| PDH 2774 | FFWSGY | 6 | 7429 |
| PDH 2775 | LFWSGF | 6 | 7430 |
| PDH 2776 | TFWSGF | 6 | 7431 |
| PDH 2777 | NFWSGF | 6 | 7432 |
| PDH 2778 | HFWSGF | 6 | 7433 |
| PDH 2779 | NFWSGS | 6 | 7434 |
| PDH 2780 | SFWSGS | 6 | 7435 |
| PDH 2781 | TFWSGS | 6 | 7436 |
| PDH 2782 | NFWSGY | 6 | 7437 |
| PDH 2783 | DFWSGY | 6 | 4254 |
| PDH 2784 | LFWSGY | 6 | 7438 |

TABLE 28-continued

Theoretical segment pool of unique DH polypeptide segments encoded by the degenerate oligonucleotides of Table 27.

| Name | Sequence | Length | SEQ ID NO |
|---|---|---|---|
| PDH 2785 | HFWSGS | 6 | 7439 |
| PDH 2786 | SFWSGY | 6 | 7440 |
| PDH 2787 | TFWSGY | 6 | 7441 |
| PDH 2788 | DFWSGS | 6 | 7442 |
| PDH 2789 | LFWSGS | 6 | 7443 |
| PDH 2790 | HFWSGY | 6 | 7444 |
| PDH 2791 | FFWSGF | 6 | 7445 |
| PDH 2792 | DYYDSSG | 7 | 7446 |
| PDH 2793 | SYYDSSG | 7 | 7447 |
| PDH 2794 | IYYDSSG | 7 | 7448 |
| PDH 2795 | HYYDSSG | 7 | 7449 |
| PDH 2796 | SYYDSSA | 7 | 7450 |
| PDH 2797 | SYYDSSD | 7 | 7451 |
| PDH 2798 | IYYDSSA | 7 | 7452 |
| PDH 2799 | AYYDSSA | 7 | 7453 |
| PDH 2800 | IYYDSSD | 7 | 7454 |
| PDH 2801 | AYYDSSD | 7 | 7455 |
| PDH 2802 | HYYDSSD | 7 | 7456 |
| PDH 2803 | VYYDSSD | 7 | 7457 |
| PDH 2804 | HYYDSSA | 7 | 7458 |
| PDH 2805 | AYYDSSG | 7 | 7459 |
| PDH 2806 | VYYDSSA | 7 | 7460 |
| PDH 2807 | LYYDSSG | 7 | 7461 |
| PDH 2808 | VYYDSSG | 7 | 7462 |
| PDH 2809 | LYYDSSD | 7 | 7463 |
| PDH 2810 | FYYDSSG | 7 | 7464 |
| PDH 2811 | LYYDSSA | 7 | 7465 |
| PDH 2812 | FYYDSSD | 7 | 7466 |
| PDH 2813 | TYYDSSG | 7 | 7467 |
| PDH 2814 | PYYDSSG | 7 | 7468 |
| PDH 2815 | FYYDSSA | 7 | 7469 |
| PDH 2816 | TYYDSSD | 7 | 7470 |
| PDH 2817 | NYYDSSG | 7 | 7471 |
| PDH 2818 | TYYDSSA | 7 | 7472 |
| PDH 2819 | PYYDSSA | 7 | 7473 |
| PDH 2820 | YYYDSSG | 7 | 4167 |
| PDH 2821 | PYYDSSD | 7 | 7474 |

TABLE 28-continued

Theoretical segment pool of unique DH polypeptide segments encoded by the degenerate oligonucleotides of Table 27.

| Name | Sequence | Length | SEQ ID NO |
|---|---|---|---|
| PDH 2822 | NYYDSSA | 7 | 7475 |
| PDH 2823 | YYYDSSD | 7 | 7476 |
| PDH 2824 | NYYDSSD | 7 | 7477 |
| PDH 2825 | YYYDSSA | 7 | 7478 |
| PDH 2826 | DYYDSSD | 7 | 7479 |
| PDH 2827 | DYYDSSA | 7 | 7480 |
| PDH 2828 | FDILTGF | 7 | 7481 |
| PDH 2829 | FDILTGS | 7 | 7482 |
| PDH 2830 | LDILTGY | 7 | 7483 |
| PDH 2831 | YDILTGF | 7 | 7484 |
| PDH 2832 | LDILTGS | 7 | 7485 |
| PDH 2833 | SDILTGF | 7 | 7486 |
| PDH 2834 | IDILTGS | 7 | 7487 |
| PDH 2835 | PDILTGS | 7 | 7488 |
| PDH 2836 | PDILTGF | 7 | 7489 |
| PDH 2837 | IDILTGF | 7 | 7490 |
| PDH 2838 | IDILTGY | 7 | 7491 |
| PDH 2839 | PDILTGY | 7 | 7492 |
| PDH 2840 | YDILTGY | 7 | 4325 |
| PDH 2841 | DDILTGF | 7 | 7493 |
| PDH 2842 | YDILTGS | 7 | 7494 |
| PDH 2843 | HDILTGY | 7 | 7495 |
| PDH 2844 | TDILTGF | 7 | 7496 |
| PDH 2845 | VDILTGY | 7 | 7497 |
| PDH 2846 | LDILTGF | 7 | 7498 |
| PDH 2847 | VDILTGS | 7 | 7499 |
| PDH 2848 | HDILTGS | 7 | 7500 |
| PDH 2849 | ADILTGS | 7 | 7501 |
| PDH 2850 | HDILTGF | 7 | 7502 |
| PDH 2851 | NDILTGS | 7 | 7503 |
| PDH 2852 | NDILTGF | 7 | 7504 |
| PDH 2853 | ADILTGY | 7 | 7505 |
| PDH 2854 | VDILTGF | 7 | 7506 |
| PDH 2855 | TDILTGY | 7 | 7507 |
| PDH 2856 | ADILTGF | 7 | 7508 |
| PDH 2857 | NDILTGY | 7 | 7509 |
| PDH 2858 | TDILTGS | 7 | 7510 |

TABLE 28-continued

Theoretical segment pool of unique DH polypeptide segments encoded by the degenerate oligonucleotides of Table 27.

| Name | Sequence | Length | SEQ ID NO |
|---|---|---|---|
| PDH 2859 | SDILTGS | 7 | 7511 |
| PDH 2860 | DDILTGY | 7 | 7512 |
| PDH 2861 | SDILTGY | 7 | 7513 |
| PDH 2862 | DDILTGS | 7 | 7514 |
| PDH 2863 | FDILTGY | 7 | 7515 |
| PDH 2864 | SYDFWSA | 7 | 7516 |
| PDH 2865 | FYDFWSG | 7 | 7517 |
| PDH 2866 | IYDFWSD | 7 | 7518 |
| PDH 2867 | LYDFWSD | 7 | 7519 |
| PDH 2868 | AYDFWSD | 7 | 7520 |
| PDH 2869 | IYDFWSA | 7 | 7521 |
| PDH 2870 | PYDFWSD | 7 | 7522 |
| PDH 2871 | AYDFWSA | 7 | 7523 |
| PDH 2872 | SYDFWSG | 7 | 7524 |
| PDH 2873 | FYDFWSA | 7 | 7525 |
| PDH 2874 | PYDFWSA | 7 | 7526 |
| PDH 2875 | YYDFWSG | 7 | 4248 |
| PDH 2876 | FYDFWSD | 7 | 7527 |
| PDH 2877 | IYDFWSG | 7 | 7528 |
| PDH 2878 | PYDFWSG | 7 | 7529 |
| PDH 2879 | YYDFWSA | 7 | 7530 |
| PDH 2880 | YYDFWSD | 7 | 7531 |
| PDH 2881 | NYDFWSD | 7 | 7532 |
| PDH 2882 | VYDFWSA | 7 | 7533 |
| PDH 2883 | NYDFWSA | 7 | 7534 |
| PDH 2884 | VYDFWSD | 7 | 7535 |
| PDH 2885 | VYDFWSG | 7 | 7536 |
| PDH 2886 | NYDFWSG | 7 | 7537 |
| PDH 2887 | DYDFWSA | 7 | 7538 |
| PDH 2888 | DYDFWSD | 7 | 7539 |
| PDH 2889 | DYDFWSG | 7 | 7540 |
| PDH 2890 | HYDFWSG | 7 | 7541 |
| PDH 2891 | TYDFWSG | 7 | 7542 |
| PDH 2892 | HYDFWSA | 7 | 7543 |
| PDH 2893 | LYDFWSG | 7 | 7544 |
| PDH 2894 | HYDFWSD | 7 | 7545 |
| PDH 2895 | TYDFWSA | 7 | 7546 |

TABLE 28-continued

Theoretical segment pool of unique DH polypeptide segments encoded by the degenerate oligonucleotides of Table 27.

| Name | Sequence | Length | SEQ ID NO |
|---|---|---|---|
| PDH 2896 | SYDFWSD | 7 | 7547 |
| PDH 2897 | TYDFWSD | 7 | 7548 |
| PDH 2898 | LYDFWSA | 7 | 7549 |
| PDH 2899 | AYDFWSG | 7 | 7550 |
| PDH 2900 | SCSSTSC | 7 | 7551 |
| PDH 2901 | HCSSTSC | 7 | 7552 |
| PDH 2902 | PCSSTSC | 7 | 7553 |
| PDH 2903 | ACSSTSC | 7 | 7554 |
| PDH 2904 | VCSSTSC | 7 | 7555 |
| PDH 2905 | LCSSTSC | 7 | 7556 |
| PDH 2906 | YCSSTSC | 7 | 3812 |
| PDH 2907 | FCSSTSC | 7 | 7557 |
| PDH 2908 | DCSSTSC | 7 | 7558 |
| PDH 2909 | RYSSSWS | 7 | 7559 |
| PDH 2910 | VYSSSWY | 7 | 7560 |
| PDH 2911 | GYSSSWY | 7 | 4435 |
| PDH 2912 | VYSSSWS | 7 | 7561 |
| PDH 2913 | TYSSSWY | 7 | 7562 |
| PDH 2914 | TYSSSWF | 7 | 7563 |
| PDH 2915 | TYSSSWS | 7 | 7564 |
| PDH 2916 | GYSSSWF | 7 | 7565 |
| PDH 2917 | LYSSSWF | 7 | 7566 |
| PDH 2918 | AYSSSWS | 7 | 7567 |
| PDH 2919 | SYSSSWF | 7 | 7568 |
| PDH 2920 | WYSSSWS | 7 | 7569 |
| PDH 2921 | WYSSSWF | 7 | 7570 |
| PDH 2922 | MYSSSWS | 7 | 7571 |
| PDH 2923 | SYSSSWS | 7 | 7572 |
| PDH 2924 | LYSSSWY | 7 | 7573 |
| PDH 2925 | AYSSSWY | 7 | 7574 |
| PDH 2926 | AYSSSWF | 7 | 7575 |
| PDH 2927 | LYSSSWS | 7 | 7576 |
| PDH 2928 | WYSSSWY | 7 | 7577 |
| PDH 2929 | VYSSSWF | 7 | 7578 |
| PDH 2930 | SYSSSWY | 7 | 7579 |
| PDH 2931 | RYSSSWF | 7 | 7580 |
| PDH 2932 | MYSSSWF | 7 | 7581 |

TABLE 28-continued

Theoretical segment pool of unique DH polypeptide segments encoded by the degenerate oligonucleotides of Table 27.

| Name | Sequence | Length | SEQ ID NO |
|---|---|---|---|
| PDH 2933 | RYSSSWY | 7 | 7582 |
| PDH 2934 | MYSSSWY | 7 | 7583 |
| PDH 2935 | GYSSSWS | 7 | 7584 |
| PDH 2936 | IYDSSGY | 7 | 7585 |
| PDH 2937 | PYDSSGS | 7 | 7586 |
| PDH 2938 | VYDSSGF | 7 | 7587 |
| PDH 2939 | PYDSSGY | 7 | 7588 |
| PDH 2940 | NYDSSGS | 7 | 7589 |
| PDH 2941 | LYDSSGY | 7 | 7590 |
| PDH 2942 | NYDSSGY | 7 | 7591 |
| PDH 2943 | LYDSSGS | 7 | 7592 |
| PDH 2944 | VYDSSGY | 7 | 7593 |
| PDH 2945 | VYDSSGS | 7 | 7594 |
| PDH 2946 | LYDSSGF | 7 | 7595 |
| PDH 2947 | NYDSSGF | 7 | 7596 |
| PDH 2948 | YYDSSGY | 7 | 4168 |
| PDH 2949 | YYDSSGS | 7 | 7597 |
| PDH 2950 | DYDSSGS | 7 | 7598 |
| PDH 2951 | TYDSSGY | 7 | 7599 |
| PDH 2952 | TYDSSGF | 7 | 7600 |
| PDH 2953 | TYDSSGS | 7 | 7601 |
| PDH 2954 | YYDSSGF | 7 | 7602 |
| PDH 2955 | AYDSSGS | 7 | 7603 |
| PDH 2956 | HYDSSGY | 7 | 7604 |
| PDH 2957 | AYDSSGY | 7 | 7605 |
| PDH 2958 | HYDSSGF | 7 | 7606 |
| PDH 2959 | HYDSSGS | 7 | 7607 |
| PDH 2960 | FYDSSGF | 7 | 7608 |
| PDH 2961 | IYDSSGF | 7 | 7609 |
| PDH 2962 | DYDSSGY | 7 | 7610 |
| PDH 2963 | DYDSSGF | 7 | 7611 |
| PDH 2964 | PYDSSGF | 7 | 7612 |
| PDH 2965 | SYDSSGS | 7 | 7613 |
| PDH 2966 | SYDSSGF | 7 | 7614 |
| PDH 2967 | AYDSSGF | 7 | 7615 |
| PDH 2968 | FYDSSGY | 7 | 7616 |
| PDH 2969 | SYDSSGY | 7 | 7617 |

TABLE 28-continued

Theoretical segment pool of unique DH polypeptide segments encoded by the degenerate oligonucleotides of Table 27.

| Name | Sequence | Length | SEQ ID NO |
|---|---|---|---|
| PDH 2970 | IYDSSGS | 7 | 7618 |
| PDH 2971 | FYDSSGS | 7 | 7619 |
| PDH 2972 | HYYGSGI | 7 | 7620 |
| PDH 2973 | SYYGSGI | 7 | 7621 |
| PDH 2974 | AYYGSGT | 7 | 7622 |
| PDH 2975 | DYYGSGI | 7 | 7623 |
| PDH 2976 | VYYGSGT | 7 | 7624 |
| PDH 2977 | AYYGSGS | 7 | 7625 |
| PDH 2978 | VYYGSGI | 7 | 7626 |
| PDH 2979 | VYYGSGS | 7 | 7627 |
| PDH 2980 | HYYGSGS | 7 | 7628 |
| PDH 2981 | LYYGSGS | 7 | 7629 |
| PDH 2982 | HYYGSGT | 7 | 7630 |
| PDH 2983 | LYYGSGT | 7 | 7631 |
| PDH 2984 | PYYGSGS | 7 | 7632 |
| PDH 2985 | SYYGSGS | 7 | 7633 |
| PDH 2986 | NYYGSGS | 7 | 7634 |
| PDH 2987 | IYYGSGS | 7 | 7635 |
| PDH 2988 | DYYGSGT | 7 | 7636 |
| PDH 2989 | PYYGSGI | 7 | 7637 |
| PDH 2990 | PYYGSGT | 7 | 7638 |
| PDH 2991 | SYYGSGT | 7 | 7639 |
| PDH 2992 | FYYGSGS | 7 | 7640 |
| PDH 2993 | YYYGSGS | 7 | 3975 |
| PDH 2994 | NYYGSGT | 7 | 7641 |
| PDH 2995 | IYYGSGT | 7 | 7642 |
| PDH 2996 | DYYGSGS | 7 | 7643 |
| PDH 2997 | TYYGSGS | 7 | 7644 |
| PDH 2998 | FYYGSGT | 7 | 7645 |
| PDH 2999 | YYYGSGT | 7 | 7646 |
| PDH 3000 | TYYGSGT | 7 | 7647 |
| PDH 3001 | YYYGSGI | 7 | 7648 |
| PDH 3002 | FYYGSGI | 7 | 7649 |
| PDH 3003 | AYYGSGI | 7 | 7650 |
| PDH 3004 | TYYGSGI | 7 | 7651 |
| PDH 3005 | IYYGSGI | 7 | 7652 |
| PDH 3006 | LYYGSGI | 7 | 7653 |
| PDH 3007 | NYYGSGI | 7 | 7654 |
| PDH 3008 | TYSSGWF | 7 | 7655 |
| PDH 3009 | TYSSGWS | 7 | 7656 |
| PDH 3010 | VYSSGWF | 7 | 7657 |
| PDH 3011 | GYSSGWF | 7 | 7658 |
| PDH 3012 | MYSSGWS | 7 | 7659 |
| PDH 3013 | SYSSGWF | 7 | 7660 |
| PDH 3014 | MYSSGWY | 7 | 7661 |
| PDH 3015 | LYSSGWY | 7 | 7662 |
| PDH 3016 | MYSSGWF | 7 | 7663 |
| PDH 3017 | WYSSGWS | 7 | 7664 |
| PDH 3018 | WYSSGWY | 7 | 7665 |
| PDH 3019 | AYSSGWS | 7 | 7666 |
| PDH 3020 | RYSSGWF | 7 | 7667 |
| PDH 3021 | LYSSGWF | 7 | 7668 |
| PDH 3022 | AYSSGWY | 7 | 7669 |
| PDH 3023 | RYSSGWY | 7 | 7670 |
| PDH 3024 | SYSSGWY | 7 | 7671 |
| PDH 3025 | RYSSGWS | 7 | 7672 |
| PDH 3026 | GYSSGWY | 7 | 4456 |
| PDH 3027 | WYSSGWF | 7 | 7673 |
| PDH 3028 | AYSSGWF | 7 | 7674 |
| PDH 3029 | GYSSGWS | 7 | 7675 |
| PDH 3030 | VYSSGWY | 7 | 7676 |
| PDH 3031 | VYSSGWS | 7 | 7677 |
| PDH 3032 | LYSSGWS | 7 | 7678 |
| PDH 3033 | TYSSGWY | 7 | 7679 |
| PDH 3034 | SYSSGWS | 7 | 7680 |
| PDH 3035 | FCSGGSC | 7 | 7681 |
| PDH 3036 | LCSGGSC | 7 | 7682 |
| PDH 3037 | SCSGGSC | 7 | 7683 |
| PDH 3038 | YCSGGSC | 7 | 3773 |
| PDH 3039 | DCSGGSC | 7 | 7684 |
| PDH 3040 | HCSGGSC | 7 | 7685 |
| PDH 3041 | PCSGGSC | 7 | 7686 |
| PDH 3042 | ACSGGSC | 7 | 7687 |
| PDH 3043 | VCSGGSC | 7 | 7688 |

TABLE 28-continued

Theoretical segment pool of unique DH polypeptide segments encoded by the degenerate oligonucleotides of Table 27.

| Name | Sequence | Length | SEQ ID NO |
|---|---|---|---|
| PDH 3044 | CSGGSCH | 7 | 7689 |
| PDH 3045 | CSGGSCL | 7 | 7690 |
| PDH 3046 | CSGGSCS | 7 | 7691 |
| PDH 3047 | CSGGSCY | 7 | 3774 |
| PDH 3048 | CSGGSCP | 7 | 7692 |
| PDH 3049 | CSGGSCF | 7 | 7693 |
| PDH 3050 | CSSTSCY | 7 | 3813 |
| PDH 3051 | CSSTSCL | 7 | 7694 |
| PDH 3052 | CSSTSCF | 7 | 7695 |
| PDH 3053 | CSSTSCH | 7 | 7696 |
| PDH 3054 | CSSTSCS | 7 | 7697 |
| PDH 3055 | CSSTSCP | 7 | 7698 |
| PDH 3056 | ICGGDCF | 7 | 7699 |
| PDH 3057 | VCGGDCS | 7 | 7700 |
| PDH 3058 | DCGGDCF | 7 | 7701 |
| PDH 3059 | SCGGDCF | 7 | 7702 |
| PDH 3060 | NCGGDCY | 7 | 7703 |
| PDH 3061 | VCGGDCY | 7 | 7704 |
| PDH 3062 | SCGGDCS | 7 | 7705 |
| PDH 3063 | NCGGDCS | 7 | 7706 |
| PDH 3064 | HCGGDCF | 7 | 7707 |
| PDH 3065 | LCGGDCS | 7 | 7708 |
| PDH 3066 | LCGGDCY | 7 | 7709 |
| PDH 3067 | ICGGDCY | 7 | 7710 |
| PDH 3068 | LCGGDCF | 7 | 7711 |
| PDH 3069 | ICGGDCS | 7 | 7712 |
| PDH 3070 | VCGGDCF | 7 | 7713 |
| PDH 3071 | HCGGDCS | 7 | 7714 |
| PDH 3072 | YCGGDCF | 7 | 7715 |
| PDH 3073 | HCGGDCY | 7 | 7716 |
| PDH 3074 | FCGGDCF | 7 | 7717 |
| PDH 3075 | YCGGDCS | 7 | 7718 |
| PDH 3076 | DCGGDCS | 7 | 7719 |
| PDH 3077 | YCGGDCY | 7 | 3866 |
| PDH 3078 | DCGGDCY | 7 | 7720 |
| PDH 3079 | PCGGDCF | 7 | 7721 |
| PDH 3080 | FCGGDCS | 7 | 7722 |

TABLE 28-continued

Theoretical segment pool of unique DH polypeptide segments encoded by the degenerate oligonucleotides of Table 27.

| Name | Sequence | Length | SEQ ID NO |
|---|---|---|---|
| PDH 3081 | FCGGDCY | 7 | 7723 |
| PDH 3082 | ACGGDCF | 7 | 7724 |
| PDH 3083 | ACGGDCY | 7 | 7725 |
| PDH 3084 | ACGGDCS | 7 | 7726 |
| PDH 3085 | PCGGDCY | 7 | 7727 |
| PDH 3086 | PCGGDCS | 7 | 7728 |
| PDH 3087 | SCGGDCY | 7 | 7729 |
| PDH 3088 | NCGGDCF | 7 | 7730 |
| PDH 3089 | TCGGDCS | 7 | 7731 |
| PDH 3090 | TCGGDCY | 7 | 7732 |
| PDH 3091 | TCGGDCF | 7 | 7733 |
| PDH 3092 | NDFWSGF | 7 | 7734 |
| PDH 3093 | HDFWSGF | 7 | 7735 |
| PDH 3094 | SDFWSGF | 7 | 7736 |
| PDH 3095 | NDFWSGY | 7 | 7737 |
| PDH 3096 | HDFWSGS | 7 | 7738 |
| PDH 3097 | DDFWSGF | 7 | 7739 |
| PDH 3098 | HDFWSGY | 7 | 7740 |
| PDH 3099 | SDFWSGY | 7 | 7741 |
| PDH 3100 | FDFWSGF | 7 | 7742 |
| PDH 3101 | PDFWSGY | 7 | 7743 |
| PDH 3102 | IDFWSGF | 7 | 7744 |
| PDH 3103 | SDFWSGS | 7 | 7745 |
| PDH 3104 | PDFWSGS | 7 | 7746 |
| PDH 3105 | TDFWSGF | 7 | 7747 |
| PDH 3106 | LDFWSGS | 7 | 7748 |
| PDH 3107 | DDFWSGY | 7 | 7749 |
| PDH 3108 | LDFWSGY | 7 | 7750 |
| PDH 3109 | FDFWSGS | 7 | 7751 |
| PDH 3110 | ADFWSGF | 7 | 7752 |
| PDH 3111 | FDFWSGY | 7 | 7753 |
| PDH 3112 | TDFWSGS | 7 | 7754 |
| PDH 3113 | PDFWSGF | 7 | 7755 |
| PDH 3114 | VDFWSGF | 7 | 7756 |
| PDH 3115 | TDFWSGY | 7 | 7757 |
| PDH 3116 | IDFWSGY | 7 | 7758 |
| PDH 3117 | DDFWSGS | 7 | 7759 |

TABLE 28-continued

Theoretical segment pool of unique DH polypeptide segments encoded by the degenerate oligonucleotides of Table 27.

| Name | Sequence | Length | SEQ ID NO |
|---|---|---|---|
| PDH 3118 | YDFWSGS | 7 | 7760 |
| PDH 3119 | YDFWSGF | 7 | 7761 |
| PDH 3120 | IDFWSGS | 7 | 7762 |
| PDH 3121 | NDFWSGS | 7 | 7763 |
| PDH 3122 | YDFWSGY | 7 | 4249 |
| PDH 3123 | LDFWSGF | 7 | 7764 |
| PDH 3124 | ADFWSGY | 7 | 7765 |
| PDH 3125 | VDFWSGS | 7 | 7766 |
| PDH 3126 | ADFWSGS | 7 | 7767 |
| PDH 3127 | VDFWSGY | 7 | 7768 |
| PDH 3128 | YDSSGYS | 7 | 7769 |
| PDH 3129 | VDSSGYF | 7 | 7770 |
| PDH 3130 | VDSSGYS | 7 | 7771 |
| PDH 3131 | ADSSGYS | 7 | 7772 |
| PDH 3132 | HDSSGYF | 7 | 7773 |
| PDH 3133 | ADSSGYY | 7 | 7774 |
| PDH 3134 | DDSSGYY | 7 | 7775 |
| PDH 3135 | DDSSGYS | 7 | 7776 |
| PDH 3136 | SDSSGYS | 7 | 7777 |
| PDH 3137 | SDSSGYF | 7 | 7778 |
| PDH 3138 | PDSSGYS | 7 | 7779 |
| PDH 3139 | SDSSGYY | 7 | 7780 |
| PDH 3140 | PDSSGYY | 7 | 7781 |
| PDH 3141 | HDSSGYY | 7 | 7782 |
| PDH 3142 | PDSSGYF | 7 | 7783 |
| PDH 3143 | FDSSGYF | 7 | 7784 |
| PDH 3144 | HDSSGYS | 7 | 7785 |
| PDH 3145 | ADSSGYF | 7 | 7786 |
| PDH 3146 | DDSSGYF | 7 | 7787 |
| PDH 3147 | LDSSGYF | 7 | 7788 |
| PDH 3148 | LDSSGYY | 7 | 7789 |
| PDH 3149 | LDSSGYS | 7 | 7790 |
| PDH 3150 | FDSSGYY | 7 | 7791 |
| PDH 3151 | FDSSGYS | 7 | 7792 |
| PDH 3152 | YDSSGYF | 7 | 7793 |
| PDH 3153 | YDSSGYY | 7 | 4169 |
| PDH 3154 | VDSSGYY | 7 | 7794 |

TABLE 28-continued

Theoretical segment pool of unique DH polypeptide segments encoded by the degenerate oligonucleotides of Table 27.

| Name | Sequence | Length | SEQ ID NO |
|---|---|---|---|
| PDH 3155 | EYCGGDC | 7 | 7795 |
| PDH 3156 | QYCGGDC | 7 | 7796 |
| PDH 3157 | AYCGGDC | 7 | 3865 |
| PDH 3158 | IYCGGDC | 7 | 7797 |
| PDH 3159 | TYCGGDC | 7 | 7798 |
| PDH 3160 | PYCGGDC | 7 | 7799 |
| PDH 3161 | LYCGGDC | 7 | 7800 |
| PDH 3162 | VYCGGDC | 7 | 7801 |
| PDH 3163 | KYCGGDC | 7 | 7802 |
| PDH 3164 | VYYDSSGF | 8 | 7803 |
| PDH 3165 | IYYDSSGF | 8 | 7804 |
| PDH 3166 | YYYDSSGY | 8 | 4164 |
| PDH 3167 | PYYDSSGF | 8 | 7805 |
| PDH 3168 | HYYDSSGF | 8 | 7806 |
| PDH 3169 | HYYDSSGY | 8 | 7807 |
| PDH 3170 | AYYDSSGF | 8 | 7808 |
| PDH 3171 | HYYDSSGS | 8 | 7809 |
| PDH 3172 | DYYDSSGY | 8 | 7810 |
| PDH 3173 | DYYDSSGS | 8 | 7811 |
| PDH 3174 | YYYDSSGS | 8 | 7812 |
| PDH 3175 | SYYDSSGF | 8 | 7813 |
| PDH 3176 | LYYDSSGF | 8 | 7814 |
| PDH 3177 | NYYDSSGF | 8 | 7815 |
| PDH 3178 | NYYDSSGY | 8 | 7816 |
| PDH 3179 | IYYDSSGY | 8 | 7817 |
| PDH 3180 | SYYDSSGS | 8 | 7818 |
| PDH 3181 | AYYDSSGS | 8 | 7819 |
| PDH 3182 | IYYDSSGS | 8 | 7820 |
| PDH 3183 | AYYDSSGY | 8 | 7821 |
| PDH 3184 | DYYDSSGF | 8 | 7822 |
| PDH 3185 | SYYDSSGY | 8 | 7823 |
| PDH 3186 | NYYDSSGS | 8 | 7824 |
| PDH 3187 | LYYDSSGY | 8 | 7825 |
| PDH 3188 | PYYDSSGS | 8 | 7826 |
| PDH 3189 | LYYDSSGS | 8 | 7827 |
| PDH 3190 | PYYDSSGY | 8 | 7828 |
| PDH 3191 | TYYDSSGY | 8 | 7829 |

TABLE 28-continued

Theoretical segment pool of unique DH polypeptide segments encoded by the degenerate oligonucleotides of Table 27.

| Name | Sequence | Length | SEQ ID NO |
|---|---|---|---|
| PDH 3192 | TYYDSSGS | 8 | 7830 |
| PDH 3193 | FYYDSSGF | 8 | 7831 |
| PDH 3194 | FYYDSSGY | 8 | 7832 |
| PDH 3195 | FYYDSSGS | 8 | 7833 |
| PDH 3196 | VYYDSSGS | 8 | 7834 |
| PDH 3197 | TYYDSSGF | 8 | 7835 |
| PDH 3198 | YYYDSSGF | 8 | 7836 |
| PDH 3199 | VYYDSSGY | 8 | 7837 |
| PDH 3200 | TYYGSGSS | 8 | 7838 |
| PDH 3201 | SYYGSGSY | 8 | 7839 |
| PDH 3202 | SYYGSGSS | 8 | 7840 |
| PDH 3203 | HYYGSGSF | 8 | 7841 |
| PDH 3204 | PYYGSGSF | 8 | 7842 |
| PDH 3205 | AYYGSGSS | 8 | 7843 |
| PDH 3206 | AYYGSGSF | 8 | 7844 |
| PDH 3207 | AYYGSGSY | 8 | 7845 |
| PDH 3208 | YYYGSGSF | 8 | 7846 |
| PDH 3209 | TYYGSGSY | 8 | 7847 |
| PDH 3210 | YYYGSGSY | 8 | 3972 |
| PDH 3211 | PYYGSGSS | 8 | 7848 |
| PDH 3212 | PYYGSGSY | 8 | 7849 |
| PDH 3213 | DYYGSGSY | 8 | 7850 |
| PDH 3214 | VYYGSGSY | 8 | 7851 |
| PDH 3215 | VYYGSGSF | 8 | 7852 |
| PDH 3216 | YYYGSGSS | 8 | 7853 |
| PDH 3217 | LYYGSGSF | 8 | 7854 |
| PDH 3218 | LYYGSGSY | 8 | 7855 |
| PDH 3219 | DYYGSGSS | 8 | 7856 |
| PDH 3220 | VYYGSGSS | 8 | 7857 |
| PDH 3221 | IYYGSGSS | 8 | 7858 |
| PDH 3222 | FYYGSGSY | 8 | 7859 |
| PDH 3223 | FYYGSGSS | 8 | 7860 |
| PDH 3224 | LYYGSGSS | 8 | 7861 |
| PDH 3225 | SYYGSGSF | 8 | 7862 |
| PDH 3226 | IYYGSGSY | 8 | 7863 |
| PDH 3227 | IYYGSGSF | 8 | 7864 |
| PDH 3228 | FYYGSGSF | 8 | 7865 |

TABLE 28-continued

Theoretical segment pool of unique DH polypeptide segments encoded by the degenerate oligonucleotides of Table 27.

| Name | Sequence | Length | SEQ ID NO |
|---|---|---|---|
| PDH 3229 | DYYGSGSF | 8 | 7866 |
| PDH 3230 | NYYGSGSS | 8 | 7867 |
| PDH 3231 | NYYGSGSY | 8 | 7868 |
| PDH 3232 | TYYGSGSF | 8 | 7869 |
| PDH 3233 | HYYGSGSY | 8 | 7870 |
| PDH 3234 | HYYGSGSS | 8 | 7871 |
| PDH 3235 | NYYGSGSF | 8 | 7872 |
| PDH 3236 | AYCSSTSC | 8 | 7873 |
| PDH 3237 | PYCSSTSC | 8 | 7874 |
| PDH 3238 | RYCSSTSC | 8 | 7875 |
| PDH 3239 | IYCSSTSC | 8 | 7876 |
| PDH 3240 | LYCSSTSC | 8 | 7877 |
| PDH 3241 | VYCSSTSC | 8 | 7878 |
| PDH 3242 | TYCSSTSC | 8 | 7879 |
| PDH 3243 | SYCSSTSC | 8 | 7880 |
| PDH 3244 | GYCSSTSC | 8 | 3809 |
| PDH 3245 | IYCSGGSC | 8 | 7881 |
| PDH 3246 | VYCSGGSC | 8 | 7882 |
| PDH 3247 | LYCSGGSC | 8 | 7883 |
| PDH 3248 | AYCSGGSC | 8 | 7884 |
| PDH 3249 | TYCSGGSC | 8 | 7885 |
| PDH 3250 | GYCSGGSC | 8 | 3770 |
| PDH 3251 | RYCSGGSC | 8 | 7886 |
| PDH 3252 | PYCSGGSC | 8 | 7887 |
| PDH 3253 | SYCSGGSC | 8 | 7888 |
| PDH 3254 | FYDFWSGY | 8 | 7889 |
| PDH 3255 | AYDFWSGF | 8 | 7890 |
| PDH 3256 | NYDFWSGF | 8 | 7891 |
| PDH 3257 | IYDFWSGF | 8 | 7892 |
| PDH 3258 | DYDFWSGS | 8 | 7893 |
| PDH 3259 | DYDFWSGY | 8 | 7894 |
| PDH 3260 | NYDFWSGY | 8 | 7895 |
| PDH 3261 | VYDFWSGF | 8 | 7896 |
| PDH 3262 | VYDFWSGS | 8 | 7897 |
| PDH 3263 | YYDFWSGF | 8 | 7898 |
| PDH 3264 | PYDFWSGF | 8 | 7899 |
| PDH 3265 | FYDFWSGS | 8 | 7900 |

TABLE 28-continued

Theoretical segment pool of unique DH polypeptide segments encoded by the degenerate oligonucleotides of Table 27.

| Name | Sequence | Length | SEQ ID NO |
|---|---|---|---|
| PDH 3266 | HYDFWSGF | 8 | 7901 |
| PDH 3267 | HYDFWSGY | 8 | 7902 |
| PDH 3268 | YYDFWSGS | 8 | 7903 |
| PDH 3269 | PYDFWSGY | 8 | 7904 |
| PDH 3270 | PYDFWSGS | 8 | 7905 |
| PDH 3271 | VYDFWSGY | 8 | 7906 |
| PDH 3272 | SYDFWSGS | 8 | 7907 |
| PDH 3273 | YYDFWSGY | 8 | 4245 |
| PDH 3274 | LYDFWSGF | 8 | 7908 |
| PDH 3275 | HYDFWSGS | 8 | 7909 |
| PDH 3276 | SYDFWSGY | 8 | 7910 |
| PDH 3277 | SYDFWSGF | 8 | 7911 |
| PDH 3278 | LYDFWSGS | 8 | 7912 |
| PDH 3279 | TYDFWSGF | 8 | 7913 |
| PDH 3280 | LYDFWSGY | 8 | 7914 |
| PDH 3281 | AYDFWSGY | 8 | 7915 |
| PDH 3282 | AYDFWSGS | 8 | 7916 |
| PDH 3283 | TYDFWSGS | 8 | 7917 |
| PDH 3284 | IYDFWSGY | 8 | 7918 |
| PDH 3285 | TYDFWSGY | 8 | 7919 |
| PDH 3286 | NYDFWSGS | 8 | 7920 |
| PDH 3287 | DYDFWSGF | 8 | 7921 |
| PDH 3288 | IYDFWSGS | 8 | 7922 |
| PDH 3289 | FYDFWSGF | 8 | 7923 |
| PDH 3290 | HDILTGYS | 8 | 7924 |
| PDH 3291 | PDILTGYY | 8 | 7925 |
| PDH 3292 | PDILTGYF | 8 | 7926 |
| PDH 3293 | TDILTGYS | 8 | 7927 |
| PDH 3294 | HDILTGYY | 8 | 7928 |
| PDH 3295 | YDILTGYF | 8 | 7929 |
| PDH 3296 | IDILTGYS | 8 | 7930 |
| PDH 3297 | IDILTGYY | 8 | 7931 |
| PDH 3298 | IDILTGYF | 8 | 7932 |
| PDH 3299 | LDILTGYF | 8 | 7933 |
| PDH 3300 | LDILTGYY | 8 | 7934 |
| PDH 3301 | LDILTGYS | 8 | 7935 |
| PDH 3302 | DDILTGYF | 8 | 7936 |
| PDH 3303 | FDILTGYF | 8 | 7937 |
| PDH 3304 | SDILTGYF | 8 | 7938 |
| PDH 3305 | ADILTGYY | 8 | 7939 |
| PDH 3306 | VDILTGYY | 8 | 7940 |
| PDH 3307 | VDILTGYS | 8 | 7941 |
| PDH 3308 | ADILTGYS | 8 | 7942 |
| PDH 3309 | DDILTGYS | 8 | 7943 |
| PDH 3310 | FDILTGYS | 8 | 7944 |
| PDH 3311 | SDILTGYS | 8 | 7945 |
| PDH 3312 | DDILTGYY | 8 | 7946 |
| PDH 3313 | SDILTGYY | 8 | 7947 |
| PDH 3314 | YDILTGYY | 8 | 4322 |
| PDH 3315 | FDILTGYY | 8 | 7948 |
| PDH 3316 | HDILTGYF | 8 | 7949 |
| PDH 3317 | NDILTGYY | 8 | 7950 |
| PDH 3318 | NDILTGYF | 8 | 7951 |
| PDH 3319 | PDILTGYS | 8 | 7952 |
| PDH 3320 | VDILTGYF | 8 | 7953 |
| PDH 3321 | TDILTGYY | 8 | 7954 |
| PDH 3322 | TDILTGYF | 8 | 7955 |
| PDH 3323 | YDILTGYS | 8 | 7956 |
| PDH 3324 | NDILTGYS | 8 | 7957 |
| PDH 3325 | ADILTGYF | 8 | 7958 |
| PDH 3326 | SCSGGSCS | 8 | 7959 |
| PDH 3327 | HCSGGSCF | 8 | 7960 |
| PDH 3328 | DCSGGSCS | 8 | 7961 |
| PDH 3329 | PCSGGSCF | 8 | 7962 |
| PDH 3330 | PCSGGSCY | 8 | 7963 |
| PDH 3331 | SCSGGSCY | 8 | 7964 |
| PDH 3332 | PCSGGSCS | 8 | 7965 |
| PDH 3333 | LCSGGSCY | 8 | 7966 |
| PDH 3334 | ACSGGSCY | 8 | 7967 |
| PDH 3335 | ACSGGSCS | 8 | 7968 |
| PDH 3336 | ACSGGSCF | 8 | 7969 |
| PDH 3337 | VCSGGSCY | 8 | 7970 |
| PDH 3338 | VCSGGSCF | 8 | 7971 |
| PDH 3339 | VCSGGSCS | 8 | 7972 |

TABLE 28-continued

Theoretical segment pool of unique DH polypeptide segments encoded by the degenerate oligonucleotides of Table 27.

| Name | Sequence | Length | SEQ ID NO |
|---|---|---|---|
| PDH 3340 | YCSGGSCS | 8 | 7973 |
| PDH 3341 | YCSGGSCF | 8 | 7974 |
| PDH 3342 | DCSGGSCF | 8 | 7975 |
| PDH 3343 | DCSGGSCY | 8 | 7976 |
| PDH 3344 | FCSGGSCS | 8 | 7977 |
| PDH 3345 | FCSGGSCY | 8 | 7978 |
| PDH 3346 | FCSGGSCF | 8 | 7979 |
| PDH 3347 | SCSGGSCF | 8 | 7980 |
| PDH 3348 | YCSGGSCY | 8 | 3771 |
| PDH 3349 | LCSGGSCF | 8 | 7981 |
| PDH 3350 | LCSGGSCS | 8 | 7982 |
| PDH 3351 | HCSGGSCS | 8 | 7983 |
| PDH 3352 | HCSGGSCY | 8 | 7984 |
| PDH 3353 | ACSSTSCY | 8 | 7985 |
| PDH 3354 | YCSSTSCF | 8 | 7986 |
| PDH 3355 | FCSSTSCY | 8 | 7987 |
| PDH 3356 | PCSSTSCF | 8 | 7988 |
| PDH 3357 | FCSSTSCS | 8 | 7989 |
| PDH 3358 | DCSSTSCF | 8 | 7990 |
| PDH 3359 | VCSSTSCS | 8 | 7991 |
| PDH 3360 | VCSSTSCF | 8 | 7992 |
| PDH 3361 | LCSSTSCS | 8 | 7993 |
| PDH 3362 | VCSSTSCY | 8 | 7994 |
| PDH 3363 | ACSSTSCS | 8 | 7995 |
| PDH 3364 | LCSSTSCY | 8 | 7996 |
| PDH 3365 | LCSSTSCF | 8 | 7997 |
| PDH 3366 | FCSSTSCF | 8 | 7998 |
| PDH 3367 | HCSSTSCY | 8 | 7999 |
| PDH 3368 | HCSSTSCS | 8 | 8000 |
| PDH 3369 | HCSSTSCF | 8 | 8001 |
| PDH 3370 | SCSSTSCF | 8 | 8002 |
| PDH 3371 | SCSSTSCS | 8 | 8003 |
| PDH 3372 | YCSSTSCS | 8 | 8004 |
| PDH 3373 | DCSSTSCY | 8 | 8005 |
| PDH 3374 | DCSSTSCS | 8 | 8006 |
| PDH 3375 | SCSSTSCY | 8 | 8007 |
| PDH 3376 | PCSSTSCS | 8 | 8008 |

TABLE 28-continued

Theoretical segment pool of unique DH polypeptide segments encoded by the degenerate oligonucleotides of Table 27.

| Name | Sequence | Length | SEQ ID NO |
|---|---|---|---|
| PDH 3377 | ACSSTSCF | 8 | 8009 |
| PDH 3378 | PCSSTSCY | 8 | 8010 |
| PDH 3379 | YCSSTSCY | 8 | 3810 |
| PDH 3380 | LYCGGDCS | 8 | 8011 |
| PDH 3381 | EYCGGDCS | 8 | 8012 |
| PDH 3382 | LYCGGDCY | 8 | 8013 |
| PDH 3383 | VYCGGDCS | 8 | 8014 |
| PDH 3384 | VYCGGDCY | 8 | 8015 |
| PDH 3385 | AYCGGDCY | 8 | 3863 |
| PDH 3386 | AYCGGDCF | 8 | 8016 |
| PDH 3387 | EYCGGDCY | 8 | 8017 |
| PDH 3388 | TYCGGDCF | 8 | 8018 |
| PDH 3389 | LYCGGDCF | 8 | 8019 |
| PDH 3390 | AYCGGDCS | 8 | 8020 |
| PDH 3391 | QYCGGDCF | 8 | 8021 |
| PDH 3392 | QYCGGDCS | 8 | 8022 |
| PDH 3393 | KYCGGDCF | 8 | 8023 |
| PDH 3394 | KYCGGDCY | 8 | 8024 |
| PDH 3395 | QYCGGDCY | 8 | 8025 |
| PDH 3396 | KYCGGDCS | 8 | 8026 |
| PDH 3397 | VYCGGDCF | 8 | 8027 |
| PDH 3398 | IYCGGDCF | 8 | 8028 |
| PDH 3399 | IYCGGDCY | 8 | 8029 |
| PDH 3400 | IYCGGDCS | 8 | 8030 |
| PDH 3401 | PYCGGDCS | 8 | 8031 |
| PDH 3402 | PYCGGDCF | 8 | 8032 |
| PDH 3403 | TYCGGDCY | 8 | 8033 |
| PDH 3404 | EYCGGDCF | 8 | 8034 |
| PDH 3405 | PYCGGDCY | 8 | 8035 |
| PDH 3406 | TYCGGDCS | 8 | 8036 |
| PDH 3407 | DYDSSGYS | 8 | 8037 |
| PDH 3408 | YYDSSGYF | 8 | 8038 |
| PDH 3409 | LYDSSGYS | 8 | 8039 |
| PDH 3410 | AYDSSGYS | 8 | 8040 |
| PDH 3411 | AYDSSGYY | 8 | 8041 |
| PDH 3412 | NYDSSGYY | 8 | 8042 |
| PDH 3413 | IYDSSGYS | 8 | 8043 |

TABLE 28-continued

Theoretical segment pool of unique DH polypeptide segments encoded by the degenerate oligonucleotides of Table 27.

| Name | Sequence | Length | SEQ ID NO |
|---|---|---|---|
| PDH 3414 | FYDSSGYF | 8 | 8044 |
| PDH 3415 | DYDSSGYY | 8 | 8045 |
| PDH 3416 | YYDSSGYS | 8 | 8046 |
| PDH 3417 | TYDSSGYY | 8 | 8047 |
| PDH 3418 | TYDSSGYS | 8 | 8048 |
| PDH 3419 | PYDSSGYF | 8 | 8049 |
| PDH 3420 | IYDSSGYY | 8 | 8050 |
| PDH 3421 | IYDSSGYF | 8 | 8051 |
| PDH 3422 | YYDSSGYY | 8 | 4165 |
| PDH 3423 | NYDSSGYS | 8 | 8052 |
| PDH 3424 | NYDSSGYF | 8 | 8053 |
| PDH 3425 | VYDSSGYY | 8 | 8054 |
| PDH 3426 | VYDSSGYF | 8 | 8055 |
| PDH 3427 | FYDSSGYY | 8 | 8056 |
| PDH 3428 | FYDSSGYS | 8 | 8057 |
| PDH 3429 | SYDSSGYY | 8 | 8058 |
| PDH 3430 | SYDSSGYS | 8 | 8059 |
| PDH 3431 | PYDSSGYS | 8 | 8060 |
| PDH 3432 | PYDSSGYY | 8 | 8061 |
| PDH 3433 | LYDSSGYY | 8 | 8062 |
| PDH 3434 | VYDSSGYS | 8 | 8063 |
| PDH 3435 | SYDSSGYF | 8 | 8064 |
| PDH 3436 | LYDSSGYF | 8 | 8065 |
| PDH 3437 | HYDSSGYY | 8 | 8066 |
| PDH 3438 | HYDSSGYS | 8 | 8067 |
| PDH 3439 | TYDSSGYF | 8 | 8068 |
| PDH 3440 | AYDSSGYF | 8 | 8069 |
| PDH 3441 | DYDSSGYF | 8 | 8070 |
| PDH 3442 | HYDSSGYF | 8 | 8071 |
| PDH 3443 | RYYGSGSY | 8 | 8072 |
| PDH 3444 | RYYGSGSS | 8 | 8073 |
| PDH 3445 | GYYGSGSS | 8 | 8074 |
| PDH 3446 | GYYGSGSY | 8 | 8075 |
| PDH 3447 | FDFWSGYS | 8 | 8076 |
| PDH 3448 | HDFWSGYF | 8 | 8077 |
| PDH 3449 | FDFWSGYY | 8 | 8078 |
| PDH 3450 | SDFWSGYS | 8 | 8079 |
| PDH 3451 | SDFWSGYY | 8 | 8080 |
| PDH 3452 | PDFWSGYS | 8 | 8081 |
| PDH 3453 | HDFWSGYS | 8 | 8082 |
| PDH 3454 | IDFWSGYY | 8 | 8083 |
| PDH 3455 | HDFWSGYY | 8 | 8084 |
| PDH 3456 | NDFWSGYF | 8 | 8085 |
| PDH 3457 | YDFWSGYS | 8 | 8086 |
| PDH 3458 | IDFWSGYS | 8 | 8087 |
| PDH 3459 | PDFWSGYY | 8 | 8088 |
| PDH 3460 | SDFWSGYF | 8 | 8089 |
| PDH 3461 | VDFWSGYS | 8 | 8090 |
| PDH 3462 | IDFWSGYF | 8 | 8091 |
| PDH 3463 | YDFWSGYY | 8 | 4246 |
| PDH 3464 | YDFWSGYF | 8 | 8092 |
| PDH 3465 | TDFWSGYY | 8 | 8093 |
| PDH 3466 | DDFWSGYS | 8 | 8094 |
| PDH 3467 | LDFWSGYS | 8 | 8095 |
| PDH 3468 | DDFWSGYY | 8 | 8096 |
| PDH 3469 | DDFWSGYF | 8 | 8097 |
| PDH 3470 | VDFWSGYY | 8 | 8098 |
| PDH 3471 | VDFWSGYF | 8 | 8099 |
| PDH 3472 | NDFWSGYY | 8 | 8100 |
| PDH 3473 | FDFWSGYF | 8 | 8101 |
| PDH 3474 | NDFWSGYS | 8 | 8102 |
| PDH 3475 | LDFWSGYY | 8 | 8103 |
| PDH 3476 | ADFWSGYY | 8 | 8104 |
| PDH 3477 | ADFWSGYS | 8 | 8105 |
| PDH 3478 | TDFWSGYS | 8 | 8106 |
| PDH 3479 | TDFWSGYF | 8 | 8107 |
| PDH 3480 | ADFWSGYF | 8 | 8108 |
| PDH 3481 | LDFWSGYF | 8 | 8109 |
| PDH 3482 | PDFWSGYF | 8 | 8110 |
| PDH 3483 | LLRYFDWY | 8 | 8111 |
| PDH 3484 | QLRYFDWY | 8 | 8112 |
| PDH 3485 | PLRYFDWL | 8 | 8113 |
| PDH 3486 | ILRYFDWF | 8 | 8114 |
| PDH 3487 | ILRYFDWY | 8 | 8115 |

TABLE 28-continued

Theoretical segment pool of unique DH polypeptide segments encoded by the degenerate oligonucleotides of Table 27.

| Name | Sequence | Length | SEQ ID NO |
|---|---|---|---|
| PDH 3488 | ALRYFDWL | 8 | 8116 |
| PDH 3489 | QLRYFDWF | 8 | 8117 |
| PDH 3490 | KLRYFDWL | 8 | 8118 |
| PDH 3491 | TLRYFDWL | 8 | 8119 |
| PDH 3492 | TLRYFDWH | 8 | 8120 |
| PDH 3493 | ELRYFDWL | 8 | 8121 |
| PDH 3494 | ELRYFDWH | 8 | 8122 |
| PDH 3495 | PLRYFDWH | 8 | 8123 |
| PDH 3496 | ELRYFDWY | 8 | 8124 |
| PDH 3497 | ELRYFDWF | 8 | 8125 |
| PDH 3498 | LLRYFDWL | 8 | 8126 |
| PDH 3499 | VLRYFDWF | 8 | 8127 |
| PDH 3500 | TLRYFDWF | 8 | 8128 |
| PDH 3501 | ALRYFDWF | 8 | 8129 |
| PDH 3502 | ILRYFDWH | 8 | 8130 |
| PDH 3503 | QLRYFDWL | 8 | 8131 |
| PDH 3504 | QLRYFDWH | 8 | 8132 |
| PDH 3505 | VLRYFDWY | 8 | 8133 |
| PDH 3506 | TLRYFDWY | 8 | 8134 |
| PDH 3507 | ILRYFDWL | 8 | 8135 |
| PDH 3508 | LLRYFDWH | 8 | 8136 |
| PDH 3509 | VLRYFDWH | 8 | 8137 |
| PDH 3510 | KLRYFDWY | 8 | 8138 |
| PDH 3511 | KLRYFDWF | 8 | 8139 |
| PDH 3512 | ALRYFDWH | 8 | 8140 |
| PDH 3513 | ALRYFDWY | 8 | 8141 |
| PDH 3514 | VLRYFDWL | 8 | 4298 |
| PDH 3515 | KLRYFDWH | 8 | 8142 |
| PDH 3516 | PLRYFDWY | 8 | 8143 |
| PDH 3517 | PLRYFDWF | 8 | 8144 |
| PDH 3518 | LLRYFDWF | 8 | 8145 |
| PDH 3519 | IYYDSSGYS | 9 | 8146 |
| PDH 3520 | TYYDSSGYS | 9 | 8147 |
| PDH 3521 | HYYDSSGYY | 9 | 8148 |
| PDH 3522 | TYYDSSGYY | 9 | 8149 |
| PDH 3523 | HYYDSSGYS | 9 | 8150 |
| PDH 3524 | NYYDSSGYF | 9 | 8151 |

TABLE 28-continued

Theoretical segment pool of unique DH polypeptide segments encoded by the degenerate oligonucleotides of Table 27.

| Name | Sequence | Length | SEQ ID NO |
|---|---|---|---|
| PDH 3525 | AYYDSSGYS | 9 | 8152 |
| PDH 3526 | DYYDSSGYF | 9 | 8153 |
| PDH 3527 | DYYDSSGYS | 9 | 8154 |
| PDH 3528 | LYYDSSGYS | 9 | 8155 |
| PDH 3529 | NYYDSSGYS | 9 | 8156 |
| PDH 3530 | HYYDSSGYF | 9 | 8157 |
| PDH 3531 | DYYDSSGYY | 9 | 8158 |
| PDH 3532 | LYYDSSGYY | 9 | 8159 |
| PDH 3533 | IYYDSSGYY | 9 | 8160 |
| PDH 3534 | LYYDSSGYF | 9 | 8161 |
| PDH 3535 | IYYDSSGYF | 9 | 8162 |
| PDH 3536 | AYYDSSGYF | 9 | 8163 |
| PDH 3537 | AYYDSSGYY | 9 | 8164 |
| PDH 3538 | FYYDSSGYS | 9 | 8165 |
| PDH 3539 | YYYDSSGYS | 9 | 8166 |
| PDH 3540 | FYYDSSGYY | 9 | 8167 |
| PDH 3541 | FYYDSSGYF | 9 | 8168 |
| PDH 3542 | YYYDSSGYY | 9 | 4162 |
| PDH 3543 | YYYDSSGYF | 9 | 8169 |
| PDH 3544 | VYYDSSGYF | 9 | 8170 |
| PDH 3545 | PYYDSSGYY | 9 | 8171 |
| PDH 3546 | PYYDSSGYS | 9 | 8172 |
| PDH 3547 | VYYDSSGYS | 9 | 8173 |
| PDH 3548 | SYYDSSGYY | 9 | 8174 |
| PDH 3549 | NYYDSSGYY | 9 | 8175 |
| PDH 3550 | VYYDSSGYY | 9 | 8176 |
| PDH 3551 | SYYDSSGYS | 9 | 8177 |
| PDH 3552 | SYYDSSGYF | 9 | 8178 |
| PDH 3553 | TYYDSSGYF | 9 | 8179 |
| PDH 3554 | PYYDSSGYF | 9 | 8180 |
| PDH 3555 | PYCSGGSCF | 9 | 8181 |
| PDH 3556 | TYCSGGSCF | 9 | 8182 |
| PDH 3557 | IYCSGGSCF | 9 | 8183 |
| PDH 3558 | VYCSGGSCS | 9 | 8184 |
| PDH 3559 | TYCSGGSCY | 9 | 8185 |
| PDH 3560 | VYCSGGSCF | 9 | 8186 |
| PDH 3561 | TYCSGGSCS | 9 | 8187 |

TABLE 28-continued

Theoretical segment pool of unique DH polypeptide segments encoded by the degenerate oligonucleotides of Table 27.

| Name | Sequence | Length | SEQ ID NO |
|---|---|---|---|
| PDH 3562 | GYCSGGSCS | 9 | 8188 |
| PDH 3563 | IYCSGGSCS | 9 | 8189 |
| PDH 3564 | GYCSGGSCY | 9 | 3768 |
| PDH 3565 | IYCSGGSCY | 9 | 8190 |
| PDH 3566 | VYCSGGSCY | 9 | 8191 |
| PDH 3567 | AYCSGGSCF | 9 | 8192 |
| PDH 3568 | GYCSGGSCF | 9 | 8193 |
| PDH 3569 | LYCSGGSCF | 9 | 8194 |
| PDH 3570 | RYCSGGSCF | 9 | 8195 |
| PDH 3571 | LYCSGGSCS | 9 | 8196 |
| PDH 3572 | RYCSGGSCY | 9 | 8197 |
| PDH 3573 | AYCSGGSCS | 9 | 8198 |
| PDH 3574 | SYCSGGSCY | 9 | 8199 |
| PDH 3575 | SYCSGGSCF | 9 | 8200 |
| PDH 3576 | AYCSGGSCY | 9 | 8201 |
| PDH 3577 | SYCSGGSCS | 9 | 8202 |
| PDH 3578 | PYCSGGSCS | 9 | 8203 |
| PDH 3579 | LYCSGGSCY | 9 | 8204 |
| PDH 3580 | RYCSGGSCS | 9 | 8205 |
| PDH 3581 | PYCSGGSCY | 9 | 8206 |
| PDH 3582 | TYCSSTSCY | 9 | 8207 |
| PDH 3583 | AYCSSTSCY | 9 | 8208 |
| PDH 3584 | AYCSSTSCS | 9 | 8209 |
| PDH 3585 | RYCSSTSCS | 9 | 8210 |
| PDH 3586 | TYCSSTSCS | 9 | 8211 |
| PDH 3587 | PYCSSTSCY | 9 | 8212 |
| PDH 3588 | PYCSSTSCS | 9 | 8213 |
| PDH 3589 | RYCSSTSCY | 9 | 8214 |
| PDH 3590 | VYCSSTSCS | 9 | 8215 |
| PDH 3591 | VYCSSTSCY | 9 | 8216 |
| PDH 3592 | LYCSSTSCF | 9 | 8217 |
| PDH 3593 | LYCSSTSCY | 9 | 8218 |
| PDH 3594 | PYCSSTSCF | 9 | 8219 |
| PDH 3595 | VYCSSTSCF | 9 | 8220 |
| PDH 3596 | IYCSSTSCY | 9 | 8221 |
| PDH 3597 | IYCSSTSCS | 9 | 8222 |
| PDH 3598 | IYCSSTSCF | 9 | 8223 |

TABLE 28-continued

Theoretical segment pool of unique DH polypeptide segments encoded by the degenerate oligonucleotides of Table 27.

| Name | Sequence | Length | SEQ ID NO |
|---|---|---|---|
| PDH 3599 | SYCSSTSCS | 9 | 8224 |
| PDH 3600 | LYCSSTSCS | 9 | 8225 |
| PDH 3601 | SYCSSTSCY | 9 | 8226 |
| PDH 3602 | SYCSSTSCF | 9 | 8227 |
| PDH 3603 | GYCSSTSCY | 9 | 3807 |
| PDH 3604 | GYCSSTSCF | 9 | 8228 |
| PDH 3605 | GYCSSTSCS | 9 | 8229 |
| PDH 3606 | RYCSSTSCF | 9 | 8230 |
| PDH 3607 | TYCSSTSCF | 9 | 8231 |
| PDH 3608 | AYCSSTSCF | 9 | 8232 |
| PDH 3609 | IYDFWSGYY | 9 | 8233 |
| PDH 3610 | NYDFWSGYY | 9 | 8234 |
| PDH 3611 | PYDFWSGYF | 9 | 8235 |
| PDH 3612 | SYDFWSGYF | 9 | 8236 |
| PDH 3613 | VYDFWSGYF | 9 | 8237 |
| PDH 3614 | VYDFWSGYY | 9 | 8238 |
| PDH 3615 | HYDFWSGYY | 9 | 8239 |
| PDH 3616 | HYDFWSGYF | 9 | 8240 |
| PDH 3617 | HYDFWSGYS | 9 | 8241 |
| PDH 3618 | IYDFWSGYS | 9 | 8242 |
| PDH 3619 | NYDFWSGYS | 9 | 8243 |
| PDH 3620 | AYDFWSGYS | 9 | 8244 |
| PDH 3621 | SYDFWSGYS | 9 | 8245 |
| PDH 3622 | PYDFWSGYS | 9 | 8246 |
| PDH 3623 | AYDFWSGYY | 9 | 8247 |
| PDH 3624 | SYDFWSGYY | 9 | 8248 |
| PDH 3625 | PYDFWSGYY | 9 | 8249 |
| PDH 3626 | FYDFWSGYY | 9 | 8250 |
| PDH 3627 | FYDFWSGYF | 9 | 8251 |
| PDH 3628 | DYDFWSGYS | 9 | 8252 |
| PDH 3629 | FYDFWSGYS | 9 | 8253 |
| PDH 3630 | DYDFWSGYF | 9 | 8254 |
| PDH 3631 | LYDFWSGYY | 9 | 8255 |
| PDH 3632 | AYDFWSGYF | 9 | 8256 |
| PDH 3633 | LYDFWSGYS | 9 | 8257 |
| PDH 3634 | DYDFWSGYY | 9 | 8258 |
| PDH 3635 | LYDFWSGYF | 9 | 8259 |

TABLE 28-continued

Theoretical segment pool of unique DH polypeptide segments encoded by the degenerate oligonucleotides of Table 27.

| Name | Sequence | Length | SEQ ID NO |
|---|---|---|---|
| PDH 3636 | YYDFWSGYY | 9 | 4243 |
| PDH 3637 | TYDFWSGYY | 9 | 8260 |
| PDH 3638 | TYDFWSGYF | 9 | 8261 |
| PDH 3639 | YYDFWSGYS | 9 | 8262 |
| PDH 3640 | YYDFWSGYF | 9 | 8263 |
| PDH 3641 | TYDFWSGYS | 9 | 8264 |
| PDH 3642 | VYDFWSGYS | 9 | 8265 |
| PDH 3643 | NYDFWSGYF | 9 | 8266 |
| PDH 3644 | IYDFWSGYF | 9 | 8267 |
| PDH 3645 | FCSGGSCYS | 9 | 8268 |
| PDH 3646 | LCSGGSCYS | 9 | 8269 |
| PDH 3647 | VCSGGSCYS | 9 | 8270 |
| PDH 3648 | ACSGGSCYS | 9 | 8271 |
| PDH 3649 | ACSGGSCYY | 9 | 8272 |
| PDH 3650 | FCSGGSCYY | 9 | 8273 |
| PDH 3651 | LCSGGSCYF | 9 | 8274 |
| PDH 3652 | LCSGGSCYY | 9 | 8275 |
| PDH 3653 | VCSGGSCYY | 9 | 8276 |
| PDH 3654 | YCSGGSCYS | 9 | 3769 |
| PDH 3655 | PCSGGSCYS | 9 | 8277 |
| PDH 3656 | PCSGGSCYY | 9 | 8278 |
| PDH 3657 | PCSGGSCYF | 9 | 8279 |
| PDH 3658 | YCSGGSCYF | 9 | 8280 |
| PDH 3659 | YCSGGSCYY | 9 | 8281 |
| PDH 3660 | SCSGGSCYY | 9 | 8282 |
| PDH 3661 | HCSGGSCYF | 9 | 8283 |
| PDH 3662 | DCSGGSCYY | 9 | 8284 |
| PDH 3663 | SCSGGSCYF | 9 | 8285 |
| PDH 3664 | DCSGGSCYS | 9 | 8286 |
| PDH 3665 | HCSGGSCYS | 9 | 8287 |
| PDH 3666 | SCSGGSCYS | 9 | 8288 |
| PDH 3667 | FCSGGSCYF | 9 | 8289 |
| PDH 3668 | ACSGGSCYF | 9 | 8290 |
| PDH 3669 | DCSGGSCYF | 9 | 8291 |
| PDH 3670 | HCSGGSCYY | 9 | 8292 |
| PDH 3671 | VCSGGSCYF | 9 | 8293 |
| PDH 3672 | FYYDSSGYYY | 10 | 8294 |

TABLE 28-continued

Theoretical segment pool of unique DH polypeptide segments encoded by the degenerate oligonucleotides of Table 27.

| Name | Sequence | Length | SEQ ID NO |
|---|---|---|---|
| PDH 3673 | YYYDSSGYYF | 10 | 8295 |
| PDH 3674 | PYYDSSGYYY | 10 | 8296 |
| PDH 3675 | VYYDSSGYYS | 10 | 8297 |
| PDH 3676 | PYYDSSGYYS | 10 | 8298 |
| PDH 3677 | FYYDSSGYYS | 10 | 8299 |
| PDH 3678 | NYYDSSGYYY | 10 | 8300 |
| PDH 3679 | NYYDSSGYYS | 10 | 8301 |
| PDH 3680 | DYYDSSGYYS | 10 | 8302 |
| PDH 3681 | HYYDSSGYYF | 10 | 8303 |
| PDH 3682 | DYYDSSGYYY | 10 | 8304 |
| PDH 3683 | NYYDSSGYYF | 10 | 8305 |
| PDH 3684 | HYYDSSGYYY | 10 | 8306 |
| PDH 3685 | LYYDSSGYYF | 10 | 8307 |
| PDH 3686 | IYYDSSGYYS | 10 | 8308 |
| PDH 3687 | YYYDSSGYYS | 10 | 8309 |
| PDH 3688 | IYYDSSGYYF | 10 | 8310 |
| PDH 3689 | YYYDSSGYYY | 10 | 4161 |
| PDH 3690 | HYYDSSGYYS | 10 | 8311 |
| PDH 3691 | TYYDSSGYYS | 10 | 8312 |
| PDH 3692 | IYYDSSGYYY | 10 | 8313 |
| PDH 3693 | TYYDSSGYYF | 10 | 8314 |
| PDH 3694 | LYYDSSGYYS | 10 | 8315 |
| PDH 3695 | TYYDSSGYYY | 10 | 8316 |
| PDH 3696 | LYYDSSGYYY | 10 | 8317 |
| PDH 3697 | AYYDSSGYYF | 10 | 8318 |
| PDH 3698 | FYYDSSGYYF | 10 | 8319 |
| PDH 3699 | AYYDSSGYYY | 10 | 8320 |
| PDH 3700 | VYYDSSGYYY | 10 | 8321 |
| PDH 3701 | SYYDSSGYYF | 10 | 8322 |
| PDH 3702 | PYYDSSGYYF | 10 | 8323 |
| PDH 3703 | SYYDSSGYYY | 10 | 8324 |
| PDH 3704 | AYYDSSGYYS | 10 | 8325 |
| PDH 3705 | DYYDSSGYYF | 10 | 8326 |
| PDH 3706 | SYYDSSGYYS | 10 | 8327 |
| PDH 3707 | VYYDSSGYYF | 10 | 8328 |
| PDH 3708 | IYDYVWGSYAS | 11 | 8329 |
| PDH 3709 | AYDYVWGSYAS | 11 | 8330 |

TABLE 28-continued

Theoretical segment pool of unique DH polypeptide segments encoded by the degenerate oligonucleotides of Table 27.

| Name | Sequence | Length | SEQ ID NO |
|---|---|---|---|
| PDH 3710 | IYDYVWGSYAY | 11 | 8331 |
| PDH 3711 | NYDYVWGSYAY | 11 | 8332 |
| PDH 3712 | NYDYVWGSYAS | 11 | 8333 |
| PDH 3713 | YYDYVWGSYAF | 11 | 8334 |
| PDH 3714 | DYDYVWGSYAF | 11 | 8335 |
| PDH 3715 | SYDYVWGSYAY | 11 | 8336 |
| PDH 3716 | DYDYVWGSYAS | 11 | 8337 |
| PDH 3717 | DYDYVWGSYAY | 11 | 8338 |
| PDH 3718 | FYDYVWGSYAS | 11 | 8339 |
| PDH 3719 | NYDYVWGSYAF | 11 | 8340 |
| PDH 3720 | YYDYVWGSYAS | 11 | 8341 |
| PDH 3721 | FYDYVWGSYAY | 11 | 8342 |
| PDH 3722 | SYDYVWGSYAS | 11 | 8343 |
| PDH 3723 | PYDYVWGSYAF | 11 | 8344 |
| PDH 3724 | TYDYVWGSYAY | 11 | 8345 |
| PDH 3725 | VYDYVWGSYAY | 11 | 8346 |
| PDH 3726 | SYDYVWGSYAF | 11 | 8347 |
| PDH 3727 | FYDYVWGSYAF | 11 | 8348 |
| PDH 3728 | HYDYVWGSYAS | 11 | 8349 |
| PDH 3729 | VYDYVWGSYAS | 11 | 8350 |
| PDH 3730 | VYDYVWGSYAF | 11 | 8351 |
| PDH 3731 | YYDYVWGSYAY | 11 | 4071 |
| PDH 3732 | AYDYVWGSYAY | 11 | 8352 |
| PDH 3733 | LYDYVWGSYAS | 11 | 8353 |
| PDH 3734 | TYDYVWGSYAF | 11 | 8354 |
| PDH 3735 | AYDYVWGSYAF | 11 | 8355 |
| PDH 3736 | HYDYVWGSYAY | 11 | 8356 |
| PDH 3737 | TYDYVWGSYAS | 11 | 8357 |
| PDH 3738 | LYDYVWGSYAF | 11 | 8358 |
| PDH 3739 | PYDYVWGSYAY | 11 | 8359 |
| PDH 3740 | PYDYVWGSYAS | 11 | 8360 |
| PDH 3741 | HYDYVWGSYAF | 11 | 8361 |
| PDH 3742 | LYDYVWGSYAY | 11 | 8362 |
| PDH 3743 | IYDYVWGSYAF | 11 | 8363 |
| PDH 3744 | NYDYVWGSYAYT | 12 | 8364 |
| PDH 3745 | NYDYVWGSYAYI | 12 | 8365 |
| PDH 3746 | IYDYVWGSYAYI | 12 | 8366 |

TABLE 28-continued

Theoretical segment pool of unique DH polypeptide segments encoded by the degenerate oligonucleotides of Table 27.

| Name | Sequence | Length | SEQ ID NO |
|---|---|---|---|
| PDH 3747 | YYDYVWGSYAYK | 12 | 8367 |
| PDH 3748 | NYDYVWGSYAYK | 12 | 8368 |
| PDH 3749 | YYDYVWGSYAYT | 12 | 4070 |
| PDH 3750 | PYDYVWGSYAYT | 12 | 8369 |
| PDH 3751 | DYDYVWGSYAYI | 12 | 8370 |
| PDH 3752 | PYDYVWGSYAYK | 12 | 8371 |
| PDH 3753 | FYDYVWGSYAYI | 12 | 8372 |
| PDH 3754 | VYDYVWGSYAYT | 12 | 8373 |
| PDH 3755 | DYDYVWGSYAYK | 12 | 8374 |
| PDH 3756 | IYDYVWGSYAYT | 12 | 8375 |
| PDH 3757 | IYDYVWGSYAYK | 12 | 8376 |
| PDH 3758 | LYDYVWGSYAYI | 12 | 8377 |
| PDH 3759 | HYDYVWGSYAYK | 12 | 8378 |
| PDH 3760 | TYDYVWGSYAYI | 12 | 8379 |
| PDH 3761 | HYDYVWGSYAYT | 12 | 8380 |
| PDH 3762 | AYDYVWGSYAYT | 12 | 8381 |
| PDH 3763 | AYDYVWGSYAYK | 12 | 8382 |
| PDH 3764 | AYDYVWGSYAYI | 12 | 8383 |
| PDH 3765 | TYDYVWGSYAYK | 12 | 8384 |
| PDH 3766 | DYDYVWGSYAYT | 12 | 8385 |
| PDH 3767 | VYDYVWGSYAYK | 12 | 8386 |
| PDH 3768 | TYDYVWGSYAYT | 12 | 8387 |
| PDH 3769 | FYDYVWGSYAYK | 12 | 8388 |
| PDH 3770 | LYDYVWGSYAYK | 12 | 8389 |
| PDH 3771 | VYDYVWGSYAYI | 12 | 8390 |
| PDH 3772 | LYDYVWGSYAYT | 12 | 8391 |
| PDH 3773 | PYDYVWGSYAYI | 12 | 8392 |
| PDH 3774 | FYDYVWGSYAYT | 12 | 8393 |
| PDH 3775 | YYDYVWGSYAYI | 12 | 8394 |
| PDH 3776 | SYDYVWGSYAYI | 12 | 8395 |
| PDH 3777 | HYDYVWGSYAYI | 12 | 8396 |
| PDH 3778 | SYDYVWGSYAYT | 12 | 8397 |
| PDH 3779 | SYDYVWGSYAYK | 12 | 8398 |

TABLE 29

Theoretical segment pool of oligonucleotide sequences encoding N2 segments of Example 14.

| Name | Degenerate Oligo | Peptide Length | | SEQ ID NO |
|---|---|---|---|---|
| N2 000 | | 0 | Not degenerate | n/a |
| N2 001 | GCT | 1 | Not degenerate | n/a |
| N2 002 | GAT | 1 | Not degenerate | n/a |
| N2 003 | GAG | 1 | Not degenerate | n/a |
| N2 004 | TTT | 1 | Not degenerate | n/a |
| N2 005 | GGC | 1 | Not degenerate | n/a |
| N2 006 | CAT | 1 | Not degenerate | n/a |
| N2 007 | ATC | 1 | Not degenerate | n/a |
| N2 008 | AAA | 1 | Not degenerate | n/a |
| N2 009 | TTG | 1 | Not degenerate | n/a |
| N2 010 | ATG | 1 | Not degenerate | n/a |
| N2 011 | CCT | 1 | Not degenerate | n/a |
| N2 012 | CAA | 1 | Not degenerate | n/a |
| N2 013 | AGG | 1 | Not degenerate | n/a |
| N2 014 | TCA | 1 | Not degenerate | n/a |
| N2 015 | ACC | 1 | Not degenerate | n/a |
| N2 016 | GTT | 1 | Not degenerate | n/a |
| N2 017 | TGG | 1 | Not degenerate | n/a |
| N2 018 | TAC | 1 | Not degenerate | n/a |
| N2 019 | GMCKHT | 2 | | n/a |
| N2 020 | GMCSVT | 2 | | n/a |
| N2 021 | GMCSHT | 2 | | n/a |
| N2 022 | GMCSVG | 2 | | n/a |
| N2 023 | GMTDYT | 2 | | n/a |
| N2 024 | KHCGAS | 2 | | n/a |
| N2 025 | KHCGRC | 2 | | n/a |
| N2 026 | KHCGWG | 2 | | n/a |
| N2 027 | KHTTTM | 2 | | n/a |
| N2 028 | KHTTYC | 2 | | n/a |
| N2 029 | KHTTWC | 2 | | n/a |
| N2 030 | KHCRGA | 2 | | n/a |
| N2 031 | KHCKGG | 2 | | n/a |
| N2 032 | KHCCWC | 2 | | n/a |
| N2 033 | KHCCMT | 2 | | n/a |
| N2 034 | KHCMCA | 2 | | n/a |
| N2 035 | GVCSWG | 2 | | n/a |
| N2 036 | GVCMKC | 2 | | n/a |
| N2 037 | GVCWSG | 2 | | n/a |
| N2 038 | SVCYAC | 2 | | n/a |
| N2 039 | GNAAHA | 2 | | n/a |
| N2 040 | BYCSAG | 2 | | n/a |
| N2 041 | RBAAWA | 2 | | n/a |
| N2 042 | RBAAYA | 2 | | n/a |
| N2 043 | SBAMAA | 2 | | n/a |
| N2 044 | VSCMAA | 2 | | n/a |
| N2 045 | GRARVG | 2 | | n/a |
| N2 046 | GRADYT | 2 | | n/a |
| N2 047 | GRABYT | 2 | | n/a |
| N2 048 | GRAKBG | 2 | | n/a |
| N2 049 | RDAGMT | 2 | | n/a |
| N2 050 | RDAGAK | 2 | | n/a |
| N2 051 | RDAGRT | 2 | | n/a |
| N2 052 | RDAGWG | 2 | | n/a |
| N2 053 | RDARGG | 2 | | n/a |
| N2 054 | RDACYA | 2 | | n/a |
| N2 055 | SDACSA | 2 | | n/a |
| N2 056 | VWACYA | 2 | | n/a |
| N2 057 | VWATYA | 2 | | n/a |
| N2 058 | VWAASA | 2 | | n/a |
| N2 059 | YHCGMC | 2 | | n/a |
| N2 060 | YHCGMG | 2 | | n/a |
| N2 061 | YHCGST | 2 | | n/a |
| N2 062 | YHCSCG | 2 | | n/a |
| N2 063 | YHCKCG | 2 | | n/a |
| N2 064 | YHCSAC | 2 | | n/a |
| N2 065 | YHCKAC | 2 | | n/a |
| N2 066 | YHCRGA | 2 | | n/a |
| N2 067 | YHCCWC | 2 | | n/a |
| N2 068 | YHCMCA | 2 | | n/a |
| N2 069 | WTCYHT | 2 | | n/a |
| N2 070 | HYCGWG | 2 | | n/a |
| N2 071 | HYCTTM | 2 | | n/a |
| N2 072 | HYCAGM | 2 | | n/a |
| N2 073 | HYCTMC | 2 | | n/a |

TABLE 29-continued

Theoretical segment pool of oligonucleotide sequences encoding N2 segments of Example 14.

| Name | Degenerate Oligo | Peptide Length | SEQ ID NO |
|---|---|---|---|
| N2 074 | VKCTWT | 2 | n/a |
| N2 075 | CNCVGC | 2 | n/a |
| N2 076 | MHAGAK | 2 | n/a |
| N2 077 | MHAGRC | 2 | n/a |
| N2 078 | MHAGWG | 2 | n/a |
| N2 079 | MHAMCA | 2 | n/a |
| N2 080 | ANAGBT | 2 | n/a |
| N2 081 | MBCYAC | 2 | n/a |
| N2 082 | MBCAWA | 2 | n/a |
| N2 083 | MHGGKA | 2 | n/a |
| N2 084 | CNABTT | 2 | n/a |
| N2 085 | CVACNA | 2 | n/a |
| N2 086 | CVAYSG | 2 | n/a |
| N2 087 | MSCAHG | 2 | n/a |
| N2 088 | CRAKBG | 2 | n/a |
| N2 089 | WSGHCA | 2 | n/a |
| N2 090 | WGGKHC | 2 | n/a |
| N2 091 | MBCATR | 2 | n/a |
| N2 092 | AYABSG | 2 | n/a |
| N2 093 | VYCAWG | 2 | n/a |
| N2 094 | BGGSAK | 2 | n/a |
| N2 095 | AHGRYT | 2 | n/a |
| N2 096 | BWCAMA | 2 | n/a |
| N2 097 | BHCTGG | 2 | n/a |
| N2 098 | TGGBHC | 2 | n/a |
| N2 099 | TGGVBT | 2 | n/a |
| N2 100 | NHCGCAGCC | 3 | n/a |
| N2 101 | BHCGGAATG | 3 | n/a |
| N2 102 | BHCGGAGGA | 3 | n/a |
| N2 103 | BHCGGAGTA | 3 | n/a |
| N2 104 | VNCGCAGGA | 3 | n/a |
| N2 105 | VBCGGAGCC | 3 | n/a |
| N2 106 | VBCGGAGGA | 3 | n/a |
| N2 107 | VBCGGACTA | 3 | n/a |
| N2 108 | VBCGGAAGG | 3 | n/a |
| N2 109 | VBCGGAAGC | 3 | n/a |
| N2 110 | VBCGGAGTA | 3 | n/a |

TABLE 29-continued

Theoretical segment pool of oligonucleotide sequences encoding N2 segments of Example 14.

| Name | Degenerate Oligo | Peptide Length | SEQ ID NO |
|---|---|---|---|
| N2 111 | VNCCTTGGA | 3 | n/a |
| N2 112 | VNCCCAGGA | 3 | n/a |
| N2 113 | VNCCCACCA | 3 | n/a |
| N2 114 | VNCAGAGGA | 3 | n/a |
| N2 115 | VNCAGCGGA | 3 | n/a |
| N2 116 | VBCACAGGA | 3 | n/a |
| N2 117 | VNCGTAGGA | 3 | n/a |
| N2 118 | BHCGGACAC | 3 | n/a |
| N2 119 | NHCAAACAA | 3 | n/a |
| N2 120 | NHCAAAAGA | 3 | n/a |
| N2 121 | BHCACACAA | 3 | n/a |
| N2 122 | VNCTTTGAG | 3 | n/a |
| N2 123 | VNCCCACTA | 3 | n/a |
| N2 124 | VNCCCATAC | 3 | n/a |
| N2 125 | BHCGGAGAG | 3 | n/a |
| N2 126 | BHCGGACTA | 3 | n/a |
| N2 127 | BHCGGATGG | 3 | n/a |
| N2 128 | BHCGGATAC | 3 | n/a |
| N2 129 | NHCAGAGGA | 3 | n/a |
| N2 130 | NHCAGCGAG | 3 | n/a |
| N2 131 | NHCAGCTGG | 3 | n/a |
| N2 132 | VHAGGAGGA | 3 | n/a |
| N2 133 | BHCGGAAGG | 3 | n/a |
| N2 134 | NHCCAAGGA | 3 | n/a |
| N2 135 | BHCACAGCT | 3 | n/a |
| N2 136 | GGABHCGGATAC | 4 | 8399 |
| N2 137 | AGABHCGGATAC | 4 | 8400 |
| N2 138 | AGCBHCGGATAC | 4 | 8401 |
| N2 139 | CCABHCGGATAC | 4 | 8402 |
| N2 140 | GGTAGAVHGTAC | 4 | 8403 |
| N2 141 | AGGAGAVHGTAC | 4 | 8404 |
| N2 142 | GGABHCGGATGG | 4 | 8405 |
| N2 143 | GGABHCGGACTA | 4 | 8406 |
| N2 144 | GGABHCACAGCT | 4 | 8407 |
| N2 145 | GGABHCACACAA | 4 | 8408 |

TABLE 30

| Theoretical segment pool of unique N2 polypeptide segments encoded by the oligonucleotides of Table 29. | | | |
|---|---|---|---|
| Name | Sequence | Length | SEQ ID NO |
| PN2 000 | | 0 | #N/A |
| PN2 001 | A | 1 | #N/A |
| PN2 002 | D | 1 | #N/A |
| PN2 003 | E | 1 | #N/A |
| PN2 004 | F | 1 | #N/A |
| PN2 005 | G | 1 | #N/A |
| PN2 006 | H | 1 | #N/A |
| PN2 007 | I | 1 | #N/A |
| PN2 008 | K | 1 | #N/A |
| PN2 009 | L | 1 | #N/A |
| PN2 010 | M | 1 | #N/A |
| PN2 011 | P | 1 | #N/A |
| PN2 012 | Q | 1 | #N/A |
| PN2 013 | R | 1 | #N/A |
| PN2 014 | S | 1 | #N/A |
| PN2 015 | T | 1 | #N/A |
| PN2 016 | V | 1 | #N/A |
| PN2 017 | W | 1 | #N/A |
| PN2 018 | Y | 1 | #N/A |
| PN2 019 | GW | 2 | #N/A |
| PN2 020 | GV | 2 | #N/A |
| PN2 021 | GT | 2 | #N/A |
| PN2 022 | GS | 2 | #N/A |
| PN2 023 | GR | 2 | #N/A |
| PN2 024 | GQ | 2 | #N/A |
| PN2 025 | GP | 2 | #N/A |
| PN2 026 | GY | 2 | #N/A |
| PN2 027 | GG | 2 | #N/A |
| PN2 028 | GF | 2 | #N/A |
| PN2 029 | GE | 2 | #N/A |
| PN2 030 | GD | 2 | #N/A |
| PN2 031 | GA | 2 | #N/A |
| PN2 032 | GL | 2 | #N/A |
| PN2 033 | GK | 2 | #N/A |
| PN2 034 | GI | 2 | #N/A |
| PN2 035 | GH | 2 | #N/A |
| PN2 036 | MG | 2 | #N/A |

TABLE 30-continued

| Theoretical segment pool of unique N2 polypeptide segments encoded by the oligonucleotides of Table 29. | | | |
|---|---|---|---|
| Name | Sequence | Length | SEQ ID NO |
| PN2 037 | MA | 2 | #N/A |
| PN2 038 | MI | 2 | #N/A |
| PN2 039 | MT | 2 | #N/A |
| PN2 040 | MV | 2 | #N/A |
| PN2 041 | FP | 2 | #N/A |
| PN2 042 | FQ | 2 | #N/A |
| PN2 043 | FR | 2 | #N/A |
| PN2 044 | FS | 2 | #N/A |
| PN2 045 | FT | 2 | #N/A |
| PN2 046 | FV | 2 | #N/A |
| PN2 047 | FW | 2 | #N/A |
| PN2 048 | FY | 2 | #N/A |
| PN2 049 | FA | 2 | #N/A |
| PN2 050 | FD | 2 | #N/A |
| PN2 051 | FE | 2 | #N/A |
| PN2 052 | FF | 2 | #N/A |
| PN2 053 | FG | 2 | #N/A |
| PN2 054 | FH | 2 | #N/A |
| PN2 055 | FK | 2 | #N/A |
| PN2 056 | FL | 2 | #N/A |
| PN2 057 | SY | 2 | #N/A |
| PN2 058 | SS | 2 | #N/A |
| PN2 059 | SR | 2 | #N/A |
| PN2 060 | SQ | 2 | #N/A |
| PN2 061 | SP | 2 | #N/A |
| PN2 062 | SW | 2 | #N/A |
| PN2 063 | SV | 2 | #N/A |
| PN2 064 | ST | 2 | #N/A |
| PN2 065 | SK | 2 | #N/A |
| PN2 066 | SI | 2 | #N/A |
| PN2 067 | SH | 2 | #N/A |
| PN2 068 | SM | 2 | #N/A |
| PN2 069 | SL | 2 | #N/A |
| PN2 070 | SA | 2 | #N/A |
| PN2 071 | SG | 2 | #N/A |
| PN2 072 | SF | 2 | #N/A |
| PN2 073 | SE | 2 | #N/A |

TABLE 30-continued

Theoretical segment pool of unique N2 polypeptide segments encoded by the oligonucleotides of Table 29.

| Name | Sequence | Length | SEQ ID NO |
|---|---|---|---|
| PN2 074 | SD | 2 | #N/A |
| PN2 075 | YH | 2 | #N/A |
| PN2 076 | YK | 2 | #N/A |
| PN2 077 | YL | 2 | #N/A |
| PN2 078 | YA | 2 | #N/A |
| PN2 079 | YE | 2 | #N/A |
| PN2 080 | YD | 2 | #N/A |
| PN2 081 | YG | 2 | #N/A |
| PN2 082 | YF | 2 | #N/A |
| PN2 083 | YY | 2 | #N/A |
| PN2 084 | YP | 2 | #N/A |
| PN2 085 | YS | 2 | #N/A |
| PN2 086 | YR | 2 | #N/A |
| PN2 087 | YT | 2 | #N/A |
| PN2 088 | YW | 2 | #N/A |
| PN2 089 | YV | 2 | #N/A |
| PN2 090 | LF | 2 | #N/A |
| PN2 091 | LD | 2 | #N/A |
| PN2 092 | LE | 2 | #N/A |
| PN2 093 | LL | 2 | #N/A |
| PN2 094 | LM | 2 | #N/A |
| PN2 095 | LK | 2 | #N/A |
| PN2 096 | LH | 2 | #N/A |
| PN2 097 | LI | 2 | #N/A |
| PN2 098 | LW | 2 | #N/A |
| PN2 099 | LT | 2 | #N/A |
| PN2 100 | LR | 2 | #N/A |
| PN2 101 | LS | 2 | #N/A |
| PN2 102 | LP | 2 | #N/A |
| PN2 103 | LQ | 2 | #N/A |
| PN2 104 | LY | 2 | #N/A |
| PN2 105 | LG | 2 | #N/A |
| PN2 106 | LA | 2 | #N/A |
| PN2 107 | RT | 2 | #N/A |
| PN2 108 | RV | 2 | #N/A |
| PN2 109 | RW | 2 | #N/A |
| PN2 110 | RP | 2 | #N/A |
| PN2 111 | RQ | 2 | #N/A |
| PN2 112 | RR | 2 | #N/A |
| PN2 113 | RS | 2 | #N/A |
| PN2 114 | RY | 2 | #N/A |
| PN2 115 | RD | 2 | #N/A |
| PN2 116 | RE | 2 | #N/A |
| PN2 117 | RF | 2 | #N/A |
| PN2 118 | RG | 2 | #N/A |
| PN2 119 | RA | 2 | #N/A |
| PN2 120 | RL | 2 | #N/A |
| PN2 121 | RM | 2 | #N/A |
| PN2 122 | RH | 2 | #N/A |
| PN2 123 | RI | 2 | #N/A |
| PN2 124 | RK | 2 | #N/A |
| PN2 125 | LV | 2 | #N/A |
| PN2 126 | IP | 2 | #N/A |
| PN2 127 | EL | 2 | #N/A |
| PN2 128 | VK | 2 | #N/A |
| PN2 129 | EI | 2 | #N/A |
| PN2 130 | EK | 2 | #N/A |
| PN2 131 | EE | 2 | #N/A |
| PN2 132 | ED | 2 | #N/A |
| PN2 133 | EG | 2 | #N/A |
| PN2 134 | EF | 2 | #N/A |
| PN2 135 | EA | 2 | #N/A |
| PN2 136 | IT | 2 | #N/A |
| PN2 137 | ET | 2 | #N/A |
| PN2 138 | EW | 2 | #N/A |
| PN2 139 | EV | 2 | #N/A |
| PN2 140 | EP | 2 | #N/A |
| PN2 141 | ES | 2 | #N/A |
| PN2 142 | ER | 2 | #N/A |
| PN2 143 | II | 2 | #N/A |
| PN2 144 | IH | 2 | #N/A |
| PN2 145 | VR | 2 | #N/A |
| PN2 146 | VT | 2 | #N/A |
| PN2 147 | KA | 2 | #N/A |

TABLE 30-continued

Theoretical segment pool of unique N2 polypeptide segments encoded by the oligonucleotides of Table 29.

| Name | Sequence | Length | SEQ ID NO |
|---|---|---|---|
| PN2 148 | KG | 2 | #N/A |
| PN2 149 | KE | 2 | #N/A |
| PN2 150 | KD | 2 | #N/A |
| PN2 151 | KI | 2 | #N/A |
| PN2 152 | KL | 2 | #N/A |
| PN2 153 | KS | 2 | #N/A |
| PN2 154 | KR | 2 | #N/A |
| PN2 155 | KP | 2 | #N/A |
| PN2 156 | KV | 2 | #N/A |
| PN2 157 | KT | 2 | #N/A |
| PN2 158 | DK | 2 | #N/A |
| PN2 159 | DH | 2 | #N/A |
| PN2 160 | DI | 2 | #N/A |
| PN2 161 | DF | 2 | #N/A |
| PN2 162 | DG | 2 | #N/A |
| PN2 163 | DD | 2 | #N/A |
| PN2 164 | DE | 2 | #N/A |
| PN2 165 | DA | 2 | #N/A |
| PN2 166 | DY | 2 | #N/A |
| PN2 167 | DV | 2 | #N/A |
| PN2 168 | DW | 2 | #N/A |
| PN2 169 | DT | 2 | #N/A |
| PN2 170 | DR | 2 | #N/A |
| PN2 171 | DS | 2 | #N/A |
| PN2 172 | DP | 2 | #N/A |
| PN2 173 | DQ | 2 | #N/A |
| PN2 174 | QQ | 2 | #N/A |
| PN2 175 | QP | 2 | #N/A |
| PN2 176 | QS | 2 | #N/A |
| PN2 177 | QR | 2 | #N/A |
| PN2 178 | QT | 2 | #N/A |
| PN2 179 | QW | 2 | #N/A |
| PN2 180 | QA | 2 | #N/A |
| PN2 181 | QE | 2 | #N/A |
| PN2 182 | QD | 2 | #N/A |
| PN2 183 | QG | 2 | #N/A |
| PN2 184 | QF | 2 | #N/A |

TABLE 30-continued

Theoretical segment pool of unique N2 polypeptide segments encoded by the oligonucleotides of Table 29.

| Name | Sequence | Length | SEQ ID NO |
|---|---|---|---|
| PN2 185 | QL | 2 | #N/A |
| PN2 186 | WG | 2 | #N/A |
| PN2 187 | WF | 2 | #N/A |
| PN2 188 | WE | 2 | #N/A |
| PN2 189 | WD | 2 | #N/A |
| PN2 190 | WA | 2 | #N/A |
| PN2 191 | WL | 2 | #N/A |
| PN2 192 | WI | 2 | #N/A |
| PN2 193 | WH | 2 | #N/A |
| PN2 194 | WV | 2 | #N/A |
| PN2 195 | WT | 2 | #N/A |
| PN2 196 | WS | 2 | #N/A |
| PN2 197 | WR | 2 | #N/A |
| PN2 198 | WQ | 2 | #N/A |
| PN2 199 | WP | 2 | #N/A |
| PN2 200 | WY | 2 | #N/A |
| PN2 201 | PR | 2 | #N/A |
| PN2 202 | PS | 2 | #N/A |
| PN2 203 | PP | 2 | #N/A |
| PN2 204 | PQ | 2 | #N/A |
| PN2 205 | PV | 2 | #N/A |
| PN2 206 | PW | 2 | #N/A |
| PN2 207 | PT | 2 | #N/A |
| PN2 208 | PY | 2 | #N/A |
| PN2 209 | PA | 2 | #N/A |
| PN2 210 | PF | 2 | #N/A |
| PN2 211 | PG | 2 | #N/A |
| PN2 212 | PD | 2 | #N/A |
| PN2 213 | PE | 2 | #N/A |
| PN2 214 | PK | 2 | #N/A |
| PN2 215 | PH | 2 | #N/A |
| PN2 216 | PI | 2 | #N/A |
| PN2 217 | PL | 2 | #N/A |
| PN2 218 | PM | 2 | #N/A |
| PN2 219 | DL | 2 | #N/A |
| PN2 220 | IY | 2 | #N/A |
| PN2 221 | VA | 2 | #N/A |

TABLE 30-continued

Theoretical segment pool of unique N2 polypeptide segments encoded by the oligonucleotides of Table 29.

| Name | Sequence | Length | SEQ ID NO |
|---|---|---|---|
| PN2 222 | VD | 2 | #N/A |
| PN2 223 | VE | 2 | #N/A |
| PN2 224 | VF | 2 | #N/A |
| PN2 225 | VG | 2 | #N/A |
| PN2 226 | VH | 2 | #N/A |
| PN2 227 | VI | 2 | #N/A |
| PN2 228 | IS | 2 | #N/A |
| PN2 229 | IR | 2 | #N/A |
| PN2 230 | VL | 2 | #N/A |
| PN2 231 | VM | 2 | #N/A |
| PN2 232 | IW | 2 | #N/A |
| PN2 233 | IV | 2 | #N/A |
| PN2 234 | VP | 2 | #N/A |
| PN2 235 | VQ | 2 | #N/A |
| PN2 236 | IK | 2 | #N/A |
| PN2 237 | VS | 2 | #N/A |
| PN2 238 | IM | 2 | #N/A |
| PN2 239 | IL | 2 | #N/A |
| PN2 240 | VV | 2 | #N/A |
| PN2 241 | VW | 2 | #N/A |
| PN2 242 | IA | 2 | #N/A |
| PN2 243 | VY | 2 | #N/A |
| PN2 244 | IE | 2 | #N/A |
| PN2 245 | ID | 2 | #N/A |
| PN2 246 | IG | 2 | #N/A |
| PN2 247 | IF | 2 | #N/A |
| PN2 248 | TQ | 2 | #N/A |
| PN2 249 | TF | 2 | #N/A |
| PN2 250 | HY | 2 | #N/A |
| PN2 251 | HR | 2 | #N/A |
| PN2 252 | HS | 2 | #N/A |
| PN2 253 | HP | 2 | #N/A |
| PN2 254 | HW | 2 | #N/A |
| PN2 255 | HT | 2 | #N/A |
| PN2 256 | HK | 2 | #N/A |
| PN2 257 | HH | 2 | #N/A |
| PN2 258 | HL | 2 | #N/A |

TABLE 30-continued

Theoretical segment pool of unique N2 polypeptide segments encoded by the oligonucleotides of Table 29.

| Name | Sequence | Length | SEQ ID NO |
|---|---|---|---|
| PN2 259 | HA | 2 | #N/A |
| PN2 260 | HG | 2 | #N/A |
| PN2 261 | HD | 2 | #N/A |
| PN2 262 | HE | 2 | #N/A |
| PN2 263 | QV | 2 | #N/A |
| PN2 264 | TY | 2 | #N/A |
| PN2 265 | TV | 2 | #N/A |
| PN2 266 | TW | 2 | #N/A |
| PN2 267 | TT | 2 | #N/A |
| PN2 268 | TR | 2 | #N/A |
| PN2 269 | TS | 2 | #N/A |
| PN2 270 | TP | 2 | #N/A |
| PN2 271 | TL | 2 | #N/A |
| PN2 272 | TM | 2 | #N/A |
| PN2 273 | TK | 2 | #N/A |
| PN2 274 | TH | 2 | #N/A |
| PN2 275 | TI | 2 | #N/A |
| PN2 276 | TG | 2 | #N/A |
| PN2 277 | TD | 2 | #N/A |
| PN2 278 | TE | 2 | #N/A |
| PN2 279 | TA | 2 | #N/A |
| PN2 280 | AA | 2 | #N/A |
| PN2 281 | AE | 2 | #N/A |
| PN2 282 | AD | 2 | #N/A |
| PN2 283 | AG | 2 | #N/A |
| PN2 284 | AF | 2 | #N/A |
| PN2 285 | AI | 2 | #N/A |
| PN2 286 | AH | 2 | #N/A |
| PN2 287 | AK | 2 | #N/A |
| PN2 288 | AM | 2 | #N/A |
| PN2 289 | AL | 2 | #N/A |
| PN2 290 | AQ | 2 | #N/A |
| PN2 291 | AP | 2 | #N/A |
| PN2 292 | AS | 2 | #N/A |
| PN2 293 | AR | 2 | #N/A |
| PN2 294 | AT | 2 | #N/A |
| PN2 295 | AW | 2 | #N/A |

TABLE 30-continued

Theoretical segment pool of unique N2 polypeptide segments encoded by the oligonucleotides of Table 29.

| Name | Sequence | Length | SEQ ID NO |
|---|---|---|---|
| PN2 296 | AV | 2 | #N/A |
| PN2 297 | AY | 2 | #N/A |
| PN2 298 | AGM | 3 | #N/A |
| PN2 299 | AGL | 3 | #N/A |
| PN2 300 | AGH | 3 | #N/A |
| PN2 301 | AGG | 3 | #N/A |
| PN2 302 | AGE | 3 | #N/A |
| PN2 303 | AGA | 3 | #N/A |
| PN2 304 | TQG | 3 | #N/A |
| PN2 305 | AGY | 3 | #N/A |
| PN2 306 | AGW | 3 | #N/A |
| PN2 307 | AGV | 3 | #N/A |
| PN2 308 | AGS | 3 | #N/A |
| PN2 309 | AGR | 3 | #N/A |
| PN2 310 | SPY | 3 | #N/A |
| PN2 311 | SPP | 3 | #N/A |
| PN2 312 | TAG | 3 | #N/A |
| PN2 313 | SPL | 3 | #N/A |
| PN2 314 | TAA | 3 | #N/A |
| PN2 315 | SPG | 3 | #N/A |
| PN2 316 | VAA | 3 | #N/A |
| PN2 317 | VAG | 3 | #N/A |
| PN2 318 | NPL | 3 | #N/A |
| PN2 319 | PAA | 3 | #N/A |
| PN2 320 | NPG | 3 | #N/A |
| PN2 321 | LAG | 3 | #N/A |
| PN2 322 | LAA | 3 | #N/A |
| PN2 323 | NPY | 3 | #N/A |
| PN2 324 | ALG | 3 | #N/A |
| PN2 325 | RLG | 3 | #N/A |
| PN2 326 | TSG | 3 | #N/A |
| PN2 327 | DTA | 3 | #N/A |
| PN2 328 | PAG | 3 | #N/A |
| PN2 329 | QGG | 3 | #N/A |
| PN2 330 | DLG | 3 | #N/A |
| PN2 331 | DTQ | 3 | #N/A |
| PN2 332 | LSG | 3 | #N/A |

TABLE 30-continued

Theoretical segment pool of unique N2 polypeptide segments encoded by the oligonucleotides of Table 29.

| Name | Sequence | Length | SEQ ID NO |
|---|---|---|---|
| PN2 333 | LSE | 3 | #N/A |
| PN2 334 | PGR | 3 | #N/A |
| PN2 335 | VLG | 3 | #N/A |
| PN2 336 | LSW | 3 | #N/A |
| PN2 337 | AFE | 3 | #N/A |
| PN2 338 | TTG | 3 | #N/A |
| PN2 339 | FTQ | 3 | #N/A |
| PN2 340 | IGV | 3 | #N/A |
| PN2 341 | NFE | 3 | #N/A |
| PN2 342 | IGS | 3 | #N/A |
| PN2 343 | IGR | 3 | #N/A |
| PN2 344 | PGS | 3 | #N/A |
| PN2 345 | IGG | 3 | #N/A |
| PN2 346 | GRG | 3 | #N/A |
| PN2 347 | IGA | 3 | #N/A |
| PN2 348 | DSG | 3 | #N/A |
| PN2 349 | IGL | 3 | #N/A |
| PN2 350 | HLG | 3 | #N/A |
| PN2 351 | HPP | 3 | #N/A |
| PN2 352 | AKQ | 3 | #N/A |
| PN2 353 | GLG | 3 | #N/A |
| PN2 354 | LFE | 3 | #N/A |
| PN2 355 | GGV | 3 | #N/A |
| PN2 356 | GGS | 3 | #N/A |
| PN2 357 | GGR | 3 | #N/A |
| PN2 358 | GGG | 3 | #N/A |
| PN2 359 | GGA | 3 | #N/A |
| PN2 360 | GGL | 3 | #N/A |
| PN2 361 | YTA | 3 | #N/A |
| PN2 362 | LTQ | 3 | #N/A |
| PN2 363 | FQG | 3 | #N/A |
| PN2 364 | LVG | 3 | #N/A |
| PN2 365 | LTA | 3 | #N/A |
| PN2 366 | LTG | 3 | #N/A |
| PN2 367 | DPY | 3 | #N/A |
| PN2 368 | DFE | 3 | #N/A |
| PN2 369 | DPG | 3 | #N/A |

TABLE 30-continued

Theoretical segment pool of unique N2 polypeptide segments encoded by the oligonucleotides of Table 29.

| Name | Sequence | Length | SEQ ID NO |
|---|---|---|---|
| PN2 370 | HTA | 3 | #N/A |
| PN2 371 | DPP | 3 | #N/A |
| PN2 372 | PGG | 3 | #N/A |
| PN2 373 | VPP | 3 | #N/A |
| PN2 374 | PGA | 3 | #N/A |
| PN2 375 | VPY | 3 | #N/A |
| PN2 376 | PGV | 3 | #N/A |
| PN2 377 | VPL | 3 | #N/A |
| PN2 378 | STG | 3 | #N/A |
| PN2 379 | STA | 3 | #N/A |
| PN2 380 | HGV | 3 | #N/A |
| PN2 381 | HGW | 3 | #N/A |
| PN2 382 | HGR | 3 | #N/A |
| PN2 383 | HGL | 3 | #N/A |
| PN2 384 | HGM | 3 | #N/A |
| PN2 385 | STQ | 3 | #N/A |
| PN2 386 | HGH | 3 | #N/A |
| PN2 387 | HGG | 3 | #N/A |
| PN2 388 | DSW | 3 | #N/A |
| PN2 389 | HGE | 3 | #N/A |
| PN2 390 | TFE | 3 | #N/A |
| PN2 391 | PGY | 3 | #N/A |
| PN2 392 | PGL | 3 | #N/A |
| PN2 393 | PGM | 3 | #N/A |
| PN2 394 | DKR | 3 | #N/A |
| PN2 395 | DKQ | 3 | #N/A |
| PN2 396 | VFE | 3 | #N/A |
| PN2 397 | PRG | 3 | #N/A |
| PN2 398 | PGH | 3 | #N/A |
| PN2 399 | PPL | 3 | #N/A |
| PN2 400 | EGG | 3 | #N/A |
| PN2 401 | RAG | 3 | #N/A |
| PN2 402 | SAA | 3 | #N/A |
| PN2 403 | FGW | 3 | #N/A |
| PN2 404 | SAG | 3 | #N/A |
| PN2 405 | FGR | 3 | #N/A |
| PN2 406 | FGH | 3 | #N/A |

TABLE 30-continued

Theoretical segment pool of unique N2 polypeptide segments encoded by the oligonucleotides of Table 29.

| Name | Sequence | Length | SEQ ID NO |
|---|---|---|---|
| PN2 407 | FGG | 3 | #N/A |
| PN2 408 | TPG | 3 | #N/A |
| PN2 409 | LPY | 3 | #N/A |
| PN2 410 | TPL | 3 | #N/A |
| PN2 411 | LPP | 3 | #N/A |
| PN2 412 | LPL | 3 | #N/A |
| PN2 413 | TPP | 3 | #N/A |
| PN2 414 | LPG | 3 | #N/A |
| PN2 415 | HRG | 3 | #N/A |
| PN2 416 | TPY | 3 | #N/A |
| PN2 417 | APY | 3 | #N/A |
| PN2 418 | IPG | 3 | #N/A |
| PN2 419 | APP | 3 | #N/A |
| PN2 420 | PQG | 3 | #N/A |
| PN2 421 | IPL | 3 | #N/A |
| PN2 422 | IPP | 3 | #N/A |
| PN2 423 | APL | 3 | #N/A |
| PN2 424 | SFE | 3 | #N/A |
| PN2 425 | APG | 3 | #N/A |
| PN2 426 | YSE | 3 | #N/A |
| PN2 427 | IFE | 3 | #N/A |
| PN2 428 | YSW | 3 | #N/A |
| PN2 429 | PKR | 3 | #N/A |
| PN2 430 | RTG | 3 | #N/A |
| PN2 431 | PKQ | 3 | #N/A |
| PN2 432 | HGY | 3 | #N/A |
| PN2 433 | TKR | 3 | #N/A |
| PN2 434 | NLG | 3 | #N/A |
| PN2 435 | VKR | 3 | #N/A |
| PN2 436 | RFE | 3 | #N/A |
| PN2 437 | SSW | 3 | #N/A |
| PN2 438 | NPP | 3 | #N/A |
| PN2 439 | SSE | 3 | #N/A |
| PN2 440 | SSG | 3 | #N/A |
| PN2 441 | YGR | 3 | #N/A |
| PN2 442 | ATG | 3 | #N/A |
| PN2 443 | ATA | 3 | #N/A |

TABLE 30-continued

Theoretical segment pool of unique N2 polypeptide segments encoded by the oligonucleotides of Table 29.

| Name | Sequence | Length | SEQ ID NO |
|---|---|---|---|
| PN2 444 | HPL | 3 | #N/A |
| PN2 445 | ISW | 3 | #N/A |
| PN2 446 | ATQ | 3 | #N/A |
| PN2 447 | ISG | 3 | #N/A |
| PN2 448 | ISE | 3 | #N/A |
| PN2 449 | DGR | 3 | #N/A |
| PN2 450 | ASW | 3 | #N/A |
| PN2 451 | DGG | 3 | #N/A |
| PN2 452 | DGE | 3 | #N/A |
| PN2 453 | HPG | 3 | #N/A |
| PN2 454 | DGH | 3 | #N/A |
| PN2 455 | DGL | 3 | #N/A |
| PN2 456 | DGM | 3 | #N/A |
| PN2 457 | LKQ | 3 | #N/A |
| PN2 458 | DGV | 3 | #N/A |
| PN2 459 | DGW | 3 | #N/A |
| PN2 460 | PVG | 3 | #N/A |
| PN2 461 | ASG | 3 | #N/A |
| PN2 462 | IRG | 3 | #N/A |
| PN2 463 | VTA | 3 | #N/A |
| PN2 464 | TSE | 3 | #N/A |
| PN2 465 | FRG | 3 | #N/A |
| PN2 466 | ASE | 3 | #N/A |
| PN2 467 | VTG | 3 | #N/A |
| PN2 468 | GTG | 3 | #N/A |
| PN2 469 | LGW | 3 | #N/A |
| PN2 470 | VTQ | 3 | #N/A |
| PN2 471 | TLG | 3 | #N/A |
| PN2 472 | YAA | 3 | #N/A |
| PN2 473 | DGY | 3 | #N/A |
| PN2 474 | ITG | 3 | #N/A |
| PN2 475 | HVG | 3 | #N/A |
| PN2 476 | RPP | 3 | #N/A |
| PN2 477 | AAG | 3 | #N/A |
| PN2 478 | RSG | 3 | #N/A |
| PN2 479 | AAA | 3 | #N/A |
| PN2 480 | TGR | 3 | #N/A |

TABLE 30-continued

Theoretical segment pool of unique N2 polypeptide segments encoded by the oligonucleotides of Table 29.

| Name | Sequence | Length | SEQ ID NO |
|---|---|---|---|
| PN2 481 | TGS | 3 | #N/A |
| PN2 482 | TGV | 3 | #N/A |
| PN2 483 | RPY | 3 | #N/A |
| PN2 484 | TGA | 3 | #N/A |
| PN2 485 | TGG | 3 | #N/A |
| PN2 486 | RPG | 3 | #N/A |
| PN2 487 | RPL | 3 | #N/A |
| PN2 488 | TGL | 3 | #N/A |
| PN2 489 | FKQ | 3 | #N/A |
| PN2 490 | FKR | 3 | #N/A |
| PN2 491 | SLG | 3 | #N/A |
| PN2 492 | LGM | 3 | #N/A |
| PN2 493 | LGA | 3 | #N/A |
| PN2 494 | NRG | 3 | #N/A |
| PN2 495 | LGG | 3 | #N/A |
| PN2 496 | LGE | 3 | #N/A |
| PN2 497 | LGY | 3 | #N/A |
| PN2 498 | LGR | 3 | #N/A |
| PN2 499 | LGS | 3 | #N/A |
| PN2 500 | LGV | 3 | #N/A |
| PN2 501 | GFE | 3 | #N/A |
| PN2 502 | LQG | 3 | #N/A |
| PN2 503 | HSG | 3 | #N/A |
| PN2 504 | HSE | 3 | #N/A |
| PN2 505 | HSW | 3 | #N/A |
| PN2 506 | DPL | 3 | #N/A |
| PN2 507 | GPL | 3 | #N/A |
| PN2 508 | HAA | 3 | #N/A |
| PN2 509 | TAG | 3 | #N/A |
| PN2 510 | GPG | 3 | #N/A |
| PN2 511 | IAA | 3 | #N/A |
| PN2 512 | HAG | 3 | #N/A |
| PN2 513 | DQG | 3 | #N/A |
| PN2 514 | GPY | 3 | #N/A |
| PN2 515 | GPP | 3 | #N/A |
| PN2 516 | VQG | 3 | #N/A |
| PN2 517 | RGR | 3 | #N/A |

TABLE 30-continued

Theoretical segment pool of unique N2 polypeptide segments encoded by the oligonucleotides of Table 29.

| Name | Sequence | Length | SEQ ID NO |
|---|---|---|---|
| PN2 518 | RGS | 3 | #N/A |
| PN2 519 | SKQ | 3 | #N/A |
| PN2 520 | RGV | 3 | #N/A |
| PN2 521 | SKR | 3 | #N/A |
| PN2 522 | RGA | 3 | #N/A |
| PN2 523 | RGG | 3 | #N/A |
| PN2 524 | RGL | 3 | #N/A |
| PN2 525 | VGL | 3 | #N/A |
| PN2 526 | VGM | 3 | #N/A |
| PN2 527 | VGH | 3 | #N/A |
| PN2 528 | FGY | 3 | #N/A |
| PN2 529 | VGE | 3 | #N/A |
| PN2 530 | VGG | 3 | #N/A |
| PN2 531 | VGA | 3 | #N/A |
| PN2 532 | YKR | 3 | #N/A |
| PN2 533 | YKQ | 3 | #N/A |
| PN2 534 | VGY | 3 | #N/A |
| PN2 535 | VGV | 3 | #N/A |
| PN2 536 | VGW | 3 | #N/A |
| PN2 537 | VGR | 3 | #N/A |
| PN2 538 | VGS | 3 | #N/A |
| PN2 539 | FTA | 3 | #N/A |
| PN2 540 | PSG | 3 | #N/A |
| PN2 541 | PSE | 3 | #N/A |
| PN2 542 | NVG | 3 | #N/A |
| PN2 543 | FGV | 3 | #N/A |
| PN2 544 | FGL | 3 | #N/A |
| PN2 545 | ILG | 3 | #N/A |
| PN2 546 | PGW | 3 | #N/A |
| PN2 547 | FSE | 3 | #N/A |
| PN2 548 | DVG | 3 | #N/A |
| PN2 549 | FSW | 3 | #N/A |
| PN2 550 | IKR | 3 | #N/A |
| PN2 551 | IKQ | 3 | #N/A |
| PN2 552 | DSE | 3 | #N/A |
| PN2 553 | FGM | 3 | #N/A |
| PN2 554 | VRG | 3 | #N/A |

TABLE 30-continued

Theoretical segment pool of unique N2 polypeptide segments encoded by the oligonucleotides of Table 29.

| Name | Sequence | Length | SEQ ID NO |
|---|---|---|---|
| PN2 555 | NKQ | 3 | #N/A |
| PN2 556 | TVG | 3 | #N/A |
| PN2 557 | NQG | 3 | #N/A |
| PN2 558 | SRG | 3 | #N/A |
| PN2 559 | YRG | 3 | #N/A |
| PN2 560 | FGE | 3 | #N/A |
| PN2 561 | PLG | 3 | #N/A |
| PN2 562 | PPG | 3 | #N/A |
| PN2 563 | NSE | 3 | #N/A |
| PN2 564 | NSG | 3 | #N/A |
| PN2 565 | PPP | 3 | #N/A |
| PN2 566 | GAG | 3 | #N/A |
| PN2 567 | PPY | 3 | #N/A |
| PN2 568 | FAA | 3 | #N/A |
| PN2 569 | NSW | 3 | #N/A |
| PN2 570 | HPY | 3 | #N/A |
| PN2 571 | PSW | 3 | #N/A |
| PN2 572 | ARG | 3 | #N/A |
| PN2 573 | SGS | 3 | #N/A |
| PN2 574 | NAA | 3 | #N/A |
| PN2 575 | NAG | 3 | #N/A |
| PN2 576 | SGW | 3 | #N/A |
| PN2 577 | GSG | 3 | #N/A |
| PN2 578 | DRG | 3 | #N/A |
| PN2 579 | RVG | 3 | #N/A |
| PN2 580 | HKR | 3 | #N/A |
| PN2 581 | HKQ | 3 | #N/A |
| PN2 582 | AQG | 3 | #N/A |
| PN2 583 | VPG | 3 | #N/A |
| PN2 584 | AKR | 3 | #N/A |
| PN2 585 | VVG | 3 | #N/A |
| PN2 586 | SGL | 3 | #N/A |
| PN2 587 | VKQ | 3 | #N/A |
| PN2 588 | SVG | 3 | #N/A |
| PN2 589 | SQG | 3 | #N/A |
| PN2 590 | LKR | 3 | #N/A |
| PN2 591 | PTG | 3 | #N/A |

TABLE 30-continued

Theoretical segment pool of unique N2 polypeptide segments encoded by the oligonucleotides of Table 29.

| Name | Sequence | Length | SEQ ID NO |
|---|---|---|---|
| PN2 592 | PGE | 3 | #N/A |
| PN2 593 | PTA | 3 | #N/A |
| PN2 594 | LLG | 3 | #N/A |
| PN2 595 | PTQ | 3 | #N/A |
| PN2 596 | TRG | 3 | #N/A |
| PN2 597 | GVG | 3 | #N/A |
| PN2 598 | IVG | 3 | #N/A |
| PN2 599 | LRG | 3 | #N/A |
| PN2 600 | HTQ | 3 | #N/A |
| PN2 601 | AVG | 3 | #N/A |
| PN2 602 | IPY | 3 | #N/A |
| PN2 603 | YQG | 3 | #N/A |
| PN2 604 | HFE | 3 | #N/A |
| PN2 605 | RRG | 3 | #N/A |
| PN2 606 | LGH | 3 | #N/A |
| PN2 607 | LGL | 3 | #N/A |
| PN2 608 | TSW | 3 | #N/A |
| PN2 609 | TKQ | 3 | #N/A |
| PN2 610 | IQG | 3 | #N/A |
| PN2 611 | HQG | 3 | #N/A |
| PN2 612 | SGY | 3 | #N/A |
| PN2 613 | DAG | 3 | #N/A |
| PN2 614 | DAA | 3 | #N/A |
| PN2 615 | SGR | 3 | #N/A |
| PN2 616 | SGV | 3 | #N/A |
| PN2 617 | SGH | 3 | #N/A |
| PN2 618 | SGM | 3 | #N/A |
| PN2 619 | SGA | 3 | #N/A |
| PN2 620 | SGE | 3 | #N/A |
| PN2 621 | SGG | 3 | #N/A |
| PN2 622 | YTQ | 3 | #N/A |
| PN2 623 | YGG | 3 | #N/A |
| PN2 624 | YGE | 3 | #N/A |
| PN2 625 | PFE | 3 | #N/A |
| PN2 626 | VSW | 3 | #N/A |
| PN2 627 | YGM | 3 | #N/A |
| PN2 628 | YGL | 3 | #N/A |

TABLE 30-continued

Theoretical segment pool of unique N2 polypeptide segments encoded by the oligonucleotides of Table 29.

| Name | Sequence | Length | SEQ ID NO |
|---|---|---|---|
| PN2 629 | YGH | 3 | #N/A |
| PN2 630 | YGW | 3 | #N/A |
| PN2 631 | YGV | 3 | #N/A |
| PN2 632 | NKR | 3 | #N/A |
| PN2 633 | VSE | 3 | #N/A |
| PN2 634 | KGG | 3 | #N/A |
| PN2 635 | VSG | 3 | #N/A |
| PN2 636 | YGY | 3 | #N/A |
| PN2 637 | RPGY | 4 | 8409 |
| PN2 638 | SAGY | 4 | 6277 |
| PN2 639 | PSGY | 4 | 6268 |
| PN2 640 | RFGY | 4 | 8410 |
| PN2 641 | RLGY | 4 | 8411 |
| PN2 642 | PYGY | 4 | 6281 |
| PN2 643 | GREY | 4 | 8412 |
| PN2 644 | GRKY | 4 | 8413 |
| PN2 645 | GHGW | 4 | 8414 |
| PN2 646 | RVGY | 4 | 8415 |
| PN2 647 | GLGL | 4 | 8416 |
| PN2 648 | GHGY | 4 | 8417 |
| PN2 649 | RDGY | 4 | 4410 |
| PN2 650 | RRVY | 4 | 8418 |
| PN2 651 | GLGW | 4 | 8419 |
| PN2 652 | GHGL | 4 | 8420 |
| PN2 653 | GLGY | 4 | 8421 |
| PN2 654 | PVGY | 4 | 8422 |
| PN2 655 | GPGY | 4 | 8423 |
| PN2 656 | GPGW | 4 | 8424 |
| PN2 657 | PDGY | 4 | 5829 |
| PN2 658 | GPGL | 4 | 8425 |
| PN2 659 | GVTA | 4 | 8426 |
| PN2 660 | GRLY | 4 | 8427 |
| PN2 661 | RRAY | 4 | 8428 |
| PN2 662 | GHTQ | 4 | 8429 |
| PN2 663 | GVGL | 4 | 8430 |
| PN2 664 | SYGY | 4 | 4434 |
| PN2 665 | RRQY | 4 | 8431 |

TABLE 30-continued

Theoretical segment pool of unique N2 polypeptide segments encoded by the oligonucleotides of Table 29.

| Name | Sequence | Length | SEQ ID NO |
|---|---|---|---|
| PN2 666 | GATQ | 4 | 8432 |
| PN2 667 | PFGY | 4 | 8433 |
| PN2 668 | GVGY | 4 | 8434 |
| PN2 669 | GVGW | 4 | 8435 |
| PN2 670 | RAGY | 4 | 6278 |
| PN2 671 | GATA | 4 | 8436 |
| PN2 672 | RYGY | 4 | 6262 |
| PN2 673 | GRAY | 4 | 8437 |
| PN2 674 | GRMY | 4 | 8438 |
| PN2 675 | GRTY | 4 | 8439 |
| PN2 676 | PPGY | 4 | 8440 |
| PN2 677 | RRPY | 4 | 8441 |
| PN2 678 | RHGY | 4 | 8442 |
| PN2 679 | GDGY | 4 | 5813 |
| PN2 680 | SVGY | 4 | 8443 |
| PN2 681 | GVTQ | 4 | 8444 |
| PN2 682 | GDGW | 4 | 8445 |
| PN2 683 | GRQY | 4 | 8446 |
| PN2 684 | GDGL | 4 | 8447 |
| PN2 685 | SHGY | 4 | 8448 |
| PN2 686 | GSGY | 4 | 6284 |
| PN2 687 | GFGY | 4 | 8449 |
| PN2 688 | GFGW | 4 | 8450 |
| PN2 689 | GSGW | 4 | 8451 |
| PN2 690 | GFGL | 4 | 8452 |
| PN2 691 | GSGL | 4 | 8453 |
| PN2 692 | RRLY | 4 | 8454 |
| PN2 693 | GFTA | 4 | 8455 |
| PN2 694 | PLGY | 4 | 8456 |
| PN2 695 | GYTQ | 4 | 8457 |
| PN2 696 | GLTQ | 4 | 8458 |

TABLE 30-continued

Theoretical segment pool of unique N2 polypeptide segments encoded by the oligonucleotides of Table 29.

| Name | Sequence | Length | SEQ ID NO |
|---|---|---|---|
| PN2 697 | GHTA | 4 | 8459 |
| PN2 698 | PHGY | 4 | 8460 |
| PN2 699 | GFTQ | 4 | 8461 |
| PN2 700 | GRVY | 4 | 8462 |
| PN2 701 | GYTA | 4 | 8463 |
| PN2 702 | GLTA | 4 | 8464 |
| PN2 703 | PAGY | 4 | 6276 |
| PN2 704 | RRKY | 4 | 8465 |
| PN2 705 | SSGY | 4 | 4186 |
| PN2 706 | GPTQ | 4 | 8466 |
| PN2 707 | SDGY | 4 | 5805 |
| PN2 708 | GPTA | 4 | 8467 |
| PN2 709 | GDTQ | 4 | 8468 |
| PN2 710 | GAGW | 4 | 8469 |
| PN2 711 | GAGY | 4 | 6270 |
| PN2 712 | GDTA | 4 | 8470 |
| PN2 713 | SFGY | 4 | 8471 |
| PN2 714 | GAGL | 4 | 8472 |
| PN2 715 | GSTQ | 4 | 8473 |
| PN2 716 | GRPY | 4 | 8474 |
| PN2 717 | SLGY | 4 | 8475 |
| PN2 718 | GSTA | 4 | 8476 |
| PN2 719 | GYGL | 4 | 8477 |
| PN2 720 | RSGY | 4 | 6269 |
| PN2 721 | RREY | 4 | 8478 |
| PN2 722 | SPGY | 4 | 8479 |
| PN2 723 | GYGY | 4 | 6260 |
| PN2 724 | RRTY | 4 | 8480 |
| PN2 725 | GYGW | 4 | 8481 |
| PN2 726 | RRMY | 4 | 8482 |

TABLE 31

Theoretical segment pool of oligonucleotides encoding JH segments of Example 15.

| Name | Degenerate Oligo | Peptide Length | Degenerate | SEQ ID NO |
|---|---|---|---|---|
| JH4 001 | TGGGGACAGGGTACATTGGTCACCGTCTCCTCA | 0 | | 8483 |
| JH1 002 | CATTGGGGACAGGGTACATTGGTCACCGTCTCCTCA | 1 | | 8484 |
| JH1 003 | ATTTGGGGACAGGGTACATTGGTCACCGTCTCCTCA | 1 | | 8485 |
| JH1 004 | TACTGGGGACAGGGTACATTGGTCACCGTCTCCTCA | 1 | | 8486 |
| JH1 005 | CCATGGGGACAGGGTACATTGGTCACCGTCTCCTCA | 1 | | 8487 |
| JH1 006 | GTCTGGGGACAGGGTACATTGGTCACCGTCTCCTCA | 1 | | 8488 |
| JH1 007 | GATTGGGGACAGGGTACATTGGTCACCGTCTCCTCA | 1 | | 8489 |
| JH1 008 | TTCTGGGGACAGGGTACATTGGTCACCGTCTCCTCA | 1 | | 8490 |
| JH1 009 | AATTGGGGACAGGGTACATTGGTCACCGTCTCCTCA | 1 | | 8491 |
| JH1 010 | AGTTGGGGACAGGGTACATTGGTCACCGTCTCCTCA | 1 | | 8492 |
| JH1 011 | ACTTGGGGACAGGGTACATTGGTCACCGTCTCCTCA | 1 | | 8493 |
| JH1 200 | GCATGGGGACAGGGTACATTGGTCACCGTCTCCTCA | 1 | | 8494 |
| JH4 013 | GATTACTGGGGACAGGGTACATTGGTCACCGTCTCCTCA | 2 | | 8495 |
| JH4 016 | GCTTACTGGGGACAGGGTACATTGGTCACCGTCTCCTCA | 2 | | 8496 |
| JH4 017 | TTCTACTGGGGACAGGGTACATTGGTCACCGTCTCCTCA | 2 | | 8497 |
| JH4 018 | GGCTATTGGGGACAGGGTACATTGGTCACCGTCTCCTCA | 2 | | 8498 |
| JH4 019 | CATTACTGGGGACAGGGTACATTGGTCACCGTCTCCTCA | 2 | | 8499 |
| JH4 023 | AGTTACTGGGGACAGGGTACATTGGTCACCGTCTCCTCA | 2 | | 8500 |
| JH4 024 | GTTTATTGGGGACAGGGTACATTGGTCACCGTCTCCTCA | 2 | | 8501 |
| JH4 025 | TACTATTGGGGACAGGGTACATTGGTCACCGTCTCCTCA | 2 | | 8502 |
| JH4 022 | CSATACTGGGGACAGGGTACATTGGTCACCGTCTCCTCA | 2 | YES | 8503 |
| JH3 012 | RACATATGGGGTCAGGGTACAATGGTCACCGTCTCCTCA | 2 | YES | 8504 |
| JH5 014 | RACCCATGGGGACAGGGTACATTGGTCACCGTCTCCTCA | 2 | YES | 8505 |
| JH3 015 | RACGTATGGGGTCAGGGTACAATGGTCACCGTCTCCTCA | 2 | YES | 8506 |
| JH4 021 | AMCTACTGGGGACAGGGTACATTGGTCACCGTCTCCTCA | 2 | YES | 8507 |
| JH4 020 | MTATACTGGGGACAGGGTACATTGGTCACCGTCTCCTCA | 2 | YES | 8508 |
| JH4 029 | TTCGATTATTGGGGACAGGGTACATTGGTCACCGTCTCCTCA | 3 | | 8509 |
| JH4 030 | ATTGACTACTGGGGACAGGGTACATTGGTCACCGTCTCCTCA | 3 | | 8510 |
| JH4 031 | GTGGACTACTGGGGACAGGGTACATTGGTCACCGTCTCCTCA | 3 | | 8511 |
| JH4 032 | TTAGATTACTGGGGACAGGGTACATTGGTCACCGTCTCCTCA | 3 | | 8512 |
| JH4 033 | TCCGATTATTGGGGACAGGGTACATTGGTCACCGTCTCCTCA | 3 | | 8513 |
| JH4 034 | CACGATTACTGGGGACAGGGTACATTGGTCACCGTCTCCTCA | 3 | | 8514 |
| JH4 035 | AGAGACTACTGGGGACAGGGTACATTGGTCACCGTCTCCTCA | 3 | | 8515 |
| JH4 036 | CCAGATTACTGGGGACAGGGTACATTGGTCACCGTCTCCTCA | 3 | | 8516 |
| JH4 037 | AACGATTACTGGGGACAGGGTACATTGGTCACCGTCTCCTCA | 3 | | 8517 |
| JH4 038 | ACTGATTACTGGGGACAGGGTACATTGGTCACCGTCTCCTCA | 3 | | 8518 |
| JH4 039 | GATGATTATTGGGGACAGGGTACATTGGTCACCGTCTCCTCA | 3 | | 8519 |

TABLE 31 -continued

Theoretical segment pool of oligonucleotides encoding JH segments of Example 15.

| Name | Degenerate Oligo | Peptide Length | Degenerate | SEQ ID NO |
|---|---|---|---|---|
| JH4 040 | GGTGATTATTGGGGACAGGGTACATTGGTCACCGTCTCCTCA | 3 | | 8520 |
| JH4 041 | GCAGACTACTGGGGACAGGGTACATTGGTCACCGTCTCCTCA | 3 | | 8521 |
| JH4 042 | TACGATTATTGGGGACAGGGTACATTGGTCACCGTCTCCTCA | 3 | | 8522 |
| JH5 043 | TTCGATCCCTGGGGACAGGGTACATTGGTCACCGTCTCCTCA | 3 | | 8523 |
| JH6 044 | ATGGATGTGTGGGGCCAGGGAACAACTGTCACCGTCTCCTCA | 3 | | 8524 |
| JH1 026 | TTMCAACACTGGGGACAGGGTACATTGGTCACCGTCTCCTCA | 3 | YES | 8525 |
| JH3 046 | STAGACGTATGGGGTCAGGGTACAATGGTCACCGTCTCCTCA | 3 | YES | 8526 |
| JH3 028 | TTMGACATATGGGGTCAGGGTACAATGGTCACCGTCTCCTCA | 3 | YES | 8527 |
| JH2 027 | TTMGACCTATGGGGGAGAGGTACCTTGGTCACCGTCTCCTCA | 3 | YES | 8528 |
| JH5 045 | TYAGACCCATGGGGACAGGGTACATTGGTCACCGTCTCCTCA | 3 | YES | 8529 |
| JH3 049 | GCCTTTGATATTTGGGGTCAGGGTACAATGGTCACCGTCTCCTCA | 4 | | 8530 |
| JH4 051 | TACTTTGACTACTGGGGACAGGGTACATTGGTCACCGTCTCCTCA | 4 | | 8531 |
| JH4 052 | AATTTCGACTACTGGGGACAGGGTACATTGGTCACCGTCTCCTCA | 4 | | 8532 |
| JH4 053 | GACTTCGACTATTGGGGACAGGGTACATTGGTCACCGTCTCCTCA | 4 | | 8533 |
| JH4 054 | CATTTCGATTACTGGGGACAGGGTACATTGGTCACCGTCTCCTCA | 4 | | 8534 |
| JH4 055 | TTCTTTGATTATTGGGGACAGGGTACATTGGTCACCGTCTCCTCA | 4 | | 8535 |
| JH4 056 | TCTTTTGATTATTGGGGACAGGGTACATTGGTCACCGTCTCCTCA | 4 | | 8536 |
| JH4 057 | AGATTCGACTACTGGGGACAGGGTACATTGGTCACCGTCTCCTCA | 4 | | 8537 |
| JH4 058 | TTGTTCGACTACTGGGGACAGGGTACATTGGTCACCGTCTCCTCA | 4 | | 8538 |
| JH4 059 | CCCTTCGACTATTGGGGACAGGGTACATTGGTCACCGTCTCCTCA | 4 | | 8539 |
| JH4 060 | ATTTTCGATTATTGGGGACAGGGTACATTGGTCACCGTCTCCTCA | 4 | | 8540 |
| JH4 061 | ACCTTTGATTACTGGGGACAGGGTACATTGGTCACCGTCTCCTCA | 4 | | 8541 |
| JH4 062 | GGATTCGATTACTGGGGACAGGGTACATTGGTCACCGTCTCCTCA | 4 | | 8542 |
| JH4 063 | GTTTTCGATTACTGGGGACAGGGTACATTGGTCACCGTCTCCTCA | 4 | | 8543 |
| JH4 064 | GCTTTTGACTACTGGGGACAGGGTACATTGGTCACCGTCTCCTCA | 4 | | 8544 |
| JH5 065 | TGGTTTGATCCATGGGGACAGGGTACATTGGTCACCGTCTCCTCA | 4 | | 8545 |
| JH6 068 | GGAATGGACGTATGGGGCCAGGGAACAACTGTCACCGTCTCCTCA | 4 | | 8546 |
| JH6 070 | YCAATGGACGTATGGGGCCAGGGAACAACTGTCACCGTCTCCTCA | 4 | YES | 8547 |
| JH6 069 | KACATGGACGTATGGGGCAAGGGTACAACTGTCACCGTCTCCTCA | 4 | YES | 8548 |
| JH3 198 | STATTCGACATATGGGGTCAGGGTACAATGGTCACCGTCTCCTCA | 4 | YES | 8549 |
| JH2 048 | KACTTCGACCTATGGGGGAGAGGTACCTTGGTCACCGTCTCCTCA | 4 | YES | 8550 |
| JH1 047 | KACTTCCAACACTGGGGACAGGGTACATTGGTCACCGTCTCCTCA | 4 | YES | 8551 |
| JH5 067 | GSATTCGACCCATGGGGACAGGGTACATTGGTCACCGTCTCCTCA | 4 | YES | 8552 |
| JH3 050 | YCATTCGACATATGGGGTCAGGGTACAATGGTCACCGTCTCCTCA | 4 | YES | 8553 |
| JH5 066 | AGMTTCGACCCATGGGGACAGGGTACATTGGTCACCGTCTCCTCA | 4 | YES | 8554 |
| JH2 072 | TGGTACTTCGACTTATGGGGGAGAGGTACCTTGGTCACCGTCTCCTCA | 5 | | 8555 |
| JH3 075 | GACGCATTTGATATATGGGGTCAGGGTACAATGGTCACCGTCTCCTCA | 5 | | 8556 |

TABLE 31 -continued

Theoretical segment pool of oligonucleotides encoding JH segments of Example 15.

| Name | Degenerate Oligo | Peptide Length | Degenerate | SEQ ID NO |
|---|---|---|---|---|
| JH3 076 | TACGCATTTGATATTTGGGGTCAGGGTACAATGGTCACCGTCTCCTCA | 5 | | 8557 |
| JH3 077 | CACGCATTCGACATCTGGGGTCAGGGTACAATGGTCACCGTCTCCTCA | 5 | | 8558 |
| JH3 078 | TTCGCATTCGATATCTGGGGTCAGGGTACAATGGTCACCGTCTCCTCA | 5 | | 8559 |
| JH3 079 | TCAGCTTTCGACATATGGGGTCAGGGTACAATGGTCACCGTCTCCTCA | 5 | | 8560 |
| JH3 080 | AGAGCCTTCGATATATGGGGTCAGGGTACAATGGTCACCGTCTCCTCA | 5 | | 8561 |
| JH3 081 | TTAGCCTTCGATATCTGGGGTCAGGGTACAATGGTCACCGTCTCCTCA | 5 | | 8562 |
| JH3 082 | GGAGCCTTCGACATATGGGGTCAGGGTACAATGGTCACCGTCTCCTCA | 5 | | 8563 |
| JH4 086 | GACTATTTTGATTACTGGGGACAGGGTACATTGGTCACCGTCTCCTCA | 5 | | 8564 |
| JH4 087 | TATTACTTTGATTACTGGGGACAGGGTACATTGGTCACCGTCTCCTCA | 5 | | 8565 |
| JH4 088 | CACTATTTCGACTATTGGGGACAGGGTACATTGGTCACCGTCTCCTCA | 5 | | 8566 |
| JH4 089 | TTCTATTTTGATTACTGGGGACAGGGTACATTGGTCACCGTCTCCTCA | 5 | | 8567 |
| JH4 090 | AGTTATTTTGACTATTGGGGACAGGGTACATTGGTCACCGTCTCCTCA | 5 | | 8568 |
| JH4 091 | AGATACTTTGATTACTGGGGACAGGGTACATTGGTCACCGTCTCCTCA | 5 | | 8569 |
| JH4 092 | TTATATTTCGACTATTGGGGACAGGGTACATTGGTCACCGTCTCCTCA | 5 | | 8570 |
| JH4 093 | CCCTACTTTGACTATTGGGGACAGGGTACATTGGTCACCGTCTCCTCA | 5 | | 8571 |
| JH4 095 | GGATATTTCGATTATTGGGGACAGGGTACATTGGTCACCGTCTCCTCA | 5 | | 8572 |
| JH4 096 | GTTTACTTTGATTATTGGGGACAGGGTACATTGGTCACCGTCTCCTCA | 5 | | 8573 |
| JH4 097 | GCTTACTTTGATTATTGGGGACAGGGTACATTGGTCACCGTCTCCTCA | 5 | | 8574 |
| JH4 098 | AACTACTTCGATTACTGGGGACAGGGTACATTGGTCACCGTCTCCTCA | 5 | | 8575 |
| JH5 099 | AATTGGTTCGATCCTTGGGGACAGGGTACATTGGTCACCGTCTCCTCA | 5 | | 8576 |
| JH5 100 | GATTGGTTTGATCCATGGGGACAGGGTACATTGGTCACCGTCTCCTCA | 5 | | 8577 |
| JH5 101 | TATTGGTTTGATCCATGGGGACAGGGTACATTGGTCACCGTCTCCTCA | 5 | | 8578 |
| JH5 102 | CACTGGTTCGATCCATGGGGACAGGGTACATTGGTCACCGTCTCCTCA | 5 | | 8579 |
| JH5 103 | TTCTGGTTTGACCCCTGGGGACAGGGTACATTGGTCACCGTCTCCTCA | 5 | | 8580 |
| JH5 104 | TCTTGGTTTGATCCCTGGGGACAGGGTACATTGGTCACCGTCTCCTCA | 5 | | 8581 |
| JH5 105 | AGATGGTTTGATCCTTGGGGACAGGGTACATTGGTCACCGTCTCCTCA | 5 | | 8582 |
| JH5 107 | GGTTGGTTCGATCCCTGGGGACAGGGTACATTGGTCACCGTCTCCTCA | 5 | | 8583 |
| JH5 109 | GCTTGGTTTGATCCATGGGGACAGGGTACATTGGTCACCGTCTCCTCA | 5 | | 8584 |
| JH6 110 | TACGGTATGGACGTTTGGGGCCAGGGAACAACTGTCACCGTCTCCTCA | 5 | | 8585 |
| JH6 112 | GATGGGATGGATGTTTGGGGCCAGGGAACAACTGTCACCGTCTCCTCA | 5 | | 8586 |
| JH3 084 | SCAGCATTCGACATATGGGGTCAGGGTACAATGGTCACCGTCTCCTCA | 5 | YES | 8587 |
| JH5 106 | MCATGGTTCGACCCATGGGGACAGGGTACATTGGTCACCGTCTCCTCA | 5 | YES | 8588 |
| JH2 073 | RGCTACTTCGACCTATGGGGGAGAGGTACCTTGGTCACCGTCTCCTCA | 5 | YES | 8589 |
| JH4 094 | AYATACTTCGACTACTGGGGACAGGGTACATTGGTCACCGTCTCCTCA | 5 | YES | 8590 |
| JH5 108 | RTATGGTTCGACCCATGGGGACAGGGTACATTGGTCACCGTCTCCTCA | 5 | YES | 8591 |
| JH6 113 | CWCGGAATGGACGTATGGGGCCAGGGAACAACTGTCACCGTCTCCTCA | 5 | YES | 8592 |
| JH6 114 | KCAGGAATGGACGTATGGGGCCAGGGAACAACTGTCACCGTCTCCTCA | 5 | YES | 8593 |

TABLE 31 -continued

Theoretical segment pool of oligonucleotides encoding JH segments of Example 15.

| Name | Degenerate Oligo | Peptide Length | Degenerate | SEQ ID NO |
|---|---|---|---|---|
| JH3 083 | RTAGCATTCGACATATGGGGTCAGGGTACAATGGTCACCGTCTCCTCA | 5 | YES | 8594 |
| JH1 071 | RAGTACTTCCAACACTGGGGACAGGGTACATTGGTCACCGTCTCCTCA | 5 | YES | 8595 |
| JH3 085 | AMCGCATTCGACATATGGGGTCAGGGTACAATGGTCACCGTCTCCTCA | 5 | YES | 8596 |
| JH2 074 | CKATACTTCGACCTATGGGGGAGAGGTACCTTGGTCACCGTCTCCTCA | 5 | YES | 8597 |
| JH6 111 | KACTACATGGACGTATGGGGCAAGGGTACAACTGTCACCGTCTCCTCA | 5 | YES | 8598 |
| JH2 116 | TACTGGTACTTCGATTTGTGGGGGAGAGGTACCTTGGTCACCGTCTCCTCA | 6 | | 8599 |
| JH2 117 | GATTGGTACTTCGATTTATGGGGGAGAGGTACCTTGGTCACCGTCTCCTCA | 6 | | 8600 |
| JH5 120 | GATAATTGGTTCGATCCATGGGGACAGGGTACATTGGTCACCGTCTCCTCA | 6 | | 8601 |
| JH5 121 | TATAACTGGTTCGATCCCTGGGGACAGGGTACATTGGTCACCGTCTCCTCA | 6 | | 8602 |
| JH5 122 | CACAATTGGTTCGACCCCTGGGGACAGGGTACATTGGTCACCGTCTCCTCA | 6 | | 8603 |
| JH5 123 | TTCAATTGGTTTGATCCCTGGGGACAGGGTACATTGGTCACCGTCTCCTCA | 6 | | 8604 |
| JH5 124 | AGCAACTGGTTCGACCCATGGGGACAGGGTACATTGGTCACCGTCTCCTCA | 6 | | 8605 |
| JH5 125 | AGAAACTGGTTTGATCCATGGGGACAGGGTACATTGGTCACCGTCTCCTCA | 6 | | 8606 |
| JH5 126 | TTAAATTGGTTCGACCCTTGGGGACAGGGTACATTGGTCACCGTCTCCTCA | 6 | | 8607 |
| JH5 127 | CCCAATTGGTTTGATCCATGGGGACAGGGTACATTGGTCACCGTCTCCTCA | 6 | | 8608 |
| JH5 128 | ATAAATTGGTTCGACCCTTGGGGACAGGGTACATTGGTCACCGTCTCCTCA | 6 | | 8609 |
| JH5 129 | ACTAACTGGTTTGACCCATGGGGACAGGGTACATTGGTCACCGTCTCCTCA | 6 | | 8610 |
| JH5 130 | GGTAACTGGTTTGACCCATGGGGACAGGGTACATTGGTCACCGTCTCCTCA | 6 | | 8611 |
| JH5 131 | GTGAACTGGTTTGATCCCTGGGGACAGGGTACATTGGTCACCGTCTCCTCA | 6 | | 8612 |
| JH5 132 | GCCAACTGGTTCGATCCCTGGGGACAGGGTACATTGGTCACCGTCTCCTCA | 6 | | 8613 |
| JH5 133 | AACAATTGGTTCGACCCATGGGGACAGGGTACATTGGTCACCGTCTCCTCA | 6 | | 8614 |
| JH6 134 | TACTACGGCATGGATGTATGGGGCCAGGGAACAACTGTCACCGTCTCCTCA | 6 | | 8615 |
| JH6 136 | GATTATGGAATGGACGTATGGGGCCAGGGAACAACTGTCACCGTCTCCTCA | 6 | | 8616 |
| JH6 137 | TTCTACGGTATGGATGTCTGGGGCCAGGGAACAACTGTCACCGTCTCCTCA | 6 | | 8617 |
| JH6 138 | CATTACGGAATGGACGTATGGGGCCAGGGAACAACTGTCACCGTCTCCTCA | 6 | | 8618 |
| JH6 139 | TTGTACGGAATGGACGTTTGGGGCCAGGGAACAACTGTCACCGTCTCCTCA | 6 | | 8619 |
| JH6 140 | AACTATGGCATGGATGTGTGGGGCCAGGGAACAACTGTCACCGTCTCCTCA | 6 | | 8620 |
| JH2 118 | CWCTGGTACTTCGACCTATGGGGGAGAGGTACCTTGGTCACCGTCTCCTCA | 6 | YES | 8621 |
| JH6 141 | SCATACGGAATGGACGTATGGGGCCAGGGAACAACTGTCACCGTCTCCTCA | 6 | YES | 8622 |
| JH1 115 | SCAGAATACTTCCAACACTGGGGACAGGGTACATTGGTCACCGTCTCCTCA | 6 | YES | 8623 |
| JH6 135 | KACTACTACATGGACGTATGGGGCAAGGGTACAACTGTCACCGTCTCCTCA | 6 | YES | 8624 |
| JH6 199 | GKATACGGAATGGACGTATGGGGCCAGGGAACAACTGTCACCGTCTCCTCA | 6 | YES | 8625 |
| JH6 142 | AKCTACGGAATGGACGTATGGGGCCAGGGAACAACTGTCACCGTCTCCTCA | 6 | YES | 8626 |
| JH2 119 | ARCTGGTACTTCGACCTATGGGGGAGAGGTACCTTGGTCACCGTCTCCTCA | 6 | YES | 8627 |
| JH6 143 | ASATACGGAATGGACGTATGGGGCCAGGGAACAACTGTCACCGTCTCCTCA | 6 | YES | 8628 |
| JH6 144 | TATTACTATGGTATGGATGTATGGGGCCAGGGAACAACTGTCACCGTCTCCTCA | 7 | | 8629 |
| JH6 145 | TATTACTATTATATGGATGTTTGGGGCAAGGGTACAACTGTCACCGTCTCCTCA | 7 | | 8630 |

TABLE 31 -continued

Theoretical segment pool of oligonucleotides encoding JH segments of Example 15.

| Name | Degenerate Oligo | Peptide Length | Degenerate | SEQ ID NO |
|---|---|---|---|---|
| JH6 146 | GATTACTACGGCATGGATGTTTGGGGCCAGGGAACAACTGTCACCGTCTCCTCA | 7 | | 8631 |
| JH6 148 | AACTACTACGGCATGGACGTATGGGGCCAGGGAACAACTGTCACCGTCTCCTCA | 7 | | 8632 |
| JH6 147 | CWCTACTACGGAATGGACGTATGGGGCCAGGGAACAACTGTCACCGTCTCCTCA | 7 | YES | 8633 |
| JH6 150 | RACTACTACTACATGGACGTATGGGGCAAGGGTACAACTGTCACCGTCTCCTCA | 7 | YES | 8634 |
| JH6 149 | YCATACTACGGAATGGACGTATGGGGCCAGGGAACAACTGTCACCGTCTCCTCA | 7 | YES | 8635 |
| JH6 151 | TATTACTACTACGGAATGGACGTTTGGGGCCAGGGAACAACTGTCACCGTCTCCTCA | 8 | | 8636 |
| JH6 152 | AATTATTATTACGGCATGGACGTCTGGGGCCAGGGAACAACTGTCACCGTCTCCTCA | 8 | | 8637 |
| JH6 153 | GATTACTATTACGGTATGGATGTCTGGGGCCAGGGAACAACTGTCACCGTCTCCTCA | 8 | | 8638 |
| JH6 154 | CACTATTACTACGGCATGGACGTATGGGGCCAGGGAACAACTGTCACCGTCTCCTCA | 8 | | 8639 |
| JH6 155 | TTCTATTATTATGGTATGGATGTTTGGGGCCAGGGAACAACTGTCACCGTCTCCTCA | 8 | | 8640 |
| JH6 156 | TCTTACTACTATGGGATGGACGTGTGGGGCCAGGGAACAACTGTCACCGTCTCCTCA | 8 | | 8641 |
| JH6 157 | AGATATTACTACGGCATGGATGTTTGGGGCCAGGGAACAACTGTCACCGTCTCCTCA | 8 | | 8642 |
| JH6 158 | TTATACTACTATGGGATGGATGTATGGGGCCAGGGAACAACTGTCACCGTCTCCTCA | 8 | | 8643 |
| JH6 159 | CCTTACTACTATGGCATGGACGTCTGGGGCCAGGGAACAACTGTCACCGTCTCCTCA | 8 | | 8644 |
| JH6 160 | ACCTATTACTATGGTATGGATGTGTGGGGCCAGGGAACAACTGTCACCGTCTCCTCA | 8 | | 8645 |
| JH6 161 | GGATACTACTATGGGATGGACGTCTGGGGCCAGGGAACAACTGTCACCGTCTCCTCA | 8 | | 8646 |
| JH6 163 | GCCTACTATTATGGCATGGACGTCTGGGGCCAGGGAACAACTGTCACCGTCTCCTCA | 8 | | 8647 |
| JH6 164 | TACTACTATTATTATATGGACGTTTGGGGCAAGGGTACAACTGTCACCGTCTCCTCA | 8 | | 8648 |
| JH6 165 | AACTACTACTACTATATGGATGTTTGGGGCAAGGGTACAACTGTCACCGTCTCCTCA | 8 | | 8649 |
| JH6 166 | GATTATTATTACTATATGGACGTCTGGGGCAAGGGTACAACTGTCACCGTCTCCTCA | 8 | | 8650 |
| JH6 162 | RTATACTACTACGGAATGGACGTATGGGGCCAGGGAACAACTGTCACCGTCTCCTCA | 8 | YES | 8651 |
| JH6 168 | RGCTACTACTACTACATGGACGTATGGGGCAAGGGTACAACTGTCACCGTCTCCTCA | 8 | YES | 8652 |
| JH6 167 | CMCTACTACTACTACATGGACGTATGGGGCAAGGGTACAACTGTCACCGTCTCCTCA | 8 | YES | 8653 |
| JH6 169 | TATTACTATTATTACGGGATGGACGTATGGGGCCAGGGAACAACTGTCACCGTCTCCTCA | 9 | | 8654 |
| JH6 170 | AATTATTATTATTATGGGATGGACGTATGGGGCCAGGGAACAACTGTCACCGTCTCCTCA | 9 | | 8655 |
| JH6 171 | GACTATTACTATTATGGAATGGATGTATGGGGCCAGGGAACAACTGTCACCGTCTCCTCA | 9 | | 8656 |
| JH6 172 | CATTATTATTATTACGGAATGGACGTTTGGGGCCAGGGAACAACTGTCACCGTCTCCTCA | 9 | | 8657 |
| JH6 173 | TTCTATTACTATTATGGCATGGATGTGTGGGGCCAGGGAACAACTGTCACCGTCTCCTCA | 9 | | 8658 |
| JH6 174 | AGCTACTACTATTATGGTATGGACGTGTGGGGCCAGGGAACAACTGTCACCGTCTCCTCA | 9 | | 8659 |
| JH6 175 | AGATATTACTACTATGGCATGGATGTCTGGGGCCAGGGAACAACTGTCACCGTCTCCTCA | 9 | | 8660 |
| JH6 176 | TTATACTACTATTACGGCATGGATGTCTGGGGCCAGGGAACAACTGTCACCGTCTCCTCA | 9 | | 8661 |
| JH6 177 | CCCTATTATTACTACGGAATGGACGTTTGGGGCCAGGGAACAACTGTCACCGTCTCCTCA | 9 | | 8662 |
| JH6 178 | ATCTATTACTATTATGGCATGGATGTATGGGGCCAGGGAACAACTGTCACCGTCTCCTCA | 9 | | 8663 |
| JH6 179 | ACCTATTACTACTATGGCATGGACGTTTGGGGCCAGGGAACAACTGTCACCGTCTCCTCA | 9 | | 8664 |
| JH6 180 | GGCTACTATTACTATGGGATGGACGTCTGGGGCCAGGGAACAACTGTCACCGTCTCCTCA | 9 | | 8665 |
| JH6 181 | GTCTACTATTATTATGGCATGGACGTATGGGGCCAGGGAACAACTGTCACCGTCTCCTCA | 9 | | 8666 |
| JH6 182 | GCTTACTATTACTACGGCATGGACGTATGGGGCCAGGGAACAACTGTCACCGTCTCCTCA | 9 | | 8667 |

TABLE 31 -continued

Theoretical segment pool of oligonucleotides encoding JH segments of Example 15.

| Name | Degenerate Oligo | Peptide Length | Degenerate | SEQ ID NO |
|---|---|---|---|---|
| JH6 183 | GATTATTATTATTACTATGGTATGGATGTGTGGGGCCAGGGAACAACTGTCACCGTCTCCTCA | 10 | | 8668 |
| JH6 184 | TACTATTACTACTATTATGGCATGGACGTCTGGGGCCAGGGAACAACTGTCACCGTCTCCTCA | 10 | | 8669 |
| JH6 185 | CACTACTACTATTATTATGGGATGGACGTATGGGGCCAGGGAACAACTGTCACCGTCTCCTCA | 10 | | 8670 |
| JH6 186 | TTCTATTATTATTATTACGGAATGGACGTCTGGGGCCAGGGAACAACTGTCACCGTCTCCTCA | 10 | | 8671 |
| JH6 187 | AGCTACTATTACTACTATGGGATGGATGTGTGGGGCCAGGGAACAACTGTCACCGTCTCCTCA | 10 | | 8672 |
| JH6 188 | AGATATTACTATTACTATGGTATGGACGTTTGGGGCCAGGGAACAACTGTCACCGTCTCCTCA | 10 | | 8673 |
| JH6 189 | TTGTACTATTACTATTATGGAATGGACGTTTGGGGCCAGGGAACAACTGTCACCGTCTCCTCA | 10 | | 8674 |
| JH6 190 | CCTTACTATTATTATTATGGGATGGATGTCTGGGGCCAGGGAACAACTGTCACCGTCTCCTCA | 10 | | 8675 |
| JH6 191 | ATATATTACTATTACTACGGGATGGATGTTTGGGGCCAGGGAACAACTGTCACCGTCTCCTCA | 10 | | 8676 |
| JH6 192 | ACCTACTATTATTATTACGGGATGGACGTTTGGGGCCAGGGAACAACTGTCACCGTCTCCTCA | 10 | | 8677 |
| JH6 193 | GGTTACTATTATTACTACGGGATGGACGTGTGGGGCCAGGGAACAACTGTCACCGTCTCCTCA | 10 | | 8678 |
| JH6 194 | GTGTATTACTATTACTACGGGATGGACGTGTGGGGCCAGGGAACAACTGTCACCGTCTCCTCA | 10 | | 8679 |
| JH6 195 | GCCTATTACTACTACTATGGGATGGATGTGTGGGGCCAGGGAACAACTGTCACCGTCTCCTCA | 10 | | 8680 |
| JH6 196 | AATTATTATTACTATTACGGTATGGACGTGTGGGGCCAGGGAACAACTGTCACCGTCTCCTCA | 10 | | 8681 |
| JH6 197 | KACTACTACTACTACTACTACATGGACGTATGGGGCAAGGGTACAACTGTCACCGTCTCCTCA | 10 | YES | 8682 |

TABLE 32

Theoretical segment pool of unique H3-JH polypeptide segments encoded by the oligonucleotides of Table 31.

| Name | Sequence | Length | SEQ ID NO |
|---|---|---|---|
| PJH4 001 | | 0 | n/a |
| PJH1 002 | H | 1 | n/a |
| PJH1 003 | I | 1 | n/a |
| PJH1 004 | Y | 1 | n/a |
| PJH1 005 | P | 1 | n/a |
| PJH1 006 | V | 1 | n/a |
| PJH1 007 | D | 1 | n/a |
| PJH1 008 | F | 1 | n/a |
| PJH1 009 | N | 1 | n/a |
| PJH1 010 | S | 1 | n/a |
| PJH1 011 | T | 1 | n/a |
| PJH1 200 | A | 1 | n/a |
| PJH4 013 | DY | 2 | n/a |
| PJH4 016 | AY | 2 | n/a |
| PJH4 017 | FY | 2 | n/a |
| PJH4 018 | GY | 2 | n/a |
| PJH4 019 | HY | 2 | n/a |

TABLE 32 -continued

Theoretical segment pool of unique H3-JH polypeptide segments encoded by the oligonucleotides of Table 31.

| Name | Sequence | Length | SEQ ID NO |
|---|---|---|---|
| PJH4 023 | SY | 2 | n/a |
| PJH4 024 | VY | 2 | n/a |
| PJH4 025 | YY | 2 | n/a |
| PJH3 012A | NI | 2 | n/a |
| PJH3 012B | DI | 2 | n/a |
| PJH3 015A | NV | 2 | n/a |
| PJH3 015B | DV | 2 | n/a |
| PJH4 020A | LY | 2 | n/a |
| PJH4 020B | IY | 2 | n/a |
| PJH4 021A | NY | 2 | n/a |
| PJH4 021B | TY | 2 | n/a |
| PJH4 022A | PY | 2 | n/a |
| PJH4 022B | RY | 2 | n/a |
| PJH5 014A | NP | 2 | n/a |
| PJH5 014B | DP | 2 | n/a |
| PJH4 029 | FDY | 3 | n/a |

TABLE 32 -continued

Theoretical segment pool of unique H3-JH polypeptide segments encoded by the oligonucleotides of Table 31.

| Name | Sequence | Length | SEQ ID NO |
|---|---|---|---|
| PJH4 030 | IDY | 3 | n/a |
| PJH4 031 | VDY | 3 | n/a |
| PJH4 032 | LDY | 3 | n/a |
| PJH4 033 | SDY | 3 | n/a |
| PJH4 034 | HDY | 3 | n/a |
| PJH4 035 | RDY | 3 | n/a |
| PJH4 036 | PDY | 3 | n/a |
| PJH4 037 | NDY | 3 | n/a |
| PJH4 038 | TDY | 3 | n/a |
| PJH4 039 | DDY | 3 | n/a |
| PJH4 040 | GDY | 3 | n/a |
| PJH4 041 | ADY | 3 | n/a |
| PJH4 042 | YDY | 3 | n/a |
| PJH5 043 | FDP | 3 | n/a |
| PJH6 044 | MDV | 3 | n/a |
| PJH1 026A | LQH | 3 | n/a |
| PJH1 026B | FQH | 3 | n/a |
| PJH2 027A | FDL | 3 | n/a |
| PJH2 027B | LDL | 3 | n/a |
| PJH3 028A | FDI | 3 | n/a |
| PJH3 028B | LDI | 3 | n/a |
| PJH3 046A | VDV | 3 | n/a |
| PJH3 046B | LDV | 3 | n/a |
| PJH5 045A | LDP | 3 | n/a |
| PJH5 045B | SDP | 3 | n/a |
| PJH3 049 | AFDI | 4 | 4539 |
| PJH4 051 | YFDY | 4 | 4567 |
| PJH4 052 | NFDY | 4 | 4580 |
| PJH4 053 | DFDY | 4 | 4581 |
| PJH4 054 | HFDY | 4 | 4582 |
| PJH4 055 | FFDY | 4 | 4583 |
| PJH4 056 | SFDY | 4 | 4584 |
| PJH4 057 | RFDY | 4 | 4585 |
| PJH4 058 | LFDY | 4 | 4586 |
| PJH4 059 | PFDY | 4 | 4587 |
| PJH4 060 | IFDY | 4 | 4588 |
| PJH4 061 | TFDY | 4 | 4589 |

TABLE 32 -continued

Theoretical segment pool of unique H3-JH polypeptide segments encoded by the oligonucleotides of Table 31.

| Name | Sequence | Length | SEQ ID NO |
|---|---|---|---|
| PJH4 062 | GFDY | 4 | 4590 |
| PJH4 063 | VFDY | 4 | 4591 |
| PJH4 064 | AFDY | 4 | 4592 |
| PJH5 065 | WFDP | 4 | 4596 |
| PJH6 068 | GMDV | 4 | 4641 |
| PJH1 047A | YFQH | 4 | 4489 |
| PJH1 047B | DFQH | 4 | 4514 |
| PJH2 048A | DFDL | 4 | 4537 |
| PJH2 048B | YFDL | 4 | 4529 |
| PJH3 050A | PFDI | 4 | 4554 |
| PJH3 050B | SFDI | 4 | 4553 |
| PJH3 198A | VFDI | 4 | 4563 |
| PJH3 198B | LFDI | 4 | 4558 |
| PJH5 066A | RFDP | 4 | 4622 |
| PJH5 066B | SFDP | 4 | 4625 |
| PJH5 067A | GFDP | 4 | 4623 |
| PJH5 067B | AFDP | 4 | 4633 |
| PJH6 069A | YMDV | 4 | 4687 |
| PJH6 069B | DMDV | 4 | 8683 |
| PJH6 070A | PMDV | 4 | 8684 |
| PJH6 070B | SMDV | 4 | 8685 |
| PJH2 072 | WYFDL | 5 | 4528 |
| PJH3 075 | DAFDI | 5 | 4538 |
| PJH3 076 | YAFDI | 5 | 4540 |
| PJH3 077 | HAFDI | 5 | 4541 |
| PJH3 078 | FAFDI | 5 | 4542 |
| PJH3 079 | SAFDI | 5 | 4543 |
| PJH3 080 | RAFDI | 5 | 4544 |
| PJH3 081 | LAFDI | 5 | 4545 |
| PJH3 082 | GAFDI | 5 | 4549 |
| PJH4 086 | DYFDY | 5 | 4566 |
| PJH4 087 | YYFDY | 5 | 4568 |
| PJH4 088 | HYFDY | 5 | 4569 |
| PJH4 089 | FYFDY | 5 | 4570 |
| PJH4 090 | SYFDY | 5 | 4571 |
| PJH4 091 | RYFDY | 5 | 4572 |
| PJH4 092 | LYFDY | 5 | 4573 |

TABLE 32 -continued

Theoretical segment pool of unique H3-JH polypeptide segments encoded by the oligonucleotides of Table 31.

| Name | Sequence | Length | SEQ ID NO |
|---|---|---|---|
| PJH4 093 | PYFDY | 5 | 4574 |
| PJH4 095 | GYFDY | 5 | 4577 |
| PJH4 096 | VYFDY | 5 | 4578 |
| PJH4 097 | AYFDY | 5 | 4579 |
| PJH4 098 | NYFDY | 5 | 4593 |
| PJH5 099 | NWFDP | 5 | 4595 |
| PJH5 100 | DWFDP | 5 | 4609 |
| PJH5 101 | YWFDP | 5 | 4610 |
| PJH5 102 | HWFDP | 5 | 4611 |
| PJH5 103 | FWFDP | 5 | 4612 |
| PJH5 104 | SWFDP | 5 | 4613 |
| PJH5 105 | RWFDP | 5 | 4614 |
| PJH5 107 | GWFDP | 5 | 4619 |
| PJH5 109 | AWFDP | 5 | 4621 |
| PJH6 110 | YGMDV | 5 | 4640 |
| PJH6 112 | DGMDV | 5 | 8686 |
| PJH1 071A | EYFQH | 5 | 4488 |
| PJH1 071B | KYFQH | 5 | 4502 |
| PJH2 073A | SYFDL | 5 | 8687 |
| PJH2 073B | GYFDL | 5 | 4533 |
| PJH2 074A | RYFDL | 5 | 4534 |
| PJH2 074B | LYFDL | 5 | 8688 |
| PJH3 083A | IAFDI | 5 | 4547 |
| PJH3 083B | VAFDI | 5 | 4550 |
| PJH3 084A | PAFDI | 5 | 4546 |
| PJH3 084B | AAFDI | 5 | 4551 |
| PJH3 085A | NAFDI | 5 | 4565 |
| PJH3 085B | TAFDI | 5 | 4548 |
| PJH4 094A | IYFDY | 5 | 4575 |
| PJH4 094B | TYFDY | 5 | 4576 |
| PJH5 106A | PWFDP | 5 | 4616 |
| PJH5 106B | TWFDP | 5 | 4618 |
| PJH5 108A | IWFDP | 5 | 4617 |
| PJH5 108B | VWFDP | 5 | 4620 |
| PJH6 111A | YYMDV | 5 | 4686 |
| PJH6 111B | DYMDV | 5 | 8689 |
| PJH6 113A | HGMDV | 5 | 8690 |

TABLE 32 -continued

Theoretical segment pool of unique H3-JH polypeptide segments encoded by the oligonucleotides of Table 31.

| Name | Sequence | Length | SEQ ID NO |
|---|---|---|---|
| PJH6 113B | LGMDV | 5 | 8691 |
| PJH6 114A | SGMDV | 5 | 8692 |
| PJH6 114B | AGMDV | 5 | 8693 |
| PJH2 116 | YWYFDL | 6 | 4527 |
| PJH2 117 | DWYFDL | 6 | 4530 |
| PJH5 120 | DNWFDP | 6 | 4594 |
| PJH5 121 | YNWFDP | 6 | 4597 |
| PJH5 122 | HNWFDP | 6 | 4598 |
| PJH5 123 | FNWFDP | 6 | 4599 |
| PJH5 124 | SNWFDP | 6 | 4600 |
| PJH5 125 | RNWFDP | 6 | 4601 |
| PJH5 126 | LNWFDP | 6 | 4602 |
| PJH5 127 | PNWFDP | 6 | 4603 |
| PJH5 128 | INWFDP | 6 | 4604 |
| PJH5 129 | TNWFDP | 6 | 4605 |
| PJH5 130 | GNWFDP | 6 | 4606 |
| PJH5 131 | VNWFDP | 6 | 4607 |
| PJH5 132 | ANWFDP | 6 | 4608 |
| PJH5 133 | NNWFDP | 6 | 4634 |
| PJH6 134 | YYGMDV | 6 | 4639 |
| PJH6 136 | DYGMDV | 6 | 8694 |
| PJH6 137 | FYGMDV | 6 | 8695 |
| PJH6 138 | HYGMDV | 6 | 8696 |
| PJH6 139 | LYGMDV | 6 | 8697 |
| PJH6 140 | NYGMDV | 6 | 8698 |
| PJH1 115A | AEYFQH | 6 | 4526 |
| PJH1 115B | PEYFQH | 6 | 4491 |
| PJH2 118A | LWYFDL | 6 | 8699 |
| PJH2 118B | HWYFDL | 6 | 4531 |
| PJH2 119A | NWYFDL | 6 | 4532 |
| PJH2 119B | SWYFDL | 6 | 8700 |
| PJH6 135A | DYYMDV | 6 | 8701 |
| PJH6 135B | YYYMDV | 6 | 4685 |
| PJH6 141A | AYGMDV | 6 | 8702 |
| PJH6 141B | PYGMDV | 6 | 8703 |
| PJH6 142A | SYGMDV | 6 | 8704 |
| PJH6 142B | IYGMDV | 6 | 8705 |

TABLE 32 -continued

Theoretical segment pool of unique H3-JH polypeptide segments encoded by the oligonucleotides of Table 31.

| Name | Sequence | Length | SEQ ID NO |
|---|---|---|---|
| PJH6 143A | TYGMDV | 6 | 8706 |
| PJH6 143B | RYGMDV | 6 | 8707 |
| PJH6 199A | GYGMDV | 6 | 8708 |
| PJH6 199B | VYGMDV | 6 | 8709 |
| PJH6 144 | YYYGMDV | 7 | 4638 |
| PJH6 145 | YYYYMDV | 7 | 4684 |
| PJH6 146 | DYYGMDV | 7 | 8710 |
| PJH6 148 | NYYGMDV | 7 | 8711 |
| PJH6 147A | LYYGMDV | 7 | 8712 |
| PJH6 147B | HYYGMDV | 7 | 8713 |
| PJH6 149A | SYYGMDV | 7 | 8714 |
| PJH6 149B | PYYGMDV | 7 | 8715 |
| PJH6 150A | NYYYMDV | 7 | 8716 |
| PJH6 150B | DYYYMDV | 7 | 8717 |
| PJH6 151 | YYYYGMDV | 8 | 4637 |
| PJH6 152 | NYYYGMDV | 8 | 4667 |
| PJH6 153 | DYYYGMDV | 8 | 4668 |
| PJH6 154 | HYYYGMDV | 8 | 4669 |
| PJH6 155 | FYYYGMDV | 8 | 4670 |
| PJH6 156 | SYYYGMDV | 8 | 4671 |
| PJH6 157 | RYYYGMDV | 8 | 4672 |
| PJH6 158 | LYYYGMDV | 8 | 4673 |
| PJH6 159 | PYYYGMDV | 8 | 4674 |
| PJH6 160 | TYYYGMDV | 8 | 4676 |
| PJH6 161 | GYYYGMDV | 8 | 4677 |
| PJH6 163 | AYYYGMDV | 8 | 4679 |
| PJH6 164 | YYYYYMDV | 8 | 4683 |
| PJH6 165 | NYYYYMDV | 8 | 4713 |
| PJH6 166 | DYYYYMDV | 8 | 4714 |
| PJH6 162A | VYYYGMDV | 8 | 4678 |
| PJH6 162B | IYYYGMDV | 8 | 4675 |
| PJH6 167A | HYYYYMDV | 8 | 4715 |
| PJH6 167B | PYYYYMDV | 8 | 4720 |
| PJH6 168A | SYYYYMDV | 8 | 4717 |
| PJH6 168B | GYYYYMDV | 8 | 4723 |
| PJH6 169 | YYYYYGMDV | 9 | 4636 |
| PJH6 170 | NYYYYGMDV | 9 | 4654 |

TABLE 32 -continued

Theoretical segment pool of unique H3-JH polypeptide segments encoded by the oligonucleotides of Table 31.

| Name | Sequence | Length | SEQ ID NO |
|---|---|---|---|
| PJH6 171 | DYYYYGMDV | 9 | 4655 |
| PJH6 172 | HYYYYGMDV | 9 | 4656 |
| PJH6 173 | FYYYYGMDV | 9 | 4657 |
| PJH6 174 | SYYYYGMDV | 9 | 4658 |
| PJH6 175 | RYYYYGMDV | 9 | 4659 |
| PJH6 176 | LYYYYGMDV | 9 | 4660 |
| PJH6 177 | PYYYYGMDV | 9 | 4661 |
| PJH6 178 | IYYYYGMDV | 9 | 4662 |
| PJH6 179 | TYYYYGMDV | 9 | 4663 |
| PJH6 180 | GYYYYGMDV | 9 | 4664 |
| PJH6 181 | VYYYYGMDV | 9 | 4665 |
| PJH6 182 | AYYYYGMDV | 9 | 4666 |
| PJH6 183 | DYYYYYGMDV | 10 | 4635 |
| PJH6 184 | YYYYYYGMDV | 10 | 4642 |
| PJH6 185 | HYYYYYGMDV | 10 | 4643 |
| PJH6 186 | FYYYYYGMDV | 10 | 4644 |
| PJH6 187 | SYYYYYGMDV | 10 | 4645 |
| PJH6 188 | RYYYYYGMDV | 10 | 4646 |
| PJH6 189 | LYYYYYGMDV | 10 | 4647 |
| PJH6 190 | PYYYYYGMDV | 10 | 4648 |
| PJH6 191 | IYYYYYGMDV | 10 | 4649 |
| PJH6 192 | TYYYYYGMDV | 10 | 4650 |
| PJH6 193 | GYYYYYGMDV | 10 | 4651 |
| PJH6 194 | VYYYYYGMDV | 10 | 4652 |
| PJH6 195 | AYYYYYGMDV | 10 | 4653 |
| PJH6 196 | NYYYYYGMDV | 10 | 4680 |
| PJH6 197A | DYYYYYYMDV | 10 | 4681 |
| PJH6 197B | YYYYYYYMDV | 10 | 4688 |

EQUIVALENTS

Those skilled in the art will recognize, or be able to ascertain using no more than routine experimentation, many equivalents to the specific embodiments and methods described herein. Such equivalents are intended to be encompassed by the scope of the following claims.

APPENDIX A

GI NUMBERS OF 3,571 SEQUENCES IN THE HEALTHY PREIMMUNE SET (HPS)

| | | | |
|---|---|---|---|
| 33628 | 1052674 | 1685242 | 1770847 |
| 37745 | 1052676 | 1685246 | 1770848 |
| 37747 | 1052683 | 1685248 | 1770851 |
| 37749 | 1052685 | 1685250 | 1770852 |
| 37751 | 1052691 | 1685252 | 1770853 |
| 37753 | 1052692 | 1685254 | 1770854 |
| 37755 | 1052693 | 1685256 | 1770855 |
| 37757 | 1052695 | 1685258 | 1770860 |
| 37759 | 1154682 | 1685260 | 1770861 |
| 37761 | 1154691 | 1685264 | 1770865 |
| 37763 | 1154698 | 1685266 | 1770866 |
| 37765 | 1154699 | 1685268 | 1770867 |
| 37767 | 1154706 | 1770744 | 1770869 |
| 37769 | 1154710 | 1770746 | 1770870 |
| 37773 | 1154713 | 1770747 | 1770872 |
| 37777 | 1154715 | 1770751 | 1770874 |
| 38383 | 1154724 | 1770755 | 1770875 |
| 38391 | 1154754 | 1770756 | 1770876 |
| 38393 | 1154769 | 1770758 | 1770877 |
| 38397 | 1154770 | 1770759 | 1770878 |
| 38401 | 1154805 | 1770761 | 1770879 |
| 185292 | 1154807 | 1770763 | 1770880 |
| 264183 | 1154808 | 1770765 | 1770881 |
| 297147 | 1154809 | 1770766 | 1770882 |
| 306949 | 1154810 | 1770770 | 1770883 |
| 306951 | 1154811 | 1770771 | 1770884 |
| 306953 | 1154813 | 1770772 | 1770885 |
| 483332 | 1154818 | 1770775 | 1770887 |
| 483333 | 1154820 | 1770776 | 1770888 |
| 483335 | 1154822 | 1770777 | 1770891 |
| 483336 | 1154824 | 1770779 | 1770892 |
| 483338 | 1154825 | 1770780 | 1770893 |
| 483339 | 1154834 | 1770783 | 1770894 |
| 483348 | 1154837 | 1770784 | 1770895 |
| 483350 | 1154838 | 1770785 | 1770896 |
| 510999 | 1154839 | 1770789 | 1770898 |
| 547164 | 1154840 | 1770791 | 1770902 |
| 587252 | 1154841 | 1770792 | 1770904 |
| 587254 | 1154843 | 1770793 | 1770905 |
| 587266 | 1154844 | 1770794 | 1770906 |
| 587276 | 1154845 | 1770795 | 1770908 |
| 587278 | 1154847 | 1770796 | 1770909 |
| 587280 | 1154848 | 1770797 | 1770910 |
| 587286 | 1197299 | 1770799 | 1770911 |
| 587288 | 1197300 | 1770800 | 1770912 |
| 587291 | 1197304 | 1770801 | 1770913 |
| 587293 | 1197307 | 1770805 | 1770914 |
| 587295 | 1197308 | 1770806 | 1770915 |
| 587299 | 1197309 | 1770807 | 1770916 |
| 587301 | 1197312 | 1770808 | 1770918 |
| 587304 | 1197313 | 1770809 | 1770922 |
| 587306 | 1197314 | 1770810 | 1770932 |
| 587308 | 1197315 | 1770811 | 1770936 |
| 587311 | 1197316 | 1770812 | 1770937 |
| 587313 | 1197318 | 1770813 | 1770950 |
| 587315 | 1197319 | 1770814 | 1770952 |
| 587317 | 1197321 | 1770815 | 1770954 |
| 1052611 | 1197322 | 1770816 | 1770958 |
| 1052620 | 1197323 | 1770817 | 1770961 |
| 1052622 | 1197324 | 1770818 | 1770962 |
| 1052626 | 1197325 | 1770820 | 1770963 |
| 1052627 | 1197326 | 1770822 | 1770964 |
| 1052634 | 1197327 | 1770824 | 1770967 |
| 1052637 | 1197328 | 1770826 | 1770969 |
| 1052639 | 1495508 | 1770829 | 1770971 |
| 1052640 | 1495511 | 1770830 | 1770972 |
| 1052642 | 1495512 | 1770831 | 1770974 |
| 1052644 | 1495516 | 1770833 | 1770976 |
| 1052655 | 1495518 | 1770835 | 1770979 |
| 1052656 | 1592729 | 1770836 | 1770981 |
| 1052657 | 1685210 | 1770837 | 1770982 |
| 1052658 | 1685220 | 1770839 | 1770983 |
| 1052659 | 1685222 | 1770840 | 1770989 |
| 1052662 | 1685228 | 1770843 | 1770992 |
| 1052668 | 1685234 | 1770844 | 1770994 |
| 1052669 | 1685238 | 1770845 | 1770995 |

APPENDIX A-continued

GI NUMBERS OF 3,571 SEQUENCES IN THE HEALTHY PREIMMUNE SET (HPS)

| | | | |
|---|---|---|---|
| 1052671 | 1685240 | 1770846 | 1770997 |
| 1770998 | 1791142 | 3170752 | 3170974 |
| 1771002 | 1791144 | 3170754 | 3170978 |
| 1771004 | 1791152 | 3170756 | 3170980 |
| 1771008 | 1791154 | 3170758 | 3170984 |
| 1771010 | 1791160 | 3170760 | 3170986 |
| 1771014 | 1791164 | 3170762 | 3170988 |
| 1771016 | 1791176 | 3170764 | 3170990 |
| 1771017 | 1791182 | 3170766 | 3170992 |
| 1771018 | 1791184 | 3170768 | 3171006 |
| 1771022 | 1791186 | 3170772 | 3171008 |
| 1771026 | 1791190 | 3170774 | 3171010 |
| 1771027 | 1791194 | 3170778 | 3171016 |
| 1771029 | 1791196 | 3170782 | 3171018 |
| 1771033 | 1791200 | 3170784 | 3171020 |
| 1771034 | 1791204 | 3170786 | 3171022 |
| 1771035 | 1791206 | 3170788 | 3171024 |
| 1771036 | 1869905 | 3170794 | 3171026 |
| 1771038 | 1869907 | 3170796 | 3171028 |
| 1771039 | 1869912 | 3170802 | 3171030 |
| 1771042 | 1869913 | 3170808 | 3171038 |
| 1771044 | 1869915 | 3170810 | 3171040 |
| 1771045 | 1869918 | 3170812 | 3171042 |
| 1771055 | 1869919 | 3170816 | 3171044 |
| 1771057 | 1934921 | 3170820 | 3171242 |
| 1771058 | 2367538 | 3170822 | 3608440 |
| 1771059 | 2388836 | 3170824 | 3608462 |
| 1771060 | 2388837 | 3170826 | 3954953 |
| 1771061 | 2388839 | 3170830 | 3954955 |
| 1771063 | 2388840 | 3170832 | 4530538 |
| 1791008 | 2388841 | 3170834 | 4530544 |
| 1791010 | 2388842 | 3170836 | 4753741 |
| 1791012 | 2388843 | 3170840 | 4959477 |
| 1791018 | 2388846 | 3170842 | 4995315 |
| 1791020 | 2388847 | 3170844 | 4995317 |
| 1791026 | 2388848 | 3170846 | 4995319 |
| 1791028 | 2388851 | 3170848 | 4995321 |
| 1791030 | 2388852 | 3170852 | 4995323 |
| 1791032 | 2388853 | 3170854 | 4995325 |
| 1791034 | 2388856 | 3170856 | 4995327 |
| 1791036 | 2388859 | 3170858 | 4995329 |
| 1791040 | 2388861 | 3170862 | 4995331 |
| 1791042 | 2388862 | 3170864 | 4995333 |
| 1791046 | 2388863 | 3170866 | 4995335 |
| 1791050 | 2388864 | 3170868 | 4995337 |
| 1791052 | 2388865 | 3170870 | 4995339 |
| 1791054 | 2388868 | 3170872 | 4995341 |
| 1791058 | 2388871 | 3170874 | 4995343 |
| 1791060 | 2388873 | 3170876 | 4995345 |
| 1791062 | 2388875 | 3170878 | 4995347 |
| 1791064 | 2388876 | 3170880 | 4995349 |
| 1791072 | 2388878 | 3170882 | 4995351 |
| 1791074 | 2773082 | 3170884 | 4995353 |
| 1791076 | 3170658 | 3170890 | 4995355 |
| 1791078 | 3170662 | 3170894 | 4995357 |
| 1791080 | 3170664 | 3170898 | 4995359 |
| 1791082 | 3170668 | 3170902 | 4995361 |
| 1791084 | 3170670 | 3170908 | 4995365 |
| 1791086 | 3170686 | 3170910 | 4995367 |
| 1791088 | 3170688 | 3170916 | 4995375 |
| 1791090 | 3170692 | 3170918 | 4995383 |
| 1791096 | 3170694 | 3170922 | 4995385 |
| 1791098 | 3170696 | 3170924 | 4995389 |
| 1791100 | 3170702 | 3170926 | 4995391 |
| 1791104 | 3170704 | 3170930 | 4995393 |
| 1791106 | 3170712 | 3170932 | 4995397 |
| 1791108 | 3170714 | 3170934 | 4995399 |
| 1791110 | 3170716 | 3170936 | 4995400 |
| 1791112 | 3170720 | 3170938 | 4995404 |
| 1791114 | 3170722 | 3170944 | 4995406 |
| 1791116 | 3170726 | 3170946 | 4995408 |
| 1791118 | 3170728 | 3170954 | 4995410 |
| 1791122 | 3170730 | 3170958 | 4995418 |
| 1791124 | 3170734 | 3170960 | 4995422 |
| 1791130 | 3170736 | 3170964 | 4995426 |
| 1791132 | 3170738 | 3170966 | 4995428 |

APPENDIX A-continued

GI NUMBERS OF 3,571 SEQUENCES IN THE HEALTHY PREIMMUNE SET (HPS)

| | | | |
|---|---|---|---|
| 1791134 | 3170740 | 3170968 | 4995430 |
| 1791136 | 3170748 | 3170970 | 4995432 |
| 4995434 | 5834089 | 6531600 | 8489286 |
| 4995436 | 5834091 | 6723523 | 8489289 |
| 4995438 | 5834093 | 6723525 | 8489291 |
| 4995440 | 5834095 | 6723527 | 11137164 |
| 4995442 | 5834097 | 6723531 | 11137170 |
| 4995446 | 5834099 | 6723535 | 11137172 |
| 4995456 | 5834101 | 6723537 | 11137174 |
| 4995462 | 5834103 | 6723543 | 11137178 |
| 4995466 | 5834105 | 6723545 | 11137183 |
| 4995470 | 5834107 | 6723549 | 11137186 |
| 4995474 | 5834109 | 6723551 | 11137188 |
| 4995476 | 5834113 | 6723558 | 11137196 |
| 4995478 | 5834115 | 6723565 | 11137200 |
| 4995480 | 5834119 | 6723581 | 11137205 |
| 4995482 | 5834121 | 6723583 | 11137215 |
| 4995484 | 5834123 | 6723595 | 11137219 |
| 4995486 | 5834125 | 6723597 | 11137229 |
| 4995488 | 5834127 | 6723599 | 11137231 |
| 4995490 | 5834129 | 7161042 | 11137242 |
| 4995492 | 5834131 | 7161061 | 11137251 |
| 4995494 | 5834133 | 7161129 | 11137253 |
| 4995496 | 5834135 | 7161136 | 11137261 |
| 4995498 | 5834137 | 7161164 | 11137262 |
| 4995500 | 5834139 | 8249510 | 11137274 |
| 4995502 | 5834141 | 8249514 | 11137276 |
| 4995504 | 5834143 | 8249518 | 11137279 |
| 4995506 | 5834145 | 8249524 | 11137281 |
| 4995508 | 5834147 | 8249528 | 11137283 |
| 4995510 | 5834149 | 8249538 | 11137285 |
| 4995512 | 5834151 | 8249546 | 11137289 |
| 4995514 | 5834153 | 8249552 | 11137290 |
| 4995516 | 5834155 | 8249554 | 11137293 |
| 4995520 | 5834159 | 8249558 | 11137295 |
| 4995524 | 5834161 | 8249560 | 11137298 |
| 4995530 | 5834163 | 8249562 | 11137301 |
| 4995535 | 5834165 | 8249566 | 11137303 |
| 4995537 | 5834169 | 8249568 | 11137305 |
| 4995539 | 5834175 | 8249608 | 11137307 |
| 4995549 | 5834177 | 8249622 | 11137309 |
| 4995555 | 5834179 | 8249632 | 11137313 |
| 4995557 | 5834183 | 8249650 | 11137315 |
| 4995563 | 5834185 | 8249652 | 11137317 |
| 4995569 | 5834187 | 8249654 | 11137319 |
| 4995575 | 5834191 | 8249656 | 11137322 |
| 4995581 | 5834193 | 8249662 | 11137326 |
| 4995589 | 5834195 | 8249674 | 11137329 |
| 4995591 | 5834197 | 8249682 | 11137333 |
| 5833973 | 5834199 | 8249698 | 11137335 |
| 5833980 | 5834201 | 8249712 | 11137339 |
| 5833984 | 5834203 | 8249716 | 11137343 |
| 5833986 | 5834205 | 8249718 | 11137348 |
| 5834003 | 5834207 | 8249730 | 11137350 |
| 5834011 | 5834209 | 8249738 | 11137352 |
| 5834015 | 5834213 | 8249740 | 11137354 |
| 5834019 | 5834215 | 8249744 | 11137359 |
| 5834031 | 6013039 | 8249754 | 11137361 |
| 5834035 | 6013043 | 8249756 | 11137363 |
| 5834037 | 6013045 | 8249760 | 11137365 |
| 5834039 | 6531445 | 8249772 | 11137367 |
| 5834041 | 6531457 | 8249778 | 11137369 |
| 5834043 | 6531461 | 8249784 | 11137371 |
| 5834047 | 6531465 | 8249786 | 11137373 |
| 5834049 | 6531481 | 8249788 | 11137375 |
| 5834051 | 6531489 | 8249790 | 11137377 |
| 5834053 | 6531493 | 8249812 | 11137379 |
| 5834055 | 6531495 | 8249816 | 11137382 |
| 5834057 | 6531507 | 8249826 | 11137386 |
| 5834059 | 6531509 | 8249828 | 11137388 |
| 5834065 | 6531511 | 8249838 | 11137392 |
| 5834069 | 6531513 | 8250248 | 11137399 |
| 5834071 | 6531517 | 8250255 | 11137403 |
| 5834073 | 6531521 | 8489274 | 11137407 |
| 5834075 | 6531525 | 8489276 | 11137411 |
| 5834077 | 6531533 | 8489278 | 11137413 |

APPENDIX A-continued

GI NUMBERS OF 3,571 SEQUENCES IN THE HEALTHY PREIMMUNE SET (HPS)

| | | | |
|---|---|---|---|
| 5834079 | 6531537 | 8489280 | 11137415 |
| 5834081 | 6531539 | 8489282 | 11137418 |
| 5834083 | 6531554 | 8489284 | 11137420 |
| 11137422 | 13172069 | 21702275 | 47846518 |
| 11137426 | 13172073 | 21702277 | 47846520 |
| 11137428 | 13172083 | 21702281 | 47846524 |
| 11137430 | 13172091 | 21702282 | 47846526 |
| 11137432 | 13172093 | 21702287 | 47846528 |
| 11137439 | 13172099 | 21702289 | 47846530 |
| 11137441 | 13172117 | 21702291 | 47846532 |
| 11137445 | 13172125 | 21702293 | 47846534 |
| 11137448 | 13172129 | 21702295 | 47846538 |
| 11137450 | 13172133 | 21702297 | 47846540 |
| 11137452 | 13172135 | 21702299 | 47846542 |
| 11137454 | 13172137 | 21702301 | 47846544 |
| 11137460 | 13172141 | 21702303 | 47846546 |
| 11137462 | 13172143 | 21702305 | 47846548 |
| 11137467 | 13172147 | 21702307 | 47846550 |
| 11137470 | 13172149 | 21702309 | 47846558 |
| 11137474 | 13172151 | 21702311 | 47846562 |
| 11137476 | 13172155 | 21702313 | 47846564 |
| 11137480 | 13172157 | 21702314 | 47846566 |
| 11137482 | 13172159 | 21702315 | 47846570 |
| 11137487 | 13172163 | 23337033 | 47846572 |
| 11137494 | 13172169 | 27370812 | 47846574 |
| 11137500 | 13172177 | 31076438 | 47846578 |
| 11137502 | 13623574 | 33873883 | 47846580 |
| 11137507 | 14289029 | 33989177 | 47846582 |
| 11137509 | 14289035 | 37987904 | 47846586 |
| 13171905 | 14289037 | 37987932 | 47846588 |
| 13171909 | 14289049 | 37987938 | 47846590 |
| 13171911 | 14289057 | 37987960 | 47846594 |
| 13171913 | 14289061 | 37987970 | 47846596 |
| 13171915 | 14289065 | 39644659 | 47846598 |
| 13171917 | 14289067 | 39645530 | 47846600 |
| 13171921 | 14289071 | 47846366 | 47846602 |
| 13171923 | 14289073 | 47846370 | 47846604 |
| 13171925 | 14289079 | 47846372 | 47846606 |
| 13171927 | 14289097 | 47846376 | 47846612 |
| 13171929 | 14289099 | 47846378 | 47846614 |
| 13171931 | 14289109 | 47846380 | 47846618 |
| 13171935 | 14289111 | 47846386 | 47846620 |
| 13171937 | 16075408 | 47846388 | 47846626 |
| 13171939 | 16075410 | 47846394 | 47846632 |
| 13171941 | 16075412 | 47846398 | 47846644 |
| 13171945 | 16075414 | 47846416 | 47846646 |
| 13171947 | 16075416 | 47846418 | 47846658 |
| 13171949 | 16075418 | 47846420 | 47846660 |
| 13171951 | 16075420 | 47846422 | 47846664 |
| 13171953 | 16075422 | 47846426 | 47846666 |
| 13171955 | 16075424 | 47846428 | 47846674 |
| 13171957 | 16075426 | 47846430 | 47846678 |
| 13171959 | 16075428 | 47846432 | 47846680 |
| 13171961 | 16075430 | 47846434 | 47846684 |
| 13171965 | 16075432 | 47846438 | 47846690 |
| 13171967 | 16075434 | 47846442 | 47846692 |
| 13171969 | 16075436 | 47846446 | 47846696 |
| 13171971 | 16075438 | 47846448 | 47846698 |
| 13171973 | 16075440 | 47846450 | 47846716 |
| 13171975 | 16075442 | 47846456 | 47846718 |
| 13171977 | 16075444 | 47846458 | 47846724 |
| 13171981 | 16075448 | 47846466 | 47846728 |
| 13171987 | 16075450 | 47846468 | 47846730 |
| 13171999 | 16075452 | 47846472 | 47846734 |
| 13172003 | 16075454 | 47846476 | 47846750 |
| 13172005 | 16075456 | 47846478 | 47846752 |
| 13172007 | 16075458 | 47846482 | 47846756 |
| 13172009 | 16075460 | 47846484 | 47846762 |
| 13172013 | 16075464 | 47846486 | 47846764 |
| 13172019 | 16075466 | 47846488 | 47846768 |
| 13172021 | 16076270 | 47846490 | 47846778 |
| 13172025 | 16076286 | 47846492 | 47846782 |
| 13172027 | 17511791 | 47846494 | 47846784 |
| 13172033 | 18044958 | 47846498 | 47846786 |
| 13172037 | 19171939 | 47846506 | 49256420 |
| 13172043 | 19550754 | 47846508 | 49256426 |

APPENDIX A-continued

GI NUMBERS OF 3,571 SEQUENCES IN THE HEALTHY PREIMMUNE SET (HPS)

| | | | |
|---|---|---|---|
| 13172045 | 19848531 | 47846510 | 49258105 |
| 13172053 | 19848533 | 47846512 | 49523831 |
| 13172061 | 19848543 | 47846514 | 49523833 |
| 13172065 | 19848545 | 47846516 | 49523835 |
| 49523837 | 54779258 | 54780723 | 145910938 |
| 49523841 | 54779260 | 54780731 | 145910942 |
| 49523843 | 54779262 | 54780733 | 145910945 |
| 49523849 | 54779264 | 54780735 | 145910949 |
| 49523851 | 54779266 | 54780741 | 145910952 |
| 49523853 | 54779268 | 54780745 | 145910955 |
| 49523855 | 54779270 | 54780753 | 145910958 |
| 49523861 | 54779272 | 54780757 | 145910966 |
| 49523865 | 54779274 | 54780759 | 145910969 |
| 49523871 | 54779276 | 54780761 | 145910972 |
| 49523873 | 54779278 | 54780763 | 145910975 |
| 49523879 | 54779280 | 54780765 | 145910983 |
| 49523881 | 54779282 | 54780767 | 145910986 |
| 49523887 | 54779284 | 54780771 | 145910989 |
| 49523895 | 54779286 | 54780775 | 145910992 |
| 49523905 | 54779288 | 54780777 | 145910995 |
| 49523919 | 54779290 | 54780779 | 145910998 |
| 49523921 | 54779292 | 54780781 | 145911001 |
| 49523923 | 54779296 | 54780783 | 145911004 |
| 49523927 | 54779298 | 54780785 | 145911013 |
| 49523929 | 54779300 | 54780787 | 145911017 |
| 49523931 | 54779302 | 54780791 | 145911020 |
| 49523946 | 54779306 | 54780793 | 145911023 |
| 49523950 | 54779308 | 54780795 | 145911026 |
| 54779136 | 54779310 | 54780801 | 145911029 |
| 54779140 | 54779314 | 54780803 | 145911032 |
| 54779142 | 54779316 | 54780805 | 145911038 |
| 54779144 | 54779318 | 54780807 | 145911041 |
| 54779146 | 54779320 | 54780809 | 145911044 |
| 54779148 | 54779322 | 54780815 | 145911047 |
| 54779150 | 54779324 | 54780817 | 145911050 |
| 54779152 | 54779328 | 54780821 | 145911053 |
| 54779156 | 54779330 | 54780825 | 145911061 |
| 54779158 | 54779332 | 54780827 | 145911064 |
| 54779160 | 54779334 | 54780831 | 145911072 |
| 54779162 | 54779336 | 54780833 | 145911075 |
| 54779166 | 54779338 | 54780835 | 145911081 |
| 54779168 | 54779340 | 54780837 | 145911086 |
| 54779170 | 54779342 | 54780839 | 145911090 |
| 54779172 | 54779344 | 54780841 | 145911092 |
| 54779174 | 54779350 | 54780843 | 145911096 |
| 54779178 | 54779354 | 54780845 | 145911102 |
| 54779180 | 54779356 | 54780847 | 145911105 |
| 54779182 | 54779358 | 54780853 | 145911108 |
| 54779184 | 54779360 | 54780857 | 145911111 |
| 54779186 | 54779362 | 54780859 | 145911133 |
| 54779188 | 54779364 | 54780861 | 145911150 |
| 54779190 | 54780155 | 54780863 | 145911156 |
| 54779192 | 54780163 | 55228577 | 145911159 |
| 54779194 | 54780167 | 55228579 | 145911162 |
| 54779196 | 54780171 | 55228584 | 145911165 |
| 54779198 | 54780177 | 55228638 | 145911171 |
| 54779200 | 54780179 | 55228640 | 145911174 |
| 54779204 | 54780185 | 55228646 | 145911177 |
| 54779206 | 54780187 | 55228650 | 145911180 |
| 54779208 | 54780191 | 55228651 | 145911183 |
| 54779210 | 54780193 | 55228652 | 145911186 |
| 54779212 | 54780209 | 60688113 | 145911190 |
| 54779214 | 54780211 | 74095346 | 145911193 |
| 54779218 | 54780213 | 74095348 | 145911199 |
| 54779220 | 54780227 | 74095350 | 145911202 |
| 54779222 | 54780229 | 74095355 | 145911205 |
| 54779224 | 54780235 | 74095358 | 145911214 |
| 54779226 | 54780237 | 91979763 | 145911217 |
| 54779228 | 54780239 | 91979789 | 145911220 |
| 54779230 | 54780243 | 91979839 | 145911223 |
| 54779232 | 54780247 | 91979849 | 145911226 |
| 54779234 | 54780251 | 111918091 | 145911235 |
| 54779236 | 54780253 | 111918116 | 145911238 |
| 54779238 | 54780259 | 111918127 | 145911248 |
| 54779240 | 54780709 | 111918184 | 145911257 |
| 54779242 | 54780711 | 111918251 | 145911287 |

APPENDIX A-continued

GI NUMBERS OF 3,571 SEQUENCES IN THE HEALTHY PREIMMUNE SET (HPS)

| | | | |
|---|---|---|---|
| 54779244 | 54780713 | 111918262 | 145911291 |
| 54779248 | 54780715 | 111918647 | 145911294 |
| 54779250 | 54780717 | 121488404 | 145911298 |
| 54779252 | 54780719 | 145910925 | 145911301 |
| 54779256 | 54780721 | 145910934 | 145911305 |
| 145911308 | 145911823 | 145912707 | 145913746 |
| 145911311 | 145911832 | 145912717 | 145913752 |
| 145911314 | 145911840 | 145912725 | 145913757 |
| 145911317 | 145911849 | 145912735 | 145913766 |
| 145911320 | 145911857 | 145912744 | 145913772 |
| 145911323 | 145911883 | 145912753 | 145913777 |
| 145911326 | 145911892 | 145912760 | 145913782 |
| 145911329 | 145911914 | 145912780 | 145913787 |
| 145911332 | 145911936 | 145912790 | 145913792 |
| 145911335 | 145911938 | 145912799 | 145913797 |
| 145911338 | 145911940 | 145912814 | 145913803 |
| 145911341 | 145911942 | 145912824 | 145913808 |
| 145911344 | 145911944 | 145912844 | 145913813 |
| 145911347 | 145911946 | 145912853 | 145913840 |
| 145911350 | 145911948 | 145912861 | 145913852 |
| 145911353 | 145911950 | 145912868 | 145913856 |
| 145911356 | 145911953 | 145912879 | 145913867 |
| 145911359 | 145911959 | 145912888 | 145913875 |
| 145911362 | 145911968 | 145912898 | 145913879 |
| 145911365 | 145911983 | 145912909 | 145913883 |
| 145911368 | 145911992 | 145912919 | 145913888 |
| 145911371 | 145912001 | 145912930 | 145913893 |
| 145911374 | 145912009 | 145912940 | 145913898 |
| 145911377 | 145912023 | 145912949 | 145913902 |
| 145911384 | 145912037 | 145912958 | 145913915 |
| 145911388 | 145912044 | 145912978 | 145913919 |
| 145911391 | 145912059 | 145912996 | 145913921 |
| 145911394 | 145912100 | 145913026 | 145913923 |
| 145911397 | 145912107 | 145913035 | 145913927 |
| 145911400 | 145912114 | 145913042 | 145913929 |
| 145911403 | 145912123 | 145913066 | 145913932 |
| 145911407 | 145912132 | 145913107 | 145913943 |
| 145911410 | 145912152 | 145913138 | 145913955 |
| 145911413 | 145912167 | 145913155 | 145913961 |
| 145911416 | 145912176 | 145913181 | 145913965 |
| 145911421 | 145912186 | 145913209 | 145913969 |
| 145911427 | 145912211 | 145913219 | 145913973 |
| 145911436 | 145912220 | 145913232 | 145913977 |
| 145911442 | 145912229 | 145913236 | 145913980 |
| 145911451 | 145912238 | 145913241 | 145913984 |
| 145911457 | 145912249 | 145913248 | 145913988 |
| 145911466 | 145912260 | 145913257 | 145913991 |
| 145911482 | 145912278 | 145913268 | 145913995 |
| 145911491 | 145912308 | 145913278 | 145914000 |
| 145911498 | 145912353 | 145913288 | 145914004 |
| 145911502 | 145912361 | 145913297 | 145914011 |
| 145911510 | 145912371 | 145913308 | 145914017 |
| 145911517 | 145912381 | 145913344 | 145914020 |
| 145911523 | 145912399 | 145913354 | 145914023 |
| 145911536 | 145912409 | 145913377 | 145914026 |
| 145911544 | 145912418 | 145913386 | 145914038 |
| 145911553 | 145912436 | 145913394 | 145914045 |
| 145911561 | 145912446 | 145913404 | 145914049 |
| 145911568 | 145912456 | 145913415 | 145914056 |
| 145911576 | 145912466 | 145913425 | 145914060 |
| 145911585 | 145912470 | 145913433 | 145914063 |
| 145911597 | 145912479 | 145913470 | 145938277 |
| 145911604 | 145912495 | 145913480 | 145938293 |
| 145911611 | 145912504 | 145913489 | 145938315 |
| 145911618 | 145912508 | 145913518 | 145938332 |
| 145911621 | 145912528 | 145913528 | 145938348 |
| 145911655 | 145912547 | 145913539 | 145938356 |
| 145911663 | 145912566 | 145913549 | 145938362 |
| 145911679 | 145912575 | 145913569 | 145938375 |
| 145911687 | 145912587 | 145913578 | 145938384 |
| 145911695 | 145912589 | 145913588 | 145938391 |
| 145911703 | 145912591 | 145913596 | 145938403 |
| 145911713 | 145912595 | 145913608 | 145938411 |
| 145911722 | 145912598 | 145913620 | 145938421 |
| 145911746 | 145912614 | 145913640 | 145938426 |
| 145911748 | 145912624 | 145913650 | 145938430 |

APPENDIX A-continued

GI NUMBERS OF 3,571 SEQUENCES IN THE HEALTHY PREIMMUNE SET (HPS)

| | | | |
|---|---|---|---|
| 145911750 | 145912635 | 145913660 | 145938438 |
| 145911752 | 145912647 | 145913670 | 145938446 |
| 145911754 | 145912674 | 145913682 | 145938454 |
| 145911768 | 145912682 | 145913687 | 145938462 |
| 145911786 | 145912691 | 145913722 | 145938470 |
| 145911795 | 145912700 | 145913730 | 145938490 |
| 145938504 | 145939392 | 145940316 | 145940902 |
| 145938513 | 145939407 | 145940325 | 145940907 |
| 145938531 | 145939416 | 145940332 | 145940912 |
| 145938537 | 145939432 | 145940340 | 145940917 |
| 145938553 | 145939449 | 145940354 | 145940921 |
| 145938562 | 145939459 | 145940362 | 145940926 |
| 145938570 | 145939470 | 145940370 | 145940940 |
| 145938577 | 145939475 | 145940379 | 145941075 |
| 145938596 | 145939484 | 145940387 | 145941079 |
| 145938621 | 145939501 | 145940399 | 145941083 |
| 145938629 | 145939514 | 145940404 | 145941090 |
| 145938639 | 145939566 | 145940411 | 145941097 |
| 145938647 | 145939578 | 145940416 | 145941111 |
| 145938674 | 145939586 | 145940428 | 145941118 |
| 145938680 | 145939593 | 145940439 | 145941131 |
| 145938689 | 145939602 | 145940441 | 145941134 |
| 145938698 | 145939609 | 145940445 | 145941137 |
| 145938706 | 145939634 | 145940448 | 145941143 |
| 145938713 | 145939643 | 145940450 | 145941151 |
| 145938721 | 145939651 | 145940452 | 145941158 |
| 145938730 | 145939657 | 145940456 | 145941167 |
| 145938737 | 145939670 | 145940461 | 145941176 |
| 145938755 | 145939678 | 145940468 | 145941194 |
| 145938771 | 145939686 | 145940482 | 145941226 |
| 145938808 | 145939694 | 145940489 | 145941231 |
| 145938830 | 145939699 | 145940494 | 145941239 |
| 145938837 | 145939704 | 145940498 | 145941247 |
| 145938865 | 145939707 | 145940508 | 145941255 |
| 145938874 | 145939711 | 145940510 | 145941262 |
| 145938892 | 145939718 | 145940515 | 145941276 |
| 145938899 | 145939724 | 145940520 | 145941296 |
| 145938906 | 145939730 | 145940530 | 145941328 |
| 145938916 | 145939738 | 145940535 | 145941336 |
| 145938926 | 145939747 | 145940541 | 145941349 |
| 145938944 | 145939753 | 145940547 | 145941358 |
| 145938952 | 145939760 | 145940552 | 145941365 |
| 145938969 | 145939766 | 145940557 | 145941373 |
| 145938986 | 145939768 | 145940567 | 145941380 |
| 145938995 | 145939770 | 145940573 | 145941388 |
| 145939005 | 145939776 | 145940583 | 145941393 |
| 145939023 | 145939778 | 145940593 | 145941399 |
| 145939030 | 145939782 | 145940597 | 145941425 |
| 145939044 | 145939788 | 145940602 | 145941459 |
| 145939053 | 145939805 | 145940613 | 145941466 |
| 145939061 | 145939817 | 145940631 | 145941474 |
| 145939069 | 145939824 | 145940636 | 145941483 |
| 145939083 | 145939834 | 145940645 | 145941488 |
| 145939085 | 145939844 | 145940650 | 145941499 |
| 145939087 | 145939858 | 145940656 | 145941505 |
| 145939093 | 145939865 | 145940662 | 145941512 |
| 145939095 | 145939872 | 145940675 | 145941518 |
| 145939097 | 145939879 | 145940681 | 145941539 |
| 145939106 | 145939900 | 145940700 | 145941544 |
| 145939132 | 145939910 | 145940706 | 145941550 |
| 145939147 | 145939921 | 145940711 | 145941558 |
| 145939155 | 145939940 | 145940727 | 145941571 |
| 145939161 | 145939949 | 145940735 | 145941577 |
| 145939169 | 145939970 | 145940742 | 145941588 |
| 145939181 | 145939986 | 145940748 | 145941597 |
| 145939189 | 145940002 | 145940756 | 145941605 |
| 145939197 | 145940029 | 145940762 | 145941618 |
| 145939206 | 145940036 | 145940774 | 145941634 |
| 145939215 | 145940043 | 145940783 | 145941639 |
| 145939231 | 145940052 | 145940789 | 145941644 |
| 145939237 | 145940070 | 145940797 | 145941650 |
| 145939252 | 145940091 | 145940804 | 145941657 |
| 145939271 | 145940115 | 145940818 | 145941669 |
| 145939285 | 145940124 | 145940825 | 145941674 |
| 145939302 | 145940133 | 145940832 | 145941680 |
| 145939309 | 145940152 | 145940838 | 145941685 |

APPENDIX A-continued

GI NUMBERS OF 3,571 SEQUENCES IN THE HEALTHY PREIMMUNE SET (HPS)

| | | | |
|---|---|---|---|
| 145939317 | 145940167 | 145940846 | 145941698 |
| 145939331 | 145940173 | 145940853 | 145941704 |
| 145939338 | 145940190 | 145940858 | 145941717 |
| 145939346 | 145940218 | 145940865 | 145941724 |
| 145939356 | 145940226 | 145940877 | 145941731 |
| 145939367 | 145940239 | 145940884 | 145941745 |
| 145939384 | 145940269 | 145940891 | 145941752 |
| 145941758 | 159034235 | 159034347 | 159034453 |
| 145941764 | 159034236 | 159034348 | 159034455 |
| 145941791 | 159034238 | 159034349 | 159034460 |
| 145941806 | 159034239 | 159034350 | 159034461 |
| 145941819 | 159034240 | 159034354 | 159034462 |
| 145941822 | 159034241 | 159034355 | 159034463 |
| 145941824 | 159034242 | 159034356 | 159034464 |
| 145941828 | 159034243 | 159034358 | 159034465 |
| 145941837 | 159034244 | 159034359 | 159034466 |
| 145941854 | 159034245 | 159034362 | 159034467 |
| 145941863 | 159034249 | 159034364 | 159034468 |
| 145941877 | 159034250 | 159034365 | 159034471 |
| 145941886 | 159034252 | 159034366 | 159034472 |
| 145941908 | 159034253 | 159034367 | 159034474 |
| 145941915 | 159034254 | 159034368 | 159034476 |
| 145941933 | 159034258 | 159034369 | 159034479 |
| 145942086 | 159034259 | 159034370 | 159034481 |
| 145942146 | 159034260 | 159034372 | 159034482 |
| 145942158 | 159034262 | 159034373 | 159034484 |
| 145942175 | 159034266 | 159034375 | 159034485 |
| 145942206 | 159034267 | 159034376 | 159034486 |
| 145942223 | 159034268 | 159034378 | 159034490 |
| 145942261 | 159034273 | 159034379 | 159034492 |
| 145942265 | 159034274 | 159034381 | 159034493 |
| 145942309 | 159034276 | 159034383 | 159034494 |
| 145942383 | 159034277 | 159034384 | 159034495 |
| 145942405 | 159034278 | 159034385 | 159034497 |
| 145942487 | 159034279 | 159034386 | 159034499 |
| 145942497 | 159034280 | 159034387 | 159034500 |
| 145942506 | 159034282 | 159034388 | 159034501 |
| 145942509 | 159034283 | 159034389 | 159034502 |
| 145942544 | 159034284 | 159034390 | 159034503 |
| 145942565 | 159034285 | 159034392 | 159034504 |
| 145942606 | 159034286 | 159034393 | 159034511 |
| 148717962 | 159034287 | 159034395 | 159034512 |
| 148717964 | 159034288 | 159034396 | 159034515 |
| 148717966 | 159034290 | 159034397 | 159034516 |
| 148910865 | 159034291 | 159034398 | 159034518 |
| 159034187 | 159034293 | 159034399 | 159034521 |
| 159034188 | 159034296 | 159034400 | 159034522 |
| 159034189 | 159034297 | 159034402 | 159034523 |
| 159034190 | 159034298 | 159034403 | 159034524 |
| 159034191 | 159034299 | 159034404 | 159034526 |
| 159034192 | 159034300 | 159034405 | 159034527 |
| 159034193 | 159034301 | 159034408 | 159034529 |
| 159034194 | 159034302 | 159034410 | 159034530 |
| 159034195 | 159034303 | 159034414 | 159034531 |
| 159034196 | 159034304 | 159034415 | 159034532 |
| 159034197 | 159034305 | 159034417 | 159034534 |
| 159034198 | 159034306 | 159034419 | 159034535 |
| 159034200 | 159034307 | 159034420 | 159034536 |
| 159034202 | 159034308 | 159034421 | 159034537 |
| 159034203 | 159034309 | 159034422 | 159034538 |
| 159034204 | 159034310 | 159034423 | 159034539 |
| 159034205 | 159034311 | 159034424 | 159034540 |
| 159034207 | 159034313 | 159034425 | 159034541 |
| 159034208 | 159034315 | 159034426 | 159034542 |
| 159034209 | 159034316 | 159034429 | 159034543 |
| 159034211 | 159034318 | 159034430 | 159034545 |
| 159034212 | 159034320 | 159034431 | 159034546 |
| 159034213 | 159034323 | 159034433 | 159034547 |
| 159034214 | 159034324 | 159034434 | 159034549 |
| 159034215 | 159034325 | 159034435 | 159034550 |
| 159034216 | 159034328 | 159034436 | 159034552 |
| 159034217 | 159034329 | 159034438 | 159034554 |
| 159034218 | 159034330 | 159034439 | 159034556 |
| 159034219 | 159034331 | 159034440 | 159034559 |
| 159034222 | 159034335 | 159034441 | 159034562 |
| 159034223 | 159034337 | 159034443 | 159034563 |

APPENDIX A-continued

GI NUMBERS OF 3,571 SEQUENCES IN THE HEALTHY PREIMMUNE SET (HPS)

| | | | | | | | |
|---|---|---|---|---|---|---|---|
| 159034224 | 159034339 | 159034444 | 159034564 | 159034686 | 159034789 | 159034894 | 159034998 |
| 159034225 | 159034340 | 159034445 | 159034565 | 159034687 | 159034790 | 159034895 | 159035002 |
| 159034226 | 159034341 | 159034446 | 159034566 | 159034688 | 159034791 | 159034897 | 159035003 |
| 159034227 | 159034342 | 159034447 | 159034568 | 159034689 | 159034793 | 159034898 | 159035005 |
| 159034228 | 159034343 | 159034448 | 159034570 | 159034690 | 159034794 | 159034899 | 159035007 |
| 159034230 | 159034344 | 159034449 | 159034571 | 159034692 | 159034795 | 159034900 | 159035008 |
| 159034231 | 159034345 | 159034450 | 159034572 | 159034693 | 159034796 | 159034901 | 159035009 |
| 159034233 | 159034346 | 159034451 | 159034573 | 159034695 | 159034798 | 159034902 | 159035010 |
| 159034575 | 159034697 | 159034801 | 159034904 | 159034696 | 159034799 | 159034903 | 159035013 |
| 159034576 | 159034698 | 159034802 | 159034905 | 159035014 | 159035117 | 159035234 | 159035362 |
| 159034578 | 159034699 | 159034804 | 159034906 | 159035015 | 159035118 | 159035235 | 159035363 |
| 159034580 | 159034700 | 159034805 | 159034907 | 159035016 | 159035120 | 159035238 | 159035364 |
| 159034581 | 159034701 | 159034809 | 159034908 | 159035017 | 159035122 | 159035239 | 159035366 |
| 159034582 | 159034704 | 159034811 | 159034909 | 159035018 | 159035123 | 159035240 | 159035368 |
| 159034584 | 159034705 | 159034812 | 159034910 | 159035021 | 159035124 | 159035241 | 159035369 |
| 159034587 | 159034706 | 159034813 | 159034911 | 159035022 | 159035125 | 159035242 | 159035370 |
| 159034588 | 159034708 | 159034815 | 159034912 | 159035023 | 159035126 | 159035245 | 159035372 |
| 159034589 | 159034709 | 159034816 | 159034913 | 159035024 | 159035128 | 159035247 | 159035373 |
| 159034591 | 159034710 | 159034817 | 159034914 | 159035025 | 159035129 | 159035250 | 159035374 |
| 159034596 | 159034711 | 159034818 | 159034917 | 159035026 | 159035130 | 159035253 | 159035378 |
| 159034599 | 159034712 | 159034819 | 159034918 | 159035027 | 159035131 | 159035256 | 159035380 |
| 159034600 | 159034713 | 159034820 | 159034919 | 159035028 | 159035133 | 159035257 | 159035382 |
| 159034601 | 159034714 | 159034821 | 159034920 | 159035031 | 159035134 | 159035260 | 159035384 |
| 159034602 | 159034717 | 159034822 | 159034923 | 159035033 | 159035135 | 159035261 | 159035385 |
| 159034604 | 159034718 | 159034823 | 159034925 | 159035034 | 159035136 | 159035262 | 159035386 |
| 159034607 | 159034720 | 159034824 | 159034926 | 159035035 | 159035137 | 159035263 | 159035390 |
| 159034609 | 159034721 | 159034825 | 159034928 | 159035036 | 159035138 | 159035264 | 159035391 |
| 159034611 | 159034722 | 159034827 | 159034929 | 159035038 | 159035139 | 159035265 | 159035393 |
| 159034612 | 159034725 | 159034828 | 159034931 | 159035039 | 159035140 | 159035267 | 159035394 |
| 159034613 | 159034726 | 159034829 | 159034934 | 159035040 | 159035143 | 159035268 | 159035395 |
| 159034617 | 159034728 | 159034831 | 159034935 | 159035041 | 159035145 | 159035269 | 159035400 |
| 159034619 | 159034729 | 159034832 | 159034936 | 159035042 | 159035146 | 159035270 | 159035401 |
| 159034620 | 159034730 | 159034833 | 159034937 | 159035043 | 159035147 | 159035272 | 159035402 |
| 159034621 | 159034731 | 159034834 | 159034938 | 159035044 | 159035149 | 159035273 | 159035403 |
| 159034622 | 159034732 | 159034835 | 159034939 | 159035045 | 159035150 | 159035274 | 159035404 |
| 159034625 | 159034733 | 159034837 | 159034940 | 159035046 | 159035151 | 159035275 | 159035405 |
| 159034626 | 159034734 | 159034838 | 159034942 | 159035047 | 159035152 | 159035277 | 159035406 |
| 159034628 | 159034736 | 159034839 | 159034945 | 159035049 | 159035155 | 159035279 | 159035407 |
| 159034629 | 159034737 | 159034840 | 159034946 | 159035050 | 159035158 | 159035280 | 159035408 |
| 159034631 | 159034738 | 159034842 | 159034947 | 159035051 | 159035159 | 159035282 | 159035413 |
| 159034632 | 159034741 | 159034843 | 159034948 | 159035052 | 159035160 | 159035284 | 159035418 |
| 159034634 | 159034742 | 159034844 | 159034950 | 159035053 | 159035162 | 159035285 | 159035420 |
| 159034635 | 159034743 | 159034845 | 159034952 | 159035054 | 159035163 | 159035287 | 159035422 |
| 159034636 | 159034744 | 159034846 | 159034953 | 159035055 | 159035164 | 159035288 | 159035423 |
| 159034637 | 159034745 | 159034847 | 159034954 | 159035056 | 159035166 | 159035289 | 159035424 |
| 159034638 | 159034747 | 159034848 | 159034955 | 159035057 | 159035170 | 159035290 | 159035425 |
| 159034640 | 159034748 | 159034849 | 159034957 | 159035058 | 159035172 | 159035292 | 159035426 |
| 159034641 | 159034749 | 159034852 | 159034959 | 159035060 | 159035173 | 159035293 | 159035427 |
| 159034642 | 159034750 | 159034853 | 159034961 | 159035061 | 159035174 | 159035294 | 159035430 |
| 159034643 | 159034751 | 159034856 | 159034962 | 159035063 | 159035175 | 159035296 | 159035432 |
| 159034647 | 159034752 | 159034858 | 159034963 | 159035064 | 159035176 | 159035299 | 159035433 |
| 159034648 | 159034754 | 159034859 | 159034964 | 159035065 | 159035177 | 159035302 | 159035435 |
| 159034649 | 159034756 | 159034860 | 159034965 | 159035066 | 159035179 | 159035303 | 159035436 |
| 159034650 | 159034758 | 159034861 | 159034967 | 159035067 | 159035180 | 159035305 | 159035437 |
| 159034651 | 159034759 | 159034862 | 159034970 | 159035072 | 159035181 | 159035307 | 159035439 |
| 159034652 | 159034760 | 159034863 | 159034971 | 159035073 | 159035182 | 159035308 | 159035441 |
| 159034653 | 159034762 | 159034864 | 159034973 | 159035074 | 159035183 | 159035309 | 159035445 |
| 159034654 | 159034763 | 159034866 | 159034974 | 159035075 | 159035185 | 159035310 | 159035446 |
| 159034657 | 159034764 | 159034869 | 159034975 | 159035076 | 159035186 | 159035312 | 159035447 |
| 159034658 | 159034765 | 159034871 | 159034976 | 159035079 | 159035187 | 159035313 | 159035449 |
| 159034659 | 159034766 | 159034872 | 159034978 | 159035080 | 159035188 | 159035314 | 159035450 |
| 159034660 | 159034767 | 159034874 | 159034980 | 159035081 | 159035191 | 159035315 | 159035451 |
| 159034661 | 159034768 | 159034876 | 159034981 | 159035083 | 159035192 | 159035316 | 159035452 |
| 159034664 | 159034771 | 159034877 | 159034982 | 159035084 | 159035193 | 159035318 | 159035453 |
| 159034665 | 159034773 | 159034879 | 159034983 | 159035085 | 159035194 | 159035319 | 159035454 |
| 159034668 | 159034774 | 159034880 | 159034984 | 159035086 | 159035195 | 159035320 | 159035456 |
| 159034669 | 159034778 | 159034882 | 159034985 | 159035087 | 159035199 | 159035321 | 159035457 |
| 159034672 | 159034779 | 159034883 | 159034987 | 159035089 | 159035201 | 159035323 | 159035458 |
| 159034673 | 159034780 | 159034885 | 159034988 | 159035090 | 159035204 | 159035327 | 159035459 |
| 159034676 | 159034781 | 159034886 | 159034989 | 159035092 | 159035205 | 159035329 | 159035461 |
| 159034677 | 159034782 | 159034887 | 159034991 | 159035097 | 159035206 | 159035330 | 159035463 |
| 159034678 | 159034783 | 159034888 | 159034992 | 159035100 | 159035207 | 159035331 | 159035464 |
| 159034679 | 159034784 | 159034889 | 159034993 | 159035101 | 159035208 | 159035334 | 159035466 |
| 159034680 | 159034786 | 159034890 | 159034995 | 159035102 | 159035209 | 159035335 | 159035468 |
| 159034681 | 159034787 | 159034892 | 159034996 | 159035103 | 159035210 | 159035338 | 159035470 |
| 159034683 | 159034788 | 159034893 | 159034997 | 159035104 | 159035211 | 159035342 | 159035472 |

APPENDIX A-continued

GI NUMBERS OF 3,571 SEQUENCES IN THE HEALTHY PREIMMUNE SET (HPS)

| | | | |
|---|---|---|---|
| 159035106 | 159035212 | 159035343 | 159035473 |
| 159035108 | 159035213 | 159035344 | 159035475 |
| 159035109 | 159035215 | 159035346 | 159035476 |
| 159035110 | 159035218 | 159035348 | 159035477 |
| 159035111 | 159035221 | 159035349 | 159035479 |
| 159035112 | 159035224 | 159035350 | 159035483 |
| 159035113 | 159035226 | 159035351 | 159035484 |
| 159035114 | 159035227 | 159035353 | 159035490 |
| 159035115 | 159035230 | 159035360 | 159035492 |
| 159035116 | 159035232 | 159035361 | 159035493 |
| 159035496 | 159035605 | 162950148 | 162950323 |
| 159035497 | 159035609 | 162950152 | 162950325 |
| 159035498 | 159035610 | 162950188 | 162950326 |
| 159035499 | 159035611 | 162950189 | 162950327 |
| 159035501 | 159035612 | 162950191 | 162950328 |
| 159035502 | 159035614 | 162950199 | 162950329 |
| 159035503 | 159035618 | 162950202 | 162950330 |
| 159035507 | 159035619 | 162950204 | 162950333 |
| 159035508 | 159035624 | 162950205 | 162950334 |
| 159035512 | 159035626 | 162950210 | 162950335 |
| 159035513 | 159035627 | 162950211 | 162950337 |
| 159035514 | 159035628 | 162950213 | 162950338 |
| 159035515 | 159035630 | 162950227 | 162950339 |
| 159035516 | 159035631 | 162950241 | 162950341 |
| 159035519 | 159035632 | 162950243 | 162950342 |
| 159035520 | 159035633 | 162950244 | 162950343 |
| 159035523 | 159035634 | 162950245 | 162950344 |
| 159035524 | 159035636 | 162950248 | 162950345 |
| 159035525 | 159035637 | 162950249 | 162950347 |
| 159035526 | 159035638 | 162950250 | 162950348 |
| 159035527 | 159035640 | 162950251 | 162950350 |
| 159035528 | 159035641 | 162950252 | 162950352 |
| 159035529 | 159035642 | 162950253 | 162950353 |
| 159035531 | 159035644 | 162950254 | 162950355 |
| 159035532 | 159035646 | 162950255 | 162950359 |
| 159035533 | 159035649 | 162950257 | 162950360 |
| 159035535 | 159035650 | 162950258 | 162950361 |
| 159035536 | 159035653 | 162950260 | 162950363 |
| 159035537 | 159035655 | 162950261 | 162950365 |
| 159035538 | 159035656 | 162950263 | 162950367 |
| 159035541 | 159035658 | 162950265 | 162950369 |
| 159035542 | 159035659 | 162950266 | 162950372 |
| 159035546 | 159035661 | 162950267 | 162950373 |
| 159035548 | 159035662 | 162950269 | 162950374 |
| 159035549 | 159035663 | 162950270 | 162950375 |
| 159035550 | 159035664 | 162950272 | 162950377 |
| 159035552 | 162950025 | 162950273 | 162950381 |
| 159035553 | 162950028 | 162950275 | 162950382 |
| 159035554 | 162950034 | 162950277 | 162950384 |
| 159035556 | 162950035 | 162950278 | 162950385 |
| 159035557 | 162950039 | 162950279 | 162950386 |
| 159035559 | 162950043 | 162950282 | 162950387 |
| 159035560 | 162950050 | 162950284 | 162950388 |
| 159035562 | 162950051 | 162950285 | 162950390 |
| 159035563 | 162950052 | 162950286 | 162950391 |
| 159035564 | 162950054 | 162950287 | 162950392 |
| 159035565 | 162950055 | 162950288 | 162950393 |
| 159035566 | 162950057 | 162950289 | 162950394 |
| 159035567 | 162950065 | 162950290 | 162950396 |
| 159035568 | 162950067 | 162950291 | 162950397 |
| 159035569 | 162950077 | 162950292 | 162950398 |
| 159035570 | 162950097 | 162950293 | 162950399 |
| 159035571 | 162950098 | 162950294 | 162950400 |
| 159035573 | 162950100 | 162950295 | 162950401 |
| 159035574 | 162950111 | 162950296 | 162950404 |
| 159035575 | 162950114 | 162950297 | 162950405 |
| 159035576 | 162950115 | 162950298 | 162950406 |
| 159035577 | 162950120 | 162950299 | 162950408 |
| 159035581 | 162950121 | 162950300 | 162950410 |
| 159035582 | 162950123 | 162950301 | 162950411 |
| 159035583 | 162950125 | 162950302 | 162950416 |
| 159035584 | 162950126 | 162950303 | 162950418 |
| 159035585 | 162950127 | 162950305 | 162950419 |
| 159035586 | 162950128 | 162950306 | 162950420 |
| 159035589 | 162950129 | 162950308 | 162950421 |
| 159035590 | 162950130 | 162950309 | 162950423 |

APPENDIX A-continued

GI NUMBERS OF 3,571 SEQUENCES IN THE HEALTHY PREIMMUNE SET (HPS)

| | | | |
|---|---|---|---|
| 159035591 | 162950132 | 162950310 | 162950425 |
| 159035592 | 162950133 | 162950311 | 162950426 |
| 159035593 | 162950134 | 162950312 | 162950428 |
| 159035594 | 162950137 | 162950313 | 162950430 |
| 159035595 | 162950138 | 162950314 | 162950431 |
| 159035596 | 162950139 | 162950315 | 162950432 |
| 159035597 | 162950140 | 162950316 | 162950433 |
| 159035598 | 162950141 | 162950317 | 162950434 |
| 159035602 | 162950143 | 162950318 | 162950435 |
| 159035603 | 162950146 | 162950319 | 162950437 |
| 159035604 | 162950147 | 162950321 | 162950438 |
| 162950439 | 162950566 | 162950674 | |
| 162950440 | 162950568 | 162950675 | |
| 162950441 | 162950570 | 162950676 | |
| 162950442 | 162950571 | 162950685 | |
| 162950444 | 162950572 | 162950686 | |
| 162950445 | 162950573 | 162950688 | |
| 162950446 | 162950574 | 162950689 | |
| 162950447 | 162950575 | 162950691 | |
| 162950449 | 162950577 | 162950692 | |
| 162950450 | 162950578 | 162950693 | |
| 162950451 | 162950579 | 162950694 | |
| 162950453 | 162950580 | 162950695 | |
| 162950454 | 162950581 | 162950696 | |
| 162950456 | 162950582 | 162950697 | |
| 162950461 | 162950583 | 162950698 | |
| 162950463 | 162950584 | 162950710 | |
| 162950464 | 162950585 | 162950714 | |
| 162950465 | 162950586 | 162950716 | |
| 162950466 | 162950587 | 162950720 | |
| 162950467 | 162950589 | 162950724 | |
| 162950469 | 162950590 | 162950725 | |
| 162950470 | 162950591 | 162950726 | |
| 162950471 | 162950592 | 162950728 | |
| 162950474 | 162950593 | 162950729 | |
| 162950476 | 162950594 | 194719560 | |
| 162950481 | 162950596 | 194719575 | |
| 162950483 | 162950597 | 218454113 | |
| 162950484 | 162950598 | 218454117 | |
| 162950485 | 162950599 | 219937557 | |
| 162950487 | 162950600 | | |
| 162950489 | 162950602 | | |
| 162950490 | 162950604 | | |
| 162950491 | 162950605 | | |
| 162950492 | 162950606 | | |
| 162950493 | 162950609 | | |
| 162950494 | 162950610 | | |
| 162950496 | 162950611 | | |
| 162950498 | 162950613 | | |
| 162950500 | 162950614 | | |
| 162950503 | 162950615 | | |
| 162950504 | 162950617 | | |
| 162950514 | 162950618 | | |
| 162950515 | 162950619 | | |
| 162950516 | 162950620 | | |
| 162950517 | 162950621 | | |
| 162950518 | 162950622 | | |
| 162950519 | 162950626 | | |
| 162950520 | 162950627 | | |
| 162950522 | 162950628 | | |
| 162950525 | 162950629 | | |
| 162950526 | 162950631 | | |
| 162950527 | 162950632 | | |
| 162950528 | 162950633 | | |
| 162950529 | 162950634 | | |
| 162950530 | 162950635 | | |
| 162950531 | 162950640 | | |
| 162950532 | 162950641 | | |
| 162950534 | 162950642 | | |
| 162950535 | 162950644 | | |
| 162950536 | 162950645 | | |
| 162950537 | 162950646 | | |
| 162950539 | 162950647 | | |
| 162950540 | 162950649 | | |
| 162950542 | 162950650 | | |
| 162950543 | 162950651 | | |

APPENDIX A-continued

| GI NUMBERS OF 3,571 SEQUENCES IN THE HEALTHY PREIMMUNE SET (HPS) | |
|---|---|
| 162950546 | 162950652 |
| 162950547 | 162950654 |
| 162950551 | 162950655 |
| 162950552 | 162950656 |
| 162950555 | 162950659 |
| 162950556 | 162950660 |
| 162950557 | 162950661 |

APPENDIX A-continued

| GI NUMBERS OF 3,571 SEQUENCES IN THE HEALTHY PREIMMUNE SET (HPS) | |
|---|---|
| 162950558 | 162950662 |
| 162950559 | 162950665 |
| 162950562 | 162950666 |
| 162950564 | 162950671 |
| 162950565 | 162950673 |

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US10889811B2). An electronic copy of the "Sequence Listing" will also be available from the USPTO upon request and payment of the fee set forth in 37 CFR 1.19(b)(3).

The invention claimed is:

1. A method of making a library comprising synthetic polynucleotides that encode an antibody heavy chain containing at least about $10^4$ unique antibody CDRH3 amino acid sequences, wherein each of the polynucleotides encoding the at least about $10^4$ unique antibody CDRH3 amino acid sequences has an antibody CDRH3 amino acid sequence represented by the following formula: [TN1]-[DH]-[N2]-[H3-JH], the method comprising:

(a) providing a theoretical segment pool containing TN1, DH, N2, and H3-JH segments, wherein the H3-JH segments are provided according to the following steps:
   (i) obtaining a set of polynucleotide sequences of human IGHJ genes and alleles;
   (ii) progressively deleting at least one nucleotide base from the 5' end of the polynucleotide sequences of (i);
   (iii) systematically adding at least one nucleotide base to the 5' end of the polynucleotide sequences from (ii); and
   (iv) translating the modified polynucleotide sequences of (iii) and selecting unique amino acid sequences to thereby provide the H3-JH theoretical segment pool;

(b) providing a reference set of preimmune CDRH3 sequences having sequence diversities and length diversities similar to naturally occurring human antibody sequences before these sequences have undergone negative selection and/or hypermutation;

(c) utilizing combinations of the TN1, DH, N2, and H3-JH segments contained in the theoretical segment pool of (a) to identify the closest match(es) to each CDRH3 sequence in the reference set of (b);

(d) selecting segments from the closest match(es) identified in step (c) for inclusion in a library comprising synthetic polynucleotides that encode an antibody heavy chain; and (e) synthesizing the synthetic polynucleotides that encode an antibody heavy chain;

wherein the diversity of the polynucleotides encoding the at least about $10^4$ unique antibody CDRH3 amino acid sequences is created by polynucleotides having CDRH3 sequences that are different from the CDRH3 sequences of other polynucleotides; and wherein the antibody heavy chain is a variable domain with framework (FRM) and complementary determining regions (CDRs) comprising FRMH1-CDRH1-FRMH2-CDRH2-FRMH3-CDRH3-FRM4.

2. The method of claim 1, wherein step (a)(ii) comprises progressive single base deletions.

3. The method of claim 1, wherein step (a)(ii) comprises progressively deleting at least one nucleotide base until only the sequence corresponding to FRM4 remains.

4. The method of claim 1, wherein step (a)(ii) comprises progressively deleting at least one nucleotide base until the polynucleotide sequence encodes only a single amino acid residue in the H3-JH segment.

5. The method of claim 1, wherein step (a)(iii) comprises systematically adding 1 or 2 nucleotide bases to the 5' end of the polynucleotide sequences from (ii).

6. The method of claim 1, wherein the unique sequences selected in step (a)(iv) do not comprise FRM4.

7. The method of claim 1, wherein the segments selected for inclusion in the synthetic library are selected according to their segment usage weight in the reference set of CDRH3 sequences.

8. The method of claim 1, wherein the segments selected for inclusion in the synthetic library are selected according to one or more physicochemical properties.

9. The method of claim 1, further comprising selecting additional TN1 and N2 segments occurring in the reference set but not in the theoretical segment pool.

10. The method of claim 1, wherein stop codons are reduced or eliminated from the library.

11. The method of claim 1, wherein the unpaired Cys residues, N-linked glycosylation motifs, and deamidation motifs are reduced or eliminated in the translation products of the library.

12. The method of claim 1, wherein the H3-JH segments are about 0 to about 10 amino acids in length.

13. The method of claim 1, wherein the theoretical segment pool contains TN1 segments corresponding to any of the TN1 polypeptides of Tables 10 and 18-26, or a polypeptide produced by translation of any of the TN1-encoding polynucleotides of Tables 25-26.

14. The method of claim 1, wherein the theoretical segment pool contains DH segments corresponding to any of the DH polypeptides of Tables 11, 17-25 and 28, or a polypeptide produced by translation of any of the DH-encoding polynucleotides of Tables 16, 25, and 27.

15. The method of claim 1, wherein the theoretical segment pool contains N2 segments corresponding to any of the N2 polypeptides of Tables 12, 18-25, and 30, or a polypeptide produced by translation of any of the N2-encoding polynucleotides of Tables 25 and 29.

16. The method of claim 1, wherein the theoretical segment pool contains H3-JH segments corresponding to any of the H3-JH polypeptides of Tables 13, 15, 18-25, and 32, or a polypeptide produced by translation of any of the H3-JH encoding polynucleotides of Tables 14, 25, and 31.

17. The method of claim 1, wherein the unique sequences of (iv) do not have stop codons, unpaired Cys residues, deamidation motifs, or Asn in the last or next to last position that can lead to N-linked glycosylation motifs.

18. The method of claim 1, wherein step (a)(iii) comprises systematically adding a NN doublet or NNN triplet at the 5' end of the sequence.

* * * * *